US010710978B2

(12) United States Patent
Gray et al.

(10) Patent No.: US 10,710,978 B2
(45) Date of Patent: Jul. 14, 2020

(54) STK4 INHIBITORS FOR TREATMENT OF HEMATOLOGIC MALIGNANCIES

(71) Applicants: Dana-Farber Cancer Institute, Inc., Boston, MA (US); Fondazione Centro San Raffaele, Milan (IT)

(72) Inventors: Nathanael S. Gray, Boston, MA (US); Sara Buhrlage, Somerville, MA (US); Kenneth Anderson, Wellesley, MA (US); Francesca Cottini, Columbus, OH (US); Giovanni Tonon, Milan (IT)

(73) Assignees: DANA-FARBER CANCER INSTITUTE, INC., Boston, MA (US); FONDAZIONE CENTRO SAN RAFFAELE, Milan (IT)

( * ) Notice: Subject to any disclaimer, the term of this patent is extended or adjusted under 35 U.S.C. 154(b) by 0 days.

(21) Appl. No.: 15/562,961

(22) PCT Filed: Mar. 31, 2016

(86) PCT No.: PCT/US2016/025320
§ 371 (c)(1),
(2) Date: Sep. 29, 2017

(87) PCT Pub. No.: WO2016/161145
PCT Pub. Date: Oct. 6, 2016

(65) Prior Publication Data
US 2018/0111916 A1    Apr. 26, 2018

Related U.S. Application Data

(60) Provisional application No. 62/140,695, filed on Mar. 31, 2015.

(51) Int. Cl.
| C07D 401/14 | (2006.01) |
| C07D 401/04 | (2006.01) |
| C07D 405/14 | (2006.01) |
| C07D 413/14 | (2006.01) |
| C07D 213/73 | (2006.01) |
| C07D 409/14 | (2006.01) |
| C07D 413/04 | (2006.01) |
| C07D 417/14 | (2006.01) |
| C07D 513/04 | (2006.01) |
| A61P 35/00 | (2006.01) |

(52) U.S. Cl.
CPC ............ C07D 401/14 (2013.01); A61P 35/00 (2018.01); C07D 213/73 (2013.01); C07D 401/04 (2013.01); C07D 405/14 (2013.01); C07D 409/14 (2013.01); C07D 413/04 (2013.01); C07D 413/14 (2013.01); C07D 417/14 (2013.01); C07D 513/04 (2013.01)

(58) Field of Classification Search
None
See application file for complete search history.

(56) References Cited

U.S. PATENT DOCUMENTS

| 8,153,804 | B2* | 4/2012 | Augeri | ................. C07D 213/73 544/238 |
| 8,440,652 | B2* | 5/2013 | Augeri | ................. C07D 401/04 514/211.05 |
| 2011/0098325 | A1* | 4/2011 | Raynham | ............ C07D 213/74 514/352 |
| 2012/0225857 | A1 | 9/2012 | Augeri et al. | |

FOREIGN PATENT DOCUMENTS

| WO | WO 2007/016674 A2 | 2/2007 |
| WO | WO 2007/139816 A2 | 12/2007 |
| WO | WO 2008/025820 A1 | 3/2008 |
| WO | WO-2008025820 A1 * | 3/2008 ........... C07D 213/73 |

OTHER PUBLICATIONS

Silva, A., Mini-Reviews in Medicinal Chemistry, 2005, vol. 5, pp. 893-014.*
Silverman, R. "The Organic Chemistry of Drug Design and Drug Action," 2004, Elsevier, pp. 29-32.*
Ardestani, A., et al., "MST1 is a key regulator of beta cell apoptosis and dysfunction in diabetes", *Nature Medicine*, 2014, vol. 20, No. 4, p. 385-397.
Cottini, F., et al., "Rescue of Hippo coactivator YAP1 triggers DNA damage—induced apoptosis in hematological cancers", *Nature Medicine*, 2014, vol. 20, No. 6, p. 599-606.
Hilton, S., et al., "Identification and characterisation of 2-aminopyridine inhibitors of checkpoint kinase 2", *Bioorganic & Medicinal Chemistry*, 2010, vol. 18, Issue 2, pp. 707-718.
Kyle, R.A., et al., "Multiple Myeloma", *New England Journal of Medicine*, 2004, vol. 351, No. 18, p. 1860-1873.
Kyle, R.A., et al., "Clinical course and prognosis of smoldering (asymptomatic) multiple myeloma", *New England Journal of Medicine*, 2007, vol. 356, No. 25, p. 2582-2590.

(Continued)

*Primary Examiner* — Heidi Reese
(74) *Attorney, Agent, or Firm* — Burns & Levinson, LLP; Daniel W. Clarke

(57) ABSTRACT

The application relates to compounds of Formula (I'):

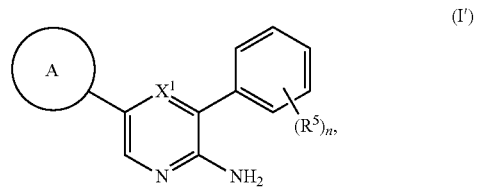

which modulate the activity of a kinase (e.g., STK4), a pharmaceutical composition comprising the compound, and a method of treating or preventing a disease or disorder associated with the modulation of a kinase, such as STK4.

24 Claims, 53 Drawing Sheets

(56) References Cited

OTHER PUBLICATIONS

Kyle, R.A., et al., "Prevalence of monoclonal gammopathy of undetermined significance", *New England Journal of Medicine*, 2006, vol. 354, No. 13, p. 1362-1369.

Salojin, K.V., et al., "Genetic Deletion of Mst1 Alters T Cell Function and Protects against Autoimmunity", *PLoS One*, 2014, vol. 9, No. 5, e98151.

\* cited by examiner

Concentration of Compound I-15 μM

Concentration of Compound I-9 μM

Concentration of Compound I-39 µM

Concentration of Compound I-6 µM

Concentration of Compound I-77 μM

Concentration of Compound I-77 μM

STK4 INHIBITORS FOR TREATMENT OF HEMATOLOGIC MALIGNANCIES

RELATED APPLICATION

This application is a U.S. National Phase application, filed under 35 U.S.C. § 371, of International Application No. PCT/US2016/025320, filed on Mar. 31, 2016, which claims the benefit of and priority to U.S. provisional application No. 62/140,695, filed Mar. 31, 2015, the contents of each of which are incorporated herein by reference in their entireties.

BACKGROUND OF THE APPLICATION

STK4 (also known as MST1) is a serine-threonine kinase that is part of the Hippo signaling pathway. STK4 is involved in multiple cellular processes including proliferation, trafficking, apoptosis, immune response and stress response (Cottini, F., et al., Nat. Med., 20 (6), 599-606 (2014); Salojin, K. V., et al., PLoS One, 9(5), e98151 (2014); Ardestani, A., et al., Nat. Med., 20 (4), 385-397, (2014)). STK4 reactivates the Hippo mediator YAP1 thereby triggering apoptosis in hematologic malignancies characterized by high levels of DNA damage. DNA double-strand break (DSB) followed by activation of DNA damage response in cancers occurs in premalignant and malignant conditions. However, progression to malignancy is prevented in pre-cancerous settings by senescence and apoptotic responses until the tumor suppressor TP53 (p53) is inactivated, thereby triggering genomic instability and enhancing tumor cell growth.

Recently, it has been shown that hematologic malignancies, including multiple myeloma, lymphoma, and leukemia, contain pervasive DNA damage that leads to activation of a p53-independent proapoptotic network centered on relocalization of ABL1 kinase. Unlike normal cells in which ABL1 kinase triggers cell death with the Hippo pathway co-activator YAP1, low levels of YAP1 in hematologic malignancies prevent nuclear ABL1-induced apoptosis (Cottini, F., et al., Nat. Med., 20 (6), 599-606, (2014)).

Downregulation of STK4 with specific shRNAs has been shown to lead to a robust increase of YAP1 protein levels compared to scrambled shRNA. Inactivation of serine-threonine kinase 4 (STK4) has also been shown to restore YAP1 levels triggering cell death in vitro and in vivo demonstrating that YAP1 is under the control of STK4. Inhibition of STK4 with small molecule inhibitors has the potential to be a treatment for cancers and other disorders. Known STK4 inhibitors have demonstrated poor kinase selectivity, cell penetration and pharmacokinetic properties. For these reasons, there remains a need for novel and potent small molecule STK4 inhibitors.

SUMMARY OF THE APPLICATION

The present application relates to compounds of any of the formulae described herein, as defined herein, that are capable of modulating a kinase (e.g., serine-threonine kinase 4 (STK4)) activity. The application also features methods of treating or preventing a disease in which a kinase (e.g., STK4) plays a role in a subject in need thereof by administering to the subject a therapeutically effective amount of a compound of any of the formulae described herein, or a pharmaceutically acceptable salt, hydrate, solvate, prodrug, stereoisomer, or tautomer thereof, as defined herein. The methods of the application can be used to treat diseases in which a kinase (e.g., STK4) plays a role by inhibiting the kinase activity.

A first aspect of the application relates to compounds of Formula (I') or (I):

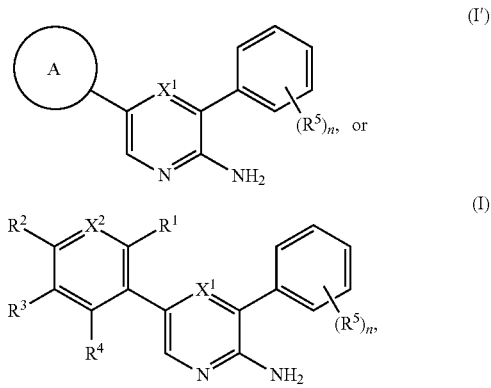

or pharmaceutically acceptable salts, hydrates, solvates, prodrugs, stereoisomers, or tautomers thereof, wherein

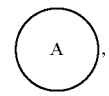

$R^1$, $R^2$, $R^3$, $R^4$, $R^5$, $X^1$, $X^2$, and n are described herein in detail below.

Another aspect of the present application relates to a pharmaceutical composition comprising, a compound of any of the formulae described herein, or a pharmaceutically acceptable salt, hydrate, solvate, prodrug, stereoisomer, or tautomer thereof, and a pharmaceutically acceptable carrier.

Another aspect of the present application relates to a method of treating or preventing a disease or disorder (e.g., cancer, a proliferation disease, an autoimmune disease, or a metabolic disease). The method comprises administering to a subject in need thereof an effective amount of a compound of any of the formulae described herein, or a pharmaceutically acceptable salt, hydrate, solvate, prodrug, stereoisomer, or tautomer thereof.

In another aspect, the present application relates to a method of treating or preventing a disease or disorder associated with the modulation of a kinase. The method comprises administering to a subject in need thereof an effective amount of a compound of any of the formulae described herein, or a pharmaceutically acceptable salt, hydrate, solvate, prodrug, stereoisomer, or tautomer thereof. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase is STK4. In some embodiments, the kinase is ITPK1.

Another aspect of the present application relates to a method of modulating a kinase. The method comprises administering to a subject in need thereof an effective amount of a compound of any of the formulae described herein, or a pharmaceutically acceptable salt, hydrate, solvate, prodrug, stereoisomer, or tautomer thereof. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the present application relates to a method of inhibiting a kinase. In some embodiments, the kinase that is inhibited is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase that is inhibited is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase that is inhibited is STK4. In some embodiments, the present application relates to a method of activating a kinase. In some embodiments, the kinase that is activated is ITPK1.

In another aspect, the present application relates to a method of treating or preventing cancer or a hematopoietic disorder. The method comprises administering to a subject in need thereof an effective amount of a compound of any of the formulae described herein, or a pharmaceutically acceptable salt, hydrate, solvate, prodrug, stereoisomer, or tautomer thereof. In some embodiments, the compound increases YAP1 levels. In some embodiments, the subject has been identified as having a hematopoietic disorder with reduced levels of YAP1.

In another aspect, the present application relates to a compound of any of the formulae described herein, or a pharmaceutically acceptable salt, hydrate, solvate, prodrug, stereoisomer, or tautomer thereof, for use in the manufacture of a medicament for treating or preventing a disease or disorder (e.g., cancer, a proliferation disease, an autoimmune disease, or a metabolic disease).

In another aspect, the present application relates to a compound of any of the formulae described herein, or a pharmaceutically acceptable salt, hydrate, solvate, prodrug, stereoisomer, or tautomer thereof, for use in the manufacture of a medicament for treating or preventing a disease or disorder associated with the modulation of a kinase. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase is STK4. In some embodiments, the kinase is ITPK1.

Another aspect of the present application relates to a compound of any of the formulae described herein, or a pharmaceutically acceptable salt, hydrate, solvate, prodrug, stereoisomer, or tautomer thereof, for use in the manufacture of a medicament for modulating a kinase. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the medicament is for inhibiting a kinase. In some embodiments, the kinase that is inhibited is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase that is inhibited is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase that is inhibited is STK4. In some embodiments, the medicament is for activating a kinase. In some embodiments, the kinase that is activated is ITPK1.

Another aspect of the present application relates to a compound of any of the formulae described herein, or a pharmaceutically acceptable salt, hydrate, solvate, prodrug, stereoisomer, or tautomer thereof, for use in the manufacture of a medicament for treating or preventing cancer or a hematopoietic disorder. In some embodiments, the compound increases YAP1 levels. In some embodiments, the medicament is for a subject which has been identified as having a hematopoietic disorder with reduced levels of YAP1.

In another aspect, the present application relates to the use of a compound of any of the formulae described herein, or a pharmaceutically acceptable salt, hydrate, solvate, prodrug, stereoisomer, or tautomer thereof, in the treatment or prevention of a disease or disorder (e.g., cancer, a proliferation disease, an autoimmune disease, or a metabolic disease).

Another aspect of the present application relates to the use of a compound of any of the formulae described herein, or a pharmaceutically acceptable salt, hydrate, solvate, prodrug, stereoisomer, or tautomer thereof, in the treatment or prevention of a disease or disorder associated with the modulation of a kinase. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase is STK4. In some embodiments, the kinase is ITPK1.

Another aspect of the present application relates to the use of a compound of any of the formulae described herein, or a pharmaceutically acceptable salt, hydrate, solvate, prodrug, stereoisomer, or tautomer thereof, in the modulation of a kinase. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the modulation is inhibition. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase is STK4. In some embodiments, the modulation is activation. In some embodiments, the kinase is ITPK1.

In another aspect, the present application relates to the use of a compound of any of the formulae described herein, or a pharmaceutically acceptable salt, hydrate, solvate, prodrug, stereoisomer, or tautomer thereof, in the treatment or prevention of cancer or a hematopoietic disorder. In some embodiments, the compound increases YAP1 levels. In some embodiments, the subject which has been identified as having a hematopoietic disorder has reduced levels of YAP1.

The present application further provides compounds and compositions with an improved efficacy and/or safety profile relative to known serine-threonine kinase 4 (STK4) inhibitors. The present application also provides agents with novel mechanisms of action toward serine-threonine kinase 4 (STK4) kinases in the treatment of various types of diseases including cancer and metastasis, proliferation diseases, autoimmune diseases, and metabolic diseases.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

BRIEF DESCRIPTION OF THE DRAWINGS

FIG. 11A-FIG. 1M are graphs showing the viability of MM.1S, KMS20, and H929 cells when treated with Compound I-2 (FIG. 11A), Compound I-3 (FIG. 11B), Compound I-9 (FIG. 11C), Compound I-12 (FIG. 11D), Compound I-13 (FIG. 11E), Compound I-23 (FIG. 11F), Compound I-27 (FIG. 11G), Compound I-28 (FIG. 11H), Compound I-72 (FIG. 11I), Compound I-74 (FIG. 11J), Compound I-76 (FIG. 11K), Compound I-45 (FIG. 11L), and Compound I-46 (FIG. 11M).

FIG. 32A is a graph showing the ratio of MEK2 to STK4 derived from the Western blotting band signals in FIG. 32B, in MM.1S cell lysates treated with 10 µM of Compound I-9, I-13, or I-27 or KIN001-305 followed by incubation with biotinylated ATP. FIG. 32B is a Western blot showing the levels of STK4 and MEK2 in MM.1S cells treated with 10 µM of Compound I-9, I-13, or I-27 or KIN001-305 followed by incubation with biotinylated ATP. The results suggest that Compounds I-9, I-27, and KIN001-305 have the highest affinity for STK4, as of ATP binding.

DETAILED DESCRIPTION OF THE APPLICATION

Compounds of the Application

Figure 1:
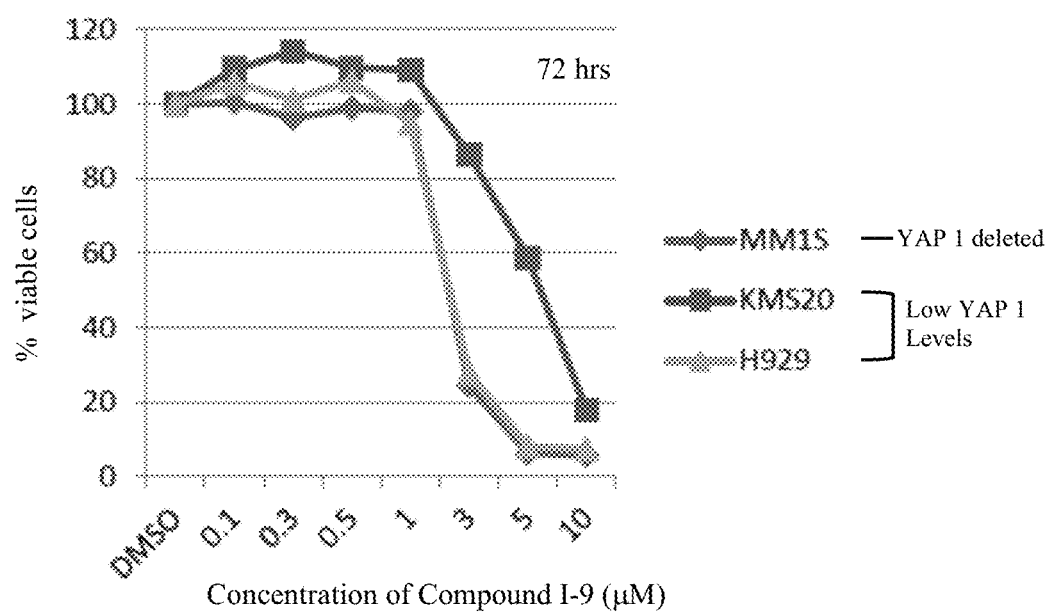
FIG. 1 is a graph showing the viability of MM.1S, KMS20 and H929 cells when treated for 72 hours with varying concentrations of Compound I-9.
Figure 2A:
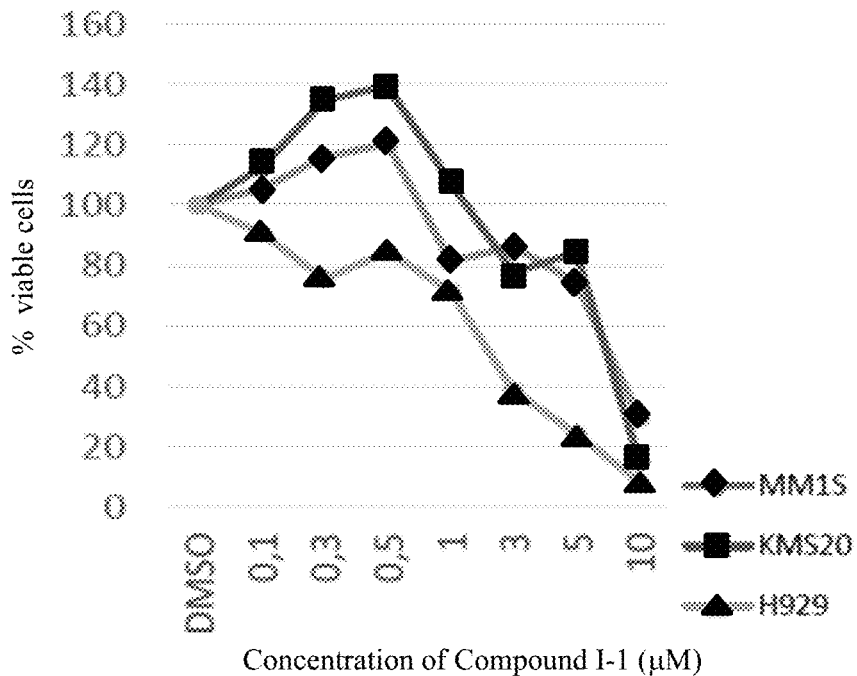
FIG. 2A and FIG. 2B are graphs showing the viability of MM.1S, KMS20 and H929 cells when treated for 72 hours with varying concentrations of Compound I-1 and Compound I-12.
Figure 2B:
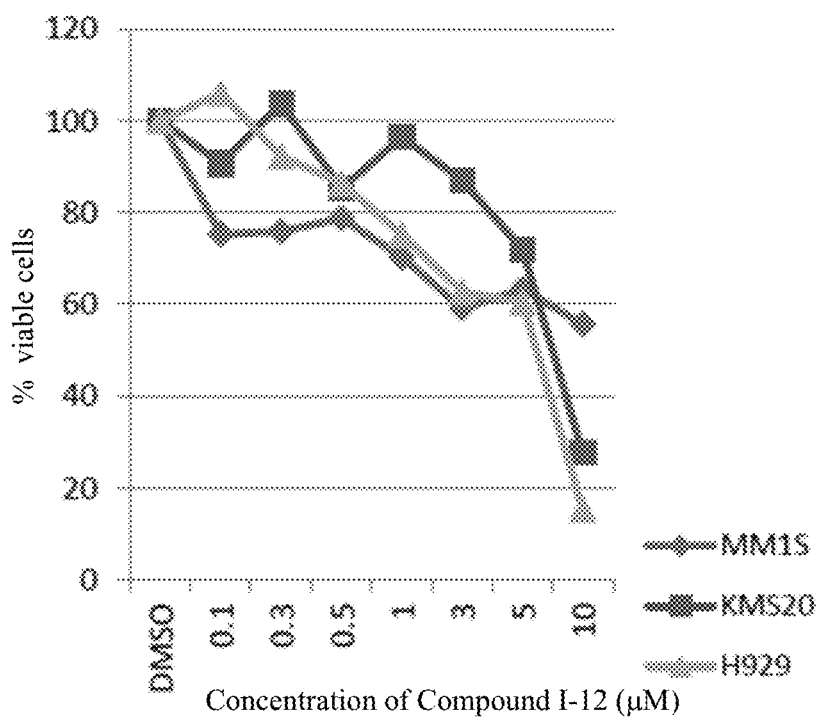
Figure 3A:
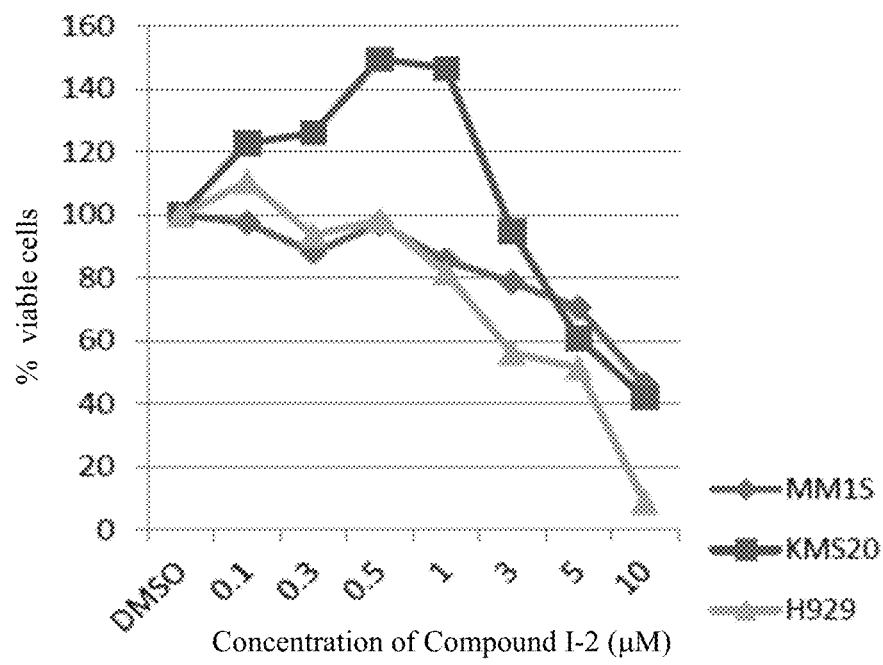
FIG. 3A and FIG. 3B are graphs showing the viability of MM.1S, KMS20 and H929 cells when treated for 72 hours with varying concentrations of Compound I-2 and Compound I-3.
Figure 3B:
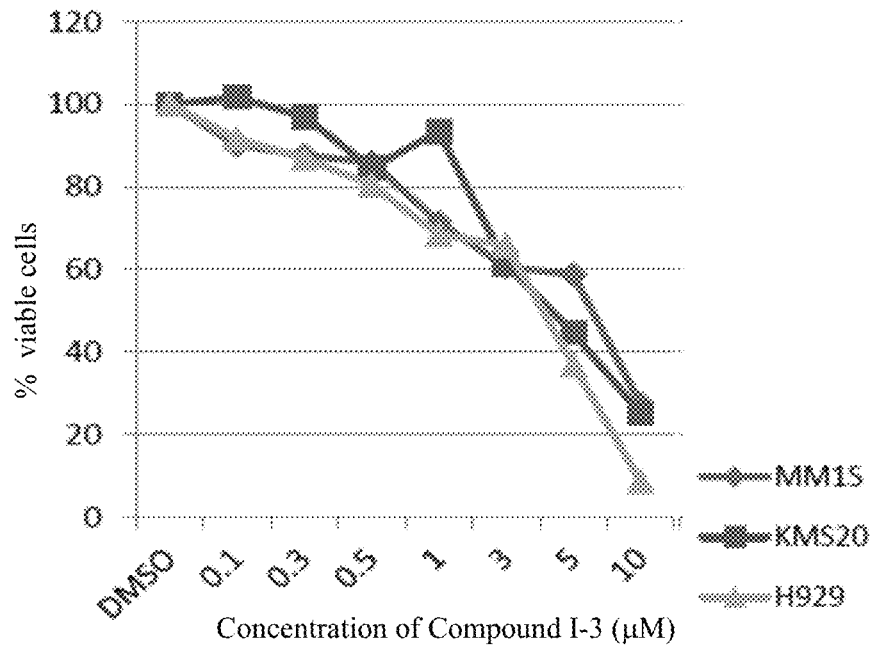
Figure 4A:
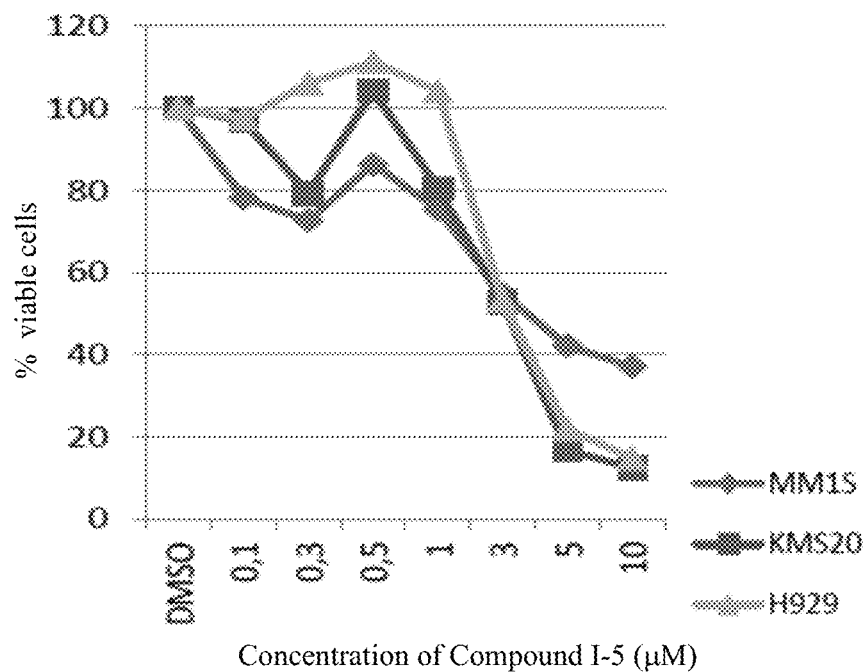
FIG. 4A and FIG. 4B are graphs showing the viability of MM.1S, KMS20 and H929 cells when treated for 72 hours with varying concentrations of Compound I-5 and Compound I-6.
Figure 4B:
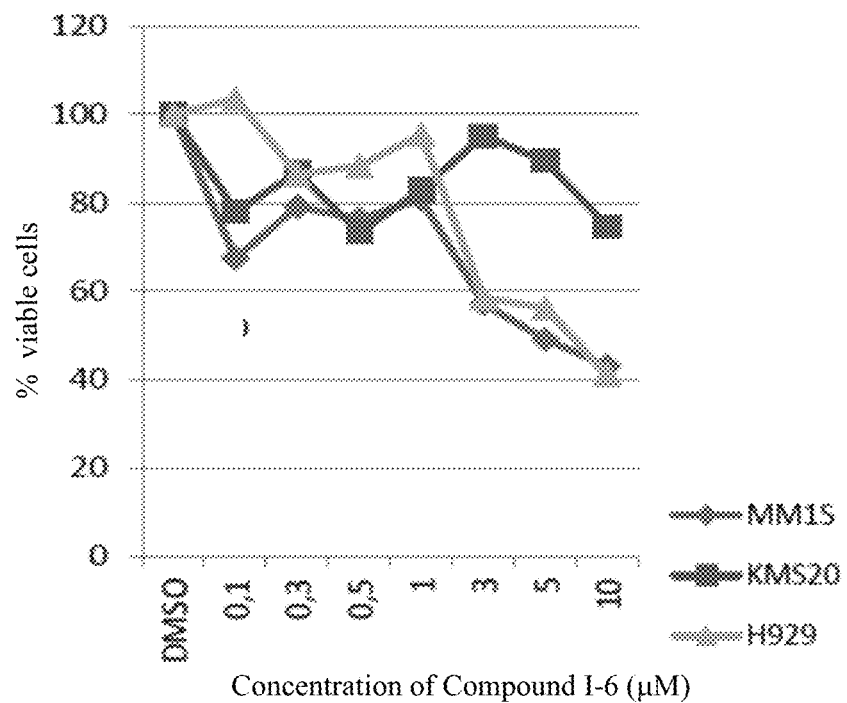
Figure 5A:
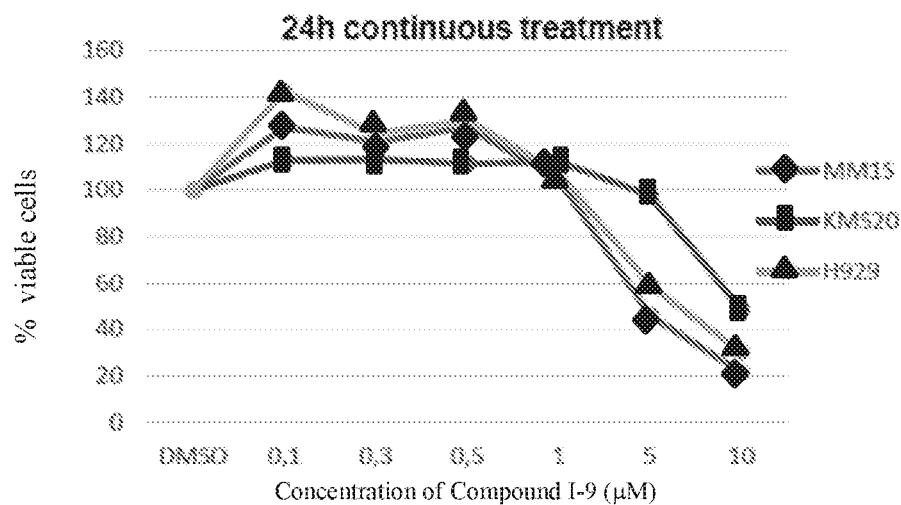
FIG. 5A is a graph showing the viability of MM.1 S, KMS20 and H929 cells when treated with varying concentrations of Compound I-9.
Figure 5B:
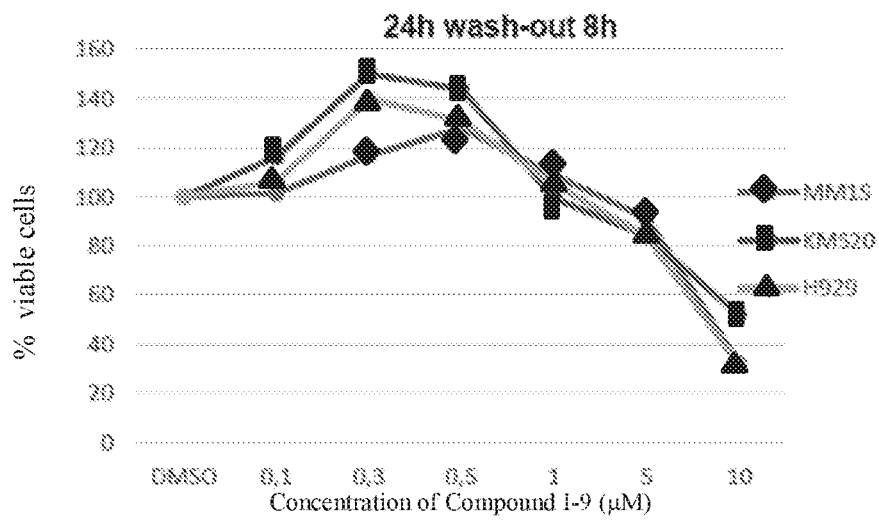
FIG. 5B is a graph showing the viability of MM.1S, KMS20 and H929 cells after being treated for 8 hours with varying concentrations of Compound I-9, followed by 16 hours in media without Compound I-9.
Figure 5C:
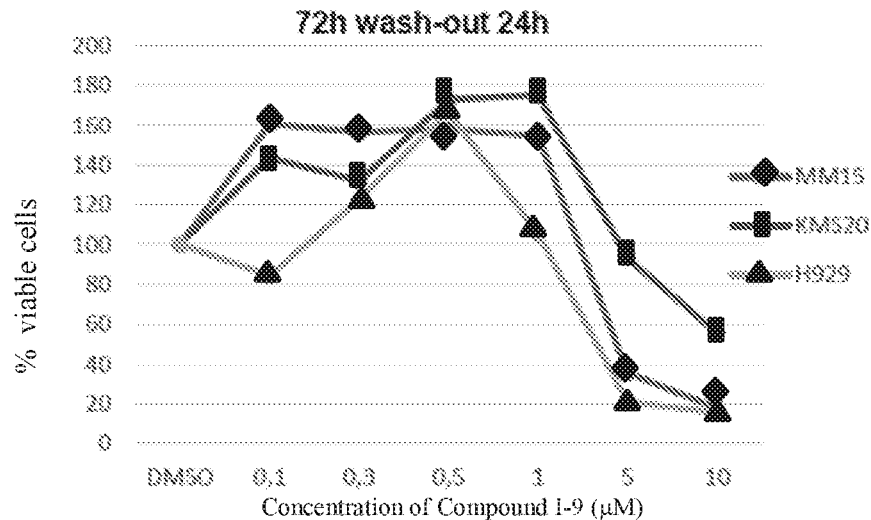
FIG. 5C is a graph showing the viability of MM.1S, KMS20 and H929 cells after being treated with varying concentrations of Compound I-9 for 24 hours, followed by 48 hours in media without Compound I-9.

A first aspect of the application relates to compounds of Formula (I'):

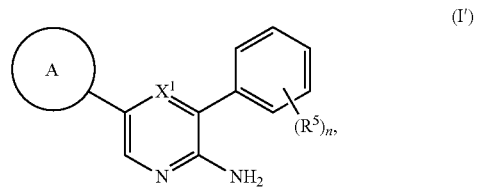

or a pharmaceutically acceptable salt, hydrate, solvate, prodrug, stereoisomer, or tautomer thereof, wherein:

is

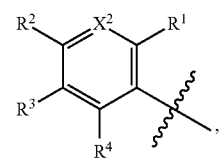

or a 5- to 6-membered heteroaryl optionally substituted with one or more substituents selected from halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_mR^{12}$, $S(O)_mNR^{11}R^{12}$, $NHS(O)_m$—$(C_3-C_7)$ cycloalkyl, and $CN$;

$X^1$ is N or CH;

$X^2$ is N or $CR^6$;

$R^1$ is H, $(C_1-C_3)$ alkyl, $(C_1-C_3)$ alkoxy, $NO_2$, halogen, O—$(C_3-C_7)$ cycloalkyl, or O-benzyl;

$R^2$ is H, $(C_1-C_2)$ alkyl, $(C_2-C_4)$ alkenyl, $(C_2-C_4)$ alkynyl, $(C_1-C_2)$ alkoxy, $(CH_2)_{0-2}$-heterocycloalkyl, halogen, $NO_2$, $CN$, $NR^9C(O)R^{10}$, $NR^9R^{10}$, $S(O)_mNR^9R^{10}$, $NHS(O)_m$—$(C_3-C_7)$ cycloalkyl, or $(CH_2)_{0-2}$-heteroaryl wherein the heteroaryl comprises a 5- to 6-membered ring and is optionally substituted with one or more substituents selected from halogen, $(C_1-C_3)$ alkyl, and $(C_1-C_3)$ alkoxy, wherein the alkyl, alkenyl, or alkynyl is optionally substituted with one or more substituents selected from $NH_2$, $NH(C_1-C_3)$ alkyl, and $N((C_1-C_3)$ alkyl$)_2$;

$R^3$ is H, halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_mR^{12}$, $S(O)_mNR^{11}R^{12}$, $NHS(O)_m$—$(C_3-C_7)$ cycloalkyl, CN, or a 5- to 6-membered heteroaryl optionally substituted with one or more substituents selected from halogen, $(C_1-C_3)$ alkyl, and $(C_1-C_3)$ alkoxy, wherein the alkyl is optionally substituted with one or more substituents selected from $NH_2$, $NH(C_1-C_3)$ alkyl, and $N((C_1-C_3)$ alkyl$)_2$;

$R^4$ is H, $(C_1-C_3)$ alkyl, $(C_1-C_3)$ alkoxy, $NO_2$, halogen, O—$(C_3-C_7)$ cycloalkyl, or O-benzyl;

$R^6$ is H, halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_mR^{12}$, $S(O)_mNR^{11}R^{12}$, $NHS(O)_m$—$(C_3-C_7)$ cycloalkyl, CN, or a 5- to 6-membered heteroaryl optionally substituted with one or more substituents selected from halogen, $(C_1-C_3)$ alkyl, and $(C_1-C_3)$ alkoxy, wherein the alkyl is optionally substituted with one or more substituents selected from $NH_2$, $NH(C_1-C_3)$ alkyl, and $N((C_1-C_3)$ alkyl$)_2$; or $R^2$ and $R^3$, together with the atoms to which they are attached, form a 6-membered heterocycloalkyl optionally substituted with one or more $R^7$, or a 5- to 6-membered heteroaryl optionally substituted with one or more $R^7$; or $R^2$ and $R^6$, together with the atoms to which they are attached, form a 6-membered heterocycloalkyl optionally substituted with one or more $R^7$, or a 5- to 6-membered heteroaryl optionally substituted with one or more $R^7$; or $R^3$ and $R^4$, together with the atoms to which they are attached, form a 5- to 6-membered heteroaryl optionally substituted with one or more $R^8$; or $R^1$ and $R^6$, together with the atoms to which they are attached, form a 5- to 6-membered heteroaryl optionally substituted with one or more $R^8$;

each $R^7$ is independently $(C_1-C_3)$ alkyl, $(C_1-C_3)$ alkoxy, or halogen, or two $R^7$, together with the carbon atom to which they are attached, form C(O);

each $R^8$ is independently $(C_1-C_3)$ alkyl, $(C_1-C_3)$ alkoxy, or halogen, or two $R^8$, together with the carbon atom to which they are attached, form C(O);

$R^9$ and $R^{10}$ are each independently H, $(C_1-C_4)$ alkyl, $(CH_2)_{0-2}$-aryl, $(CH_2)_{0-2}$-heteroaryl, $(CH_2)_{0-2}$—$(C_3-C_7)$ cycloalkyl, or $(CH_2)_{0-2}$-heterocycloalkyl;

$R^{11}$ and $R^{12}$ are each independently H, $(C_1-C_4)$ alkyl, $(C_3-C_7)$ cycloalkyl, or heterocycloalkyl;

each $R^5$ is independently $(C_1-C_4)$ alkyl, $C(O)NR^{14}R^{15}$, CN, OH, or halogen; or two adjacent $R^5$, together with the atoms to which they are attached, form a 5- to 6-membered heterocycloalkyl optionally substituted with one or more $R^{13}$, or a 5- to 6-membered heteroaryl optionally substituted with one or more $R^{13}$;

each $R^{13}$ is independently $(C_1-C_4)$ alkyl, $(C_1-C_4)$ alkoxy, or halogen, or two $R^{13}$, together with the carbon atom to which they are attached, form C(O);

$R^{14}$ and $R^{15}$ are each independently H or $(C_1-C_4)$ alkyl;

m is 0, 1, or 2; and n is 1, 2, 3, 4, or 5;

wherein at least one of $R^1$, $R^2$, $R^3$, $R^4$, and $R^6$ is not H; and provided that when $R^2$ is $S(O)_2NR^9R^{10}$ or F, then $R^4$ and $R^1$ are not simultaneously H, and when $R^2$ is $S(O)_2NR^9R^{10}$, then $R^4$ or $R^1$ is not Cl.

(0a') In some embodiments of Formula (I'),

is

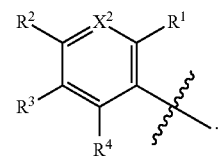

(0b') In some embodiments of Formula (I'),

is a 5- to 6-membered heteroaryl optionally substituted with one or more substituents selected from halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_mR^{12}$, $S(O)_mNR^{11}R^{12}$, $NHS(O)_m$—$(C_3-C_7)$ cycloalkyl, and CN. In further embodiments, the heteroaryl comprises a 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more substituents selected from halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_mR^{12}$, $S(O)_mNR^{11}R^{12}$, NHS$(O)_m$—$(C_3-C_7)$ cycloalkyl, and CN. In further embodiments,

is thiazolyl substituted with one or more halogen.

(1a') In some embodiments of Formula (I'), $X^1$ is CH.

(1b') In some embodiments of Formula (I'), $X^1$ is N.

(1c') In some embodiments of Formula (I'), $X^2$ is $CR^6$. In further embodiments, $X^2$ is CH.

(1d') In some embodiments of Formula (I'), $X^2$ is N.

(2a') In some embodiments of Formula (I'), $R^1$ is H, halogen (e.g., F, Cl, Br, or I), or $NO_2$. In further embodiments, $R^1$ is H. In other embodiments, $R^1$ is halogen. In further embodiments, $R^1$ is F or Cl. In other embodiments, $R^1$ is $NO_2$.

(2b') In some embodiments of Formula (I'), $R^1$ and $R^6$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^1$ and $R^6$, together with the atoms to which they are attached, form an optionally substituted 5- to 6-membered heteroaryl selected from

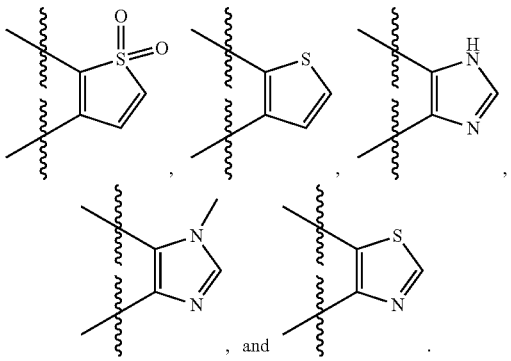

, and .

(2c') In some embodiments of Formula (I'), $R^1$ is ($C_1$-$C_3$) alkyl (e.g., methyl, ethyl, propyl, or i-propyl).

(2d') In some embodiments of Formula (I'), $R^1$ is ($C_1$-$C_3$) alkoxy (e.g., $OCH_3$, $OCH_2CH_3$, $OCH_2CH_2CH_3$, or OCH ($CH_3)CH_3$). In further embodiments, $R^1$ is $OCH_3$.

(2e') In some embodiments of Formula (I'), $R^1$ is O—($C_3$-$C_7$) cycloalkyl, wherein the ($C_3$-$C_7$) cycloalkyl is selected from cyclopropyl, cyclobutyl, cyclopentyl, cyclohexyl, and cycloheptyl. In further embodiments, $R^1$ is O-cyclopentyl or O-cyclohexyl.

(2f') In some embodiments of Formula (I'), $R^1$ is O-benzyl.

(3') In some embodiments of Formula (I'), $R^2$ is H, $NO_2$, CN, halogen (e.g., F, Cl, Br, or I), ($C_1$-$C_2$) alkyl (e.g., methyl or ethyl) wherein the alkyl is optionally substituted with one or more substituents selected from $NH_2$, NH($C_1$-$C_3$) alkyl, and N(($C_1$-$C_3$) alkyl)$_2$, ($C_1$-$C_2$) alkoxy (e.g., $OCH_3$ or $OCH_2CH_3$), $(CH_2)_{0-2}$-heterocycloalkyl, $NR^9C(O)R^{10}$, or $NR^9R^{10}$. In further embodiments, $R^2$ is H, halogen (e.g., F, Cl, Br, or I), or ($C_1$-$C_2$) alkoxy (e.g., $OCH_3$ or $OCH_2CH_3$).

(3a1') In some embodiments of Formula (I'), $R^2$ is H or halogen (e.g., F, Cl, Br, or I). In further embodiments, $R^2$ is H. In other embodiments, $R^2$ is halogen. In further embodiments, $R^2$ is F or Cl.

(3a2') In some embodiments of Formula (I'), $R^2$ is $NO_2$.

(3a3') In some embodiments of Formula (I'), $R^2$ is CN.

(3b1') In some embodiments of Formula (I'), $R^2$ is ($C_1$-$C_2$) alkyl (e.g., methyl or ethyl) wherein the alkyl is optionally substituted with one or more substituents selected from $NH_2$, NH($C_1$-$C_3$) alkyl, and N(($C_1$-$C_3$) alkyl)$_2$. In other embodiments, $R^2$ is methyl or ethyl, each of which is optionally substituted with one to two substituents selected from $NH_2$, NH($C_1$-$C_3$) alkyl, and N(($C_1$-$C_3$) alkyl)$_2$. In yet other embodiments, $R^2$ is methyl or ethyl, each of which is optionally substituted with one substituent selected from $NH_2$, NH($C_1$-$C_3$) alkyl, and N(($C_1$-$C_3$) alkyl)$_2$. In further embodiments, $R^2$ is methyl optionally substituted with one substituent selected from $NH_2$, NH($C_1$-$C_3$) alkyl, and N(($C_1$-$C_3$) alkyl)$_2$. In further embodiments, $R^2$ is $CH_2NH_2$, $CH_2NHCH_3$, or $CH_2N(CH_3)_2$. In further embodiments, $R^2$ is $CH_2N(CH_3)_2$.

(3b2') In some embodiments of Formula (I'), $R^2$ is ($C_2$-$C_4$) alkenyl (e.g., ethenyl, propenyl, or butenyl) wherein the alkenyl is optionally substituted with one or more substituents selected from $NH_2$, NH($C_1$-$C_3$) alkyl, and N(($C_1$-$C_3$) alkyl)$_2$.

(3b3') In some embodiments of Formula (I'), $R^2$ is ($C_2$-$C_4$) alkynyl (e.g., ethynyl, propynyl, or butynyl) wherein the alkynyl is optionally substituted with one or more substituents selected from $NH_2$, NH($C_1$-$C_3$) alkyl, and N(($C_1$-$C_3$) alkyl)$_2$.

(3c') In some embodiments of Formula (I'), $R^2$ is ($C_1$-$C_2$) alkoxy (e.g., $OCH_3$ or $OCH_2CH_3$). In further embodiments, $R^2$ is $OCH_3$.

(3d1') In some embodiments of Formula (I'), $R^2$ is $(CH_2)_{0-2}$-heterocycloalkyl. In further embodiments, $R^2$ is $(CH_2)_{0-1}$-heterocycloalkyl. In further embodiments, $R^2$ is $(CH_2)_0$-heterocycloalkyl. In further embodiments, $R^2$ is $(CH_2)_1$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In other embodiments, $R^2$ is morpholinyl or $CH_2$-morpholinyl.

(3d2') In some embodiments of Formula (I'), $R^2$ is a $(CH_2)_{0-2}$-heteroaryl optionally substituted with one or more substituents selected from halogen, ($C_1$-$C_3$) alkyl, and ($C_1$-$C_3$) alkoxy. In further embodiments, $R^2$ is $(CH_2)_0$-heteroaryl. $R^2$ is $(CH_2)_1$-heteroaryl. In further embodiments, the heteroaryl comprises a 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more substituents selected from halogen, ($C_1$-$C_3$) alkyl, and ($C_1$-$C_3$) alkoxy. In further embodiments, $R^2$ is thiazolyl optionally substituted with one or more substituents selected from halogen, ($C_1$-$C_3$) alkyl, and ($C_1$-$C_3$) alkoxy.

(3e1') In some embodiments of Formula (I'), $R^2$ is $NR^9C(O)R^{10}$. In further embodiments, $R^2$ is $NHC(O)CH_3$.

(3e2') In some embodiments of Formula (I'), $R^2$ is $NR^9R^{10}$. In further embodiments, $R^2$ is $NH_2$, NH($C_1$-$C_4$) alkyl, N(($C_1$-$C_4$) alkyl)$_2$, NH—$(CH_2)_{0-2}$-aryl, or NH—$(CH_2)_{0-2}$-heteroaryl. In further embodiments, $R^2$ is NH—$CH_2$-phenyl.

(3f1') In some embodiments of Formula (I'), $R^2$ is $S(O)_m NR^9R^{10}$. In further embodiments, $R^2$ is $S(O)_2NR^9R^{10}$. In further embodiments, $R^2$ is $S(O)_2NCH_3$-cyclopropyl.

(3f2') In some embodiments of Formula (I'), $R^2$ is NHS$(O)_m$—($C_3$-$C_7$) cycloalkyl wherein the ($C_3$-$C_7$) cycloalkyl is selected from cyclopropyl, cyclobutyl, cyclopentyl, cyclohexyl, and cycloheptyl. In further embodiments, $R^2$ is NHS$(O)_2$—($C_3$-$C_7$) cycloalkyl. In further embodiments, $R^2$ is NHS$(O)_2$-cyclopropyl.

(3g') In some embodiments of Formula (I'), $R^2$ and $R^3$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(3h') In some embodiments of Formula (I'), $R^2$ and $R^3$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(3i') In some embodiments of Formula (I'), $R^2$ and $R^6$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(3j') In some embodiments of Formula (1'), $R^2$ and $R^6$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(4a') In some embodiments of Formula (I'), $R^3$ is H, halogen (e.g., F, Cl, Br, or I), CN, or $NO_2$. In further embodiments, $R^3$ is H. In other embodiments, $R^3$ is halogen. In further embodiments, $R^3$ is F or Cl. In other embodiments, $R^3$ is $NO_2$. In other embodiments, $R^3$ is CN.

(4b') In some embodiments of Formula (I'), $R^3$ is $(C_1-C_3)$ alkyl (e.g., methyl, ethyl, propyl, or i-propyl), wherein the alkyl is optionally substituted with one or more substituents selected from $NH_2$, $NH(C_1-C_3)$ alkyl, and $N((C_1-C_3)$ alkyl$)_2$. In other embodiments, $R^3$ is methyl, or ethyl, each of which is optionally substituted with one or two substituents selected from $NH_2$, $NH(C_1-C_3)$ alkyl, and $N((C_1-C_3)$ alkyl$)_2$. In yet other embodiments, $R^3$ is methyl or ethyl, each of which is optionally substituted with one substituent selected from $NH_2$, $NH(C_1-C_3)$ alkyl, and $N((C_1-C_3)$ alkyl$)_2$. In further embodiments, $R^3$ is methyl optionally substituted with one substituent selected from $NH_2$, $NH(C_1-C_3)$ alkyl, and $N((C_1-C_3)$ alkyl$)_2$. In further embodiments, $R^3$ is $CH_2NH_2$, $CH_2NHCH_3$, or $CH_2N(CH_3)_2$. In further embodiments, $R^3$ is $CH_2N(CH_3)_2$.

(4c') In some embodiments of Formula (I'), $R^3$ is $(C_1-C_3)$ alkoxy (e.g., $OCH_3$, $OCH_2CH_3$, $OCH_2CH_2CH_3$, or $OCH(CH_3)CH_3$). In further embodiments, $R^3$ is $OCH_3$.

(4d') In some embodiments of Formula (I'), $R^3$ is $C(O)NR^{11}R^{12}$ or $C(O)OR^{11}$. In further embodiments, $R^3$ is $C(O)NR^{11}R^{12}$. In further embodiments, $R^3$ is $C(O)NHCH_3$ or $C(O)NHCH_2CH_3$. In other embodiments, $R^3$ is $C(O)OR^{11}$. In further embodiments, $R^3$ is $C(O)OCH_3$.

(4e') In some embodiments of Formula (I'), $R^3$ is $NR^{11}C(O)R^{12}$. In further embodiments, $R^3$ is $NHC(O)CH_3$.

(4f1') In some embodiments of Formula (I'), $R^3$ is $S(O)_m R^{12}$ or $S(O)_m NR^{11}R^2$. In other embodiments, $R^3$ is $S(O)_2 R^{12}$. In other embodiments, $R^3$ is $S(O)_2 NR^{11}R^{12}$. In further embodiments, $R^3$ is $S(O)_2NH$-cyclopropyl.

(4f2') In some embodiments of Formula (I'), $R^3$ is $NHS(O)_m—(C_3-C_7)$ cycloalkyl wherein the $(C_3-C_7)$ cycloalkyl is selected from cyclopropyl, cyclobutyl, cyclopentyl, cyclohexyl, and cycloheptyl. In further embodiments, $R^3$ is $NHS(O)_2—(C_3-C_7)$ cycloalkyl. In further embodiments, $R^3$ is $NHS(O)_2$-cyclopropyl.

(4g') In some embodiments of Formula (I'), $R^3$ and $R^4$, together with the atoms to which they are attached, form a 5- to 6-membered heteroaryl optionally substituted with one or more $R^8$. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^3$ and $R^4$, together with the atoms to which they are attached, form an optionally substituted 5- to 6-membered heteroaryl selected from

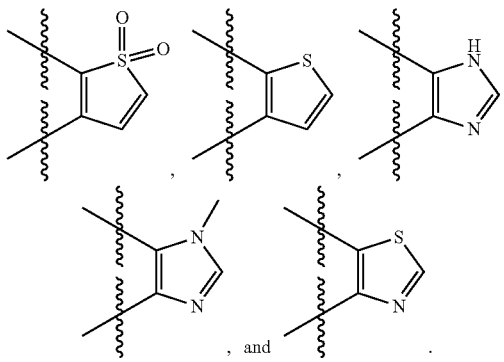

, and (4h') In some embodiments of Formula (I'), $R^2$ and $R^3$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(4i') In some embodiments of Formula (I'), $R^2$ and $R^3$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(4j') In some embodiments of Formula (I'), $R^3$ is a 5- to 6-membered heteroaryl optionally substituted with one or more substituents selected from halogen, $(C_1-C_3)$ alkyl, and $(C_1-C_3)$ alkoxy. In further embodiments, the heteroaryl comprises a 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more substituents selected from halogen, $(C_1-C_3)$ alkyl, and $(C_1-C_3)$ alkoxy. In further embodiments, $R^3$ is thiazolyl optionally substituted with one or more substituents selected from halogen, $(C_1-C_3)$ alkyl, and $(C_1-C_3)$ alkoxy.

(5a') In some embodiments of Formula (I'), $R^4$ is H, halogen (e.g., F, Cl, Br, or I), or $NO_2$. In further embodiments, $R^4$ is H. In other embodiments, $R^4$ is halogen. In further embodiments, $R^4$ is F or Cl. In other embodiments, $R^4$ is $NO_2$.

(5b') In some embodiments of Formula (I'), $R^3$ and $R^4$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In another embodiment, $R^3$ and $R^4$, together with the atoms to which they are attached, form an optionally substituted 5- to 6-membered heteroaryl selected from

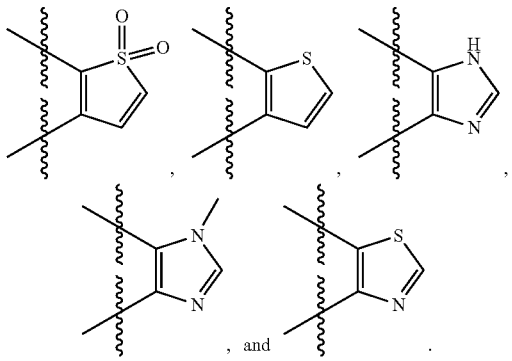

, and .

(5c') In some embodiments of Formula (I'), $R^4$ is $(C_1-C_3)$ alkyl (e.g., methyl, ethyl, propyl, or i-propyl).

(5d') In some embodiments of Formula (I'), $R^4$ is $(C_1-C_3)$ alkoxy (e.g., $OCH_3$, $OCH_2CH_3$, $OCH_2CH_2CH_3$, or $OCH(CH_3)CH_3$). In further embodiments, $R^4$ is $OCH_3$.

(5e') In some embodiments of Formula (I'), $R^4$ is O—$(C_3-C_7)$ cycloalkyl, wherein the $(C_3-C_7)$ cycloalkyl is selected from cyclopropyl, cyclobutyl, cyclopentyl, cyclohexyl, and cycloheptyl. In further embodiments, $R^4$ is O-cyclopentyl or O-cyclohexyl.

(5f') In some embodiments of Formula (I'), $R^4$ is O-benzyl.

(6a') In some embodiments of Formula (I'), $R^6$ is H, halogen (e.g., F, Cl, Br, or I), CN, or $NO_2$. In further embodiments, $R^6$ is H. In other embodiments, $R^6$ is halogen. In further embodiments, $R^6$ is F or Cl. In other embodiments, $R^6$ is $NO_2$. In other embodiments, $R^6$ is CN.

(6b') In some embodiments of Formula (I'), $R^6$ is $(C_1-C_3)$ alkyl (e.g., methyl, ethyl, propyl, or i-propyl), wherein the alkyl is optionally substituted with one or more substituents selected from $NH_2$, $NH(C_1-C_3)$ alkyl, and $N((C_1-C_3)$ alkyl$)_2$. In other embodiments, $R^6$ is methyl or ethyl, each of which is optionally substituted with one or two substituents selected from $NH_2$, $NH(C_1-C_3)$ alkyl, and $N((C_1-C_3)$ alkyl$)_2$. In yet other embodiments, $R^6$ is methyl or ethyl, each of which is optionally substituted with one substituent selected from $NH_2$, $NH(C_1-C_3)$ alkyl, and $N((C_1-C_3)$ alkyl$)_2$. In other embodiments, $R^6$ is methyl optionally substituted with one substituent selected from $NH_2$, $NH(C_1-$ $C_3)$ alkyl, and $N((C_1-C_3)$ alkyl$)_2$. In further embodiments, $R^6$ is $CH_2NH_2$, $CH_2NHCH_3$, or $CH_2N(CH_3)_2$. In further embodiments, $R^6$ is $CH_2N(CH_3)_2$.

(6c') In some embodiments of Formula (I'), $R^6$ is $(C_1-C_3)$ alkoxy (e.g., $OCH_3$, $OCH_2CH_3$, $OCH_2CH_2CH_3$, or $OCH(CH_3)CH_3$). In further embodiments, $R^6$ is $OCH_3$.

(6d') In some embodiments of Formula (I'), $R^6$ is C(O)$NR^{11}R^{12}$ or C(O)$OR^{11}$. In further embodiments, $R^6$ is C(O)$NR^{11}R^{12}$. In further embodiments, $R^6$ is C(O)$NHCH_3$ or C(O)$NHCH_2CH_3$. In other embodiments, $R^6$ is C(O)$OR^{11}$. In further embodiments, $R^6$ is C(O)$OCH_3$.

(6e') In some embodiments of Formula (I'), $R^6$ is $NR^{11}$C(O)$R^{12}$. In further embodiments, $R^6$ is NHC(O)$CH_3$.

(6f1') In some embodiments of Formula (I'), $R^6$ is S(O)$_m$ $R^{12}$ or S(O)$_m NR^{11}R^{12}$. In further embodiments, $R^6$ is S(O)$_2$ $R^{12}$. In further embodiments, $R^6$ is S(O)$_2 NR^{11}R^{12}$. In further embodiments, $R^6$ is S(O)$_2$NH-cyclopropyl.

(6f2') In some embodiments of Formula (I'), $R^6$ is NHS(O)$_m$—$(C_3-C_7)$ cycloalkyl wherein the $(C_3-C_7)$ cycloalkyl is selected from cyclopropyl, cyclobutyl, cyclopentyl, cyclohexyl, and cycloheptyl. In further embodiments, $R^6$ is NHS(O)$_2$—$(C_3-C_7)$ cycloalkyl. In further embodiments, $R^6$ is NHS(O)$_2$-cyclopropyl.

(6g1') In some embodiments of Formula (I'), $R^1$ and $R^6$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^1$ and $R^6$, together with the atoms to which they are attached, form an optionally substituted 5- to 6-membered heteroaryl selected from

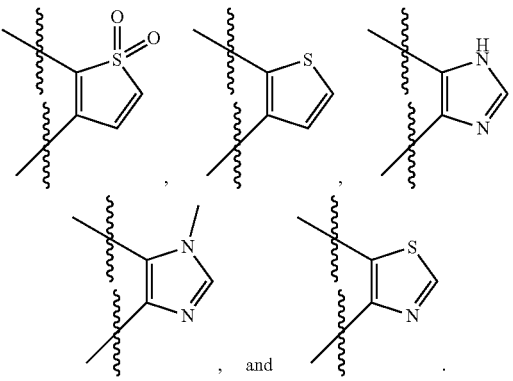

, and .

(6g2') In some embodiments of Formula (I'), $R^2$ and $R^6$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(6g3') In other embodiments of Formula (I'), $R^2$ and $R^6$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(6h') In some embodiments of Formula (I'), $R^6$ is a 5- to 6-membered heteroaryl optionally substituted with one or more substituents selected from halogen, $(C_1\text{-}C_3)$ alkyl, and $(C_1\text{-}C_3)$ alkoxy. In further embodiments, the heteroaryl comprises a 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more substituents selected from halogen, $(C_1\text{-}C_3)$ alkyl, and $(C_1\text{-}C_3)$ alkoxy. In further embodiments, $R^6$ is thiazolyl optionally substituted with one or more substituents selected from halogen, $(C_1\text{-}C_3)$ alkyl, and $(C_1\text{-}C_3)$ alkoxy.

(7a') In some embodiments of Formula (I'), at least one $R^7$ is $(C_1\text{-}C_3)$ alkyl (e.g., methyl, ethyl, propyl, or i-propyl). In further embodiments, at least one $R^7$ is methyl.

(7b') In some embodiments of Formula (I'), at least one $R^7$ is $(C_1\text{-}C_3)$ alkoxy (e.g., $OCH_3$, $OCH_2CH_3$, $OCH_2CH_2CH_3$, or $OCH(CH_3)CH_3$). In further embodiments, at least one $R^7$ is $OCH_3$.

(7c') In some embodiments of Formula (I'), at least one $R^7$ is halogen (e.g., F, Cl, Br, or I). In further embodiments, at least one $R^7$ is F or Cl. In other embodiments, two $R^7$, together with the carbon atom to which they are attached, form C(O).

(8a') In some embodiments of Formula (I'), at least one $R^8$ is $(C_1\text{-}C_3)$ alkyl (e.g., methyl, ethyl, propyl, or i-propyl). In further embodiments, at least one $R^8$ is methyl.

(8b') In some embodiments of Formula (I'), at least one $R^8$ is $(C_1\text{-}C_3)$ alkoxy (e.g., $OCH_3$, $OCH_2CH_3$, $OCH_2CH_2CH_3$, or $OCH(CH_3)CH_3$). In further embodiments, at least one $R^8$ is $OCH_3$.

(8c') In some embodiments of Formula (I'), at least one $R^8$ is halogen (e.g., F, Cl, Br, or I). In further embodiments, at least one $R^8$ is F or Cl. In other embodiments, two $R^8$, together with the carbon atom to which they are attached, form C(O).

(9a') In some embodiments of Formula (I'), $R^9$ is H or $(C_1\text{-}C_4)$ alkyl (e.g., methyl, ethyl, propyl, i-propyl, butyl, i-butyl, or tert-butyl). In further embodiments, $R^9$ is H. In other embodiments, $R^9$ is methyl or ethyl.

(9b') In some embodiments of Formula (I'), $R^9$ is $(CH_2)_{0\text{-}2}$-aryl or $(CH_2)_{0\text{-}2}$-heteroaryl. In further embodiments, $R^9$ is $(CH_2)_{0\text{-}1}$-aryl or $(CH_2)_{0\text{-}1}$-heteroaryl. In further embodiments, $R^9$ is $(CH_2)_{0\text{-}1}$-aryl. In further embodiments, $R^9$ is $(CH_2)$-aryl. In further embodiments, $R^9$ is benzyl (e.g., $CH_2$-phenyl). In other embodiments, $R^9$ is $(CH_2)_{0\text{-}1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(9c') In some embodiments of Formula (I'), $R^9$ is $(CH_2)_{0\text{-}2}$—$(C_3\text{-}C_7)$ cycloalkyl or $(CH_2)_{0\text{-}2}$-heterocycloalkyl. In further embodiments, $R^9$ is $(CH_2)_{0\text{-}1}$—$(C_3\text{-}C_7)$ cycloalkyl or $(CH_2)_{0\text{-}1}$-heterocycloalkyl. In further embodiments, $R^9$ is $(C_3\text{-}C_7)$ cycloalkyl. In other embodiments, $R^9$ is $(C_3\text{-}C_5)$ cycloalkyl. In further embodiments, $R^9$ is cyclopropyl. In other embodiments, $R^9$ is heterocycloalkyl or $(CH_2)$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^9$ is morpholinyl or $CH_2$-morpholinyl.

(10a') In some embodiments of Formula (I'), $R^{10}$ is H or $(C_1\text{-}C_4)$ alkyl (e.g., methyl, ethyl, propyl, i-propyl, butyl, i-butyl, or tert-butyl). In further embodiments, $R^{10}$ is H. In other embodiments, $R^{10}$ is methyl or ethyl.

(10b') In some embodiments of Formula (I'), $R^{10}$ is $(CH_2)_{0\text{-}2}$-aryl or $(CH_2)_{0\text{-}2}$-heteroaryl. In further embodiments, $R^{10}$ is $(CH_2)_{0\text{-}1}$-aryl or $(CH_2)_{0\text{-}1}$-heteroaryl. In further embodiments, $R^{10}$ is $(CH_2)_{0\text{-}1}$-aryl. In further embodiments, $R^{10}$ is $(CH_2)$-aryl. In further embodiments, $R^{10}$ is benzyl (e.g., $CH_2$-phenyl). In other embodiments, $R^{10}$ is $(CH_2)_{0\text{-}1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(10c') In some embodiments of Formula (I'), $R^{10}$ is $(CH_2)_{0\text{-}2}$—$(C_3\text{-}C_7)$ cycloalkyl or $(CH_2)_{0\text{-}2}$-heterocycloalkyl. In further embodiments, $R^{10}$ is $(CH_2)_{0\text{-}1}$—$(C_3\text{-}C_7)$ cycloalkyl or $(CH_2)_{0\text{-}1}$-heterocycloalkyl. In further embodiments, $R^{10}$ is $(C_3\text{-}C_7)$ cycloalkyl. In other embodiments, $R^{10}$ is $(C_3\text{-}C_5)$ cycloalkyl. In further embodiments, $R^{10}$ is cyclopropyl. In other embodiments, $R^{10}$ is heterocycloalkyl or $(CH_2)$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^{10}$ is morpholinyl or $CH_2$-morpholinyl.

(11a') In some embodiments of Formula (I'), $R^{11}$ is H or $(C_1\text{-}C_4)$ alkyl (e.g., methyl, ethyl, propyl, i-propyl, butyl, i-butyl, or tert-butyl). In further embodiments, $R^{11}$ is H. In further embodiments, $R^{11}$ is methyl or ethyl.

(11b') In some embodiments of Formula (I'), $R^{11}$ is $(C_3\text{-}C_7)$ cycloalkyl or heterocycloalkyl. In further embodiments, $R^{11}$ is $(C_3\text{-}C_7)$ cycloalkyl. In further embodiments, $R^{11}$ is cyclopropyl. In other embodiments, $R^{11}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(12a') In some embodiments of Formula (I'), $R^{12}$ is H or $(C_1\text{-}C_4)$ alkyl (e.g., methyl, ethyl, propyl, i-propyl, butyl, i-butyl, or tert-butyl). In further embodiments, $R^{12}$ is H. In further embodiments, $R^{12}$ is methyl or ethyl.

(12b') In some embodiments of Formula (I'), $R^{12}$ is $(C_3-C_7)$ cycloalkyl or heterocycloalkyl. In further embodiments, $R^{12}$ is $(C_3-C_7)$ cycloalkyl. In further embodiments, $R^{12}$ is cyclopropyl. In other embodiments, $R^{12}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(13a') In some embodiments of Formula (I'), at least one $R^5$ is $(C_1-C_4)$ alkyl (e.g., methyl, ethyl, propyl, i-propyl, butyl, i-butyl, or tert-butyl). In further embodiments, at least one $R^5$ is methyl or ethyl.

(13b') In some embodiments of Formula (I'), at least one $R^5$ is $C(O)NR^{14}R^{15}$. In further embodiments, at least one $R^5$ is $C(O)NR^{14}R^{15}$ and is at the para-position on the phenyl ring.

(13c') In some embodiments of Formula (I'), at least one $R^5$ is CN, OH, or halogen (e.g., F, Cl, Br, or I). In further embodiments, at least one $R^5$ is CN. In other embodiments, at least one $R^5$ is OH. In other embodiments, at least one $R^5$ is halogen. In further embodiments, at least one $R^5$ is F or Cl.

(13d') In some embodiments of Formula (I'), two adjacent $R^5$, together with the atoms to which they are attached, form a 5- to 6-membered heterocycloalkyl optionally substituted with one or more $R^{13}$. In further embodiments, the heterocycloalkyl comprises a 5- to 6-membered ring and 1 to 3 heteroatoms selected from N, O, and S, and is optionally substituted with one or more $R^{13}$. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl, each of which is optionally substituted with one or more $R^{13}$.

(13e') In some embodiments of Formula (I'), two adjacent $R^5$, together with the atoms to which they are attached, form a 5- to 6-membered heteroaryl optionally substituted with one or more $R^{13}$. In further embodiments, the heteroaryl comprises one 5- to 6-membered ring and 1 to 3 heteroatoms selected from N, O, and S, and is optionally substituted with one or more $R^{13}$. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^{13}$.

(14a') In some embodiments of Formula (I'), two $R^{13}$, together with the carbon atom to which they are attached, form C(O). In other embodiments, at least one $R^{13}$ is halogen. In further embodiments, at least one $R^{13}$ is F or Cl.

(14b') In some embodiments of Formula (I'), at least one $R^{13}$ is $(C_1-C_4)$ alkyl (e.g., methyl, ethyl, propyl, i-propyl, butyl, i-butyl, or tert-butyl). In further embodiments, at least one $R^{13}$ is methyl or ethyl.

(14c') In some embodiments of Formula (I'), at least one $R^{13}$ is $(C_1-C_4)$ alkoxy (e.g., $OCH_3$, $OCH_2CH_3$, $OCH_2CH_2CH_3$, $OCH(CH_3)CH_3$, $O(CH_2)_3CH_3$, $OCH_2CH(CH_3)CH_3$, or $OC(CH_3)_3$). In further embodiments, at least one $R^{13}$ is $OCH_3$ or $OCH_2CH_3$.

(15a') In some embodiments of Formula (I'), $R^{14}$ is H or $(C_1-C_4)$ alkyl (e.g., methyl, ethyl, propyl, i-propyl, butyl, i-butyl, or tert-butyl). In further embodiments, $R^{14}$ is H. In further embodiments, $R^{14}$ is methyl or ethyl.

(16a') In some embodiments of Formula (I'), $R^{is}$ is H or $(C_1-C_4)$ alkyl (e.g., methyl, ethyl, propyl, i-propyl, butyl, i-butyl, or tert-butyl). In further embodiments, $R^{15}$ is H. In further embodiments, $R^{15}$ is methyl or ethyl.

(17a') In some embodiments of Formula (I'), m is 0, 1, or 2. In other embodiments, m is 1 or 2. In a further embodiment, m is 2.

(18a') In some embodiments of Formula (I'), n is 1, 2, 3, 4, or 5. In other embodiments, n is 1, 2, or 3. In other embodiments, n is 1 or 2. In other embodiments, n is 2 or 3.

In some embodiments of Formula (I'), at least one of $R^1$, $R^2$, $R^3$, $R^4$, and $R^6$ is not H.

In some embodiments of Formula (I'), when $R^2$ is $S(O)_2NR^9R^{10}$ or F, then $R^4$ and $R^1$ are not simultaneously H. In other embodiments of Formula (I'), when $R^2$ is $S(O)_2NR^9R^{10}$, then $R^4$ or $R^1$ is not Cl.

In some embodiments of Formula (I'), each of the substituents defined for any one of

, $X^1$, $X^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, m, and n can be combined with any of the substituents defined for the remainder of

, $X^1$, $X^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, m, and n.

(11') In some embodiments of Formula (I'), $X^1$ and $X^2$ are defined as in (1a') and (1c'), respectively, or (1b') and (1c'), respectively.

(12') In some embodiments of Formula (I'), $X^1$ and $X^2$ are defined as in (1a') and (1d'), respectively, or (1b') and (1d'), respectively.

(13') In some embodiments of Formula (I'), $X^1$ and $X^2$ are defined as in (1a') and (1c'), respectively, and $R^5$ is defined as in (13a') or (13b').

(14') In some embodiments of Formula (I'), $X^1$ and $X^2$ are defined as in (1a') and (1c'), respectively, and $R^5$ is defined as in (13b') or (13c').

(15') In some embodiments of Formula (I'), $X^1$, $X^2$ and $R^5$ are defined as in (1a'), (1c'), and (13b'), respectively.

(16') In some embodiments of Formula (I'), $X^1$, $X^2$ and $R^5$ are defined as in (1a'), (1c'), and (13d'), respectively.

(17') In some embodiments of Formula (I'), $X^1$, $X^2$ and $R^5$ are defined as in (1a'), (1c'), and (13e'), respectively.

(18') In some embodiments of Formula (I'), $X^1$, $X^2$ and $R^1$ are defined as in (1a'), (1c'), and (2a'), respectively.

(19') In some embodiments of Formula (I'), $X^1$, $X^2$ and $R^1$ are defined as in (1a'), (1c'), and (2d'), respectively.

(20') In some embodiments of Formula (I'), $X^1$, $X^2$ and $R^1$ are defined as in (1a'), (1c'), and (2b'), respectively.

(21') In some embodiments of Formula (I'), $X^1$, $X^2$ and $R^4$ are defined as in (1a'), (1c'), and (5a'), respectively.

(22') In some embodiments of Formula (I'), $X^1$, $X^2$ and $R^4$ are defined as in (1a'), (1c'), and (5d'), respectively.

(23') In some embodiments of Formula (I'), $X^1$, $X^2$ and $R^4$ are defined as in (1a'), (1c'), and (5b'), respectively.

(24') In some embodiments of Formula (I'), $X^1$, $X^2$ and $R^3$ are defined as in (1a'), (1c'), and (4a'), respectively.

(25') In some embodiments of Formula (I'), $X^1$ and $X^2$ are defined as in (1a') and (1c'), respectively, and $R^3$ is defined as in (4b') or (4c').

(26') In some embodiments of Formula (I'), $X^1$ and $X^2$ are defined as in (1a') and (1c'), respectively, and $R^3$ is defined as in (4d') or (4e').

(27-1') In some embodiments of Formula (I'), $X^1$, $X^2$ and $R^3$ are defined as in (1a'), (1c'), and (4f1'), respectively.

(27-2') In some embodiments of Formula (I'), $X^1$, $X^2$ and $R^3$ are defined as in (1a'), (1c'), and (4f2'), respectively.

(27-3') In some embodiments of Formula (I'), $X^1$, $X^2$ and $R^3$ are defined as in (1a'), (1c'), and (4j'), respectively.

(28') In some embodiments of Formula (I'), $X^1$, $X^2$ and $R^3$ are defined as in (1a'), (1c'), and (4g'), respectively.

(29') In some embodiments of Formula (I'), $X^1$ and $X^2$ are defined as in (1a') and (1c'), respectively, and $R^3$ is defined as in (4h') or (4i').

(30') In some embodiments of Formula (I'), $X^1$, $X^2$ and $R^6$ are defined as in (1a'), (1c'), and (6a'), respectively.

(31') In some embodiments of Formula (I'), $X^1$ and $X^2$ are defined as in (1a') and (1c'), respectively, and $R^6$ is defined as in (6b') or (6c').

(32') In some embodiments of Formula (I'), $X^1$ and $X^2$ are defined as in (1a') and (1c'), respectively, and $R^6$ is defined as in (6d') or (6e').

(33-1') In some embodiments of Formula (I'), $X^1$, $X^2$ and $R^6$ are defined as in (1a'), (1c'), and (6f1'), respectively.

(33-2') In some embodiments of Formula (I'), $X^1$, $X^2$ and $R^6$ are defined as in (1a'), (1c'), and (6f2'), respectively.

(33-3') In some embodiments of Formula (I'), $X^1$, $X^2$ and $R^6$ are defined as in (1a'), (1c'), and (6h'), respectively.

(34') In some embodiments of Formula (I'), $X^1$ and $X^2$ are defined as in (1a') and (1c'), respectively, and $R^6$ is defined as in (6g1'), (6g2'), or (6g3').

(35') In some embodiments of Formula (I'), $X^1$, $X^2$ and $R^2$ are defined as in (1a'), (1c'), and (3'), respectively. In further embodiments of Formula (I'), $X^1$, $X^2$ and $R^2$ are defined as in (1a'), (1c'), and (3a1'), respectively. In further embodiments of Formula (I'), $X^1$, $X^2$ and $R^2$ are defined as in (1a'), (1c'), and (3a2'), respectively. In further embodiments of Formula (I'), $X^1$, $X^2$ and $R^2$ are defined as in (1a'), (1c'), and (3a3'), respectively.

(36-1') In some embodiments of Formula (I'), $X^1$ and $X^2$ are defined as in (1a') and (1c'), respectively, and $R^2$ is defined as in (3b1') or (3c').

(36-2') In some embodiments of Formula (I'), $X^1$ and $X^2$ are defined as in (1a') and (1c'), respectively, and $R^2$ is defined as in (3b2').

(36-3') In some embodiments of Formula (I'), $X^1$ and $X^2$ are defined as in (1a') and (1c'), respectively, and $R^2$ is defined as in (3b3').

(37-1') In some embodiments of Formula (I'), $X^1$, $X^2$ and $R^2$ are defined as in (1a'), (1c'), and (3d1'), respectively.

(37-2') In some embodiments of Formula (I'), $X^1$, $X^2$ and $R^2$ are defined as in (1a'), (1c'), and (3d2'), respectively.

(38') In some embodiments of Formula (I'), $X^1$ and $X^2$ are defined as in (1a') and (1c'), respectively, and $R^2$ is defined as in (3e1') or (3e2').

(39-1') In some embodiments of Formula (I'), $X^1$, $X^2$ and $R^2$ are defined as in (1a'), (1c'), and (3f1'), respectively.

(39-2') In some embodiments of Formula (I'), $X^1$, $X^2$ and $R^2$ are defined as in (1a'), (1c'), and (3f2'), respectively.

(40') In some embodiments of Formula (I'), $X^1$ and $X^2$ are defined as in (1a') and (1c'), respectively, and $R^2$ is defined as in (3g') or (3h').

(41') In some embodiments of Formula (I'), $X^1$ and $X^2$ are defined as in (1a') and (1c'), respectively, and $R^2$ is defined as in (3i') or (3j').

(42') In some embodiments of Formula (I'), $X^1$, $X^2$, $R^1$, and $R^5$ are defined as in (1a'), (1c'), (2a'), and (13d'), respectively.

(43') In some embodiments of Formula (I'), $X^1$, $X^2$, $R^1$, and $R^5$ are defined as in (1a'), (1c'), (2b'), and (13d'), respectively.

(44') In some embodiments of Formula (I'), $X^1$, $X^2$, $R^1$, and $R^5$ are defined as in (1a'), (1c'), (2d'), and (13d'), respectively.

(45') In some embodiments of Formula (I'), $X^1$, $X^2$, $R^4$, and $R^5$ are defined as in (1a'), (1c'), (5a'), and (13d'), respectively.

(46') In some embodiments of Formula (I'), $X^1$, $X^2$, $R^4$, and $R^5$ are defined as in (1a'), (1c'), (5b'), and (13d'), respectively.

(47') In some embodiments of Formula (I'), $X^1$, $X^2$, $R^4$, and $R^5$ are defined as in (1a'), (1c'), (5d'), and (13d'), respectively.

(48') In some embodiments of Formula (I'), $X^1$, $X^2$, $R^3$, and $R^5$ are defined as in (1a'), (1c'), (4a'), and (13d'), respectively.

(49') In some embodiments of Formula (I'), $X^1$, $X^2$, and $R^5$ are defined as in (1a'), (1c'), and (13d'), respectively, and $R^3$ is defined as in (4b') or (4c').

(50') In some embodiments of Formula (I'), $X^1$, $X^2$, and $R^5$ are defined as in (1a'), (1c'), and (13d'), respectively, and $R^3$ is defined as in (4d') or (4e').

(51') In some embodiments of Formula (I'), $X^1$, $X^2$, $R^3$, and $R^5$ are defined as in (1a'), (1c'), (4f), and (13d'), respectively.

(52') In some embodiments of Formula (I'), $X^1$, $X^2$, $R^3$, and $R^5$ are defined as in (1a'), (1c'), (4g'), and (13d'), respectively.

(53') In some embodiments of Formula (I'), $X^1$, $X^2$, and $R^5$ are defined as in (1a'), (1c'), and (13d'), respectively, and $R^3$ is defined as in (4h') or (4i').

(54') In some embodiments of Formula (I'), $X^1$, $X^2$, $R^6$, and $R^5$ are defined as in (1a'), (1c'), (6a'), and (13d'), respectively.

(55') In some embodiments of Formula (I'), $X^1$, $X^2$, and $R^5$ are defined as in (1a'), (1c'), and (13d'), respectively, and $R^6$ is defined as in (6b') or (6c').

(55a') In some embodiments of Formula (I'), $X^1$, $X^2$, and $R^5$ are defined as in (1a'), (1c'), and (13d'), respectively, and $R^6$ is defined as in (6d') or (6e').

(55b') In some embodiments of Formula (I'), $X^1$, $X^2$, $R^6$, and $R^5$ are defined as in (1a'), (1c'), (6f), and (13d'), respectively.

(55c') In some embodiments of Formula (I'), $X^1$, $X^2$, $R^6$, and $R^5$ are defined as in (1a'), (1c'), (6g1'), and (13d'), respectively.

(55d') In some embodiments of Formula (I'), $X^1$, $X^2$, and $R^5$ are defined as in (1a'), (1c'), and (13d'), respectively, and $R^6$ is defined as in (6g2') or (6g3').

(56') In some embodiments of Formula (I'), $X^1$, $X^2$, $R^2$, and $R^5$ are defined as in (1a'), (1c'), (3'), and (13d'), respectively. In further embodiments of Formula (I'), $X^1$, $X^2$, $R^2$, and $R^5$ are defined as in (1a'), (1c'), (3a'), and (13d'), respectively.

(57') In some embodiments of Formula (I'), is

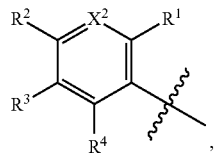

and $X^1, X^2, R^1, R^2, R^3, R^4, R^5, R^6, R^7, R^8, R^9, R^{10}, R^{11}, R^{12}, R^{13}, R^{14}, R^5, m$, and n are each as defined above.

In one embodiment, the compounds of Formula (I') have the structure of Formula (I):

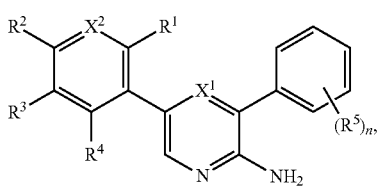

(I)

or a pharmaceutically acceptable salt, hydrate, solvate, prodrug, stereoisomer, or tautomer thereof, wherein:

$X^1$ is N or CH;

$X^2$ is N or $CR^6$;

$R^1$ is H, $(C_1\text{-}C_3)$ alkyl, $(C_1\text{-}C_3)$ alkoxy, $NO_2$, or halogen;

$R^2$ is H, $(C_1\text{-}C_2)$ alkyl, $(C_1\text{-}C_2)$ alkoxy, $(CH_2)_{0\text{-}2}$-heterocycloalkyl, halogen, $NR^9C(O)R^{10}$, $NR^9R^{10}$, or $S(O)_m NR^9R^{10}$, wherein the alkyl is optionally substituted with one or more substituents selected from $NH_2$, $NH(C_1\text{-}C_3)$ alkyl, and $N((C_1\text{-}C_3)$ alkyl$)_2$;

$R^3$ is H, halogen, $(C_1\text{-}C_3)$ alkyl, $(C_1\text{-}C_3)$ alkoxy, $NO_2$, $C(O)NR^{11}R^{12}$, $NR^{11}C(O)R^{12}$, $C(O)OR^{11}$, $S(O)_m R^{12}$, $S(O)_m NR^{11}R^{12}$, or CN, wherein the alkyl is optionally substituted with one or more substituents selected from $NH_2$, $NH(C_1\text{-}C_3)$ alkyl, and $N((C_1\text{-}C_3)$ alkyl$)_2$;

$R^4$ is H, $(C_1\text{-}C_3)$ alkyl, $(C_1\text{-}C_3)$ alkoxy, $NO_2$, or halogen;

$R^6$ is H, halogen, $(C_1\text{-}C_3)$ alkyl, $(C_1\text{-}C_3)$ alkoxy, $NO_2$, $C(O)NR^{11}R^{12}$, $NR^{11}C(O)R^{12}$, $C(O)OR^{11}$, $S(O)_m R^{12}$, $S(O)_m NR^{11}R^{12}$, or CN, wherein the alkyl is optionally substituted with one or more substituents selected from $NH_2$, $NH(C_1\text{-}C_3)$ alkyl, and $N((C_1\text{-}C_3)$ alkyl$)_2$; or $R^2$ and $R^3$, together with the atoms to which they are attached, form a 6-membered heterocycloalkyl optionally substituted with one or more $R^7$, or a 5- to 6-membered heteroaryl optionally substituted with one or more $R^7$; or $R^2$ and $R^6$, together with the atoms to which they are attached, form a 6-membered heterocycloalkyl optionally substituted with one or more $R^7$, or a 5- to 6-membered heteroaryl optionally substituted with one or more $R^7$; or $R^3$ and $R^4$, together with the atoms to which they are attached, form a 5- to 6-membered heteroaryl optionally substituted with one or more $R^8$; or $R^1$ and $R^6$, together with the atoms to which they are attached, form a 5- to 6-membered heteroaryl optionally substituted with one or more $R^8$;

each $R^7$ is independently $(C_1\text{-}C_3)$ alkyl, $(C_1\text{-}C_3)$ alkoxy, or halogen, or two $R^7$, together with the carbon atom to which they are attached, form C(O);

each $R^8$ is independently $(C_1\text{-}C_3)$ alkyl, $(C_1\text{-}C_3)$ alkoxy, or halogen, or two $R^8$, together with the carbon atom to which they are attached, form C(O);

$R^9$ and $R^{10}$ are each independently H, $(C_1\text{-}C_4)$ alkyl, $(CH_2)_{0\text{-}2}$-aryl, $(CH_2)_{0\text{-}2}$-heteroaryl, $(CH_2)_{0\text{-}2}$—$(C_3\text{-}C_7)$ cycloalkyl, or $(CH_2)_{0\text{-}2}$-heterocycloalkyl;

$R^{11}$ and $R^{12}$ are each independently H, $(C_1\text{-}C_4)$ alkyl, $(C_3\text{-}C_7)$ cycloalkyl, or heterocycloalkyl;

each $R^5$ is independently $(C_1\text{-}C_4)$ alkyl, $C(O)NR^{14}R^{15}$, CN, OH, or halogen; or two adjacent $R^5$, together with the atoms to which they are attached, form a 5- to 6-membered heterocycloalkyl optionally substituted with one or more $R^{13}$, or a 5- to 6-membered heteroaryl optionally substituted with one or more $R^{13}$;

each $R^{13}$ is independently $(C_1\text{-}C_4)$ alkyl, $(C_1\text{-}C_4)$ alkoxy, or halogen, or two $R^{13}$, together with the carbon atom to which they are attached, form C(O);

$R^{14}$ and $R^{15}$ are each independently H or $(C_1\text{-}C_4)$ alkyl;

m is 0, 1, or 2; and n is 1, 2, 3, 4, or 5;

wherein at least one of $R^1, R^2, R^3, R^4$, and $R^6$ is not H; and provided that when $R^2$ is $S(O)_2 NR^9 R^{10}$ or F, then $R^4$ and $R^1$ are not simultaneously H, and when $R^2$ is $S(O)_2 NR^9 R^{10}$, then $R^4$ or $R^1$ is not Cl.

(1a) In some embodiments of Formula (I), $X^1$ is CH.

(1b) In some embodiments of Formula (I), $X^1$ is N.

(1c) In some embodiments of Formula (I), $X^2$ is $CR^6$. In further embodiments, $X^2$ is CH.

(1d) In some embodiments of Formula (I), $X^2$ is N.

(2a) In some embodiments of Formula (I), $R^1$ is H, halogen (e.g., F, Cl, Br, or I), or $NO_2$. In further embodiments, $R^1$ is H. In other embodiments, $R^1$ is halogen. In further embodiments, $R^1$ is F or Cl. In other embodiments, $R^1$ is $NO_2$.

(2b) In some embodiments of Formula (I), $R^1$ and $R^6$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^1$ and $R^6$, together with the atoms to which they are attached, form an optionally substituted 5- to 6-membered heteroaryl selected from

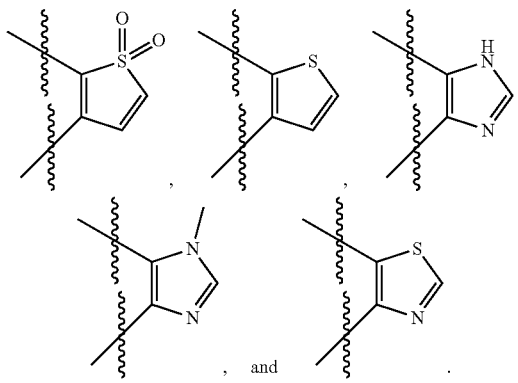

(2c) In some embodiments of Formula (I), $R^1$ is $(C_1\text{-}C_3)$ alkyl (e.g., methyl, ethyl, propyl, or i-propyl).

(2d) In some embodiments of Formula (I), $R^1$ is $(C_1\text{-}C_3)$ alkoxy (e.g., $OCH_3$, $OCH_2CH_3$, $OCH_2CH_2CH_3$, or $OCH(CH_3)CH_3$). In further embodiments, $R^1$ is $OCH_3$.

(3) In some embodiments of Formula (I), $R^2$ is H, halogen (e.g., F, Cl, Br, or I), ($C_1$-$C_2$) alkyl (e.g., methyl or ethyl) wherein the alkyl is optionally substituted with one or more substituents selected from $NH_2$, $NH(C_1$-$C_3)$ alkyl, and $N((C_1$-$C_3)$ alkyl)$_2$, ($C_1$-$C_2$) alkoxy (e.g., $OCH_3$ or $OCH_2CH_3$), $(CH_2)_{0-2}$-heterocycloalkyl, $NR^9C(O)R^{10}$, or $NR^9R^{10}$. In further embodiments, $R^2$ is H, halogen (e.g., F, Cl, Br, or I), or ($C_1$-$C_2$) alkoxy (e.g., $OCH_3$ or $OCH_2CH_3$).

(3a) In some embodiments of Formula (I), $R^2$ is H or halogen (e.g., F, Cl, Br, or I). In further embodiments, $R^2$ is H. In other embodiments, $R^2$ is halogen. In further embodiments, $R^2$ is F or Cl.

(3b) In some embodiments of Formula (I), $R^2$ is ($C_1$-$C_2$) alkyl (e.g., methyl or ethyl) wherein the alkyl is optionally substituted with one or more substituents selected from $NH_2$, $NH(C_1$-$C_3)$ alkyl, and $N((C_1$-$C_3)$ alkyl)$_2$. In other embodiments, $R^2$ is methyl or ethyl, each of which is optionally substituted with one to two substituents selected from $NH_2$, $NH(C_1$-$C_3)$ alkyl, and $N((C_1$-$C_3)$ alkyl)$_2$. In yet other embodiments, $R^2$ is methyl or ethyl, each of which is optionally substituted with one substituent selected from $NH_2$, $NH(C_1$-$C_3)$ alkyl, and $N((C_1$-$C_3)$ alkyl)$_2$. In further embodiments, $R^2$ is methyl optionally substituted with one substituent selected from $NH_2$, $NH(C_1$-$C_3)$ alkyl, and $N((C_1$-$C_3)$ alkyl)$_2$. In further embodiments, $R^2$ is $CH_2NH_2$, $CH_2NHCH_3$, or $CH_2N(CH_3)_2$. In further embodiments, $R^2$ is $CH_2N(CH_3)_2$.

(3c) In some embodiments of Formula (I), $R^2$ is ($C_1$-$C_2$) alkoxy (e.g., $OCH_3$ or $OCH_2CH_3$). In further embodiments, $R^2$ is $OCH_3$.

(3d) In some embodiments of Formula (I), $R^2$ is $(CH_2)_{0-2}$-heterocycloalkyl. In further embodiments, $R^2$ is $(CH_2)_{0-1}$-heterocycloalkyl. In further embodiments, $R^2$ is $(CH_2)_0$-heterocycloalkyl. In further embodiments, $R^2$ is $(CH_2)_1$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In other embodiments, $R^2$ is morpholinyl or $CH_2$-morpholinyl.

(3e1) In some embodiments of Formula (I), $R^2$ is $NR^9C(O)R^{10}$. In further embodiments, $R^2$ is $NHC(O)CH_3$.

(3e2) In some embodiments of Formula (I), $R^2$ is $NR^9R^{10}$. In further embodiments, $R^2$ is $NH_2$, $NH(C_1$-$C_4)$ alkyl, $N((C_1$-$C_4)$ alkyl)$_2$, $NH$—$(CH_2)_{0-2}$-aryl, or $NH$—$(CH_2)_{0-2}$-heteroaryl. In further embodiments, $R^2$ is $NH$—$CH_2$-phenyl.

(3f) In some embodiments of Formula (I), $R^2$ is $S(O)_m NR^9R^{10}$. In further embodiments, $R^2$ is $S(O)_2NR^9R^{10}$. In further embodiments, $R^2$ is $S(O)_2NCH_3$-cyclopropyl.

(3g) In some embodiments of Formula (I), $R^2$ and $R^3$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(3h) In some embodiments of Formula (I), $R^2$ and $R^3$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(3i) In some embodiments of Formula (I), $R^2$ and $R^6$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(3j) In some embodiments of Formula (I), $R^2$ and $R^6$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(4a) In some embodiments of Formula (I), $R^3$ is H, halogen (e.g., F, Cl, Br, or I), CN, or $NO_2$. In further embodiments, $R^3$ is H. In other embodiments, $R^3$ is halogen. In further embodiments, $R^3$ is F or Cl. In other embodiments, $R^3$ is $NO_2$. In other embodiments, $R^3$ is CN.

(4b) In some embodiments of Formula (I), $R^3$ is ($C_1$-$C_3$) alkyl (e.g., methyl, ethyl, propyl, or i-propyl), wherein the alkyl is optionally substituted with one or more substituents selected from $NH_2$, $NH(C_1$-$C_3)$ alkyl, and $N((C_1$-$C_3)$ alkyl)$_2$. In other embodiments, $R^3$ is methyl, or ethyl, each of which is optionally substituted with one or two substituents selected from $NH_2$, $NH(C_1$-$C_3)$ alkyl, and $N((C_1$-$C_3)$ alkyl)$_2$. In yet other embodiments, $R^3$ is methyl or ethyl, each of which is optionally substituted with one substituent selected from $NH_2$, $NH(C_1$-$C_3)$ alkyl, and $N((C_1$-$C_3)$ alkyl)$_2$. In further embodiments, $R^3$ is methyl optionally substituted with one substituent selected from $NH_2$, $NH(C_1$-$C_3)$ alkyl, and $N((C_1$-$C_3)$ alkyl)$_2$. In further embodiments, $R^3$ is $CH_2NH_2$, $CH_2NHCH_3$, or $CH_2N(CH_3)_2$. In further embodiments, $R^3$ is $CH_2N(CH_3)_2$.

(4c) In some embodiments of Formula (I), $R^3$ is ($C_1$-$C_3$) alkoxy (e.g., $OCH_3$, $OCH_2CH_3$, $OCH_2CH_2CH_3$, or $OCH(CH_3)CH_3$). In further embodiments, $R^3$ is $OCH_3$.

(4d) In some embodiments of Formula (I), $R^3$ is $C(O)NR^{11}R^{12}$ or $C(O)OR^{11}$. In further embodiments, $R^3$ is $C(O)NR^{11}R^{12}$. In further embodiments, $R^3$ is $C(O)NHCH_3$ or $C(O)NHCH_2CH_3$. In other embodiments, $R^3$ is $C(O)OR^{11}$. In further embodiments, $R^3$ is $C(O)OCH_3$.

(4e) In some embodiments of Formula (I), $R^3$ is $NR^{11}C(O)R^{12}$. In further embodiments, $R^3$ is $NHC(O)CH_3$.

(4f) In some embodiments of Formula (I), $R^3$ is $S(O)_m R^{12}$ or $S(O)_m NR^{11}R^{12}$. In other embodiments, $R^3$ is $S(O)_2R^{12}$. In other embodiments, $R^3$ is $S(O)_2NR^{11}R^{12}$. In further embodiments, $R^3$ is $S(O)_2NH$-cyclopropyl.

(4g) In some embodiments of Formula (I), $R^3$ and $R^4$, together with the atoms to which they are attached, form a 5- to 6-membered heteroaryl optionally substituted with one or more $R^8$. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^3$ and $R^4$, together with the atoms to which they are attached, form an optionally substituted 5- to 6-membered heteroaryl selected from

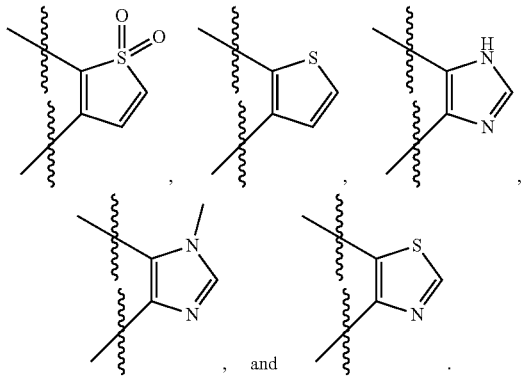

, and

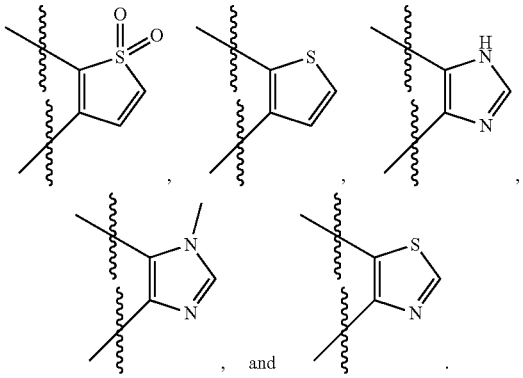

, and (4h) In some embodiments of Formula (I), $R^2$ and $R^3$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(4i) In some embodiments of Formula (I), $R^2$ and $R^3$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(5a) In some embodiments of Formula (I), $R^4$ is H, halogen (e.g., F, Cl, Br, or I), or $NO_2$. In further embodiments, $R^4$ is H. In other embodiments, $R^4$ is halogen. In further embodiments, $R^4$ is F or Cl. In other embodiments, $R^4$ is $NO_2$.

(5b) In some embodiments of Formula (I), $R^3$ and $R^4$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In another embodiment, $R^3$ and $R^4$, together with the atoms to which they are attached, form an optionally substituted 5- to 6-membered heteroaryl selected from (5c) In some embodiments of Formula (I), $R^4$ is $(C_1-C_3)$ alkyl (e.g., methyl, ethyl, propyl, or i-propyl).

(5d) In some embodiments of Formula (I), $R^4$ is $(C_1-C_3)$ alkoxy (e.g., $OCH_3$, $OCH_2CH_3$, $OCH_2CH_2CH_3$, or $OCH(CH_3)CH_3$). In further embodiments, $R^4$ is $OCH_3$.

(6a) In some embodiments of Formula (I), $R^6$ is H, halogen (e.g., F, Cl, Br, or I), CN, or $NO_2$. In further embodiments, $R^6$ is H. In other embodiments, $R^6$ is halogen. In further embodiments, $R^6$ is F or Cl. In other embodiments, $R^6$ is $NO_2$. In other embodiments, $R^6$ is CN.

(6b) In some embodiments of Formula (I), $R^6$ is $(C_1-C_3)$ alkyl (e.g., methyl, ethyl, propyl, or i-propyl), wherein the alkyl is optionally substituted with one or more substituents selected from $NH_2$, $NH(C_1-C_3)$ alkyl, and $N((C_1-C_3)$ alkyl$)_2$. In other embodiments, $R^6$ is methyl or ethyl, each of which is optionally substituted with one or two substituents selected from $NH_2$, $NH(C_1-C_3)$ alkyl, and $N((C_1-C_3)$ alkyl$)_2$. In yet other embodiments, $R^6$ is methyl or ethyl, each of which is optionally substituted with one substituent selected from $NH_2$, $NH(C_1-C_3)$ alkyl, and $N((C_1-C_3)$ alkyl$)_2$. In other embodiments, $R^6$ is methyl optionally substituted with one substituent selected from $NH_2$, $NH(C_1-C_3)$ alkyl, and $N((C_1-C_3)$ alkyl$)_2$. In further embodiments, $R^6$ is $CH_2NH_2$, $CH_2NHCH_3$, or $CH_2N(CH_3)_2$. In further embodiments, $R^6$ is $CH_2N(CH_3)_2$.

(6c) In some embodiments of Formula (I), $R^6$ is $(C_1-C_3)$ alkoxy (e.g., $OCH_3$, $OCH_2CH_3$, $OCH_2CH_2CH_3$, or $OCH(CH_3)CH_3$). In further embodiments, $R^6$ is $OCH_3$.

(6d) In some embodiments of Formula (I), $R^6$ is $C(O)NR^{11}R^{12}$ or $C(O)OR^{11}$. In further embodiments, $R^6$ is $C(O)NR^{11}R^{12}$. In further embodiments, $R^6$ is $C(O)NHCH_3$ or $C(O)NHCH_2CH_3$. In other embodiments, $R^6$ is $C(O)OR^{11}$. In further embodiments, $R^6$ is $C(O)OCH_3$.

(6e) In some embodiments of Formula (I), $R^6$ is $NR^{11}C(O)R^{12}$. In further embodiments, $R^6$ is $NHC(O)CH_3$.

(6f) In some embodiments of Formula (I), $R^6$ is $S(O)_mR^{12}$ or $S(O)_mNR^{11}R^{12}$. In further embodiments, $R^6$ is $S(O)_2R^{12}$. In further embodiments, $R^6$ is $S(O)_2NR^{11}R^{12}$. In further embodiments, $R^6$ is $S(O)_2NH$-cyclopropyl.

(6g1) In some embodiments of Formula (I), $R^1$ and $R^6$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^1$ and $R^6$, together with the atoms to which they are attached, form an optionally substituted 5- to 6-membered heteroaryl selected from

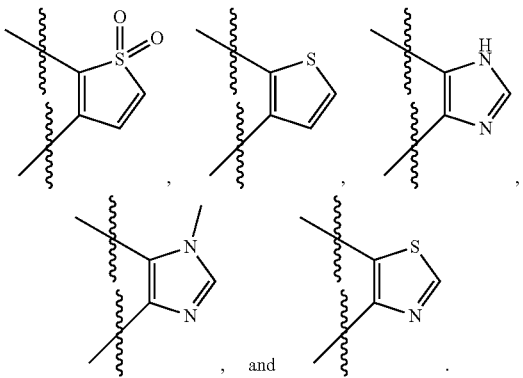

, and (6g2) In some embodiments of Formula (I), $R^2$ and $R^6$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(6g3) In other embodiments of Formula (I), $R^2$ and $R^6$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(7a) In some embodiments of Formula (I), at least one $R^7$ is $(C_1-C_3)$ alkyl (e.g., methyl, ethyl, propyl, or i-propyl). In further embodiments, at least one $R^7$ is methyl.

(7b) In some embodiments of Formula (I), at least one $R^7$ is $(C_1-C_3)$ alkoxy (e.g., $OCH_3$, $OCH_2CH_3$, $OCH_2CH_2CH_3$, or $OCH(CH_3)CH_3$). In further embodiments, at least one $R^7$ is $OCH_3$.

(7c) In some embodiments of Formula (I), at least one $R^7$ is halogen (e.g., F, Cl, Br, or I). In further embodiments, at least one $R^7$ is F or Cl. In other embodiments, two $R^7$, together with the carbon atom to which they are attached, form C(O).

(8a) In some embodiments of Formula (I), at least one $R^8$ is $(C_1-C_3)$ alkyl (e.g., methyl, ethyl, propyl, or i-propyl). In further embodiments, at least one $R^8$ is methyl.

(8b) In some embodiments of Formula (I), at least one $R^8$ is $(C_1-C_3)$ alkoxy (e.g., $OCH_3$, $OCH_2CH_3$, $OCH_2CH_2CH_3$, or $OCH(CH_3)CH_3$). In further embodiments, at least one $R^8$ is $OCH_3$.

(8c) In some embodiments of Formula (I), at least one $R^8$ is halogen (e.g., F, Cl, Br, or I). In further embodiments, at least one $R^8$ is F or Cl. In other embodiments, two $R^8$, together with the carbon atom to which they are attached, form C(O).

(9a) In some embodiments of Formula (I), $R^9$ is H or $(C_1-C_4)$ alkyl (e.g., methyl, ethyl, propyl, i-propyl, butyl, i-butyl, or tert-butyl). In further embodiments, $R^9$ is H. In other embodiments, $R^9$ is methyl or ethyl.

(9b) In some embodiments of Formula (I), $R^9$ is $(CH_2)_{0-2}$-aryl or $(CH_2)_{0-2}$-heteroaryl. In further embodiments, $R^9$ is $(CH_2)_{0-1}$-aryl or $(CH_2)_{0-1}$-heteroaryl. In further embodiments, $R^9$ is $(CH_2)_{0-1}$-aryl. In further embodiments, $R^9$ is $(CH_2)$-aryl. In further embodiments, $R^9$ is benzyl (e.g., $CH_2$-phenyl). In other embodiments, $R^9$ is $(CH_2)_{0-1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(9c) In some embodiments of Formula (I), $R^9$ is $(CH_2)_{0-2}$—$(C_3-C_7)$ cycloalkyl or $(CH_2)_{0-2}$-heterocycloalkyl. In further embodiments, $R^9$ is $(CH_2)_{0-1}$—$(C_3-C_7)$ cycloalkyl or $(CH_2)_{0-1}$-heterocycloalkyl. In further embodiments, $R^9$ is $(C_3-C_7)$ cycloalkyl. In other embodiments, $R^9$ is $(C_3-C_5)$ cycloalkyl. In further embodiments, $R^9$ is cyclopropyl. In other embodiments, $R^9$ is heterocycloalkyl or $(CH_2)$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^9$ is morpholinyl or $CH_2$-morpholinyl.

(10a) In some embodiments of Formula (I), $R^{10}$ is H or $(C_1-C_4)$ alkyl (e.g., methyl, ethyl, propyl, i-propyl, butyl, i-butyl, or tert-butyl). In further embodiments, $R^{10}$ is H. In other embodiments, $R^{10}$ is methyl or ethyl.

(10b) In some embodiments of Formula (I), $R^{10}$ is $(CH_2)_{0-2}$-aryl or $(CH_2)_{0-2}$-heteroaryl. In further embodiments, $R^{10}$ is $(CH_2)_{0-1}$-aryl or $(CH_2)_{0-1}$-heteroaryl. In further embodiments, $R^{10}$ is $(CH_2)_{0-1}$-aryl. In further embodiments, $R^{10}$ is $(CH_2)$-aryl. In further embodiments, $R^{10}$ is benzyl (e.g., $CH_2$-phenyl). In other embodiments, $R^{10}$ is $(CH_2)_{0-1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(10c) In some embodiments of Formula (I), $R^{10}$ is $(CH_2)_{0-2}$—$(C_3-C_7)$ cycloalkyl or $(CH_2)_{0-2}$-heterocycloalkyl. In further embodiments, $R^{10}$ is $(CH_2)_{0-1}$—$(C_3-C_7)$ cycloalkyl or $(CH_2)_{0-1}$-heterocycloalkyl. In further embodiments, $R^{10}$ is $(C_3-C_7)$ cycloalkyl. In other embodiments, $R^{10}$ is $(C_3-C_5)$ cycloalkyl. In further embodiments, $R^{10}$ is cyclopropyl. In other embodiments, $R^{10}$ is heterocycloalkyl or $(CH_2)$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^{10}$ is morpholinyl or $CH_2$-morpholinyl.

(11a) In some embodiments of Formula (I), $R^{11}$ is H or $(C_1-C_4)$ alkyl (e.g., methyl, ethyl, propyl, i-propyl, butyl, i-butyl, or tert-butyl). In further embodiments, $R^{11}$ is H. In further embodiments, $R^{11}$ is methyl or ethyl.

(11b) In some embodiments of Formula (I), $R^{11}$ is $(C_3-C_7)$ cycloalkyl or heterocycloalkyl. In further embodiments, $R^{11}$ is $(C_3-C_7)$ cycloalkyl. In further embodiments, $R^{11}$ is cyclopropyl. In other embodiments, $R^{11}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(12a) In some embodiments of Formula (I), $R^{12}$ is H or $(C_1-C_4)$ alkyl (e.g., methyl, ethyl, propyl, i-propyl, butyl, i-butyl, or tert-butyl). In further embodiments, $R^{12}$ is H. In further embodiments, $R^{12}$ is methyl or ethyl.

(12b) In some embodiments of Formula (I), $R^{12}$ is $(C_3-C_7)$ cycloalkyl or heterocycloalkyl. In further embodiments, $R^{12}$ is $(C_3-C_7)$ cycloalkyl. In further embodiments, $R^{12}$ is cyclopropyl. In other embodiments, $R^{12}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(13a) In some embodiments of Formula (I), at least one $R^5$ is $(C_1-C_4)$ alkyl (e.g., methyl, ethyl, propyl, i-propyl, butyl, i-butyl, or tert-butyl). In further embodiments, at least one $R^5$ is methyl or ethyl.

(13b) In some embodiments of Formula (I), at least one $R^5$ is $C(O)NR^{14}R^{15}$. In further embodiments, at least one $R^5$ is $C(O)NR^{14}R^{15}$ and is at the para-position on the phenyl ring.

(13c) In some embodiments of Formula (I), at least one $R^5$ is CN, OH, or halogen (e.g., F, Cl, Br, or I). In further embodiments, at least one $R^5$ is CN. In other embodiments, at least one $R^5$ is OH. In other embodiments, at least one $R^5$ is halogen. In further embodiments, at least one $R^5$ is F or Cl.

(13d) In some embodiments of Formula (I), two adjacent $R^5$, together with the atoms to which they are attached, form a 5- to 6-membered heterocycloalkyl optionally substituted with one or more $R^{13}$. In further embodiments, the heterocycloalkyl comprises a 5- to 6-membered ring and 1 to 3 heteroatoms selected from N, O, and S, and is optionally substituted with one or more $R^{13}$. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl, each of which is optionally substituted with one or more $R^{13}$.

(13e) In some embodiments of Formula (I), two adjacent $R^5$, together with the atoms to which they are attached, form a 5- to 6-membered heteroaryl optionally substituted with one or more $R^{13}$. In further embodiments, the heteroaryl comprises one 5- to 6-membered ring and 1 to 3 heteroatoms selected from N, O, and S, and is optionally substituted with one or more $R^{13}$. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^{13}$.

(14a) In some embodiments of Formula (I), two $R^{13}$, together with the carbon atom to which they are attached, form C(O). In other embodiments, at least one $R^{13}$ is halogen. In further embodiments, at least one $R^{13}$ is F or Cl.

(14b) In some embodiments of Formula (I), at least one $R^{13}$ is $(C_1-C_4)$ alkyl (e.g., methyl, ethyl, propyl, i-propyl, butyl, i-butyl, or tert-butyl). In further embodiments, at least one $R^{13}$ is methyl or ethyl.

(14c) In some embodiments of Formula (I), at least one $R^{13}$ is $(C_1-C_4)$ alkoxy (e.g., $OCH_3$, $OCH_2CH_3$, $OCH_2CH_2CH_3$, $OCH(CH_3)CH_3$, $O(CH_2)_3CH_3$, $OCH_2CH(CH_3)CH_3$, or $OC(CH_3)_3$). In further embodiments, at least one $R^{13}$ is $OCH_3$ or $OCH_2CH_3$.

(15a) In some embodiments of Formula (I), $R^{14}$ is H or $(C_1-C_4)$ alkyl (e.g., methyl, ethyl, propyl, i-propyl, butyl, i-butyl, or tert-butyl). In further embodiments, $R^{14}$ is H. In further embodiments, $R^{14}$ is methyl or ethyl.

(16a) In some embodiments of Formula (I), $R^{15}$ is H or $(C_1-C_4)$ alkyl (e.g., methyl, ethyl, propyl, i-propyl, butyl, i-butyl, or tert-butyl). In further embodiments, $R^{15}$ is H. In further embodiments, $R^{15}$ is methyl or ethyl.

(17a) In some embodiments of Formula (I), m is 0, 1, or 2. In other embodiments, m is 1 or 2. In a further embodiment, m is 2.

(18a) In some embodiments of Formula (I), n is 1, 2, 3, 4, or 5. In other embodiments, n is 1, 2, or 3. In other embodiments, n is 1 or 2. In other embodiments, n is 2 or 3.

In some embodiments of Formula (I), at least one of $R^1$, $R^2$, $R^3$, $R^4$, and $R^6$ is not H.

In some embodiments of Formula (I), when $R^2$ is $S(O)_2NR^9R^{10}$ or F, then $R^4$ and $R^1$ are not simultaneously H. In other embodiments of Formula (I), when $R^2$ is $S(O)_2NR^9R^{10}$, then $R^4$ or $R^1$ is not Cl.

In some embodiments of Formula (I), each of the substituents defined for any one of $X^1$, $X^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, m, and n can be combined with any of the substituents defined for the remainder of $X^1$, $X^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^5$, m, and n.

(11) In some embodiments of Formula (I), $X^1$ and $X^2$ are defined as in (1a) and (1c), respectively, or (1b) and (1c), respectively.

(12) In some embodiments of Formula (I), $X^1$ and $X^2$ are defined as in (1a) and (1d), respectively, or (1b) and (1d), respectively.

(13) In some embodiments of Formula (I), $X^1$ and $X^2$ are defined as in (1a) and (1c), respectively, and $R^5$ is defined as in (13a) or (13b).

(14) In some embodiments of Formula (I), $X^1$ and $X^2$ are defined as in (1a) and (1c), respectively, and $R^5$ is defined as in (13b) or (13c).

(15) In some embodiments of Formula (I), $X^1$, $X^2$ and $R^5$ are defined as in (1a), (1c), and (13b), respectively.

(16) In some embodiments of Formula (I), $X^1$, $X^2$ and $R^5$ are defined as in (1a), (1c), and (13d), respectively.

(17) In some embodiments of Formula (I), $X^1$, $X^2$ and $R^5$ are defined as in (1a), (1c), and (13e), respectively.

(18) In some embodiments of Formula (I), $X^1$, $X^2$ and $R^1$ are defined as in (1a), (1c), and (2a), respectively.

(19) In some embodiments of Formula (I), $X^1$, $X^2$ and $R^1$ are defined as in (1a), (1c), and (2d), respectively.

(20) In some embodiments of Formula (I), $X^1$, $X^2$ and $R^1$ are defined as in (1a), (1c), and (2b), respectively.

(21) In some embodiments of Formula (I), $X^1$, $X^2$ and $R^4$ are defined as in (1a), (1c), and (5a), respectively.

(22) In some embodiments of Formula (I), $X^1$, $X^2$ and $R^4$ are defined as in (1a), (1c), and (5d), respectively.

(23) In some embodiments of Formula (I), $X^1$, $X^2$ and $R^4$ are defined as in (1a), (1c), and (5b), respectively.

(24) In some embodiments of Formula (I), $X^1$, $X^2$ and $R^3$ are defined as in (1a), (1c), and (4a), respectively.

(25) In some embodiments of Formula (I), $X^1$ and $X^2$ are defined as in (1a) and (1c), respectively, and $R^3$ is defined as in (4b) or (4c).

(26) In some embodiments of Formula (I), $X^1$ and $X^2$ are defined as in (1a) and (1c), respectively, and $R^3$ is defined as in (4d) or (4e).

(27) In some embodiments of Formula (I), $X^1$, $X^2$ and $R^3$ are defined as in (1a), (1c), and (4f), respectively.

(28) In some embodiments of Formula (I), $X^1$, $X^2$ and $R^3$ are defined as in (1a), (1c), and (4g), respectively.

(29) In some embodiments of Formula (I), $X^1$ and $X^2$ are defined as in (1a) and (1c), respectively, and $R^3$ is defined as in (4h) or (4i).

(30) In some embodiments of Formula (I), $X^1$, $X^2$ and $R^6$ are defined as in (1a), (1c), and (6a), respectively.

(31) In some embodiments of Formula (I), $X^1$ and $X^2$ are defined as in (1a) and (1c), respectively, and $R^6$ is defined as in (6b) or (6c).

(32) In some embodiments of Formula (I), $X^1$ and $X^2$ are defined as in (1a) and (1c), respectively, and $R^6$ is defined as in (6d) or (6e).

(33) In some embodiments of Formula (I), $X^1$, $X^2$ and $R^6$ are defined as in (1a), (1c), and (6f), respectively.

(34) In some embodiments of Formula (I), $X^1$ and $X^2$ are defined as in (1a) and (1c), respectively, and $R^6$ is defined as in (6g1), (6g2), or (6g3).

(35) In some embodiments of Formula (I), $X^1$, $X^2$ and $R^2$ are defined as in (1a), (1c), and (3), respectively. In further embodiments of Formula (I), $X^1$, $X^2$ and $R^2$ are defined as in (1a), (1c), and (3a), respectively.

(36) In some embodiments of Formula (I), $X^1$ and $X^2$ are defined as in (1a) and (1c), respectively, and $R^2$ is defined as in (3b) or (3c).

(37) In some embodiments of Formula (I), $X^1$, $X^2$ and $R^2$ are defined as in (1a), (1c), and (3d), respectively.

(38) In some embodiments of Formula (I), $X^1$ and $X^2$ are defined as in (1a) and (1c), respectively, and $R^2$ is defined as in (3e1) or (3e2).

(39) In some embodiments of Formula (I), $X^1$, $X^2$ and $R^2$ are defined as in (1a), (1c), and (3f), respectively.

(40) In some embodiments of Formula (I), $X^1$ and $X^2$ are defined as in (1a) and (1c), respectively, and $R^2$ is defined as in (3g) or (3h).

(41) In some embodiments of Formula (I), $X^1$ and $X^2$ are defined as in (1a) and (1c), respectively, and $R^2$ is defined as in (3i) or (3j).

(42) In some embodiments of Formula (I), $X^1$, $X^2$, $R^1$, and $R^5$ are defined as in (1a), (1c), (2a), and (13d), respectively.

(43) In some embodiments of Formula (I), $X^1$, $X^2$, $R^1$, and $R^5$ are defined as in (1a), (1c), (2b), and (13d), respectively.

(44) In some embodiments of Formula (I), $X^1$, $X^2$, $R^1$, and $R^5$ are defined as in (1a), (1c), (2d), and (13d), respectively.

(45) In some embodiments of Formula (I), $X^1$, $X^2$, $R^4$, and $R^5$ are defined as in (1a), (1c), (5a), and (13d), respectively.

(46) In some embodiments of Formula (I), $X^1$, $X^2$, $R^4$, and $R^5$ are defined as in (1a), (1c), (5b), and (13d), respectively.

(47) In some embodiments of Formula (I), $X^1$, $X^2$, $R^4$, and $R^5$ are defined as in (1a), (1c), (5d), and (13d), respectively.

(48) In some embodiments of Formula (I), $X^1$, $X^2$, $R^3$, and $R^5$ are defined as in (1a), (1c), (4a), and (13d), respectively.

(49) In some embodiments of Formula (I), $X^1$, $X^2$, and $R^5$ are defined as in (1a), (1c), and (13d), respectively, and $R^3$ is defined as in (4b) or (4c).

(50) In some embodiments of Formula (I), $X^1$, $X^2$, and $R^5$ are defined as in (1a), (1c), and (13d), respectively, and $R^3$ is defined as in (4d) or (4e).

(51) In some embodiments of Formula (I), $X^1$, $X^2$, $R^3$, and $R^5$ are defined as in (1a), (1c), (4f), and (13d), respectively.

(52) In some embodiments of Formula (I), $X^1$, $X^2$, $R^3$, and $R^5$ are defined as in (1a), (1c), (4g), and (13d), respectively.

(53) In some embodiments of Formula (I), $X^1$, $X^2$, and $R^5$ are defined as in (1a), (1c), and (13d), respectively, and $R^3$ is defined as in (4h) or (4i).

(54) In some embodiments of Formula (I), $X^1$, $X^2$, $R^6$, and $R^5$ are defined as in (1a), (1c), (6a), and (13d), respectively.

(55) In some embodiments of Formula (I), $X^1$, $X^2$, and $R^5$ are defined as in (1a), (1c), and (13d), respectively, and $R^6$ is defined as in (6b) or (6c).

(55a) In some embodiments of Formula (I), $X^1$, $X^2$, and $R^5$ are defined as in (1a), (1c), and (13d), respectively, and $R^6$ is defined as in (6d) or (6e).

(55b) In some embodiments of Formula (I), $X^1$, $X^2$, $R^6$, and $R^5$ are defined as in (1a), (1c), (6f), and (13d), respectively.

(55c) In some embodiments of Formula (I), $X^1$, $X^2$, $R^6$, and $R^5$ are defined as in (1a), (1c), (6g1), and (13d), respectively.

(55d) In some embodiments of Formula (I), $X^1$, $X^2$, and $R^5$ are defined as in (1a), (1c), and (13d), respectively, and $R^6$ is defined as in (6g2) or (6g3).

(56) In some embodiments of Formula (I), $X^1$, $X^2$, $R^2$, and $R^5$ are defined as in (1a), (1c), (3), and (13d), respectively. In further embodiments of Formula (I), $X^1$, $X^2$, $R^2$, and $R^5$ are defined as in (1a), (1c), (3a), and (13d), respectively.

In one embodiment, the compounds of Formula (I) have the structure of Formula (Ia) or (Ib):

or pharmaceutically acceptable salts, hydrates, solvates, prodrugs, stereoisomers, or tautomers thereof, wherein:

$R^1$ is H, $(C_1-C_3)$ alkyl, $(C_1-C_3)$ alkoxy, $NO_2$, or halogen;

$R^2$ is H, $(C_1-C_2)$ alkyl, $(C_1-C_2)$ alkoxy, $(CH_2)_{0-2}$-heterocycloalkyl, halogen, $NR^9C(O)R^{10}$, $NR^9R^{10}$, or $S(O)_m NR^9R^{10}$, wherein the alkyl is optionally substituted with one or more substituents selected from $NH_2$, $NH(C_1-C_3)$ alkyl, and $N((C_1-C_3)$ alkyl$)_2$;

R³ is H, halogen, (C₁-C₃) alkyl, (C₁-C₃) alkoxy, NO₂, C(O)NR¹¹R¹², NR¹¹C(O)R¹², C(O)OR¹¹, S(O)ₘR¹², S(O)ₘNR¹¹R¹², or CN, wherein the alkyl is optionally substituted with one or more substituents selected from NH₂, NH(C₁-C₃) alkyl, and N((C₁-C₃) alkyl)₂;

R⁴ is H, (C₁-C₃) alkyl, (C₁-C₃) alkoxy, NO₂, or halogen;

R⁶ is H, halogen, (C₁-C₃) alkyl, (C₁-C₃) alkoxy, NO₂, C(O)NR¹¹R¹², NR¹¹C(O)R¹², C(O)OR¹¹, S(O)ₘR¹², S(O)ₘNR¹¹R¹², or CN, wherein the alkyl is optionally substituted with one or more substituents selected from NH₂, NH(C₁-C₃) alkyl, and N((C₁-C₃) alkyl)₂; or R² and R³, together with the atoms to which they are attached, form a 6-membered heterocycloalkyl optionally substituted with one or more R⁷, or a 5- to 6-membered heteroaryl optionally substituted with one or more R⁷; or R² and R⁶, together with the atoms to which they are attached, form a 6-membered heterocycloalkyl optionally substituted with one or more R⁷, or a 5- to 6-membered heteroaryl optionally substituted with one or more R⁷; or R³ and R⁴, together with the atoms to which they are attached, form a 5- to 6-membered heteroaryl optionally substituted with one or more R⁸; or R¹ and R⁶, together with the atoms to which they are attached, form a 5- to 6-membered heteroaryl optionally substituted with one or more R⁸;

each R⁷ is independently (C₁-C₃) alkyl, (C₁-C₃) alkoxy, or halogen, or two R⁷, together with the carbon atom to which they are attached, form C(O);

each R⁸ is independently (C₁-C₃) alkyl, (C₁-C₃) alkoxy, or halogen, or two R⁸, together with the carbon atom to which they are attached, form C(O);

R⁹ and R¹⁰ are each independently H, (C₁-C₄) alkyl, (CH₂)₀₋₂-aryl, (CH₂)₀₋₂-heteroaryl, (CH₂)₀₋₂—(C₃-C₇) cycloalkyl, or (CH₂)₀₋₂-heterocycloalkyl;

R¹¹ and R¹² are each independently H, (C₁-C₄) alkyl, (C₃-C₇) cycloalkyl, or heterocycloalkyl;

each R⁵ is independently (C₁-C₄) alkyl, C(O)NR¹⁴R¹⁵, CN, OH, or halogen;

R¹³ is (C₁-C₄) alkyl, (C₁-C₄) alkoxy, or halogen;

R¹⁴ and R¹⁵ are each independently H or (C₁-C₄) alkyl;

m is 0, 1, or 2; and n is 1, 2, 3, 4, or 5;

wherein at least one of R¹, R², R³, R⁴, and R⁶ is not H; and provided that when R² is S(O)₂NR⁹R¹⁰ or F, then R⁴ and R¹ are not simultaneously H, and when R² is S(O)₂NR⁹R¹⁰, then R⁴ or R¹ is not Cl.

(56a) In some embodiments of Formulae (Ia) and (Ib), R¹ is H, halogen (e.g., F, Cl, Br, or I), or NO₂. In further embodiments, R¹ is H. In other embodiments, R¹ is halogen. In further embodiments, R¹ is F or Cl. In other embodiments, R¹ is NO₂.

(56b) In some embodiments of Formulae (Ia) and (Ib), R¹ and R⁶, together with the atoms to which they are attached, form a 5- to 6-membered heteroaryl optionally substituted with one or more R⁸. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more R⁸. In another embodiment, R¹ and R⁶, together with the atoms to which they are attached, form an optionally substituted 5- to 6-membered heteroaryl selected from

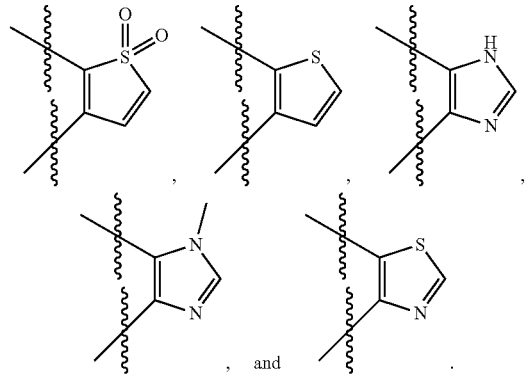

(56c) In some embodiments of Formulae (Ia) and (Ib), R¹ is (C₁-C₃) alkyl (e.g., methyl, ethyl, propyl, or i-propyl).

(56d) In some embodiments of Formulae (Ia) and (Ib), R¹ is (C₁-C₃) alkoxy (e.g., OCH₃, OCH₂CH₃, OCH₂CH₂CH₃, or OCH(CH₃)CH₃). In further embodiments, R¹ is OCH₃.

(57) In some embodiments of Formulae (Ia) and (Ib), R² is H, halogen (e.g., F, Cl, Br, or I), (C₁-C₂) alkyl (e.g., methyl or ethyl) wherein the alkyl is optionally substituted with one or more substituents selected from NH₂, NH(C₁-C₃) alkyl, and N((C₁-C₃) alkyl)₂, (C₁-C₂) alkoxy (e.g., OCH₃ or OCH₂CH₃), (CH₂)₀₋₂-heterocycloalkyl, NR⁹C(O)R¹⁰, or NR⁹R¹⁰. In further embodiments, R² is H, halogen (e.g., F, Cl, Br, or I), or (C₁-C₂) alkoxy (e.g., OCH₃ or OCH₂CH₃).

(57a) In some embodiments of Formulae (Ia) and (Ib), R² is H or halogen (e.g., F, Cl, Br, or I). In further embodiments, R² is H. In other embodiments, R² is halogen. In further embodiments, R² is F or Cl.

(57b) In some embodiments of Formulae (Ia) and (Ib), R² is (C₁-C₂) alkyl (e.g., methyl or ethyl) wherein the alkyl is optionally substituted with one or more substituents selected from NH₂, NH(C₁-C₃) alkyl, and N((C₁-C₃) alkyl)₂. In other embodiments, R² is methyl or ethyl, each of which is optionally substituted with one to two substituents selected from NH₂, NH(C₁-C₃) alkyl, and N((C₁-C₃) alkyl)₂. In yet other embodiments, R² is methyl or ethyl, each of which is optionally substituted with one substituent selected from NH₂, NH(C₁-C₃) alkyl, and N((C₁-C₃) alkyl)₂. In further embodiments, R² is methyl optionally substituted with one substituent selected from NH₂, NH(C₁-C₃) alkyl, and N((C₁-C₃) alkyl)₂. In further embodiments, R² is CH₂NH₂, CH₂NHCH₃, or CH₂N(CH₃)₂. In further embodiments, R² is CH₂N(CH₃)₂.

(57c) In some embodiments of Formulae (Ia) and (Ib), R² is (C₁-C₂) alkoxy (e.g., OCH₃ or OCH₂CH₃). In further embodiments, R² is OCH₃.

(57d) In some embodiments of Formulae (Ia) and (Ib), R² is (CH₂)₀₋₂-heterocycloalkyl. In further embodiments, R² is (CH₂)₀₋₁-heterocycloalkyl. In further embodiments, R² is (CH₂)O-heterocycloalkyl. In further embodiments, R² is (CH₂)₁-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In other embodiments, R² is morpholinyl or CH₂-morpholinyl.

(57e1) In some embodiments of Formulae (Ia) and (Ib), $R^2$ is $NR^9C(O)R^{10}$. In further embodiments, $R^2$ is $NHC(O)CH_3$.

(57e2) In some embodiments of Formulae (Ia) and (Ib), $R^2$ is $NR^9R^{10}$. In further embodiments, $R^2$ is $NH_2$, $NH(C_1-C_4)$ alkyl, $N((C_1-C_4)$ alkyl$)_2$, $NH-(CH_2)_{0-2}$-aryl, or $NH-(CH_2)_{0-2}$-heteroaryl. In further embodiments, $R^2$ is $NH-CH_2$-phenyl.

(57f) In some embodiments of Formulae (Ia) and (Ib), $R^2$ is $S(O)_mNR^9R^{10}$. In further embodiments, $R^2$ is $S(O)_2NR^9R^{10}$. In further embodiments, $R^2$ is $S(O)_2NCH_3$-cyclopropyl.

(57g) In some embodiments of Formulae (Ia) and (Ib), $R^2$ and $R^3$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(57h) In some embodiments of Formulae (Ia) and (Ib), $R^2$ and $R^3$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(57i) In some embodiments of Formulae (Ia) and (Ib), $R^2$ and $R^6$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(57j) In some embodiments of Formulae (Ia) and (Ib), $R^2$ and $R^6$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(58a) In some embodiments of Formulae (Ia) and (Ib), $R^3$ is H, halogen (e.g., F, Cl, Br, or I), CN, or $NO_2$. In further embodiments, $R^3$ is H. In other embodiments, $R^3$ is halogen. In further embodiments, $R^3$ is F or Cl. In other embodiments, $R^3$ is $NO_2$. In other embodiments, $R^3$ is CN.

(58b) In some embodiments of Formulae (Ia) and (Ib), $R^3$ is $(C_1-C_3)$ alkyl (e.g., methyl, ethyl, propyl, or i-propyl), wherein the alkyl is optionally substituted with one or more substituents selected from $NH_2$, $NH(C_1-C_3)$ alkyl, and $N((C_1-C_3)$ alkyl$)_2$. In other embodiments, $R^3$ is methyl, or ethyl, each of which is optionally substituted with one or two substituents selected from $NH_2$, $NH(C_1-C_3)$ alkyl, and $N((C_1-C_3)$ alkyl$)_2$. In yet other embodiments, $R^3$ is methyl or ethyl, each of which is optionally substituted with one substituent selected from $NH_2$, $NH(C_1-C_3)$ alkyl, and $N((C_1-C_3)$ alkyl$)_2$. In further embodiments, $R^3$ is methyl optionally substituted with one substituent selected from $NH_2$, $NH(C_1-C_3)$ alkyl, and $N((C_1-C_3)$ alkyl$)_2$. In further embodiments, $R^3$ is $CH_2NH_2$, $CH_2NHCH_3$, or $CH_2N(CH_3)_2$. In further embodiments, $R^3$ is $CH_2N(CH_3)_2$.

(58c) In some embodiments of Formulae (Ia) and (Ib), $R^3$ is $(C_1-C_3)$ alkoxy (e.g., $OCH_3$, $OCH_2CH_3$, $OCH_2CH_2CH_3$, or $OCH(CH_3)CH_3$). In further embodiments, $R^3$ is $OCH_3$.

(58d) In some embodiments of Formulae (Ia) and (Ib), $R^3$ is $C(O)NR^{11}R^{12}$ or $C(O)OR^{11}$. In further embodiments, $R^3$ is $C(O)NR^{11}R^{12}$. In further embodiments, $R^3$ is $C(O)NHCH_3$ or $C(O)NHCH_2CH_3$. In other embodiments, $R^3$ is $C(O)OR^{11}$. In further embodiments, $R^3$ is $C(O)OCH_3$.

(58e) In some embodiments of Formulae (Ia) and (Ib), $R^3$ is $NR^1C(O)R^2$. In further embodiments, $R^3$ is $NHC(O)CH_3$.

(58f) In some embodiments of Formulae (Ia) and (Ib), $R^3$ is $S(O)_mR^{12}$ or $S(O)_mNR^{11}R^{12}$. In other embodiments, $R^3$ is $S(O)_2R^{12}$. In other embodiments, $R^3$ is $S(O)_2NR^{11}R^{12}$. In further embodiments, $R^3$ is $S(O)_2NH$-cyclopropyl.

(58g) In some embodiments of Formulae (Ia) and (Ib), $R^3$ and $R^4$, together with the atoms to which they are attached, form a 5- to 6-membered heteroaryl optionally substituted with one or more $R^8$. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^3$ and $R^4$, together with the atoms to which they are attached, form an optionally substituted 5- to 6-membered heteroaryl selected from

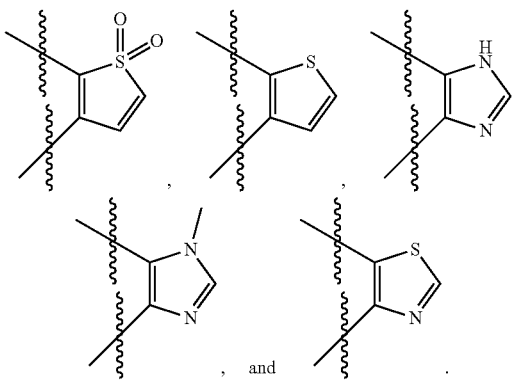

, and

.

(58h) In some embodiments of Formulae (Ia) and (Ib), $R^2$ and $R^3$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(58i) In some embodiments of Formulae (Ia) and (Ib), $R^2$ and $R^3$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(59a) In some embodiments of Formulae (Ia) and (Ib), $R^4$ is H, halogen (e.g., F, Cl, Br, or I), or $NO_2$. In further embodiments, $R^4$ is H. In other embodiments, $R^4$ is halogen. In further embodiments, $R^4$ is F or Cl. In other embodiments, $R^4$ is $NO_2$.

(59b) In some embodiments of Formulae (Ia) and (Ib), $R^3$ and $R^4$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In another embodiment, $R^3$ and $R^4$, together with the atoms to which they are attached, form an optionally substituted 5- to 6-membered heteroaryl selected from

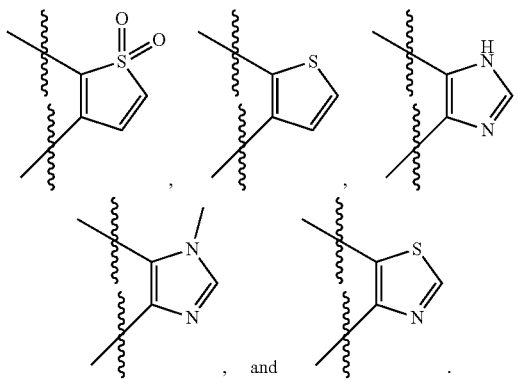

, and (59c) In some embodiments of Formulae (Ia) and (Ib), $R^4$ is ($C_1$-$C_3$) alkyl (e.g., methyl, ethyl, propyl, or i-propyl).

(59d) In some embodiments of Formulae (Ia) and (Ib), $R^4$ is ($C_1$-$C_3$) alkoxy (e.g., $OCH_3$, $OCH_2CH_3$, $OCH_2CH_2CH_3$, or $OCH(CH_3)CH_3$). In further embodiments, $R^4$ is $OCH_3$.

(60a) In some embodiments of Formulae (Ia) and (Ib), $R^6$ is H, halogen (e.g., F, Cl, Br, or I), CN, or $NO_2$. In further embodiments, $R^6$ is H. In other embodiments, $R^6$ is halogen. In further embodiments, $R^6$ is F or Cl. In another embodiment, $R^6$ is $NO_2$. In other embodiments, $R^6$ is CN.

(60b) In some embodiments of Formulae (Ia) and (Ib), $R^6$ is ($C_1$-$C_3$) alkyl (e.g., methyl, ethyl, propyl, or i-propyl), wherein the alkyl is optionally substituted with one or more substituents selected from $NH_2$, $NH(C_1$-$C_3)$ alkyl, and $N((C_1$-$C_3)$ alkyl$)_2$. In other embodiments, $R^6$ is methyl or ethyl, each of which is optionally substituted with one or two substituents selected from $NH_2$, $NH(C_1$-$C_3)$ alkyl, and $N((C_1$-$C_3)$ alkyl$)_2$. In yet other embodiments, $R^6$ is methyl or ethyl, each of which is optionally substituted with one substituent selected from $NH_2$, $NH(C_1$-$C_3)$ alkyl, and $N((C_1$-$C_3)$ alkyl$)_2$. In other embodiments, $R^6$ is methyl optionally substituted with one substituent selected from $NH_2$, $NH(C_1$-$C_3)$ alkyl, and $N((C_1$-$C_3)$ alkyl$)_2$. In further embodiments, $R^6$ is $CH_2NH_2$, $CH_2NHCH_3$, or $CH_2N(CH_3)_2$. In further embodiments, $R^6$ is $CH_2N(CH_3)_2$.

(60c) In some embodiments of Formulae (Ia) and (Ib), $R^6$ is ($C_1$-$C_3$) alkoxy (e.g., $OCH_3$, $OCH_2CH_3$, $OCH_2CH_2CH_3$, or $OCH(CH_3)CH_3$). In further embodiments, $R^6$ is $OCH_3$.

(60d) In some embodiments of Formulae (Ia) and (Ib), $R^6$ is $C(O)NR^{11}R^{12}$ or $C(O)OR^{11}$. In further embodiments, $R^6$ is $C(O)NR^{11}R^{12}$. In further embodiments, $R^6$ is $C(O)NHCH_3$ or $C(O)NHCH_2CH_3$. In other embodiments, $R^6$ is $C(O)OR^{11}$. In further embodiments, $R^6$ is $C(O)OCH_3$.

(60e) In some embodiments of Formulae (Ia) and (Ib), $R^6$ is $NR^{11}C(O)R^{12}$. In further embodiments, $R^6$ is $NHC(O)CH_3$.

(60f) In some embodiments of Formulae (Ia) and (Ib), $R^6$ is $S(O)_mR^{12}$ or $S(O)_mNR^{11}R^{12}$. In further embodiments, $R^6$ is $S(O)_2R^{12}$. In further embodiments, $R^6$ is $S(O)_2NR^{11}R^{12}$. In further embodiments, $R^6$ is $S(O)_2NH$-cyclopropyl.

(60g1) In some embodiments of Formulae (Ia) and (Ib), $R^1$ and $R^6$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^1$ and $R^6$, together with the atoms to which they are attached, form an optionally substituted 5- to 6-membered heteroaryl selected from

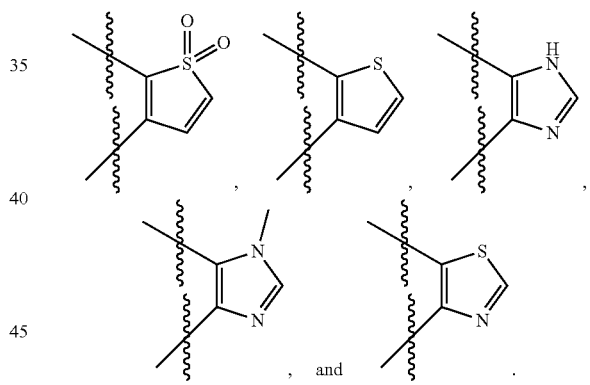

, and (60g2) In some embodiments of Formulae (Ia) and (Ib), $R^2$ and $R^6$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(60g3) In some embodiments of Formulae (Ia) and (Ib), $R^2$ and $R^6$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(61a) In some embodiments of Formulae (Ia) and (Ib), at least one $R^7$ is ($C_1$-$C_3$) alkyl (e.g., methyl, ethyl, propyl, or i-propyl). In further embodiments, at least one $R^7$ is methyl.

(61b) In some embodiments of Formulae (Ia) and (Ib), at least one $R^7$ is ($C_1$-$C_3$) alkoxy (e.g., $OCH_3$, $OCH_2CH_3$, $OCH_2CH_2CH_3$, or $OCH(CH_3)CH_3$). In further embodiments, at least one $R^7$ is $OCH_3$.

(61c) In some embodiments of Formulae (Ia) and (Ib), at least one $R^7$ is halogen (e.g., F, Cl, Br, or I). In further embodiments, at least one $R^7$ is F or Cl. In other embodiments, two $R^7$, together with the carbon atom to which they are attached, form C(O).

(62a) In some embodiments of Formulae (Ia) and (Ib), at least one $R^8$ is ($C_1$-$C_3$) alkyl (e.g., methyl, ethyl, propyl, or i-propyl). In further embodiments, at least one $R^8$ is methyl.

(62b) In some embodiments of Formulae (Ia) and (Ib), at least one $R^8$ is ($C_1$-$C_3$) alkoxy (e.g., $OCH_3$, $OCH_2CH_3$, $OCH_2CH_2CH_3$, or $OCH(CH_3)CH_3$). In further embodiments, at least one $R^8$ is $OCH_3$.

(62c) In some embodiments of Formulae (Ia) and (Ib), at least one $R^8$ is halogen (e.g., F, Cl, Br, or I). In further embodiments, at least one $R^8$ is F or Cl. In other embodiments, two $R^8$, together with the carbon atom to which they are attached, form C(O).

(63a) In some embodiments of Formulae (Ia) and (Ib), $R^9$ is H or ($C_1$-$C_4$) alkyl (e.g., methyl, ethyl, propyl, i-propyl, butyl, i-butyl, or tert-butyl). In further embodiments, $R^9$ is H. In other embodiments, $R^9$ is methyl or ethyl.

(63b) In some embodiments of Formulae (Ia) and (Ib), $R^9$ is $(CH_2)_{0-2}$-aryl or $(CH_2)_{0-2}$-heteroaryl. In further embodiments, $R^9$ is $(CH_2)_{0-1}$-aryl or $(CH_2)_{0-1}$-heteroaryl. In further embodiments, $R^9$ is $(CH_2)_{0-1}$-aryl. In further embodiments, $R^9$ is $(CH_2)$-aryl. In further embodiments, $R^9$ is benzyl (e.g., $CH_2$-phenyl). In other embodiments, $R^9$ is $(CH_2)_{0-1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(63c) In some embodiments of Formulae (Ia) and (Ib), $R^9$ is $(CH_2)_{0-2}$—($C_3$-$C_7$) cycloalkyl or $(CH_2)_{0-2}$-heterocycloalkyl. In further embodiments, $R^9$ is $(CH_2)_{0-1}$—($C_3$-$C_7$) cycloalkyl or $(CH_2)_{0-1}$-heterocycloalkyl. In further embodiments, $R^9$ is ($C_3$-$C_7$) cycloalkyl. In other embodiments, $R^9$ is ($C_3$-$C_5$) cycloalkyl. In further embodiments, $R^9$ is cyclopropyl. In other embodiments, $R^9$ is heterocycloalkyl or $(CH_2)$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^9$ is morpholinyl or $CH_2$-morpholinyl.

(64a) In some embodiments of Formulae (Ia) and (Ib), $R^{10}$ is H or ($C_1$-$C_4$) alkyl (e.g., methyl, ethyl, propyl, i-propyl, butyl, i-butyl, or tert-butyl). In further embodiments, $R^{10}$ is H. In other embodiments, $R^{10}$ is methyl or ethyl.

(64b) In some embodiments of Formulae (Ia) and (Ib), $R^{10}$ is $(CH_2)_{0-2}$-aryl or $(CH_2)_{0-2}$-heteroaryl. In further embodiments, $R^{10}$ is $(CH_2)_{0-1}$-aryl or $(CH_2)_{0-1}$-heteroaryl. In further embodiments, $R^{10}$ is $(CH_2)_{0-1}$-aryl. In further embodiments, $R^{10}$ is $(CH_2)$-aryl. In further embodiments, $R^{10}$ is benzyl (e.g., $CH_2$-phenyl). In other embodiments, $R^{10}$ is $(CH_2)_{0-1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(64c) In some embodiments of Formulae (Ia) and (Ib), $R^{10}$ is $(CH_2)_{0-2}$—($C_3$-$C_7$) cycloalkyl or $(CH_2)_{0-2}$-heterocycloalkyl. In further embodiments, $R^{10}$ is $(CH_2)_{0-1}$—($C_3$-$C_7$) cycloalkyl or $(CH_2)_{0-1}$-heterocycloalkyl. In further embodiments, $R^{10}$ is ($C_3$-$C_7$) cycloalkyl. In other embodiments, $R^{10}$ is ($C_3$-$C_5$) cycloalkyl. In further embodiments, $R^{10}$ is cyclopropyl. In other embodiments, $R^{10}$ is heterocycloalkyl or $(CH_2)$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^{10}$ is morpholinyl or $CH_2$-morpholinyl.

(65a) In some embodiments of Formulae (Ia) and (Ib), $R^{11}$ is H or ($C_1$-$C_4$) alkyl (e.g., methyl, ethyl, propyl, i-propyl, butyl, i-butyl, or tert-butyl). In further embodiments, $R^{11}$ is H. In further embodiments, $R^{11}$ is methyl or ethyl.

(65b) In some embodiments of Formulae (Ia) and (Ib), $R^{11}$ is ($C_3$-$C_7$) cycloalkyl or heterocycloalkyl. In further embodiments, $R^{11}$ is ($C_3$-$C_7$) cycloalkyl. In further embodiments, $R^{11}$ is cyclopropyl. In other embodiments, $R^{11}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(66a) In some embodiments of Formulae (Ia) and (Ib), $R^{12}$ is H or ($C_1$-$C_4$) alkyl (e.g., methyl, ethyl, propyl, i-propyl, butyl, i-butyl, or tert-butyl). In further embodiments, $R^{12}$ is H. In further embodiments, $R^{12}$ is methyl or ethyl.

(66b) In some embodiments of Formulae (Ia) and (Ib), $R^{12}$ is ($C_3$-$C_7$) cycloalkyl or heterocycloalkyl. In further embodiments, $R^{12}$ is ($C_3$-$C_7$) cycloalkyl. In further embodiments, $R^{12}$ is cyclopropyl. In other embodiments, $R^{12}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(67a) In some embodiments of Formulae (Ia) and (Ib), at least one $R^5$ is ($C_1$-$C_4$) alkyl (e.g., methyl, ethyl, propyl, i-propyl, butyl, i-butyl, or tert-butyl). In further embodiments, at least one $R^5$ is methyl or ethyl.

(67b) In some embodiments of Formulae (Ia) and (Ib), at least one $R^5$ is $C(O)NR^{14}R^{15}$. In further embodiments, at least one $R^5$ is $C(O)NR^{14}R^{15}$ and is at the para-position on the phenyl ring.

(67c) In some embodiments of Formulae (Ia) and (Ib), at least one $R^5$ is CN, OH, or halogen (e.g., F, Cl, Br, or I). In further embodiments, at least one $R^5$ is CN. In other embodiments, at least one $R^5$ is OH. In other embodiments, at least one $R^5$ is halogen. In further embodiments, at least one $R^5$ is F or Cl.

(68a) In some embodiments of Formulae (Ia) and (Ib), at least one $R^{13}$ is halogen. In further embodiments, at least one $R^{13}$ is F or Cl.

(68b) In some embodiments of Formulae (Ia) and (Ib), at least one $R^{13}$ is ($C_1$-$C_4$) alkyl (e.g., methyl, ethyl, propyl, i-propyl, butyl, i-butyl, or tert-butyl). In further embodiments, at least one $R^{13}$ is methyl or ethyl.

(68c) In some embodiments of Formulae (Ia) and (Ib), at least one $R^{13}$ is ($C_1$-$C_4$) alkoxy (e.g., $OCH_3$, $OCH_2CH_3$, $OCH_2CH_2CH_3$, $OCH(CH_3)CH_3$, $O(CH_2)_3CH_3$, $OCH_2CH(CH_3)CH_3$, or $OC(CH_3)_3$). In further embodiments, at least one $R^{13}$ is $OCH_3$ or $OCH_2CH_3$.

(69a) In some embodiments of Formulae (Ia) and (Ib), $R^{14}$ is H or ($C_1$-$C_4$) alkyl (e.g., methyl, ethyl, propyl, i-propyl, butyl, i-butyl, or tert-butyl). In further embodiments, $R^{14}$ is H. In further embodiments, $R^{14}$ is methyl or ethyl.

(70a) In some embodiments of Formulae (Ia) and (Ib), $R^{15}$ is H or ($C_1$-$C_4$) alkyl (e.g., methyl, ethyl, propyl, i-propyl, butyl, i-butyl, or tert-butyl). In further embodiments, $R^{15}$ is H. In further embodiments, $R^{15}$ is methyl or ethyl.

(71a) In some embodiments of Formulae (Ia) and (Ib), m is 0, 1, or 2. In other embodiments, m is 1, or 2. In a further embodiment, m is 2.

(72a) In some embodiments of Formulae (Ia) and (Ib), n is 1, 2, 3, 4, or 5. In other embodiments, n is 1, 2, or 3. In other embodiments, n is 1 or 2. In other embodiments, n is 2 or 3.

In some embodiments of Formulae (Ia) and (Ib), at least one of $R^1$, $R^2$, $R^3$, $R^4$, and $R^6$ is not H.

In some embodiments of Formulae (Ia) and (Ib), when $R^2$ is $S(O)_2NR^9R^{10}$ or F, then $R^4$ and $R^1$ are not simultaneously H. In other embodiments of Formulae (Ia) and (Ib), when $R^2$ is $S(O)_2NR^9R^{10}$, then $R^4$ or $R^1$ is not Cl.

In some embodiments of Formulae (Ia) and (Ib), each of the substituents defined for any one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, m, and n can be combined with any of the substituents defined for the remainder of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, m, and n. In some embodiments, any of the substituents defined for any one, two, or more of $R^1$, $R^2$, $R^3$, $R^4$, $R^5$, and $R^6$ can be combined with any of the substituents defined for the remainder of $R^1$, $R^2$, $R^3$, $R^4$, $R^5$, and $R^6$ as described in (42)-(56).

In another embodiment, the compounds of Formula (I) have the structure of Formula (Ic) or (Id):

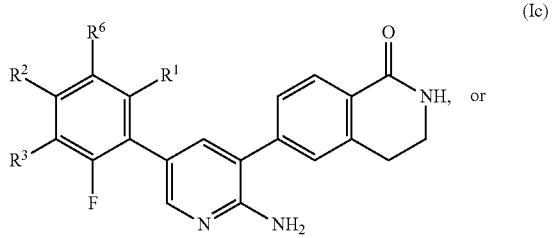

(Ic)

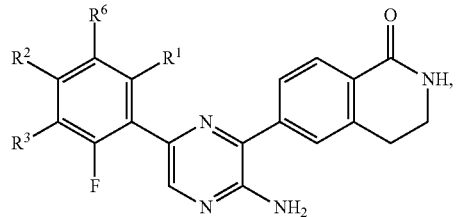

(Id)

or pharmaceutically acceptable salts, hydrates, solvates, prodrugs, stereoisomers, or tautomers thereof, wherein:

$R^1$ is H, ($C_1$-$C_3$) alkyl, ($C_1$-$C_3$) alkoxy, $NO_2$, or halogen;

$R^2$ is H, ($C_1$-$C_2$) alkyl, ($C_1$-$C_2$) alkoxy, $(CH_2)_{0-2}$-heterocycloalkyl, halogen, $NR^9C(O)R^{10}$, $NR^9R^{10}$, or $S(O)_m NR^9R^{10}$, wherein the alkyl is optionally substituted with one or more substituents selected from $NH_2$, $NH(C_1$-$C_3)$ alkyl, and $N((C_1$-$C_3)$ alkyl)$_2$;

$R^3$ is H, halogen, ($C_1$-$C_3$) alkyl, ($C_1$-$C_3$) alkoxy, $NO_2$, $C(O)NR^{11}R^{12}$, $NR^{11}C(O)R^{12}$, $C(O)OR^{11}$, $S(O)_m R^{12}$, $S(O)_m NR^{11}R^{12}$, or CN, wherein the alkyl is optionally substituted with one or more substituents selected from $NH_2$, $NH(C_1$-$C_3)$ alkyl, and $N((C_1$-$C_3)$ alkyl)$_2$;

$R^6$ is H, halogen, ($C_1$-$C_3$) alkyl, ($C_1$-$C_3$) alkoxy, $NO_2$, $C(O)NR^{11}R^{12}$, $NR^{11}C(O)R^{12}$, $C(O)OR^{11}$, $S(O)_m R^{12}$, $S(O)_m NR^{11}R^{12}$, or CN, wherein the alkyl is optionally substituted with one or more substituents selected from $NH_2$, $NH(C_1$-$C_3)$ alkyl, and $N((C_1$-$C_3)$ alkyl)$_2$; or $R^2$ and $R^3$, together with the atoms to which they are attached, form a 6-membered heterocycloalkyl optionally substituted with one or more $R^7$, or a 5- to 6-membered heteroaryl optionally substituted with one or more $R^7$; or $R^2$ and $R^6$, together with the atoms to which they are attached, form a 6-membered heterocycloalkyl optionally substituted with one or more $R^7$, or a 5- to 6-membered heteroaryl optionally substituted with one or more $R^7$; or $R^1$ and $R^6$, together with the atoms to which they are attached, form a 5- to 6-membered heteroaryl optionally substituted with one or more $R^8$; or each $R^7$ is independently ($C_1$-$C_3$) alkyl, ($C_1$-$C_3$) alkoxy, or halogen, or two $R^7$, together with the carbon atom to which they are attached, form C(O);

each $R^8$ is independently ($C_1$-$C_3$) alkyl, ($C_1$-$C_3$) alkoxy, or halogen, or two $R^8$, together with the carbon atom to which they are attached, form C(O);

$R^9$ and $R^{10}$ are each independently H, ($C_1$-$C_4$) alkyl, $(CH_2)_{0-2}$-aryl, $(CH_2)_{0-2}$-heteroaryl, $(CH_2)_{0-2}$—($C_3$-$C_7$) cycloalkyl, or $(CH_2)_{0-2}$-heterocycloalkyl;

$R^{11}$ and $R^{12}$ are each independently H, ($C_1$-$C_4$) alkyl, ($C_3$-$C_7$) cycloalkyl, or heterocycloalkyl; and m is 0, 1, or 2.

(73a) In some embodiments of Formulae (Ic) and (Id), $R^1$ is H, halogen (e.g., F, Cl, Br, or I), or $NO_2$. In further embodiments, $R^1$ is H. In other embodiments, $R^1$ is halogen. In further embodiments, $R^1$ is F or Cl. In other embodiments, $R^1$ is $NO_2$.

(73b) In some embodiments of Formulae (Ic) and (Id), $R^1$ and $R^6$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more R$^8$. In further embodiments, R$^1$ and R$^6$, together with the atoms to which they are attached, form an optionally substituted 5- to 6-membered heteroaryl selected from

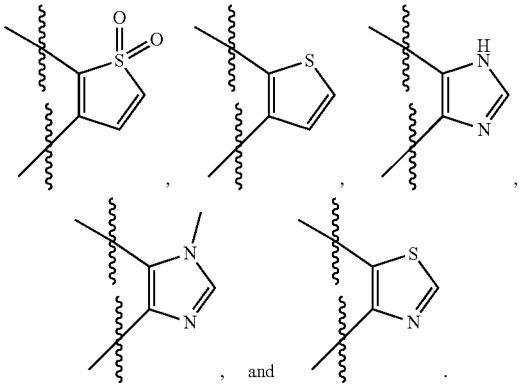

, and (73c) In some embodiments of Formulae (Ic) and (Id), R$^1$ is (C$_1$-C$_3$) alkyl (e.g., methyl, ethyl, propyl, or i-propyl).

(73d) In some embodiments of Formulae (Ic) and (Id), R$^1$ is (C$_1$-C$_3$) alkoxy (e.g., OCH$_3$, OCH$_2$CH$_3$, OCH$_2$CH$_2$CH$_3$, or OCH(CH$_3$)CH$_3$). In further embodiments, R$^1$ is OCH$_3$.

(74) In some embodiments of Formulae (Ic) and (Id), R$^2$ is H, halogen (e.g., F, Cl, Br, or I), (C$_1$-C$_2$) alkyl (e.g., methyl or ethyl) wherein the alkyl is optionally substituted with one or more substituents selected from NH$_2$, NH(C$_1$-C$_3$) alkyl, and N((C$_1$-C$_3$) alkyl)$_2$, (C$_1$-C$_2$) alkoxy (e.g., OCH$_3$ or OCH$_2$CH$_3$), (CH$_2$)$_{0-2}$-heterocycloalkyl, NR$^9$C(O)R$^{10}$, or NR$^9$R$^{10}$. In further embodiments, R$^2$ is H, halogen (e.g., F, Cl, Br, or I), or (C$_1$-C$_2$) alkoxy (e.g., OCH$_3$ or OCH$_2$CH$_3$).

(74a) In some embodiments of Formulae (Ic) and (Id), R$^2$ is H or halogen (e.g., F, Cl, Br, or I). In further embodiments, R$^2$ is H. In other embodiments, R$^2$ is halogen. In further embodiments, R$^2$ is F or Cl.

(74b) In some embodiments of Formulae (Ic) and (Id), R$^2$ is (C$_1$-C$_2$) alkyl (e.g., methyl or ethyl) wherein the alkyl is optionally substituted with one or more substituents selected from NH$_2$, NH(C$_1$-C$_3$) alkyl, and N((C$_1$-C$_3$) alkyl)$_2$. In other embodiments, R$^2$ is methyl or ethyl, each of which is optionally substituted with one to two substituents selected from NH$_2$, NH(C$_1$-C$_3$) alkyl, and N((C$_1$-C$_3$) alkyl)$_2$. In yet other embodiments, R$^2$ is methyl or ethyl, each of which is optionally substituted with one substituent selected from NH$_2$, NH(C$_1$-C$_3$) alkyl, and N((C$_1$-C$_3$) alkyl)$_2$. In further embodiments, R$^2$ is methyl optionally substituted with one substituent selected from NH$_2$, NH(C$_1$-C$_3$) alkyl, and N((C$_1$-C$_3$) alkyl)$_2$. In further embodiments, R$^2$ is CH$_2$NH$_2$, CH$_2$NHCH$_3$, or CH$_2$N(CH$_3$)$_2$. In further embodiments, R$^2$ is CH$_2$N(CH$_3$)$_2$.

(74c) In some embodiments of Formulae (Ic) and (Id), R$^2$ is (C$_1$-C$_2$) alkoxy (e.g., OCH$_3$ or OCH$_2$CH$_3$). In further embodiments, R$^2$ is OCH$_3$.

(74d) In some embodiments of Formulae (Ic) and (Id), R$^2$ is (CH$_2$)$_{0-2}$-heterocycloalkyl. In further embodiments, R$^2$ is (CH$_2$)$_{0-1}$-heterocycloalkyl. In further embodiments, R$^2$ is (CH$_2$)$_0$-heterocycloalkyl. In further embodiments, R$^2$ is (CH$_2$)$_1$-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In other embodiments, R$^2$ is morpholinyl or CH$_2$-morpholinyl.

(74e1) In some embodiments of Formulae (Ic) and (Id), R$^2$ is NR$^9$C(O)R$^{10}$. In further embodiments, R$^2$ is NHC(O)CH$_3$.

(74e2) In some embodiments of Formulae (Ic) and (Id), R$^2$ is NR$^9$R$^{10}$. In further embodiments, R$^2$ is NH$_2$, NH(C$_1$-C$_4$) alkyl, N((C$_1$-C$_4$) alkyl)$_2$, NH—(CH$_2$)$_{0-2}$-aryl, or NH—(CH$_2$)$_{0-2}$-heteroaryl. In further embodiments, R$^2$ is NH—CH$_2$-phenyl.

(74f) In some embodiments of Formulae (Ic) and (Id), R$^2$ is S(O)$_m$NR$^9$R$^{10}$. In further embodiments, R$^2$ is S(O)$_2$NR$^9$R$^{10}$. In further embodiments, R$^2$ is S(O)$_2$NCH$_3$-cyclopropyl.

(74g) In some embodiments of Formulae (Ic) and (Id), R$^2$ and R$^3$, together with the atoms to which they are attached, form a 6-membered heterocycloalkyl optionally substituted with one or more R$^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more R$^7$. In further embodiments, the heterocycloalkyl is morpholinyl, which is optionally substituted with one or more R$^7$.

(74h) In some embodiments of Formulae (Ic) and (Id), R$^2$ and R$^3$, together with the atoms to which they are attached, form a 5- to 6-membered heteroaryl optionally substituted with one or more R$^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more R$^7$. In further embodiments, the heteroaryl is thiazolyl, which is optionally substituted with one or more R$^7$.

(74i) In some embodiments of Formulae (Ic) and (Id), R$^2$ and R$^6$, together with the atoms to which they are attached, form a 6-membered heterocycloalkyl optionally substituted with one or more R$^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more R$^7$. In further embodiments, the heterocycloalkyl is morpholinyl, which is optionally substituted with one or more R$^7$.

(74j) In some embodiments of Formulae (Ic) and (Id), R$^2$ and R$^6$, together with the atoms to which they are attached, form a 5- to 6-membered heteroaryl optionally substituted with one or more R$^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more R$^7$. In further embodiments, the heteroaryl is thiazolyl, which is optionally substituted with one or more R$^7$.

(75a) In some embodiments of Formulae (Ic) and (Id), R$^3$ is H, halogen (e.g., F, Cl, Br, or I), CN, or NO$_2$. In further embodiments, R$^3$ is H. In other embodiments, R$^3$ is halogen. In further embodiments, R$^3$ is F or Cl. In other embodiments, R$^3$ is NO$_2$. In other embodiments, R$^3$ is CN.

(75b) In some embodiments of Formulae (Ic) and (Id), R$^3$ is (C$_1$-C$_3$) alkyl (e.g., methyl, ethyl, propyl, or i-propyl), wherein the alkyl is optionally substituted with one or more substituents selected from $NH_2$, $NH(C_1-C_3)$ alkyl, and $N((C_1-C_3)$ alkyl$)_2$. In other embodiments, $R^3$ is methyl, or ethyl, each of which is optionally substituted with one or two substituents selected from $NH_2$, $NH(C_1-C_3)$ alkyl, and $N((C_1-C_3)$ alkyl$)_2$. In yet other embodiments, $R^3$ is methyl or ethyl, each of which is optionally substituted with one substituent selected from $NH_2$, $NH(C_1-C_3)$ alkyl, and $N((C_1-C_3)$ alkyl$)_2$. In further embodiments, $R^3$ is methyl optionally substituted with one substituent selected from $NH_2$, $NH(C_1-C_3)$ alkyl, and $N((C_1-C_3)$ alkyl$)_2$. In further embodiments, $R^3$ is $CH_2NH_2$, $CH_2NHCH_3$, or $CH_2N(CH_3)_2$. In further embodiments, $R^3$ is $CH_2N(CH_3)_2$.

(75c) In some embodiments of Formulae (Ic) and (Id), $R^3$ is $(C_1-C_3)$ alkoxy (e.g., $OCH_3$, $OCH_2CH_3$, $OCH_2CH_2CH_3$, or $OCH(CH_3)CH_3$). In further embodiments, $R^3$ is $OCH_3$.

(75d) In some embodiments of Formulae (Ic) and (Id), $R^3$ is $C(O)NR^{11}R^{12}$ or $C(O)OR^{11}$. In further embodiments, $R^3$ is $C(O)NR^{11}R^{12}$. In further embodiments, $R^3$ is $C(O)NHCH_3$ or $C(O)NHCH_2CH_3$. In other embodiments, $R^3$ is $C(O)OR^{11}$. In further embodiments, $R^3$ is $C(O)OCH_3$.

(75e) In some embodiments of Formulae (Ic) and (Id), $R^3$ is $NR^{11}C(O)R^{12}$. In further embodiments, $R^3$ is $NHC(O)CH_3$.

(75f) In some embodiments of Formulae (Ic) and (Id), $R^3$ is $S(O)_mR^{12}$ or $S(O)_mNR^{11}R^{12}$. In other embodiments, $R^3$ is $S(O)_2R^{12}$. In other embodiments, $R^3$ is $S(O)_2NR^{11}R^{12}$. In further embodiments, $R^3$ is $S(O)_2NH$-cyclopropyl.

(75h) In some embodiments of Formulae (Ic) and (Id), $R^2$ and $R^3$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(75i) In some embodiments of Formulae (Ic) and (Id), $R^2$ and $R^3$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(76a) In some embodiments of Formulae (Ic) and (Id), $R^6$ is H, halogen (e.g., F, Cl, Br, or I), CN, or $NO_2$. In further embodiments, $R^6$ is H. In other embodiments, $R^6$ is halogen. In further embodiments, $R^6$ is F or Cl. In other embodiments, $R^6$ is $NO_2$. In further embodiments, $R^6$ is CN.

(76b) In some embodiments of Formulae (Ic) and (Id), $R^6$ is $(C_1-C_3)$ alkyl (e.g., methyl, ethyl, propyl, or i-propyl), wherein the alkyl is optionally substituted with one or more substituents selected from $NH_2$, $NH(C_1-C_3)$ alkyl, and $N((C_1-C_3)$ alkyl$)_2$. In other embodiments, $R^6$ is methyl or ethyl, each of which is optionally substituted with one or two substituents selected from $NH_2$, $NH(C_1-C_3)$ alkyl, and $N((C_1-C_3)$ alkyl$)_2$. In yet other embodiments, $R^6$ is methyl or ethyl, each of which is optionally substituted with one substituent selected from $NH_2$, $NH(C_1-C_3)$ alkyl, and $N((C_1-C_3)$ alkyl$)_2$. In further embodiments, $R^6$ is methyl optionally substituted with one substituent selected from $NH_2$, $NH(C_1-C_3)$ alkyl, and $N((C_1-C_3)$ alkyl$)_2$. In further embodiments, $R^6$ is $CH_2NH_2$, $CH_2NHCH_3$, or $CH_2N(CH_3)_2$. In further embodiments, $R^6$ is $CH_2N(CH_3)_2$.

(76c) In some embodiments of Formulae (Ic) and (Id), $R^6$ is $(C_1-C_3)$ alkoxy (e.g., $OCH_3$, $OCH_2CH_3$, $OCH_2CH_2CH_3$, or $OCH(CH_3)CH_3$). In further embodiments, $R^6$ is $OCH_3$.

(76d) In some embodiments of Formulae (Ic) and (Id), $R^6$ is $C(O)NR^{11}R^{12}$ or $C(O)OR^{11}$. In further embodiments, $R^6$ is $C(O)NR^{11}R^{12}$. In further embodiments, $R^6$ is $C(O)NHCH_3$ or $C(O)NHCH_2CH_3$. In other embodiments, $R^6$ is $C(O)OR^{11}$. In further embodiments, $R^6$ is $C(O)OCH_3$.

(76e) In some embodiments of Formulae (Ic) and (Id), $R^6$ is $NR^{11}C(O)R^{12}$. In further embodiments, $R^6$ is $NHC(O)CH_3$.

(76f) In some embodiments of Formulae (Ic) and (Id), $R^6$ is $S(O)_mR^{12}$ or $S(O)_mNR^{11}R^{12}$. In further embodiments, $R^6$ is $S(O)_2R^{12}$. In further embodiments, $R^6$ is $S(O)_2NR^{11}R^{12}$. In further embodiments, $R^6$ is $S(O)_2NH$-cyclopropyl.

(76g1) In some embodiments of Formulae (Ic) and (Id), $R^1$ and $R^6$, together with the atoms to which they are attached, form a 5- to 6-membered heteroaryl optionally substituted with one or more $R^8$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^8$. In further embodiments, $R^1$ and $R^6$, together with the atoms to which they are attached, form an optionally substituted 5- to 6-membered heteroaryl selected from

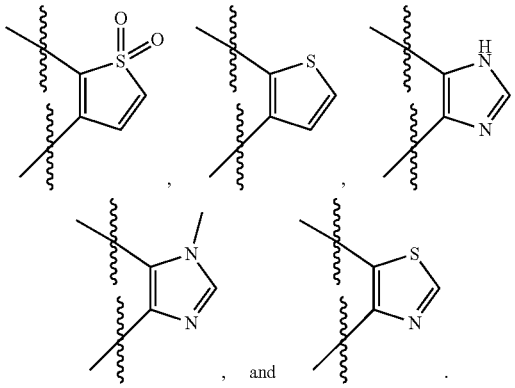

(76g2) In some embodiments of Formulae (Ic) and (Id), $R^2$ and $R^6$, together with the atoms to which they are attached, form a 6-membered heterocycloalkyl optionally substituted with one or more $R^7$. In further embodiments, the heterocycloalkyl comprises 1 to 3 heteroatoms selected from N, O, and S. In further embodiments, the heterocycloalkyl is selected from piperidinyl, piperazinyl, and morpholinyl, each of which is optionally substituted with one or more $R^7$. In further embodiments, the heterocycloalkyl is morpholinyl, which is optionally substituted with one or more $R^7$.

(76g3) In other embodiments of Formulae (Ic) and (Id), $R^2$ and $R^6$, together with the atoms to which they are attached, form a 5- to 6-membered heteroaryl optionally substituted with one or more $R^7$. In further embodiments, the heteroaryl comprises 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl, each of which is optionally substituted with one or more $R^7$. In further embodiments, the heteroaryl is thiazolyl, which is optionally substituted with one or more $R^7$.

(77a) In some embodiments of Formulae (Ic) and (Id), at least one $R^7$ is ($C_1$-$C_3$) alkyl (e.g., methyl, ethyl, propyl, or i-propyl). In further embodiments, at least one $R^7$ is methyl.

(77b) In some embodiments of Formulae (Ic) and (Id), at least one $R^7$ is ($C_1$-$C_3$) alkoxy (e.g., $OCH_3$, $OCH_2CH_3$, $OCH_2CH_2CH_3$, or $OCH(CH_3)CH_3$). In further embodiments, at least one $R^7$ is $OCH_3$.

(77c) In some embodiments of Formulae (Ic) and (Id), at least one $R^7$ is halogen (e.g., F, Cl, Br, or I). In further embodiments, at least one $R^7$ is F or Cl. In other embodiments, two $R^7$, together with the carbon atom to which they are attached, form C(O).

(78a) In some embodiments of Formulae (Ic) and (Id), at least one $R^8$ is ($C_1$-$C_3$) alkyl (e.g., methyl, ethyl, propyl, or i-propyl). In further embodiments, at least one $R^8$ is methyl.

(78b) In some embodiments of Formulae (Ic) and (Id), at least one $R^8$ is ($C_1$-$C_3$) alkoxy (e.g., $OCH_3$, $OCH_2CH_3$, $OCH_2CH_2CH_3$, or $OCH(CH_3)CH_3$). In further embodiments, at least one $R^8$ is $OCH_3$.

(78c) In some embodiments of Formulae (Ic) and (Id), at least one $R^8$ is halogen (e.g., F, Cl, Br, or I). In further embodiments, at least one $R^8$ is F or Cl. In other embodiments, two $R^8$, together with the carbon atom to which they are attached, form C(O).

(79a) In some embodiments of Formulae (Ic) and (Id), $R^9$ is H or ($C_1$-$C_4$) alkyl (e.g., methyl, ethyl, propyl, i-propyl, butyl, i-butyl, or tert-butyl). In further embodiments, $R^9$ is H. In other embodiments, $R^9$ is methyl or ethyl.

(79b) In some embodiments of Formulae (Ic) and (Id), $R^9$ is $(CH_2)_{0-2}$-aryl or $(CH_2)_{0-2}$-heteroaryl. In further embodiments, $R^9$ is $(CH_2)_{0-1}$-aryl or $(CH_2)_{0-1}$-heteroaryl. In further embodiments, $R^9$ is $(CH_2)_{0-1}$-aryl. In further embodiments, $R^9$ is $(CH_2)$-aryl. In further embodiments, $R^9$ is benzyl (e.g., $CH_2$-phenyl). In other embodiments, $R^9$ is $(CH_2)_{0-1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(79c) In some embodiments of Formulae (Ic) and (Id), $R^9$ is $(CH_2)_{0-2}$—($C_3$-$C_7$) cycloalkyl or $(CH_2)_{0-2}$-heterocycloalkyl. In further embodiments, $R^9$ is $(CH_2)_{0-1}$—($C_3$-$C_7$) cycloalkyl or $(CH_2)_{0-1}$-heterocycloalkyl. In further embodiments, $R^9$ is ($C_3$-$C_7$) cycloalkyl. In other embodiments, $R^9$ is ($C_3$-$C_5$) cycloalkyl. In further embodiments, $R^9$ is cyclopropyl. In other embodiments, $R^9$ is heterocycloalkyl or ($CH_2$)-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^9$ is morpholinyl or $CH_2$-morpholinyl.

(80a) In some embodiments of Formulae (Ic) and (Id), $R^{10}$ is H or ($C_1$-$C_4$) alkyl (e.g., methyl, ethyl, propyl, i-propyl, butyl, i-butyl, or tert-butyl). In further embodiments, $R^{10}$ is H. In other embodiments, $R^{10}$ is methyl or ethyl.

(80b) In some embodiments of Formulae (Ic) and (Id), $R^{10}$ is $(CH_2)_{0-2}$-aryl or $(CH_2)_{0-2}$-heteroaryl. In further embodiments, $R^{10}$ is $(CH_2)_{0-1}$-aryl or $(CH_2)_{0-1}$heteroaryl. In further embodiments, $R^{10}$ is $(CH_2)_{0-1}$-aryl. In further embodiments, $R^{10}$ is $(CH_2)$-aryl. In further embodiments, $R^{10}$ is benzyl (e.g., $CH_2$-phenyl). In other embodiments, $R^{10}$ is $(CH_2)_{0-1}$-heteroaryl. In further embodiments, the heteroaryl comprises one 5- to 6-membered ring and 1 to 3 heteroatoms selected from N, O, and S. In further embodiments, the heteroaryl is selected from pyridinyl, pyrazinyl, pyrimidinyl, pyrrolyl, pyrazolyl, imidazolyl, oxazolyl, isooxazolyl, dioxazolyl, oxadiazolyl, thiazolyl, isothiazolyl, dithiazolyl, thiadiazolyl, thiophenyl, and furanyl.

(80c) In some embodiments of Formulae (Ic) and (Id), $R^{10}$ is $(CH_2)_{0-2}$—($C_3$-$C_7$) cycloalkyl or $(CH_2)_{0-2}$-heterocycloalkyl. In further embodiments, $R^{10}$ is $(CH_2)_{0-1}$—($C_3$-$C_7$) cycloalkyl or $(CH_2)_{0-1}$-heterocycloalkyl. In further embodiments, $R^{10}$ is ($C_3$-$C_7$) cycloalkyl. In other embodiments, $R^{10}$ is ($C_3$-$C_5$) cycloalkyl. In further embodiments, $R^{10}$ is cyclopropyl. In other embodiments, $R^{10}$ is heterocycloalkyl or ($CH_2$)-heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl. In further embodiments, $R^{10}$ is morpholinyl or $CH_2$-morpholinyl.

(81a) In some embodiments of Formulae (Ic) and (Id), $R^{11}$ is H or ($C_1$-$C_4$) alkyl (e.g., methyl, ethyl, propyl, i-propyl, butyl, i-butyl, or tert-butyl). In further embodiments, $R^{11}$ is H. In further embodiments, $R^{11}$ is methyl or ethyl.

(81b) In some embodiments of Formulae (Ic) and (Id), $R^{11}$ is ($C_3$-$C_7$) cycloalkyl or heterocycloalkyl. In further embodiments, $R^{11}$ is ($C_3$-$C_7$) cycloalkyl. In further embodiments, $R^{11}$ is cyclopropyl. In other embodiments, $R^{11}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(82a) In some embodiments of Formulae (Ic) and (Id), $R^{12}$ is H or ($C_1$-$C_4$) alkyl (e.g., methyl, ethyl, propyl, i-propyl, butyl, i-butyl, or tert-butyl). In further embodiments, $R^{12}$ is H. In further embodiments, $R^{12}$ is methyl or ethyl.

(82b) In some embodiments of Formulae (Ic) and (Id), $R^{12}$ is ($C_3$-$C_7$) cycloalkyl or heterocycloalkyl. In further embodiments, $R^{12}$ is ($C_3$-$C_7$) cycloalkyl. In further embodiments, $R^{12}$ is cyclopropyl. In other embodiments, $R^{12}$ is heterocycloalkyl. In further embodiments, the heterocycloalkyl comprises a 5- to 6-membered ring and 1 to 3 heteroatoms selected from N, O, and S. In further embodiments, the heterocycloalkyl is selected from pyrrolidinyl, pyrazolidinyl, imidazolidinyl, triazolidinyl, oxazolidinyl, isoxazolidinyl, dioxazolidinyl, oxadiazolidinyl, thiazolidinyl, isothiazolidinyl, dithiazolidinyl, thiadiazolidinyl, piperidinyl, piperazinyl, and morpholinyl.

(83a) In some embodiments of Formulae (Ic) and (Id), $R^{14}$ is H or ($C_1$-$C_4$) alkyl (e.g., methyl, ethyl, propyl, i-propyl, butyl, i-butyl, or tert-butyl). In further embodiments, $R^{14}$ is H. In further embodiments, $R^{14}$ is methyl or ethyl.

(84a) In some embodiments of Formulae (Ic) and (Id), $R^{15}$ is H or ($C_1$-$C_4$) alkyl (e.g., methyl, ethyl, propyl, i-propyl, butyl, i-butyl, or tert-butyl). In further embodiments, $R^{15}$ is H. In further embodiments, $R^{15}$ is methyl or ethyl.

(85a) In some embodiments of Formulae (Ic) and (Id), m is 0, 1, or 2. In other embodiments, m is 1, or 2. In further embodiments, m is 2.

In some embodiments of Formulae (Ic) and (Id), each of the substituents defined for any one of $R^1$, $R^2$, $R^3$, $R^6$, $R^7$, $R^8$, $R^9$, $R^{10}$, $R^{11}$, $R^{12}$, $R^{14}$, $R^{15}$, and m can be combined with any of the substituents defined for the remainder of $R^1$, $R^2$, $R^3$, $R^6$, $R^7$, $R^8$, $R^9$, $R^{10}$, $R^{11}$, $R^{12}$, $R^{14}$, $R^{15}$, and m.

In some embodiments of the Formulae above, $X^1$ is N. In other embodiments, $X^1$ is CH.

In some embodiments of the Formulae above, $X^2$ is N. In other embodiments, $X^2$ is $CR^6$. In further embodiments, $X^2$ is CH.

In some embodiments of the Formulae above, two adjacent $R^5$, together with the atoms to which they are attached, form a 5- to 6-membered heterocycloalkyl substituted with two or more $R^{13}$, and two $R^{13}$, together with the carbon atom to which they are attached, form C(O). In other embodiments, two adjacent $R^5$, together with the atoms to which they are attached, form an optionally substituted 5-membered heteroaryl.

In some embodiments of the Formulae above, $R^5$ is selected from OH, CN, Cl, and $C(O)NH_2$.

In some embodiments of the Formulae above, $R^1$ is selected from H, F, Cl, $NO_2$, and $OCH_3$.

In some embodiments of the Formulae above, $R^4$ is selected from H, F, Cl, $NO_2$, and $OCH_3$.

In some embodiments of the Formulae above, $R^2$ is selected from H, $CH_3$, F, Cl, NHBn, $CH_2N(CH_3)_2$, $NHC(O)CH_3$, morpholinyl, $CH_2$-morpholinyl, $NO_2$, $S(O)_2N(CH_3)$ cyclopropyl, and $OCH_3$.

In some embodiments of the Formulae above, $R^3$ is selected from H, F, Cl, $NO_2$, CN, $C(O)NHCH_2CH_3$, $NHC(O)(CH_3)_2$, $CH_2N(CH_3)_2$, $C(O)OCH_3$, $S(O)_2N(CH_3)$cyclopropyl, and $OCH_3$.

In some embodiments of the Formulae above, $R^6$ is selected from H, F, Cl, $NO_2$, CN, $C(O)NHCH_2CH_3$, $NHC(O)(CH_3)_2$, $CH_2N(CH_3)_2$, $C(O)OCH_3$, $S(O)_2N(CH_3)$cyclopropyl, and $OCH_3$.

In some embodiments of the Formulae above, $R^1$ and $R^6$, together with the atoms to which they are attached, form an optionally substituted 5- to 6-membered heteroaryl.

In some embodiments of the Formulae above, $R^2$ and $R^3$, together with the atoms to which they are attached, form an optionally substituted 6-membered heterocycloalkyl.

In some embodiments of the Formulae above, $R^2$ and $R^3$, together with the atoms to which they are attached, form an optionally substituted 5- to 6-membered heteroaryl.

Non-limiting illustrative compounds of the application include:

| Compound Number | Structure | Compound Name |
| --- | --- | --- |
| I-1 | 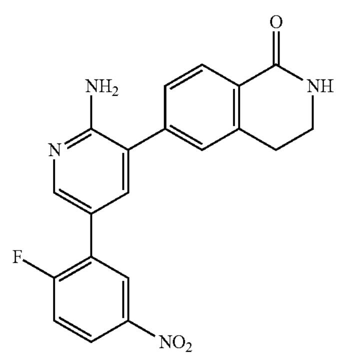 [SMILES: Nc1ncc(-c2cc([N+](=O)[O-])ccc2F)cc1-c1ccc2c(c1)CCNC2=O] | 6-(2-amino-5-(2-fluoro-5-nitrophenyl)pyridin-3-yl)-3,4-dihydroisoquinolin-1(2H)-one |
| I-2 | 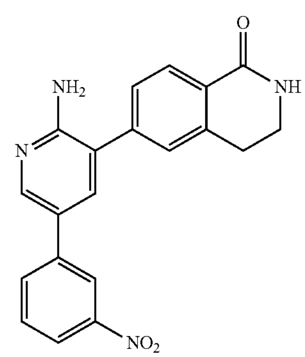 [SMILES: Nc1ncc(-c2cccc([N+](=O)[O-])c2)cc1-c1ccc2c(c1)CCNC2=O] | 6-(2-amino-5-(3-nitrophenyl)pyridin-3-yl)-3,4-dihydroisoquinolin-1(2H)-one |

-continued

| Compound Number | Structure | Compound Name |
|---|---|---|
| I-3 | 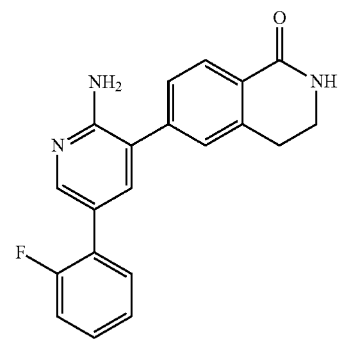 [SMILES: Nc1ncc(-c2ccccc2F)cc1-c1ccc2c(c1)CCNC2=O] | 6-(2-amino-5-(2-fluorophenyl)pyridin-3-yl)-3,4-dihydroisoquinolin-1(2H)-one |
| I-4 | 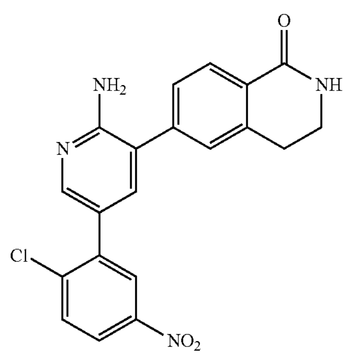 [SMILES: Nc1ncc(-c2cc([N+](=O)[O-])ccc2Cl)cc1-c1ccc2c(c1)CCNC2=O] | 6-(2-amino-5-(2-chloro-5-nitrophenyl)pyridin-3-yl)-3,4-dihydroisoquinolin-1(2H)-one |
| I-5 | 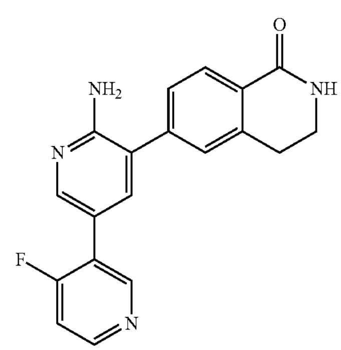 [SMILES: Nc1ncc(-c2cnccc2F)cc1-c1ccc2c(c1)CCNC2=O] | 6-(6-amino-4'-fluoro-[3,3'-bipyridin]-5-yl)-3,4-dihydroisoquinolin-1(2H)-one |
| I-6 | 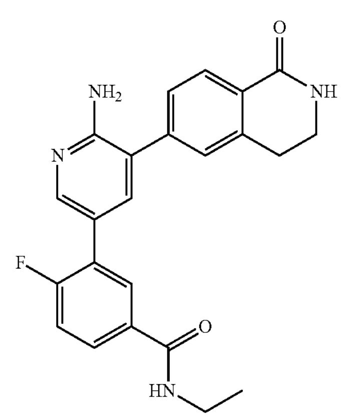 [SMILES: CCNC(=O)c1ccc(F)c(-c2cnc(N)c(-c3ccc4c(c3)CCNC4=O)c2)c1] | 3-(6-amino-5-(1-oxo-1,2,3,4-tetrahydroisoquinolin-6-yl)pyridin-3-yl)-N-ethyl-4-fluorobenzamide |

-continued

| Compound Number | Structure | Compound Name |
|---|---|---|
| I-7 | 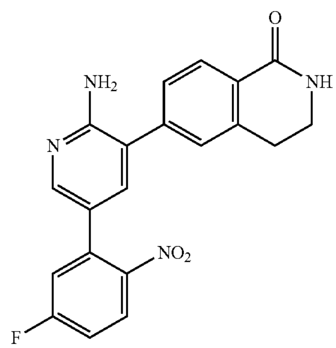 [SMILES: Nc1ncc(-c2cc(F)ccc2[N+](=O)[O-])cc1-c1ccc2c(c1)CCNC2=O] | 6-(2-amino-5-(5-fluoro-2-nitrophenyl)pyridin-3-yl)-3,4-dihydroisoquinolin-1(2H)-one |
| I-8 | 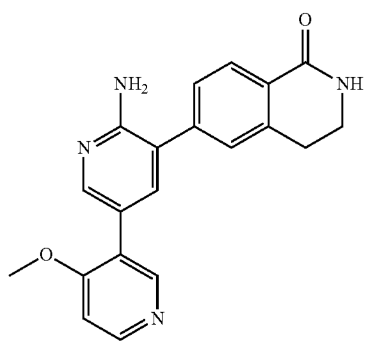 [SMILES: COc1ccncc1-c1cnc(N)c(-c2ccc3c(c2)CCNC3=O)c1] | 6-(6-amino-4'-methoxy-[3,3'-bipyridin]-5-yl)-3,4-dihydroisoquinolin-1(2H)-one |
| I-9 | 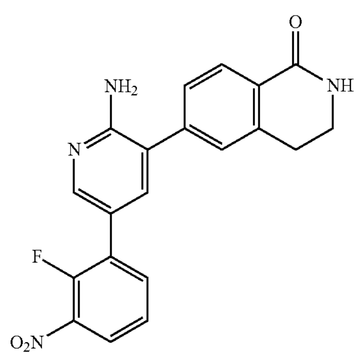 [SMILES: Nc1ncc(-c2cccc([N+](=O)[O-])c2F)cc1-c1ccc2c(c1)CCNC2=O] | 6-(2-amino-5-(2-fluoro-3-nitrophenyl)pyridin-3-yl)-3,4-dihydroisoquinolin-1(2H)-one |
| I-10 | 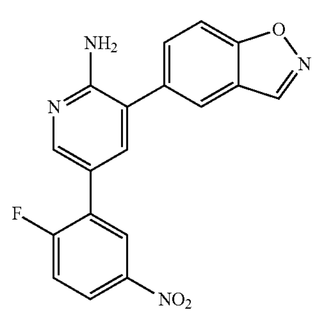 [SMILES: Nc1ncc(-c2cc([N+](=O)[O-])ccc2F)cc1-c1ccc2oncc2c1] | 3-(benzo[d]isoxazol-5-yl)-5-(2-fluoro-5-nitrophenyl)pyridin-2-amine |

-continued

| Compound Number | Structure | Compound Name |
|---|---|---|
| I-11 | 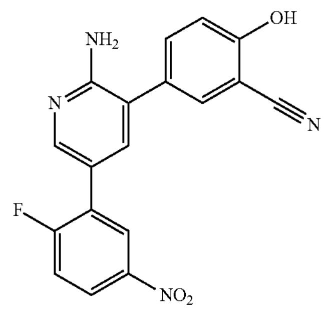 [SMILES: N#Cc1cc(-c2cc(-c3cc([N+](=O)[O-])ccc3F)cnc2N)ccc1O] | 5-(2-amino-5-(2-fluoro-5-nitrophenyl)pyridin-3-yl)-2-hydroxybenzonitrile |
| I-12 | 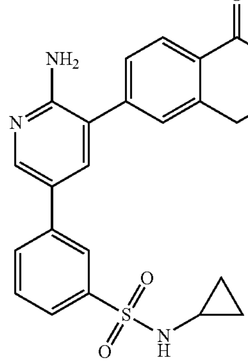 | 3-(6-amino-5-(1-oxo-1,2,3,4-tetrahydroisoquinolin-6-yl)pyridin-3-yl)-N-cyclopropylbenzenesulfonamide |
| I-13 | 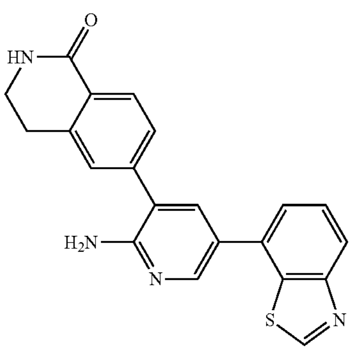 [SMILES: Nc1ncc(-c2cccc3ncsc23)cc1-c1ccc2c(c1)CCNC2=O] | 6-(2-amino-5-(benzo[d]thiazol-7-yl)pyridin-3-yl)-3,4-dihydroisoquinolin-1(2H)-one |
| I-14 | 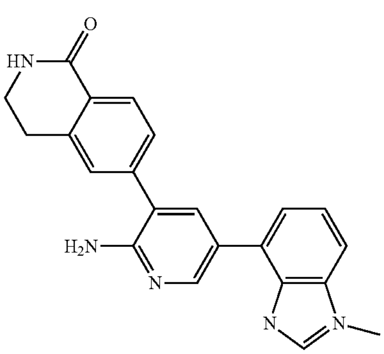 | 6-(2-amino-5-(1-methyl-1H-benzo[d]imidazol-4-yl)pyridin-3-yl)-3,4-dihydroisoquinolin-1(2H)-one |

-continued

| Compound Number | Structure | Compound Name |
|---|---|---|
| I-15 | 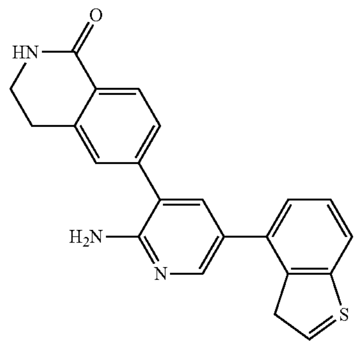 | 6-(2-amino-5-(benzo[b]thiophen-4-yl)pyridin-3-yl)-3,4-dihydroisoquinolin-1(2H)-one |
| I-16 | 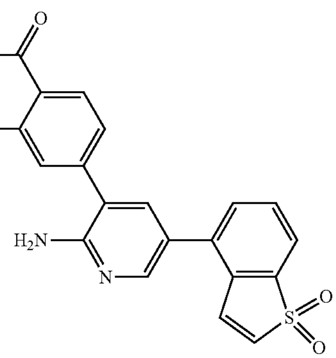 | 6-(2-amino-5-(1,1-dioxidobenzo[b]thiophen-4-yl)pyridin-3-yl)-3,4-dihydroisoquinolin-1(2H)-one |
| I-17 | 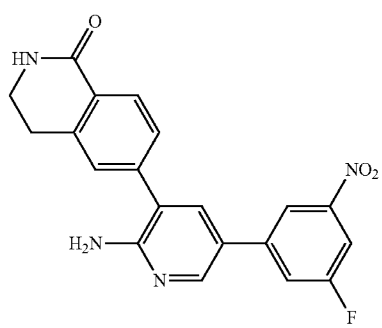 [SMILES: Nc1ncc(-c2cc(F)cc([N+](=O)[O-])c2)cc1-c1ccc2c(c1)CCNC2=O] | 6-(2-amino-5-(3-fluoro-5-nitrophenyl)pyridin-3-yl)-3,4-dihydroisoquinolin-1(2H)-one |
| I-18 | 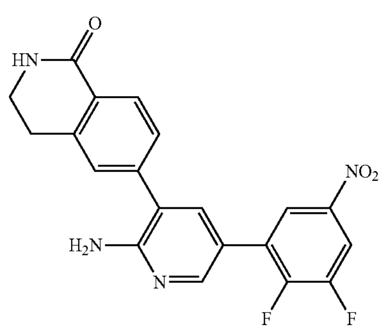 [SMILES: Nc1ncc(-c2cc([N+](=O)[O-])cc(F)c2F)cc1-c1ccc2c(c1)CCNC2=O] | 6-(2-amino-5-(2,3-difluoro-5-nitrophenyl)pyridin-3-yl)-3,4-dihydroisoquinolin-1(2H)-one |

-continued

| Compound Number | Structure | Compound Name |
|---|---|---|
| I-19 | 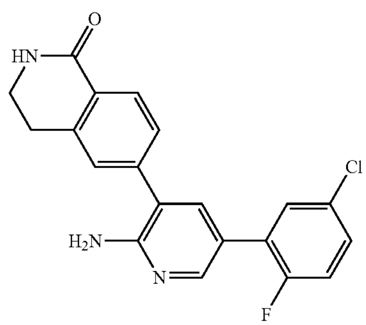 [SMILES: Nc1ncc(-c2cc(Cl)ccc2F)cc1-c1ccc2c(c1)CCNC2=O] | 6-(2-amino-5-(5-chloro-2-fluorophenyl)pyridin-3-yl)-3,4-dihydroisoquinolin-1(2H)-one |
| I-20 | 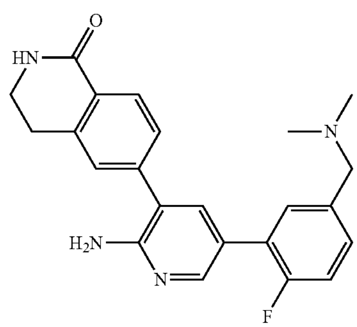 [SMILES: CN(C)Cc1ccc(F)c(-c2cnc(N)c(-c3ccc4c(c3)CCNC4=O)c2)c1] | 6-(2-amino-5-(5-((dimethylamino)methyl)-2-fluorophenyl)pyridin-3-yl)-3,4-dihydroisoquinolin-1(2H)-one |
| I-21 | 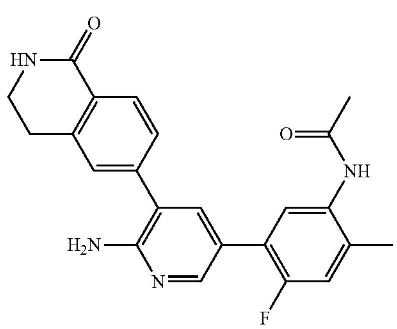 [SMILES: CC(=O)Nc1cc(-c2cnc(N)c(-c3ccc4c(c3)CCNC4=O)c2)c(F)cc1C] | N-(5-(6-amino-5-(1-oxo-1,2,3,4-tetrahydroisoquinolin-6-yl)pyridin-3-yl)-4-fluoro-2-methylphenyl)acetamide |
| I-22 | 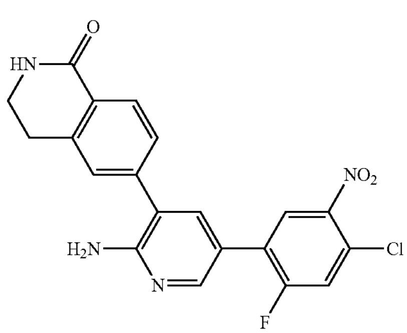 [SMILES: Nc1ncc(-c2cc([N+](=O)[O-])c(Cl)cc2F)cc1-c1ccc2c(c1)CCNC2=O] | 6-(2-amino-5-(4-chloro-2-fluoro-5-nitrophenyl)pyridin-3-yl)-3,4-dihydroisoquinolin-1(2H)-one |

-continued

| Compound Number | Structure | Compound Name |
|---|---|---|
| I-23 | 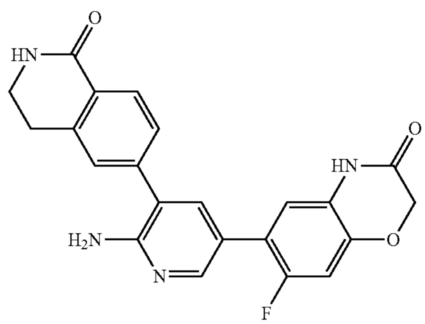 [SMILES: Nc1ncc(-c2cc3c(cc2F)OCC(=O)N3)cc1-c1ccc2c(c1)CCNC2=O] | 6-(6-amino-5-(1-oxo-1,2,3,4-tetrahydroisoquinolin-6-yl)pyridin-3-yl)-7-fluoro-2H-benzo[b][1,4]oxazin-3(4H)-one |
| I-24 | 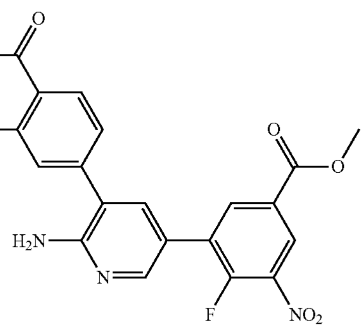 | methyl 3-(6-amino-5-(1-oxo-1,2,3,4-tetrahydroisoquinolin-6-yl)pyridin-3-yl)-4-fluoro-5-nitrobenzoate |
| I-25 | 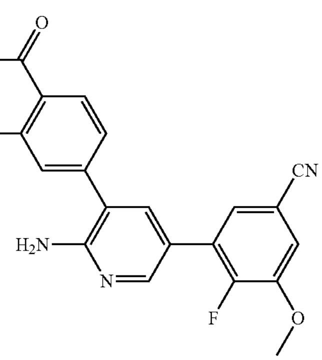 | 3-(6-amino-5-(1-oxo-1,2,3,4-tetrahydroisoquinolin-6-yl)pyridin-3-yl)-4-fluoro-5-methoxybenzonitrile |
| I-26 | 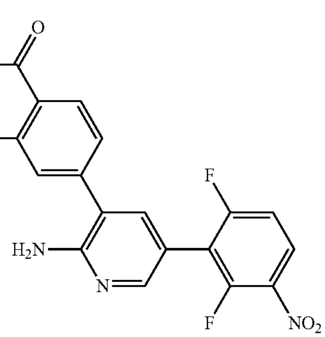 | 6-(2-amino-5-(2,6-difluoro-3-nitrophenyl)pyridin-3-yl)-3,4-dihydroisoquinolin-1(2H)-one |

-continued

| Compound Number | Structure | Compound Name |
|---|---|---|
| I-27 | 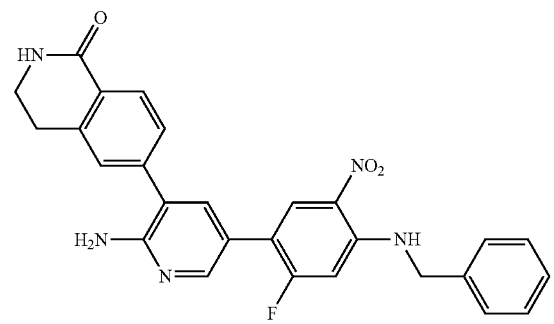 [SMILES: Nc1ncc(-c2cc([N+](=O)[O-])c(NCc3ccccc3)cc2F)cc1-c1ccc2c(c1)CCNC2=O] | 6-(2-amino-5-(4-(benzylamino)-2-fluoro-5-nitrophenyl)pyridin-3-yl)-3,4-dihydroisoquinolin-1(2H)-one |
| I-28 | 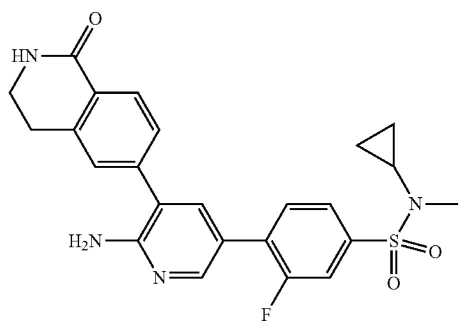 [SMILES: CN(C1CC1)S(=O)(=O)c1ccc(-c2cnc(N)c(-c3ccc4c(c3)CCNC4=O)c2)c(F)c1] | 4-(6-amino-5-(1-oxo-1,2,3,4-tetrahydroisoquinolin-6-yl)pyridin-3-yl)-N-cyclopropyl-3-fluoro-N-methylbenzenesulfonamide |
| I-29 | 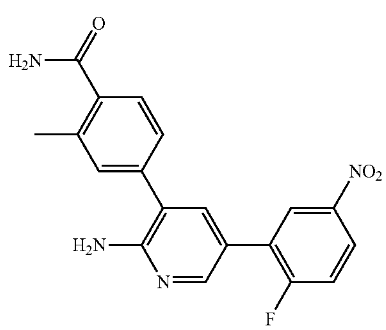 [SMILES: Cc1cc(-c2cc(-c3cc([N+](=O)[O-])ccc3F)cnc2N)ccc1C(N)=O] | 4-(2-amino-5-(2-fluoro-5-nitrophenyl)pyridin-3-yl)-2-methylbenzamide |
| I-30 | 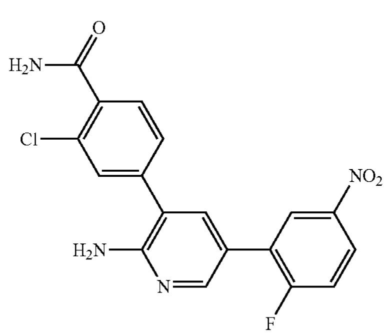 [SMILES: NC(=O)c1ccc(-c2cc(-c3cc([N+](=O)[O-])ccc3F)cnc2N)cc1Cl] | 4-(2-amino-5-(2-fluoro-5-nitrophenyl)pyridin-3-yl)-2-chlorobenzamide |

-continued

| Compound Number | Structure | Compound Name |
|---|---|---|
| I-31 | 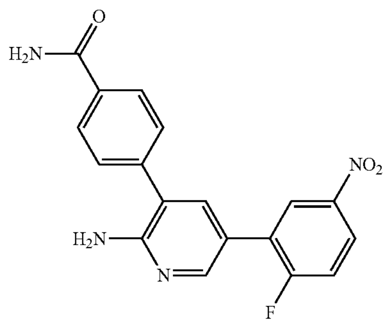 [SMILES: NC(=O)c1ccc(-c2cc(-c3cc([N+](=O)[O-])ccc3F)cnc2N)cc1] | 4-(2-amino-5-(2-fluoro-5-nitrophenyl)pyridin-3-yl)benzamide |
| I-32 | 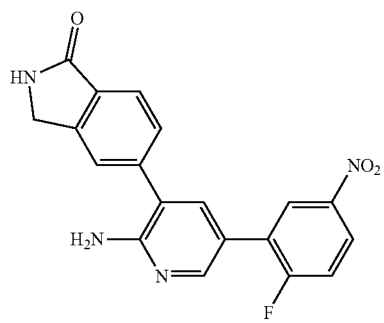 [SMILES: Nc1ncc(-c2cc([N+](=O)[O-])ccc2F)cc1-c1ccc2c(c1)CNC2=O] | 5-(2-amino-5-(2-fluoro-5-nitrophenyl)pyridin-3-yl)isoindolin-1-one |
| I-33 | 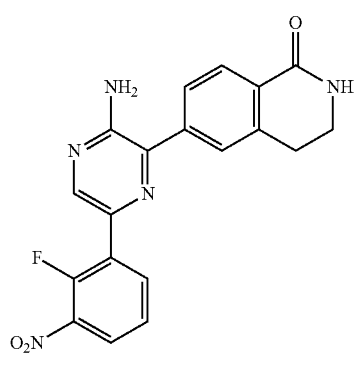 [SMILES: Nc1ncc(-c2cccc([N+](=O)[O-])c2F)nc1-c1ccc2c(c1)CCNC2=O] | 6-(3-amino-6-(2-fluoro-3-nitrophenyl)pyrazin-2-yl)-3,4-dihydroisoquinolin-1(2H)-one |
| I-34 | 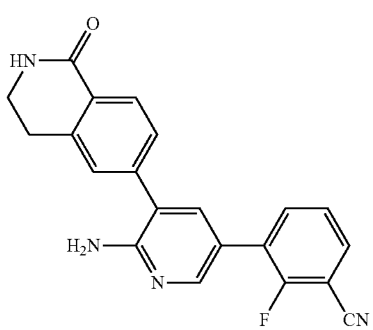 [SMILES: N#Cc1cccc(-c2cnc(N)c(-c3ccc4c(c3)CCNC4=O)c2)c1F] | 3-(6-amino-5-(1-oxo-1,2,3,4-tetrahydroisoquinolin-6-yl)pyridin-3-yl)-2-fluorobenzonitrile |

-continued

| Compound Number | Compound Name |
|---|---|
| I-35 | 3-(6-amino-5-(1-oxo-1,2,3,4-tetrahydroisoquinolin-6-yl)pyridin-3-yl)-4-fluorobenzonitrile |
| I-36 | 6-(6-amino-4'-fluoro-5'-nitro-[3,3'-bipyridin]-5-yl)-3,4-dihydroisoquinolin-1(2H)-one |
| I-37 | 6-(2-amino-5-(5-((dimethylamino)methyl)-2-fluoro-3-nitrophenyl)pyridin-3-yl)-3,4-dihydroisoquinolin-1(2H)-one |
| I-38 | 6-(2-amino-5-(4-((dimethylamino)methyl)-2-fluoro-5-nitrophenyl)pyridin-3-yl)-3,4-dihydroisoquinolin-1(2H)-one |

-continued

| Compound Number | Structure | Compound Name |
|---|---|---|
| I-39 | 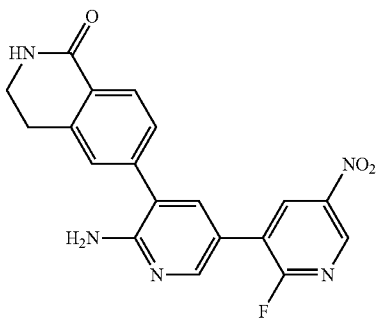 [SMILES: Nc1ncc(-c2cc([N+](=O)[O-])cnc2F)cc1-c1ccc2c(c1)CCNC2=O] | 6-(6-amino-2'-fluoro-5'-nitro-[3,3'-bipyridin]-5-yl)-3,4-dihydroisoquinolin-1(2H)-one |
| I-40 | 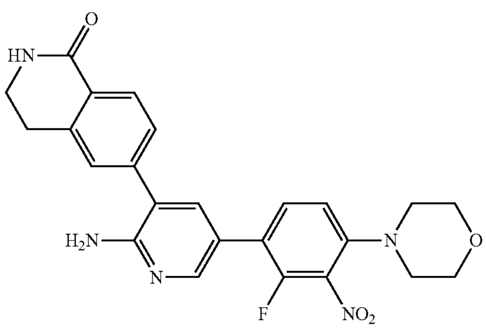 [SMILES: Nc1ncc(-c2ccc(N3CCOCC3)c([N+](=O)[O-])c2F)cc1-c1ccc2c(c1)CCNC2=O] | 6-(2-amino-5-(2-fluoro-4-morpholino-3-nitrophenyl)pyridin-3-yl)-3,4-dihydroisoquinolin-1(2H)-one |
| I-41 | 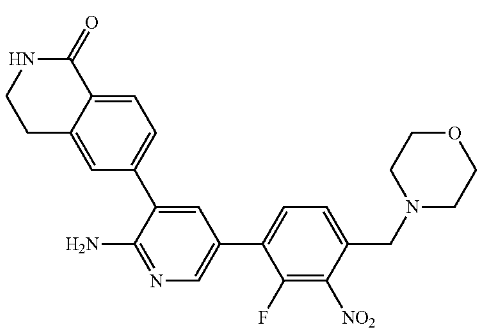 [SMILES: Nc1ncc(-c2ccc(CN3CCOCC3)c([N+](=O)[O-])c2F)cc1-c1ccc2c(c1)CCNC2=O] | 6-(2-amino-5-(2-fluoro-4-(morpholinomethyl)-3-nitrophenyl)pyridin-3-yl)-3,4-dihydroisoquinolin-1(2H)-one |
| I-42 | 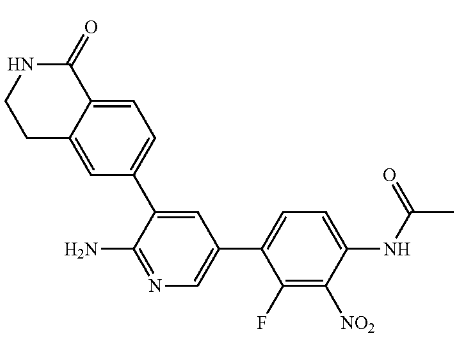 [SMILES: CC(=O)Nc1ccc(-c2cnc(N)c(-c3ccc4c(c3)CCNC4=O)c2)c(F)c1[N+](=O)[O-]] | N-(4-(6-amino-5-(1-oxo-1,2,3,4-tetrahydroisoquinolin-6-yl)pyridin-3-yl)-3-fluoro-2-nitrophenyl)acetamide |

-continued

| Compound Number | Structure | Compound Name |
|---|---|---|
| I-43 | 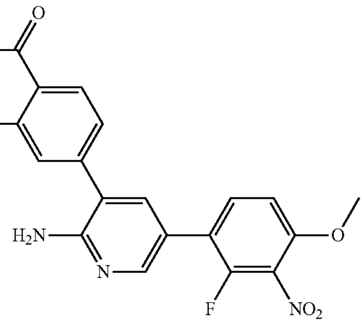 | 6-(2-amino-5-(2-fluoro-4-methoxy-3-nitrophenyl)pyridin-3-yl)-3,4-dihydroisoquinolin-1(2H)-one |
| I-44 | 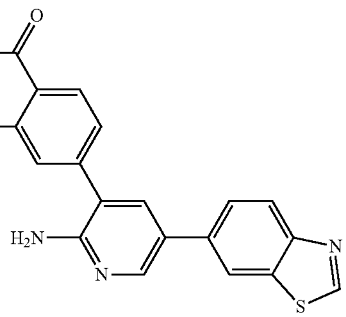 | 6-(2-amino-5-(benzo[d]thiazol-6-yl)pyridin-3-yl)-3,4-dihydroisoquinolin-1(2H)-one |
| I-45 | 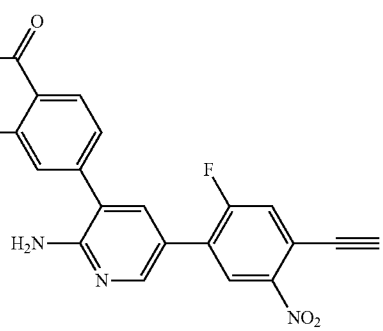 | 6-(2-amino-5-(4-ethynyl-2-fluoro-5-nitrophenyl)pyridin-3-yl)-3,4-dihydroisoquinolin-1(2H)-one |
| I-46 | 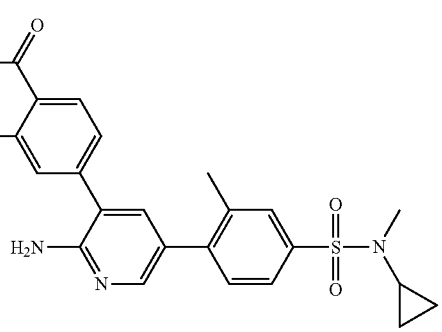 | 4-(6-amino-5-(1-oxo-1,2,3,4-tetrahydroisoquinolin-6-yl)pyridin-3-yl)-N-cyclopropyl-N,3-dimethylbenzenesulfonamide |

| Compound Number | Structure | Compound Name |
|---|---|---|
| I-47 | 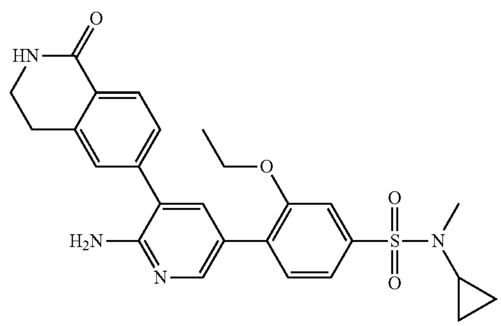 [SMILES: CCOc1cc(S(=O)(=O)N(C)C2CC2)ccc1-c1cnc(N)c(-c2ccc3c(c2)CCNC3=O)c1] | 4-(6-amino-5-(1-oxo-1,2,3,4-tetrahydroisoquinolin-6-yl)pyridin-3-yl)-N-cyclopropyl-3-ethoxy-N-methylbenzenesulfonamide |
| I-48 | 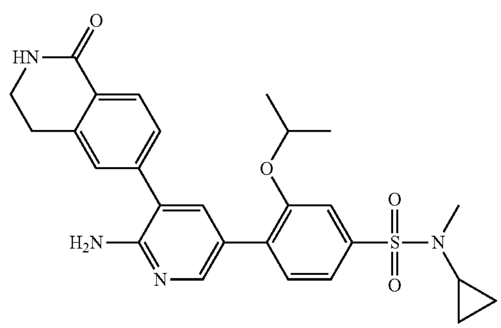 [SMILES: CC(C)Oc1cc(S(=O)(=O)N(C)C2CC2)ccc1-c1cnc(N)c(-c2ccc3c(c2)CCNC3=O)c1] | 4-(6-amino-5-(1-oxo-1,2,3,4-tetrahydroisoquinolin-6-yl)pyridin-3-yl)-N-cyclopropyl-3-isopropoxy-N-methylbenzenesulfonamide |
| I-49 | 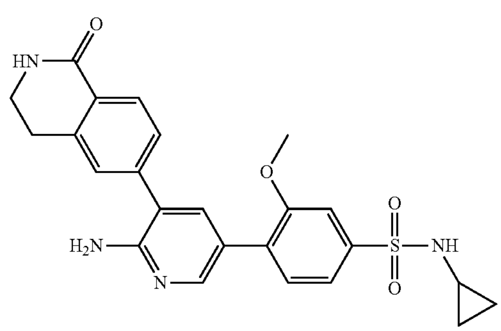 [SMILES: COc1cc(S(=O)(=O)NC2CC2)ccc1-c1cnc(N)c(-c2ccc3c(c2)CCNC3=O)c1] | 4-(6-amino-5-(1-oxo-1,2,3,4-tetrahydroisoquinolin-6-yl)pyridin-3-yl)-N-cyclopropyl-3-methoxybenzenesulfonamide |
| I-50 | 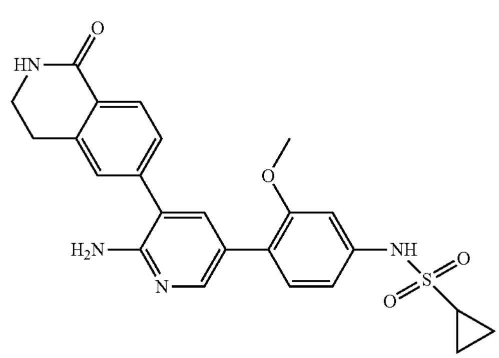 [SMILES: COc1cc(NS(=O)(=O)C2CC2)ccc1-c1cnc(N)c(-c2ccc3c(c2)CCNC3=O)c1] | N-(4-(6-amino-5-(1-oxo-1,2,3,4-tetrahydroisoquinolin-6-yl)pyridin-3-yl)-3-methoxyphenyl)cyclopropanesulfonamide |

-continued

| Compound Number | Structure | Compound Name |
|---|---|---|
| I-51 | 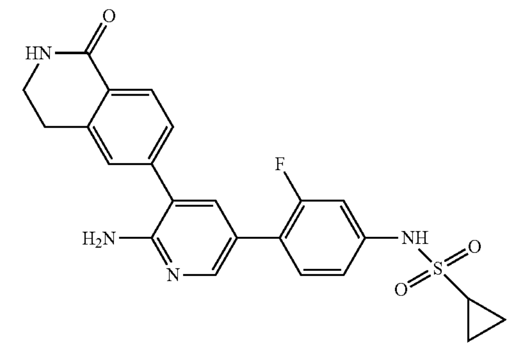 [SMILES: Nc1ncc(-c2ccc(NS(=O)(=O)C3CC3)cc2F)cc1-c1ccc2c(c1)CCNC2=O] | N-(4-(6-amino-5-(1-oxo-1,2,3,4-tetrahydroisoquinolin-6-yl)pyridin-3-yl)-3-fluorophenyl)cyclopropanesulfonamide |
| I-52 | 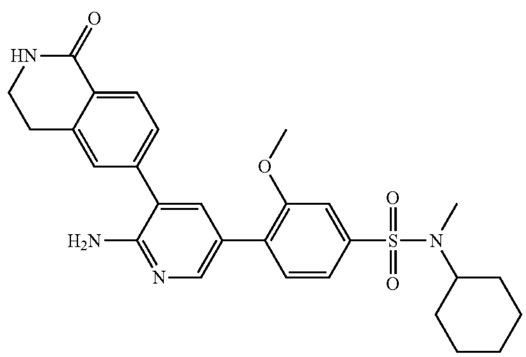 [SMILES: COc1cc(S(=O)(=O)N(C)C2CCCCC2)ccc1-c1cnc(N)c(-c2ccc3c(c2)CCNC3=O)c1] | 4-(6-amino-5-(1-oxo-1,2,3,4-tetrahydroisoquinolin-6-yl)pyridin-3-yl)-N-cyclohexyl-3-methoxy-N-methylbenzenesulfonamide |
| I-53 | 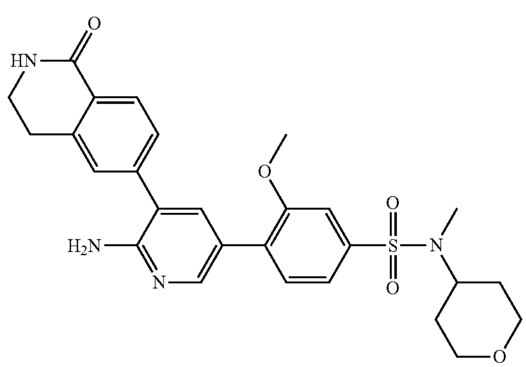 [SMILES: COc1cc(S(=O)(=O)N(C)C2CCOCC2)ccc1-c1cnc(N)c(-c2ccc3c(c2)CCNC3=O)c1] | 4-(6-amino-5-(1-oxo-1,2,3,4-tetrahydroisoquinolin-6-yl)pyridin-3-yl)-3-methoxy-N-methyl-N-(tetrahydro-2H-pyran-4-yl)benzenesulfonamide |
| I-54 | 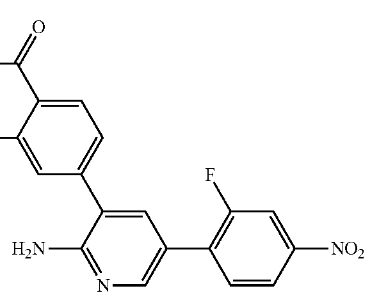 | 6-(2-amino-5-(2-fluoro-4-nitrophenyl)pyridin-3-yl)-3,4-dihydroisoquinolin-1(2H)-one |

-continued

| Compound Number | Structure | Compound Name |
| --- | --- | --- |
| I-55 | 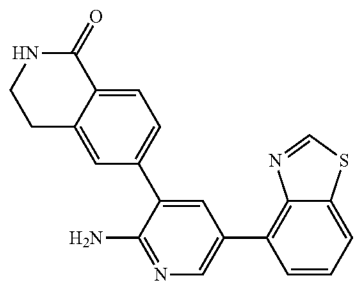 [SMILES: Nc1ncc(-c2cccc3scnc23)cc1-c1ccc2c(c1)CCNC2=O] | 6-(2-amino-5-(benzo[d]thiazol-4-yl)pyridin-3-yl)-3,4-dihydroisoquinolin-1(2H)-one |
| I-56 | 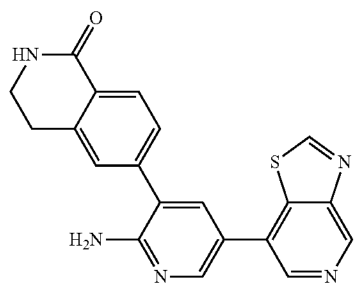 [SMILES: Nc1ncc(-c2cncc3ncsc23)cc1-c1ccc2c(c1)CCNC2=O] | 6-(2-amino-5-(thiazolo[4,5-c]pyridin-7-yl)pyridin-3-yl)-3,4-dihydroisoquinolin-1(2H)-one |
| I-57 | 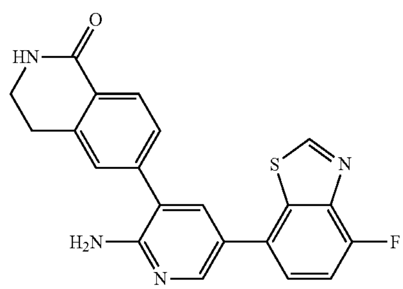 [SMILES: Nc1ncc(-c2ccc(F)c3ncsc23)cc1-c1ccc2c(c1)CCNC2=O] | 6-(2-amino-5-(4-fluorobenzo[d]thiazol-7-yl)pyridin-3-yl)-3,4-dihydroisoquinolin-1(2H)-one |
| I-58 | 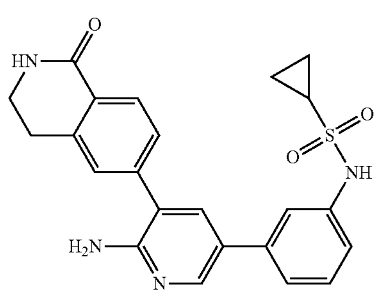 [SMILES: Nc1ncc(-c2cccc(NS(=O)(=O)C3CC3)c2)cc1-c1ccc2c(c1)CCNC2=O] | N-(3-(6-amino-5-(1-oxo-1,2,3,4-tetrahydroisoquinolin-6-yl)pyridin-3-yl)phenyl)cyclopropanesulfonamide |
| I-59 | 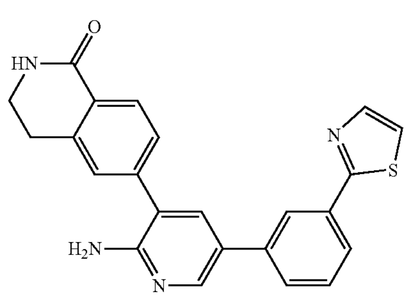 [SMILES: Nc1ncc(-c2cccc(-c3nccs3)c2)cc1-c1ccc2c(c1)CCNC2=O] | 6-(2-amino-5-(3-(thiazol-2-yl)phenyl)pyridin-3-yl)-3,4-dihydroisoquinolin-1(2H)-one |

-continued

| Compound Number | Structure | Compound Name |
|---|---|---|
| I-60 | 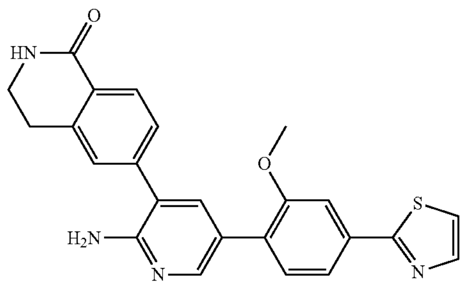 [SMILES: COc1cc(-c2nccs2)ccc1-c1cnc(N)c(-c2ccc3c(c2)CCNC3=O)c1] | 6-(2-amino-5-(2-methoxy-4-(thiazol-2-yl)phenyl)pyridin-3-yl)-3,4-dihydroisoquinolin-1(2H)-one |
| I-61 | 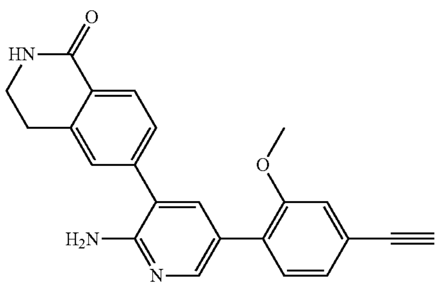 [SMILES: C#Cc1ccc(-c2cnc(N)c(-c3ccc4c(c3)CCNC4=O)c2)c(OC)c1] | 4-(6-amino-5-(1-oxo-1,2,3,4-tetrahydroisoquinolin-6-yl)pyridin-3-yl)-3-methoxybenzonitrile |
| I-62 | 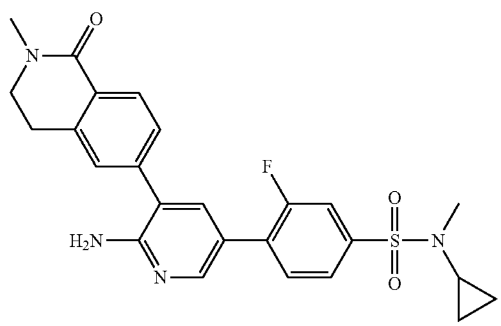 [SMILES: CN1CCc2cc(-c3cc(-c4ccc(S(=O)(=O)N(C)C5CC5)cc4F)cnc3N)ccc2C1=O] | 4-(6-amino-5-(2-methyl-1-oxo-1,2,3,4-tetrahydroisoquinolin-6-yl)pyridin-3-yl)-N-cyclopropyl-3-fluoro-N-methylbenzenesulfonamide |
| I-63 | 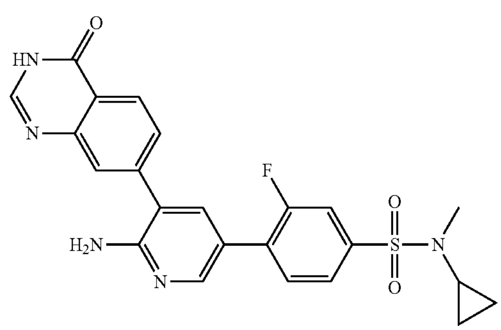 | 4-(6-amino-5-(4-oxo-3,4-dihydroquinazolin-7-yl)pyridin-3-yl)-N-cyclopropyl-3-fluoro-N-methylbenzenesulfonamide |
| I-64 | 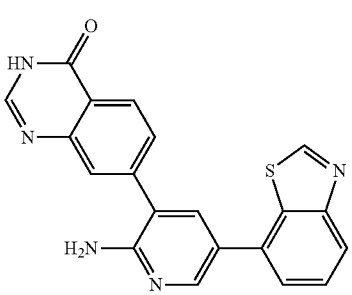 [SMILES: Nc1ncc(-c2cccc3ncsc23)cc1-c1ccc2c(=O)[nH]cnc2c1] | 7-(2-amino-5-(benzo[d]thiazol-7-yl)pyridin-3-yl)quinazolin-4(3H)-one |

| Compound Number | Structure | Compound Name |
|---|---|---|
| I-65 | 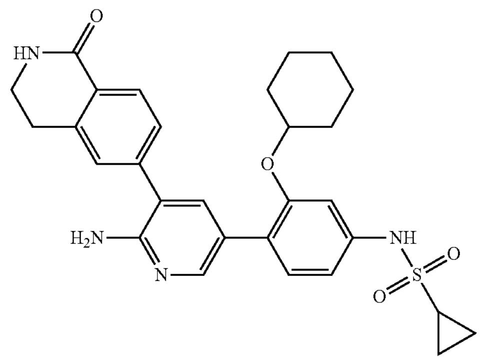 [SMILES: Nc1ncc(-c2ccc(NS(=O)(=O)C3CC3)cc2OC2CCCCC2)cc1-c1ccc2c(c1)CCNC2=O] | N-(4-(6-amino-5-(1-oxo-1,2,3,4-tetrahydroisoquinolin-6-yl)pyridin-3-yl)-3-(cyclohexyloxy)phenyl)cyclopropanesulfonamide |
| I-66 | 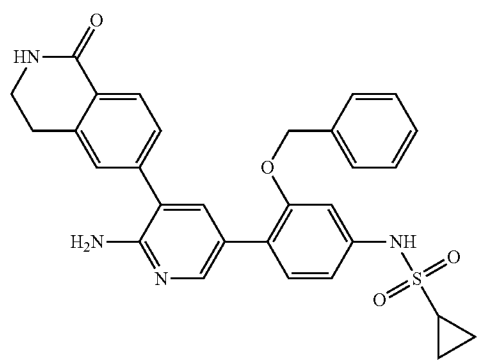 [SMILES: Nc1ncc(-c2ccc(NS(=O)(=O)C3CC3)cc2OCc2ccccc2)cc1-c1ccc2c(c1)CCNC2=O] | N-(4-(6-amino-5-(1-oxo-1,2,3,4-tetrahydroisoquinolin-6-yl)pyridin-3-yl)-3-(benzyloxy)phenyl)cyclopropanesulfonamide |
| I-67 | 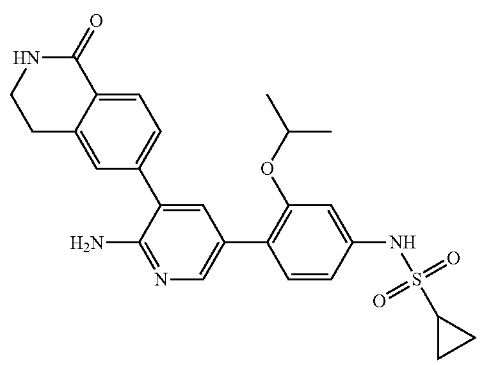 [SMILES: CC(C)Oc1cc(NS(=O)(=O)C2CC2)ccc1-c1cnc(N)c(-c2ccc3c(c2)CCNC3=O)c1] | N-(4-(6-amino-5-(1-oxo-1,2,3,4-tetrahydroisoquinolin-6-yl)pyridin-3-yl)-3-isopropoxyphenyl)cyclopropanesulfonamide |
| I-68 | 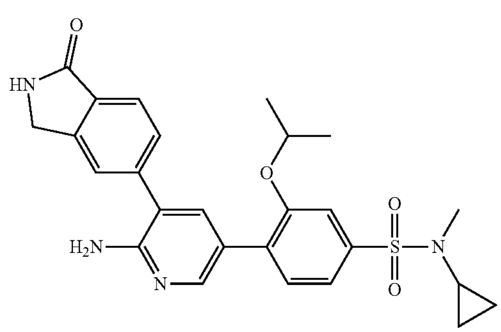 [SMILES: CC(C)Oc1cc(S(=O)(=O)N(C)C2CC2)ccc1-c1cnc(N)c(-c2ccc3c(c2)CNC3=O)c1] | 4-(6-amino-5-(1-oxoisoindolin-5-yl)pyridin-3-yl)-N-cyclopropyl-3-isopropoxy-N-methylbenzenesulfonamide |

-continued

| Compound Number | Structure | Compound Name |
|---|---|---|
| I-69 | 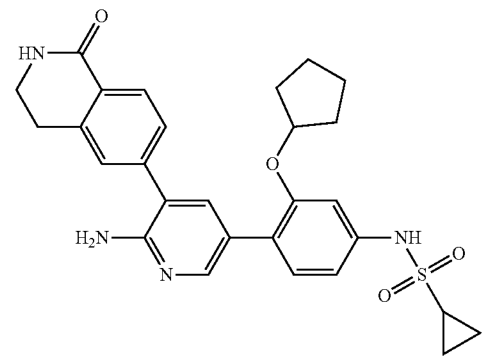 [SMILES: Nc1ncc(-c2ccc(NS(=O)(=O)C3CC3)cc2OC2CCCC2)cc1-c1ccc2c(c1)CCNC2=O] | N-(4-(6-amino-5-(1-oxo-1,2,3,4-tetrahydroisoquinolin-6-yl)pyridin-3-yl)-3-(cyclopentyloxy)phenyl)cyclopropanesulfonamide |
| I-70 | 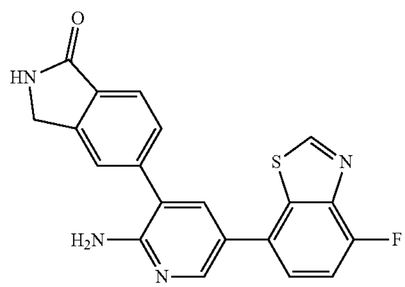 [SMILES: Nc1ncc(-c2ccc(F)c3ncsc23)cc1-c1ccc2c(c1)CNC2=O] | 5-(2-amino-5-(4-fluorobenzo[d]thiazol-7-yl)pyridin-3-yl)isoindolin-1-one |
| I-71 | 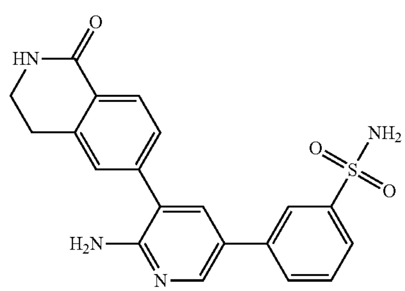 [SMILES: Nc1ncc(-c2cccc(S(N)(=O)=O)c2)cc1-c1ccc2c(c1)CCNC2=O] | 3-(6-amino-5-(1-oxo-1,2,3,4-tetrahydroisoquinolin-6-yl)pyridin-3-yl)benzenesulfonamide |
| I-72 | 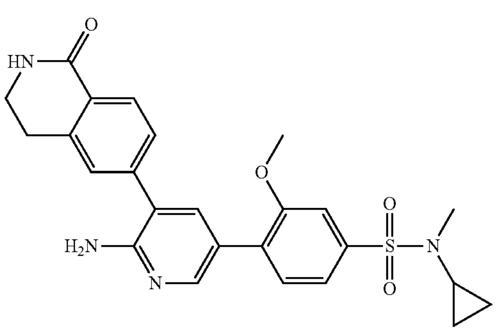 [SMILES: COc1cc(S(=O)(=O)N(C)C2CC2)ccc1-c1cnc(N)c(-c2ccc3c(c2)CCNC3=O)c1] | 4-(6-amino-5-(1-oxo-1,2,3,4-tetrahydroisoquinolin-6-yl)pyridin-3-yl)-N-cyclopropyl-3-methoxy-N-methylbenzenesulfonamide |
| I-73 | 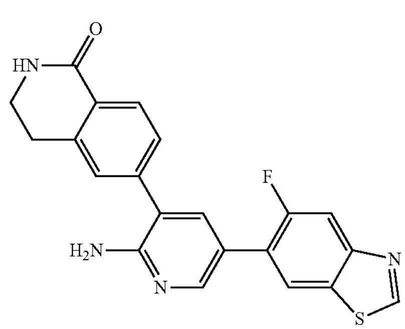 [SMILES: Nc1ncc(-c2cc3scnc3cc2F)cc1-c1ccc2c(c1)CCNC2=O] | 6-(2-amino-5-(5-fluorobenzo[d]thiazol-6-yl)pyridin-3-yl)-3,4-dihydroisoquinolin-1(2H)-one |

| Compound Number | Structure | Compound Name |
|---|---|---|
| I-74 | 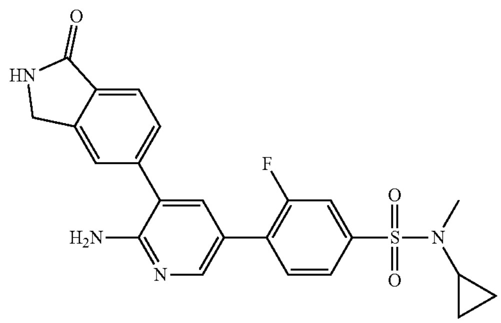 [SMILES: CN(C1CC1)S(=O)(=O)c1ccc(-c2cnc(N)c(-c3ccc4c(c3)CNC4=O)c2)c(F)c1] | 4-(6-amino-5-(1-oxoisoindolin-5-yl)pyridin-3-yl)-N-cyclopropyl-3-fluoro-N-methylbenzenesulfonamide |
| I-75 | 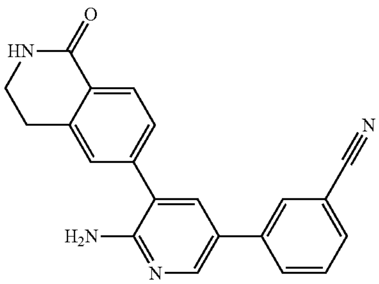 [SMILES: N#Cc1cccc(-c2cnc(N)c(-c3ccc4c(c3)CCNC4=O)c2)c1] | 3-(6-amino-5-(1-oxo-1,2,3,4-tetrahydroisoquinolin-6-yl)pyridin-3-yl)benzonitrile |
| I-76 | 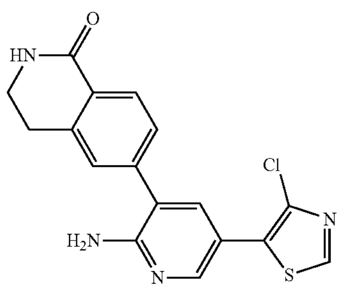 [SMILES: Nc1ncc(-c2scnc2Cl)cc1-c1ccc2c(c1)CCNC2=O] | 6-(2-amino-5-(4-chlorothiazol-5-yl)pyridin-3-yl)-3,4-dihydroisoquinolin-1(2H)-one |
| I-77 | 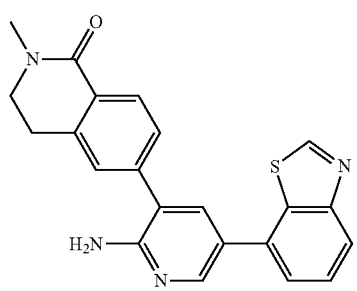 [SMILES: CN1CCc2cc(-c3cc(-c4cccc5ncsc45)cnc3N)ccc2C1=O] | 6-(2-amino-5-(4-chlorothiazol-5-yl)pyridin-3-yl)-3,4-dihydroisoquinolin-1(2H)-one |

The compounds of the application are capable of modulating serine-threonine kinase 4 (STK4) activity. In one embodiment, the compounds of the present application are capable of inhibiting or decreasing serine-threonine kinase 4 (STK4) activity.

In some embodiments, the compounds of the present application are inhibitors of STK4. In this context the inhibitor of STK4 prevents STK4 from reducing YAP1 levels. In other embodiments, the compounds of the present application are inhibitors that prevent or reduce expression of STK4.

In some embodiments, the compounds of the present application are inactivators of STK4. In one embodiment, the compounds of the present application prevent STK4 from reducing YAP1 levels.

In some embodiments, the compounds of the present application prevent or reduce expression of STK4.

In some embodiments, the compounds of the present application are antagonists of STK4. In various embodiments the antagonists prevent or reduce phosphorylation activity of STK4. In one embodiment, the compounds of the present application prevent or reduce phosphorylation activity of STK4.

In other embodiments, the compounds of the present application bind upstream of STK4 in the STK4/YAP1 pathway and have an effect on the pathway that causes STK4 to be unable to reduce YAP1 levels.

In other embodiments, the compounds of the present application bind downstream of STK4 in the STK4/YAP1 pathway and have an effect on the pathway that causes STK4 to be unable to reduce YAP1 levels.

In some embodiments, the compounds of the present application are capable of modulating one or more kinases. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the compounds of the present application are capable of inhibiting one or more kinases. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase is STK4. In some embodiments, the compounds of the present application are capable of activating one or more kinases. In some embodiments, the kinase is ITPK1. In some embodiment, the compounds of the present invention modulate a group of specific kinases selectively over other kinase enzymes. In certain embodiments, the compounds of the application are inhibitors of a specific group of kinases (e.g., STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, or ZC3/MINK) that exhibit at least 2-fold, 3-fold, 5-fold, 10-fold, 25-fold, 50-fold or 100-fold selectivity over other kinases. In various embodiments, the compounds of the application exhibit up to 1000-fold selectivity over other kinases. In certain embodiments, the compounds of the application are activators of a specific group of kinases (e.g., ITPK1) that exhibit at least 2-fold, 3-fold, 5-fold, 10-fold, 25-fold, 50-fold or 100-fold selectivity over other kinases. In various embodiments, the compounds of the application exhibit up to 1000-fold selectivity over other kinases.

In some embodiments, the compounds of the present application are selective over other kinases. As used herein "selective modulator", "selective activator", "selective inhibitor" or "selective compound" refers to a compound, for example a compound of the application, that effectively modulates, activates or inhibits a specific kinase or a specific group of kinases to a greater extent than any other kinase enzyme.

A "selective modulator", "selective activator", "selective inhibitor" or "selective compound" can be identified, for example, by comparing the ability of a compound to modulate, activate or inhibit the activity of a specific kinase to its ability to inhibit the other kinases. In some embodiments, the selectivity can identified by measuring the $EC_{50}$ or $IC_{50}$ of the compounds.

In some embodiments, the compounds of the present application are selective STK4 modulators. As used herein "selective STK4 modulator", "selective STK4 inhibitor" or "selective STK4 compound" refers to a compound, for example a compound of the application, that effectively modulates or inhibits STK4 kinase to a greater extent than any other kinase enzyme, particularly any enzyme from the STK/MST kinase family (e.g., STK3 (MST2), STK24 (MST3), MST4).

A "selective STK4 modulator", "selective STK4 inhibitor" or "selective STK4 compound" can be identified, for example, by comparing the ability of a compound to inhibit STK4 kinase activity to its ability to inhibit the other members of the STK/MST kinase family or other kinases. For example, a substance may be assayed for its ability to inhibit STK4 kinase activity, as well as STK3 (MST2), STK24 (MST3), MST4, and other kinases. In some embodiments, the selectivity can identified by measuring the $EC_{50}$ or $IC_{50}$ of the compounds.

In certain embodiments, the compounds of the application are STK4 inhibitors that exhibit at least 2-fold, 3-fold, 5-fold, 10-fold, 25-fold, 50-fold or 100-fold selectivity over other kinases (e.g., STK3 (MST2), STK24 (MST3), and MST4). In various embodiments, the compounds of the application exhibit up to 1000-fold selectivity over other kinases.

As used herein, "selective STK4/STK3 inhibitor" or "selective STK4/STK3 compound" refers to a compound, for example a compound of the application, that effectively inhibits STK4 and STK3 (MST2) kinase to a greater extent than any other kinase enzyme, particularly any enzyme from the STK/MST kinase family (e.g., STK24 (MST3), MST4).

A "selective STK4/STK3 inhibitor," can be identified, for example, by comparing the ability of a compound to inhibit STK4 and STK3 kinase activity to its ability to inhibit the other members of the STK/MST kinase family or other kinases. For example, a substance may be assayed for its ability to inhibit STK4/STK3 kinase activity, as well as STK24 (MST3), MST4, and other kinases. In some embodiments, the selectivity can identified by measuring the $EC_{50}$ or $IC_{50}$ of the compounds.

In certain embodiments, the compounds of the application are STK4 and STK3 inhibitors that exhibit at least 2-fold, 3-fold, 5-fold, 10-fold, 25-fold, 50-fold or 100-fold selectivity over other kinases (e.g., STK24 (MST3), MST4). In various embodiments, the compounds of the application exhibit up to 1000-fold selectivity over other kinases.

In certain embodiments, the compounds of the application exhibit at least 2-fold, 3-fold, 5-fold, 10-fold, 25-fold, 50-fold or 100-fold selectivity over other kinases. In various embodiments, the compounds of the application exhibit up to 1000-fold selectivity over other kinases.

In certain embodiments, the compounds of the application exhibit at least 2-fold, 3-fold, 5-fold, 10-fold, 25-fold, 50-fold or 100-fold selectivity over the STK/MST kinase family, STK3 (MST2), STK24 (MST3), and MST4. In various embodiments, the compounds of the application exhibit up to 1000-fold selectivity over the STK/MST kinase family, STK3 (MST2), STK24 (MST3), and MST4.

In certain embodiments, the compounds of the application exhibit at least 2-fold, 3-fold, 5-fold, 10-fold, 25-fold, 50-fold or 100-fold selectivity over STK3 (MST2). In various embodiments, the compounds of the application exhibit up to 1000-fold selectivity over STK3 (MST2).

In certain embodiments, the compounds of the application exhibit at least 2-fold, 3-fold, 5-fold, 10-fold, 25-fold, 50-fold or 100-fold selectivity over STK24 (MST3). In various embodiments, the compounds of the application exhibit up to 1000-fold selectivity over STK24 (MST3).

In certain embodiments, the compounds of the application exhibit at least 2-fold, 3-fold, 5-fold, 10-fold, 25-fold, 50-fold or 100-fold selectivity over MST4. In various embodiments, the compounds of the application exhibit up to 1000-fold selectivity over MST4.

In some embodiments, the inhibition of serine-threonine kinase 4 (STK4) activity is measured by $IC_{50}$.

In some embodiments, the inhibition of serine-threonine kinase 4 (STK4) activity is measured by $EC_{50}$.

Potency of the inhibitor can be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining a in cells expressing a, or a fragment of any thereof.

In some embodiments, the compounds of the application are capable of inhibiting cell growth in the presence of stromal cell culture supernatant (SC-CS). In some embodiments, the compounds of the application are capable of inhibiting myeloma cell growth in the presence of stromal cell culture supernatant (SC-CS). Stromal cell culture supernatant (SC-CS) contains many growth factors and anti-apoptotic factors, including interleukin-6 (IL-6) and insulin-like growth factor-1 (IGF1), and is able to decrease or abrogate the activity of conventional anti-myeloma agents (e.g., dexamethasone). Since myeloma cells grow in the bone marrow microenvironment, the ability to inhibit myeloma cell proliferation in the presence of SC-CS impacts the therapeutic efficacy of a reagent.

DEFINITIONS

Listed below are definitions of various terms used to describe this application. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (v) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl)$_2$ where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the application, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)— heteroaryl,
—C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl,
—OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$,
—OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl,
—NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)— heterocycloalkyl,
—NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$— heterocycloalkyl, NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, NHC(O)NH-heterocycloalkyl,
NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, C(NH)NH—C$_3$-C$_{12}$-cycloalkyl, —C(NH)NH-aryl, —C(NH)NH-heteroaryl, —C(NH)NHheterocycloalkyl,
—S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be further substituted.

As defined herein, "KIN001-305" is a compound having the following structure:

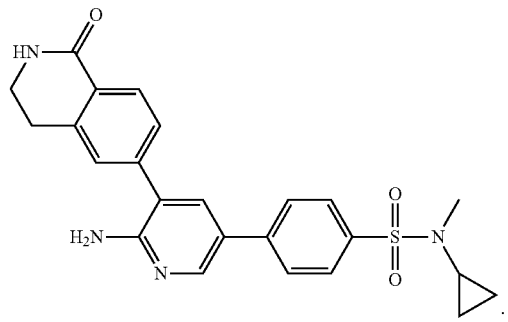 [SMILES: CN(C1CC1)S(=O)(=O)c1ccc(-c2cnc(N)c(-c3ccc4c(c3)CCNC4=O)c2)cc1]

As defined herein, "BMS536924" is a compound having the following structure:

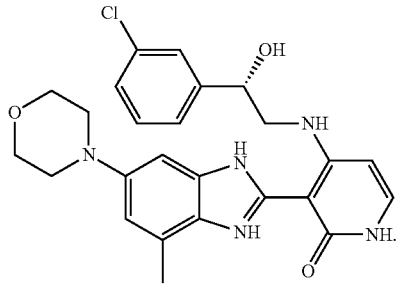 [SMILES: Cc1cc(N2CCOCC2)cc2[nH]c(-c3c(NC[C@@H](O)c4cccc(Cl)c4)cc[nH]c3=O)nc12]

As defined herein, "Lenalidomide" is a compound having the following structure:

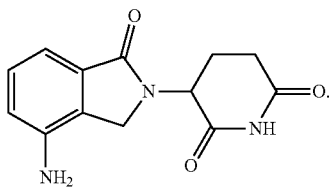 [SMILES: Nc1cccc2c1CN(C1CCC(=O)NC1=O)C2=O]

As defined herein, "Pomalidomide" is a compound having the following structure:

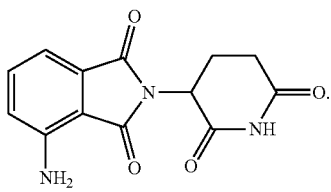 [SMILES: Nc1cccc2c1C(=O)N(C1CCC(=O)NC1=O)C2=O]

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "hematopoietic disorder" as used herein refers to any type of disorder that affects hematopoietic cells. These include but are not limited to hematopoietic cancers. Non limiting examples of hematopoietic cancers include multiple myeloma, leukaemias and lymphomas. A non-limiting list of further hematopoietic disorders include, but are not limited to, aplastic anemia, myelodysplasia, and related bone marrow failure syndromes, polycythemia vera and other myeloproliferative diseases, acute and chronic myeloid leukemia, malignancies of lymphoid cells, less common hematologic malignancies, and plasma cell disorders.

The term "hematopoietic cells" as used herein includes all the blood cell types including those from the myeloid lineage (monocytes and macrophages, neutrophils, basophils, eosinophils, erythrocytes, megakaryocytes/platelets, dendritic cells), and lymphoid lineages (T-cells, B-cells, NK-cells).

Multiple myeloma is a malignant neoplasm of plasma cells in the bone marrow associated with an overproduction of monoclonal (M)-protein often causing characteristic osteolytic lesions, anemia, renal failure, and hypercalcemia. (Kyle, R. A., et al., Multiple myeloma., N. Engl. J. Med. 2004; 351(18):1860-1873) Monoclonal gammopathy of unknown significance (MGUS) is an asymptomatic plasma cell dyscrasia that is present in more than 3% of the general white population older than age 50 and has an average multiple myeloma progression risk of 1% per year. (Kyle, R. A., et al., Prevalence of monoclonal gammopathy of undetermined significance, N. Engl. J. Med 2006; 354(13):1362-1369). Smoldering multiple myeloma (SMM) is another asymptomatic plasma cell disorder but carries a higher risk of progression to frank multiple myeloma (10% per year the first 5 years) compared with MGUS. (Kyle, R. A., et al., Clinical course and prognosis of smoldering (asymptomatic) multiple myeloma, N. Engl. J. Med. 2007; 356(25):2582-2590). It will be appreciated that the present application is useful for MGUS and SMM as well as multiple myeloma.

Leukaemias are described as lymphoid or myeloid leukaemias, depending on which type of hematopoitic cell the abnormal leukaemia cells develop from. Leukaemias start in the bone marrow and the abnormal cells can spread from there into the bloodstream and to other parts of the body. Non limiting examples of leukaemia include acute lymphoblastic leukaemia (ALL), adult T cell leukaemia (AIL), acute myeloblastic leukaemia (AML), chronic lymphocytic leukaemia (CLL) and chronic myeloid leukaemia (CML).

Lymphomas start in lymphocytes. Abnormal lymphocytes can build up in lymph nodes, bone marrow and/or the spleen. Non limiting examples of lymphomas include non-Hodgkin's lymphomas such as Waldestrom Macroglobulinemia, Burkitt lymphoma, Mantle cell lymphoma, diffuse large B cell lymphoma and follicular lymphoma.

The term "YAP1 level" as used herein preferably refers to YAP1 level in hematopoietic cells.

The term "reduced level" or "reduced YAP1 level" as used herein refers to reduced level of YAP 1 relative to that of a non-diseased cell, preferably a non-diseased hematopoietic cell, or relative to YAP1 levels of a group of reference patients. The reference patients may be presenting with "high" levels for YAP 1, and reduced level is relative to such high levels. The non-diseased cell may be from the same subject to be treated.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the application, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The application also provides for a pharmaceutical composition comprising a compound of the present application, or a pharmaceutically acceptable ester, salt, or prodrug thereof, together with a pharmaceutically acceptable carrier.

In another aspect, the application provides a kit comprising a compound capable of inhibiting STK4 activity selected from one or more compounds of the present application, or a pharmaceutically acceptable salt, hydrate, solvate, prodrug, stereoisomer, or tautomer thereof, and instructions for use in treating cancer.

In another aspect, the application provides a method of synthesizing a compound of the present application.

The synthesis of the compounds of the application can be found herein and in the Examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3$H, $^2$H, $^{14}$C, $^{13}$C, $^{18}$F, $^{35}$S, $^{32}$P, $^{125}$I, and $^{131}$I) introduced into the compound. Such compounds are useful for drug metabolism studies and diagnostics, as well as therapeutic applications.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base.

Alternatively, the salt forms of the compounds of the application can be prepared using salts of the starting materials or intermediates.

The free acid or free base forms of the compounds of the application can be prepared from the corresponding base addition salt or acid addition salt from, respectively. For example a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Prodrug derivatives of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like).

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present application can be conveniently prepared, or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present application. Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application. All crystal forms of the compounds described herein are expressly included in the present application.

In the present specification, the structural formula of the compound represents a certain isomer for convenience in some cases, but the present application includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present application. Furthermore, so-called metabolite which is produced by degradation of the present compound in vivo is included in the scope of the present application.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of Synthesizing the Compounds

The compounds of the present application may be made by a variety of methods, including standard chemistry. The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof. Suitable synthetic routes are depicted in the Scheme I below.

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry*: Reactions, Mechanisms, and Structure, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application.

The compounds of the present application may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of the present application.

Those skilled in the art will recognize if a stereocenter exists in the compounds of the present application. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

Preparation of the Compounds

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below. Compounds of the present application can be synthesized by following the steps outlined in General Scheme 1 which comprise different sequences of assembling intermediates IIa, IIb, IIc, IId, and IIe. Starting materials are either commercially available or made by known procedures in the reported literature or as illustrated.

General Scheme 1

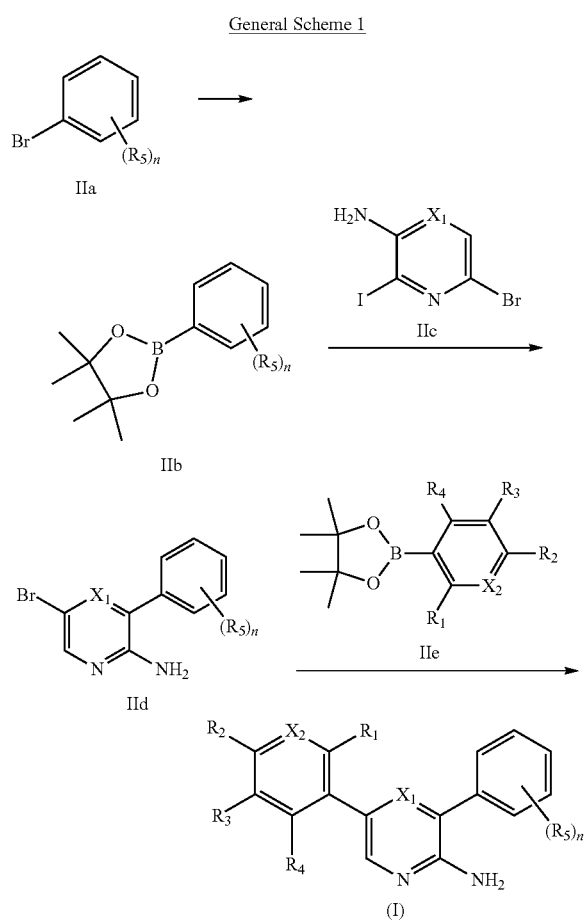

wherein $R_2$-$R_5$, $X_1$, $X_2$, and n are defined as in Formula (I).

The general way of preparing target molecules of Formula (I) by using intermediates IIa, IIb, IIc, IId, and IIe is outlined in General Scheme 1. Treatment of IIa with a palladium catalyst (i.e., Pd(dppf)Cl$_2$) and a base, i.e., KOAc, in solvent, i.e., dioxane, at elevated temperatures provides intermediate IIb. Coupling of IIb and IIc in the presence of a palladium catalyst (i.e., Pd(PPh$_3$)$_2$Cl$_2$) and a base, i.e., K$_2$CO$_3$, in solvent, i.e., dimethylformamide (DMF), at elevated temperatures provides intermediate IId. Treatment of IId and IIe with a palladium catalyst (i.e., Pd(PPh$_3$)$_2$Cl$_2$) and a base, i.e., K$_2$CO$_3$, in solvent, i.e., dioxane, at elevated temperatures provides compounds of Formula (I).

Biological Assays

The biological activities of the compounds of the present application can be measured by various biochemical or cellular assays known to one of ordinary skill in the art. Non-limiting examples of biochemical and cellular assays are listed herein below.

Cell Proliferation Assays and Growth Assays

MM.1S, KMS20 and H929 MM cells are counted and diluted to a final concentration. The cell are plated and mixed with an equal volume of culture media containing DMSO or increasing concentration of a compound of the present application diluted in DMSO. Cells with increasing drug concentration and DMSO are then harvested at different time points. Viability is assessed by a cell proliferation assay.

Western Blotting

MM.1S, KMS20 and H929 cells are counted, diluted and plated. Cells are then harvested with DMSO or different concentration of a compound of the present application for 6 hrs, 24 hrs or 48 hrs. MM cells are then collected and centrifuged at RT and the pellets are re-suspended in lysis buffer. Cell lysates are subjected to sodium dodecyl sulfate-polyacrylamide gel electrophoresis SDS-PAGE, transferred to nitrocellulose membranes, and immunoblotted with different antibodies.

Apoptosis Assays

Apoptosis is quantified using Annexin-V-FITC-PI (propidium iodide) staining. In particular, cells are washed twice, resuspended in buffer, and stained with specific antibodies for 20 minutes. After adding additional binding buffer, samples are acquired and analyzed. The percentage of cells treated with a compound of the present application undergoing apoptosis is defined as the sum of early apoptotic and late apoptotic cells.

Methods of Use

Another aspect of the application provides a method of treating or preventing a disease, the method comprising administering to a subject in need thereof an effective amount of a compound of the present application, or a pharmaceutically acceptable salt, hydrate, solvate, prodrug, stereoisomer, or tautomer thereof. In one embodiment, the disease is mediated by serine-threonine kinase 4 (STK4) (e.g., serine-threonine kinase 4 (STK4) plays a role in the initiation or development of the disease). In one embodiment, the disease is cancer or a proliferation disease. In another embodiment, the disease is an autoimmune disease. In another embodiment, the disease is a metabolic disease.

In another aspect, the application provides a method of treating a disease, comprising administering to a subject in need thereof an effective amount of a compound of the present application, or a pharmaceutically acceptable salt, hydrate, solvate, prodrug, stereoisomer, or tautomer thereof. In one embodiment, the disease is mediated by serine-threonine kinase 4 (STK4). In one embodiment, the disease is cancer or a proliferation disease. In another embodiment, the disease is an autoimmune disease. In another embodiment, the disease is a metabolic disease.

Another aspect of the application provides a method of preventing a disease, comprising administering to a subject in need thereof an effective amount of a compound of the present application, or a pharmaceutically acceptable salt, hydrate, solvate, prodrug, stereoisomer, or tautomer thereof. In one embodiment, the disease is mediated by serine-threonine kinase 4 (STK4). In one embodiment, the disease is cancer or a proliferation disease. In another embodiment, the disease is an autoimmune disease. In another embodiment, the disease is a metabolic disease.

In another aspect, the application provides a method of treating a disease or disorder associated- with modulation of serine-threonine kinase 4 (STK4) comprising, administering to a subject in need thereof an effective amount of a compound of the present application, or a pharmaceutically acceptable salt, hydrate, solvate, prodrug, stereoisomer, or tautomer thereof. In one embodiment, the disease is cancer or a proliferation disease. In another embodiment, the disease is an autoimmune disease. In another embodiment, the disease is a metabolic disease.

In certain embodiments, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In another aspect, the application provides a method of treating or preventing a disease or disorder associated with the modulation of a kinase, the method comprising administering to a subject in need thereof an effective amount of a compound of the present application, or a pharmaceutically acceptable salt, hydrate, solvate, prodrug, stereoisomer, or tautomer thereof. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase is STK4. In some embodiments, the kinase is ITPK1. In another embodiment, the subject is administered an additional therapeutic agent.

In another embodiment, the kinase mediated disorder is cancer. In a further embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

Another aspect of the present application relates to a method of modulating a kinase, comprising administering to a subject in need thereof an effective amount of a compound of the present application. In some embodiments, the kinase is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, ZC3/MINK, and ITPK1. In some embodiments, the present application relates to a method of inhibiting a kinase. In some embodiments, the kinase that is inhibited is selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the kinase that is inhibited is selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the kinase that is inhibited is STK4. In some embodiments, the present application relates to a method of activating a kinase. In some embodiments, the kinase that is activated is ITPK1. In other embodiments, the compound and the additional therapeutic agent are administered simultaneously or sequentially. In some embodiments, the compound is an inhibitor of a kinase selected from STK4, CaMKK2, CK1g2, CK1g3, GCK, GSK3A, GSK3B, HPK1, KHS1, LOK, MAP3K1, NuaK1, PIP4K2C, PIP5K3, SLK, ZC1/HGK, ZC2/TNIK, and ZC3/MINK. In some embodiments, the compound is an inhibitor of a kinase selected from STK4, CaMKK2, CK1g2, CK1g3, GCK, GSK3A, GSK3B, HPK1, KHS1, LOK, MAP3K1, PIP4K2C, PIP5K3, and SLK. In some embodiments, the compound is an inhibitor of STK4. In some embodiments, the compound is an activator of ITPK1.

In some embodiments, the inhibition of a kinase treats or prevents cancer. In a further embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In another aspect, the application provides a method of treating or preventing cancer, wherein the cancer cell comprise activated STK4, comprising administering to a subject in need thereof an effective amount of a compound of the present application, or a pharmaceutically acceptable salt, hydrate, solvate, prodrug, stereoisomer, or tautomer thereof.

In another embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

Another aspect of the application provides a method of inhibiting serine-threonine kinase 4 (STK4) comprising, administering to a subject in need thereof an effective amount of a compound of the present application, or a pharmaceutically acceptable salt, hydrate, solvate, prodrug, stereoisomer, or tautomer thereof.

In another aspect, the application provides a method of treating cancer, the method comprising administering, to a subject in need thereof an effective amount of a compound of the present application, or a pharmaceutically acceptable salt, hydrate, solvate, prodrug, stereoisomer, or tautomer thereof.

In another embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

Another aspect of the application provides a method of treating a hematopoietic disorder, the method comprising administering, to a subject in need thereof an effective amount of a compound of the present application, or a pharmaceutically acceptable salt, hydrate, solvate, prodrug, stereoisomer, or tautomer thereof.

In certain embodiments, the hematopoietic disorder is myeloma, leukaemias including acute lymphoblastic leukaemia (ALL), adult T cell leukaemia (AIL), acute myeloblastic leukaemia (AML), chronic lymphocytic leukaemia (CLL) and chronic myeloid leukaemia (CML), lymphomas including non-Hodgkin's lymphomas such as Waldestrom Macroglobulinemia, Burkitt lymphoma, Mantle cell lymphoma, diffuse large B cell lymphoma and follicular lymphoma, aplastic Anemia, myelodysplasia and related bone marrow failure syndromes, polycythemia vera, acute and chronic myeloid leukemia, malignancies of lymphoid cells, less common hematologic malignancies, and plasma cell disorders.

In one embodiment, the hematopoietic disorder is selected from the group consisting of multiple myeloma, leukemia, or lymphoma. In another embodiment, the hematopoietic disorder is multiple myeloma. In yet another embodiment, the hematopoietic disorder is leukemia. In another embodiment, the hematopoietic disorder is lymphoma.

In another aspect, the application provides a method of treating a hematopoietic disorder, comprising administering to said subject an effective amount of a compound of the present application, or a pharmaceutically acceptable salt, hydrate, solvate, prodrug, stereoisomer, or tautomer thereof that increases YAP1 levels, wherein said subject has been identified as having a hematopoietic disorder with reduced levels of YAP1. In a further embodiment, the subject has further been identified as having nuclear localization of ABL in cells associated with the disorder.

In certain embodiments, the hematopoietic disorder is myeloma, leukaemias including acute lymphoblastic leukaemia (ALL), adult T cell leukaemia (AIL), acute myeloblastic leukaemia (AML), chronic lymphocytic leukaemia (CLL) and chronic myeloid leukaemia (CML), lymphomas including non-Hodgkin's lymphomas such as Waldestrom Macroglobulinemia, Burkitt lymphoma, Mantle cell lymphoma, diffuse large B cell lymphoma and follicular lymphoma, aplastic Anemia, myelodysplasia and related bone marrow failure syndromes, polycythemia vera, acute and chronic myeloid leukemia, malignancies of lymphoid cells, less common hematologic malignancies, and plasma cell disorders.

In one embodiment, the hematopoietic disorder is selected from the group consisting of multiple myeloma, leukemia, or lymphoma. In another embodiment, the hematopoietic disorder is multiple myeloma. In yet another embodiment, the hematopoietic disorder is leukemia. In another embodiment, the hematopoietic disorder is lymphoma.

Another aspect of the application relates to the use in the manufacture of a medicament for treating or preventing a disease in which serine-threonine kinase 4 (STK4) plays a role. In one embodiment, the medicament is a compound of the present application, or a pharmaceutically acceptable salt, hydrate, solvate, prodrug, stereoisomer, or tautomer thereof.

In certain embodiments, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In another aspect, the application relates to a compound of the present application, or a pharmaceutically acceptable salt, hydrate, solvate, prodrug, stereoisomer, or tautomer thereof for use in the manufacture of a medicament for treating or preventing a disease associated with inhibiting serine-threonine kinase 4 (STK4).

In certain embodiments, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

Another aspect of the application relates to a compound of the present application, or a pharmaceutically acceptable salt, hydrate, solvate, prodrug, stereoisomer, or tautomer thereof for use in the manufacture of a medicament for treating or preventing hematopoietic disorders.

In certain embodiments, the hematopoietic disorder is myeloma, leukaemias including acute lymphoblastic leukaemia (ALL), adult T cell leukaemia (AIL), acute myeloblastic leukaemia (AML), chronic lymphocytic leukaemia (CLL) and chronic myeloid leukaemia (CML), lymphomas including non-Hodgkin's lymphomas such as Waldestrom Macroglobulinemia, Burkitt lymphoma, Mantle cell lymphoma, diffuse large B cell lymphoma and follicular lymphoma, aplastic Anemia, myelodysplasia and related bone marrow failure syndromes, polycythemia vera, acute and chronic myeloid leukemia, malignancies of lymphoid cells, less common hematologic malignancies, and plasma cell disorders.

In one embodiment, the hematopoietic disorder is selected from the group consisting of multiple myeloma, leukemia, or lymphoma. In another embodiment, the hematopoietic disorder is multiple myeloma. In yet another embodiment, the hematopoietic disorder is leukemia. In another embodiment, the hematopoietic disorder is lymphoma.

In another aspect, the application relates to the use of a compound of the present application, or a pharmaceutically acceptable salt, hydrate, solvate, prodrug, stereoisomer, or tautomer thereof in the treatment or prevention of a disease associated with inhibiting serine-threonine kinase 4 (STK4).

In certain embodiments, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In another aspect, the application relates to the use of a compound of the present application, or a pharmaceutically acceptable salt, hydrate, solvate, prodrug, stereoisomer, or tautomer thereof in the treatment or prevention of a disease in which serine-threonine kinase 4 (STK4) plays a role.

In certain embodiments, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In another aspect, the application provides a method of inhibiting serine-threonine kinase 4 (STK4), comprising contacting STK4 with a compound of the present application, or a pharmaceutically acceptable salt, hydrate, solvate, prodrug, stereoisomer, or tautomer thereof.

In another aspect, the application provides a method of inhibiting serine-threonine kinase 4 (STK4), the method comprising administering to a subject in need thereof an effective amount of a compound of the present application, or a pharmaceutically acceptable salt, hydrate, solvate, prodrug, stereoisomer, or tautomer thereof.

In certain embodiments, the disease is cancer or a proliferation disease.

In a further embodiment, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In another aspect, the application provides a method of treating a kinase mediated disorder, the method comprising administering to a subject in need thereof an effective amount of a compound of the present application, or a pharmaceutically acceptable salt, hydrate, solvate, prodrug, stereoisomer, or tautomer thereof. In one embodiment, the compound is an inhibitor of STK4. In another embodiment, the subject is administered an additional therapeutic agent. In other embodiments, the compound and the additional therapeutic agent are administered simultaneously or sequentially.

In another embodiment, the kinase mediated disorder is cancer. In a further embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In another aspect, the application provides a method of treating or preventing cancer, wherein the cancer cell comprise activated STK4, comprising administering to a subject in need thereof an effective amount of a compound of the present application, or a pharmaceutically acceptable salt, hydrate, solvate, prodrug, stereoisomer, or tautomer thereof.

In another embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

Another aspect of the application provides a method of treating or preventing cancer in a subject, wherein the subject is identified as being in need of STK4 inhibition for the treatment of cancer, comprising administering to the subject an effective amount of a compound of the present application, or a pharmaceutically acceptable salt, hydrate, solvate, prodrug, stereoisomer, or tautomer thereof.

In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In still another aspect, the application provides a method of treating cancer in a subject, wherein the subject is identified as being in need of STK4 inhibition for the treatment of cancer, comprising administering to the subject in need thereof an effective amount of a compound of the present application, or a pharmaceutically acceptable salt, hydrate, solvate, prodrug, stereoisomer, or tautomer thereof.

In certain embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In another embodiment, the cancer is multiple myeloma, leukemia, or lymphoma.

In certain embodiments, the application provides a method of treating any of the disorders described herein, wherein the subject is a human. In certain embodiments, the application provides a method of preventing any of the disorders described herein, wherein the subject is a human.

As inhibitors of serine-threonine kinase 4 (STK4), the compounds and compositions of this application are particularly useful for treating or lessening the severity of a disease, condition, or disorder where serine-threonine kinase 4 (STK4) is implicated in the disease, condition, or disorder. In one aspect, the present application provides a method for treating or lessening the severity of a disease, condition, or disorder where serine-threonine kinase 4 (STK4) is implicated in the disease state. In another aspect, the present application provides a method for treating or lessening the severity of a serine-threonine kinase 4 (STK4) disease, condition, or disorder where inhibition of enzymatic activity is implicated in the treatment of the disease. In another aspect, this application provides a method for treating or lessening the severity of a disease, condition, or disorder with compounds that inhibit enzymatic activity by binding to serine-threonine kinase 4 (STK4). Another aspect provides a method for treating or lessening the severity of a serine-threonine kinase 4 (STK4) disease, condition, or disorder by inhibiting enzymatic activity of the kinase with a serine-threonine kinase 4 (STK4) inhibitor.

In some embodiments, said method is used to treat or prevent a condition selected from autoimmune diseases, proliferative and hyperproliferative diseases, and metabolic diseases. In other embodiments, said condition is a proliferative disorder.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx;

small intestine; colorectal, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more compounds of the application in the manufacture of a medicament for the treatment of cancer, including without limitation the various types of cancer disclosed herein.

In some embodiments, the compounds of this application are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

Another aspect of this application provides a method for the treatment or lessening the severity of a disease selected from a proliferative or hyperproliferative disease, or a neurodegenerative disease, comprising administering an effective amount of a compound of the application, or a pharmaceutically acceptable composition comprising a compound, to a subject in need thereof.

As inhibitors of STK4 kinase, the compounds and compositions of this application are also useful in biological samples. One aspect of the application relates to inhibiting kinase activity in a biological sample, which method comprises contacting said biological sample with a compound of the application or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of kinase activity in a biological sample is useful for a variety of purposes that are known to one of skill in the art. Examples of such purposes include, but are not limited to, blood transfusion, organ-transplantation, and biological specimen storage.

Another aspect of this application relates to the study of STK4 kinases in biological and pathological phenomena; the study of intracellular signal transduction pathways mediated by such kinase; and the comparative evaluation of new kinase inhibitors. Examples of such uses include, but are not limited to, biological assays such as enzyme assays and cell-based assays.

The activity of the compounds as STK4 kinase inhibitors may be assayed in vitro, in vivo, or in a cell line. In vitro assays include assays that determine inhibition of the kinase activity of the activated kinase. Alternate in vitro assays quantitate the ability of the inhibitor to bind to the kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this application as an inhibitor of various kinases are set forth in the Examples below.

In accordance with the foregoing, the present application further provides a method for preventing or treating any of the diseases or disorders described above in a subject in need of such treatment, which method comprises administering to said subject a therapeutically effective amount of a compound of the application, or a pharmaceutically acceptable salt, hydrate, solvate, prodrug, stereoisomer, or tautomer thereof. For any of the above uses, the required dosage will vary depending on the mode of administration, the particular condition to be treated and the effect desired.

Pharmaceutical Compositions

In another aspect, the application provides a pharmaceutical composition comprising a compound of the present application, or a pharmaceutically acceptable ester, salt, or prodrug thereof, together with a pharmaceutically acceptable carrier.

Compounds of the application can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the application can be administered in therapeutically effective amounts in a combinational therapy with one or more therapeutic agents (pharmaceutical combinations) or modalities, e.g., non-drug therapies. For example, synergistic effects can occur with other antiproliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the application can be used in combination with other pharmaceutically active compounds, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one aspect of the application, the compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g., Mer/Nyk, Rse); RET; and platelet-derived growth factor receptor (PDGFR) (e.g., PDGF.alpha.-R, PDG.beta.-R, CSFI-RIFMS, SCF-R/C-KIT, VEGF-R/FLT, NEK/FLK 1, FLT3/FLK2/STK-1). Non-receptor tyrosine kinase families include, but are not limited to, BCR-ABL (e.g., p43.sup.abl, ARG); BTK (e.g. TTK/EMT, TEC); CSK, FAK, FPS, JAK, SRC, BMX, FER, CDK and SYK.

In another aspect of the application, the subject compounds may be administered in combination with one or more agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g., small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the application are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cyclophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the application are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the application, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the application can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the application may advantageously be used in conjunction with one or more adjunctive therapeutic agents. Examples of suitable agents for adjunctive therapy include a $5HT_1$ agonist, such as a triptan (e.g., sumatriptan or naratriptan); an adenosine A1 agonist; an EP ligand; an NMDA modulator, such as a glycine antagonist; a sodium channel blocker (e.g. lamotrigine); a substance P antagonist (e.g., an $NK_1$ antagonist); a cannabinoid; acetaminophen or phenacetin; a 5-lipoxygenase inhibitor; a leukotriene receptor antagonist; a DMARD (e.g., methotrexate); gabapentin and related compounds; a tricyclic antidepressant (e.g., amitryptilline); a neuron stabilizing antiepileptic drug; a mono-aminergic uptake inhibitor (e.g., venlafaxine); a matrix metalloproteinase inhibitor; a nitric oxide synthase (NOS) inhibitor, such as an iNOS or an nNOS inhibitor; an inhibitor of the release, or action, of tumor necrosis factor a; an antibody therapy, such as a monoclonal antibody therapy; an antiviral agent, such as a nucleoside inhibitor (e.g., lamivudine) or an immune system modulator (e.g., interferon); an opioid analgesic; a local anesthetic; a stimulant, including caffeine; an $H_2$-antagonist (e.g., ranitidine); a proton pump inhibitor (e.g., omeprazole); an antacid (e.g., aluminum or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g., codeine, hydrocodone, carmiphen, carbetapentane, or dextramethorphan); a diuretic; or a sedating or non-sedating antihistamine.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present application, disorders are treated or prevented in a subject, such as a human or other animal, by administering to the subject a therapeutically effective amount of a compound of the application, in such amounts and for such time as is necessary to achieve the desired result. The term "therapeutically effective amount" of a compound of the application, as used herein, means a sufficient amount of the compound so as to decrease the symptoms of a disorder in a subject. As is well understood in the medical arts a therapeutically effective amount of a compound of this application will be at a reasonable benefit/risk ratio applicable to any medical treatment.

In general, compounds of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present application may range from about 0.1 mg/Kg to about 500 mg/Kg, alternatively from about 1 to about 50 mg/Kg. In general, treatment regimens according to the present application comprise administration to a patient in need of such treatment from about 10 mg to about 1000 mg of the compound(s) of this application per day in single or multiple doses. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The application also provides for a pharmaceutical combinations, e.g., a kit, comprising a) a first agent which is a compound of the application as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the application and a co-agent, are both administered to a patient simultaneously in the form of a single entity or dosage. The term "non-fixed combination" means that the active ingredients, e.g., a compound of the application and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

In certain embodiments, these compositions optionally further comprise one or more additional therapeutic agents. For example, chemotherapeutic agents or other antiproliferative agents may be combined with the compounds of this application to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The kinase inhibitors or pharmaceutical salts thereof may be formulated into pharmaceutical compositions for administration to animals or humans. These pharmaceutical compositions, which comprise an amount of the inhibitor effective to treat or prevent a kinase-mediated condition and a pharmaceutically acceptable carrier, are another embodiment of the present application.

In another aspect, the application provides a kit comprising a compound capable of inhibiting kinase activity selected from one or more compounds of the present application, or pharmaceutically acceptable salts, hydrates, solvates, prodrugs, stereoisomers, or tautomers thereof, and instructions for use in treating cancer. In certain embodiments, the kit further comprises components for performing a test to determine whether a subject has reduced levels of YAP1.

In another aspect, the application provides a kit comprising a compound capable of inhibiting serine-threonine kinase 4 (STK4) activity selected from a compound of the present application, or a pharmaceutically acceptable salt, hydrate, solvate, prodrug, stereoisomer, or tautomer thereof.

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

EXAMPLES

Analytical Methods, Materials, and Instrumentation

Unless otherwise noted, reagents and solvents were used as received from commercial suppliers. Proton nuclear magnetic resonance ($^1$H NMR) spectra were obtained on Bruker AVANCE spectrometer at 400 MHz for proton. Spectra are given in ppm ($\delta$) and coupling constants, J, are reported in Hertz. The solvent peak was used as the reference peak for proton spectra. Chemical shifts are reported relative to chloroform ($\delta$=7.24) or dimethyl sulfoxide ($\delta$=2.50) for $^1$H NMR and dimethyl sulfoxide ($\delta$=39.51) for $^{13}$C NMR. Data are reported as (br=broad, s=singlet, d=doublet, t=triplet, q=quartet, m=multiplet). LC-MS spectra were obtained on Agilent 1100 HPLC LC-MS ion trap electrospray ionization (ESI) mass spectrometer.

Abbreviations used in the following examples and elsewhere herein are:

atm atmosphere
br broad
(BPin)$_2$ Bis(pinacolato)diboron
DIPEA N,N-diisopropylethylamine
dppf 1,1'-bis(diphenylphosphino)ferrocene
DCM dichloromethane
DMA N,N-dimethylacetamide
DMF N,N-dimethylformamide
EDCI N-(3-Dimethylaminopropyl)-N'-ethylcarbodiimide hydrochloride
ESI electrospray ionization
h hour(s)

HOBT hydroxybenzotriazole
HPLC high-performance liquid chromatography
KOAc Potassium Acetate
LCMS liquid chromatography-mass spectrometry
m multiplet
MeI methyl iodide
MHz megahertz
min minutes
NBS N-bromosuccinimide
NIS N-iodosuccinimide
NMR nuclear magnetic resonance
ppm parts per million
Py pyridine
TEA triethylamine
TFFA trifluoroacetic anhydride
TLC thin layer chromatography Example 1: 6-(2-amino-5-(2-fluoro-5-nitrophenyl)pyridin-3-yl)-3,4-dihydroisoquinolin-1(2H)-one (I-1)

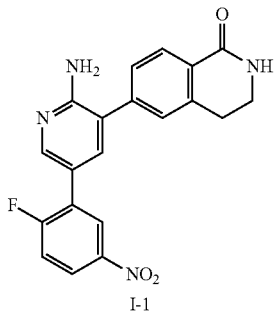

I-1

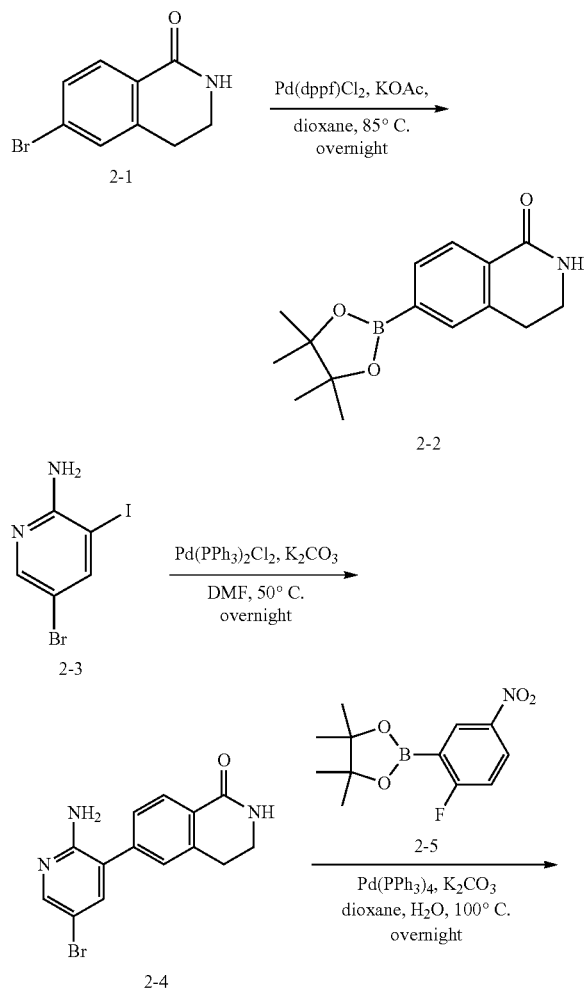

Step 1. 6-(4,4,5,5-tetramethyl-1,3,2-dioxaborolan-2-yl)-3,4-dihydroisoquinolin-1(2H)-one (2-2)

A mixture of 2-1 (3.0 g, 13.3 mmol), (BPin)$_2$ (5.0 g, 19.7 mmol), Pd(dppf)Cl$_2$ (820 mg, 1.12 mmol), KOAc (4.81 g, 49.0 mmol) and dioxane (70 mL) was stirred at 85° C. overnight. Upon completion, the mixture was concentrated and the resulting residue was extracted with ethyl acetate (150 mL×3). The combined organic layers were washed with brine (80 mL×3), dried with Na$_2$SO$_4$, filtered, and concentrated. The residue was then purified by silica gel chromatography (Pet Ether/ethyl acetate=1/5, ethyl acetate) to obtain intermediate 2-2 (light brown solid, 2.8 g, 78% yield). LCMS (m/z): 274 [M+H]$^+$.

Step 2. 6-(2-amino-5-bromopyridin-3-yl)-3,4-dihydroisoquinolin-1(2H)-one (2-4)

A mixture of 2-3 (1.0 g, 3.35 mmol), 2-2 (914 mg, 3.35 mmol), Pd(PPh$_3$)$_2$Cl$_2$ (234 mg, 0.34 mmol), K$_2$CO$_3$ (1.40 g, 10.1 mmol), DMF (20 mL) and H$_2$O (4 mL) was stirred at 55° C. overnight under N$_2$. Upon completion, the resulting mixture was concentrated and the resulting residue was extracted with DCM (50 mL×3). The combined organic phases were washed with H$_2$O (100 mL) and brine (100 mL), dried with Na$_2$SO$_4$, filtered, and concentrated. The residue was purified by silica gel chromatography (ethyl acetate) to give intermediate 2-4 (light yellow solid, 1.1 g, 70% yield). LCMS (m/z): 318 [M+H]$^+$.

Step 3. 6-(2-amino-5-(2-fluoro-5-nitrophenyl)pyridin-3-yl)-3,4-dihydroisoquinolin-1(2H)-one (I-1)

A mixture of 2-4 (155 mg, 0.487 mmol), 2-5 (270 mg, 1.01 mmol), Pd(PPh$_3$)$_4$ (63 mg, 0.0545 mmol), K$_2$CO$_3$ (229 mg, 1.66 mmol), dioxane (5 mL) and H$_2$O (1 mL) was stirred at 100° C. overnight. Upon completion, the mixture was extracted with ethyl acetate (100 mL×3), the combined organic phases were washed with brine (50 mL×3), dried with Na$_2$SO$_4$, filtered, and concentrated. The resulting residue was purified by prep-HPLC (C18 column, CH$_3$CN/H$_2$O, containing 0.05% NH$_4$HCO$_3$) to afford compound I-1 (white solid, 62 mg, 21% yield). LCMS (m/z): 379 [M+H]$^+$. $^1$H NMR (DMSO-d$_6$, 400 MHz): δ 8.50 (m, 1H), 8.31 (s, 1H), 8.29 (m, 1H), 8.07 (s, 1H), 7.96 (d, J=7.6 Hz, 1H), 7.60 (t, J=9.2 Hz, 1H), 7.50 (d, J=8.4 Hz, 1H), 7.47 (s, 1H), 3.41 (t, J=6.4 Hz, 2H), 2.96 (t, J=6.4 Hz, 2H).

Example 2: 6-(2-amino-5-(3-nitrophenyl)pyridin-3-yl)-3,4-dihydroisoquinolin-1(2H)-one (I-2)

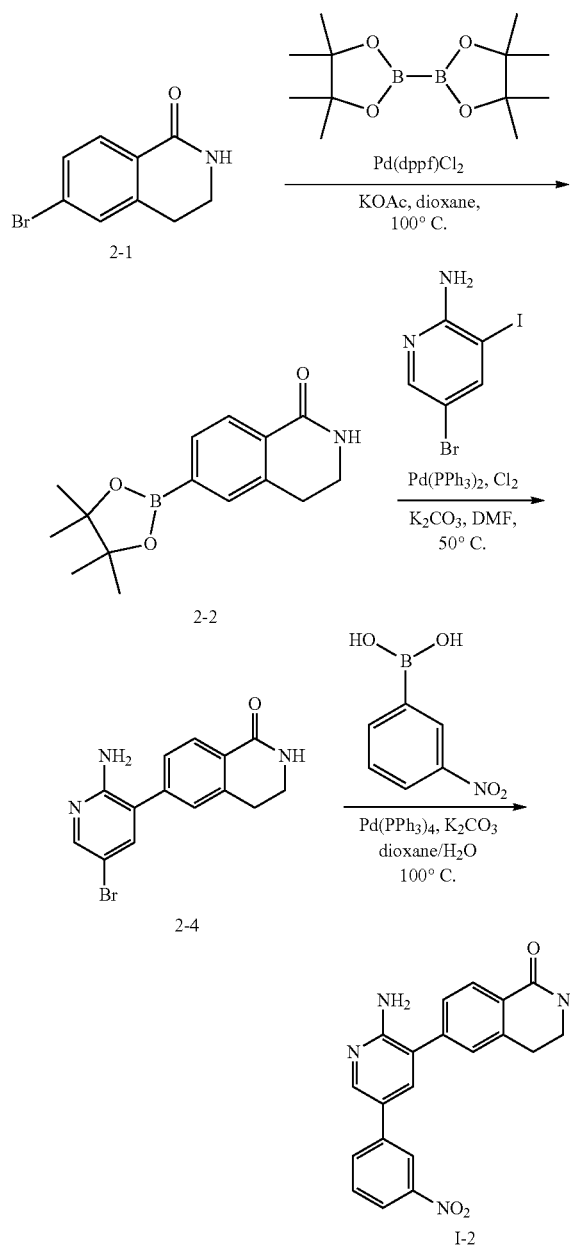

Step 1. 6-(4,4,5,5-tetramethyl-1,3,2-dioxaborolan-2-yl)-3,4-dihydroisoquinolin-1(2H)-one (2-2)

To a stirred mixture of 6-bromo-3,4-dihydroisoquinolin-1(2H)-one (2-1, 500.0 mg, 2.22 mmol), bis(pinacolato)diborane (846.7 mg, 3.33 mmol) and KOAc (653.3 mg, 6.66 mmol) in dioxane (10 mL) under argon was added Pd(dppf)Cl₂ (181.1 mg, 0.22 mol). The resulting mixture was heated at 100° C. overnight, then cooled to r.t, filtered and concentrated. The resulting residue was purified by flash column chromatography (Pet Ether/ethyl acetate=2/1 to 1/1) to obtain intermediate 2-2 (yellow solid, 0.4 g, 66% yield). LCMS (m/z): 274 [M+H]⁺.

Step 2. 6-(2-amino-5-bromopyridin-3-yl)-3,4-dihydroisoquinolin-1(2H)-one (2-4)

To a stirred mixture of 6-(4,4,5,5-tetramethyl-1,3,2-dioxaborolan-2-yl)-3,4-dihydroisoquinolin-1(2H)-one (2-2) (400.0 mg, 1.46 mmol), 5-bromo-3-iodopyridin-2-amine (2-3, 438.1 mg, 1.46 mmol) and K₂CO₃ (653.3 mg, 5.84 mmol) in DMF (8 mL) under an atmosphere of argon was added Pd(PPh₃)₂Cl₂ (102.5 mg, 0.14 mol). The resulting mixture was heated at 50° C. overnight, then cooled to r.t and diluted with saturated NaHCO₃ solution (20 mL). The mixture was then extracted with ethyl acetate (4x×30 mL). The combined ethyl acetate extracts were washed with brine (5×20 mL), dried with MgSO₄, filtered and concentrated in vacuo. The resulting residue was purified by flash column chromatography (DCM/MeOH=100/3) to provide intermediate 2-4 (yellow solid, 0.37 g, 79% yield).

Step 3. 6-(2-amino-5-(3-nitrophenyl)pyridin-3-yl)-3,4-dihydroisoquinolin-1(2H)-one (I-2)

To a stirred mixture of 6-(2-amino-5-bromopyridin-3-yl)-3,4-dihydroisoquinolin-1(2H)-one (2-4, 100.0 mg, 0.31 mmol), 3-nitrophenylboronic acid (105.3 mg, 0.63 mmol) and K₂CO₃ (130.4 mg, 0.95 mmol) in dioxane/H₂O (2/0.25 mL) under an atmosphere of argon was added Pd(PPh₃)₄ (34.6 mg, 0.03 mol). This mixture was heated at 100° C. overnight and then cooled, filtered and concentrated in vacuo. The resulting residue was purified by prep-HPLC (C18 column, CH₃CN/H₂O, containing 0.05% NH₄HCO₃) to afford compound I-2, (off-white solid, 27 mg, 23% yield). LCMS (m/z): 361 [M+H]⁺. ¹H NMR (400 MHz, DMSO) δ: 8.55 (s, 1H), 8.51 (d, J=2.4 Hz, 1H), 8.20-8.23 (m, 2H), 8.15 (s, 1H), 8.03 (s, 1H), 7.98 (d, J=8.0 Hz, 1H), 7.76 (t, J=8.0 Hz, 1H), 7.54-7.57 (m, 2H), 3.45-3.41 (m, 2H), 2.99 (t, J=6.8 Hz, 2H).

Example 3: 6-(2-amino-5-(2-fluorophenyl)pyridin-3-yl)-3,4-dihydroisoquinolin-1(2H)-one (I-3)

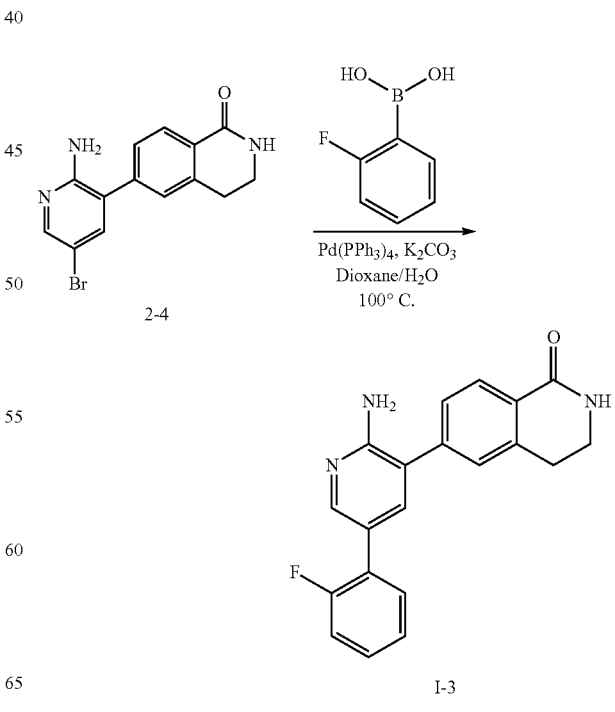

To a stirred mixture of 6-(2-amino-5-bromopyridin-3-yl)-3,4-dihydroisoquinolin-1(2H)-one (2-4, 150.0 mg, 0.47 mmol), 2-fluorophenylboronic acid (105.3 mg, 0.94 mmol) and K$_2$CO$_3$ (195.9 mg, 1.42 mmol) in dioxane/H$_2$O (3/0.37 mL) under argon was added Pd(PPh$_3$)$_4$(54.3 mg, 0.05 mol). This mixture was heated at 100° C. overnight and then cooled, filtered and concentrated in vacuo. The resulting residue was purified by prep-HPLC (C18 column, CH$_3$CN/ H$_2$O, containing 0.05% NH$_4$HCO$_3$) to afford I-3 (white solid, 72 mg, 46% yield). LCMS (m/z): 334 [M+H]$^+$. $^1$H NMR (400 MHz, CDCl$_3$) δ: 8.26 (d, J=8.0 Hz, 1H), 8.07 (d, J=1.6 Hz, 1H), 7.96 (s, 1H), 7.38-7.49 (m, 4H), 7.21-7.31 (m, 2H), 6.41 (s, 1H), 3.66-3.70 (m, 2H), 3.12 (t, J=6.8 Hz, 2H).

Example 4: 6-(2-amino-5-(2-chloro-5-nitrophenyl) pyridin-3-yl)-3,4-dihydroisoquinolin-1(2H)-one (I-4)

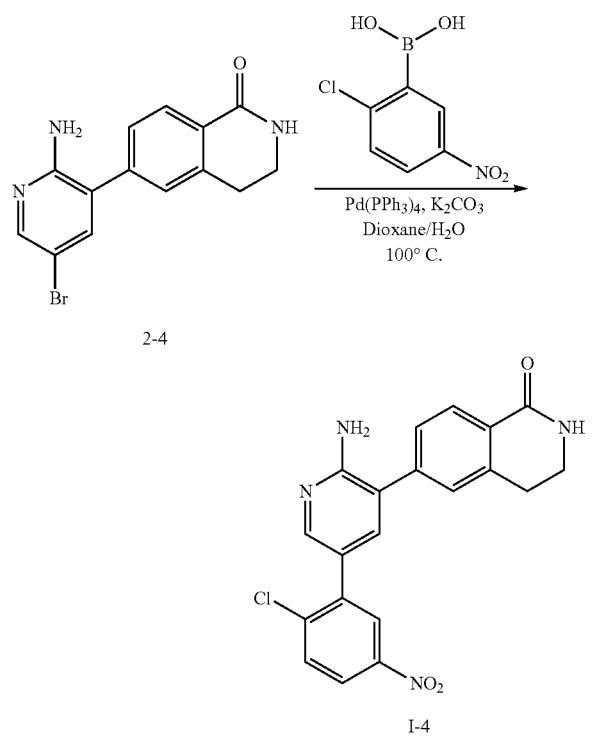

To a stirred mixture of 6-(2-amino-5-bromopyridin-3-yl)-3,4-dihydroisoquinolin-1(2H)-one (2-4, 100.0 mg, 0.31 mmol), 2-chloro-5-nitrophenylboronic acid (126.6 mg, 0.63 mmol) and K$_2$CO$_3$ (130.4 mg, 0.95 mmol) in dioxane/H$_2$O (2/0.25 mL) under an atmosphere of argon was added Pd(PPh$_3$)$_4$ (34.6 mg, 0.03 mol). This mixture was heated at 100° C. overnight and then cooled, filtered and concentrated in vacuo. The resulting residue was then purified by Prep-HPLC (C18 column, CH$_3$CN/H$_2$O, containing 0.05% NH$_4$HCO$_3$) to provide compound I-4 (white solid, 28 mg, 23% yield). LCMS (m/z): 395 [M+H]$^+$. $^1$H NMR (400 MHz, MeOD) δ: 8.43 (d, J=2.8 Hz, 1H), 8.31 (dd, J$_1$=8.4 Hz, J$_2$=2.8 Hz, 1H), 8.18 (d, J=2.4 Hz, 1H), 8.12 (d, J=8.0 Hz, 1H), 8.05 (d, J=2.0 Hz, 1H), 7.86 (d, J=8.8 Hz, 1H), 7.57 (dd, J$_1$=8.0 Hz, J$_2$=1.6 Hz, 1H), 7.54 (s, 1H), 3.58 (t, J=6.8 Hz, 2H), 3.10 (t, J=6.8 Hz, 2H).

Example 5: 6-(6-amino-4'-fluoro-3,3'-bipyridin-5-yl)-3,4-dihydroisoquinolin-1(2H)-one (I-5)

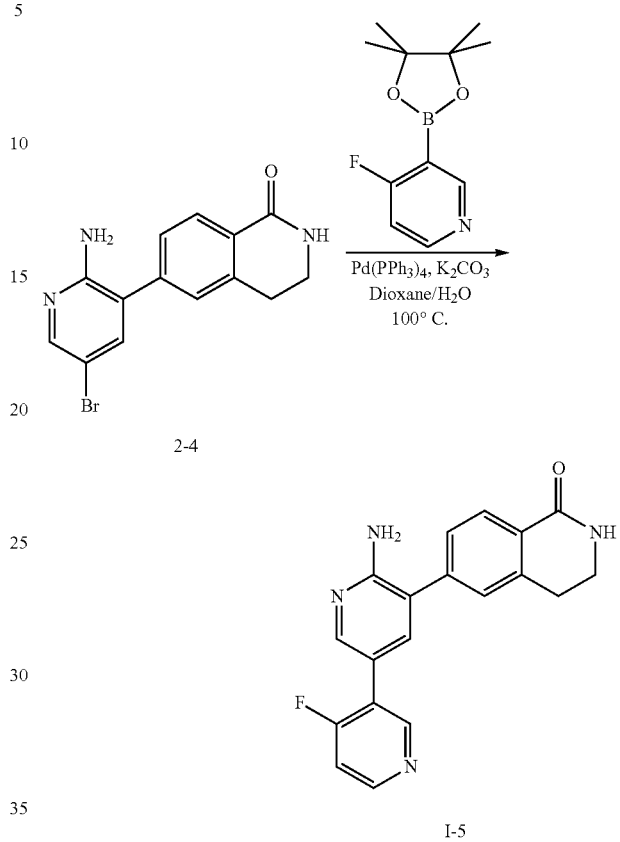

To a stirred mixture of 6-(2-amino-5-bromopyridin-3-yl)-3,4-dihydroisoquinolin-1(2H)-one (2-4, 150.0 mg, 0.47 mmol), 4-fluoro-3-(4,4,5,5-tetramethyl-1,3-dioxolan-2-yl) pyridine (211.5 mg, 0.94 mmol) and K$_2$CO$_3$ (195.9 mg, 1.42 mmol) in dioxane/H$_2$O (3/0.37 mL) under an atmosphere of argon was added Pd(PPh$_3$)$_4$(54.3 mg, 0.05 mol). The resulting mixture was heated at 100° C. overnight and then cooled, filtered and concentrated in vacuo. The resulting residue was purified by prep-HPLC (C18 column, CH$_3$CN/H$_2$O, containing 0.05% NH$_4$HCO$_3$) to provide compound I-5 (white solid, 26 mg, 16% yield). $^1$H NMR (400 MHz, MeOD) δ: 8.73 (d, J=10.4 Hz, 1H), 8.53 (dd, J$_1$=7.2 Hz, J$_2$=6.4 Hz, 1H), 8.24 (t, J=1.6 Hz, 1H), 8.08 (d, J=7.6 Hz, 1H), 7.71-7.72 (m, 1H), 7.54 (d, J=8.0 Hz, 1H), 7.50 (s, 1H), 7.34-7.38 (m, 1H), 3.58 (t, J=3.2 Hz, 2H), 3.09 (t, J=6.8 Hz, 2H). LCMS (m/z): 335 [M+H]$^+$.

Example 6: 3-(6-amino-5-(1-oxo-1,2,3,4-tetrahydroisoquinolin-6-yl)pyridin-3-yl)-N-ethyl-4-fluorobenzamide (I-6)

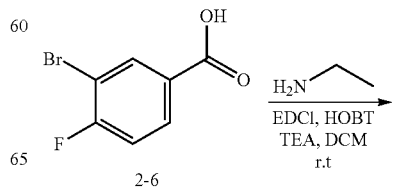

-continued

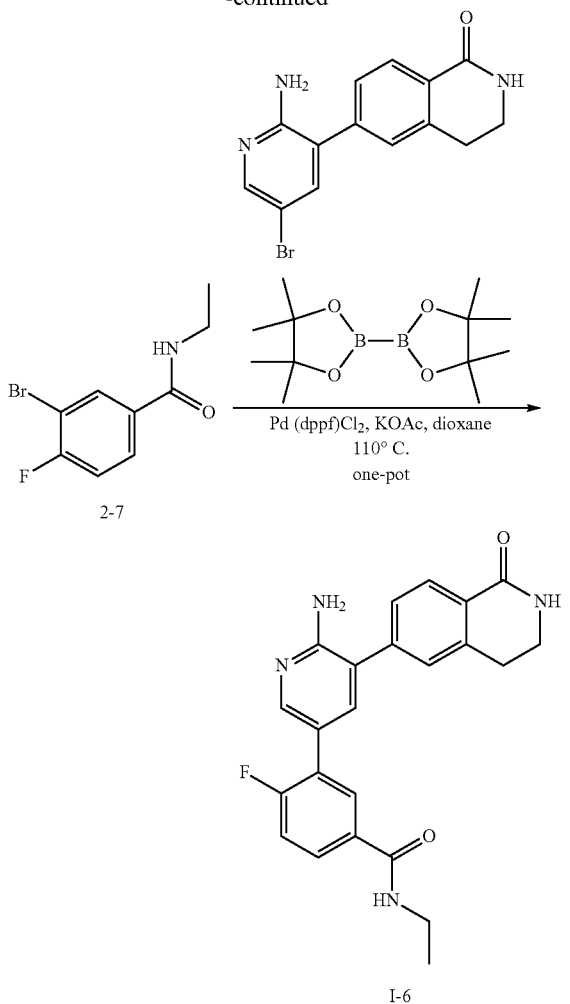

cooled, filtered and concentrated in vacuo. Purification of the resulting residue by prep-HPLC (C18 column, CH₃CN/H₂O, containing 0.05% NH₄HCO₃) afforded compound I-6, (white solid, 30 mg, 24% yield). ¹H NMR (400 MHz, MeOD) δ: 8.25 (s, 1H), 8.19 (s, 1H), 8.13 (d, J=8.0 Hz, 1H), 8.09 (dd, J₁=7.2 Hz, J₂=2.4 Hz, 1H), 7.92-7.96 (m, 1H), 7.58 (dd, J₁=8.0 Hz, J₂=1.6 Hz, 1H), 7.54 (s, 1H), 7.37-7.41 (m, 1H), 3.59 (t, J=6.4 Hz, 2H), 3.44 (q, J=7.2 Hz, 2H), 3.11 (t, J=6.4 Hz, 2H), 1.25 (t, J=7.2 Hz, 3H). LCMS (m/z): 405 [M+H]⁺.

Example 7: 6-(2-amino-5-(5-fluoro-2-nitrophenyl)pyridin-3-yl)-3,4-dihydroisoquinolin-1(2H)-one
(I-7)

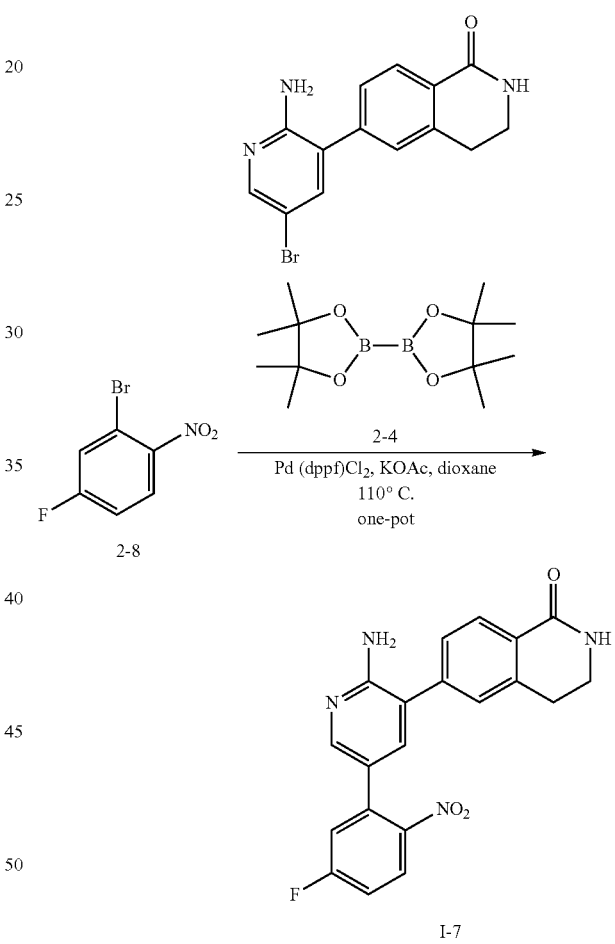

Step 1. 3-bromo-N-ethyl-4-fluorobenzamide (2-7)

A mixture of 3-bromo-4-fluorobenzoic acid (2-6, 1 g, 4.6 mmol), ethylamine (2 M solution in THF (4.6 ml, 9.2 mmol), EDCI (0.78 g, 5.0 mmol), HOBT (0.31 g, 2.3 mmol), triethylamine (1.9 ml, 13.8 mmol) and DCM (25 mL) was stirred at r.t overnight. Upon reaction completion, the mixture was diluted with dichloromethane (50 mL), washed with water (50 mL) and saturated sodium bicarbonate solution (50 mL×2), dried over anhydrous sodium sulfate, and concentrated. The resulting residue was then purified by flash column chromatography (Pet Ether/ethyl acetate=5/1) to provide intermediate 2-7 (white solid, 0.84 g, 75% yield). LCMS (m/z): 246 [M+H]⁺.

Step 2. 3-(6-amino-5-(1-oxo-1,2,3,4-tetrahydroisoquinolin-6-yl)pyridin-3-yl)-N-ethyl-4-fluorobenzamide (I-6)

To a mixture of 3-bromo-N-ethyl-4-fluorobenzamide (2-7, 116.0 mg, 0.47 mmol), 6-(2-amino-5-bromopyridin-3-yl)-3,4-dihydroisoquinolin-1 (2H)-one (2-4, 100.0 mg, 0.31 mmol), bis(pinacolato)diborane (157.5 mg, 0.62 mmol) and KOAc (91.1 mg, 0.93 mmol) in dioxane (2 mL) under argon was added Pd(dppf)Cl₂ (25.3 mg, 0.03 mol). The resulting reaction mixture was stirred at 110° C. for 2 h and then To a mixture of 2-bromo-4-fluoro-1-nitrobenzene (2-8, 116.0 mg, 0.71 mmol), 6-(2-amino-5-bromopyridin-3-yl)-3,4-dihydroisoquinolin-1(2H)-one (2-4, 150.0 mg, 0.47 mmol), bis(pinacolato)diborane (238.8 mg, 0.94 mmol) and KOAc (138.2 mg, 1.41 mmol) in dioxane (3 mL) under an atmosphere of argon was added Pd(dppf)Cl₂ (38.3 mg, 0.05 mol). The resulting reaction mixture was stirred at 110° C. overnight and then cooled, filtered and concentrated in vacuo. The resulting residue was purified by prep-HPLC (C18 column, CH₃CN/H₂O, containing 0.05% NH₄HCO₃) to provide compound I-7 (yellow solid, 17 mg, 10% yield). ¹H NMR (400 MHz, MeOD) δ: 8.09 (dd, J=8.8 Hz, J₂=5.2 Hz, 1H), 7.91-7.98 (m, 3H), 7.57 (dd, J₁=9.6 Hz, J₂=3.2 Hz, 1H), 7.41-7.46 (m, 4H), 6.15 (s, 2H), 3.41 (t, J=6.4 Hz, 2H), 2.96 (t, J=6.4 Hz, 2H). LCMS (m/z): 379 [M+H]⁺.

Example 8: 6-(6-amino-4'-methoxy-3,3'-bipyridin-5-yl)-3,4-dihydroisoquinolin-1(2H)-one (I-8)

Example 9: 6-(2-amino-5-(2-fluoro-3-nitrophenyl)pyridin-3-yl)-3,4-dihydroisoquinolin-1(2H)-one (I-9)

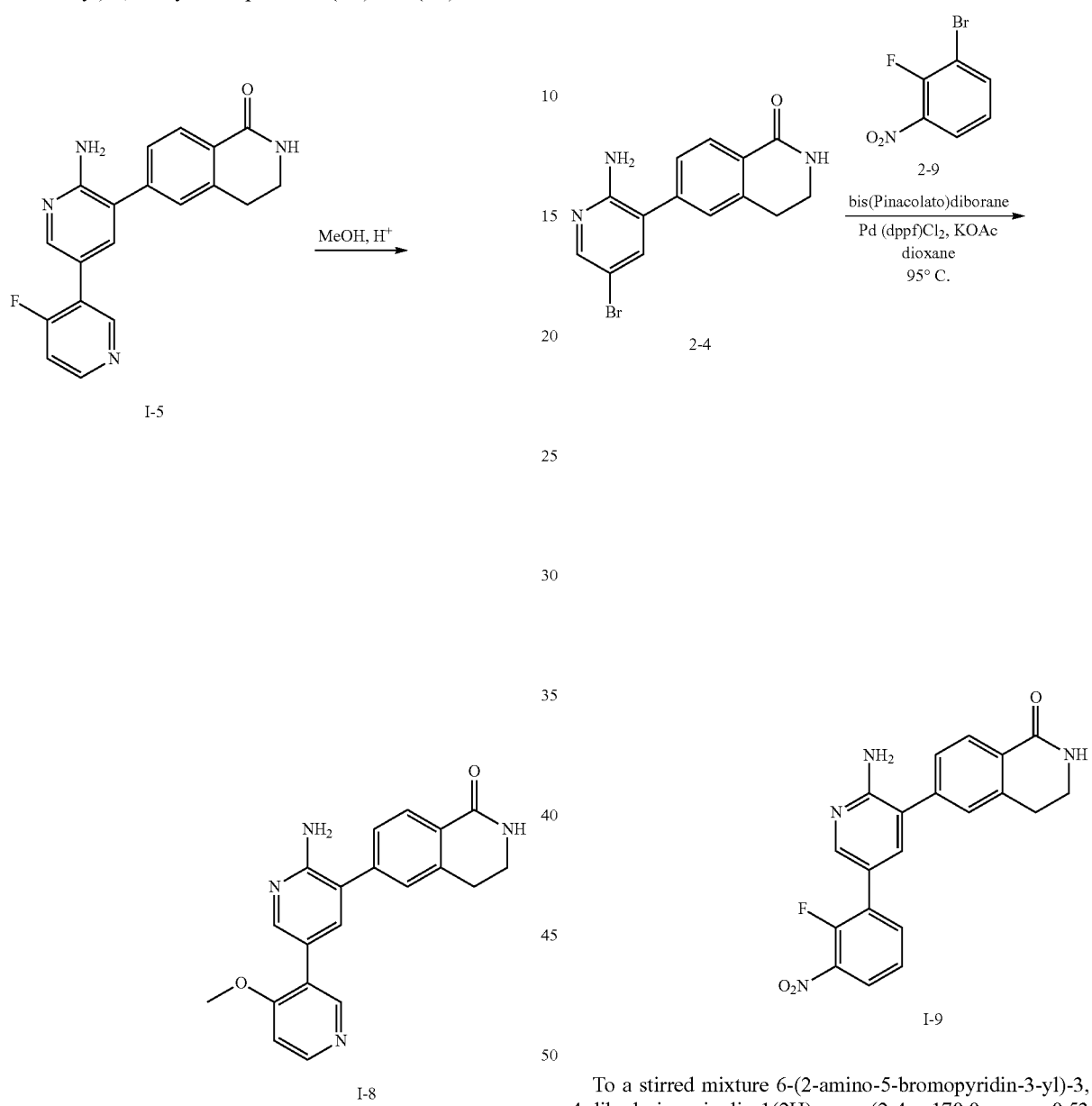

To a solution of 6-(2-amino-5-(2-fluorophenyl)pyridin-3-yl)-3,4-dihydroisoquinolin-1(2H)-one (I-5, 26 mg, 0.078 mmol) in methanol (0.5 mL) was added a solution of hydrochloric acid in methanol (3.0 M, 0.5 mL) in one portion at r.t. The reaction mixture was stirred at r.t for 1 h and then concentrated under reduced pressure. The resulting residue was purified by prep-TLC (DCM/MeOH=10/1) to provide compound I-8 (white solid, 25 mg, 93% yield). ¹H NMR (400 MHz, MeOD) δ: 8.41 (d, J=6.0 Hz, 1H), 8.38 (s, 1H), 8.14 (d, J=2.0 Hz, 1H), 8.06 (d, J=8.0 Hz, 1H), 7.65 (d, J=8.0 Hz, 1H), 7.52 (dd, J₁=8.0 Hz, J₂=1.2 Hz, 1H), 7.48 (s, 1H), 7.18 (d, J=6.0 Hz, 1H), 3.96 (s, 3H), 3.57 (t, J=6.4 Hz, 2H), 3.08 (t, J=6.6 Hz, 2H). LCMS (m/z): 347 [M+H]⁺.

To a stirred mixture 6-(2-amino-5-bromopyridin-3-yl)-3,4-dihydroisoquinolin-1(2H)-one (2-4, 170.0 mg, 0.53 mmol), 1-bromo-2-fluoro-3-nitrobenzene (234.9 mg, 1.07 mmol), bis(pinacolato)diborane (271 mg, 1.07 mmol) and KOAc (157.3 mg, 1.60 mmol) in dioxane (3 mL) under an atmosphere of argon was added Pd(dppf)Cl₂ (43.3 mg, 0.05 mol). The resulting mixture was heated at 95° C. for 2 h and then cooled, filtered and concentrated in vacuo. The resulting residue was purified by prep-TLC (ethyl acetate/PE=1/1) and prep-HPLC (C18 column, CH₃CN/H₂O, containing 0.05% NH₄HCO₃) to provide compound I-9 (yellow solid, 11 mg, 5.4% yield). ¹H NMR (400 MHz, MeOD) δ: 8.32 (d, J=2.4 Hz, 1H), 8.30 (d, J=2.0 Hz, 1H), 8.08 (d, J=7.6 Hz, 1H), 7.98-8.01 (m, 1H), 7.79 (d, J=2.4 Hz, 1H), 7.56 (dd, J₁=7.6 Hz, J₂=1.2 Hz, 1H), 7.47-7.52 (m, 2H), 3.58 (t, J=6.4 Hz, 2H), 3.09 (t, J=7.2 Hz, 2H). LCMS (m/z): 379 [M+H]⁺.

Example 10: 5-(2-amino-5-(2-fluoro-5-nitrophenyl)pyridin-3-yl)-2-hydroxybenzonitrile (I-11)

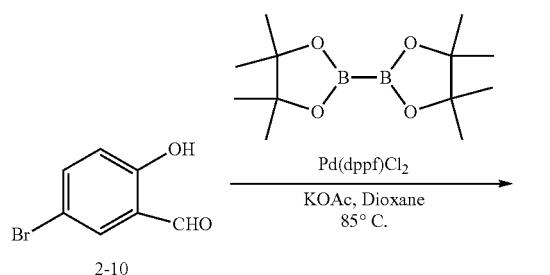

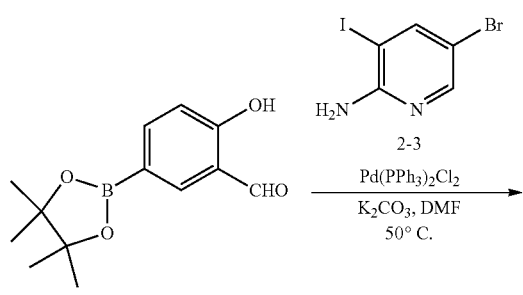

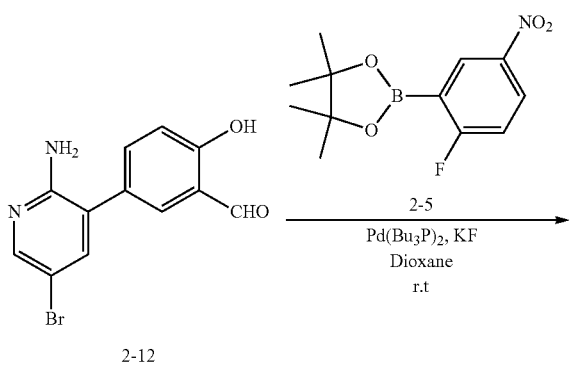

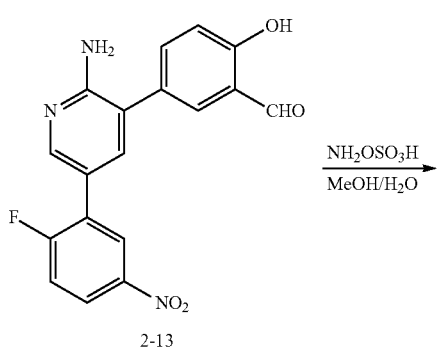

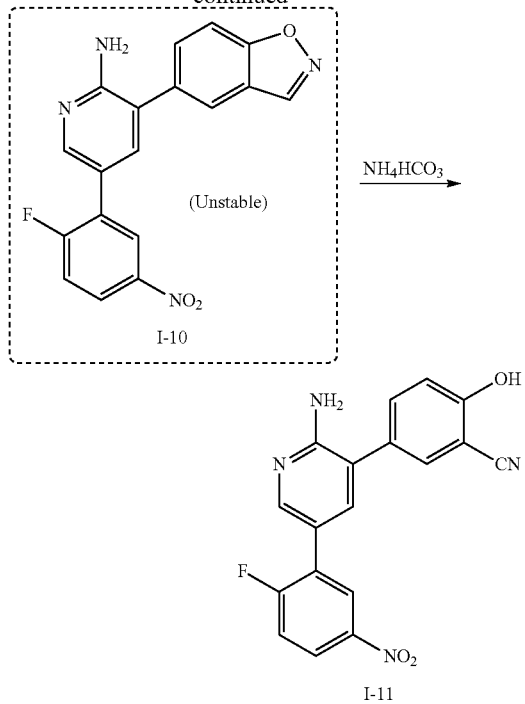

Step 1. 2-hydroxy-5-(4,4,5,5-tetramethyl-1,3,2-dioxaborolan-2-yl)benzaldehyde (2-11)

To a stirred mixture of 5-bromo-2-hydroxybenzaldehyde (2-10, 500 mg, 2.5 mmol), bis(pinacolato)diborane (762 mg, 3.0 mmol) and KOAc (735 mg, 7.5 mmol) in dioxane (10 mL) under an atmosphere of argon was added Pd(dppf)Cl$_2$ (288 mg, 0.25 mol). The resulting mixture was heated at 85° C. for 1h, and then cooled filtered, and concentrated in vacuo. The resulting residue was purified by silica gel chromatography (Pet Ether/ethyl acetate=5/1) to provide intermediate 2-11 (yellow solid, 500 mg, 80% yield). LCMS (m/z): 249 [M+H]$^+$.

Step 2. 5-(2-amino-5-bromopyridin-3-yl)-2-hydroxybenzaldehyde (2-12)

To a stirred mixture 2-hydroxy-5-(4,4,5,5-tetramethyl-1,3,2-dioxaborolan-2-yl)benzaldehyde (2-11, 500 mg, 2.0 mmol), 5-bromo-3-iodopyridin-2-amine (2-3, 720 mg, 2.4 mmol) and K$_2$CO$_3$ (828 mg, 6.0 mmol) in DMF (10 mL) under an atmosphere of argon was added Pd(PPh$_3$)$_2$Cl$_2$ (140 mg, 0.2 mol). The resulting mixture was heated at 50° C. overnight, then cooled and diluted with saturated NaHCO$_3$ solution (20 mL). The resulting mixture was extracted with ethyl acetate (2×30 mL) and the combined ethyl acetate extracts were washed with brine (5×50 mL), dried with MgSO$_4$, filtered and concentrated in vacuo. Purification of the resulting residue using silica gel chromatography (Pet Ether/ethyl acetate=3/1 to 1/1) provided intermediate 2-12 (300 mg, 51% yield) as a yellow solid. LCMS (m/z): 293 [M+H]$^+$.

Step 3. 5-(2-amino-5-(2-fluoro-5-nitrophenyl)pyridin-3-yl)-2-hydroxybenzaldehyde (2-13)

To a stirred mixture 5-(2-amino-5-bromopyridin-3-yl)-2-hydroxybenzaldehyde (2-12, 300 mg, 1.03 mmol), 2-(2- fluoro-5-nitrophenyl)-4,4,5,5-tetramethyl-1,3,2-dioxaborolane (2-5, 329 mg, 1.23 mmol) and KF (179 mg, 3.1 mmol) in dioxane (6 mL) under an atmosphere of argon was added bis(tri-tert-butylphosphine)palladium(0) (52 mg, 0.1 mol). The resulting mixture was stirred at r.t for 1 h, and then filtered and concentrated in vacuo. The resulting residue was purified by prep-TLC (Pet Ether/ethyl acetate=1/1) to provide intermediate 2-13 (180 mg, 42% yield) as a yellow solid. LCMS (m/z): 354 [M+H]$^+$.

Step 4. 5-(2-amino-5-(2-fluoro-5-nitrophenyl)pyridin-3-yl)-2-hydroxybenzonitrile (I-11)

A mixture of 5-(2-amino-5-(2-fluoro-5-nitrophenyl)pyridin-3-yl)-2-hydroxybenzaldehyde (2-13, 50 mg, 0.141 mmol), hydroxylamine-O-sulfonic acid (17.5 mg, 0.155 mmol) and 60 ml MeOH/H$_2$O (2/1) was stirred at room temperature overnight. Upon reaction completion, the reaction mixture was diluted with saturated NaHCO$_3$ solution (20 ml), extracted with DCM (20 ml×3), dried over anhydrous sodium sulfate, and concentrated. The crude product was purified by silica gel chromatography (Pet Ether/ethyl acetate=3/1) to provide compound I-11 (300 mg, 22% yield) as a yellow oil. $^1$H NMR (400 MHz, DMSO) δ: 8.43 (dd, J=6.8 Hz, J$_2$=2.8 Hz, 1H), 8.21-8.25 (m, 2H), 7.57-7.62 (m, 3H), 7.51-7.54 (m, 1H), 6.94-6.97 (m, 1H), 6.07 (s, 2H). LCMS (m/z): 351 [M+H]$^+$.

Example 11: 3-(6-amino-5-(1-oxo-1,2,3,4-tetrahydroisoquinolin-6-yl)pyridin-3-yl)-N-cyclopropylbenzenesulfonamide (I-12)

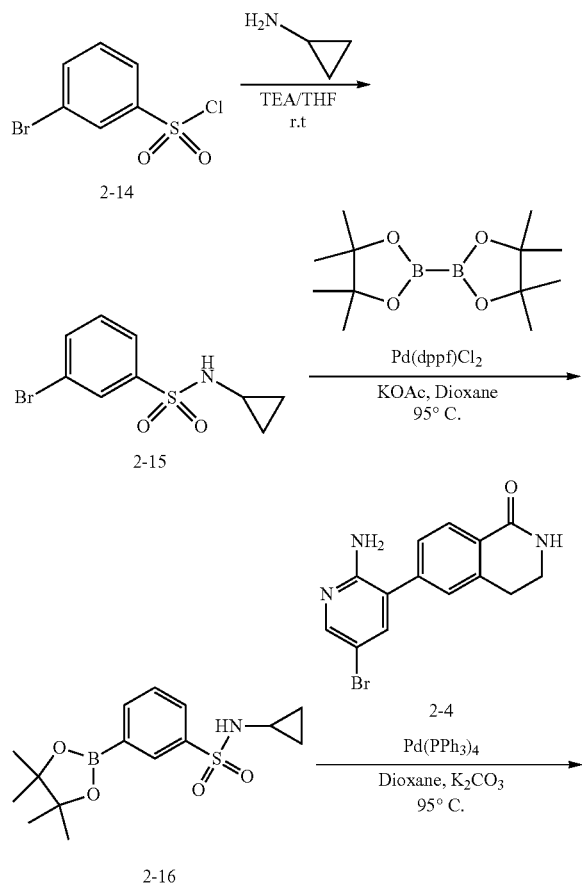

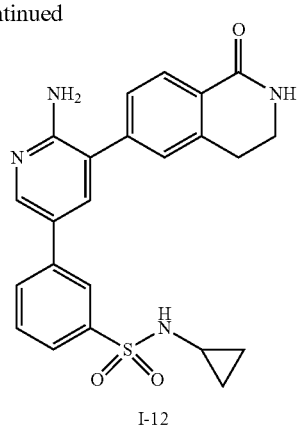

I-12

Step 1. 3-bromo-N-cyclopropylbenzenesulfonamide (2-15)

A mixture of 3-bromobenzene-1-sulfonyl chloride (2-14, 500 mg, 1.96 mmol), cyclopropanamine (2M in THF, 1.18 ml, 2.35 mmol), triethylamine (0.82 ml, 5.88 mmol) and DCM (10 mL) was stirred at r.t overnight. Upon reaction completion, the reaction mixture was diluted with dichloromethane (20 mL), washed with water (20 mL) and saturated sodium bicarbonate solution (20 mL×2), dried over anhydrous sodium sulfate, and concentrated to provide intermediate 2-15 (520 mg, 96% yield) as an off-white solid. LCMS (m/z): 276 [M+H]$^+$.

Step 2. N-cyclopropyl-3-(4,4,5,5-tetramethyl-1,3,2-dioxaborolan-2-yl)benzenesulfonamide (2-16)

To a stirred mixture 3-bromo-N-cyclopropylbenzenesulfonamide (2-15, 520.0 mg, 1.88 mmol), bis(pinacolato)-diborane (0.54 g, 2.26 mmol) and KOAc (0.56 g, 5.67 mmol) in dioxane (10 mL) under an atmosphere of argon was added Pd(dppf)Cl$_2$ (132 mg, 0.188 mol). The resulting mixture was heated at 95° C. overnight and then cooled filtered and concentrated in vacuo. Purification of the resulting residue using prep-TLC (Pet Ether/ethyl acetate=1/1) afforded intermediate 2-16 (380 mg, 62% yield) as a yellow solid. LCMS (m/z): 324 [M+H]$^+$.

Step 3. 3-(6-amino-5-(1-oxo-1,2,3,4-tetrahydroisoquinolin-6-yl)pyridin-3-yl)-N-cyclopropylbenzenesulfonamide (I-12)

To a stirred mixture N-cyclopropyl-3-(4,4,5,5-tetramethyl-1,3,2-dioxaborolan-2-yl) benzenesulfonamide (2-16, 200.0 mg, 0.62 mmol), 6-(2-amino-5-bromopyridin-3-yl)-3,4-dihydroisoquinolin-1(2H)-one (2-4, 196.5 mg, 0.62 mmol) and K2CO$_3$(256.7 mg, 1.86 mmol) in dioxane (4 mL) under an atmosphere of argon was added Pd(PPh$_3$)$_4$(71.6 mg, 0.062 mol). This mixture was heated at 95° C. for 1 h and then cooled, filtered and concentrated in vacuo. Purification of the resulting residue using prep-HPLC (C18 column, CH$_3$CN/H$_2$O, containing 0.05% NH$_4$HCO$_3$) afforded compound I-12 (42 mg, 16% yield) as a white solid. $^1$H NMR (400 MHz, DMSO) δ: 8.39 (d, J=2.0 Hz, 1H), 7.33 (d, J=8.4 Hz, 1H), 8.03 (s, 1H), 7.93-8.00 (m, 3H), 7.90 (d, J=2.4 Hz, 1H), 7.71-7.74 (m, 2H), 7.65 (t, J=7.6 Hz, 1H), 7.51 (d, J=8.0 Hz, 1H), 7.49 (s, 1H), 6.05 (s, 2H), 3.40-3.44 (m, 2H), 2.10-2.12 (m, 1H). LCMS (m/z): 435 [M+H]$^+$.

Example 12: 6-(2-amino-5-(benzo[d]thiazol-7-yl)pyridin-3-yl)-3,4-dihydroisoquinolin-1(2H)-one (I-13)

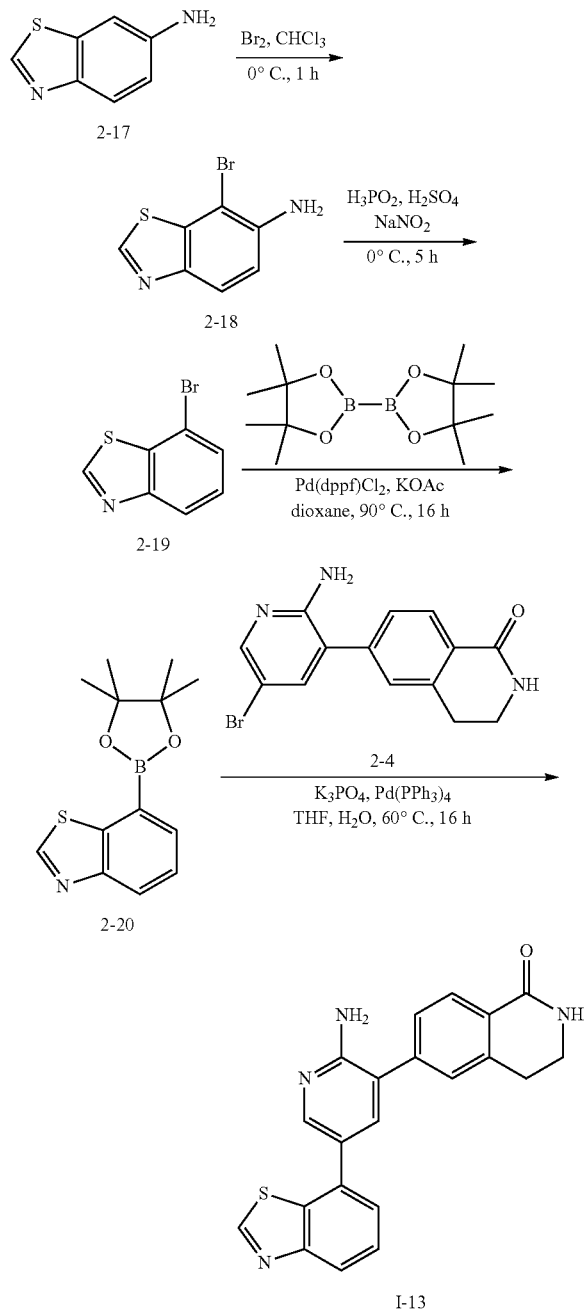

I-13

Step 1. 7-bromobenzo[d]thiazol-6-amine (2-18)

A mixture of benzo[d]thiazol-6-amine (2-17, 1 g, 6.6 mmol) and $Br_2$ (1.06 g, 6.6 mmol) in $CHCl_3$ (5 mL) was stirred at 0° C. for 1 h. Upon reaction completion, the resulting mixture was concentrated under reduced pressure to provide intermediate 2-18 (yellow solid, 1.2 g, 75% yield). LCMS (m/z): 229 [M+H]$^+$.

Step 2. 7-bromobenzo[d]thiazole (2-19)

To 7-bromobenzo[d]thiazol-6-amine (2-18, 1 g, 4.4 mmol) in $H_2SO_4$ (5 ml) was added $NaNO_2$ (605 mg, 8.8 mmol) at 0° C. and the resulting reaction mixture was stirred for 20 min. $H_3PO_2$ (5 ml) was then added at 0° C., and the mixture was stirred for 1 h. Upon reaction completion, the mixture was washed with saturated $NaHCO_3$, extracted with ethyl acetate (50 mL×3), and the combined organic phases were concentrated under reduced pressure to provide intermediate 2-19 (yellow solid, 400 mg, 42% yield). LCMS (m/z): 214 [M+H]$^+$.

Step 3. 7-(4,4,5,5-tetramethyl-1,3,2-dioxaborolan-2-yl)benzo[d]thiazole (2-20)

A mixture of 7-bromobenzo[d]thiazole (2-19, 200 mg, 0.95 mmol), 4,4,4',4',5,5,5',5'-octamethyl-2,2'-bi(1,3,2-dioxaborolane) (2-57, 240 mg, 0.95 mmol), KOAc (186 mg, 1.9 mmol), and Pd(dppf)$Cl_2$ (60 mg, 0.095 mmol) in 1,4-dioxane (5 ml) was stirred for 16 h at 90° C. Upon reaction completion, the resulting mixture was washed with $H_2O$, extracted with ethyl acetate (50 mL×3), concentrated under reduced pressure. The resulting residue was purified via silica gel chromatography (Pet Ether/ethyl acetate=10/1) to obtain intermediate 2-20 (yellow solid, 200 mg, 81% yield). LCMS (m/z): 262 [M+H]$^+$.

Step 4. 6-(2-amino-5-(benzo[d]thiazol-7-yl)pyridin-3-yl)-3,4-dihydroisoquinolin-1(2H)-one (I-13)

A mixture of 7-(4,4,5,5-tetramethyl-1,3,2-dioxaborolan-2-yl)benzo[d]thiazole (2-20, 82 mg, 0.315 mmol) and 6-(2-amino-5-bromopyridin-3-yl)-3,4-dihydroisoquinolin-1 (2H)-one (2-4, 100 mg, 0.315 mmol), $K_3PO_4$ (133 mg, 0.63 mmol), Pd(PPh$_3$)$_4$ (36 mg, 0.0315 mmol) in THF (2 mL) and $H_2O$ (0.1 mL) was stirred at 60° C. for 16 h. Upon reaction completion, the resulting mixture was concentrated under reduced pressure and the residue was purified by prep-HPLC (C18 column, $CH_3CN/H_2O$, containing 0.05% $NH_4HCO_3$) to provide compound I-13 (white solid, 49 mg, 42% yield). $^1$H NMR (DMSO-d$_6$, 500 MHz) δ 9.44 (s, 1H), 8.38 (s, 1H), 8.05-8.07 (m, 3H), 7.72 (d, J=2.0 Hz, 1H), 7.64 (d, J=6.5 Hz, 2H), 7.50-7.53 (m, 2H), 6.13 (s, 2H), 3.17 (t, J=7 Hz, 2H), 2.97 (t, J=6.5 Hz, 2H). HPLC: 100% (@254 nm). LCMS (m/z): 373 [M+H]$^+$.

Example 13: 6-(2-amino-5-(1-methyl-1H-benzo[d]imidazol-4-yl)pyridin-3-yl)-3,4-dihydroisoquinolin-1(2H)-one (I-14)

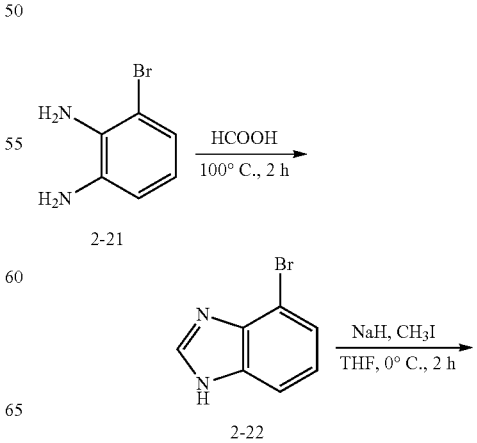

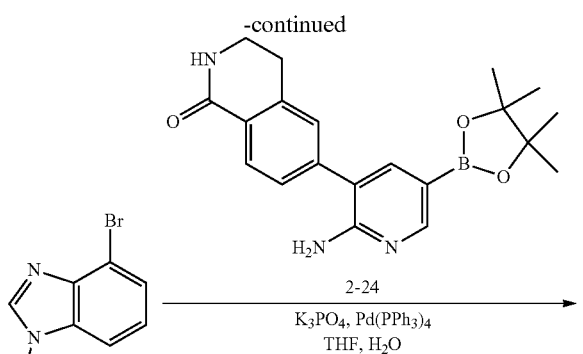

NMR (DMSO-d$_6$, 500 MHz) δ 8.76 (d, J=2.5 Hz, 1H), 8.20 (t, J=2.5 Hz, 2H), 7.95 (t, J=8 Hz, 2H), 7.33-7.51 (m, 4H), 7.32 (t, J=7.5 Hz, 1H), 5.90 (s, 2H), 3.87 (s, 3H), 3.49-3.44 (m, 2H), 2.97 (t, J=6 Hz, 2H). HPLC: 100% (@254 nm). LCMS (m/z): 370 [M+H]$^+$.

Example 14: 6-(2-amino-5-(benzo[b]thiophen-4-yl)pyridin-3-yl)-3,4-dihydroisoquinolin-1(2H)-one (I-15)

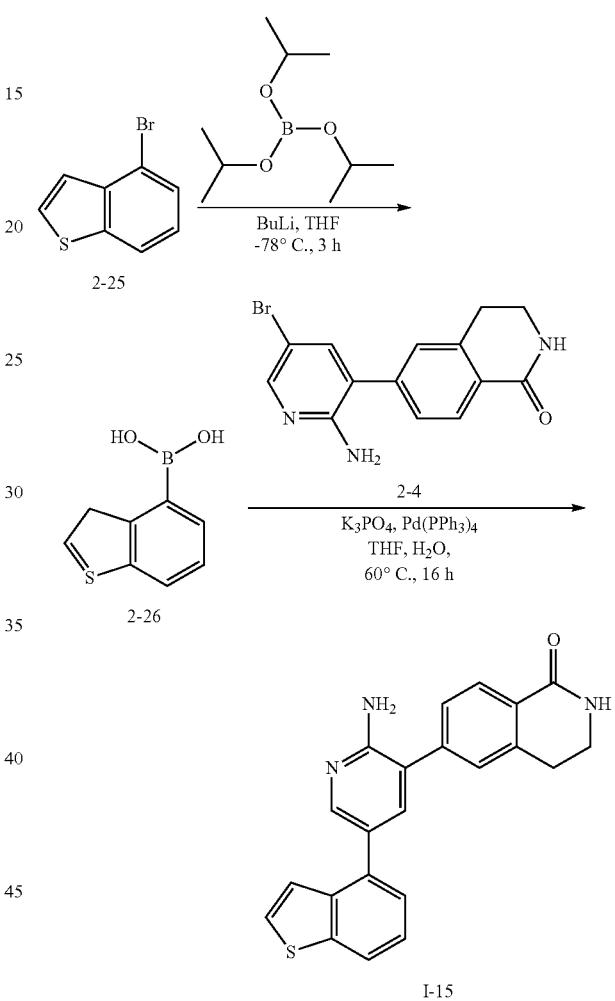

Step 1. 4-bromo-1H-benzo[d]imidazole (2-22)

A solution of 3-bromobenzene-1,2-diamine (2-21, 400 mg, 2.15 mmol) in HCOOH (5 mL) was stirred at 100° C. for 2 h. Upon reaction completion, the resulting mixture was concentrated under reduced pressure to provide intermediate 2-22 (yellow solid, 410 mg, 97% yield). LCMS (m/z): 197 [M+H]$^+$.

Step 2. 4-bromo-1-methyl-1H-benzo[d]imidazole (2-23)

A mixture of 4-bromo-1H-benzo[d]imidazole (2-22, 100 mg, 0.51 mmol), NaH (25 mg, 1.02 mmol) and CH$_3$I (142 mg, 0.51 mmol) in THF (5 mL) was stirred at 0° C. for 2 h. Upon reaction completion, the resulting mixture was concentrated under reduced pressure to provide intermediate 2-23 (yellow solid, 50 mg, 46% yield). LCMS (m/z): 211 [M+H]$^+$.

Step 3. 6-(2-amino-5-(1-methyl-1H-benzo[d]imidazol-4-yl)pyridin-3-yl)-3,4-dihydroisoquinolin-1(2H)-one (I-14)

A mixture of 4-bromo-1-methyl-1H-benzo[d]imidazole (2-23, 50 mg, 0.23 mmol) and 6-(2-amino-5-(4,4,5,5-tetramethyl-1,3,2-dioxaborolan-2-yl)pyridin-3-yl)-3,4-dihydroisoquinolin-1(2H)-one (2-24, 83 mg, 0.23 mmol), K3PO$_4$ (98 mg, 0.46 mmol), Pd(PPh$_3$)$_4$(36 mg, 0.0315 mmol) in THF (2 mL) and H$_2$O (0.1 mL) was stirred at 60° C. for 16 h. Upon reaction completion, the resulting mixture was concentrated under reduced pressure and purified by prep-HPLC(C18 column, CH$_3$CN/H$_2$O, containing 0.05% NH$_4$HCO$_3$) to provide compound I-14 (white solid, 10 mg, 9% yield). $^1$H Step 1. benzo[b]thiophen-4-ylboronic acid (2-26)

A mixture of 4-bromobenzo[b]thiophene (2-25, 140 mg, 0.65 mmol), triisopropyl borate (122 mg, 0.65 mmol), and n-BuLi (0.52 mL, 0.65 mmol, 1.5M) in THF (5 mL) was stirred at −78° C. for 2 h. Upon reaction completion, the resulting mixture was washed with H$_2$O, extracted with ethyl acetate (50 mL×3), concentrated under reduced pressure to provide intermediate 2-26 (yellow solid, 60 mg, 49% yield). LCMS (m/z): 177 [M+H]$^+$.

Step 2. 6-(2-amino-5-(benzo[b]thiophen-4-yl)pyridin-3-yl)-3,4-dihydroisoquinolin-1(2H)-one (I-15)

A mixture of benzo[b]thiophen-4-ylboronic acid (2-26, 60 mg, 0.71 mmol), 6-(2-amino-5-bromopyridin-3-yl)-3,4-dihydroisoquinolin-1(2H)-one (2-4, 100 mg, 0.31 mmol), Pd(PPh₃)₄(30 mg, 0.0315 mmol) in THF (2 mL) and H₂O (0.1 mL) was stirred at 60° C. for 16 h, Upon reaction completion, the resulting mixture was concentrated under reduced pressure and residue was purified by prep-HPLC (C18 column, CH₃CN/H₂O, containing 0.05% NH₄HCO₃) to get provide compound I-15 (white solid, 60 mg, 50% yield). ¹H NMR (DMSO-d₆, 500 MHz) δ 8.40 (d, J=2.5 Hz, 1H), 8.00 (s, 1H), 7.93-7.95 (m, 2H), 7.75-7.77 (m, 3H), 7.50 (t, J=4 Hz, 2H), 7.31-7.36 (m, 2H), 6.12 (s, 2H), 3.42 (t, J=6 Hz, 4H), 2.99 (t, J=6 Hz, 2H). HPLC: 99% (@254 nm). LCMS (m/z): 372 [M+H]⁺.

Example 15: 6-(2-amino-5-(1,1-Dioxo-benzo[b]thiophen-4-yl)pyridin-3-yl)-3,4-dihydroisoquinolin-1(2H)-one (I-16)

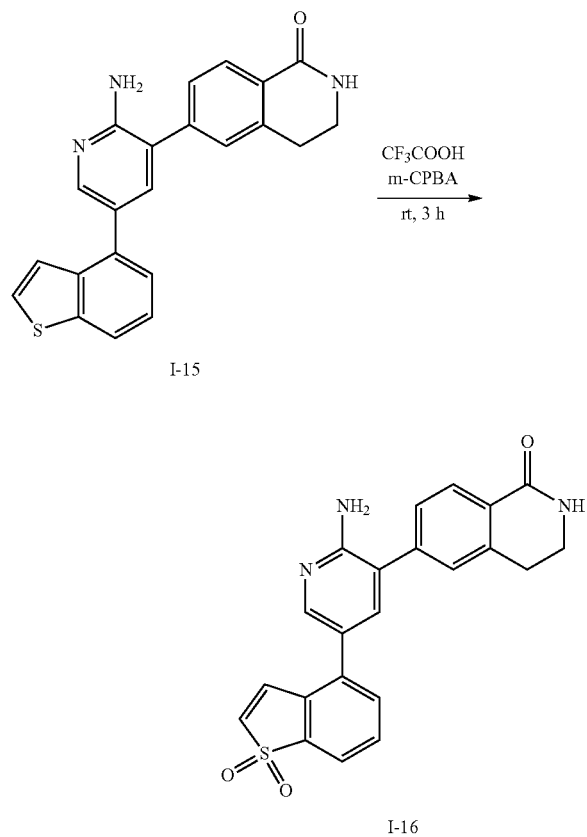

A mixture of 6-(2-amino-5-(benzo[b]thiophen-4-yl)pyridin-3-yl)-3,4-dihydroisoquinolin-1(2H)-one (I-15, 50 mg, 0.13 mmol), m-CPBA (46 mg, 0.26 mmol), and TFA (0.1 mL) in DCM (2 mL) was stirred at rt for 3 h. Upon reaction completion, the mixture was concentrated under reduced pressure and the resulting residue was purified by prep-HPLC (C18 column, CH₃CN/H₂O, containing 0.05% NH₄HCO₃) to provide compound I-16 (white solid, 5 mg, 9% yield). ¹H NMR (DMSO-d₆, 500 MHz) δ 8.48 (d, J=2.5 Hz, 1H), 7.96 (s, 1H), 7.95 (d, J=8 Hz, 1H), 7.90 (d, J=7.5 Hz, 1H), 7.81 (s, 1H), 7.79 (d, J=2.5 Hz, 1H), 7.70 (t, J=7.5 Hz, 2H), 7.44-7.46 (m, 2H), 6.54 (s, 2H), 3.42-3.43 (m, 2H), 2.99 (t, J=6.5 Hz, 2H). HPLC: 100% (@254 nm). LCMS: 404 (M+H)⁺.

Example 16: 6-(2-amino-5-(3-fluoro-5-nitrophenyl)pyridin-3-yl)-3,4-dihydroisoquinolin-1(2H)-one (I-17)

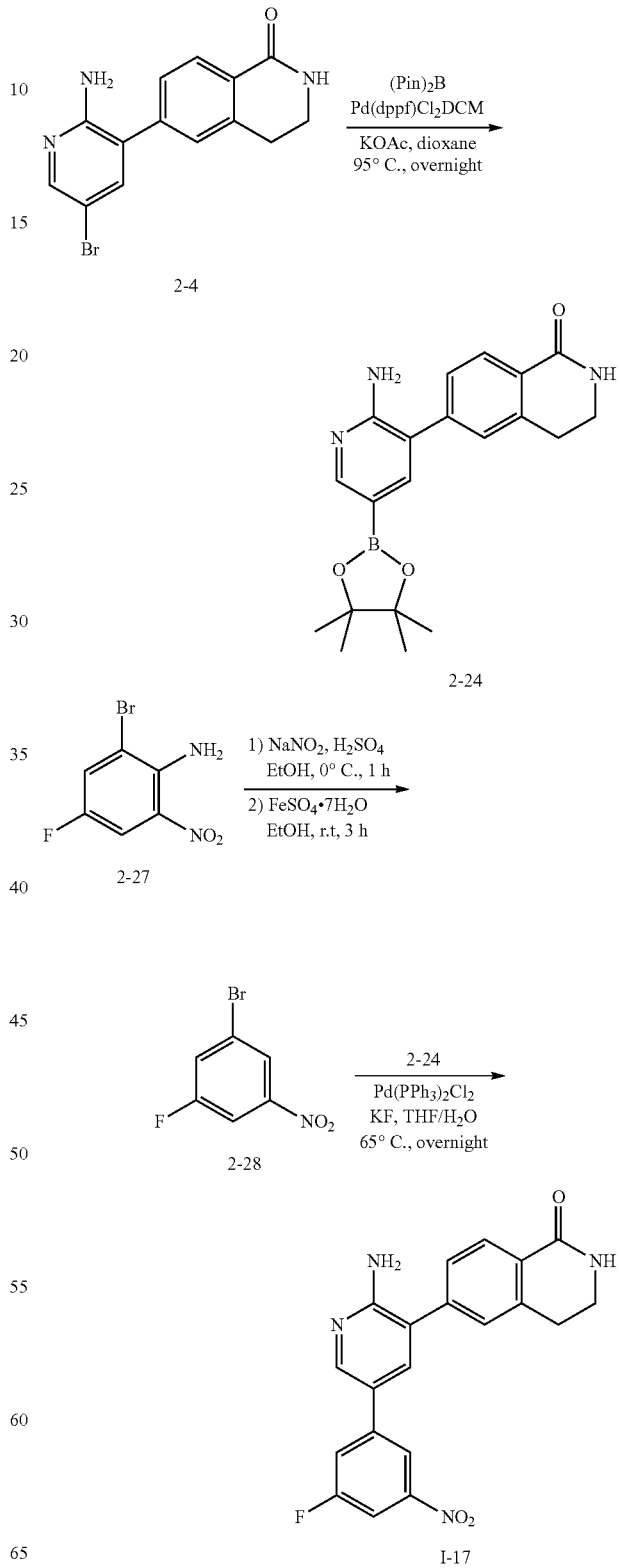

Step 1. 6-(2-amino-5-(4,4,5,5-tetramethyl-1,3,2-dioxaborolan-2-yl)pyridin-3-yl)-3,4-dihydroisoquinolin-1(2H)-one (2-24)

A mixture of 2-4 (1.58 g, 5 mmol), (PinB)₂ (2.28 g, 9 mmol), Pd(dppf)Cl₂DCM (408 mg, 0.5 mmol), KOAc (980 mg, 10 mmol) and dioxane (3 mL) was degassed with N₂ and stirred at 95° C. overnight. The resulting mixture was filtered and the filtrate was concentrated and purified by column chromatography on silica gel eluting with PE/ethyl acetate from 3/1 to 1/1 to provide intermediate 2-24 (yellow solid, 1.39 g, 76% yield). LCMS (m/z): 366 [M+H]⁺.

Step 2. 1-bromo-3-fluoro-5-nitrobenzene (2-28)

To a solution of 2-27 (702 mg, 3 mmol) in EtOH (3 mL) at 0° C., was added 6 ml 60% H₂SO₄ followed by slow addition (in portions) of NaNO₂ (414 mg, 6 mmol). Upon reaction completion of the addition, the stirring was continued for 1 h while the temperature was kept during 0-5° C. FeSO₄·7H₂O (4.38 g, 6 mmol) was then added and the resulting mixture was stirred for another 3h. The mixture was then concentrated, water was added and the resulting aqueous mixture was extracted with DCM (20 mL×3). The combined organic layers were washed with brine (20 mL), dried over Na₂SO₄, filtered and concentrated. The resulting residue was purified by prep-TLC and eluted with DCM/MeOH=60/1 to provide intermediate 2-28 (yellow solid, 448 mg, 68% yield).

Step 3. 6-(2-amino-5-(3-fluoro-5-nitrophenyl)pyridin-3-yl)-3,4-dihydroisoquinolin-1(2H)-one (I-17)

A mixture of 2-28 (216 mg, 1 mmol), 2-24 (317 mg, 1 mmol), Pd(PPh₃)₂Cl₂ (70 mg, 0.1 mmol), KF (116 mg, 2 mmol), THF (2 mL) and H₂O (0.5 mL) was degassed with N₂ and stirred at 65° C. overnight. The resulting mixture was filtered and the filtrate was concentrated and purified by prep-HPLC eluting with CH₃CN/H₂O (with 0.5% NH₄HCO₃) to provide compound I-17 (off-white solid, 125 mg, 33% yield). ¹H NMR (DMSO-d₆, 400 MHz): δ 8.51 (d, J=2.8 Hz, 1H), 8.36 (s, 1H), 8.14 (dt, J₁=8.0 Hz, J₂=2.0 Hz, 1H), 7.98-8.00 (m, 2H), 7.93 (d, J=8.0 Hz, 1H), 7.87 (d, J=2.4 Hz, 1H), 7.53 (d, J=8.0 Hz, 1H), 7.50 (s, 1H), 6.21 (s, 2H), 3.42 (dt, J₁=6.4 Hz, J₂=2.4 Hz, 2H), 2.98 (t, J=6.4 Hz, 2H). HPLC: 100% (254 nm). LCMS (m/z): 379 [M+H]⁺.

Example 17: 6-(2-amino-5-(2,3-difluoro-5-nitrophenyl)pyridin-3-yl)-3,4-dihydroisoquinolin-1(2H)-one (I-18)

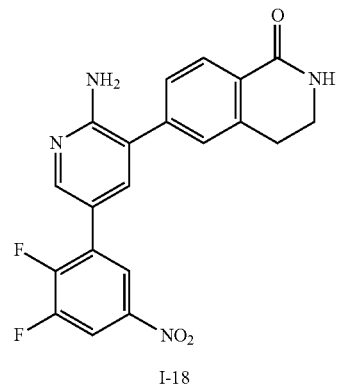

I-18

A mixture of 1-bromo-2,3-difluoro-5-nitrobenzene (2-29, 90 mg, 0.379 mmol) and 6-(2-amino-5-(4,4,5,5-tetramethyl-1,3,2-dioxaborolan-2-yl)pyridin-3-yl)-3,4-dihydroisoquinolin-1(2H)-one (2-24, 139 mg, 0.379 mmol), K₃PO₄ (160 mg, 0.758 mmol), Pd(PPh₃)₄ (43 mg, 0.0379 mmol) in THF (2 mL) and H₂O (0.1 mL) was stirred at 60° C. for 16 h. Upon reaction completion, the resulting mixture was concentrated under reduced pressure and purified by prep-HPLC (C18 column, CH₃CN/H₂O, containing 0.05% NH₄HCO₃) to obtain compound I-18 (white solid, 12 mg, 6% yield). ¹H NMR (DMSO-d₆, 500 MHz) δ 8.41-8.48 (m, 2H), 8.36 (s, 1H), 8.05 (s, 1H), 7.96-7.97 (m, 2H), 7.49-7.53 (m, 2H), 7.17 (s, 2H), 3.40-3.43 (m, 2H), 2.97 (t, J=6.5 Hz, 2H). HPLC: 100% (@254 nm). LCMS (m/z): 397 [M+H]⁺.

Example 18: 6-(2-amino-5-(5-chloro-2-fluorophenyl)pyridin-3-yl)-3,4-dihydroisoquinolin-1(2H)-one (I-19)

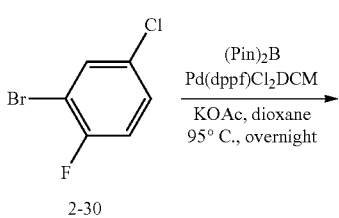

2-30

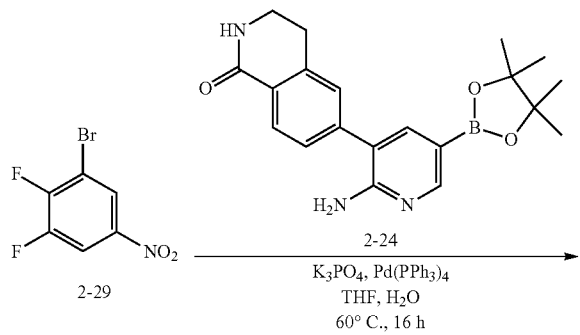

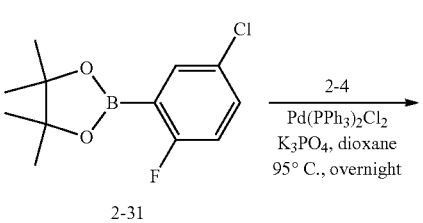

2-31

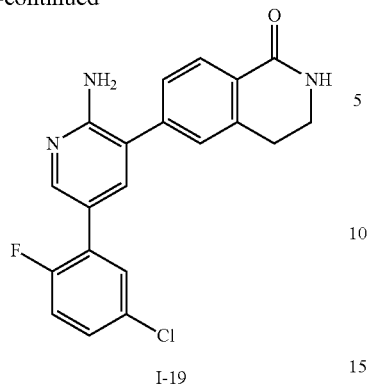

I-19

Step 1. 2-(5-chloro-2-fluorophenyl)-4,4,5,5-tetramethyl-1,3,2-dioxaborolane (2-31)

A mixture of 2-30 (1.04 g, 5 mmol), (PinB)$_2$ (2.28 g, 9 mmol), Pd(dppf)Cl$_2$DCM (408 mg, 0.5 mmol), KOAc (980 mg, 10 mmol) and dioxane (5 mL) was degassed with N$_2$ and stirred at 95° C. overnight. The resulting mixture was filtered and the filtrate was concentrated and purified by column chromatography on silica gel eluting with PE/ethyl acetate from 20/1 to 10/1 to provide intermediate 2-31 (806 mg, 63% yield) as a yellow solid. LCMS (m/z): 173 [M−H−82]−.

Step 2. 6-(2-amino-5-(5-chloro-2-fluorophenyl)pyridin-3-yl)-3,4-dihydroisoquinolin-1(2H)-one (I-19)

A mixture of 2-31 (384 mg, 1.5 mmol), 2-4 (317 mg, 1 mmol), Pd(PPh$_3$)$_2$Cl$_2$ (70 mg, 0.1 mmol), K$_3$PO$_4$ (424 mg, 2 mmol) and dioxane (3 mL) was degassed with N$_2$ and stirred at 95° C. overnight. The resulting mixture was filtered and the filtrate was concentrated and purified by prep-HPLC eluting with CH$_3$CN/H$_2$O (with 0.5% NH$_4$HCO$_3$) from 9/1 to 1/9 to provide compound I-19 (off-white solid, 128 mg, 34% yield). $^1$H NMR (DMSO-d$_6$, 500 MHz): δ 8.22 (t, J=1.6 Hz, 1H), 7.99 (s, 1H), 7.92 (d, J=6.4 Hz, 1H), 7.70 (dd, J$_1$=5.6 Hz, J$_2$=3.6 Hz, 1H), 7.59 (s, 1H), 7.50 (d, J=6.4 Hz, 1H), 7.47 (s, 1H), 7.39-7.42 (m, 1H), 7.35 (t, J=8.0 Hz, 1H), 6.12 (s, 2H), 3.41 (dt, J$_1$=5.2 Hz, J$_2$=2.4 Hz, 2H), 2.96 (t, J=5.2 Hz, 2H). HPLC: 100% (254 nm). LCMS (m/z): 368 [M+H]+.

Example 19: 6-(2-amino-5-(5-((dimethylamino)methyl)-2-fluorophenyl)pyridin-3-yl)-3,4-dihydroisoquinolin-1(2H)-one (I-20)

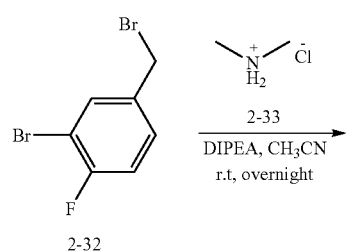

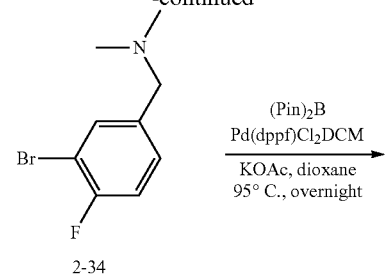

2-34

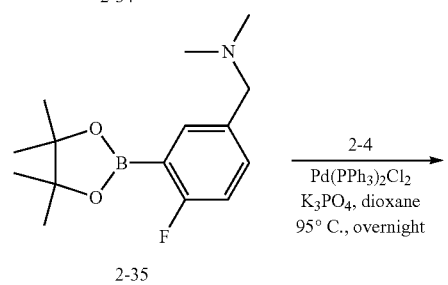

2-35

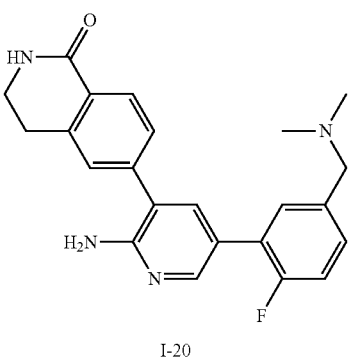

I-20

Step 1. (3-bromo-4-fluorophenyl)-N,N-dimethylmethanamine (2-34)

To a solution of 2-33 (1.34 g, 5 mmol) in CH$_3$CN (15 mL) at 0° C., 2-32 (490 mg, 6 mmol) was added slowly DIPEA (1.29 g, 10 mmol). Upon completion of the addition, the mixture was stirred at r.t overnight. The reaction mixture was concentrated and water (20 mL) was added. The resulting mixture was extracted with DCM (20 mL×3) and the combined organic layers were washed with brine (20 mL), dried over Na$_2$SO$_4$, filtered and concentrated. The resulting residue was purified via column chromatography on silica gel eluting with PE/ethyl acetate from 20/1 to 15/1 to provide intermediate 2-34 (off-white solid, 947 mg, 82% yield). LCMS (m/z): 232 [M+H]+.

Step 2. (4-fluoro-3-(4,4,5,5-tetramethyl-1,3,2-dioxaborolan-2-yl)phenyl)-N,N-dimethylmethanamine (2-35)

A mixture of 2-34 (462 mg, 2 mmol), (Pin)$_2$B (914 mg, 3.6 mmol), Pd(dppf)Cl$_2$DCM (183 mg, 0.2 mmol), KOAc (392 mg, 4 mmol) and dioxane (3 mL) was degassed with N$_2$ and stirred at 95° C. overnight. The resulting mixture was filtered and the filtrate was concentrated and purified via column chromatography on silica gel eluting with PE/ethyl acetate from 20/1 to 10/1 to provide intermediate 2-35 (yellow solid, 273 mg, 49% yield). LCMS (m/z): 198 [M+H-82]+.

Step 3. 6-(2-amino-5-(5-((dimethylamino)methyl)-2-fluorophenyl)pyridin-3-yl)-3,4-dihydroisoquinolin-1(2H)-one (I-20)

A mixture of 2-35 (209 mg, 0.75 mmol), 2-4 (158 mg, 0.5 mmol), Pd(PPh₃)₂Cl₂ (35 mg, 0.05 mmol), K₃PO₄ (212 mg, 1 mmol) and dioxane (2 mL) was degassed with N₂ and stirred at 95° C. overnight. The resulting mixture was filtered and the filtrate was concentrated and purified via prep-HPLC eluting with CH₃CN/H₂O (with 0.5% NH₄HCO₃) to provide compound I-20 (off-white solid, 101 mg, 52% yield). $^1$H NMR (DMSO-d₆, 500 MHz): δ 8.19 (t, J=1.6 Hz, 1H), 7.98 (s, 1H), 7.92 (d, J=6.4 Hz, 1H), 7.54 (s, 1H), 7.43-7.49 (m, 3H), 7.20-7.26 (m, 2H), 6.01 (s, 2H), 3.40-3.42 (m, 4H), 2.96 (t, J=4.8 Hz, 2H), 2.15 (s, 6H). HPLC: 100% (254 nm). LCMS (m/z): 391 [M+H]⁺.

Example 20: N-(5-(6-amino-5-(1-oxo-1,2,3,4-tetrahydroisoquinolin-6-yl)pyridin-3-yl)-4-fluoro-2-methylphenyl)acetamide (I-21)

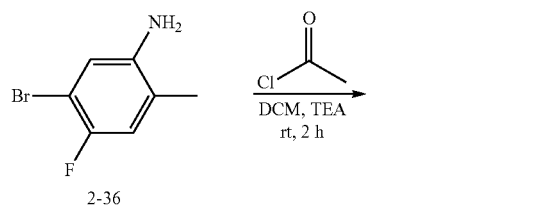

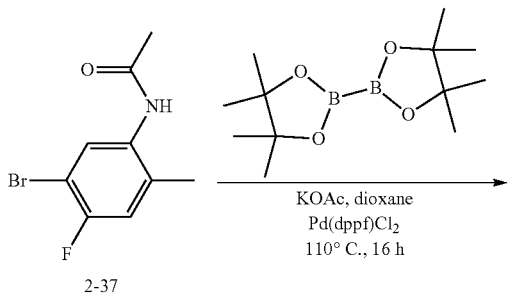

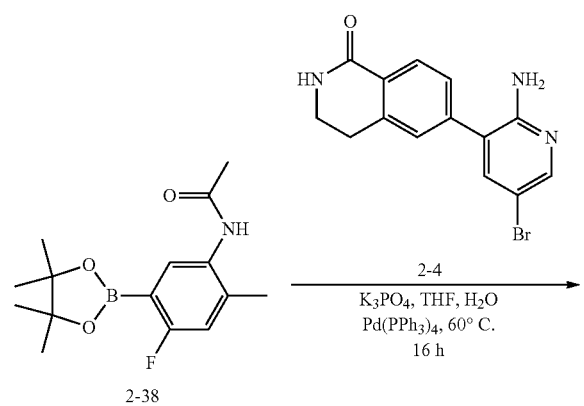

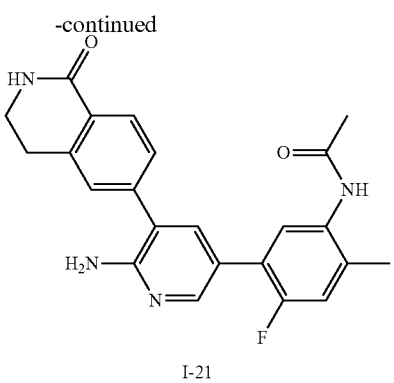

I-21

Step 1. N-(5-bromo-4-fluoro-2-methylphenyl)acetamide (2-37)

A mixture of 3-bromo-4-fluoro-2-methylaniline (2-36, 200 mg, 0.98 mmol), K₂CO₃ (272 mg, 1.96 mmol) and acetyl chloride (77 mg, 0.98 mmol) in DCM (5 mL) was stirred at rt for 2 h. Upon reaction completion, the resulting mixture was filtered and the filtrate was concentrated under reduced pressure to provide intermediate 2-37 (yellow solid, 220 mg, 92% yield). LCMS (m/z): 246 [M+H]⁺.

Step 2. N-(4-fluoro-2-methyl-5-(4,4,5,5-tetramethyl-1,3,2-dioxaborolan-2-yl)phenyl)acetamide (2-38)

A mixture of N-(5-bromo-4-fluoro-2-methylphenyl)acetamide (2-37, 100 mg, 0.4 mmol), 4,4,4',4',5,5,5',5'-octamethyl-2,2'-bi(1,3,2-dioxaborolane) (2-57, 102 mg, 0.4 mmol), KOAc (98 mg, 0.8 mmol), and Pd(dppf)Cl₂ (40 mg, 0.04 mmol) in 1,4-dioxane (5 mL) was stirred for 16 h at 110° C. Upon reaction completion, the resulting mixture was washed with H₂O, extracted with ethyl acetate (50 mL×3), concentrated under reduced pressure, and purified via silica gel chromatography (Pet Ether/ethyl acetate=10/1) to obtain intermediate 2-38 (white solid, 85 mg, 70% yield). LCMS (m/z): 294 [M+H]⁺.

Step 3. N-(5-(6-amino-5-(1-oxo-1,2,3,4-tetrahydroisoquinolin-6-yl)pyridin-3-yl)-4-fluoro-2-methylphenyl)acetamide (1-21)

A mixture of N-(4-fluoro-2-methyl-5-(4,4,5,5-tetramethyl-1,3,2-dioxaborolan-2-yl)phenyl)acetamide (2-38, 82 mg, 0.28 mmol), 6-(2-amino-5-bromopyridin-3-yl)-3,4-dihydroisoquinolin-1(2H)-one (2-4, 90 mg, 0.28 mmol), K₃PO₄ (119 mg, 0.56 mmol), Pd(PPh₃)₄ (32 mg, 0.028 mmol) in THF (2 mL), and H₂O (0.1 mL) was stirred at 60° C. for 16 h. Upon reaction completion, the resulting mixture was concentrated under reduced pressure and the resulting residue was purified using prep-HPLC (C18 column, CH₃CN/H₂O, containing 0.05% NH₄HCO₃) to provide compound I-21 (white solid, 20 mg, 17% yield). $^1$H NMR (DMSO-d₆, 400 MHz) δ 9.36 (s, 1H), 8.13 (s, 1H), 7.89-7.95 (m, 2H), 7.44-7.50 (m, 4H), 7.15 (d, J=11.2 Hz, 1H), 5.97 (s, 2H), 3.38-3.41 (m, 2H), 2.95 (t, J=6.4 Hz, 2H). HPLC: 98% (@254 nm). LCMS (m/z): 405 [M+H]⁺.

Example 21: 6-(2-amino-5-(4-chloro-2-fluoro-5-nitrophenyl)pyridin-3-yl)-3,4-dihydroisoquinolin-1(2H)-one (I-22)

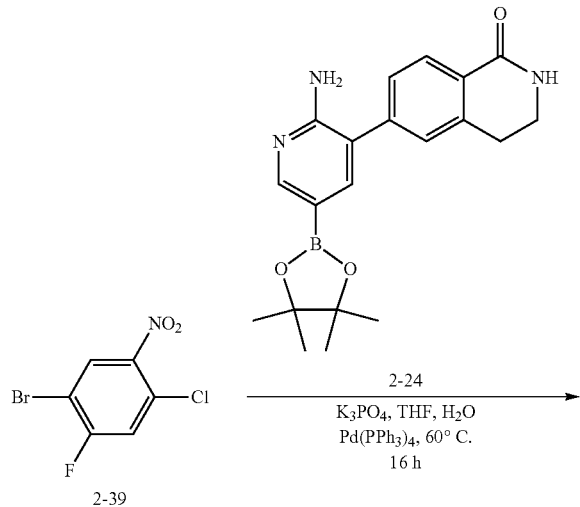

A mixture of 1-bromo-4-chloro-2-fluoro-5-nitrobenzene (2-39, 95 mg, 0.379 mmol) and 6-(2-amino-5-(4,4,5,5-tetramethyl-1,3,2-dioxaborolan-2-yl)pyridin-3-yl)-3,4-dihydroisoquinolin-1(2H)-one (2-24, 100 mg, 0.379 mmol), $K_3PO_4$ (160 mg, 0.758 mmol), $Pd(PPh_3)_4$ (43 mg, 0.0379 mmol) in THF (2 mL) and $H_2O$ (0.1 mL) was stirred at 60° C. for 16 h. Upon reaction completion, the resulting mixture was concentrated under reduced pressure and the residue was purified via prep-HPLC (C18 column, $CH_3CN/H_2O$, containing 0.05% TFA) to provide compound I-22 (white solid, 35 mg, 22% yield). $^1H$ NMR (DMSO-$d_6$, 400 MHz) δ 8.45 (d, J=7.6 Hz, 1H), 7.94-8.03 (m, 3H), 7.84 (s, 1H), 7.49-7.53 (m, 2H), 6.85 (s, 2H), 3.38 (s, 2H), 2.97 (t, J=4 Hz, 2H). HPLC: 96% (@254 nm). LCMS (m/z): 413 [M+H]$^+$.

Example 22: 6-(6-amino-5-(1-oxo-1,2,3,4-tetrahydroisoquinolin-6-yl)pyridin-3-yl)-7-fluoro-2H-benzo[b][1,4]oxazin-3(4H)-one (I-23)

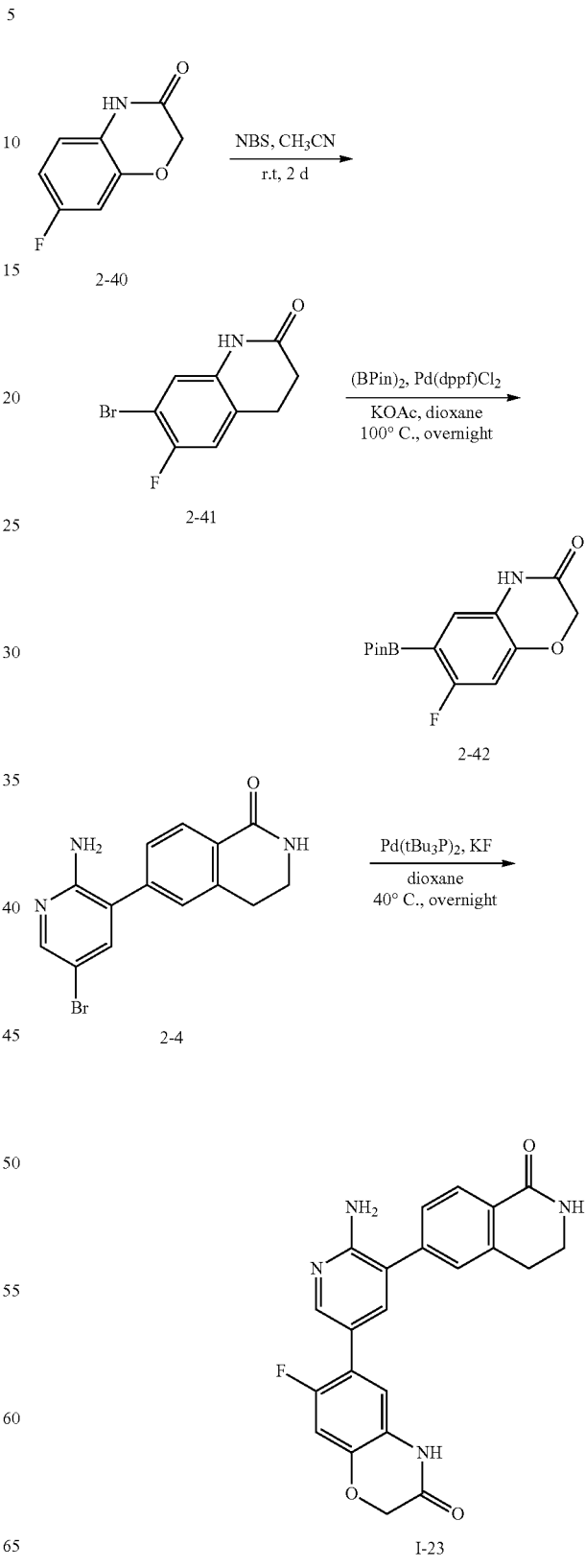

Step 1. 7-bromo-6-fluoro-3,4-dihydroquinolin-2(1H)-one (2-41)

To a mixture of 2-40 (630 mg, 3.77 mmol) in CH$_3$CN (60 mL) was added NBS (1.5 g, 8.43 mmol) and the resulting mixture was stirred at r.t for 2 d. Upon reaction completion, the resulting mixture was concentrated to remove the solvent. The resulting residue was extracted with ethyl acetate (80 mL×3) and the combined organic phases were washed with brine (50 mL×2), dried with Na$_2$SO$_4$, filtered and concentrated to provide intermediate 2-41 (light brown solid, 700 mg, 89% yield). LCMS (m/z): 246 [M+H]$^+$.

Step 2. 7-fluoro-6-(4,4,5,5-tetramethyl-1,3,2-dioxaborolan-2-yl)-2H-benz[b][1,4]oxazin-3(4H)-one (2-42)

A mixture of 2-41 (51 mg, 2.07 mmol), (BPin)$_2$ (900 mg, 3.54 mmol), KOAc (610 mg, 6.22 mmol), Pd(dppf)Cl$_2$-DCM (180 mg, 0.208 mmol) and dioxane (15 mL) was stirred at 100° C. overnight under N$_2$. Upon reaction completion, the resulting mixture was concentrated and the resulting residue was purified via silica gel chromatography (Pet Ether/ethyl acetate=4/1, 2/1) to provide intermediate 2-42 (white solid, 390 mg, 64% yield). LCMS (m/z): 294 [M+H]$^+$.

Step 3. 6-(6-amino-5-(1-oxo-1,2,3,4-tetrahydroisoquinolin-6-yl)pyridin-3-yl)-7-fluoro-2H-benzo[b][1,4]oxazin-3(4H)-one (I-23)

A mixture of 2-4 (40 mg, 0.126 mmol), 2-42 (75 mg, 0.256 mmol), Pd(t-Bu$_3$P)$_3$ (7 mg, 0.0137 mmol), KF (30 mg, 0.516 mmol) and dioxane (5 mL) was stirred at 40° C. under an N$_2$ atmosphere overnight. Upon reaction completion, the resulting mixture was concentrated and the resulting residue was purified via prep-TLC (DCM/MeOH=10/1) and prep-HPLC (C18 column, CH$_3$CN/H$_2$O, containing 0.05% NH$_4$HCO$_3$) to provide compound I-23 (white solid, 11 mg, 22% yield). $^1$H NMR (DMSO-d6, 500 MHz): δ 0.73 (bs, 1H), 8.09 (s, 1H), 7.98 (s, 1H), 7.92 (d, J=8.0 Hz, 1H), 7.45 (m, 3H), 7.01 (d, J=11.5 Hz, 1H), 6.97 (d, J=8.0 Hz, 1H), 6.00 (s, 2H), 4.63 (s, 2H), 3.41 (m, 2H), 2.96 (t, J=6.5 Hz, 2H). LCMS (m/z): 405 [M+H]$^+$.

Example 23: Methyl-3-(6-amino-5-(1-oxo-1,2,3,4-tetrahydroisoquinolin-6-yl)pyridin-3-yl)-4-fluoro-5-nitrobenzoate (I-24)

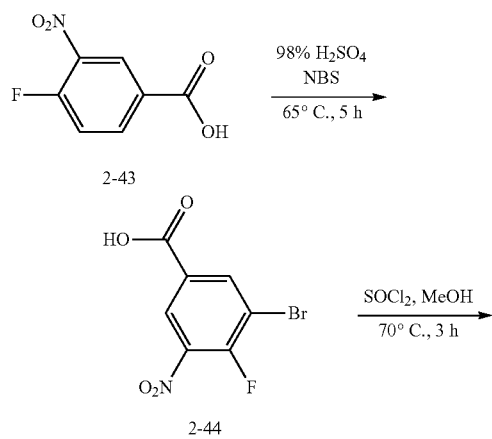

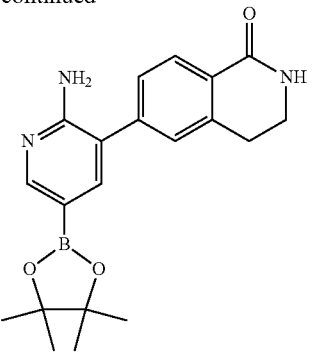

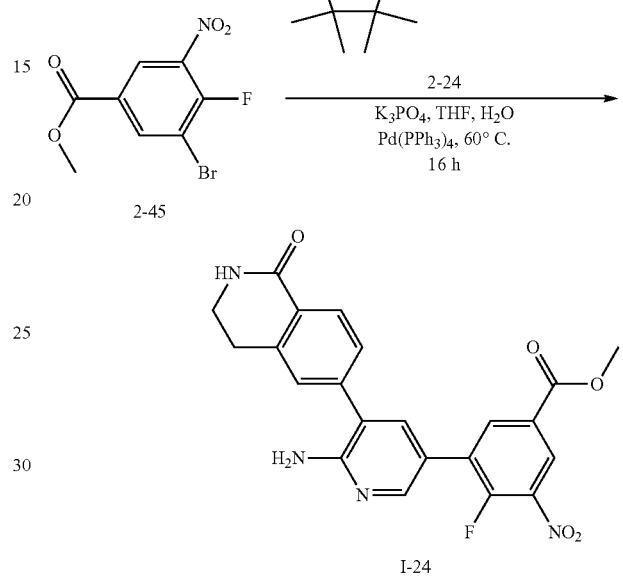

Step 1. N-(5-bromo-4-fluoro-2-methylphenyl)acetamide (2-44)

A mixture of 4-fluoro-3-nitrobenzoic acid (2-43, 2.5 g, 13.5 mmol) and NBS (2.4 g, 13.5 mmol) in 98% H$_2$SO$_4$ (5 mL) was stirred at 65° C. for 5 h. Upon reaction completion, water (25 mL) was added and the resulting mixture was filtered and the solid was collected. The solid obtained was dried to provide intermediate 2-44 (white solid, 2.8 g, 80% yield). LCMS (m/z): 262 [M−H]$^−$.

Step 2. methyl 3-bromo-4-fluoro-5-nitrobenzoate (2-45)

A mixture of N-(5-bromo-4-fluoro-2-methylphenyl)acetamide (2-44, 1 g, 3.8 mmol) and SOCl$_2$(456 mg, 3.8 mmol) in MeOH (10 mL) was stirred at 70° C. for 3 h. Upon reaction completion, the resulting mixture concentrated under reduced pressure to provide intermediate 2-45 (white solid, 900 mg, 91% yield). LCMS (m/z): 276 [M−H]$^−$.

Step 3. Methyl-3-(6-amino-5-(1-oxo-1,2,3,4-tetrahydroisoquinolin-6-yl)pyridin-3-yl)-4-fluoro-5-nitrobenzoate (I-24)

A mixture of methyl 3-bromo-4-fluoro-5-nitrobenzoate (2-45, 104 mg, 0.379 mmol), 6-(2-amino-5-(4,4,5,5-tetramethyl-1,3,2-dioxaborolan-2-yl)pyridin-3-yl)-3,4-dihydroisoquinolin-1(2H)-one (2-24, 100 mg, 0.379 mmol), K$_3$PO$_4$ (160 mg, 0.758 mmol), Pd(PPh$_3$)$_4$ (43 mg, 0.0379 mmol) in THF (2 mL) and H$_2$O (0.1 mL) was stirred at 60° C. for 16 h. Upon reaction completion, the mixture was concentrated under reduced pressure and the resulting residue was purified via prep-HPLC (C18 column, CH₃CN/H₂O, containing 0.05% NH₄HCO₃) to provide compound I-24 (white solid, 30 mg, 25% yield). ¹H NMR (DMSO-d6, 500 MHz) δ 8.55 (d, J=4.5 Hz, 1H), 8.45 (d, J=4 Hz, 1H), 8.34 (s, 1H), 8.30 (s, 1H), 7.94-7.98 (m, 2H), 7.49-7.52 (m, 2H), 7.17 (s, 2H), 3.93 (s, 3H), 3.40-3.43 (m, 2H), 2.97 (t, J=6.5 Hz, 2H). HPLC: 96% (@254 nm). LCMS (m/z): 437 [M+H]⁺.

Example 24: 3-(6-amino-5-(5-oxo-5,6,7,8-tetrahydronaphthalen-2-yl)pyridin-3-yl)-4-fluoro-5-methoxybenzonitrile (I-25)

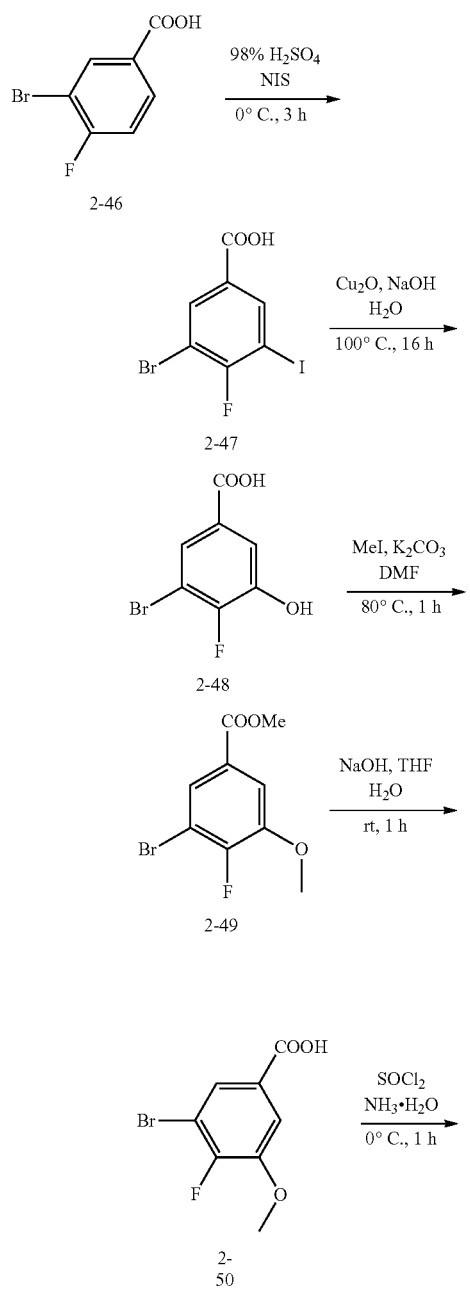

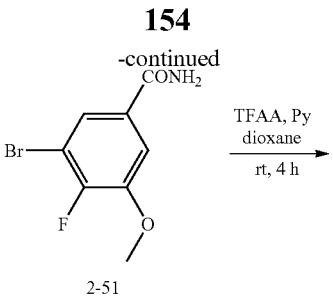

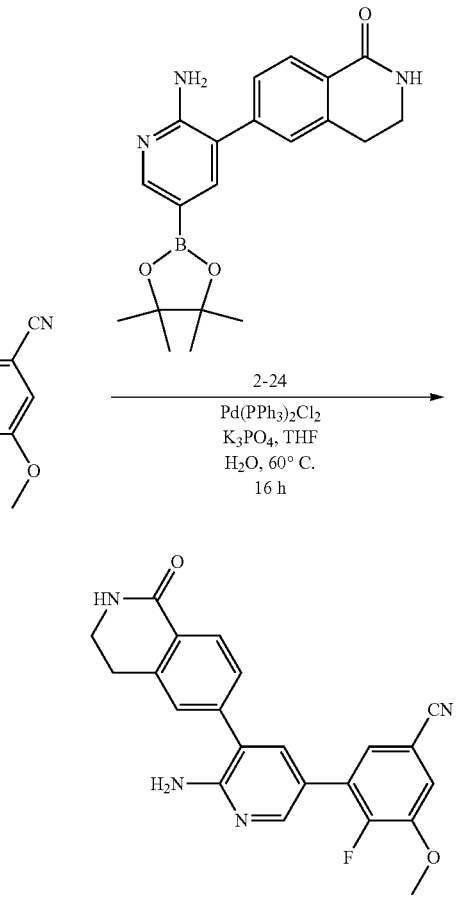

Step 1. N-(5-bromo-4-fluoro-2-methylphenyl)acetamide (2-47)

A mixture of 3-bromo-4-fluorobenzoic acid (2-46, 3 g, 13.7 mmol) and NIS (3.09 g, 13.7 mmol) in 98% H₂SO₄ (5 mL) was stirred at 0° C. for 3 h. Upon reaction completion, water (25 mL) was added and the resulting mixture was filtered and the resulting solid was collected. The solid was then dried to provide intermediate 2-47 (white solid, 3.7 g, 80% yield). LCMS (m/z): 344 [M−H]⁻.

Step 2. 3-bromo-4-fluoro-5-hydroxybenzoic acid (2-48)

A mixture of N-(5-bromo-4-fluoro-2-methylphenyl)acetamide (2-47, 1 g, 2.9 mmol), NaOH (464 mg, 11.6 mmol), and Cu₂O (83 mg, 0.58 mmol) in H₂O (5 mL) was stirred at 100° C. for 16 h. Upon reaction completion, the mixture was acidified with concentrated HCl and then extracted with ethyl acetate (150 mL×3). The combined organic phases were concentrated under reduced pressure and the resulting residue was purified via silica gel chromatography (Pet Ether/ethyl acetate=1/1) to obtain intermediate 2-48 (white solid, 600 mg, 80% yield). LCMS (m/z): 233 [M−H]⁻;

Step 3. methyl 3-bromo-4-fluoro-5-methoxybenzoate (2-49)

A mixture of 3-bromo-4-fluoro-5-hydroxybenzoic acid (2-48, 500 mg, 2.14 mmol), MeI (758 mg, 5.34 mmol) and $K_2CO_3$ (886 mg, 6.42 mmol) in DMF (5 mL) was stirred at 80° C. for 1 h. Upon reaction completion, the resulting mixture was washed with water and extracted with ethyl acetate (150 mL×3). The combined organic phases were then concentrated under reduced pressure and the resulting residue was purified via silica gel chromatography (Pet Ether/ethyl acetate=1/1) to provide intermediate 2-49 (yellow solid, 450 mg, 80% yield). LCMS (m/z): 263 [M+H]⁺.

Step 4. 3-bromo-4-fluoro-5-methoxybenzoic acid (2-50)

A mixture of methyl 3-bromo-4-fluoro-5-methoxybenzoate (2-49, 400 mg, 1.56 mmol), NaOH (183 mg, 4.58 mmol) in THF (5 mL), and $H_2O$ (5 mL) was stirred at rt for 1 h. Upon reaction completion, the reaction mixture acidified with concentrated HCl, washed with water, extracted with ethyl acetate (150 mL×3). The combined organic phases were then concentrated under reduced pressure and the resulting residue was purified via silica gel chromatography (Pet Ether/ethyl acetate=1/1) to obtain intermediate 2-50 (yellow solid, 350 mg, 92% yield). LCMS (m/z): 249 [M+H]⁺.

Step 5. 3-bromo-4-fluoro-5-methoxybenzamide (2-51)

A mixture of 3-bromo-4-fluoro-5-methoxybenzoic acid (2-50, 350 mg, 1.4 mmol) and $SOCl_2$ (336 mg, 2.8 mmol) in DCM (5 mL) was stirred at rt for 1 h and $NH_3 \cdot H_2O$ (1 mL) was then added. The resulting mixture was stirred at rt for 2 h. Upon reaction completion, the reaction mixture was washed with water and extracted with ethyl acetate (150 mL×3). The combined organic phases were concentrated under reduced pressure and the resulting residue was purified via silica gel chromatography (Pet Ether/ethyl acetate=1/1) to obtain intermediate 2-51 (white solid, 300 mg, 86% yield). LCMS (m/z): 248 [M+H]⁺.

Step 6. 3-bromo-4-fluoro-5-methoxybenzonitrile (2-52)

A mixture of 3-bromo-4-fluoro-5-methoxybenzamide (2-51, 300 mg, 1.2 mmol), TFAA (471 mg, 2.4 mmol), and pyridine (474 mg, 6.0 mmol) in dioxane (5 mL) was stirred at r.t for 4 h. Upon reaction completion, the reaction mixture was washed with water and extracted with ethyl acetate (150 mL×3). The combined organic phases were concentrated under reduced pressure and the resulting residue was purified via silica gel chromatography (Pet Ether/ethyl acetate=1/1) to obtain intermediate 2-52 (white solid, 180 mg, 65% yield). LCMS (m/z): 230 [M+H]⁺.

Step 7. 3-(6-amino-5-(5-oxo-5,6,7,8-tetrahydronaphthalen-2-yl)pyridin-3-yl)-4-fluoro-5-methoxybenzonitrile (I-25)

A mixture of 3-bromo-4-fluoro-5-methoxybenzonitrile (2-52, 62 mg, 0.27 mmol), 6-(2-amino-5-(4,4,5,5-tetramethyl-1,3,2-dioxaborolan-2-yl)pyridin-3-yl)-3,4-dihydroisoquinolin-1(2H)-one (2-24, 100 mg, 0.27 mmol), $K_3PO_4$ (114 mg, 0.54 mmol), $Pd(PPh_3)_2Cl_2$ (19 mg, 0.027 mmol) in THF (2 mL) and $H_2O$ (0.1 mL) was stirred at 60° C. for 16 h. Upon reaction completion, the reaction mixture was concentrated under reduced pressure and the resulting residue was purified via prep-HPLC (C18 column, $CH_3CN/H_2O$, containing 0.05% $NH_4HCO_3$) to provide compound I-25 (white solid, 25 mg, 24% yield). ¹H NMR (DMSO-d₆, 500 MHz) δ 8.24 (s, 1H), 7.97 (s, 1H), 7.75 (d, J=4.5 Hz, 1H), 7.65 (d, J=7 Hz, 1H), 7.61 (s, 1H), 7.47-7.50 (m, 2H), 6.15 (s, 2H), 3.41 (t, J=2 Hz, 2H), 2.97 (t, J=6.5 Hz, 2H). HPLC: 99% (@254 nm). LCMS (m/z): 389 [M+H]⁺.

Example 25: 6-(2-amino-5-(2,6-difluoro-3-nitrophenyl)pyridin-3-yl)-3,4-dihydroisoquinolin-1(2H)-one (I-26)

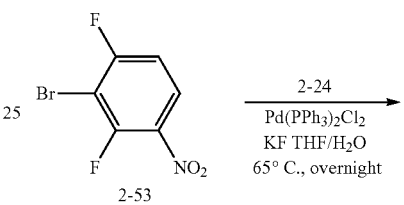

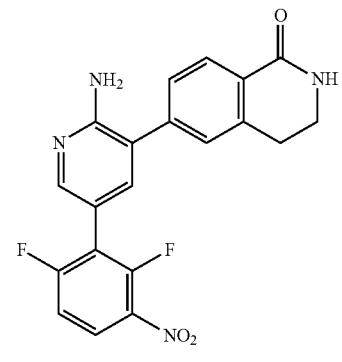

I-26

A mixture of 2-47 (178 mg, 0.75 mmol), 2-24 (182 mg, 0.5 mmol), $Pd(PPh_3)_2Cl_2$ (35 mg, 0.05 mmol), KF (58 mg, 1 mmol), THF (2 mL) and $H_2O$ (0.5 mL) was degassed with $N_2$ and stirred at 65° C. overnight. The resulting mixture was filtered, the filtrate was concentrated, and the resulting residue was purified via prep-HPLC eluting with $CH_3CN/H_2O$ (with 0.5% $NH_4HCO_3$) to provide compound I-26 (off-white solid, 121 mg, 61% yield). ¹H NMR (DMSO-d₆, 400 MHz): δ 8.24 (q, J=5.8 Hz, 1H), 8.12 (s, 1H), 7.99 (s, 1H), 7.92 (d, J=3.6 Hz, 1H), 7.54 (s, 1H), 7.43-7.50 (m, 3H), 6.24 (s, 2H), 3.41 (t, J=5.6 Hz, 2H), 2.96 (t, J=5.6 Hz, 2H). HPLC: 100% (254 nm). LCMS (m/z): 397 [M+H]⁺.

Example 26: 6-(2-amino-5-(4-(benzylamino)-2-fluoro-5-nitrophenyl)pyridin-3-yl)-3,4-dihydroisoquinolin-1(2H)-one (I-27)

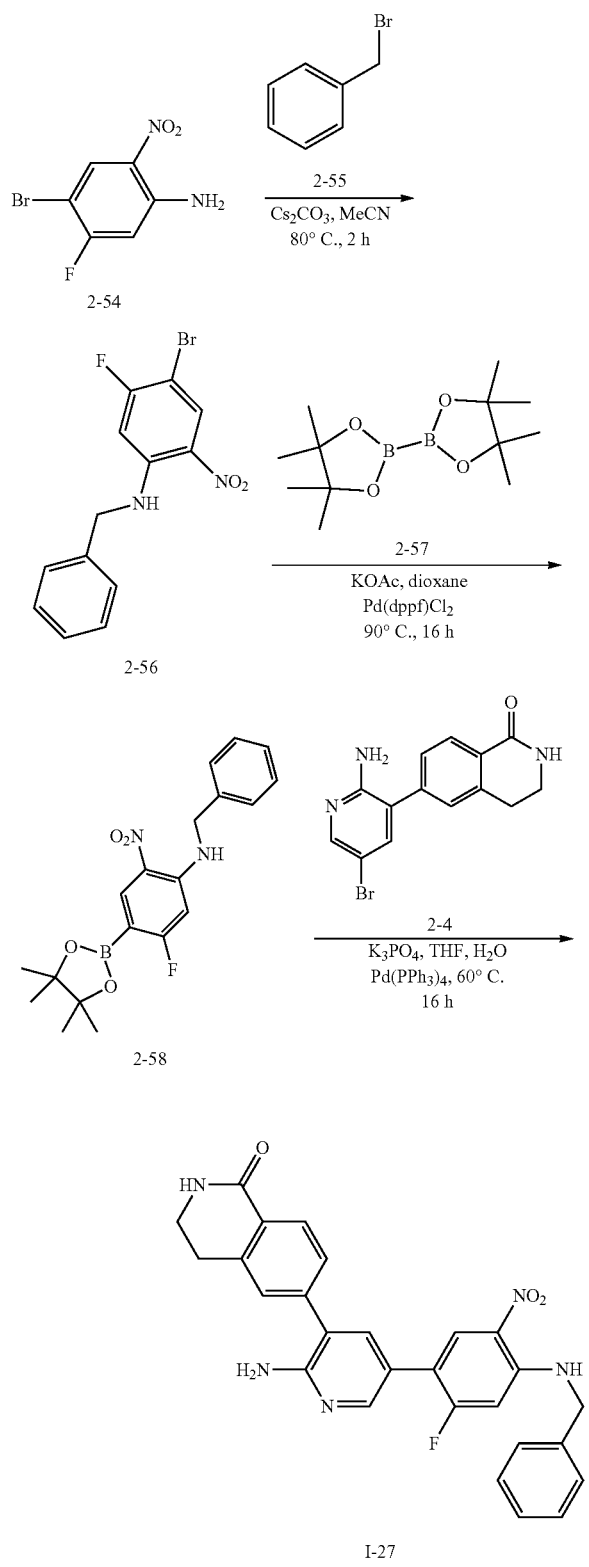

Step 1. N-benzyl-4-bromo-5-fluoro-2-nitroaniline (2-56)

A mixture of 4-bromo-5-fluoro-2-nitroaniline (2-54, 300 mg, 1.28 mmol), Cs₂CO₃ (832 mg, 2.56 mmol) and (bromomethyl)benzene (2-55, 218 mg, 1.28 mmol) in MeCN (5 mL) was stirred at 80° C. for 3 h. Upon reaction completion, the mixture was purified using silica gel chromatography (Pet Ether/ethyl acetate=1/1) to obtain intermediate 2-56 (yellow solid, 180 mg, 43% yield). LCMS (m/z): 325 [M+H]$^+$.

Step 2. N-benzyl-5-fluoro-2-nitro-4-(4,4,5,5-tetramethyl-1,3,2-dioxaborolan-2-yl)aniline (2-58)

A mixture of N-benzyl-4-bromo-5-fluoro-2-nitroaniline (2-56, 180 mg, 0.76 mmol), 4,4,4',4',5,5,5',5'-octamethyl-2,2'-bi(1,3,2-dioxaborolane) (2-57, 194 mg, 0.76 mmol), KOAc (149 mg, 1.52 mmol), and Pd(dppf)Cl₂ (54 mg, 0.076 mmol) in 1,4-dioxane (5 mL) was stirred for 16 h at 100° C. Upon reaction completion, the reaction mixture was washed with H₂O and extracted with ethyl acetate (50 mL×3). The combined organic phases were concentrated under reduced pressure and the resulting residue was purified via silica gel chromatography (Pet Ether/ethyl acetate=10/1) to obtain provide intermediate 2-58 (yellow solid, 160 mg, 80% yield). LCMS (m/z): 373 [M+H]$^+$.

Step 3. 6-(2-amino-5-(4-(benzylamino)-2-fluoro-5-nitrophenyl)pyridin-3-yl)-3,4-dihydroisoquinolin-1(2H)-one (I-27)

A mixture of N-benzyl-5-fluoro-2-nitro-4-(4,4,5,5-tetramethyl-1,3,2-dioxaborolan-2-yl)aniline (2-58, 117 mg, 0.315 mmol), 6-(2-amino-5-bromopyridin-3-yl)-3,4-dihydroisoquinolin-1(2H)-one (2-4, 100 mg, 0.315 mmol), KF (36 mg, 0.63 mmol), Pd(PPh₃)₄ (36 mg, 0.0315 mmol) in THF (2 mL) and H₂O (0.1 mL) was stirred at 60° C. for 16 h. Upon reaction completion, the reaction mixture was concentrated under reduced pressure and the resulting residue was purified via prep-HPLC (C18 column, CH₃CN/H₂O, containing 0.05% NH₄HCO₃) to provide compound I-27 (yellow solid, 25 mg, 16% yield). $^1$H NMR (DMSO-d₆, 500 MHz) δ 8.92 (s, 1H), 8.35 (d, J=9 Hz, 1H), 8.18 (s, 1H), 8.03 (s, 1H), 7.95 (d, J=8 Hz, 1H), 7.86 (s, 1H), 7.47-7.49 (m, 2H), 7.29-7.38 (m, 5H), 7.27 (s, 1H), 6.86 (d, J=13.5 Hz, 1H), 4.68 (d, J=5 Hz, 2H), 2.95 (t, J=6.5 Hz, 2H). HPLC: 100% (@254 nm). LCMS (m/z): 484 [M+H]$^+$.

Example 27: 4-(6-amino-5-(1-oxo-1,2,3,4-tetrahydroisoquinolin-6-yl)pyridin-3-yl)-N-cyclopropyl-3-fluoro-N-methylbenzenesulfonamide (I-28)

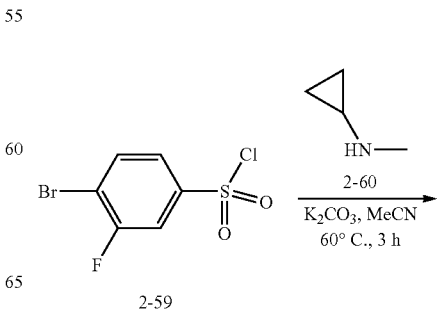

159

-continued

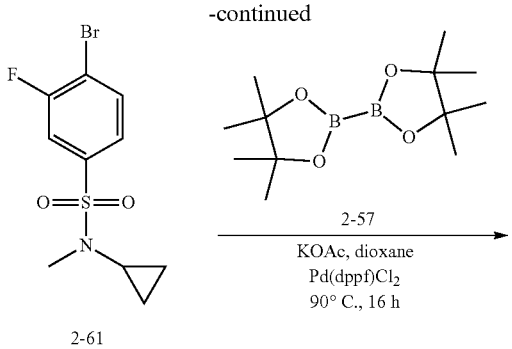

Step 1. 4-bromo-N-cyclopropyl-3-fluoro-N-methyl-benzenesulfonamide (2-61)

A mixture of 4-bromo-3-fluorobenzene-1-sulfonyl chloride (2-59, 250 mg, 0.919 mmol), K2CO3 (254 mg, 1.84 mmol) and N-methylcyclopropanamine (2-60, 85 mg, 1.19 mmol) in MeCN (5 mL) was stirred at 60° C. for 3 h. Upon reaction completion, the reaction mixture was purified via silica gel chromatography (Pet Ether/ethyl acetate=1/1) to obtain intermediate 2-61 (white solid, 250 mg, 89% yield). LCMS (m/z): 308 [M+H]$^+$.

160

Step 2. N-cyclopropyl-3-fluoro-N-methyl-4-(4,4,5,5-tetramethyl-1,3,2-dioxaborolan-2-yl)benzenesulfonamide (2-62)

A mixture of 4-bromo-N-cyclopropyl-3-fluoro-N-methyl-benzenesulfonamide (2-61, 220 mg, 0.71 mmol), 4,4,4',4',5,5,5',5'-octamethyl-2,2'-bi(1,3,2-dioxaborolane) (2-57, 182 mg, 0.71 mmol), KOAc (139 mg, 1.42 mmol), and Pd(dppf)Cl$_2$ (51 mg, 0.071 mmol) in 1,4-dioxane (5 mL) was stirred for 16 h at 100° C. Upon reaction completion, the reaction mixture was washed with H$_2$O and extracted with ethyl acetate (50 mL×3). The combined organic phases were concentrated under reduced pressure and the resulting residue was purified via silica gel chromatography (Pet Ether/ethyl acetate=10/1) to obtain intermediate 2-62 (yellow solid, 180 mg, 70% yield). LCMS (m/z): 356 [M+H]$^+$, 274 [M-82+H]$^+$.

Step 3. 4-(6-amino-5-(1-oxo-1,2,3,4-tetrahydroisoquinolin-6-yl)pyridin-3-yl)-N-cyclopropyl-3-fluoro-N-methylbenzenesulfonamide (I-28)

A mixture of N-cyclopropyl-3-fluoro-N-methyl-4-(4,4,5,5-tetramethyl-1,3,2-dioxaborolan-2-yl)benzenesulfonamide (2-62, 100 mg, 0.28 mmol), 6-(2-amino-5-bromopyridin-3-yl)-3,4-dihydroisoquinolin-1(2H)-one (2-4, 89 mg, 0.28 mmol), KF (32 mg, 0.56 mmol), Pd(PPh$_3$)$_2$Cl$_2$ (19 mg, 0.028 mmol) in THF (2 mL) and H$_2$O (0.1 mL) was stirred at 60° C. for 16 h. Upon reaction completion, the reaction mixture was concentrated under reduced pressure and the resulting residue was purified via prep-HPLC (C18 column, CH$_3$CN/H$_2$O, containing 0.05% TFA) to provide compound I-28 (yellow solid, 20 mg, 15% yield). $^1$H NMR (DMSO-d$_6$, 400 MHz) δ 8.34 (s, 1H), 7.92-8.02 (m, 4H), 7.52-7.73 (m, 2H), 7.50-7.51 (m, 2H), 7.20 (s, 2H), 3.40-3.43 (m, 2H), 2.95 (t, J=6.5 Hz, 2H), 1.89-1.93 (m, 1H), 0.71-0.79 (m, 4H). HPLC: 100% (@254 nm). LCMS (m/z): 467 [M+H]$^+$.

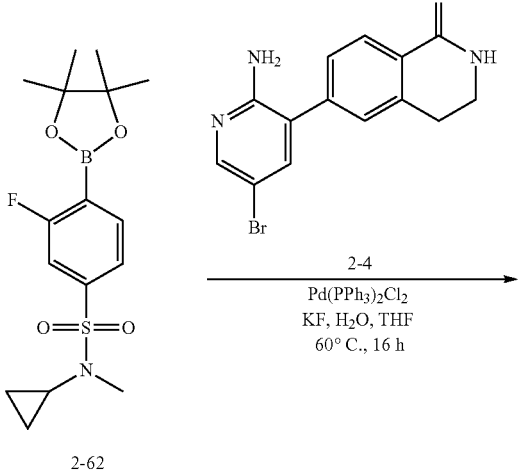

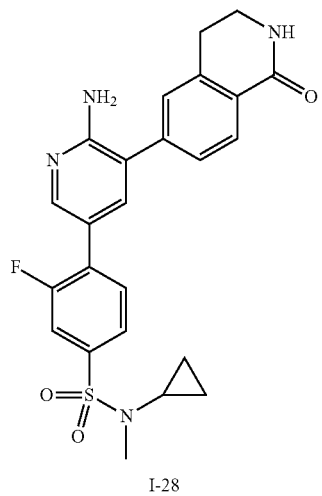

Example 28: 4-(2-amino-5-(2-fluoro-5-nitrophenyl)pyridin-3-yl)-2-methylbenzamide (I-29)

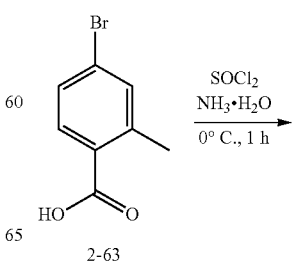

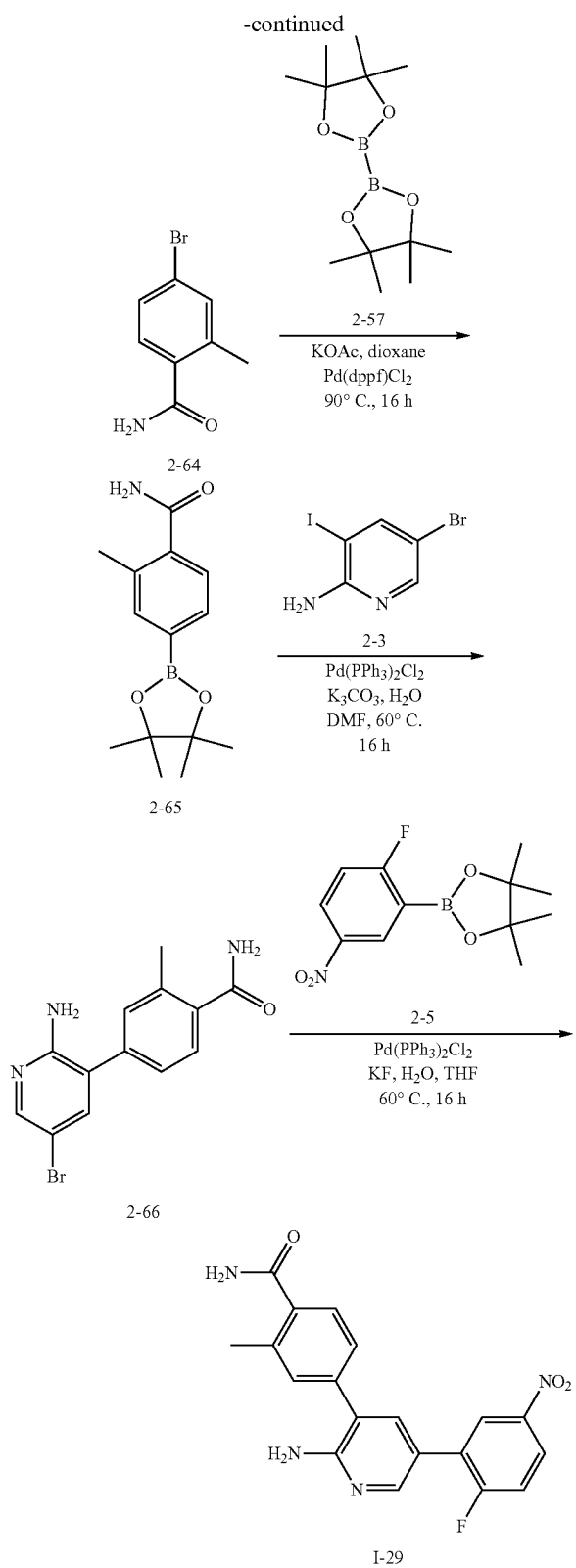

stirred at r.t for 1 h, and then NH$_3$.H$_2$O (1 mL) was added. Upon reaction completion, the resulting mixture was washed with water and extracted with ethyl acetate (150 mL×3). The combined organic phases were concentrated under reduced pressure and the resulting residue was purified via silica gel chromatography (Pet Ether/ethyl acetate=1/1) to obtain intermediate 2-64 (white solid, 940 mg, 95% yield). LCMS (m/z): 214 [M+H]$^+$.

Step 2. 2-methyl-4-(4,4,5,5-tetramethyl-1,3,2-dioxaborolan-2-yl)benzamide (2-65)

A mixture of 4-bromo-2-methylbenzamide (2-64, 500 mg, 2.19 mmol), 4,4,4',4',5,5,5',5'-octamethyl-2,2'-bi(1,3,2-dioxaborolane) (2-57, 557 mg, 2.19 mmol), KOAc (429 mg, 4.38 mmol), and Pd(dppf)Cl$_2$ (153 mg, 0.219 mmol) in dioxane (5 ml) was stirred for 16 h at 60° C. Upon reaction completion, the resulting mixture was washed with H$_2$O and extracted with ethyl acetate (50 mL×3). The combined organic phases were concentrated under reduced pressure and the resulting residue was purified via silica gel chromatography (PE/ethyl acetate=10/1) to obtain intermediate 2-65 (white solid, 450 mg, 78% yield). LCMS (m/z): 262 [M+H]$^+$.

Step 3. 4-(2-amino-5-bromopyridin-3-yl)-2-methylbenzamide (2-66)

A mixture of 2-methyl-4-(4,4,5,5-tetramethyl-1,3,2-dioxaborolan-2-yl)benzamide (2-65, 400 mg, 1.75 mmol), 5-bromo-3-iodopyridin-2-amine (2-3, 521 mg, 1.75 mmol), K$_2$CO$_3$ (483 mg, 3.5 mmol), Pd(PPh$_3$)$_2$Cl$_2$ (122 mg, 0.175 mmol) in DMF (2 mL) and H$_2$O (0.1 mL) was stirred at 60° C. for 16 h. Upon reaction completion, the resulting mixture was concentrated under reduced pressure and the resulting residue was purified via prep-HPLC (C18 column, CH$_3$CN/H$_2$O, containing 0.05% TFA) to provide intermediate 2-66 (yellow solid, 350 mg, 75% yield). LCMS (m/z): 306 [M+H]$^+$.

Step 4. 4-(2-amino-5-(2-fluoro-5-nitrophenyl)pyridin-3-yl)-2-methylbenzamide (I-29)

A mixture of 4-(2-amino-5-bromopyridin-3-yl)-2-methylbenzamide (2-66, 100 mg, 0.33 mmol), 2-(2-fluoro-5-nitrophenyl)-4,4,5,5-tetramethyl-1,3,2-dioxaborolane (2-5, 88 mg, 0.33 mmol), KF (38 mg, 0.66 mmol), Pd(PPh$_3$)$_2$Cl$_2$ (29 mg, 0.033 mmol) in THF (2 mL) and H$_2$O (0.1 mL) was stirred at 60° C. for 16 h. Upon reaction completion, the resulting mixture was concentrated under reduced pressure and the resulting residue was purified via prep-HPLC (C18 column, CH$_3$CN/H$_2$O, containing 0.05% NH$_4$HCO$_3$) to provide compound I-29 (white solid, 25 mg, 21% yield). $^1$H NMR (DMSO-d$_6$, 500 MHz) δ 8.42-8.44 (m, 1H), 8.28 (s, 1H), 8.22-8.25 (m, 1H), 7.74 (s, 1H), 7.58-7.62 (m, 2H), 7.49 (d, J=8 Hz, 1H), 7.37-7.41 (m, 3H), 6.09 (s, 2H), 2.44 (s, 3H). HPLC: 100% (@254 nm). LCMS (m/z): 367 [M+H]$^+$.

Step 1. 4-bromo-2-methylbenzamide (2-64)

A mixture of 4-bromo-2-methylbenzoic acid (2-63, 1 g, 4.6 mmol) and SOCl$_2$ (1.2 g, 9.2 mmol) in DCM (5 mL) was

Example 29: 4-(2-amino-5-(2-fluoro-5-nitrophenyl)pyridin-3-yl)-2-chlorobenzamide (I-30)

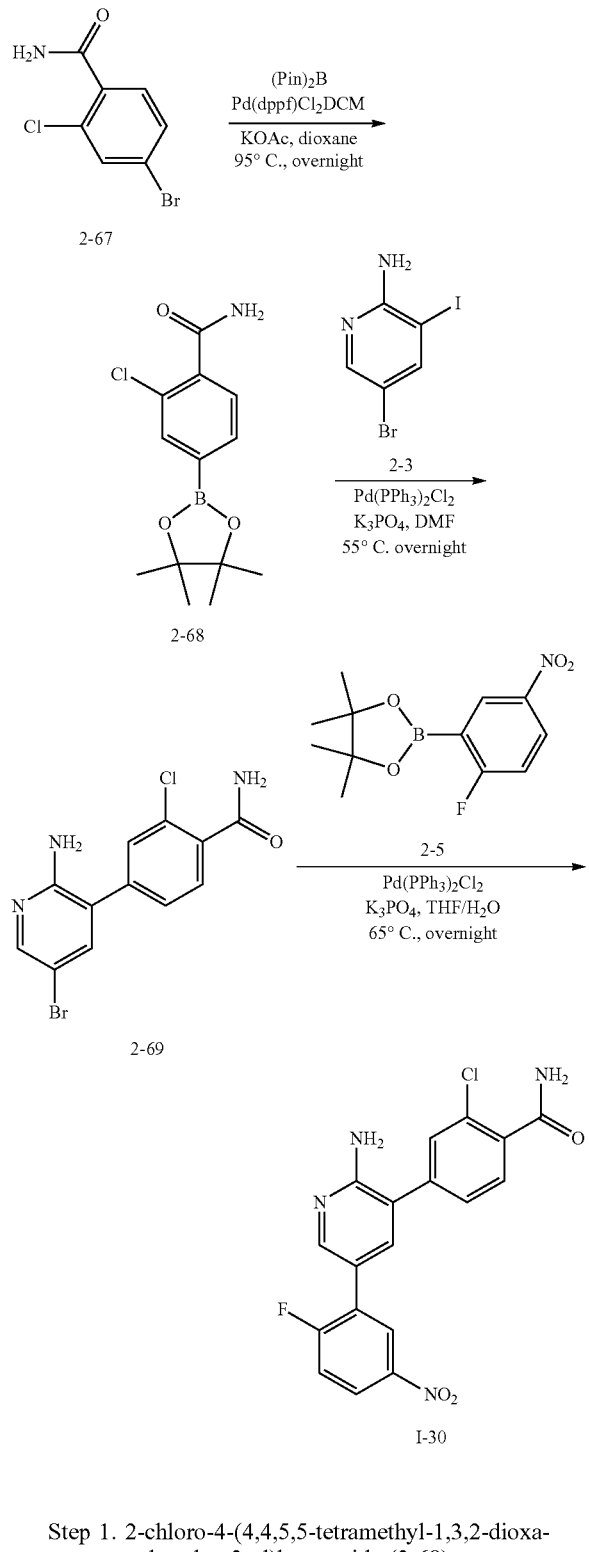

Step 1. 2-chloro-4-(4,4,5,5-tetramethyl-1,3,2-dioxaborolan-2-yl)benzamide (2-68)

A mixture of 2-67 (1.17 g, 5 mmol), (Pin)$_2$B (2.28 g, 9 mmol), Pd(dppf)Cl$_2$DCM (408 mg, 0.5 mmol), KOAc (980 mg, 10 mmol) and dioxane (5 ml) was degassed with N$_2$ and stirred at 95° C. overnight. The resulting mixture was filtered and the filtrate was concentrated and purified via column chromatography on silica gel eluting with DCM/MeOH from 20/1 to 10/1 to give intermediate 2-68 (yellow solid, 1.01 g, 72% yield). LCMS (m/z): 282 [M+H]$^+$.

Step 2. 4-(2-amino-5-bromopyridin-3-yl)-2-chlorobenzamide (2-69)

A mixture of 2-68 (1.01 g, 3.6 mmol), 2-3 (897 mg, 3 mmol), Pd(PPh$_3$)$_2$Cl$_2$ (210 mg, 0.3 mmol), K$_3$PO$_4$ (1.27 g, 6 mmol) and DMF (15 mL) was degassed with N$_2$ and stirred at 45° C. overnight. The resulting mixture was filtered and the filtrate was concentrated and purified via column chromatography on silica gel eluting with PE/ethyl acetate from 2/1 to 1/2 to provide intermediate 2-69 (yellow solid, 381 mg, 39% yield). LCMS (m/z): 326 [M+H]$^+$.

Step 3. 4-(2-amino-5-(2-fluoro-5-nitrophenyl)pyridin-3-yl)-2-chlorobenzamide (I-30)

A mixture of 2-69 (381 mg, 1.2 mmol), 2-5 (448 mg, 1.7 mmol), Pd(PPh$_3$)$_2$Cl$_2$ (84 mg, 0.12 mmol), K$_3$PO$_4$ (508 mg, 2.4 mmol), THF (2 mL) and H$_2$O (0.5 mL) was degassed with N$_2$ and stirred at 65° C. overnight. The resulting mixture was filtered and the filtrate was concentrated and purified via prep-HPLC eluting with CH$_3$CN/H$_2$O (with 0.5% NH$_4$HCO$_3$) to provide compound I-30 (yellow solid, 194 mg, 42% yield). $^1$H NMR (DMSO-d6, 400 MHz): δ 8.46 (dd, J$_1$=6.8 Hz, J$_2$=4.0 Hz, 1H), 8.30 (t, J=1.6 Hz, 1H), 8.22-8.26 (m, 1H), 7.88 (s, 1H), 7.64 (bs, 2H), 7.60 (t, J=8.0 Hz, 2H), 7.55 (s, 2H), 6.21 (s, 2H). HPLC: 100% (254 nm). LCMS (m/z): 387 [M+H]$^+$.

Example 30: 4-(2-amino-5-(2-fluoro-5-nitrophenyl)pyridin-3-yl)benzamide (I-31)

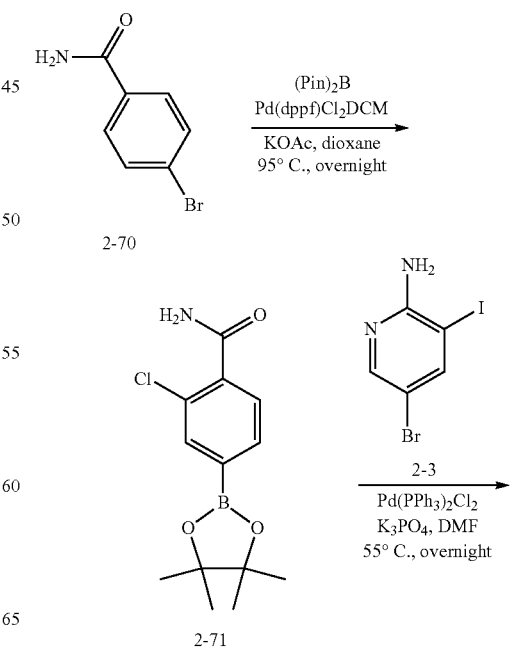

-continued

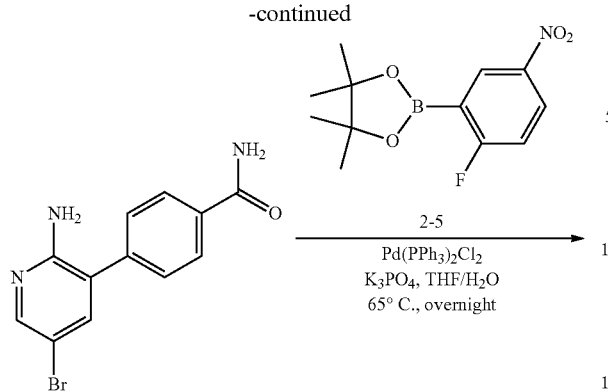

2-72

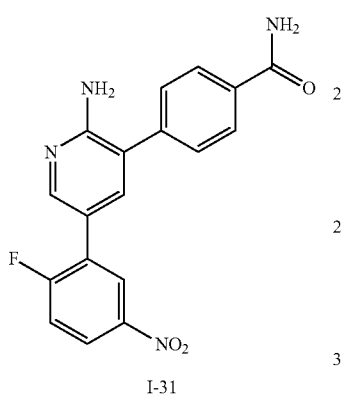

I-31

Step 1. 4-(4,4,5,5-tetramethyl-1,3,2-dioxaborolan-2-yl)benzamide (2-71)

A mixture of 2-70 (1.0 g, 5 mmol), (PinB)$_2$ (2.28 g, 9 mmol), Pd(dppf)Cl$_2$DCM (408 mg, 0.5 mmol), KOAc (980 mg, 10 mmol) and dioxane (5 mL) was degassed with N$_2$ and stirred at 95° C. overnight. The resulting mixture was filtered and the filtrate was concentrated and purified via column chromatography on silica gel eluting with DCM/MeOH from 20/1 to 10/1 to give intermediate 2-71 (yellow solid, 975 mg, 79% yield). LCMS (m/z): 248 [M+H]$^+$.

Step 2. 4-(2-amino-5-bromopyridin-3-yl)benzamide (2-72)

A mixture of 2-71 (975 mg, 3.95 mmol), 2-3 (98 mg, 3.29 mmol), Pd(PPh$_3$)$_2$Cl$_2$ (230 mg, 0.33 mmol), K3PO$_4$ (1.4 g, 6.6 mmol) and DMF (5 mL) was degassed with N$_2$ and stirred at 45° C. overnight. The resulting mixture was filtered and the filtrate was concentrated and the resulting residue was purified via column chromatography on silica gel eluting with PE/ethyl acetate from 2/1 to 1/2 to provide intermediate 2-72 (yellow solid, 509 mg, 53% yield). LCMS (m/z): 248 [M+H]$^+$.

Step 3. 4-(2-amino-5-(2-fluoro-5-nitrophenyl)pyridin-3-yl)benzamide (I-31)

A mixture of 2-72 (292 mg, 1 mmol), 2-5 (374 mg, 1.4 mmol), Pd(PPh$_3$)$_2$Cl$_2$ (70 mg, 0.1 mmol), K$_3$PO$_4$ (424 mg, 2 mmol), THF (2 mL) and H$_2$O (0.5 mL) was degassed with N$_2$ and stirred at 65° C. overnight. The resulting mixture was filtered and the filtrate was concentrated and purified via prep-HPLC eluting with CH$_3$CN/H$_2$O (with 0.5% NH$_4$HCO$_3$) to provide compound I-31 (yellow solid, 165 mg, 47% yield). $^1$H NMR (DMSO-d$_6$, 400 MHz): δ 8.45 (dd, J$_1$=6.4 Hz, J$_2$=2.4 Hz, 1H), 8.29 (t, J=2.0 Hz, 1H), 8.22-8.26 (m, 1H), 8.06 (s, 1H), 8.00 (d, J=8.4 Hz, 2H), 7.67 (s, 1H), 7.58-7.63 (m, 3H), 7.44 (s, 1H), 6.17 (s, 2H). HPLC: 100% (254 nm). LCMS (m/z): 353 [M+H]$^+$.

Example 31: 5-(2-amino-5-(2-fluoro-5-nitrophenyl)pyridin-3-yl)isoindolin-1-one (I-32)

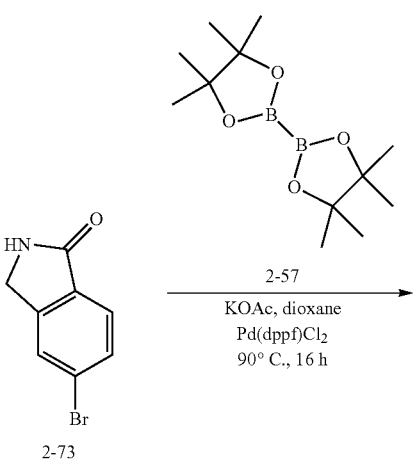

2-73

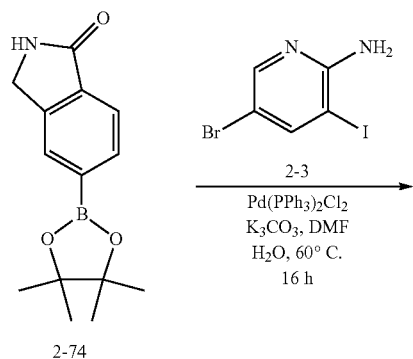

2-74

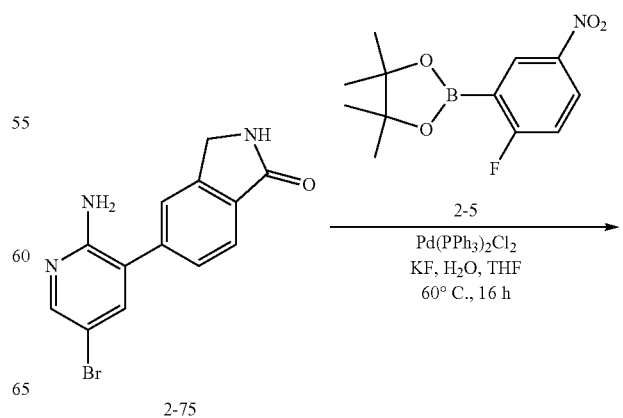

2-75

-continued

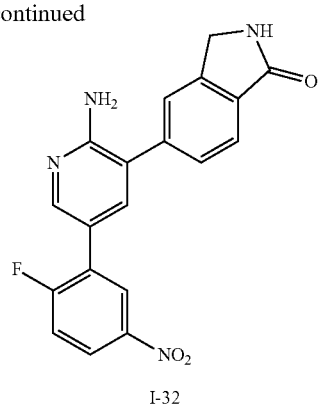

I-32

Step 1. 5-(4,4,5,5-tetramethyl-1,3,2-dioxaborolan-2-yl)isoindolin-1-one (2-74)

A mixture of 5-bromoisoindolin-1-one (2-73, 200 mg, 0.95 mmol), 4,4,4',4',5,5,5',5'-octamethyl-2,2'-bi(1,3,2-dioxaborolane) (2-57, 241 mg, 0.95 mmol), KOAc (186 mg, 1.9 mmol), and Pd(dppf)Cl$_2$ (69 mg, 0.095 mmol) in dioxane (5 ml) was stirred for 16 h at 60° C. Upon reaction completion, the resulting mixture was washed with H$_2$O and extracted with ethyl acetate (50 mL×3). The combined organic phases were concentrated under reduced pressure and the resulting residue was purified via silica gel chromatography (Pet Ether/ethyl acetate=10/1) to obtain intermediate 2-74 (white solid, 300 mg, 88% yield). LCMS (m/z): 260 [M+H]$^+$.

Step 2. 5-(2-amino-5-bromopyridin-3-yl)isoindolin-1-one (2-75)

A mixture of 5-(4,4,5,5-tetramethyl-1,3,2-dioxaborolan-2-yl)isoindolin-1-one (2-74, 200 mg, 0.55 mmol) and 5-bromo-3-iodopyridin-2-amine (2-3, 166 mg, 0.55 mmol), K$_2$CO$_3$ (152 mg, 1.1 mmol), Pd(PPh$_3$)$_2$Cl$_2$ (38 mg, 0.055 mmol) in DMF (2 mL) and H$_2$O (0.1 mL) was stirred at 60° C. for 16 h. Upon reaction completion, the resulting mixture was concentrated under reduced pressure and the resulting residue was purified via prep-HPLC to obtain intermediate 2-75 (yellow solid, 100 mg, 59% yield). LCMS (m/z): 304 [M+H]$^+$.

Step 3. 5-(2-amino-5-(2-fluoro-5-nitrophenyl)pyridin-3-yl)isoindolin-1-one (I-32)

A mixture of 5-(2-amino-5-bromopyridin-3-yl)isoindolin-1-one (2-75, 100 mg, 0.33 mmol), 2-(2-fluoro-5-nitrophenyl)-4,4,5,5-tetramethyl-1,3,2-dioxaborolane (2-5, 88 mg, 0.33 mmol), KF (38 mg, 0.66 mmol), Pd(PPh$_3$)$_2$Cl$_2$ (29 mg, 0.033 mmol) in THF (2 mL) and H$_2$O (0.1 mL) was stirred at 60° C. for 16 h. Upon reaction completion, the resulting mixture was concentrated under reduced pressure and the resulting residue was purified via prep-HPLC (C18 column, CH$_3$CN/H$_2$O, containing 0.05% NH$_4$HCO$_3$) to provide compound I-32 (white solid, 5 mg, 4% yield). $^1$H NMR (DMSO-d$_6$, 400 MHz) δ8.61 (s, 1H), 8.44-8.46 (m, 1H), 8.29 (d, J=2 Hz, 1H), 8.23-8.26 (m, 1H), 7.75 (t, J=8 Hz, 2H), 7.68 (s, 1H), 7.61 (t, J=10 Hz, 2H), 6.20 (s, 2H), 4.42 (s, 2H). HPLC: 100% (@254 nm). LCMS (m/z): 365 [M+H]$^+$.

Example 32: 6-(3-amino-6-(2-fluoro-3-nitrophenyl)pyrazin-2-yl)-3,4-dihydroisoquinolin-1(2H)-one

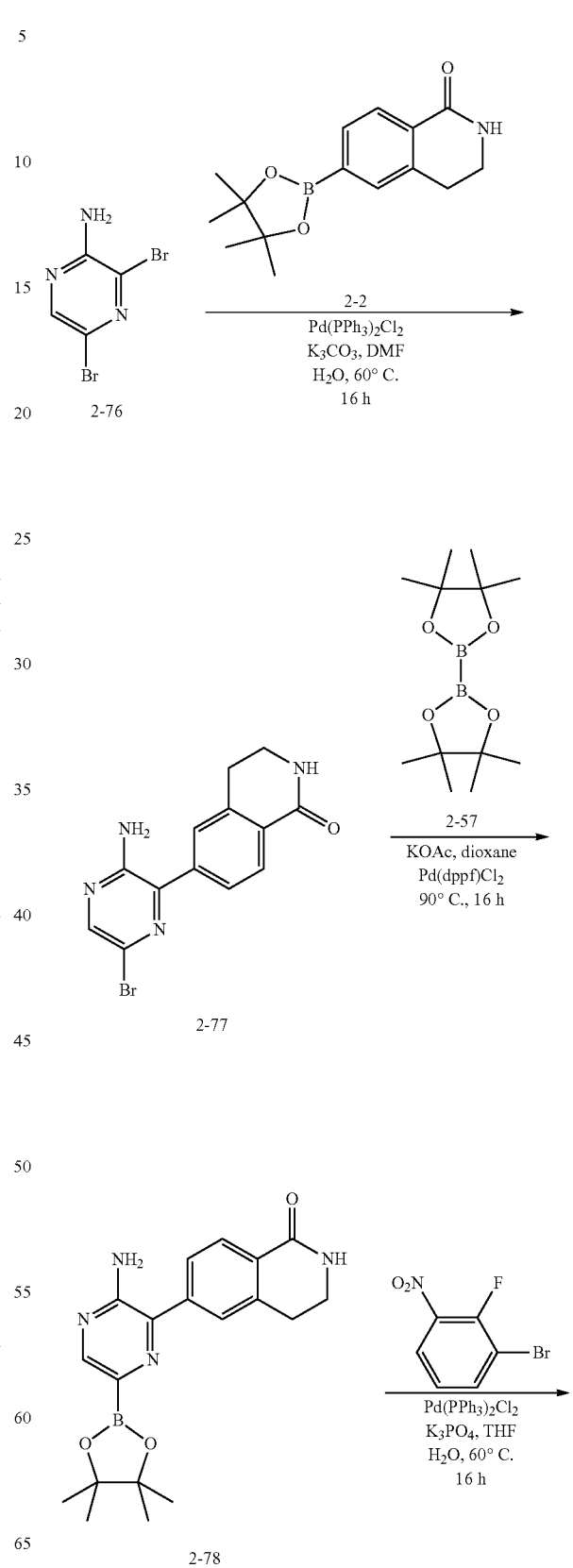

-continued

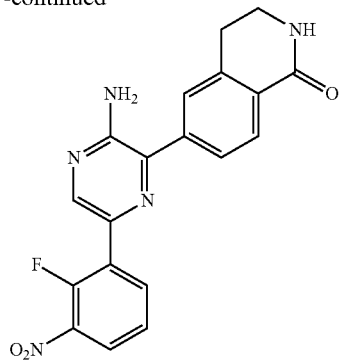

Step 1. 6-(3-amino-6-bromopyrazin-2-yl)-3,4-dihydroisoquinolin-1(2H)-one (2-77)

A mixture of 3,5-dibromopyrazin-2-amine (2-76, 274 mg, 1.09 mmol), 6-(4,4,5,5-tetramethyl-1,3,2-dioxaborolan-2-yl)-3,4-dihydroisoquinolin-1(2H)-one (2-2, 300 mg, 1.09 mmol), $K_2CO_3$ (300 mg, 2.18 mmol), $Pd(PPh_3)_2Cl_2$ (8 mg, 0.0109 mmol) in DMF (2 mL) and $H_2O$ (0.1 mL) was stirred at 60° C. for 16 h. Upon reaction completion, the resulting mixture was concentrated under reduced pressure and the resulting residue was purified via prep-HPLC to obtain intermediate 2-77 (yellow solid, 150 mg, 43% yield). LCMS (m/z): 319 $[M+H]^+$.

Step 2. 6-(3-amino-6-(4,4,5,5-tetramethyl-1,3,2-dioxaborolan-2-yl)pyrazin-2-yl)-3,4-dihydroisoquinolin-1(2H)-one (2-78)

A mixture of 6-(3-amino-6-bromopyrazin-2-yl)-3,4-dihydroisoquinolin-1(2H)-one (2-77, 150 mg, 0.47 mmol), 4,4,4',4',5,5,5',5'-octamethyl-2,2'-bi(1,3,2-dioxaborolane) (2-57, 120 mg, 0.47 mmol), KOAc (92 mg, 0.94 mmol), and $Pd(dppf)Cl_2$ (34 mg, 0.047 mmol) in dioxane (5 ml) was stirred for 16 h at 100° C. Upon reaction completion, the resulting mixture was washed with $H_2O$ and extracted with ethyl acetate (50 mL×3). The combined organic phases were concentrated under reduced pressure and the resulting residue was purified via silica gel chromatography (Pet Ether/ethyl acetate=10/1) to obtain intermediate 2-78 (white solid, 90 mg, 52% yield). LCMS (m/z): 367 $[M+H]^+$.

Step 3. 6-(3-amino-6-(2-fluoro-3-nitrophenyl)pyrazin-2-yl)-3,4-dihydroisoquinolin-1(2H)-one (I-33)

A mixture of 6-(3-amino-6-(4,4,5,5-tetramethyl-1,3,2-dioxaborolan-2-yl)pyrazin-2-yl)-3,4-dihydroisoquinolin-1(2H)-one (2-78, 90 mg, 0.24 mmol), 1-bromo-2-fluoro-3-nitrobenzene (52 mg, 0.24 mmol), KF (28 mg, 0.48 mmol), $Pd(PPh_3)_2Cl_2$ (17 mg, 0.024 mmol) in THF (2 mL) and $H_2O$ (0.1 mL) was stirred at 60° C. for 16 h. Upon reaction completion, the resulting mixture was concentrated under reduced pressure and the resulting residue was purified via prep-HPLC (C18 column, $CH_3CN/H_2O$, containing 0.05% $NH_4HCO_3$) to provide compound I-33 (white solid, 14 mg, 4% yield). $^1H$ NMR (DMSO-$d_6$, 400 MHz) δ 8.46 (d, J=2.8 Hz, 1H), 8.25-8.29 (m, 1H), 8.09-8.14 (m, 1H), 8.02 (s, 1H), 7.96 (d, J=8 Hz, 1H), 7.73 (d, J=8 Hz, 1H), 7.70 (s, 1H), 7.53 (t, J=8 Hz, 1H), 6.78 (s, 2H), 3.40-3.44 (m, 2H), 2.30 (t, J=6.4 Hz, 2H). HPLC: 100% (@254 nm). LCMS (m/z): 380 $[M+H]^+$.

Example 33: 3-(6-amino-5-(1-oxo-1,2,3,4-tetrahydroisoquinolin-6-yl)pyridin-3-yl)-2-fluorobenzonitrile (I-34)

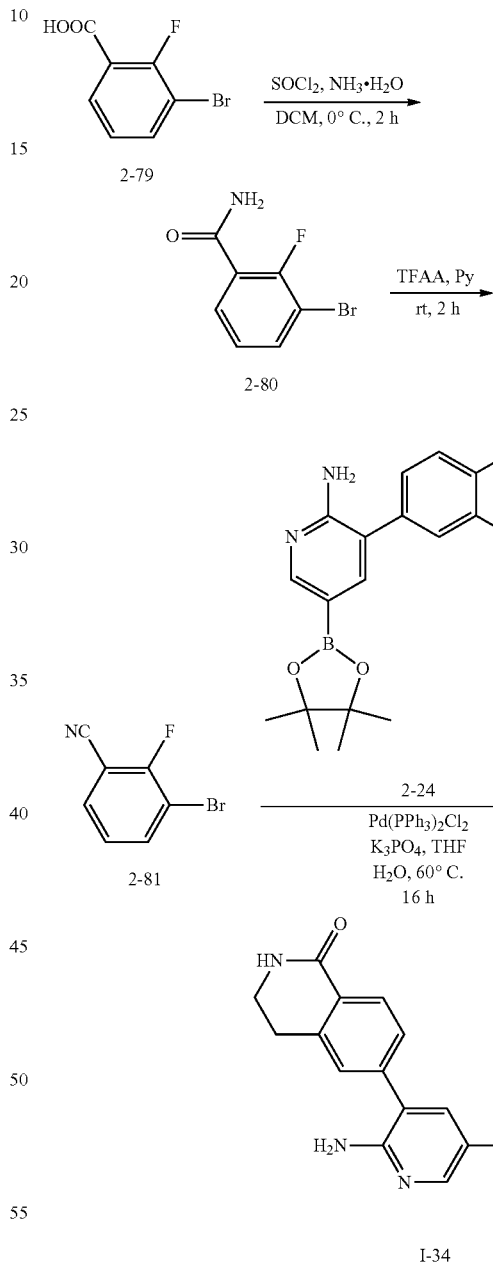

Step 1. 3-bromo-2-fluorobenzamide (2-80)

A mixture of 3-bromo-2-fluorobenzoic acid (2-79, 400 mg, 1.83 mmol) and $SOCl_2$ (4.39 mg, 3.66 mmol) in DCM (5 mL) was stirred at r.t for 1 h, and then $NH_3.H_2O$ (1 mL) was added. The resulting mixture was then stirred at r.t for 2 h. Upon reaction completion, the resulting mixture was washed with water and extracted with ethyl acetate (150 mL×3). The combined organic phases were concentrated under reduced pressure and the resulting residue was purified via silica gel chromatography (Pet Ether/ethyl acetate=1/1) to obtain intermediate-2-80 (white solid, 300 mg, 75% yield). LCMS (m/z): 218 [M+H]$^+$.

Step 2. 3-bromo-2-fluorobenzonitrile (2-81)

A mixture of 3-bromo-2-fluorobenzamide (2-80, 260 mg, 1.2 mmol), TFAA (471 mg, 2.4 mmol) and pyridine (Py) (474 mg, 6.0 mmol) in dioxane (5 mL) was stirred at r.t for 4 h. Upon reaction completion, the resulting mixture was washed with water and extracted with ethyl acetate (150 mL×3). The combined organic phases were concentrated under reduced pressure and the resulting residue was purified via silica gel chromatography (Pet Ether/ethyl acetate=1/1) to obtain intermediate 2-81 (white solid, 100 mg, 42% yield).

Step 3. 3-(6-amino-5-(1-oxo-1,2,3,4-tetrahydroiso-quinolin-6-yl)pyridin-3-yl)-2-fluorobenzonitrile (1-34)

A mixture of 3-bromo-2-fluorobenzonitrile (2-81, 53 mg, 0.27 mmol), 6-(2-amino-5-(4,4,5,5-tetramethyl-1,3,2-dioxa-borolan-2-yl)pyridin-3-yl)-3,4-dihydroisoquinolin-1(2H)-one (2-24, 100 mg, 0.27 mmol), K$_3$PO$_4$ (114 mg, 0.54 mmol), Pd(PPh$_3$)$_2$Cl$_2$(19 mg, 0.027 mmol) in THF (2 mL) and H$_2$O (0.1 mL) was stirred at 60° C. for 16 h. Upon reaction completion, the resulting mixture was concentrated under reduced pressure and the resulting residue was purified via prep-HPLC (C18 column, CH$_3$CN/H$_2$O, containing 0.05% TFA) to provide compound I-34 (white solid, 40 mg, 42% yield). $^1$H NMR (DMSO-d6, 400 MHz) δ 8.24 (s, 1H), 7.85-7.99 (m, 4H), 7.62 (s, 1H), 7.44-7.49 (m, 3H), 6.12 (s, 2H), 3.39-3.41 (m, 2H), 2.97 (t, J=6.4 Hz, 2H). HPLC: 99% (@254 nm). LCMS (m/z): 359 [M+H]$^+$.

Example 34: 3-(6-amino-5-(1-oxo-1,2,3,4-tetrahy-droisoquinolin-6-yl)pyridin-3-yl)-4-fluorobenzoni-trile (I-35)

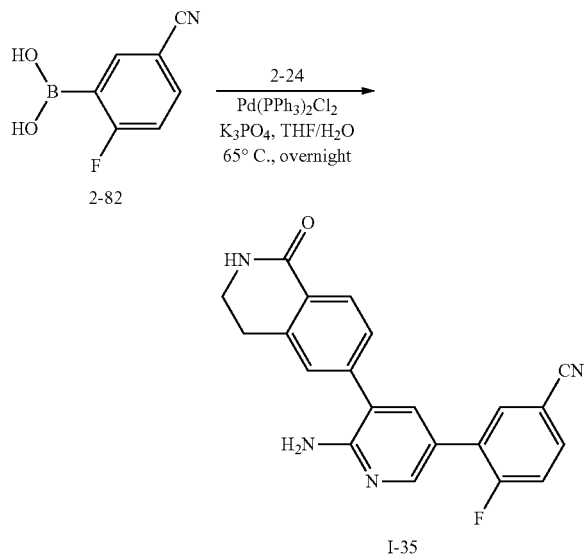

A mixture of 2-82 (247 mg, 1.5 mmol), 2-24 (317 mg, 1 mmol), Pd(PPh$_3$)$_2$Cl$_2$ (70 mg, 0.1 mmol), K$_3$PO$_4$ (424 mg, 2 mmol), THF (2 mL) and H$_2$O (0.5 mL) was degassed with N$_2$ and stirred at 65° C. overnight. The mixture was filtered and the filtrate was concentrated and purified via prep-HPLC eluting with CH$_3$CN/H$_2$O (with 0.5% NH$_4$HCO$_3$) to provide compound I-35 (yellow solid, 161 mg, 45% yield). $^1$H NMR (DMSO-d6, 400 MHz): δ 8.26 (t, J=2.0 Hz, 1H), 8.20 (dd, J$_1$=7.2 Hz, J$_2$=2.0 Hz, 1H), 7.97 (s, 1H), 7.92 (d, J=8.0 Hz, 1H), 7.84-7.88 (m, 1H), 7.65 (s, 1H), 7.47-7.56 (m, 3H), 6.15 (s, 2H), 3.41 (dt, J$_1$=6.4 Hz, J$_2$=2.4 Hz, 2H), 2.96 (t, J=6.4 Hz, 2H). HPLC: 100% (254 nm). LCMS (m/z): 359 [M+H]$^+$.

Example 35: 6-(2-amino-5-(benzo[d]thiazol-6-yl) pyridin-3-yl)-3,4-dihydroisoquinolin-1(2H)-one (I-44)

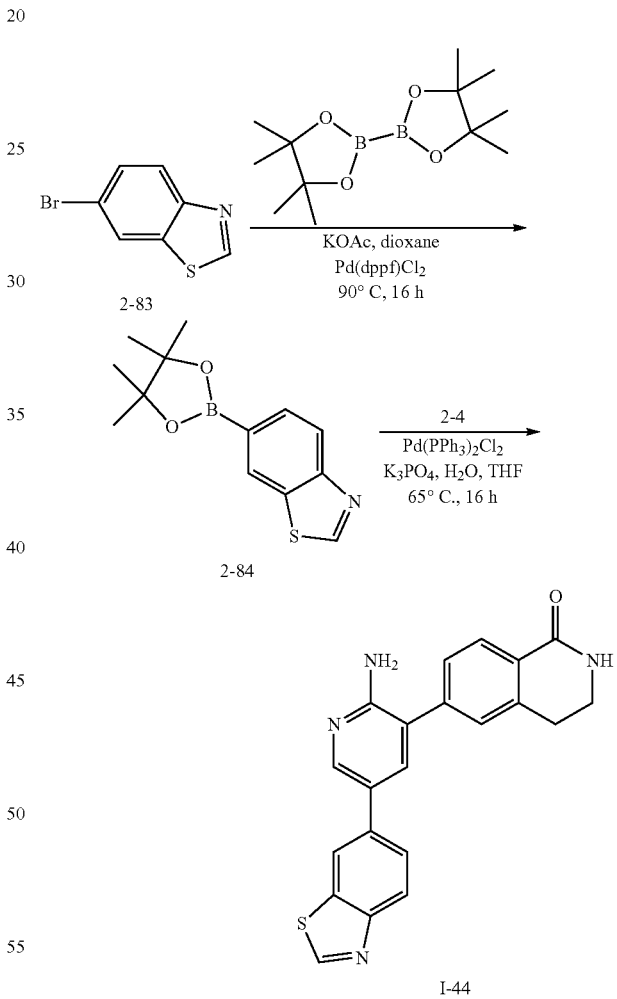

Step 1. 6-(4,4,5,5-tetramethyl-1,3,2-dioxaborolan-2-yl)benzo[d]thiazole

The mixture of 6-bromobenzo[d]thiazole (2-83, 200 mg, 0.94 mmol), 4,4,4',4',5,5,5',5'-octamethyl-2,2'-bi(1,3,2-di-oxaborolane) (239 mg, 0.94 mmol), KOAc (184 mg, 1.88 mmol), Pd(dppf)Cl$_2$ (68 mg, 0.094 mmol) in 1,4-dioxane (5 ml) was stirred for 16 h at 105° C. under N$_2$, after completion, added water, the mixture was extracted with ethyl acetate (50 mL×3), combined the organic phase, concentrated under reduced pressure, the residue was purified by silica gel chromatography (Pet Ether/ethyl acetate=10/1) to obtain title compound 2-84 (yellow solid, 120 mg, 48% yield). LCMS: 262 (M+H)+.

Step 2. 6-(2-amino-5-(benzo[d]thiazol-6-yl)pyridin-3-yl)-3,4-dihydroisoquinolin-1(2H)-one The mixture of 6-(4,4,5,5-tetramethyl-1,3,2-dioxaborolan-2-yl)benzo[d]thiazole (2-84, 80 mg, 0.31 mmol) and 6-(2-amino-5-(benzo[d]thiazol-6-yl)pyridin-3-yl)-3,4-dihydroisoquinolin-1(2H)-one (2-4, 97 mg, 0.31 mmol), K$_3$PO$_4$ (129 mg, 0.61 mmol), Pd(PPh$_3$)$_2$Cl$_2$ (21 mg, 0.031 mmol) in THF (2 mL) and H$_2$O (0.1 mL) was stirred at 65° C. for 16 h under N$_2$, after completion, filtered, concentrated under reduced pressure, the residue was purified by prep-HPLC (C18 column, CH$_3$CN/H$_2$O, containing 0.05% TFA) to get title compound I-44 (white solid, 11 mg, 10%). LCMS: 373 (M+H)+; HPLC: 100% (254 nm); $^1$H NMR (DMSO-d$_6$, 400 MHz) δ 9.40 (s, 1H), 8.49 (d, J=1.5 Hz, 1H), 8.44 (d, J=2.4 Hz, 1H), 8.10 (d, J=8.6 Hz, 1H), 8.01-7.70 (m, 3H), 7.61-7.42 (m, 2H), 5.99 (s, 2H), 3.63-3.36 (m, 2H), 2.98 (t, J=6.5 Hz, 2H).

Example 36: 6-(2-amino-5-(4-ethynyl-2-fluoro-5-nitrophenyl)pyridin-3-yl)-3,4-dihydroisoquinolin-1(2H)-one (I-45)

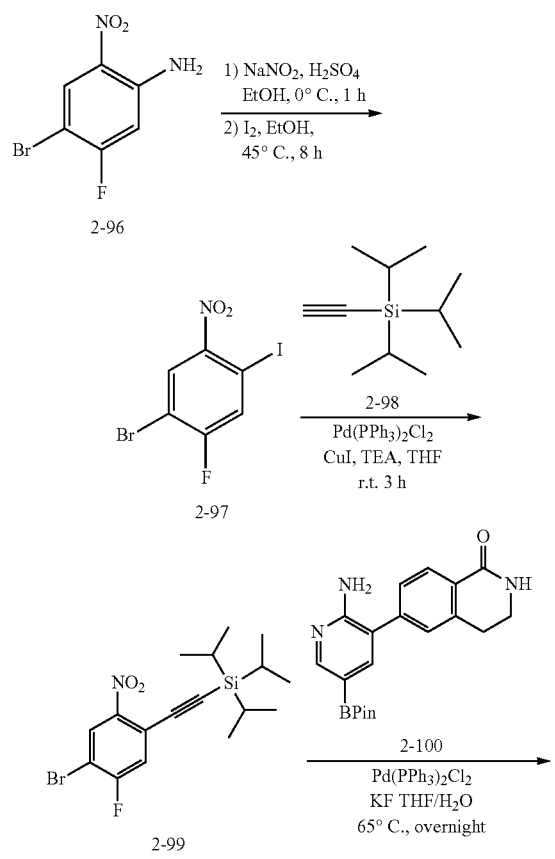

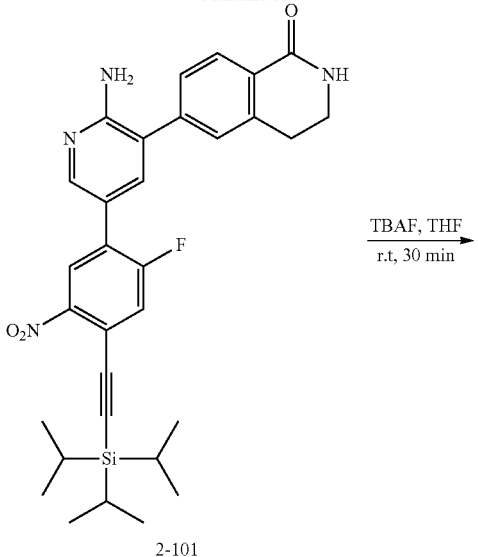

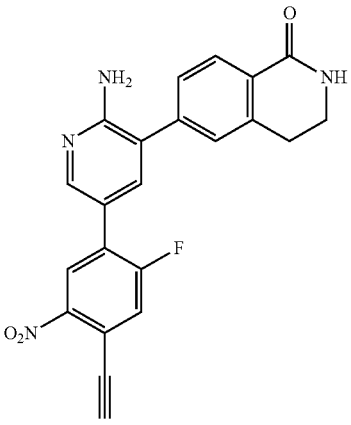

Step 1. 1-bromo-2-fluoro-4-iodo-5-nitrobenzene (2-97)

To a solution of 2-96 (700 mg, 2.99 mmol) in EtOH (20 mL) at 0° C., was added 4 mL 60% H$_2$SO$_4$, then NaNO$_2$ (414 mg, 5.98 mmol) was added slowly in portions. Upon completion of the addition, the stirring was continued for 1 h while the temperature was kept during 0-5° C. I2 (918 mg, 3.59 mmol) was then added and the resulting mixture was stirred at 45° C. for another 8 h. The reaction mixture was concentrated, water (30 mL) was added, and then the mixture was extracted with DCM (30 mL×3). The combined organic layers were washed with brine (30 mL), dried over Na$_2$SO$_4$, filtered and concentrated. The residue was purified by prep-TLC (Pet Ether/ethyl acetate=30/1 to give 2-97 (yellow solid, 221 mg, yield 28%).

Step 2. ((4-bromo-5-fluoro-2-nitrophenyl)ethynyl)triisopropylsilane (2-99)

A mixture of 2-97 (100 mg, 0.29 mmol), 2-98 (79 mg, 0.43 mmol), Pd(PPh$_3$)$_2$Cl$_2$ (20 mg, 0.03 mmol), CuI (22 mg, 0.12 mmol), TEA (59 mg, 0.58 mmol) and THF (4 mL) was degassed with N$_2$. The mixture was stirred at r.t for 3 h. The mixture was filtered, the filtrate was concentrated, and then purified by prep-TLC (Pet Ether/ethyl acetate=50/1) to give 2-99 (yellow solid, 107 mg, yield 93%). LCMS: t=2.85 min, no mass peak.

Step 3. 6-(2-amino-5-(2-fluoro-5-nitro-4-((triisopropylsilyl)ethynyl)phenyl)pyridin-3-yl)-3,4-dihydroisoquinolin-1(2H)-one (2-101)

A mixture of 2-99 (107 mg, 0.27 mmol), 2-100 (108 mg, 0.30 mmol), Pd(PPh$_3$)$_2$Cl$_2$ (21 mg, 0.03 mmol), KF (35 mg, 0.60 mmol), THF (4 mL) and H$_2$O (1 mL) was degassed with N$_2$. The mixture was stirred at 65° C. overnight. The mixture was filtered, the filtrate was concentrated, and purified by prep-TLC with Pet Ether/Acetone=1/1 to give 2-101 (yellow solid, 102 mg, yield 61%). LCMS (m/z): 559 [M+H]$^+$.

Step 4. 6-(2-amino-5-(4-ethynyl-2-fluoro-5-nitrophenyl)pyridin-3-yl)-3,4-dihydroisoquinolin-1(2H)-one (I-45)

To a solution of 2-101 (100 mg, 0.18 mmol) in THF (2 mL) at 0° C., TBAF (1 M in THF, 0.27 mL, 0.27 mmol) was added and the resulting mixture was stirred at 0° C. for 15 min. The mixture was concentrated and purified by prep-TLC with DCM/MeOH=8/1 to give I-45 (yellow solid, 66 mg, yield 92%). HPLC: 100% (254 nm); LCMS (m/z): 403 [M+H]$^+$; $^1$H NMR (DMSO-d6, 400 MHz): δ 8.36 (d, J=4.8 Hz, 1H), 8.31 (t, J=2.0 Hz, 1H), 7.97 (s, 1H), 7.92 (d, J=6.0 Hz, 1H), 8.79 (d, J=10.8 Hz, 1H), 7.68 (s, 1H), 7.48 (dd, J$_1$=8.0 Hz, J$_2$=1.6 Hz, 1H), 7.46 (s, 1H), 6.26 (s, 2H), 4.87 (s, 1H), 3.41 (td, J$_1$=6.4 Hz, J$_2$=2.4 Hz, 2H), 2.96 (t, J=6.4 Hz, 2H).

Example 37: 4-(6-amino-5-(1-oxo-1,2,3,4-tetrahydroisoquinolin-6-yl)pyridin-3-yl)-N-cyclopropyl-N,3-dimethylbenzenesulfonamide (I-46)

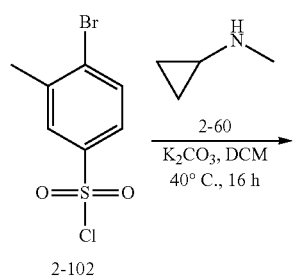

Step 1. 4-bromo-N-cyclopropyl-N,3-dimethylbenzenesulfonamide (2-103)

The mixture of 4-bromo-3-methylbenzene-1-sulfonyl chloride (2-102, 200 mg, 0.75 mmol), K$_2$CO$_3$ (205 mg, 1.49 mmol) and N-methylcyclopropanamine (2-60, 106 mg, 1.49 mmol) in DCM (20 mL) was stirred at 40° C. for 16 h. Upon reaction completion, the resulting mixture was filtered and then concentrated under reduced pressure to get title compound 2-103 (yellow oil, 210 mg, 93% yield). LCMS: 304 [M+H]$^+$.

Step 2. 4-(6-amino-5-(1-oxo-1,2,3,4-tetrahydroisoquinolin-6-yl)pyridin-3-yl)-N-cyclopropyl-N,3-dimethylbenzenesulfonamide (I-46)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 90 mg, 0.24 mmol), 4-bromo-N-cyclopropyl-N,3-dimethylbenzenesulfonamide (2-103, 73 mg, 0.24 mmol), K$_3$PO$_4$ (101 mg, 0.48 mmol), Pd(PPh$_3$)$_2$Cl$_2$ (16 mg, 0.024 mol) in THF (2 mL) and H$_2$O (0.1 mL) was stirred at 65° C. for 16 h under N$_2$ atmosphere. Upon reaction comple-

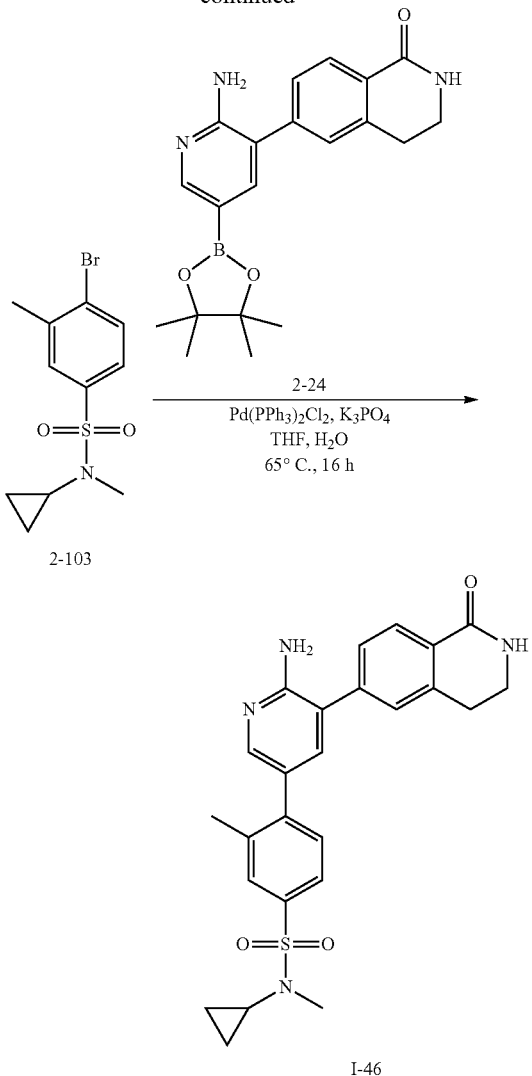

tion, the resulting mixture was filtered, concentrated under reduced pressure, and the resulting residue was purified by prep-HPLC (C18 column, CH₃CN/H₂O, containing 0.05% NH₄HCO₃) to get title compound I-46 (white solid, 25 mg, 22%). LCMS: 357 (M+H)+; HPLC: 100% (254 nm); $^1$H NMR (400 MHz, DMSO-d6) δ 8.06 (d, J=2.4 Hz, 1H), 7.99-7.85 (m, 2H), 7.71 (s, 1H), 7.65 (dd, J=8.0, 1.7 Hz, 1H), 7.55 (d, J=8.1 Hz, 1H), 7.51-7.41 (m, 3H), 6.01 (s, 2H), 3.48-3.37 (m, 2H), 2.93 (dd, J=24.6, 18.1 Hz, 2H), 2.69 (s, 3H), 2.43 (s, 3H), 1.86 (tt, J=7.0, 3.6 Hz, 1H), 0.80-0.63 (m, 4H).

Example 38: 4-(6-amino-5-(1-oxo-1,2,3,4-tetrahydroisoquinolin-6-yl)pyridin-3-yl)-N-cyclopropyl-3-ethoxy-N-methylbenzenesulfonamide (I-47)

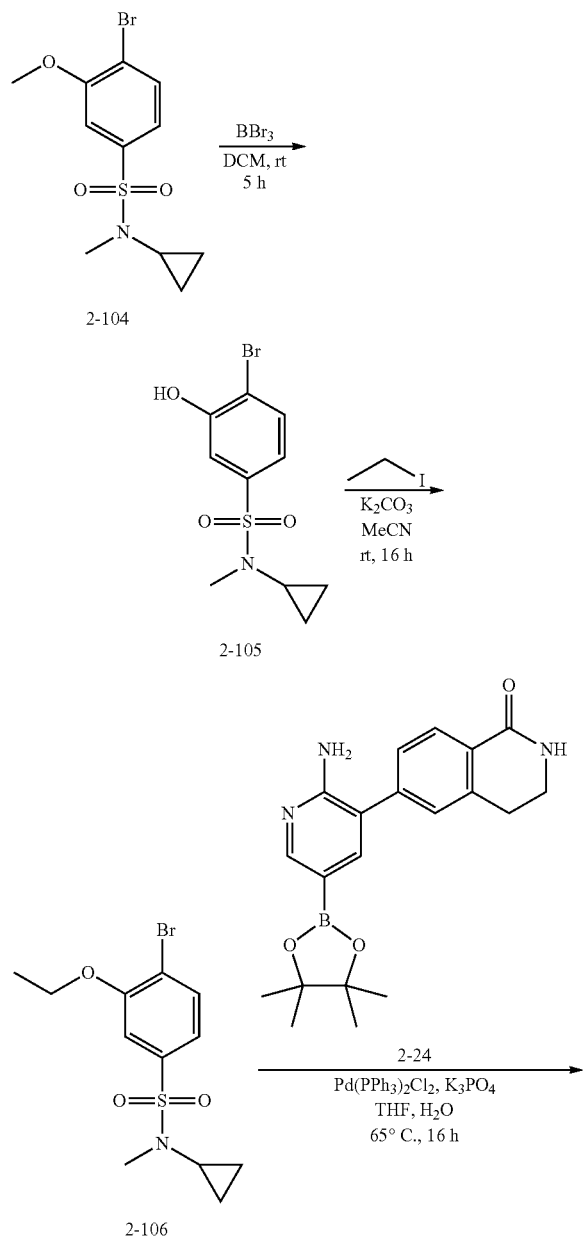

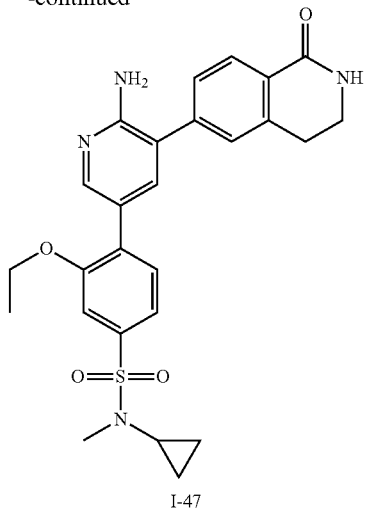

Step 1. 4-bromo-N-cyclopropyl-3-hydroxy-N-methylbenzenesulfonamide (2-105)

The mixture of 4-bromo-N-cyclopropyl-3-methoxy-N-methylbenzenesulfonamide (2-104, 200 mg, 0.63 mmol), and BBr₃ (6.3 mL, 1.0 M) in DCM (20 mL) was stirred at rt for 5 h. Upon reaction completion, the resulting mixture was quenched with water, extracted with ethyl acetate (100 mL×3) and concentrated under reduced pressure. The resulting residue was purified by column chromatography (Pet Ether/ethyl acetate=2/1) to get title compound 2-105 (white solid, 140 mg, 73% yield). LCMS: 306 [M+H]⁺.

Step 2. 4-bromo-N-cyclopropyl-3-ethoxy-N-methylbenzenesulfonamide 2-106)

The mixture of 4-bromo-N-cyclopropyl-3-hydroxy-N-methylbenzenesulfonamide (2-105, 130 mg, 0.426 mmol), K₂CO₃ (117 mg, 0.852 mmol) and iodoethane (99 mg, 0.639 mmol) in MeCN (5 mL) was stirred at rt for 16 h. Upon reaction completion, the resulting mixture was filtered, and concentrated under reduced pressure. The resulting residue was purified by silica gel chromatography (Pet Ether/ethyl acetate=1/1) to obtain title compound 2-106 (yellow solid, 95 mg, 67% yield). LCMS: 334 [M+H]⁺.

Step 3. 4-(6-amino-5-(1-oxo-1,2,3,4-tetrahydroisoquinolin-6-yl)pyridin-3-yl)-N-cyclopropyl-3-ethoxy-N-methylbenzenesulfonamide (1-47)

The mixture of 6-(2-amino-5-(4,4,5,5-tetramethyl-1,3,2-dioxaborolan-2-yl)pyridin-3-yl)-3,4-dihydroisoquinolin-1 (2H)-one (2-24, 70 mg, 0.19 mmol), 4-bromo-N-cyclopropyl-3-ethoxy-N-methylbenzenesulfonamide (2-106, 63 mg, 0.19 mmol), K₃PO₄ (80 mg, 0.38 mmol), Pd(PPh₃)₂Cl₂ (13 mg, 0.019 mol) in THF (2 mL) and H₂O (0.1 mL) was stirred at 65° C. for 16 h under N₂ atmosphere. Upon reaction completion, the resulting mixture was filtered, and concentrated under reduced pressure. The resulting residue was purified by prep-HPLC (C18 column, CH₃CN/H₂O, containing 0.05% NH₄HCO₃) to get title compound I-47 (white solid, 25 mg, 26%). LCMS: 493 [M+H]⁺; HPLC: 100% (254 nm); $^1$H NMR (400 MHz, DMSO-d₆) δ 8.28 (d, J=2.2 Hz, 1H), 8.00-7.83 (m, 2H), 7.66 (dd, J=7.1, 5.2 Hz, 2H), 7.53-7.36 (m, 3H), 7.32 (s, 1H), 5.99 (s, 2H), 4.16 (q, J=6.9 Hz, 2H), 3.41 (t, J=5.2 Hz, 2H), 2.96 (t, J=6.4 Hz, 2H), 2.70 (s, 3H), 1.88 (dd, J=8.4, 4.8 Hz, 1H), 1.35 (t, J=6.9 Hz, 3H), 0.84-0.57 (m, 4H).

Example 39: 4-(6-amino-5-(1-oxo-1,2,3,4-tetrahydroisoquinolin-6-yl)pyridin-3-yl)-N-cyclopropyl-3-isopropoxy-N-methylbenzenesulfonamide (I-48)

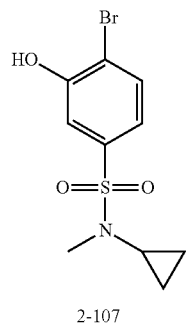
2-107

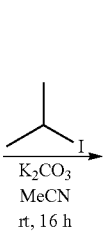

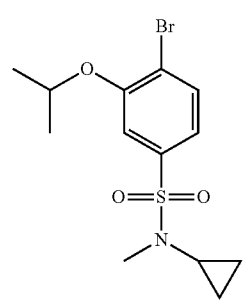
2-108

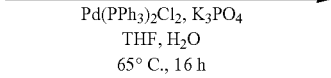

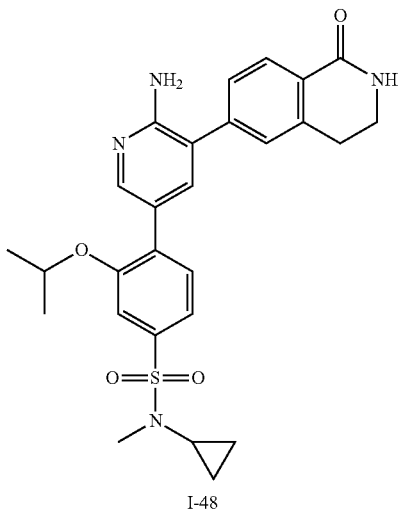
I-48

Step 1. 4-bromo-N-cyclopropyl-3-isopropoxy-N-methylbenzenesulfonamide (2-108)

The mixture of 4-bromo-N-cyclopropyl-3-hydroxy-N-methylbenzenesulfonamide (2-107, 130 mg, 0.426 mmol), $K_2CO_3$ (117 mg, 0.852 mmol) and 2-iodopropane (99 mg, 0.582 mmol) in MeCN (5 mL) was stirred at rt for 16 h. Upon reaction completion, the resulting mixture was filtered and concentrated under reduced pressure. The resulting residue was purified by silica gel chromatography (Pet Ether/ethyl acetate=1/1) to obtain title compound 2-108 (yellow solid, 95 mg, 64% yield). LCMS: 348 [M+H]$^+$.

Step 2. 4-(6-amino-5-(1-oxo-1,2,3,4-tetrahydroisoquinolin-6-yl)pyridin-3-yl)-N-cyclopropyl-3-isopropoxy-N-methylbenzenesulfonamide (I-48)

The mixture of 6-(2-amino-5-(4,4,5,5-tetramethyl-1,3,2-dioxaborolan-2-yl)pyridin-3-yl)-3,4-dihydroisoquinolin-1 (2H)-one (2-24, 60 mg, 0.16 mmol), 4-bromo-N-cyclopropyl-3-isopropoxy-N-methylbenzenesulfonamide (2-108, 57 mg, 0.16 mmol), $K_3PO_4$ (69 mg, 0.33 mmol), Pd(PPh$_3$)$_2$Cl$_2$ (11 mg, 0.016 mol) in THF (2 mL) and H$_2$O (0.1 mL) was stirred at 65° C. for 16 h under N$_2$ atmosphere. Upon reaction completion, the resulting mixture was filtered, concentrated under reduced pressure. The resulting residue was purified by prep-HPLC (C18 column, CH$_3$CN/H$_2$O, containing 0.05% NH$_4$HCO$_3$) to get title compound I-48 (white solid, 20 mg, 24%). LCMS: 507 (M+H)$^+$; HPLC: 100% (254 nm); $^1$H NMR (400 MHz, DMSO-d6) δ 8.27 (d, J=2.2 Hz, 1H), 7.93 (d, J=8.0 Hz, 2H), 7.65 (dd, J=13.5, 5.1 Hz, 2H), 7.47 (d, J=8.2 Hz, 1H), 7.45 (s, 1H), 7.39 (d, J=8.2 Hz, 1H), 7.33 (s, 1H), 5.98 (s, 2H), 4.94-4.42 (m, 1H), 3.41 (d, J=6.6 Hz, 2H), 2.96 (t, J=6.5 Hz, 2H), 2.69 (d, J=15.2 Hz, 3H), 1.87 (d, J=3.5 Hz, 1H), 1.29 (d, J=6.0 Hz, 6H), 0.88-0.55 (m, 4H).

Example 40: 4-(6-amino-5-(1-oxo-1,2,3,4-tetrahydroisoquinolin-6-yl)pyridin-3-yl)-N-cyclopropyl-3-methoxybenzenesulfonamide (I-49)

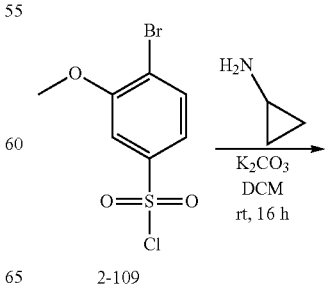
2-109

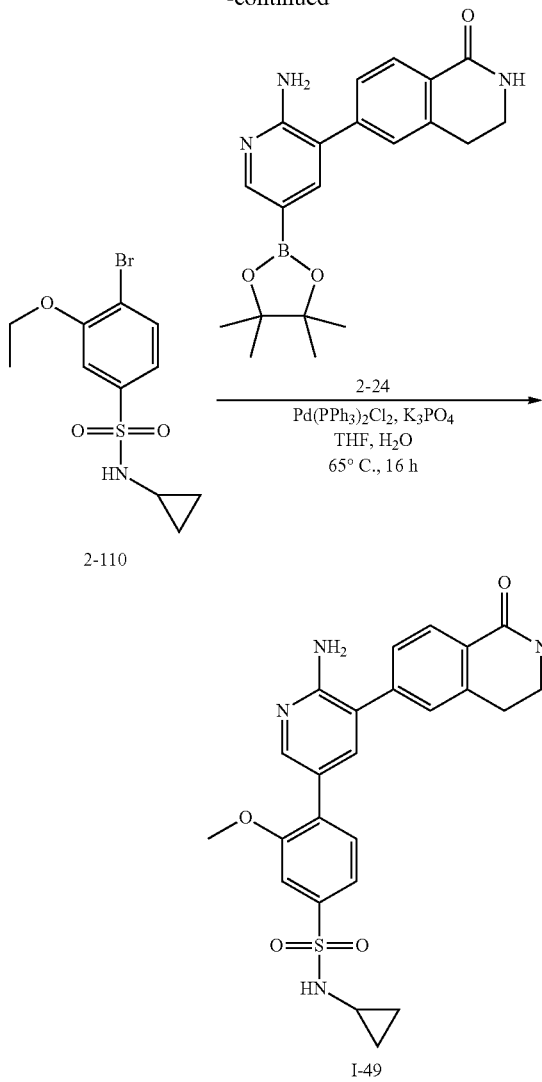

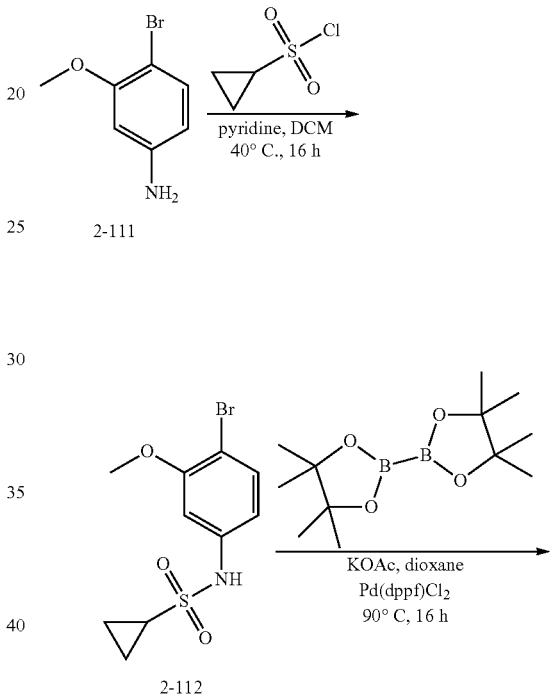

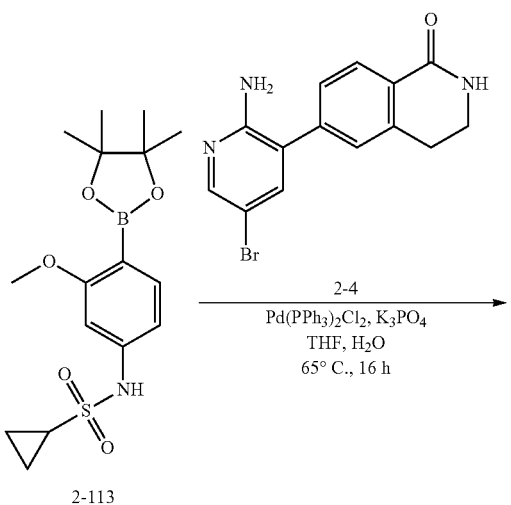

under reduced pressure. The resulting residue was purified by prep-HPLC (C18 column, CH₃CN/H₂O, containing 0.05% NH₄HCO₃) to get title compound I-49 (white solid, 10 mg, 13%). LCMS: 465 [M+H]$^+$; HPLC: 100% (254 nm); $^1$H NMR (400 MHz, DMSO-$d_6$) δ 8.20 (s, 1H), 7.92 (d, J=8.2 Hz, 3H), 7.74-7.53 (m, 2H), 7.51-7.26 (m, 4H), 5.96 (s, 2H), 3.85 (s, 3H), 3.41 (s, 2H), 2.96 (t, J=6.2 Hz, 2H), 2.13 (s, 1H), 0.61-0.29 (m, 4H).

Example 41: N-(4-(6-amino-5-(1-oxo-1,2,3,4-tetrahydroisoquinolin-6-yl)pyridin-3-yl)-3-methoxyphenyl)cyclopropanesulfonamide (I-50)

Step 1. 4-bromo-N-cyclopropyl-N,3-dimethylbenzenesulfonamide (2-110)

The mixture of 4-bromo-3-methoxybenzene-1-sulfonyl chloride (2-109, 99 mg, 0.35 mmol), K₂CO₃ (69 mg, 0.70 mmol) and cyclopropanamine (29 mg, 0.52 mmol) in DCM (20 mL) was stirred at rt for 16 h. Upon reaction completion, the resulting mixture was filtered, then concentrated under reduced pressure to get title compound 2-110 (yellow oil, 100 mg, 94% yield). LCMS: 306 [M+H]$^+$.

Step 2. 4-(6-amino-5-(1-oxo-1,2,3,4-tetrahydroisoquinolin-6-yl)pyridin-3-yl)-N-cyclopropyl-3-methoxybenzenesulfonamide (I-49)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 60 mg, 0.16 mmol), 4-bromo-N-cyclopropyl-3-methoxybenzenesulfonamide (2-110, 50 mg, 0.16 mmol), K3PO4 (69 mg, 0.33 mmol), Pd(PPh₃)₂Cl₂ (11 mg, 0.016 mol) in THF (2 mL) and H₂O (0.1 mL) was stirred at 65° C. for 16 h under N₂ atmosphere. Upon reaction completion, the resulting mixture was filtered and concentrated

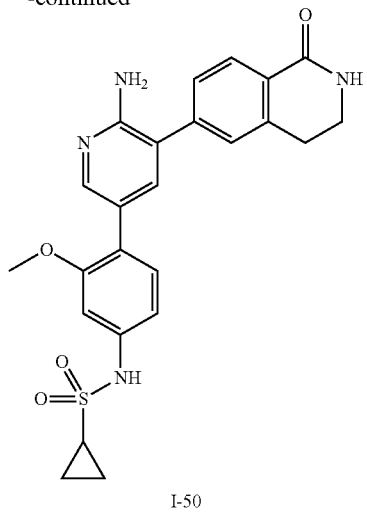

I-50

Step 1. N-(4-bromo-3-methoxyphenyl)cyclopropane sulfonamide (2-112)

The mixture of 4-bromo-3-methoxyaniline (2-111, 1 g, 4.97 mmol), pyridine (785 mg, 9.94 mmol) and cyclopropanesulfonyl chloride (696 mg, 4.97 mmol) in DCM (20 mL) was stirred at 40° C. rt for 16 h. Upon reaction completion, the resulting mixture was filtered, concentrated to remove the solvent. The resulting residue was purified by silica gel chromatography (Pet Ether/ethyl acetate=1/1) to obtain title compound 2-112 (yellow solid, 1.2 g, 79% yield). LCMS: 306 [M+H]+.

Step 2. N-(3-methoxy-4-(4,4,5,5-tetramethyl-1,3,2-dioxaborolan-2-yl)phenyl) cyclopropanesulfonamide (2-113)

The mixture of N-(4-bromo-3-methoxyphenyl)cyclopropanesulfonamide (2-112, 1 g, 3.27 mmol), 4,4,4',4',5,5,5',5'-octamethyl-2,2'-bi(1,3,2-dioxaborolane) (1.66 g, 6.54 mmol), KOAc (640 mg, 6.54 mmol), and Pd(dppf)Cl₂ (277 mg, 0.34 mmol) in 1,4-dioxane (15 ml) was stirred for 16 h at 90° C. under N₂ atmosphere. Upon reaction completion, the resulting mixture was the mixture was extracted with ethyl acetate (50 mL×3) and the combined organic phases were concentrated under reduced pressure. The resulting residue was purified by silica gel chromatography (Pet Ether/ethyl acetate=10/1) to obtain title compound 2-113 (yellow solid, 700 mg, 61% yield). LCMS: 354 [M+H]+.

Step 3. N-(4-(6-amino-5-(1-oxo-1,2,3,4-tetrahydroisoquinolin-6-yl)pyridin-3-yl)-3-methoxyphenyl) cyclopropanesulfonamide (I-50)

The mixture of N-(3-methoxy-4-(4,4,5,5-tetramethyl-1,3,2-dioxaborolan-2-yl)phenyl)cyclopropanesulfonamide (2-113, 200 mg, 0.566 mmol), 6-(2-amino-5-bromopyridin-3-yl)-3,4-dihydroisoquinolin-1(2H)-one (2-4, 179 mg, 0.566 mmol), K₃PO₄ (240 mg, 1.132 mmol), Pd(PPh₃)₂Cl₂ (40 mg, 0.056 mol) in THF (2 mL), and H₂O (0.1 mL) was stirred at 65° C. for 16 h under N₂ atmosphere. Upon reaction completion, the resulting mixture was filtered and concentrated under reduced pressure. The resulting residue was purified by prep-HPLC (C18 column, CH₃CN/H₂O, containing 0.05% NH₄HCO₃) to get title compound I-50 (white solid, 70 mg, 27%). LCMS: 465 [M+H]+; HPLC: 100% (254 nm); ¹H NMR (400 MHz, DMSO-d₆) δ 9.78 (s, 1H), 8.09 (s, 1H), 8.04-7.84 (m, 2H), 7.52-7.39 (m, 3H), 7.28 (d, J=8.1 Hz, 1H), 6.96 (s, 1H), 6.88 (d, J=8.1 Hz, 1H), 5.79 (s, 2H), 3.74 (s, 3H), 3.41-3.39 (m, 2H), 2.95 (t, J=6.2 Hz, 2H), 2.67 (d, J=6.8 Hz, 1H), 0.97 (d, J=5.0 Hz, 4H).

Example 42: N-(4-(6-amino-5-(1-oxo-1,2,3,4-tetrahydroisoquinolin-6-yl)pyridin-3-yl)-3-fluorophenyl) cyclopropanesulfonamide (I-51)

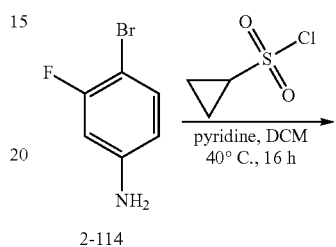

2-114

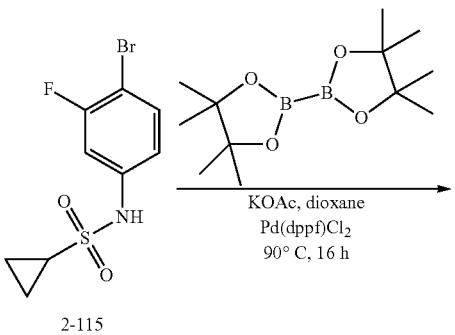

2-115

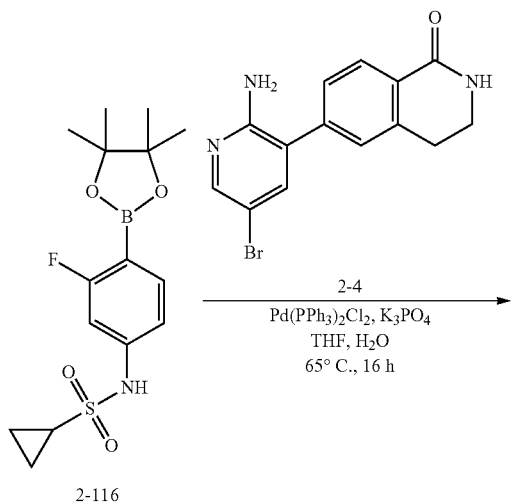

2-116

-continued

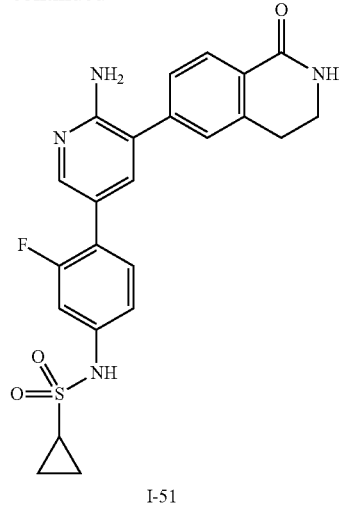

I-51

Step 1. N-(4-bromo-3-fluorophenyl)cyclopropanesulfonamide (2-115)

The mixture of 4-bromo-3-fluoroaniline (2-114, 1 g, 5.3 mmol), pyridine (837 mg, 10.6 mmol) and cyclopropanesulfonyl chloride (742 mg, 5.3 mmol) in DCM (20 mL) was stirred at 40° C. for 16 h. Upon reaction completion, the resulting mixture was filtered and concentrated under reduced pressure. The resulting residue was purified by silica gel chromatography (Pet Ether/ethyl acetate=1/1) to obtain title compound 2-115 (yellow solid, 1.2 g, 77% yield). LCMS: 294 [M+H]$^+$.

Step 2. N-(3-fluoro-4-(4,4,5,5-tetramethyl-1,3,2-dioxaborolan-2-yl)phenyl) cyclopropanesulfonamide (2-116)

The mixture of N-(4-bromo-3-fluorophenyl)cyclopropanesulfonamide (2-115, 1 g, 3.4 mmol), 4,4,4',4',5,5,5',5'-octamethyl-2,2'-bi(1,3,2-dioxaborolane) (1.7 g, 6.8 mmol), KOAc (666 mg, 6.8 mmol), and Pd(dppf)Cl$_2$(277 mg, 0.34 mmol) in 1,4-dioxane (15 ml) was stirred for 16 h at 90° C. under N$_2$ atmosphere. Upon reaction completion, water was added H$_2$O and the resulting mixture was extracted with ethyl acetate (50 mL×3). The combined organic phases were concentrated under reduced pressure. The resulting residue was purified by silica gel chromatography (Pet Ether/ethyl acetate=10/1) to obtain title compound 2-116 (yellow solid, 700 mg, 62% yield). LCMS: 342 [M+H]$^+$.

Step 3. N-(4-(6-amino-5-(1-oxo-1,2,3,4-tetrahydroisoquinolin-6-yl)pyridin-3-yl)-3-fluorophenyl) cyclopropanesulfonamide (I-51)

The mixture of N-(3-fluoro-4-(4,4,5,5-tetramethyl-1,3,2-dioxaborolan-2-yl)phenyl)cyclopropanesulfonamide (2-116, 300 mg, 0.88 mmol), 6-(2-amino-5-bromopyridin-3-yl)-3,4-dihydroisoquinolin-(2H)-one (2-4, 279 mg, 0.88 mmol), KF (102 mg, 1.76 mmol), Pd(PPh$_3$)$_2$Cl$_2$ (62 mg, 0.088 mol) in THF (2 mL), and H$_2$O (0.1 mL) was stirred at 65° C. for 16 h under N$_2$ atmosphere. Upon reaction completion, the resulting mixture was filtered and concentrated under reduced pressure. The resulting residue was purified by prep-HPLC (C18 column, CH$_3$CN/H$_2$O, containing 0.05% NH$_4$HCO$_3$) to get title compound I-51 (white solid, 125 mg, 31%). LCMS: 453 [M+H]$^+$; HPLC: 100% (254 nm); $^1$H NMR (400 MHz, DMSO-d$_6$) δ 9.47 (s, 1H), 8.16 (s, 1H), 7.97 (s, 1H), 7.92 (d, J=7.8 Hz, 1H), 7.64-7.32 (m, 4H), 7.22-6.99 (m, 2H), 5.97 (s, 2H), 3.40 (d, J=4.1 Hz, 2H), 2.96 (t, J=6.4 Hz, 2H), 2.78-2.64 (m, 1H), 0.97 (d, J=6.3 Hz, 4H).

Example 43: 4-(6-amino-5-(1-oxo-1,2,3,4-tetrahydroisoquinolin-6-yl)pyridin-3-yl)-N-cyclohexyl-3-methoxy-N-methylbenzenesulfonamide (I-52)

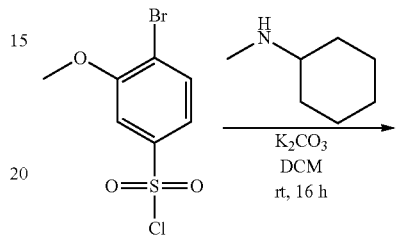

2-109

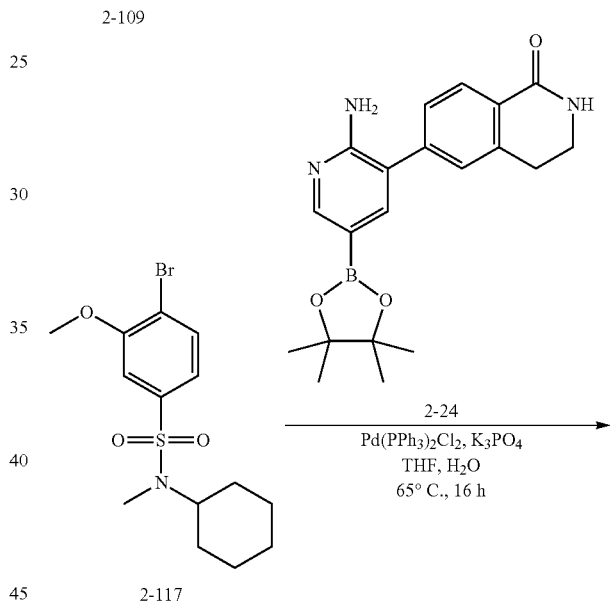

2-117

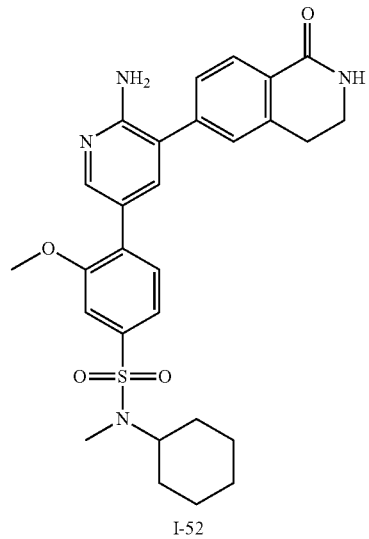

I-52

Step 1. 4-bromo-N-cyclohexyl-3-methoxy-N-methylbenzenesulfonamide (2-117)

The mixture of 4-bromo-3-methoxybenzene-1-sulfonyl chloride (2-109, 180 mg, 0.63 mmol), K₂CO₃ (174 mg, 1.26 mmol) and N-methylcyclohexanamine (72 mg, 0.63 mmol) in DCM (20 mL) was stirred at 40° C. for 16 h. Upon reaction completion, the resulting mixture was filtered and then concentrated under reduced pressure to get title compound 2-117 (yellow solid, 210 mg, 92% yield). LCMS: 362 [M+H]⁺.

Step 2. 4-(6-amino-5-(1-oxo-1,2,3,4-tetrahydroisoquinolin-6-yl)pyridin-3-yl)-N-cyclohexyl-3-methoxy-N-methylbenzenesulfonamide (I-52)

The mixture of 6-(2-amino-5-(4,4,5,5-tetramethyl-1,3,2-dioxaborolan-2-yl)pyridin-3-yl)-3,4-dihydroisoquinolin-1 (2H)-one (2-24, 70 mg, 0.19 mmol), 4-bromo-N-cyclohexyl-3-methoxy-N-methylbenzenesulfonamide (2-117, 69 mg, 0.19 mmol), K3PO₄ (91 mg, 0.38 mmol), Pd(PPh₃)₂Cl₂ (13 mg, 0.019 mol) in THF (2 mL), and H₂O (0.1 mL) was stirred at 65° C. for 16 h under N₂ atmosphere. Upon reaction completion, the resulting mixture was filtered and concentrated under reduced pressure. The resulting residue was purified by prep-HPLC (C18 column, CH₃CN/H₂O, containing 0.05% NH₄HCO₃) to get title compound I-52 (white solid, 16 mg, 16%). LCMS: 521 [M+H]⁺; HPLC: 100% (254 nm); ¹H NMR (400 MHz, DMSO-d6) δ 8.26 (d, J=2.1 Hz, 1H), 8.03 (dd, J=18.1, 5.0 Hz, 2H), 7.70 (d, J=8.0 Hz, 1H), 7.59-7.42 (m, 3H), 7.39 (s, 1H), 3.71 (s, 1H), 3.45 (t, J=6.6 Hz, 2H), 3.00 (t, J=6.6 Hz, 2H), 2.73 (s, 3H), 1.61-1.63 (m, 3H), 1.42-1.13 (m, 6H), 1.00 (d, J=13.2 Hz, 1H).

Example 44: 4-(6-amino-5-(1-oxo-1,2,3,4-tetrahydroisoquinolin-6-yl)pyridin-3-yl)-3-methoxy-N-methyl-N-(tetrahydro-2H-pyran-4-yl)benzenesulfonamide (I-53)

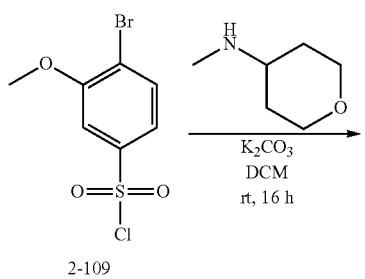

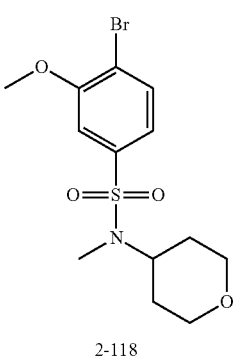

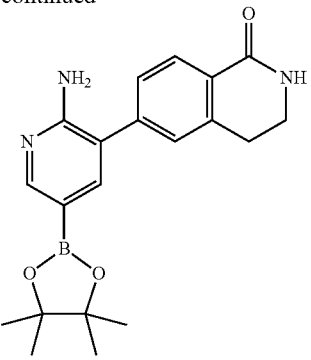

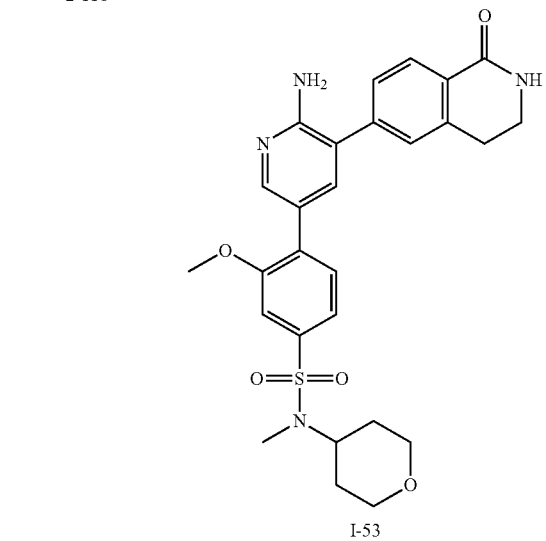

Step 1. 4-bromo-3-methoxy-N-methyl-N-(tetrahydro-2H-pyran-4-yl)benzenesulfonamide (2-118)

The mixture of 4-bromo-3-methoxybenzene-1-sulfonyl chloride (2-109, 180 mg, 0.63 mmol), K₂CO₃ (174 mg, 1.26 mmol) and N-methyltetrahydro-2H-pyran-4-amine (73 mg, 0.63 mmol) in DCM (20 mL) was stirred at 40° C. for 16 h. Upon reaction completion, the resulting mixture was filtered and then concentrated under reduced pressure to get title compound 2-118 (yellow solid, 210 mg, 91% yield). LCMS: 364 [M+H]⁺.

Step 2. 4-(6-amino-5-(1-oxo-1,2,3,4-tetrahydroisoquinolin-6-yl)pyridin-3-yl)-3-methoxy-N-methyl-N-(tetrahydro-2H-pyran-4-yl)benzenesulfonamide (1-53)

The mixture of 6-(2-amino-5-(4,4,5,5-tetramethyl-1,3,2-dioxaborolan-2-yl)pyridin-3-yl)-3,4-dihydroisoquinolin-1 (2H)-one (2-24, 70 mg, 0.19 mmol), 4-bromo-3-methoxy-N-methyl-N-(tetrahydro-2H-pyran-4-yl) benzenesulfonamide (2-118, 69 mg, 0.19 mmol), K₃PO₄ (91 mg, 0.38 mmol), Pd(PPh$_3$)$_2$Cl$_2$ (13 mg, 0.019 mol) in THF (2 mL), and H$_2$O (0.1 mL) was stirred at 65° C. for 16 h under N$_2$ atmosphere. Upon reaction completion, the resulting mixture was filtered and concentrated under reduced pressure. The resulting residue was purified by prep-HPLC (C18 column, CH$_3$CN/H$_2$O, containing 0.05% NH$_4$HCO$_3$) to get title compound I-53 (white solid, 15 mg, 15%). LCMS: 523 [M+H]$^+$; HPLC: 100% (254 nm); $^1$H NMR (400 MHz, DMSO-d$_6$) δ 8.27 (d, J=2.1 Hz, 1H), 8.08 (d, J=2.1 Hz, 1H), 8.00 (d, J=8.0 Hz, 1H), 7.70 (d, J=8.0 Hz, 1H), 7.51 (dd, J=7.5, 5.4 Hz, 3H), 7.42 (d, J=1.5 Hz, 1H), 4.02 (t, J=11.7 Hz, 1H), 3.89 (s, 3H), 3.45 (t, J=6.6 Hz, 2H), 3.35 (t, J=11.3 Hz, 2H), 3.00 (t, J=6.6 Hz, 2H), 2.76 (d, J=11.1 Hz, 3H), 1.72-1.52 (m, 2H), 1.24 (t, J=23.2 Hz, 2H).

Example 45: 6-(2-amino-5-(2-fluoro-4-nitrophenyl)pyridin-3-yl)-3,4-dihydroisoquinolin-1(2H)-one (I-54)

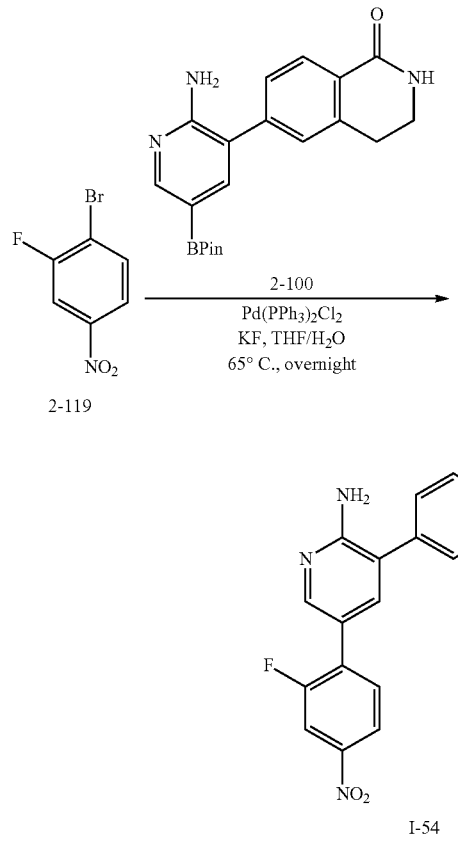

A mixture of 2-119 (44 mg, 0.20 mmol), 2-100 (73 mg, 0.20 mmol), Pd(PPh$_3$)$_2$Cl$_2$ (14 mg, 0.02 mmol), KF (24 mg, 0.40 mmol), THF (2 mL), and H$_2$O (0.5 mL) was degassed with N$_2$. The resulting mixture was stirred at 65° C. overnight. Upon completion, the mixture was filtered and the filtrate was concentrated. The resulting residue was purified by prep-TLC with DCM/MeOH=10/1 to give I-54 (yellow solid, 42 mg, yield 55%). HPLC: 100% (254 nm); LCMS (m/z): 379 [M+H]$^+$; $^1$H NMR (DMSO-d$_6$, 400 MHz): δ 8.33 (t, J=2.4 Hz, 1H), 8.19 (dd, J$_1$=11.2 Hz, J$_2$=2.4 Hz, 1H), 8.12 (dd, J$_1$=8.8 Hz, J$_2$=2.4 Hz, 1H), 7.91-7.96 (m, 3H), 7.68 (t, J=2.4 Hz, 1H), 7.48 (dd, J$_1$=8.0 Hz, J$_2$=1.6 Hz, 1H), 7.47 (s, 1H), 6.28 (s, 2H), 3.41 (td, J$_1$=6.4 Hz, J$_2$=2.8 Hz, 2H), 2.97 (t, J=6.4 Hz, 2H).

Example 46: 6-(2-amino-5-(benzo[d]thiazol-4-yl)pyridin-3-yl)-3,4-dihydroisoquinolin-1(2H)-one (I-55)

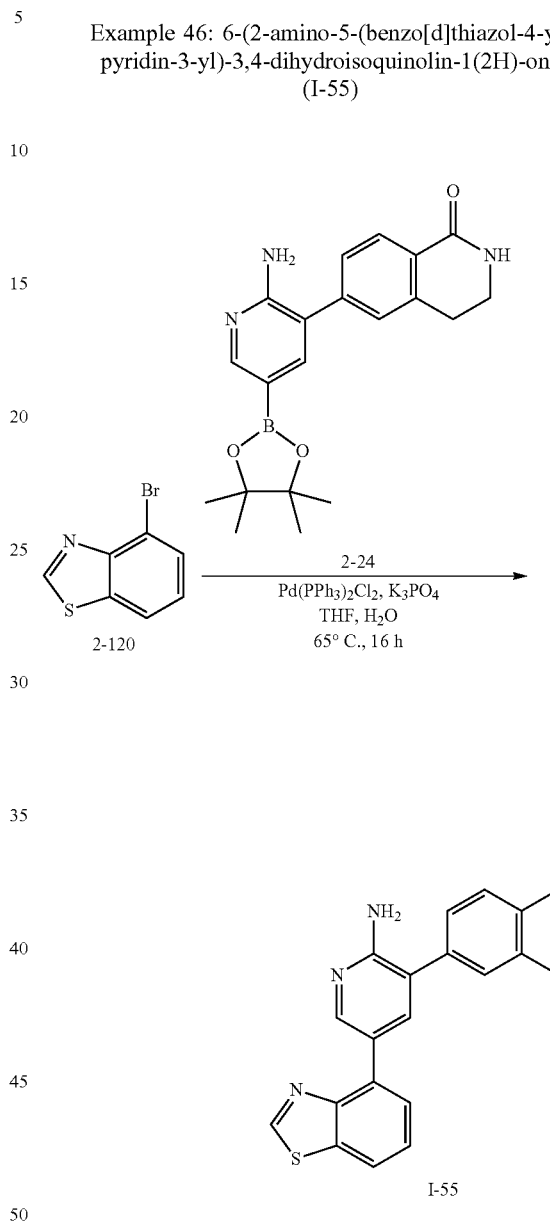

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 70 mg, 0.19 mmol), 4-bromobenzo[d]thiazole (2-120, 41 mg, 0.19 mmol), K$_3$PO$_4$ (91 mg, 0.38 mmol), Pd(PPh$_3$)$_2$C12 (13 mg, 0.019 mol) in THF (2 mL), and H$_2$O (0.1 mL) was stirred at 65° C. for 16 h under N$_2$ atmosphere. Upon reaction completion, the resulting mixture was filtered and concentrated under reduced pressure. The resulting residue was purified by prep-HPLC (C18 column, CH$_3$CN/H$_2$O, containing 0.05% NH$_4$HCO$_3$) to get title compound I-55 (white solid, 20 mg, 28%). LCMS: 373 [M+H]$^+$; HPLC: 100% (254 nm); $^1$H NMR (400 MHz, DMSO-d$_6$) δ 9.40 (s, 1H), 8.53 (d, J=2.3 Hz, 1H), 8.11 (dd, J=8.0, 1.0 Hz, 1H), 7.94 (dd, J=7.4, 5.1 Hz, 3H), 7.69 (dd, J=7.5, 1.1 Hz, 1H), 7.59-7.39 (m, 3H), 5.96 (s, 2H), 3.42 (td, J=6.6, 2.7 Hz, 2H), 2.97 (t, J=6.5 Hz, 2H).

Example 47: 6-(2-amino-5-(thiazolo[4,5-c]pyridin-7-yl)pyridin-3-yl)-3,4-dihydroisoquinolin-1(2H)-one (I-56)

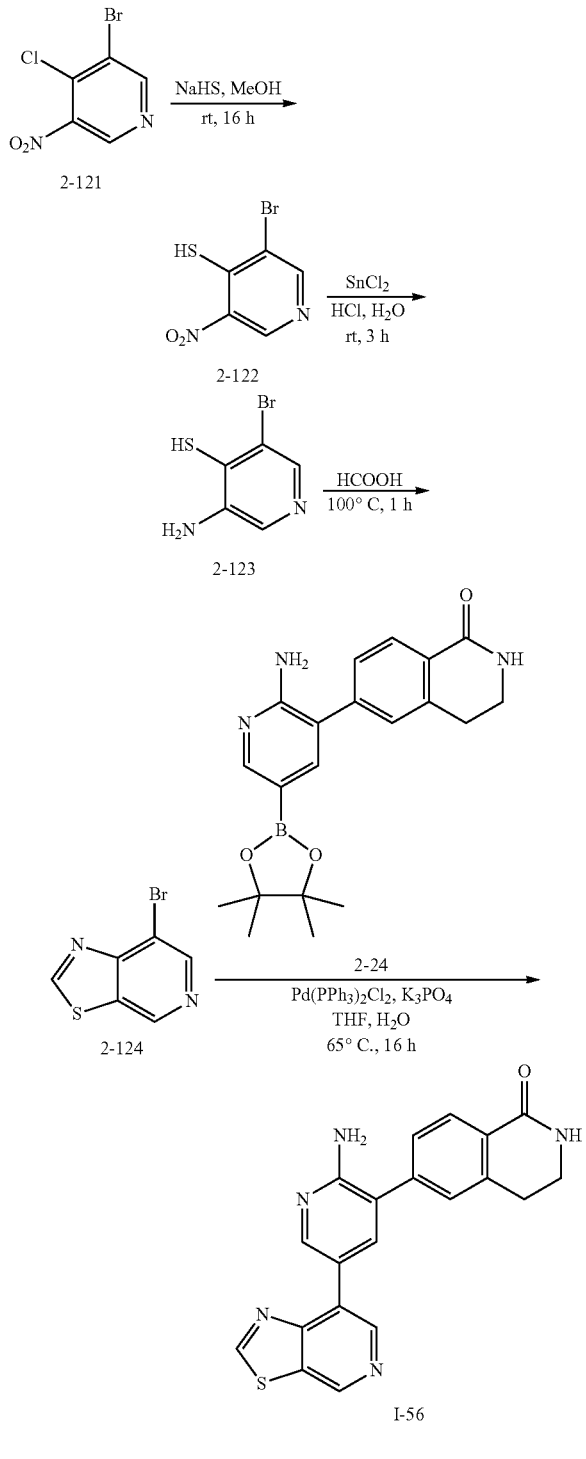

Step 1. 3-bromo-5-nitropyridine-4-thiol (2-122)

The mixture of 3-bromo-4-chloro-5-nitropyridine (2-121, 1.7 g, 7.2 mmol) and NaHS (0.8 g 14.4 mmol) in MeOH (20 mL) was stirred at rt for 16 h. Upon reaction completion, saturated NaOH (100 mL, 20%) was added and the resulting mixture was filtered. The filtrate was acidified with saturated HCl and the resulting solid was separated and dried to get title compound 2-122 (red solid, 1.5 g, 59% yield). LCMS: 235 [M+H]+.

Step 2. 3-amino-5-bromopyridine-4-thiol (2-123)

The mixture of 3-bromo-5-nitropyridine-4-thiol (2-122, 900 mg, 3.84 mmol), HCl (36%, 4 mL), and SnCl$_2$ (1.46 g, 7.69 mmol) in H$_2$O (4 mL) was stirred at rt for 3 h. Upon reaction completion, the resulting mixture was filtered and the filtrate was concentrated under reduced pressure to get title compound 2-123 (yellow solid, 600 mg, 60% yield). LCMS: 205 [M+H]+.

Step 3. 7-bromothiazolo[4,5-c]pyridine (2-124)

The mixture of 3-amino-5-bromopyridine-4-thiol (2-123, 500 mg, 2.45 mmol) and Zn (79 mg, 1.22 mmol) in HCOOH (4 mL) was stirred at 100° C. for 1 h. Upon reaction completion, the resulting mixture was the mixture was concentrated under reduced pressure. The resulting residue was purified by silica gel chromatography (Pet Ether/ethyl acetate=1/1) to obtain title compound 2-124 (yellow solid, 150 mg, 27% yield). LCMS: 215 [M+H]+.

Step 4. 6-(2-amino-5-(thiazolo[4,5-c]pyridin-7-yl) pyridin-3-yl)-3,4-dihydroisoquinolin-1(2H)-one (I-56)

The mixture of 6-(2-amino-5-(4,4,5,5-tetramethyl-1,3,2-dioxaborolan-2-yl)pyridin-3-yl)-3,4-dihydroisoquinolin-1 (2H)-one (2-24, 68 mg, 0.186 mmol), 7-bromothiazolo[4,5-c]pyridine (2-124, 40 mg, 0.186 mmol), K$_3$PO$_4$ (79 mg, 0.372 mmol), Pd(PPh$_3$)$_2$Cl$_2$ (13 mg, 0.0018 mmol) in THF (2 mL), and H$_2$O (0.1 mL) was stirred at 65° C. for 16 h under N$_2$ atmosphere. Upon reaction completion, the resulting mixture was filtered and concentrated under reduced pressure. The resulting residue was purified by prep-HPLC (C18 column, CH$_3$CN/H$_2$O, containing 0.05% NH$_4$HCO$_3$) to get title compound I-56 (white solid, 7 mg, 10%). LCMS: 374 [M+H]+; HPLC: 100% (254 nm); $^1$H NMR (400 MHz, DMSO-d$_6$) δ 9.58 (s, 1H), 9.31 (s, 1H), 8.73 (s, 1H), 8.43 (d, J=2.4 Hz, 1H), 7.97 (s, 1H), 7.94 (d, J=7.8 Hz, 1H), 7.79 (d, J=2.3 Hz, 1H), 7.52 (d, J=9.4 Hz, 2H), 6.22 (s, 2H), 3.42 (s, 2H), 2.97 (t, J=6.4 Hz, 2H).

Example 48: 6-(2-amino-5-(4-fluorobenzo[d]thiazol-7-yl)pyridin-3-yl)-3,4-dihydroisoguinolin-1 (2H)-one (I-57)

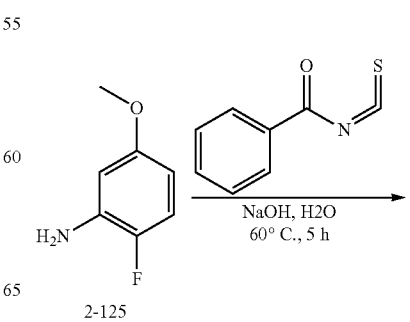

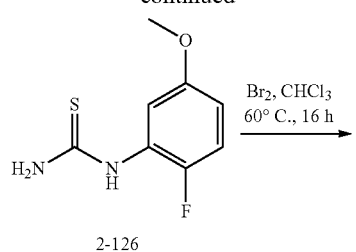

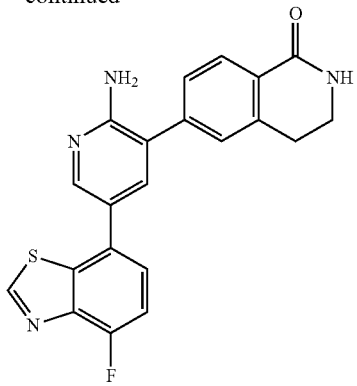

Step 1. 1-(2-fluoro-5-methoxyphenyl)thiourea (2-126)

The mixture of 2-fluoro-5-methoxyaniline (2-125, 1.0 g, 7.0 mmol) and benzoyl isothiocyanate (1.4 g, 8.5 mmol) in acetone (20 mL) was stirred at 60° C. for 2 h. Upon reaction completion, the resulting mixture was cooled to room temperature and then poured into ice water (20 mL). The resulting precipitate was collected, dried, and then added into the solution of NaOH (0.74 g, 3.04 mmol) in water (20 mL) at 80° C. The resulting mixture was then stirred at 80° C. for 2 h. After the reaction was cooled to room temperature, the pH was adjusted to 10 with concentrated hydrochloric acid. The resulting precipitate was collected by filtration, washed with saturated NaHCO$_3$ and water, and then dried under reduced pressure to get title compound 2-126 (white solid, 900 mg, 64% yield). LCMS: 201 [M+H]$^+$.

Step 2. 4-fluoro-7-methoxybenzo[d]thiazol-2-amine (2-127)

The mixture of 1-(2-fluoro-5-methoxyphenyl)thiourea (2-126, 900 mg, 4.5 mmol) and Br$_2$ (720 mg, 4.5 mmol) in CHCl$_3$ (20 mL) was stirred at 60° C. for 16 h. Upon reaction completion, the resulting mixture was concentrated under reduced pressure and water (100 mL) was added. The resulting mixture was extracted with ethyl acetate (100 mL×3) and the combined organic phases were concentrated under reduced pressure. The resulting residue was purified by column chromatography (Pet Ether/ethyl acetate=1/1) to get title compound 2-127 (yellow solid, 545 mg, 61% yield). LCMS: 199 [M+H]$^+$.

Step 3. 4-fluoro-7-methoxybenzo[d]thiazole (2-128)

The mixture of 4-fluoro-7-methoxybenzo[d]thiazol-2-amine (2-127, 500 mg, 2.5 mmol), and isopentyl nitrite (2-91a, 295 mg, 2.5 mmol) in dioxane (2 mL) was stirred at 80° C. for 1 h. Upon reaction completion, the resulting mixture was concentrated under reduced pressure and the resulting residue was purified by column chromatography (Pet Ether/ethyl acetate=2/1) to get title compound 2-128 (yellow solid, 400 mg, 86% yield).

Step 4. 4-fluorobenzo[d]thiazol-7-ol (2-129)

The mixture of 4-fluoro-7-methoxybenzo[d]thiazole (2-128, 350 mg, 1.91 mmol) and AlCl$_3$ (786 mg, 5.73 mmol)

in DCM (20 mL) was stirred at rt for 32 h. Upon reaction completion, water (100 mL) was added water (100 mL) and the resulting mixture was extracted with ethyl acetate (100 mL×3). The combined organic phases were concentrated under reduced pressure and the resulting residue was purified by column chromatography (Pet Ether/ethyl acetate=1/1) to get title compound 2-129 (yellow solid, 270 mg, 83% yield). LCMS: 170 [M+H]⁺.

Step 5. 4-fluorobenzo[d]thiazol-7-yl trifluoromethanesulfonate (2-130)

The mixture of 4-fluorobenzo[d]thiazol-7-ol (2-129, 200 mg, 1.18 mmol), DIPEA (304 mg, 2.36 mmol), and trifluoromethanesulfonic anhydride (332 mg, 1.18 mmol) in DCM (20 mL) was stirred at rt for 32 h. Upon reaction completion, water (100 mL) was added and the resulting mixture was extracted with ethyl acetate (100 mL×3). The combined organic phases were concentrated under reduced pressure and the resulting residue was purified by column chromatography (Pet Ether/ethyl acetate=1/1) to get title compound 2-130 (yellow solid, 160 mg, 48% yield). LCMS: 302 [M+H]⁺.

Step 6. 6-(2-amino-5-(4-fluorobenzo[d]thiazol-7-yl)pyridin-3-yl)-3,4-dihydroisoquinolin-1(2H)-one (I-57)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 70 mg, 0.192 mmol), 4-fluorobenzo[d]thiazol-7-yl trifluoromethanesulfonate (2-130, 60 mg, 0.192 mmol), K₂CO₃ (50 mg, 0.382 mmol), Pd(PPh₃)₂Cl₂ (13 mg, 0.018 mmol) in THF (2 mL), and H₂O (0.1 mL) was stirred at 85° C. for 16 h under N₂. Upon reaction completion, the resulting mixture was filtered and concentrated under reduced pressure. The resulting residue was purified by prep-HPLC (C18 column, CH₃CN/H₂O, containing 0.05% NH₄HCO₃) to get title compound I-57 (white solid, 20 mg, 25%). LCMS: 391 [M+H]⁺; HPLC: 100% (254 nm); ¹H NMR (400 MHz, DMSO-d₆) δ 9.47 (s, 1H), 8.34 (d, J=2.4 Hz, 1H), 8.05-7.81 (m, 2H), 7.68 (d, J=2.4 Hz, 1H), 7.62 (dd, J=8.3, 4.5 Hz, 1H), 7.49 (t, J=9.5 Hz, 3H), 6.11 (s, 2H), 3.41 (d, J=3.9 Hz, 2H), 2.96 (t, J=6.4 Hz, 2H).

Example 49: N-(3-(6-amino-5-(1-oxo-1,2,3,4-tetrahydroisoquinolin-6-yl)pyridin-3-yl)phenyl) cyclopropanesulfonamide (I-58)

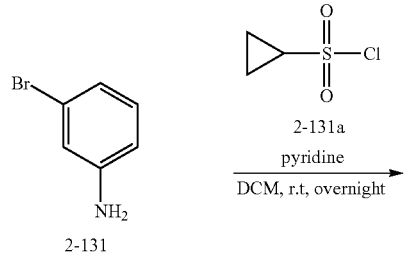

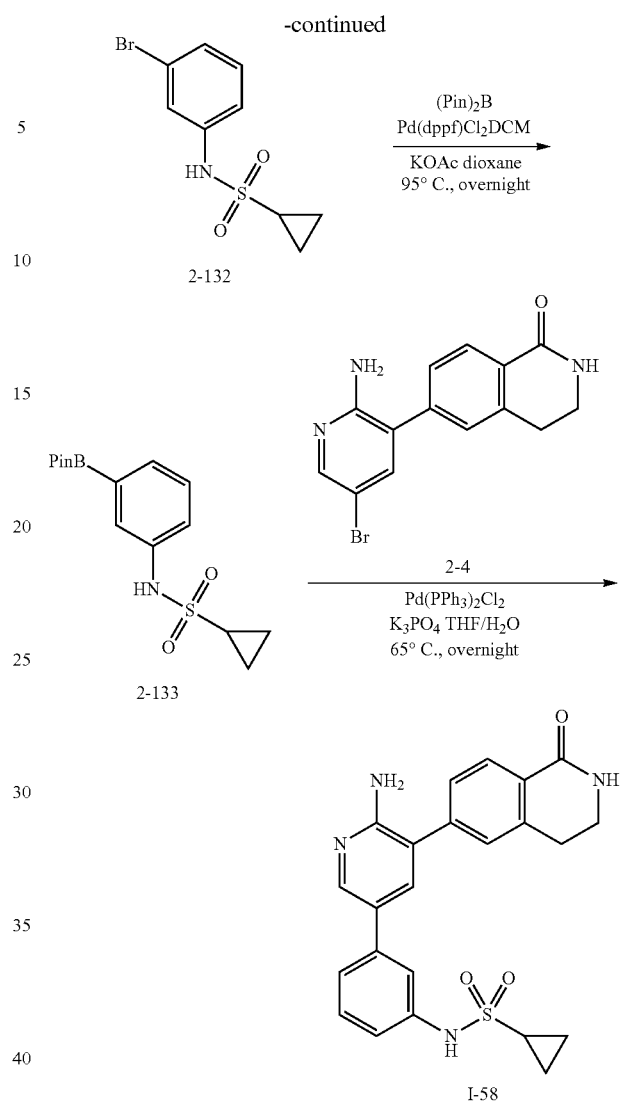

Step 1. N-(3-bromophenyl)cyclopropanesulfonamide (2-132)

To a solution of 2-131 (340 mg, 2.0 mmol) and pyridine (320 mg, 4.0 mmol) in DCM (10 mL), was added 2-131a (850 mg, 6.0 mmol) and the resulting mixture was stirred at r.t overnight Upon reaction completion, the reaction mixture was concentrated, water (20 mL) was added, the resulting mixture was extracted with DCM (20 mL×3). The combined organic layers were washed with brine (20 mL), dried over Na₂SO₄, filtered and concentrated under reduced pressure. The resulting residue was purified by Prep-TLC with Pet Ether/ethyl acetate (2/1) to give 2-132 (yellow solid, 96 mg, yield 64%). LCMS (m/z): 293 [M+NH₄]⁺.

Step 2. N-(3-(4,4,5,5-tetramethyl-1,3,2-dioxaborolan-2-yl)phenyl)cyclopropanesulfonamide (2-133)

A mixture of 2-132 (210 mg, 0.76 mmol), Pin₂B₂ (252 mg, 0.99 mmol), Pd(dppf)Cl₂DCM (62 mg, 0.076 mmol), KOAc (149 mg, 1.52 mmol) and dioxane (5 mL) was degassed with N₂. The reaction mixture was stirred at 95° C.

overnight. The resulting mixture was filtered, the filtrate was concentrated, and the resulting residue was purified by prep-TLC eluting with Pet Ether/ethyl acetate=1/3 to give 2-133 (yellow solid, 201 mg, yield 82%). LCMS (m/z): 341 [M+NH₄]⁺.

Step 3. N-(3-(6-amino-5-(1-oxo-1,2,3,4-tetrahydroisoquinolin-6-yl)pyridin-3-yl)phenyl) cyclopropanesulfonamide (I-58)

A mixture of 2-133 (122 mg, 0.38 mmol), 2-4 (100 mg, 0.31 mmol), Pd(PPh₃)₂Cl₂ (21 mg, 0.03 mmol), K₃PO₄ (131 mg, 0.62 mmol), THF (2 mL) and H₂O (0.5 mL) was degassed with N₂ and the resulting mixture was stirred at 65° C. overnight. Upon reaction completion reaction mixture was filtered, the filtrate was concentrated, and the resulting residue was purified by prep-TLC eluting with THF/Pet Ether=3/1 to give 1-58 (off-white solid, 30 mg, yield 22%). HPLC: 100% (254 nm); LCMS (m/z): 435 [M+H]⁺; ¹H NMR (DMSO-d₆, 400 MHz): δ 9.73 (bs, 1H), 8.27 (d, J=2.4 Hz, 1H), 7.96 (s, 1H), 7.93 (d, J=8.0 Hz, 1H), 7.58 (d, J=2.0 Hz, 1H), 7.44-7.50 (m, 3H), 7.35-7.40 (m, 2H), 7.19 (td, J=7.2 Hz, 2.0 Hz, 1H), 5.94 (s, 2H), 3.39-3.45 (m, 2H), 2.97 (t, J=6.4 Hz, 2H), 2.67 (p, J=2.4 Hz, 1H), 0.94 (d, J=6.4 Hz, 4H).

Example 50: 6-(2-amino-5-(3-(thiazol-2-yl)phenyl)pyridin-3-yl)-3,4-dihydroisoquinolin-1(2H)-one (I-59)

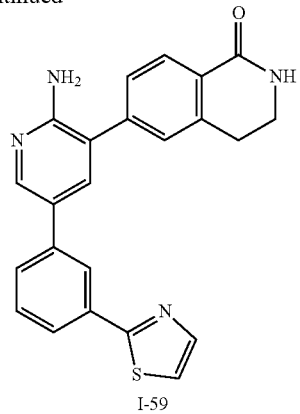
I-59

Step 1. 2-(3-bromophenyl)thiazole (2-135)

The mixture of 3-bromobenzothioamide (2-134, 1 g, 4.6 mmol), and 2-bromo-1,1-diethoxyethane (911 mg, 4.6 mmol) in THF (12 mL) was stirred at 75° C. for 2 d. Upon reaction completion, the resulting mixture was concentrated to remove the solvent and the resulting residue was purified by column chromatography (Pet Ether/ethyl acetate=2/1) to get title compound 2-135 (yellow oil, 800 mg, 72% yield). LCMS: 240[M+H]⁺.

Step 2. 2-(3-(4,4,5,5-tetramethyl-1,3,2-dioxaborolan-2-yl)phenyl)thiazole (2-136)

The mixture of 2-(3-bromophenyl)thiazole (2-135, 100 mg, 0.42 mmol), 4,4,4',4',5,5,5',5'-octamethyl-2,2'-bi(1,3,2-dioxaborolane) (106 mg, 0.42 mmol), KOAc (82 mg, 0.84 mmol), Pd(dppf)Cl₂ (30 mg, 0.042 mmol) in 1,4-dioxane (5 ml) was stirred for 16 h at 90° C. under N₂ atmosphere. Upon reaction completion, H₂O was added and the resulting mixture was extracted with ethyl acetate (50 mL×3) and the combined organic phases were concentrated under reduced pressure. The resulting residue was purified by silica gel chromatography (Pet Ether/ethyl acetate=10/1) to obtain title compound 2-136 (yellow oil, 90 mg, 75% yield). LCMS: 288 [M+H]⁺.

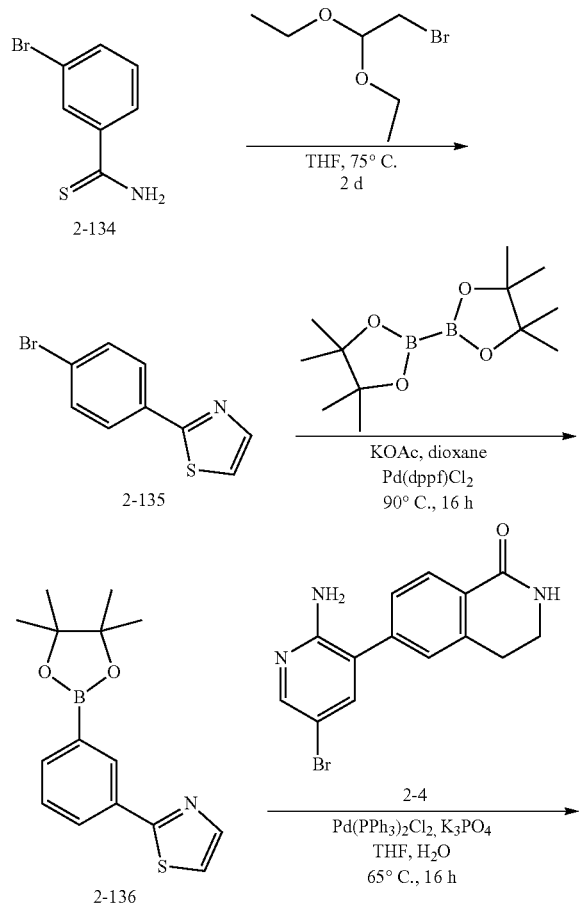

Step 3. 6-(2-amino-5-(3-(thiazol-2-yl)phenyl)pyridin-3-yl)-3,4-dihydroisoquinolin-1(2H)-one (I-59)

The mixture of 2-(3-(4,4,5,5-tetramethyl-1,3,2-dioxaborolan-2-yl)phenyl)thiazole (2-136, 45 mg, 0.157 mmol), 6-(2-amino-5-bromopyridin-3-yl)-3,4-dihydroisoquinolin-1(2H)-one (2-4, 50 mg, 0.157 mmol), K₃PO₄ (67 mg, 0.315 mmol), Pd(PPh₃)₂Cl₂ (11 mg, 0.0157 mmol) in THF (2 mL), and H₂O (0.1 mL) was stirred at 65° C. for 16 h under N₂ atmosphere. Upon reaction completion, the resulting mixture was filtered, concentrated under reduced pressure, and the resulting residue was purified by prep-HPLC (C18 column, CH₃CN/H₂O, containing 0.05% NH₄HCO₃) to get title compound I-59 (white solid, 25 mg, 40%). LCMS: 399 [M+H]⁺; HPLC: 100% (254 nm); ¹H NMR (400 MHz, DMSO-d₆) δ 8.39 (d, J=2.4 Hz, 1H), 8.15 (s, 1H), 8.00-7.70 (m, 7H), 7.60-7.45 (m, 3H), 5.97 (s, 2H), 3.38 (d, J=25.4 Hz, 2H), 2.98 (t, J=6.5 Hz, 2H).

199

Example 51: 6-(2-amino-5-(2-methoxy-4-(thiazol-2-yl)phenyl)pyridin-3-yl)-3,4-dihydroisoquinolin-1(2H)-one (I-60)

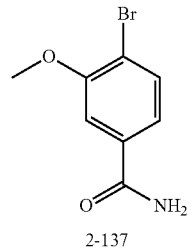

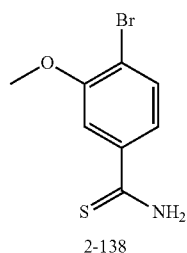

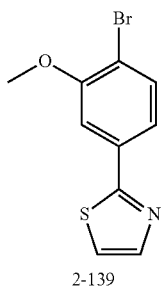

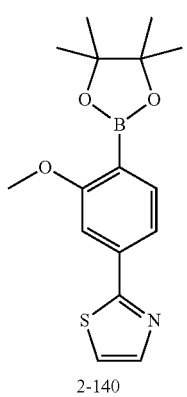

200

-continued

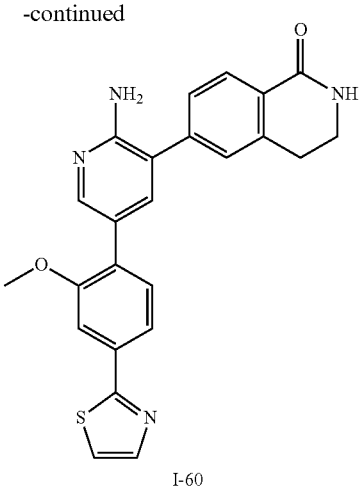

I-60

Step 1. 4-bromo-3-methoxybenzothioamide (2-138)

The mixture of 4-bromo-3-methoxybenzamide (2-137, 700 mg, 3.05 mmol), and lawesson reagent (1.2 g, 3.05 mmol) in toluene (25 8 mL) was stirred at 90° C. for 5 min. Upon reaction completion, the resulting mixture was concentrated under reduced pressure and the resulting residue was purified by column chromatography (Pet Ether/ethyl acetate=2/1) to get title compound 2-138 (yellow solid, 500 mg, 67% yield). LCMS: 246[M+H]$^+$.

Step 2. 2-(4-bromo-3-methoxyphenyl)thiazole (2-139)

The mixture of 4-bromo-3-methoxybenzothioamide (2-138, 500 mg, 2.0 mmol) and 2-bromo-1,1-diethoxyethane (479 mg, 2.44 mmol) in DMF (3 mL) was stirred at 120° C. for 30 min. Upon reaction completion, the resulting mixture was purified by column chromatography (Pet Ether/ethyl acetate=2/1) to get title compound 2-139 (yellow solid, 400 mg, 72% yield). LCMS: 270[M+H]$^+$.

Step 3. 2-(3-methoxy-4-(4,4,5,5-tetramethyl-1,3,2-dioxaborolan-2-yl)phenyl)thiazole (2-140)

The mixture of 2-(4-bromo-3-methoxyphenyl)thiazole (2-139, 240 mg, 0.89 mmol), 4,4,4',4',5,5,5',5'-octamethyl-2,2'-bi(1,3,2-dioxaborolane) (226 mg, 0.89 mmol), KOAc (174 mg, 1.78 mmol), and Pd(dppf)Cl$_2$ (65 mg, 0.089 mmol) in 1,4-dioxane (5 ml) was stirred for 16 h at 90° C. under N$_2$ atmosphere. Upon reaction completion, H$_2$O was added and the resulting mixture was extracted with ethyl acetate (50 mL×3). The combined organic phases were concentrated under reduced pressure and the resulting residue was purified by silica gel chromatography (Pet Ether/ethyl acetate=10/1) to obtain title compound 2-140 (yellow oil, 110 mg, 39% yield). LCMS: 318[M+H]$^+$.

Step 4. 6-(2-amino-5-(2-methoxy-4-(thiazol-2-yl)phenyl)pyridin-3-yl)-3,4-dihydroisoquinolin-1(2H)-one (I-60)

The mixture of 2-(3-methoxy-4-(4,4,5,5-tetramethyl-1,3,2-dioxaborolan-2-yl)phenyl)thiazole (2-140, 50 mg, 0.157 mmol), 6-(2-amino-5-bromopyridin-3-yl)-3,4-dihydroisoquinolin-1(2H)-one (2-4, 50 mg, 0.157 mmol), K$_3$PO$_4$ (67 mg, 0.315 mmol), Pd(PPh₃)₂Cl₂ (11 mg, 0.0157 mmol) in THF (2 mL), and H₂O (0.1 mL) was stirred at 65° C. for 16 h under N₂ atmosphere. Upon reaction completion, the resulting mixture was filtered, concentrated under reduced pressure, and the resulting residue was purified by prep-HPLC (C18 column, CH₃CN/H₂O, containing 0.05% NH₄HCO₃) to get title compound I-60 (white solid, 25 mg, 37%). LCMS: 429 [M+H]⁺; HPLC: 100% (254 nm); ¹H NMR (400 MHz, DMSO-d6) δ 8.20 (d, J=2.3 Hz, 1H), 7.93 (dd, J=7.1, 5.6 Hz, 3H), 7.81 (d, J=3.2 Hz, 1H), 7.63 (d, J=1.5 Hz, 1H), 7.59-7.53 (m, 2H), 7.52-7.36 (m, 3H), 5.90 (s, 2H), 3.89 (s, 3H), 3.41 (td, J=6.7, 2.6 Hz, 2H), 2.97 (t, J=6.5 Hz, 2H).

Example 52: 4-(6-amino-5-(1-oxo-1,2,3,4-tetrahydroisoquinolin-6-yl)pyridin-3-yl)-3-methoxybenzonitrile (I-61)

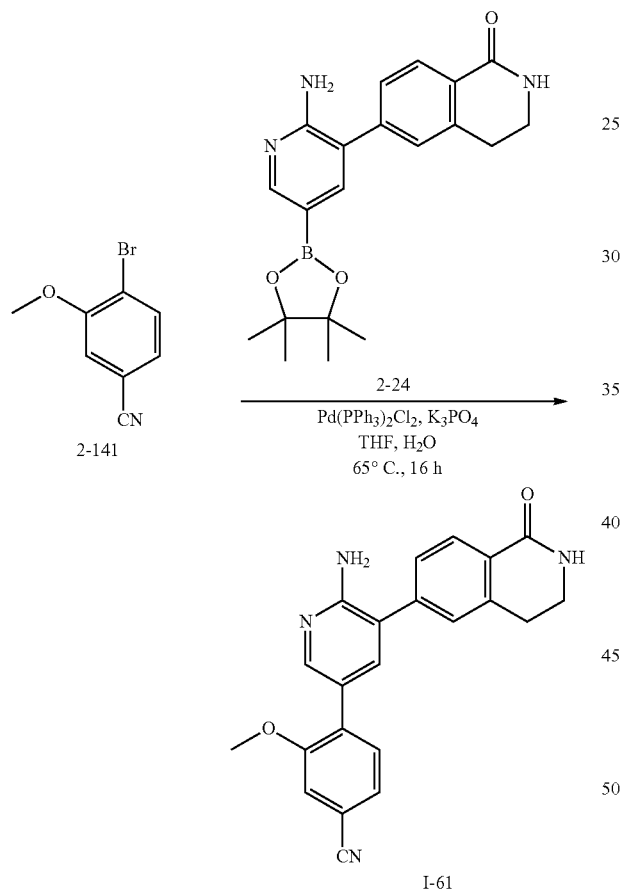

The mixture of 6-(2-amino-5-(4,4,5,5-tetramethyl-1,3,2-dioxaborolan-2-yl)pyridin-3-yl)-3,4-dihydroisoquinolin-1 (2H)-one (2-24, 60 mg, 0.16 mmol), 4-bromo-3-methoxybenzonitrile (2-141, 34 mg, 0.16 mmol), K₃PO₄ (67 mg, 0.315 mmol), Pd(PPh₃)₂Cl₂ (11 mg, 0.0157 mmol) in THF (2 mL), and H₂O (0.1 mL) was stirred at 65° C. for 16 h under N₂ atmosphere. Upon reaction completion, the resulting mixture was filtered, concentrated under reduced pressure, and the resulting residue was purified by prep-HPLC (C18 column, CH₃CN/H₂O, containing 0.05% NH₄HCO₃) to get title compound I-61 (white solid, 23 mg, 38%). LCMS: 371 [M+H]⁺; HPLC: 100% (254 nm); ¹H NMR (400 MHz, DMSO-d6) δ 8.19 (d, J=2.3 Hz, 1H), 7.94 (s, 1H), 7.91 (d, J=7.9 Hz, 1H), 7.59-7.52 (m, 3H), 7.50-7.39 (m, 3H), 6.00 (s, 2H), 3.85 (s, 3H), 3.52-3.37 (m, 2H), 2.96 (t, J=6.5 Hz, 2H).

Example 53: 4-(6-amino-5-(2-methyl-1-oxo-1,2,3,4-tetrahydroisoquinolin-6-yl)pyridin-3-yl)-N-cyclopropyl-3-fluoro-N-methylbenzenesulfonamide (1-62)

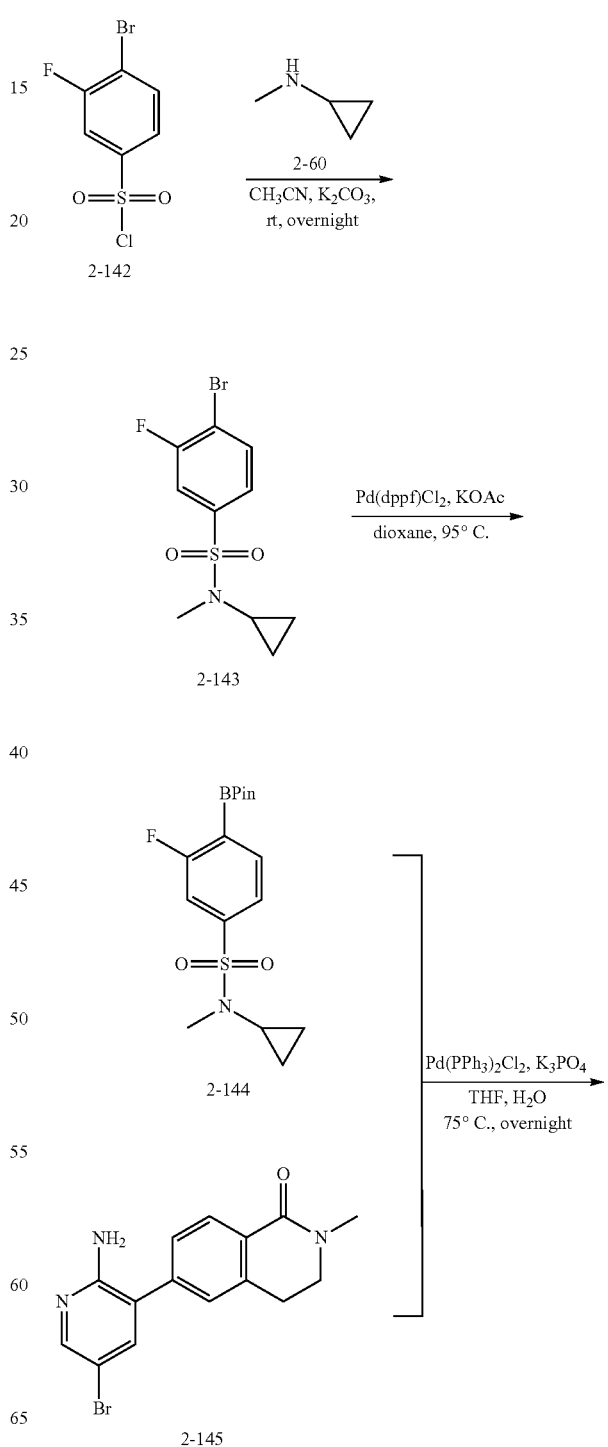

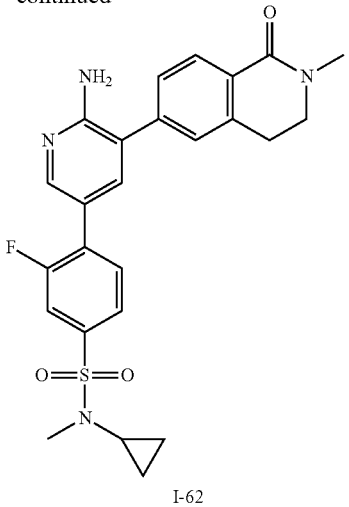

I-62

Step 1. 4-bromo-N-cyclopropyl-3-fluoro-N-methyl-benzenesulfonamide (2-143)

A mixture of 4-bromo-3-fluorobenzene-1-sulfonyl chloride (2-142, 0.5 g, 1.84 mmol), N-methylcyclopropanamine (2-60, 0.156 g, 2.2 mmol), and $K_2CO_3$ (0.51 g, 3.68 mmol) in $CH_3CN$ (10 mL) was stirred at rt overnight. The mixture was filtered and concentrated to give the crude product. The crude was purified by silica gel column chromatography eluting with ethyl acetate/Pet Ether=0-20% to give 0.55 g desired product 2-143 as a white solid (97% yield). LCMS: 308 [M+H]$^+$.

Step 2. 4-(N-cyclopropyl-N-methylsulfamoyl)-2-fluorophenylboronic acid (2-144)

4-bromo-N-cyclopropyl-3-fluoro-N-methylbenzenesulfonamide (2-143, 0.2 g, 0.65 mmol), 4,4,4',4',5,5,5',5'-octamethyl-2,2'-bi(1,3,2-dioxaborolane) (0.33 g, 1.3 mmol), Pd(dppf) $Cl_2$ (53 mg, 0.065 mmol), and KOAc (0.127 g, 1.3 mmol) in 20 mL 1,4-dioxane was stirred at 95° C. under $N_2$ atmosphere overnight. The reaction mixture was filtered and concentrated to give the crude product. The crude produce was purified by silica gel column chromatography eluting with ethyl acetate/Pet Ether=0-50% to give 0.1 g desired product 2-144 as a colorless oil (56% yield). LCMS: 274 [M+H]$^+$.

Step 3. 4-(6-amino-5-(2-methyl-1-oxo-1,2,3,4-tetrahydroisoquinolin-6-yl)pyridin-3-yl)-N-cyclopropyl-3-fluoro-N-methylbenzenesulfonamide (I-62)

A mixture of 4-(N-cyclopropyl-N-methylsulfamoyl)-2-fluorophenylboronic acid (2-144, 49 mg, 0.18 mmol), 6-(2-amino-5-bromopyridin-3-yl)-2-methyl-3,4-dihydroisoquinolin-1(2H)-one (2-145, 50 mg, 0.15 mmol) $K_3PO_4$ (63 mg, 0.3 mmol), Pd(PPh$_3$)$_2$Cl$_2$ (10 mg, 0.015 mmol), and $H_2O$ (2 mL) in THF (20 mL) was stirred at 75° C. under $N_2$ atmosphere overnight. The resulting mixture was filtered and concentrated to give the crude product. The crude product was purified by prep-HPLC to give 8 mg product I-62 as a white solid (9% yield). LCMS: 481 [M+H]$^+$. HPLC: 100% (214 nm and 254 nm); $^1$H NMR (CDCl$_3$, 400 MHz) δ: 8.33 (s, 1H), 8.20 (d, J=8.0 Hz, 1H), 7.60-7.70 (m, 4H), 7.47-7.49 (q, J=8.0 Hz, J=1.2 Hz, 1H), 7.32 (s, 1H), 4.82 (s, 2H), 3.62 (t, J=6.4 Hz, 2H), 3.19 (s, 3H), 3.08 (t, J=6.8 Hz, 2H), 2.81 (s, 3H), 1.87-1.91 (m, 1H), 0.91-0.95 (m, 2H), 0.72-0.77 (m, 2H).

Example 54: 4-(6-amino-5-(4-oxo-3,4-dihydroquinazolin-7-yl)pyridin-3-yl)-N-cyclopropyl-3-fluoro-N-methylbenzenesulfonamide (I-63)

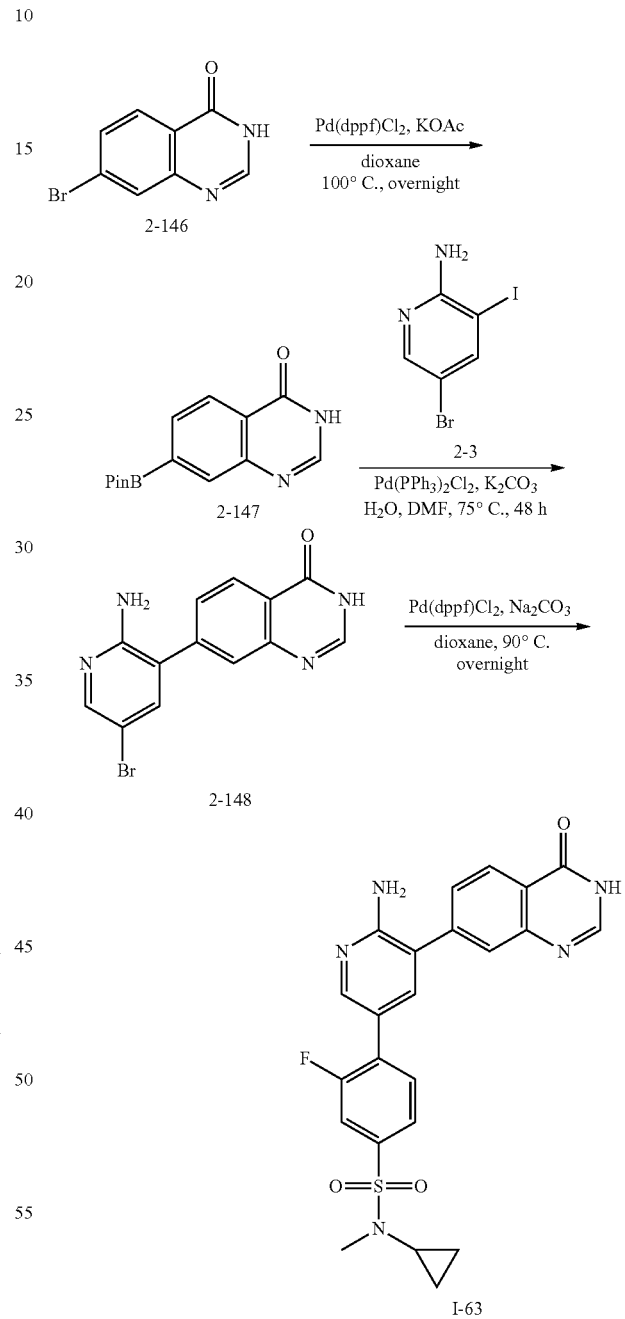

Step 1. 7-(4,4,5,5-tetramethyl-1,3,2-dioxaborolan-2-yl)quinazolin-4(3H)-one (2-147)

7-bromoquinazolin-4(3H)-one (2-146, 0.9 g, 4 mmol), 4,4,4',4',5,5,5',5'-octamethyl-2,2'-bi (1,3,2-dioxaborolane) (2.03 g, 8 mmol), Pd(dppf)Cl$_2$ (326 mg, 0.8 mmol), and KOAc (0.8 g, 8 mmol), in 50 mL 1,4-dioxane was stirred at 100° C. under N₂ atmosphere overnight. The resulting mixture was filtered and concentrated to give the crude product which was purified by silica gel column chromatography eluting with ethyl acetate to give 0.91 g product 2-147 as a brown solid (83% yield). LCMS: 273 [M+H]⁺.

Step 2. 7-(2-amino-5-bromopyridin-3-yl)quinazolin-4(3H)-one (2-148)

7-(4,4,5,5-tetramethyl-1,3,2-dioxaborolan-2-yl)quinazolin-4(3H)-one (2-147, 216 mg, 0.8 mmol), 5-bromo-3-iodopyridin-2-amine (2-3, 240 mg, 0.8 mmol), K₂CO₃ (224 mg, 1.6 mmol), H₂O (0.6 mL) and Pd(PPh₃)₂Cl₂ (168 mg, 0.24 mmol) in 10 mL DMF was stirred at 75° C. under N₂ atmosphere for 48h. The resulting mixture was filtered and concentrated to give the crude product which was purified by silica gel column chromatography eluting with MeOH/DCM=0-15% to give 0.1 g product 2-148 as a white solid (39% yield). LCMS: 317 [M+H]⁺.

Step 3. 4-(6-amino-5-(4-oxo-3,4-dihydroquinazolin-7-yl)pyridin-3-yl)-N-cyclopropyl-3-fluoro-N-methylbenzenesulfonamide (1-63)

7-(2-amino-5-bromopyridin-3-yl)quinazolin-4(3H)-one (2-148, 50 mg, 0.158 mmol), 4-(N-cyclopropyl-N-methylsulfamoyl)-2-fluorophenylboronic acid (2-144, 52 mg, 0.19 mmol), Na₂CO₃ (33 mg, 0.316 mmol), Pd(dppf)Cl₂ (13 mg, 0.016 mmol), and H₂O (0.5 mL) in 15 mL 1,4-dioxane was stirred at 90° C. under N₂ atmosphere overnight. The resulting mixture was filtered and concentrated to give the crude product which was purified by prep-HPLC to give 10 mg product 1-63 as a white solid (13% yield). LCMS: 466 [M+H]⁺. HPLC: 100% (214 nm and 254 nm); ¹H NMR (DMSO-d6, 400 MHz) δ 12.29 (s, 1H), 8.34 (s, 1H), 8.20 (d, J=8.0 Hz, 1H), 8.15 (s, 1H), 7.93 (t, J=8.0 Hz, 1H), 7.79 (s, 1H), 7.72 (s, 1H), 7.67 (d, J=8.8 Hz, 5H), 6.28 (s, 2H), 2.72 (s, 3H), 1.90-1.95 (m, 1H), 0.75-0.80 (m, 2H), 0.69-0.73 (m, 2H).

Example 55: 7-(2-amino-5-(benzo[d]thiazol-7-yl)pyridin-3-yl)quinazolin-4(3H)-one (I-64)

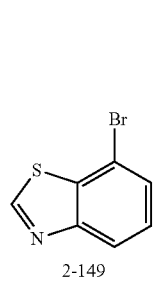 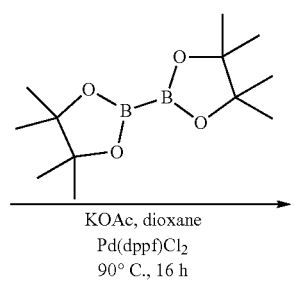

Step 1. 7-(4,4,5,5-tetramethyl-1,3,2-dioxaborolan-2-yl)benzo[d]thiazole (2-150)

The mixture of 7-bromobenzo[d]thiazole (2-149, 240 mg, 1.13 mmol), 4,4,4',4',5,5,5',5'-octamethyl-2,2'-bi(1,3,2-dioxaborolane) (572 mg, 2.25 mmol), KOAc (220 mg, 2.25 mmol), and Pd(dppf)Cl₂ (82 mg, 0.113 mmol) in 1,4-dioxane (5 ml) was stirred for 16 h at 90° C. under N₂ atmosphere. Upon reaction completion, H₂O was added and the resulting mixture was extracted with ethyl acetate (50 mL×3). The combined the organic phases were concentrated under reduced pressure and the resulting residue was purified by silica gel chromatography (Pet Ether/ethyl acetate=10/1) to obtain title compound 2-150 (yellow oil, 130 mg, 44% yield). LCMS: 262[M+H]⁺.

Step 2. 7-(2-amino-5-(benzo[d]thiazol-7-yl)pyridin-3-yl)quinazolin-4(3H)-one (I-64)

The mixture of 7-(4,4,5,5-tetramethyl-1,3,2-dioxaborolan-2-yl)benzo[d]thiazole (2-150, 60 mg, 0.22 mmol), 7-(2-amino-5-bromopyridin-3-yl)quinazolin-4(3H)-one (2-148, 72 mg, 0.22 mmol), K3PO₄ (93 mg, 0.44 mmol), Pd(PPh₃)₂Cl₂ (15 mg, 0.022 mmol) in THF (2 mL), and H₂O (0.1 mL) was stirred at 65° C. for 16 h under N₂ atmosphere. Upon reaction completion, the resulting mixture was filtered, concentrated under reduced pressure, and the resulting residue was purified by prep-HPLC (C18 column, CH₃CN/H₂O, containing 0.05% NH₄HCO₃) to get title compound I-64 (white solid, 5 mg, 6%). LCMS: 372 [M+H]⁺; HPLC: 100% (254 nm); ¹H NMR (400 MHz, DMSO-d₆) δ 12.54 (s, 1H), 9.44 (s, 1H), 8.41 (s, 1H), 8.21 (d, J=8.3 Hz, 1H), 8.15 (s, 1H), 8.06 (s, 1H), 7.80 (d, J=9.9 Hz, 2H), 7.69 (d, J=8.0 Hz, 1H), 7.64 (d, J=2.8 Hz, 2H), 6.18 (s, 2H).

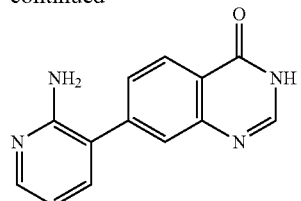

2-148

Pd(PPh₃)₂Cl₂, K₃PO₄
THF, H₂O
65° C., 16 h

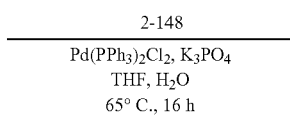

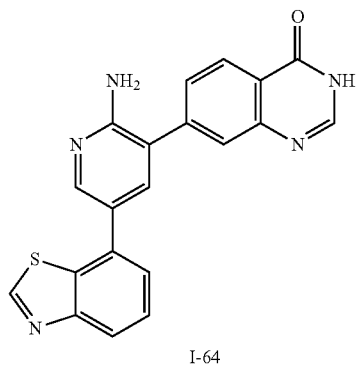

207

Example 56: N-(4-(6-amino-5-(1-oxo-1,2,3,4-tetrahydroisoquinolin-6-yl)pyridin-3-yl)-3-(cyclohexyloxy)phenyl)cyclopropanesulfonamide (1-65)

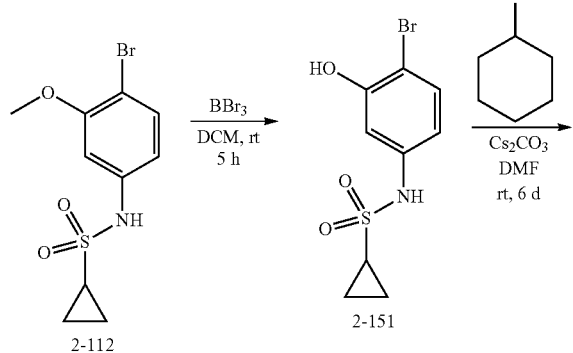

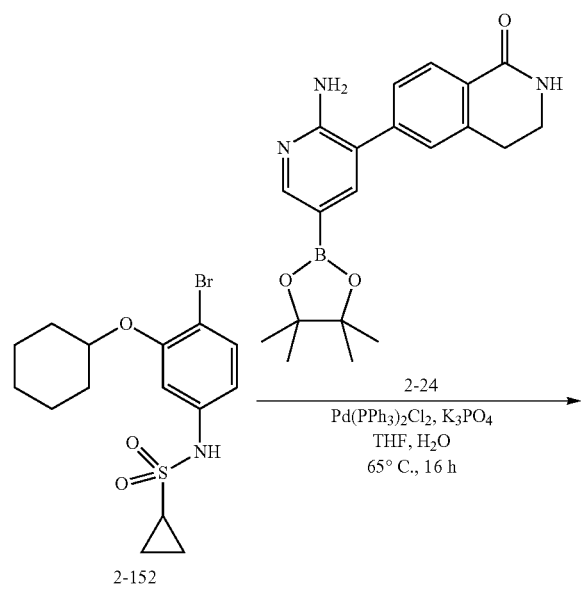

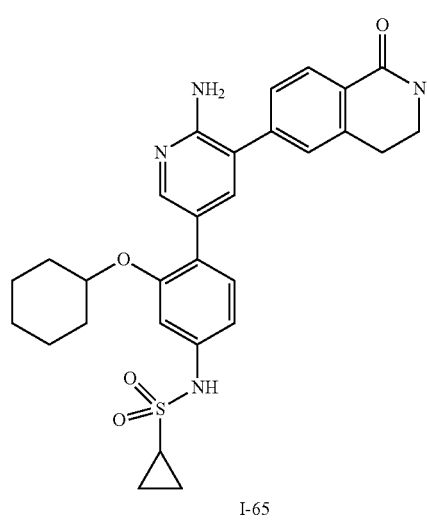

208

Step 1. N-(4-bromo-3-hydroxyphenyl)cyclopropanesulfonamide (2-151)

The mixture of N-(4-bromo-3-methoxyphenyl)cyclopropanesulfonamide (2-112, 700 mg, 2.29 mmol), and BBr$_3$ (6.3 mL, 1.0 M) in DCM (20 mL) was stirred at rt for 5 h. Upon reaction completion, water was added and the resulting mixture was extracted with ethyl acetate (100 mL×3). The combined the organic phases were concentrated under reduced pressure and the resulting residue was purified by column chromatography (Pet Ether/ethyl acetate=2/1) to get title compound 2-151 (yellow solid, 500 mg, 75% yield). LCMS: 292 [M+H]$^+$.

Step 2. N-(4-bromo-3-(cyclohexyloxy)phenyl)cyclopropanesulfonamide (2-152)

The mixture of N-(4-bromo-3-hydroxyphenyl)cyclopropanesulfonamide (2-151, 500 mg, 1.72 mmol), Cs$_2$CO$_3$ (1.7 mg, 5.16 mmol) and iodocyclohexane (720 mg, 3.43 mmol) in DMF (5 mL) was stirred at rt for 6 d. Upon reaction completion, the resulting mixture was filtered, concentrated under reduced pressure, and the resulting residue was purified by silica gel chromatography (Pet Ether/ethyl acetate=1/1) to obtain title compound 2-152 (yellow solid, 60 mg, 9% yield). LCMS: 374 [M+H]$^+$.

Step 3. N-(4-(6-amino-5-(1-oxo-1,2,3,4-tetrahydroisoquinolin-6-yl)pyridin-3-yl)-3-(cyclohexyloxy)phenyl)cyclopropanesulfonamide (1-65)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 54 mg, 0.15 mmol), N-(4-bromo-3-(cyclohexyloxy)phenyl)cyclopropanesulfonamide (2-152, 56 mg, 0.15 mmol), K$_3$PO$_4$ (64 mg, 0.30 mmol), Pd(PPh$_3$)$_2$Cl$_2$ (10 mg, 0.015 mol) in THF (2 mL), and H$_2$O (0.1 mL) was stirred at 65° C. for 16 h under N$_2$ atmosphere. Upon reaction completion, the resulting mixture was filtered, concentrated under reduced pressure, and the resulting residue was purified by prep-HPLC (C18 column, CH$_3$CN/H$_2$O, containing 0.05% NH$_4$HCO$_3$) to get title compound I-65 (white solid, 20 mg, 25%). LCMS: 533 [M+H]$^+$; HPLC: 100% (254 nm); $^1$H NMR (400 MHz, DMSO-d6) δ 9.71 (s, 1H), 8.17 (s, 1H), 7.97 (s, 1H), 7.91 (d, J=7.9 Hz, 1H), 7.55 (s, 1H), 7.49-7.38 (m, 2H), 7.31 (d, J=8.2 Hz, 1H), 6.96 (s, 1H), 6.86 (d, J=8.1 Hz, 1H), 5.81 (s, 2H), 4.29 (s, 1H), 3.41 (s, 2H), 2.95 (t, J=6.2 Hz, 2H), 2.77-2.57 (m, 1H), 1.85 (s, 2H), 1.73-1.18 (m, 8H), 0.96 (d, J=6.3 Hz, 4H).

Example 57: N-(4-(6-amino-5-(1-oxo-,2,3,4-tetrahydroisoquinolin-6-yl)pyridin-3-yl)-3-(benzyloxy)phenyl)cyclopropanesulfonamide (1-66)

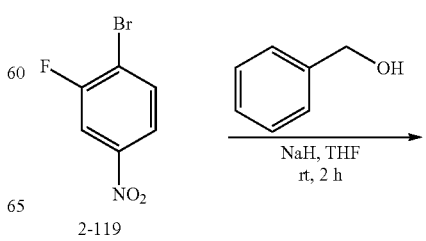

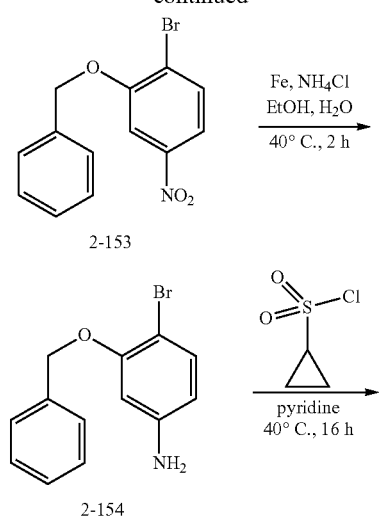

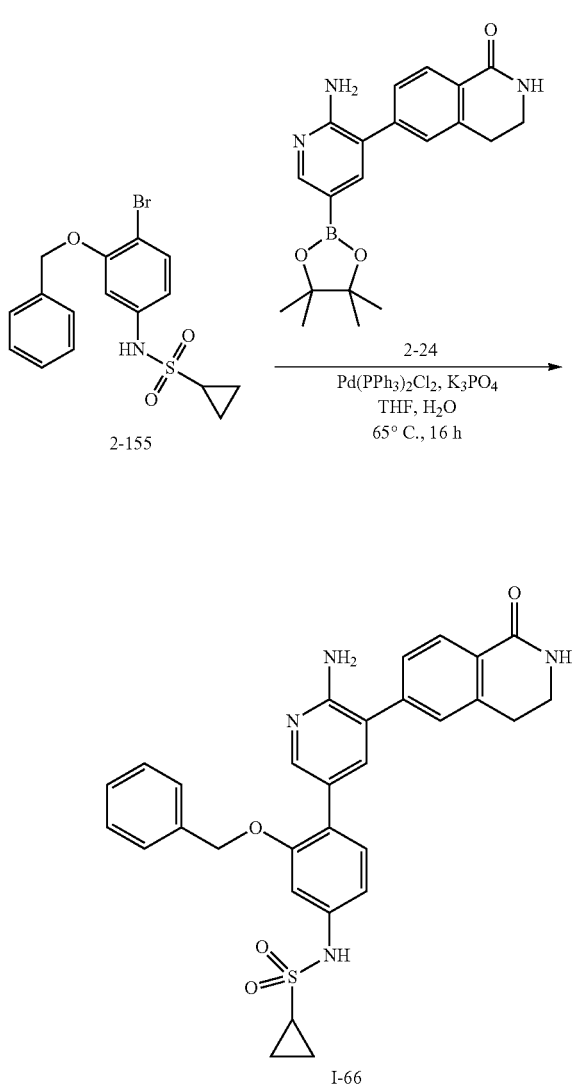

Step 1. 2-(benzyloxy)-1-bromo-4-nitrobenzene (2-153)

The mixture of phenylmethanol (243 mg, 2.27 mmol), and NaH (60%) (163 mg, 6.81 mmol) in THF (20 mL) was stirred at rt for 10 min. 1-Bromo-2-fluoro-4-nitrobenzene (2-119, 243 mg, 2.27 mmol) was then added and the resulting mixture was stirred at rt for 2 h. Upon reaction completion, water was added and the resulting mixture was extracted with ethyl acetate (100 mL×3). The combined organic phases were concentrated under reduced pressure and the resulting residue was purified by column chromatography (Pet Ether/ethyl acetate=2/1) to get title compound 2-153 (yellow solid, 300 mg, 39% yield).

Step 2. 3-(benzyloxy)-4-bromoaniline (2-154)

The mixture of 2-(benzyloxy)-1-bromo-4-nitrobenzene (2-153, 300 mg, 0.97 mmol), $NH_4Cl$ (544 mg, 9.7 mmol), Fe (546 mg, 9.7 mmol) in EtOH (20 mL) and $H_2O$ (5 mL) was stirred at 40° C. for 2 h. Upon reaction completion, the resulting mixture was filtered and the filtrate was concentrated under reduced pressure to get title compound 2-154 (yellow solid, 260 mg, 96% yield). LCMS: 278 $[M+H]^+$.

Step 3. N-(3-(benzyloxy)-4-bromophenyl)cyclopropanesulfonamide (2-155)

The mixture of 3-(benzyloxy)-4-bromoaniline (2-154, 250 mg, 0.9 mmol), cyclopropanesulfonyl chloride (315 mg, 2.25 mmol), and pyridine (284 mg, 3.6 mmol) in DCM (20 mL) was stirred at 40° C. for 16 h. Upon reaction completion, water was added and the resulting mixture was extracted with ethyl acetate (100 mL×3). The combined organic phases were concentrated under reduced pressure and the resulting residue was purified by column chromatography (Pet Ether/ethyl acetate=2/1) to get title compound 2-155 (yellow solid, 160 mg, 47% yield). LCMS: 382 $[M+H]^+$.

Step 4. N-(4-(6-amino-5-(1-oxo-1,2,3,4-tetrahydroisoquinolin-6-yl)pyridin-3-yl)-3-(benzyloxy)phenyl)cyclopropanesulfonamide (I-66)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 57 mg, 0.157 mmol), N-(3-(benzyloxy)-4-bromophenyl)cyclopropanesulfonamide (2-155, 60 mg, 0.157 mmol), $K_3PO_4$ (67 mg, 0.314 mmol), $Pd(PPh_3)_2Cl_2$ (11 mg, 0.016 mol) in THF (2 mL), and $H_2O$ (0.1 mL) was stirred at 65° C. for 16 h under $N_2$ atmosphere. Upon reaction completion, the resulting mixture was filtered, concentrated under reduced pressure, and the residue was purified by prep-HPLC (C18 column, $CH_3CN/H_2O$, containing 0.05% $NH_4HCO_3$) to get title compound 1-66 (white solid, 20 mg, 23%). LCMS: 541 $[M+H]^+$; HPLC: 100% (254 nm); $^1H$ NMR (400 MHz, DMSO-d6) δ 9.79 (s, 1H), 8.14 (s, 1H), 7.96 (s, 1H), 7.87 (d, J=7.4 Hz, 1H), 7.71-7.18 (m, 9H), 7.08 (s, 1H), 6.91 (d, J=8.0 Hz, 1H), 5.79 (s, 2H), 5.07 (s, 2H), 3.39 (d, J=13.2 Hz, 2H), 2.92 (s, 2H), 2.65 (s, 1H), 0.95 (s, 4H).

Example 58: 3-(6-amino-5-(1-oxo-1,2,3,4-tetrahydroisoquinolin-6-yl)pyridin-3-yl)benzenesulfonamide (I-71)

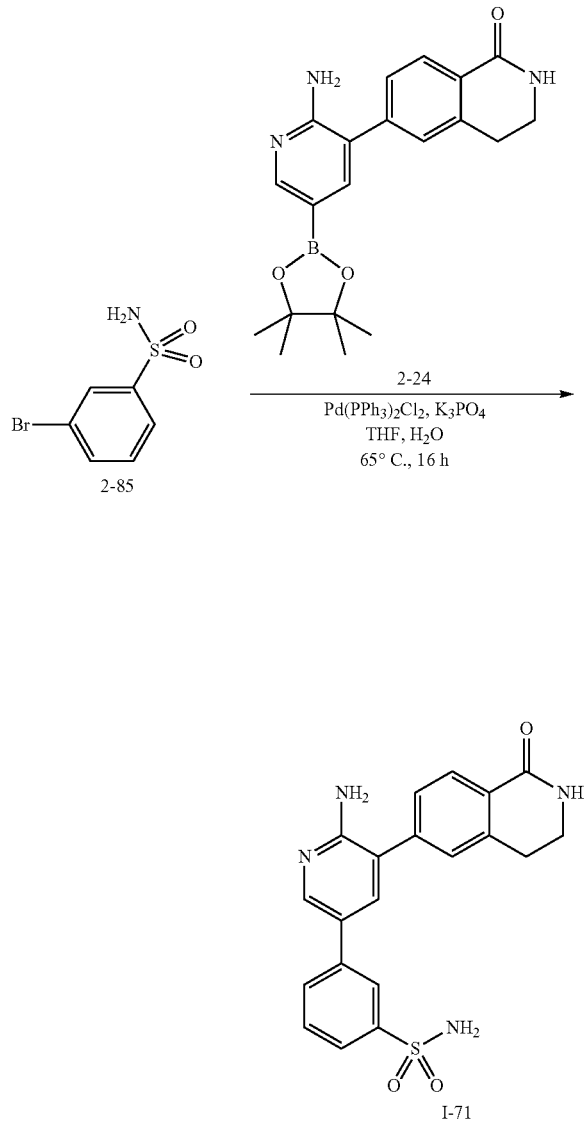

The mixture of 6-(2-amino-5-(4,4,5,5-tetramethyl-1,3,2-dioxaborolan-2-yl)pyridin-3-yl)-3,4-dihydroisoquinolin-1 (2H)-one (2-24, 60 mg, 0.16 mmol), 3-bromobenzenesulfonamide (2-85, 40 mg, 0.16 mmol), $K_3PO_4$ (70 mg, 0.32 mmol), $Pd(PPh_3)_2Cl_2$ (10 mg, 0.016 mmol) in THF (2 mL), and $H_2O$ (0.1 mL) was stirred at 65° C. for 16 h under $N_2$ atmosphere. Upon reaction completion, the resulting mixture was filtered, concentrated under reduced pressure, and the resulting residue was purified by prep-HPLC (C18 column, $CH_3CN/H_2O$, containing 0.05% TFA) to get title compound I-71 (white solid, 12 mg, 18%). LCMS: 395 [M+H]$^+$; HPLC: 100% (254 nm); $^1$H NMR (DMSO-d6, 400 MHz) δ 8.41 (d, J=2 Hz, 1H), 8.13 (s, 1H), 7.96-8.02 (m, 4H), 7.80 (d, J=8 Hz, 1H), 7.67 (t, J=8 Hz, 1H), 7.52-7.55 (m, 2H), 7.38 (s, 2H), 7.05 (s, 2H), 3.41-3.44 (m, 2H), 2.99 (t, J=6.4 Hz, 2H).

Example 59: 4-(6-amino-5-(1-oxo-1,2,3,4-tetrahydroisoquinolin-6-yl)pyridin-3-yl)-N-cyclopropyl-3-methoxy-N-methylbenzenesulfonamide (I-72)

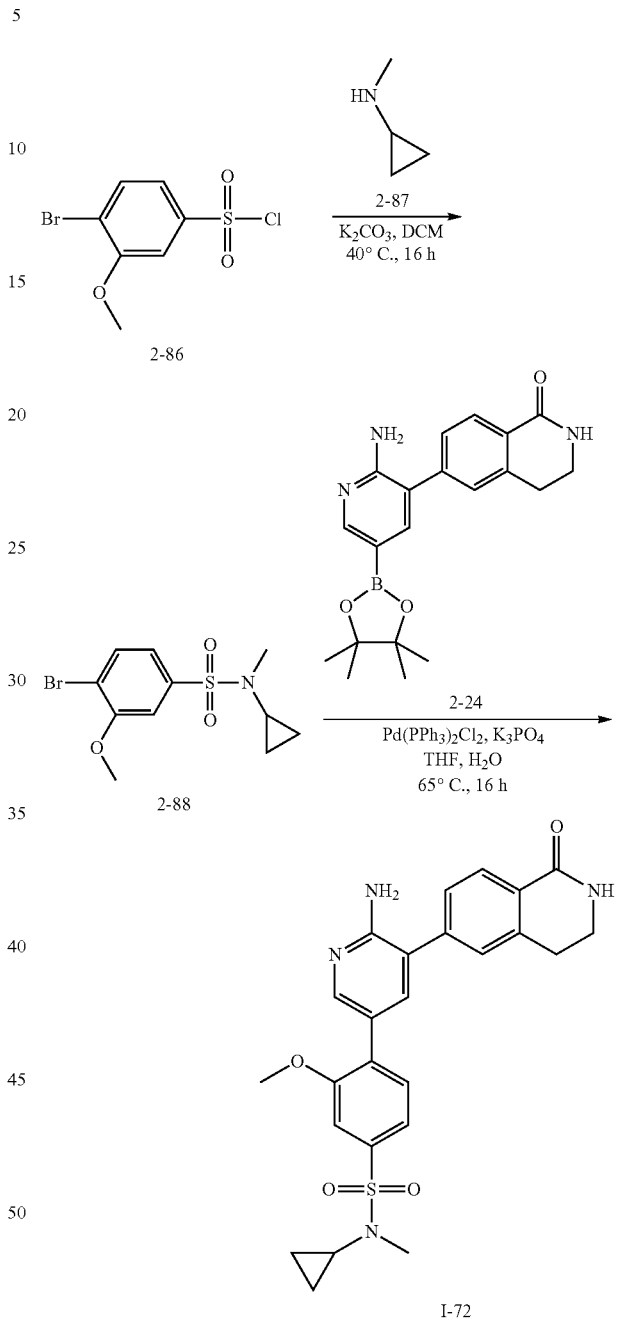

Step 1. 4-bromo-N-cyclopropyl-3-methoxy-N-methylbenzenesulfonamide (2-88)

The mixture of 4-bromo-3-methoxybenzene-1-sulfonyl chloride (2-86, 300 mg, 1.05 mmol), $K_2CO_3$ (290 mg, 2.1 mmol) and N-methylcyclopropanamine (2-87, 149 mg, 2.01 mmol) in DCM (10 mL) was stirred at 40° C. for 16 h. Upon reaction completion, the resulting mixture was filtered and then concentrated under reduced pressure to get title compound 2-88 (yellow oil, 310 mg, 92% yield). LCMS: 320 [M+H]$^+$.

Step 2. 4-(6-amino-5-(1-oxo-1,2,3,4-tetrahydroiso-quinolin-6-yl)pyridin-3-yl)-N-cyclopropyl-3-methoxy-N-methylbenzenesulfonamide (I-72)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 80 mg, 0.22 mmol), 4-bromo-N-cyclopropyl-3-methoxy-N-methylbenzenesulfonamide (2-88, 80 mg, 0.22 mmol), $K_3PO_4$ (93 mg, 0.44 mmol), $Pd(PPh_3)_2Cl_2$ (15 mg, 0.022 mmol) in THF (2 mL), and $H_2O$ (0.1 mL) was stirred at 65° C. for 16 h under $N_2$ atmosphere. Upon reaction completion, the resulting mixture was filtered, concentrated under reduced pressure, and the resulting residue was purified by prep-HPLC (C18 column, $CH_3CN/H_2O$, containing 0.05% $NH_4HCO_3$) to get title compound I-72 (white solid, 49 mg, 47%). LCMS: 479 [M+H]$^+$; HPLC: 100% (254 nm); $^1$H NMR (DMSO-d6, 400 MHz) δ 8.22 (t, J=7.5 Hz, 1H), 8.01-7.87 (m, 2H), 7.65 (d, J=8.0 Hz, 1H), 7.58 (d, J=2.3 Hz, 1H), 7.48-7.40 (m, 3H), 7.33 (s, 1H), 6.00 (s, 2H), 3.88 (s, 3H), 3.41 (dd, J=6.6, 4.2 Hz, 2H), 2.96 (t, J=6.5 Hz, 2H), 2.69 (d, J=15.0 Hz, 3H), 1.90 (ddd, J=10.4, 6.8, 3.6 Hz, 1H), 0.84-0.63 (m, 4H)

Example 60: 6-(2-amino-5-(5-fluorobenzo[d]thiazol-6-yl)pyridin-3-yl)-3,4-dihydroisoquinolin-1(2H)-one (I-73)

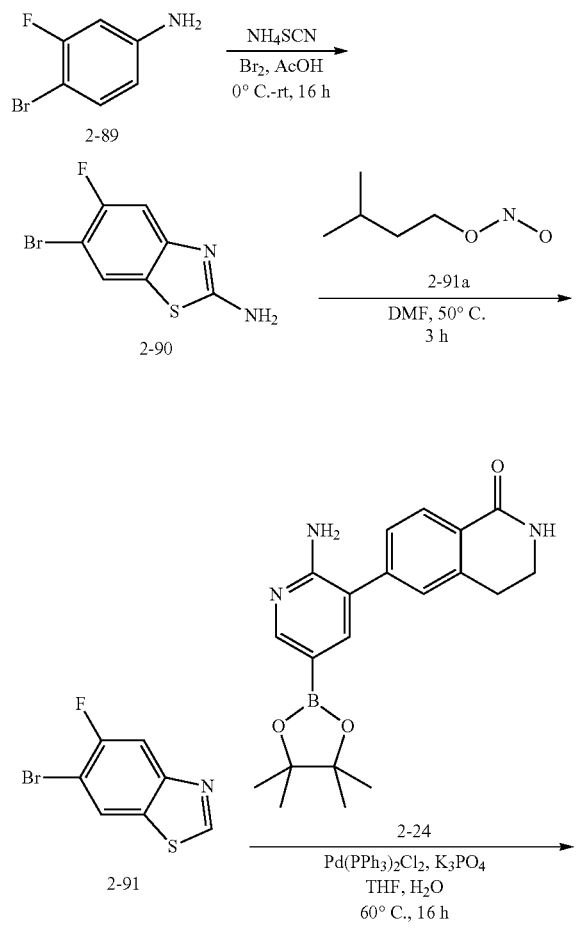

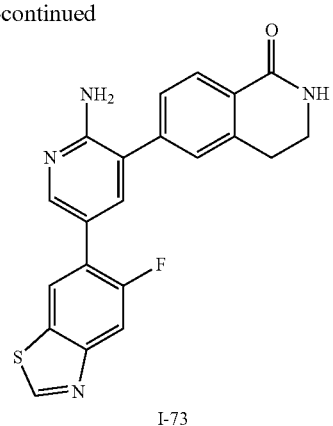

I-73

Step 1. 6-bromo-5-fluorobenzo[d]thiazol-2-amine (2-90)

The mixture of 4-bromo-3-fluoroaniline (2-89, 1.5 g, 7.9 mmol), $K_2CO_3$ (290 mg, 2.1 mmol), and $NH_4SCN$ (900 mg, 11.9 mmol) in AcOH (20 mL) was stirred at 0° C. for 10 min, then $Br_2$ (1.9 g, 11.6 mmol) was added and stirred at rt for 16 h. Upon reaction completion, the mixture was concentrated under reduced pressure and saturated KOH (1N, 100 mL) was added. The resulting mixture was extracted with ethyl acetate (100 mL×3) and the combined organic phases were concentrated under reduced pressure. The resulting residue was purified by column chromatography (Pet Ether/ethyl acetate=1/1) to get title compound 2-90 (white solid, 1 g, 51% yield). LCMS: 247 [M+H]$^+$.

Step 2. 6-bromo-5-fluorobenzo[d]thiazole (2-91)

The mixture of 6-bromo-5-fluorobenzo[d]thiazol-2-amine (2-90, 500 mg, 2.03 mmol) and isopentyl nitrite (2-91a, 357 mg, 3.04 mmol) in DMF (5 mL) was stirred at 50° C. for 3 h. Upon reaction completion, the resulting mixture was the mixture was extracted with ethyl acetate (100 mL×3) and the organic phases were concentrated under reduced pressure. The resulting residue was purified by column chromatography (Pet Ether/ethyl acetate=2/1) to get title compound 2-91 (yellow solid, 410 mg, 87% yield). LCMS: 232 [M+H]$^+$.

Step 3. 6-(2-amino-5-(5-fluorobenzo[d]thiazol-6-yl)pyridin-3-yl)-3,4-dihydroisoquinolin-1(2H)-one (I-73)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 100 mg, 0.27 mmol), 6-bromo-5-fluorobenzo[d]thiazole (2-91, 62 mg, 0.27 mmol), $K_3PO_4$ (114 mg, 0.54 mmol), $Pd(PPh_3)_2Cl_2$ (18 mg, 0.027 mmol) in THF (2 mL), and $H_2O$ (0.1 mL) was stirred at 60° C. for 16 h under $N_2$ atmosphere. Upon reaction completion, the resulting mixture was filtered, concentrated under reduced pressure, the resulting residue was purified by prep-HPLC (C18 column, $CH_3CN/H_2O$, containing 0.05% $NH_4HCO_3$) to get title compound I-73 (yellow solid, 17 mg, 16%). LCMS: 391 [M+H]$^+$; HPLC: 100% (254 nm); $^1$H NMR (400 MHz, DMSO-d6) δ 9.46 (s, 1H), 8.41 (d, J=7.7 Hz, 1H), 8.27 (t, J=2.2 Hz, 1H), 8.07-7.89 (m, 3H), 7.64 (s, 1H), 7.57-7.34 (m, 2H), 6.06 (s, 2H), 3.41 (dd, J=6.5, 3.8 Hz, 2H), 2.97 (t, J=6.6 Hz, 2H).

Example 61: 4-(6-amino-5-(1-oxoisoindolin-5-yl)pyridin-3-yl)-N-cyclopropyl-3-fluoro-N-methylbenzenesulfonamide (I-74)

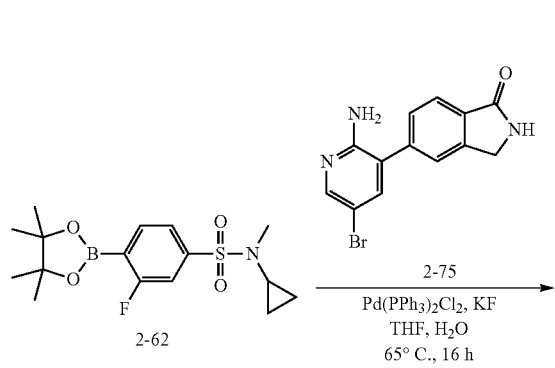

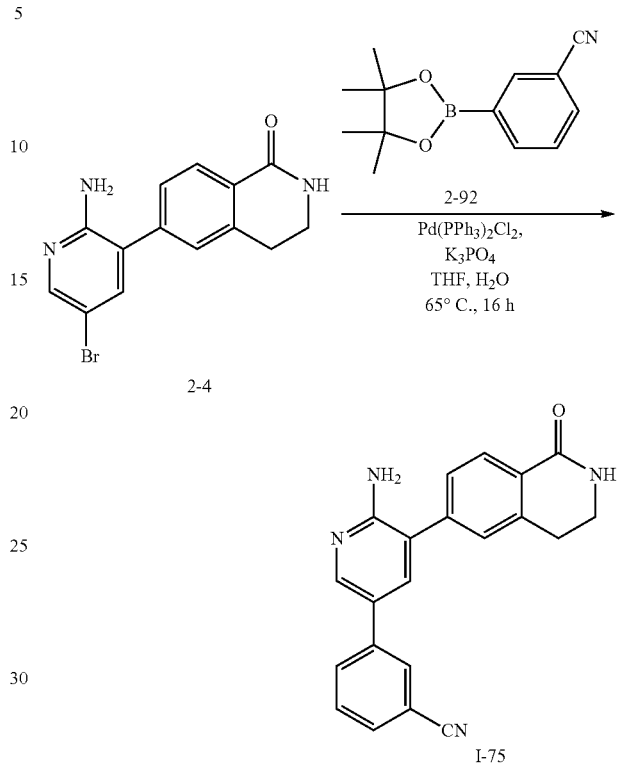

The mixture of 5-(2-amino-5-bromopyridin-3-yl)isoindolin-1-one (2-75, 50 mg, 0.16 mmol) and N-cyclopropyl-3-fluoro-N-methyl-4-(4,4,5,5-tetramethyl-1,3,2-dioxaborolan-2-yl)benzenesulfonamide (2-62, 58 mg, 0.16 mmol), KF (19 mg, 0.33 mmol), Pd(PPh$_3$)$_2$Cl$_2$ (11 mg, 0.016 mmol) in THF (2 mL), and H$_2$O (0.1 mL) was stirred at 60° C. for 16 h under N$_2$ atmosphere. Upon reaction completion, the resulting mixture was filtered, concentrated under reduced pressure, and the resulting residue was purified by prep-HPLC (C18 column, CH$_3$CN/H$_2$O, containing 0.05% NH$_4$HCO$_3$) to get title compound I-74 (yellow solid, 15 mg, 20%). LCMS: 453 [M+H]$^+$; HPLC: 100% (254 nm); $^1$H NMR (400 MHz, DMSO-d$_6$) δ 8.60 (s, 1H), 8.31 (s, 1H), 7.91 (t, J=7.8 Hz, 1H), 7.79-7.39 (m, 6H), 6.21 (s, 2H), 4.51 (d, J=67.5 Hz, 2H), 2.70 (d, J=15.1 Hz, 3H), 1.92 (ddd, J=10.3, 6.6, 3.5 Hz, 1H), 0.73 (ddd, J=14.8, 11.7, 5.4 Hz, 4H).

Example 62: 3-(6-amino-5-(1-oxo-1,2,3,4-tetrahydroisoquinolin-6-yl)pyridin-3-yl)benzonitrile (I-75)

The mixture of 6-(2-amino-5-bromopyridin-3-yl)-3,4-dihydroisoquinolin-1(2H)-one (2-4, 80 mg, 0.25 mmol), 3-(4,4,5,5-tetramethyl-1,3,2-dioxaborolan-2-yl)benzonitrile (2-92, 58 mg, 0.25 mmol), K$_3$PO$_4$ (106 mg, 0.50 mmol), Pd(PPh$_3$)$_2$Cl$_2$ (17 mg, 0.025 mmol) in THF (2 mL), and H$_2$O (0.1 mL) was stirred at 65° C. for 16 h under N$_2$ atmosphere. Upon reaction completion, the resulting mixture was filtered, concentrated under reduced pressure, and the resulting residue was purified by prep-HPLC (C18 column, CH$_3$CN/H$_2$O, containing 0.05% NH$_4$HCO$_3$) to get title compound I-75 (white solid, 25 mg, 29%). LCMS: 453 [M+H]$^+$; HPLC: 100% (254 nm); $^1$H NMR (400 MHz, DMSO-d$_6$) δ 8.42 (d, J=2.3 Hz, 1H), 8.20 (s, 1H), 8.02 (t, J=10.3 Hz, 1H), 7.95 (d, J=8.8 Hz, 1H), 7.93 (d, J=7.9 Hz, 1H), 7.79 (d, J=2.4 Hz, 1H), 7.73 (d, J=7.7 Hz, 1H), 7.60 (t, J=7.8 Hz, 1H), 7.56-7.44 (m, 2H), 6.05 (s, 2H), 3.41 (tt, J=10.6, 5.2 Hz, 2H), 2.97 (t, J=6.5 Hz, 2H).

Example 63: 6-(2-amino-5-(4-chlorothiazol-5-yl)pyridin-3-yl)-3,4-dihydroisoquinolin-1(2H)-one (I-76)

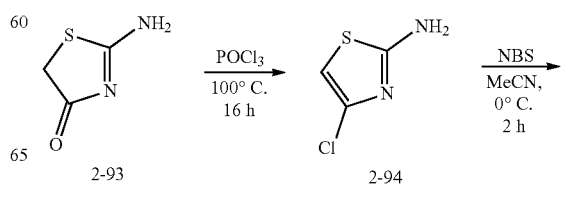

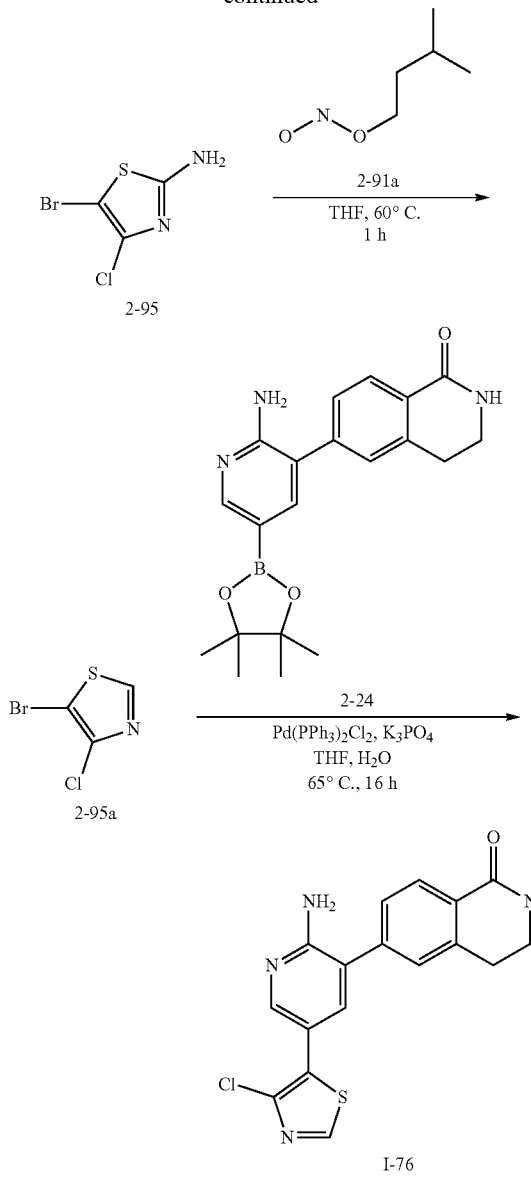

Step 1. 4-chlorothiazol-2-amine (2-94)

2-aminothiazol-4(5H)-one (2-93, 2 g, 17 mmol) in POCl₃ (10 mL) was stirred at 100° C. for 16 h. Upon reaction completion, the resulting mixture was concentrated under reduced pressure, the residue was extracted with ethyl acetate (100 mL×5), and the combined organic phases were washed with sat.NaHCO₃ and concentrated under reduced pressure to get title compound 2-94 (yellow solid, 500 mg, 21% yield). LCMS: 135 [M+H]$^+$.

Step 2. 5-bromo-4-chlorothiazol-2-amine (2-95)

The mixture of 4-chlorothiazol-2-amine (2-94, 100 mg, 0.74 mmol), and NBS (133 mg) in MeCN (5 mL) was stirred at 0° C. for 2 h. Upon reaction completion, the resulting mixture was concentrated under reduced pressure and the resulting residue was purified by column chromatography (Pet Ether/ethyl acetate=2/1) to get title compound 2-95 (yellow solid, 20 mg, 13% yield). LCMS: 213 [M+H]$^+$.

Step 3. 5-bromo-4-chlorothiazole (2-95a)

The mixture of 5-bromo-4-chlorothiazol-2-amine (2-95, 20 mg, 0.094 mmol) and isopentyl nitrite (2-91a, 11 mg, 0.094 mmol) in THF (2 mL) was stirred at 50° C. for 1 h. Upon reaction completion, the resulting mixture was concentrated under reduced pressure and the resulting residue was purified by column chromatography (Pet Ether/ethyl acetate=2/1) to get title compound 2-95a (yellow solid, 15 mg, 78% yield) used directly in the next step.

Step 4. 6-(2-amino-5-(4-chlorothiazol-5-yl)pyridin-3-yl)-3,4-dihydroisoquinolin-1(2H)-one (I-76)

The mixture of 6-(2-amino-5-(4,4,5,5-tetramethyl-1,3,2-dioxaborolan-2-yl)pyridin-3-yl)-3,4-dihydroisoquinolin-1(2H)-one (2-24, 35 mg, 0.095 mmol), 5-bromo-4-chlorothiazole (2-95a, 20 mg, 0.095 mmol), K₃PO₄ (40 mg, 0.19 mmol), Pd(PPh₃)₂Cl₂ (6 mg, 0.0095 mmol) in THF (2 mL), and H₂O (0.1 mL) was stirred at 65° C. for 16 h under N₂ atmosphere. Upon reaction completion, the resulting mixture was filtered, concentrated under reduced pressure, and the resulting residue was purified by prep-HPLC (C18 column, CH₃CN/H₂O, containing 0.05% NH₄HCO₃) to get title compound I-76 (white solid, 2 mg, 6%). LCMS: 357 [M+H]$^+$; HPLC: 100% (254 nm); $^1$H NMR (400 MHz, DMSO-d₆) δ 9.09 (s, 1H), 8.25 (d, J=2.4 Hz, 1H), 7.91-7.95 (m, 2H), 7.59 (d, J=2.4 Hz, 1H), 7.44-7.46 (m, 1H), 6.23 (s, 2H), 3.31-3.51 (m, 2H), 2.96 (t, J=6.0 Hz, 2H).

Example 64: Biochemical Studies

STK4 (MST1), STK3 (MST2); STK24 (MST3) and MST4 Assays

Biochemical IC₅₀s were measured at Invitrogen using Z-lyte technology. Briefly, for STK4, the 2×STK4 (MST1)/Ser/Thr 07 mixture was prepared in 50 mM HEPES pH 7.5, 0.01% BRIJ35, 10 mM MgCl2, 1 mM EGTA. The final 10 µL Kinase Reaction consisted of 6.25-160 ng STK4 (MST1) and 2 µM Ser/Thr 07 in 50 mM HEPES pH 7.5, 0.01% BRIJ-35, 10 mM MgCl2, 1 mM EGTA. After the 1 hour Kinase Reaction incubation, 5 µL of a 1:100000 dilution of Development Reagent A was added. Compounds were screened in a 10 point titration with 3-fold serial dilutions starting at a concentration of 10 µM. The biochemical IC₅₀s against other STK family members were measured similarly. The ATP concentration used matched the Km for each kinase.

Table 1 shows the STK4, STK3, STK24, and MST4 activity of compounds of the application. ++++ indicates an IC₅₀ less than 40 nM, +++ indicates an IC₅₀ between about 40 nM and about 200 nM, ++ indicates a IC₅₀ between about 200 nM and about 900 nM, and + indicates an IC₅₀ of greater than 900 nM.

TABLE 1

| | STK4, STK3, STK24, and MST4 Assay data | | | |
|---|---|---|---|---|
| Compound Number | STK4 (MST1) IC₅₀ (nM) | STK3 (MST2) IC₅₀ (nM) | STK24 (MST3) IC₅₀ (nM) | MST4 IC₅₀ (nM) |
| I-1 | ++++ | +++ | + | + |
| I-2 | ++++ | − | + | − |

TABLE 1-continued

STK4, STK3, STK24, and MST4 Assay data

| Compound Number | STK4 (MST1) IC$_{50}$ (nM) | STK3 (MST2) IC$_{50}$ (nM) | STK24 (MST3) IC$_{50}$ (nM) | MST4 IC$_{50}$ (nM) |
|---|---|---|---|---|
| I-3 | +++ | − | + | − |
| I-4 | + | − | + | − |
| I-5 | ++ | − | + | − |
| I-6 | + | − | + | − |
| I-7 | + | − | − | − |
| I-8 | + | − | − | − |
| I-9 | ++++ | ++++ | + | − |
| I-11 | + | | | |
| I-12 | +++ | +++ | ++ | − |
| I-13 | ++++ | +++ | + | − |
| I-14 | +++ | − | − | − |
| I-15 | ++++ | − | − | − |
| I-17 | +++ | − | − | − |
| I-18 | +++ | − | − | − |
| I-22 | +++ | +++ | − | − |
| I-23 | ++++ | +++ | − | − |
| I-27 | +++ | − | − | − |
| I-28 | ++++ | ++++ | +++ | − |
| I-30 | ++ | − | − | − |
| I-31 | ++ | − | − | − |
| I-39 | ++ | − | − | − |
| I-44 | +++ | | | |
| I-45 | +++ | − | − | − |
| I-46 | ++++ | − | − | − |
| I-47 | ++++ | − | − | − |
| I-48 | ++++ | − | − | − |
| I-49 | ++++ | − | − | − |
| I-50 | ++++ | − | ++ | − |
| I-51 | ++++ | − | +++ | − |
| I-52 | +++ | − | − | − |
| I-53 | +++ | − | − | − |
| I-54 | +++ | − | − | − |
| I-55 | +++ | − | − | − |
| I-56 | ++ | − | − | − |
| I-57 | ++++ | − | − | − |
| I-58 | ++++ | − | − | − |
| I-59 | ++++ | − | − | − |
| I-60 | +++ | − | − | − |
| I-61 | ++++ | − | − | − |
| I-62 | ++++ | − | − | − |
| I-63 | ++++ | − | − | − |
| I-64 | +++ | − | − | − |
| I-65 | ++++ | − | + | − |
| I-66 | +++ | − | − | − |
| I-67 | ++++ | − | − | − |
| I-68 | ++++ | − | − | − |
| I-69 | ++++ | − | − | − |
| I-70 | +++ | − | − | − |
| I-74 | ++++ | ++++ | + | − |
| I-75 | +++ | +++ | ++ | − |
| I-76 | ++++ | +++ | + | − |
| I-77 | +++ | − | − | − |
| I-78 | ++++ | +++ | − | − |
| I-79 | +++ | − | − | − |
| I-80 | ++++ | ++++ | +++ | − |
| I-81 | +++ | − | − | − |
| I-71 | ++ | − | − | − |
| I-72 | ++++ | ++++ | +++ | − |
| I-73 | +++ | − | − | − |
| I-74 | +++ | − | − | − |
| I-75 | +++ | − | − | − |
| I-76 | +++ | − | − | − |
| KIN00I-305 | ++++ | | | |
| BMS536924 | +++ | | | |

Kinase Selectivity Studies

To directly test the kinase selectivity of a compound of the present application over other human protein kinases, the compounds were tested in an Ambit KINOSCAN assay. Ambit KINOSCAN assay is an ATP site dependent competition assay. T7 kinase-tagged phage strains were grown in parallel in 24- or 96-well blocks in an *E. coli* host derived from the BL21 strain. *E. Coli* were grown to log phase and infected with T7 phage from a frozen stock and incubated with shaking at about 32° C. until lysis (~90 min). The lysates were centrifuged (6,000 g) and filtered (0.2 μM) to remove cell debris. Streptavidin-coated magnetic beads were treated with biotinylated small molecule ligands for 30 min at about 25° C. to generate affinity resins for kinase assays. The liganded beads were blocked with excess biotin and washed with blocking buffer (Seablock (Pierce), 1% BSA, 0.05% Tween 20, 1 mM DTT) to remove unbound ligand and to reduce non-specific phage binding. Binding reactions were assembled by combining phage lysates, liganded affinity beads, and test compounds (i.e., compounds of the present application) in 1× binding buffer (20% SeaBlock, 0.17×PBS, 0.05% Tween 20, 6 nM DTT). Test compounds were prepared 1000× stocks in DMSO and rapidly diluted into the aqueous environment (0.1% DMSO final). DMSO (0.1%) was used as a control. All reactions were carried out in polystyrene 96-well plates that had been pre-treated with blocking buffer in a final volume of 0.1 ml. The assay plates were incubated at about 25° C. with shaking for about 1 h, long enough for binding reactions to reach equilibrium, and the affinity beads were then washed four times with wash buffer (1×PBS, 0.05% Tween 20, 1 mM DTT) to remove unbound phage. After the final wash, the beads were resuspended in elution buffer (1×PBS, 0.05% Tween 20, 2 μM nonbiotinylated affinity ligand) and incubated at about 25° C. with shaking for about 30 minutes. The phage titer in the eluates was measured by standard plaque assays or quantitative PCR. Binding data were fit to the equation $PFU=L=((H-L)\times(K_{d(Test)}/K_{d(Test)}=[test])))$, where L is the lower baseline, H is the upper baseline, $K_{d(test)}$ is the biding constant for the interaction between the test compound and the kinase, and [test] is the free test compound concentration. Binding constants are measured in duplicate on the same day of testing. For more details on the Ambit KINOSCAN assay see Fabian, M. A., et al. "A Small Molecule-Kinase Interaction Map for Clinical Kinase Inhibitors" *Nat. Biotechol.* 23(3), 2005, 329-336. (Also see Davis, M. I., et al. "Comprehensive analysis of kinase inhibitor selectivity." *Nat. Biotechnol.* 29(11), 2011, 1046-1051)

Table 2 shows the activity of Compound I-1 of the application in an Ambit KINOSCAN assay.

TABLE 2

Kinase Selectivity Data

| Kinase | percent control (%) at 1 uM | IC$_{50}$ (nM) |
|---|---|---|
| CSNK1G3 | 0 | 4.68 |
| DYRK1A | 0 | |
| GSK3A | 0 | |
| CIT | 0.05 | |
| CSNK1E | 0.1 | 201 |
| DRAK1 | 0.15 | |
| BMPR1B | 0.75 | |
| DYRK1B | 0.75 | |
| MST2 | 1.2 | 42.6 |
| CLK1 | 1.6 | |
| CSNK1A1L | 1.7 | |
| VRK2 | 2.4 | |
| DCAMKL3 | 2.5 | |
| CLK4 | 2.6 | |
| IRAK1 | 2.8 | 110 |
| DYRK2 | 3 | |
| CSNK1A1 | 3.7 | |
| MINK | 3.8 | |
| CSNK1G2 | 4 | |

TABLE 2-continued

Kinase Selectivity Data

| Kinase | percent control (%) at 1 uM | $IC_{50}$ (nM) |
|---|---|---|
| CSNK1G1 | 4.6 | |
| CLK2 | 5 | |

KiNativ Assay

Biochemical $IC_{50}$s of the compounds of the present disclosure against various kinases were measured in a KiNativ assay. Compounds were screened in duplicate at 10 μM in H929 live cell. $IC_{50}$ was measured via Mass spectroscopy (MS).

Table 3 shows the activity of Compound I-9, I-13, and I-28 of the application in an Ambit KINOSCAN assay.

TABLE 3

KiNativ Assay $IC_{50}$ data of Compounds I-9, I-13, and I-28

| Kinase(s) | I-9 (10 μM) | % inhibition | I-13 (10 μM) | % inhibition | I-28 (10 μM) | % inhibition |
|---|---|---|---|---|---|---|
| ABL, ARG | 75.7 | 75-90 | 53.5 | 50-75 | 13.3 | 0.0 |
| ACK | −17.3 | 0.0 | 23.3 | 0.0 | −18.8 | 0.0 |
| AKT1 | 32.8 | 0.0 | 26.4 | 0.0 | 11.1 | 0.0 |
| AKT2, AKT3 | −1.3 | 0.0 | 19.0 | 0.0 | 14.9 | 0.0 |
| AMPKa1, AMPKa2 | 52.0 | 50-75 | 1.8 | 0.0 | −1.6 | 0.0 |
| ARAF | 9.5 | 0.0 | 16.7 | 0.0 | 8.0 | 0.0 |
| ATR | 37.5 | ND | −16.1 | 0.0 | −37.5 | 0.0 |
| AurA | 68.5 | 50-75 | 17.4 | 0.0 | 27.5 | 0.0 |
| AurA | 75.7 | 75-90 | 14.7 | 0.0 | 33.1 | 0.0 |
| AurA, AurB, AurC | 66.2 | 50-75 | 17.7 | 0.0 | 21.4 | 0.0 |
| AurB | 53.4 | 50-75 | 20.7 | 0.0 | 32.7 | 0.0 |
| BARK1 | 2.8 | 0.0 | 21.8 | 0.0 | 22.3 | 0.0 |
| BRAF | 3.3 | 0.0 | 10.2 | 0.0 | −4.6 | 0.0 |
| CaMK1d | −2.8 | 0.0 | 16.2 | 0.0 | 15.2 | 0.0 |
| CaMK2a, CaMK2b, CaMK2d, CaMK2g | 3.3 | 0.0 | −4.1 | 0.0 | 1.4 | 0.0 |
| CaMK2d | −5.7 | 0.0 | −4.3 | 0.0 | −31.0 | 0.0 |
| CaMK2g | −23.0 | 0.0 | −13.6 | 0.0 | −13.0 | 0.0 |
| CaMKK2 | 71.8 | 50-75 | 74.9 | 50-75 | 57.0 | 50-75 |
| CDC2 | −24.7 | 0.0 | −15.0 | 0.0 | −26.5 | 0.0 |
| CDK11, CDK8 | 35.5 | ND | 59.3 | 50-75 | 4.9 | 0.0 |
| CDK2 | 68.5 | 50-75 | 33.3 | 0.0 | 27.6 | 0.0 |
| CDK5 | 78.7 | 75-90 | 20.0 | 0.0 | 17.0 | 0.0 |
| CDK7 | 78.2 | 75-90 | 32.9 | 0.0 | 12.3 | 0.0 |
| CDK9 | 65.8 | 50-75 | 41.1 | 35-50 | 28.9 | 0.0 |
| CHK1 | 14.9 | 0.0 | −8.9 | 0.0 | 27.5 | 0.0 |
| CHK2 | 80.9 | 75-90 | 19.7 | 0.0 | 6.8 | 0.0 |
| CK1a | 84.6 | 75-90 | −17.4 | 0.0 | 37.8 | 35-50 |
| CK1d, CK1e | >95 | >90 | 58.9 | ND | 68.2 | 50-75 |
| CK1g1 | >85 | 75-90 | >85 | 75-90 | >85 | 75-90 |
| CK1g2 | >90 | >90 | >90 | >90 | >90 | >90 |
| CK1g3 | 93.0 | >90 | 90.4 | >90 | 93.8 | >90 |
| CLK2 | >95 | >90 | 19.1 | 0.0 | 42.7 | 35-50 |
| CSK | −4.5 | 0.0 | 4.7 | 0.0 | 3.7 | 0.0 |
| DGKH | 44.2 | ND | 25.7 | 0.0 | 10.9 | 0.0 |
| DNAPK | 79.4 | 75-90 | 44.7 | 35-50 | 42.6 | 35-50 |
| DNAPK | 94.0 | >90 | 59.4 | 50-75 | 82.1 | 75-90 |
| eEF2K | −94.7 | 0.0 | −45.5 | 0.0 | −15.1 | 0.0 |
| EphB2 | −25.0 | 0.0 | 22.1 | 0.0 | −2.0 | 0.0 |
| Erk1 | 50.5 | 50-75 | 75.0 | 75-90 | 11.0 | 0.0 |
| Erk2 | 60.2 | 50-75 | 74.6 | 50-75 | 13.9 | 0.0 |
| FER | 27.4 | 0.0 | 4.2 | 0.0 | −3.9 | 0.0 |
| FRAP | 72.7 | 50-75 | 32.5 | 0.0 | 35.3 | 35-50 |
| FYN, SRC, YES | 28.3 | 0.0 | 0.3 | 0.0 | 2.2 | 0.0 |
| GCK | 91.5 | | 77.3 | 75-90 | 84.7 | 75-90 |
| GCN2 domain2 | 15.5 | 0.0 | 13.5 | 0.0 | −32.1 | 0.0 |
| GPRK5 | 19.6 | 0.0 | −12.0 | 0.0 | 10.7 | 0.0 |
| GSK3A | 97.2 | >90 | 91.6 | >90 | 93.5 | >90 |
| GSK3B | 97.2 | >90 | 88.4 | 75-90 | 96.4 | >90 |
| HPK1 | 97.5 | >90 | 52.1 | 50-75 | 90.8 | >90 |
| IKKa | −18.4 | 0.0 | 2.6 | 0.0 | 6.4 | 0.0 |
| IKKb | −15.0 | 0.0 | −3.3 | 0.0 | 6.8 | 0.0 |
| IKKe, TBK1 | 21.2 | 0.0 | −9.9 | 0.0 | −14.8 | 0.0 |
| ILK | −19.0 | 0.0 | 1.6 | 0.0 | −5.8 | 0.0 |
| IRAK1 | 82.6 | 75-90 | 28.5 | 0.0 | 67.8 | 50-75 |
| IRAK4 | −14.1 | 0.0 | −6.4 | 0.0 | −0.7 | 0.0 |
| IRE1 | −50.1 | 0.0 | −17.0 | 0.0 | −34.1 | 0.0 |
| JAK1 domain1 | −44.3 | 0.0 | −22.4 | 0.0 | −38.6 | 0.0 |
| JAK1 domain2 | −4.9 | 0.0 | −16.0 | 0.0 | −33.7 | 0.0 |
| JAK3 domain2 | 2.6 | 0.0 | −12.8 | 0.0 | 15.2 | 0.0 |
| JNK1, JNK2, JNK3 | −24.2 | 0.0 | 6.0 | 0.0 | −12.9 | 0.0 |
| KHS1 | 79.5 | 75-90 | 47.7 | 35-50 | 75.6 | 75-90 |
| KHS2 | 69.5 | 50-75 | 1.7 | 0.0 | 68.3 | 50-75 |
| KSR1, KSR2 | −51.3 | 0.0 | −6.2 | 0.0 | −14.5 | 0.0 |
| LATS1 | 33.1 | 0.0 | 14.7 | 0.0 | 4.8 | 0.0 |
| LKB1 | 4.5 | 0.0 | 4.3 | 0.0 | −0.6 | 0.0 |
| LOK | 98.5 | >90 | 61.5 | 50-75 | 85.5 | 75-90 |
| LYN | −12.4 | 0.0 | −41.4 | 0.0 | −10.3 | 0.0 |
| MAP2K1 | −55.8 | 0.0 | −27.4 | 0.0 | −5.5 | 0.0 |
| MAP2K1, MAP2K2 | 4.9 | 0.0 | 3.3 | 0.0 | 0.5 | 0.0 |
| MAP2K1, MAP2K2 | −13.5 | 0.0 | −15.0 | 0.0 | −0.9 | 0.0 |
| MAP2K2 | −8.7 | 0.0 | −36.7 | 0.0 | −23.7 | 0.0 |
| MAP2K3 | −34.2 | 0.0 | 1.1 | 0.0 | 1.4 | 0.0 |
| MAP2K4 | 72.9 | 50-75 | 48.2 | 35-50 | 32.5 | 0.0 |
| MAP2K5 | 75.2 | 75-90 | 13.4 | 0.0 | 58.0 | 50-75 |
| MAP2K6 | 6.8 | 0.0 | 4.3 | 0.0 | 27.6 | 0.0 |
| MAP2K7 | 14.6 | 0.0 | 15.1 | 0.0 | −0.5 | 0.0 |
| MAP3K1 | 95.6 | >90 | 90.2 | >90 | 91.1 | >90 |
| MAP3K2 | 0.3 | 0.0 | −23.5 | 0.0 | 7.0 | 0.0 |
| MAP3K2, MAP3K3 | 43.2 | 35-50 | 0.2 | 0.0 | 33.8 | 0.0 |
| MAP3K4 | −9.6 | 0.0 | 3.0 | 0.0 | −8.8 | 0.0 |
| MAP3K5 | 30.6 | 0.0 | 25.6 | 0.0 | −6.2 | 0.0 |
| MAPKAPK2, MAPKAPK3 | 4.0 | 0.0 | 2.5 | 0.0 | −5.0 | 0.0 |
| MARK1, MARK2 | 40.7 | 35-50 | 2.9 | 0.0 | −1.3 | 0.0 |
| MARK2 | 63.5 | 50-75 | 32.3 | 0.0 | 4.6 | 0.0 |
| MARK2, MARK3 | 70.2 | 50-75 | 14.8 | 0.0 | −7.8 | 0.0 |
| MARK3 | 78.3 | 75-90 | 46.2 | 35-50 | 14.5 | 0.0 |
| MARK4 | >75 | 75-90 | 39.8 | ND | 23.1 | 0.0 |
| MAST3 | 31.2 | 0.0 | 22.0 | 0.0 | 14.2 | 0.0 |
| MASTL | −18.4 | 0.0 | −2.0 | 0.0 | 10.2 | 0.0 |
| MLK3 | 62.9 | 50-75 | −3.9 | 0.0 | 11.7 | 0.0 |
| MLKL | 66.9 | 50-75 | 15.2 | 0.0 | 23.9 | 0.0 |
| MPSK1 | 55.2 | ND | −28.8 | 0.0 | −9.1 | 0.0 |
| MSK1 domain1 | 2.0 | 0.0 | 9.5 | 0.0 | 5.4 | 0.0 |
| MSK2 domain1 | −36.5 | 0.0 | −6.1 | 0.0 | 2.9 | 0.0 |
| MST1 | 95.4 | >90 | 89.0 | 75-90 | 94.5 | >90 |
| MST1, MST2 | 99.0 | >90 | 89.4 | 75-90 | 97.5 | >90 |
| MST2 | 88.9 | 75-90 | 85.5 | 75-90 | 89.3 | 75-90 |
| MST3 | 40.4 | 35-50 | −1.8 | 0.0 | 72.3 | 50-75 |
| MST4 | 47.0 | ND | 29.3 | 0.0 | 63.9 | 50-75 |
| MST4, YSK1 | 33.0 | 0.0 | −17.0 | 0.0 | 76.7 | 75-90 |
| NDR1 | 3.5 | 0.0 | 13.0 | 0.0 | 24.6 | 0.0 |
| NDR2 | −9.5 | 0.0 | 4.0 | 0.0 | 24.2 | 0.0 |
| NEK1 | −34.0 | 0.0 | 6.2 | 0.0 | −14.1 | 0.0 |
| NEK3 | −42.8 | 0.0 | 5.3 | 0.0 | −27.2 | 0.0 |
| NEK4 | 67.0 | 50-75 | 4.7 | 0.0 | −2.8 | 0.0 |
| NEK6, NEK7 | −35.7 | 0.0 | −20.1 | 0.0 | −10.5 | 0.0 |
| NEK7 | −39.5 | 0.0 | −20.2 | 0.0 | 16.0 | 0.0 |
| NEK8 | 11.6 | 0.0 | 10.6 | 0.0 | −3.4 | 0.0 |
| NEK9 | −38.3 | 0.0 | −10.0 | 0.0 | −4.7 | 0.0 |
| NuaK1 | 91.0 | >90 | 71.7 | 50-75 | 55.6 | 50-75 |

TABLE 3-continued

KiNativ Assay IC$_{50}$ data of Compounds I-9, I-13, and I-28

| Kinase(s) | I-9 (10 μM) | % inhibition | I-13 (10 μM) | % inhibition | I-28 (10 μM) | % inhibition |
|---|---|---|---|---|---|---|
| NuaK1 | >90 | >90 | 83.7 | 75-90 | 66.7 | 50-75 |
| NuaK2 | 58.7 | 50-75 | 53.9 | 50-75 | 11.2 | 0.0 |
| OSR1 | -11.8 | 0.0 | 1.4 | 0.0 | 22.8 | 0.0 |
| p38a | -132.7 | | -36.3 | 0.0 | -25.8 | 0.0 |
| p38a | 75.8 | 75-90 | 30.4 | 0.0 | 32.4 | 0.0 |
| p38d, p38g | -11.0 | 0.0 | -43.7 | 0.0 | 7.7 | 0.0 |
| p70S6K | -71.5 | 0.0 | -14.3 | 0.0 | -22.7 | 0.0 |
| p70S6Kb | -84.5 | 0.0 | -17.4 | 0.0 | -14.4 | 0.0 |
| PAN3 | -7.1 | 0.0 | -4.0 | 0.0 | -45.1 | 0.0 |
| PDK1 | 28.1 | 0.0 | 17.5 | 0.0 | 5.9 | 0.0 |
| PEK | -100.2 | >100 | -40.8 | 0.0 | -15.7 | 0.0 |
| PFTAIRE1 | 74.6 | 50-75 | 49.2 | 35-50 | 22.2 | 0.0 |
| PHKg2 | -30.7 | 0.0 | -27.5 | 0.0 | 17.3 | 0.0 |
| PI4KA, PI4KAP2 | -5.5 | 0.0 | -16.1 | 0.0 | -13.2 | 0.0 |
| PI4KB | -13.8 | 0.0 | 34.8 | 0.0 | 16.7 | 0.0 |
| PIK3C3 | 51.2 | ND | 24.8 | 0.0 | -107.4 | >100 |
| PIK3CB | 14.6 | 0.0 | 23.1 | 0.0 | 1.9 | 0.0 |
| PIK3CG | 16.3 | 0.0 | 12.4 | 0.0 | 1.7 | 0.0 |
| PIP4K2A | 10.2 | 0.0 | 2.3 | 0.0 | 3.2 | 0.0 |
| PIP4K2C | 65.7 | 50-75 | 42.0 | 35-50 | 11.8 | 0.0 |
| PIP5K3 | 92.0 | >90 | 92.5 | >90 | 83.4 | 75-90 |
| PITSLRE | 38.9 | 35-50 | -3.6 | 0.0 | -6.3 | 0.0 |
| PKCi | 18.5 | 0.0 | 21.4 | 0.0 | 12.7 | 0.0 |
| PKCz | 27.0 | 0.0 | 15.5 | 0.0 | 6.2 | 0.0 |
| PKD2 | 46.2 | 35-50 | 52.1 | 50-75 | 38.9 | 35-50 |
| PKD3 | 74.2 | 50-75 | 69.4 | 50-75 | 36.6 | 35-50 |
| PKN1 | 56.9 | 50-75 | 19.0 | 0.0 | 40.5 | 35-50 |
| PKR | -36.7 | 0.0 | -21.7 | 0.0 | -0.8 | 0.0 |
| PLK1 | 14.2 | 0.0 | 6.6 | 0.0 | 15.2 | 0.0 |
| PRP4 | 70.2 | 50-75 | 73.4 | 50-75 | 3.7 | 0.0 |
| PRPK | -5.0 | 0.0 | -6.4 | 0.0 | 10.1 | 0.0 |
| QSK | 72.8 | 50-75 | 47.8 | 35-50 | 30.1 | 0.0 |
| RIPK3 | -33.4 | 0.0 | -25.9 | 0.0 | -120.8 | ND |
| ROCK1, ROCK2 | -55.8 | 0.0 | -11.4 | 0.0 | 20.8 | 0.0 |
| RSK1 domain1 | 24.0 | 0.0 | 3.3 | 0.0 | 15.6 | 0.0 |
| RSK1 domain1, RSK2 domain1, RSK3 domain1 | 58.7 | 50-75 | 13.1 | 0.0 | 13.3 | 0.0 |
| RSK1 domain2 | 1.0 | 0.0 | -7.7 | 0.0 | 3.8 | 0.0 |
| RSK2 domain1 | 69.9 | 50-75 | 19.2 | 0.0 | 20.3 | 0.0 |
| RSK2 domain2 | -23.2 | 0.0 | 3.8 | 0.0 | -20.0 | 0.0 |
| RSKL1 | 0.2 | 0.0 | 1.6 | 0.0 | -26.1 | 0.0 |
| SGK2 | -5.4 | 0.0 | 22.1 | 0.0 | -30.3 | 0.0 |
| SGK3 | 51.6 | 50-75 | 13.1 | 0.0 | 9.9 | 0.0 |
| SLK | 95.3 | >90 | 49.2 | 35-50 | 58.9 | 50-75 |
| SMG1 | 94.7 | >90 | 61.0 | 50-75 | 42.9 | 35-50 |
| SNRK | 43.7 | 35-50 | 6.2 | 0.0 | 0.0 | 0.0 |
| SRPK1 | 32.8 | 0.0 | 10.8 | 0.0 | 19.5 | 0.0 |
| SRPK2 | 18.9 | 0.0 | -14.0 | 0.0 | 8.5 | 0.0 |
| STLK3 | -22.9 | 0.0 | 1.1 | 0.0 | 13.5 | 0.0 |
| STLK5 | -14.9 | 0.0 | 9.9 | 0.0 | 6.3 | 0.0 |
| STLK6 | -47.7 | 0.0 | -10.8 | 0.0 | 1.4 | 0.0 |
| TAO1, TAO3 | 67.5 | 50-75 | 10.3 | 0.0 | 85.5 | 75-90 |
| TAO2 | 35.3 | 35-50 | -19.7 | 0.0 | 61.5 | 50-75 |
| TBK1 | 23.7 | 0.0 | -23.1 | 0.0 | 3.4 | 0.0 |
| TLK1 | 28.8 | 0.0 | 8.6 | 0.0 | 1.8 | 0.0 |
| TLK2 | 34.0 | 0.0 | 12.6 | 0.0 | 14.2 | 0.0 |
| TYK2 domain2 | 29.9 | 0.0 | 0.6 | 0.0 | 3.8 | 0.0 |
| ULK1 | -19.6 | 0.0 | -23.4 | 0.0 | -54.6 | 0.0 |
| Wnk1, Wnk2, Wnk3 | -105.5 | >100 | -69.3 | 0.0 | -31.8 | 0.0 |
| ZAK | 42.0 | 35-50 | 44.9 | 35-50 | 18.2 | 0.0 |
| ZC1/HGK, ZC2/TNIK, ZC3/MINK | 96.7 | >90 | 97.0 | >90 | 94.5 | >90 |

Table 4 shows the activity of Compounds I-50, I-51, and I-65 of the application in an Ambit KINOSCAN assay.

TABLE 4

KiNativ Assay IC$_{50}$ data

| Kinase | I-50 (10 μM) | % inhibition | I-51 (10 μM) | % inhibition | I-65 (10 μM) | % inhibition |
|---|---|---|---|---|---|---|
| ABL, ARG | -53.7 | 0.0 | -3.0 | 0.0 | -2.8 | 0.0 |
| ACK | 11.3 | 0.0 | -39.0 | 0.0 | 30.7 | 0.0 |
| AGK | 11.5 | 0.0 | -12.1 | 0.0 | -21.2 | 0.0 |
| AKT1 | 2.1 | 0.0 | -15.2 | 0.0 | 1.6 | 0.0 |
| ALK2, ALK4, ALK7, BMPR1B, TGFbR1 | 84.0 | 75-90 | 76.2 | 75-90 | 91.0 | >90 |
| AMPKa1, AMPKa2 | -8.2 | 0.0 | -20.5 | 0.0 | 39.0 | 35-40 |
| ATM | 34.6 | 0.0 | 40.3 | 35-40 | 48.0 | 35-40 |
| ATR | 17.1 | 0.0 | 15.0 | 0.0 | 28.1 | 0.0 |
| AurA | 18.0 | 0.0 | 46.7 | 35-40 | 45.4 | 35-40 |
| AurA | 11.9 | 0.0 | 43.2 | 35-40 | 40.2 | 35-40 |
| AurA, AurB, AurC | 17.8 | 0.0 | 53.2 | 50-75 | 42.9 | 35-40 |
| AurB | 7.7 | 0.0 | 31.8 | 0.0 | 21.0 | 0.0 |
| BARK1 | -19.4 | 0.0 | -5.1 | 0.0 | 3.9 | 0.0 |
| BRAF | -35.8 | 0.0 | -41.8 | 0.0 | -41.5 | 0.0 |
| CaMK1d | 10.6 | 0.0 | -1.7 | 0.0 | 0.4 | 0.0 |
| CaMK2a, CaMK2b, CaMK2d, CaMK2g | 26.8 | 0.0 | 19.2 | 0.0 | 12.8 | 0.0 |
| CaMK2d | 15.9 | 0.0 | 2.3 | 0.0 | 4.2 | 0.0 |
| CaMK2g | 15.6 | 0.0 | -6.4 | 0.0 | -12.0 | 0.0 |
| CaMK4 | -17.9 | 0.0 | -61.2 | 0.0 | -21.0 | 0.0 |

TABLE 4-continued

KiNativ Assay IC$_{50}$ data

| Kinase | I-50 (10 μM) | % inhibition | I-51 (10 μM) | % inhibition | I-65 (10 μM) | % inhibition |
|---|---|---|---|---|---|---|
| CaMKK2 | 88.3 | 75-90 | 78.5 | 75-90 | 85.6 | 75-90 |
| CDC2 | 13.7 | 0.0 | 18.5 | 0.0 | −0.5 | 0.0 |
| CDK11, CDK8 | 38.1 | 35-40 | 31.8 | 0.0 | 31.3 | 0.0 |
| CDK2 | 17.3 | 0.0 | 35.0 | 35-40 | 21.6 | 0.0 |
| CDK5 | 11.3 | 0.0 | 37.2 | 35-40 | 4.9 | 0.0 |
| CDK6 | 15.0 | 0.0 | 10.7 | 0.0 | 0.5 | 0.0 |
| CDK7 | 19.4 | 0.0 | 17.4 | 0.0 | 29.9 | 0.0 |
| CHK1 | −9.6 | 0.0 | −20.1 | 0.0 | −16.0 | 0.0 |
| CHK2 | 19.3 | 0.0 | 14.1 | 0.0 | 11.2 | 0.0 |
| CK1a | −20.9 | 0.0 | −34.7 | 0.0 | −65.1 | 0.0 |
| CK1g2 | 79.9 | 75-90 | 84.1 | 75-90 | 74.5 | 50-75 |
| CK1g3 | 77.1 | 75-90 | 88.2 | 75-90 | 87.2 | 75-90 |
| CLK2 | 10.8 | 0.0 | 65.3 | 50-75 | 69.4 | 50-75 |
| CLK3 | 1.5 | 0.0 | 23.3 | 0.0 | 40.0 | 35-40 |
| CSK | −4.3 | 0.0 | 6.9 | 0.0 | 0.1 | 0.0 |
| DGKH | 6.3 | 0.0 | 2.7 | 0.0 | 7.3 | 0.0 |
| DNAPK | 8.2 | 0.0 | 52.3 | 50-75 | 78.3 | 75-90 |
| DNAPK | −31.5 | 0.0 | 2.5 | 0.0 | 26.7 | 0.0 |
| eEF2K | −1.0 | 0.0 | 7.7 | 0.0 | −21.7 | 0.0 |
| EphB2 | 8.2 | 0.0 | 8.8 | 0.0 | 20.3 | 0.0 |
| Erk1 | 29.0 | 0.0 | 29.2 | 0.0 | −30.7 | 0.0 |
| Erk2 | 34.5 | 0.0 | 31.8 | 0.0 | −29.6 | 0.0 |
| Erk5 | −2.8 | 0.0 | −13.2 | 0.0 | −6.5 | 0.0 |
| FER | 16.3 | 0.0 | 13.4 | 0.0 | 63.6 | 50-75 |
| FRAP | 21.5 | 0.0 | 25.1 | 0.0 | 47.9 | 35-40 |
| FYN, SRC, YES | −2.0 | 0.0 | −36.4 | 0.0 | −8.4 | 0.0 |
| GAK | 51.1 | 50-75 | 50.4 | 50-75 | 7.7 | 0.0 |
| GCK | 95.2 | >90 | 93.9 | >90 | 92.5 | >90 |
| GCN2 domain2 | −12.3 | 0.0 | −5.1 | 0.0 | 43.5 | 35-40 |
| GPRK6 | −40.5 | 0.0 | 4.7 | 0.0 | 23.1 | 0.0 |
| GSK3A | 77.4 | 75-90 | 85.2 | 75-90 | 86.0 | 75-90 |
| GSK3B | 81.1 | 75-90 | 90.2 | >90 | 90.0 | >90 |
| HPK1 | 90.4 | >90 | 83.5 | 75-90 | 95.5 | >90 |
| IKKa | −1.9 | 0.0 | −17.3 | 0.0 | −34.3 | 0.0 |
| IKKb | −26.2 | 0.0 | −19.5 | 0.0 | −36.0 | 0.0 |
| IKKe, TBK1 | 33.9 | 0.0 | 26.7 | 0.0 | 81.8 | 75-90 |
| ILK | −18.8 | 0.0 | −31.3 | 0.0 | −35.0 | 0.0 |
| IRAK1 | 51.2 | 50-75 | 65.0 | 50-75 | 27.8 | 0.0 |
| IRAK4 | 19.6 | 0.0 | 16.4 | 0.0 | 32.9 | 0.0 |
| IRE1 | −8.7 | 0.0 | −43.1 | 0.0 | −6.3 | 0.0 |
| ITPK1 | −239.4 | | −282.8 | | −500.9 | >100 |
| JAK1 domain1 | −19.8 | 0.0 | −8.2 | 0.0 | 2.1 | 0.0 |
| JAK1 domain2 | −23.3 | 0.0 | −6.4 | 0.0 | 10.1 | 0.0 |
| JAK2 domain2 | −71.2 | 0.0 | −300.1 | | 18.8 | 0.0 |
| JAK3 domain2 | −20.2 | 0.0 | 13.4 | 0.0 | 52.1 | 50-75 |
| JNK1, JNK2, JNK3 | 26.8 | 0.0 | 29.3 | 0.0 | 6.4 | 0.0 |
| KHS1 | 77.8 | 75-90 | 72.7 | 50-75 | 73.3 | 50-75 |
| KSR1, KSR2 | −18.4 | 0.0 | −5.2 | 0.0 | −5.7 | 0.0 |
| LATS1 | 2.9 | 0.0 | 3.9 | 0.0 | 33.8 | 0.0 |
| LATS2 | 1.1 | 0.0 | 16.1 | 0.0 | −0.2 | 0.0 |
| LKB1 | −1.1 | 0.0 | 5.1 | 0.0 | 27.4 | 0.0 |
| LOK | 91.6 | >90 | 96.9 | >90 | 98.7 | >90 |
| LYN | 9.7 | 0.0 | −21.9 | 0.0 | −1.3 | 0.0 |
| LZK | 1.3 | 0.0 | 11.3 | 0.0 | 43.1 | 35-40 |
| MAP2K1 | 17.8 | 0.0 | −26.2 | 0.0 | 21.2 | 0.0 |
| MAP2K1, MAP2K2 | −4.3 | 0.0 | −2.3 | 0.0 | 21.0 | 0.0 |
| MAP2K1, MAP2K2 | −42.2 | 0.0 | −79.8 | 0.0 | 10.7 | 0.0 |
| MAP2K3 | −5.7 | 0.0 | 0.9 | 0.0 | −6.1 | 0.0 |
| MAP2K4 | 37.5 | 35-40 | 44.2 | 35-40 | −15.3 | 0.0 |
| MAP2K5 | −12.1 | 0.0 | −4.0 | 0.0 | 15.0 | 0.0 |
| MAP2K6 | 10.9 | 0.0 | −3.5 | 0.0 | −15.0 | 0.0 |
| MAP2K7 | 16.4 | 0.0 | 12.2 | 0.0 | 3.3 | 0.0 |
| MAP3K1 | 86.7 | 75-90 | 95.8 | >90 | 48.5 | 35-40 |
| MAP3K15 | 46.7 | 35-40 | 36.4 | 35-40 | 29.7 | 0.0 |
| MAP3K2 | −39.1 | 0.0 | −11.2 | 0.0 | −3.9 | 0.0 |
| MAP3K2, MAP3K3 | 12.0 | 0.0 | 26.7 | 0.0 | 23.3 | 0.0 |
| MAP3K3 | −5.7 | 0.0 | −29.3 | 0.0 | −28.3 | 0.0 |

TABLE 4-continued

KiNativ Assay IC$_{50}$ data

| Kinase | I-50 (10 μM) | % inhibition | I-51 (10 μM) | % inhibition | I-65 (10 μM) | % inhibition |
|---|---|---|---|---|---|---|
| MAP3K4 | 9.5 | 0.0 | 24.2 | 0.0 | 10.3 | 0.0 |
| MAP3K5 | 27.5 | 0.0 | 16.3 | 0.0 | −12.4 | 0.0 |
| MAP3K6 | −5.4 | 0.0 | 24.4 | 0.0 | −7.2 | 0.0 |
| MAPKAPK2, MAPKAPK3 | −34.3 | 0.0 | −65.2 | 0.0 | −52.2 | 0.0 |
| MARK1, MARK2 | −29.5 | 0.0 | 9.3 | 0.0 | −29.4 | 0.0 |
| MARK2 | −8.6 | 0.0 | 24.6 | 0.0 | −45.1 | 0.0 |
| MARK2, MARK3 | 0.4 | 0.0 | 14.9 | 0.0 | −17.2 | 0.0 |
| MARK3 | −17.3 | 0.0 | 4.8 | 0.0 | −22.7 | 0.0 |
| MARK4 | 6.8 | 0.0 | 22.2 | 0.0 | −1.1 | 0.0 |
| MAST1, MAST2 | 2.6 | 0.0 | −2.9 | 0.0 | 3.0 | 0.0 |
| MAST3 | −0.5 | 0.0 | 7.0 | 0.0 | −7.5 | 0.0 |
| MASTL | −1.4 | 0.0 | 14.6 | 0.0 | −9.6 | 0.0 |
| MELK | 45.9 | 35-40 | 49.5 | 35-40 | 56.5 | 50-75 |
| MER, TYRO3 | −2.0 | 0.0 | −11.0 | 0.0 | 4.6 | 0.0 |
| MLK3 | 40.9 | 35-40 | 42.3 | 35-40 | 82.7 | 75-90 |
| MLK4 | 30.2 | 0.0 | 14.2 | 0.0 | 56.9 | 50-75 |
| MLKL | 8.2 | 0.0 | 51.4 | 50-75 | 0.2 | 0.0 |
| MPSK1 | 15.7 | 0.0 | 43.9 | 35-40 | 72.8 | 50-75 |
| MSK1 domain1 | 0.1 | 0.0 | 11.4 | 0.0 | −52.5 | 0.0 |
| MSK2 domain1 | −2.8 | 0.0 | −8.0 | 0.0 | −83.6 | 0.0 |
| MST1 | 97.5 | >90 | 96.3 | >90 | 96.7 | >90 |
| MST1, MST2 | 98.7 | >90 | 98.4 | >90 | 98.7 | >90 |
| MST2 | 97.5 | >90 | 95.3 | >90 | 97.3 | >90 |
| MST3 | 20.0 | 0.0 | 53.3 | 50-75 | 31.5 | 0.0 |
| MST4 | −68.1 | 0.0 | 33.9 | 0.0 | 47.7 | 35-40 |
| MST4, YSK1 | 35.4 | 35-40 | 68.1 | 50-75 | 46.3 | 35-40 |
| NDR1 | 20.2 | 0.0 | 16.8 | 0.0 | −14.5 | 0.0 |
| NDR2 | 4.5 | 0.0 | 8.4 | 0.0 | −8.7 | 0.0 |
| NEK1 | 16.8 | 0.0 | 30.2 | 0.0 | 9.3 | 0.0 |
| NEK3 | −9.9 | 0.0 | −13.0 | 0.0 | −18.4 | 0.0 |
| NEK4 | 25.1 | 0.0 | 25.8 | 0.0 | 23.7 | 0.0 |
| NEK6, NEK7 | −54.5 | 0.0 | −63.6 | 0.0 | −78.6 | 0.0 |
| NEK7 | −18.9 | 0.0 | −50.3 | 0.0 | −80.0 | 0.0 |
| NEK8 | −8.1 | 0.0 | −8.1 | 0.0 | −1.7 | 0.0 |
| NEK9 | 5.9 | 0.0 | −20.8 | 0.0 | −27.8 | 0.0 |
| NuaK1 | 67.9 | 50-75 | 71.9 | 50-75 | 66.8 | 50-75 |
| NuaK1 | 61.5 | 50-75 | 68.8 | 50-75 | 61.5 | 50-75 |
| NuaK2 | 40.8 | 35-40 | 45.1 | 35-40 | 48.7 | 35-40 |
| OSR1 | 16.6 | 0.0 | 8.8 | 0.0 | 26.8 | 0.0 |
| p38a | 12.1 | 0.0 | 8.7 | 0.0 | −11.0 | 0.0 |
| p38a | −12.9 | 0.0 | −24.7 | 0.0 | −44.2 | 0.0 |
| p38d, p38g | 7.4 | 0.0 | 2.3 | 0.0 | −8.5 | 0.0 |
| p70S6K | 2.4 | 0.0 | −21.6 | 0.0 | 11.1 | 0.0 |
| p70S6Kb | 14.0 | 0.0 | 5.5 | 0.0 | 32.0 | 0.0 |
| PAK2 | 20.2 | 0.0 | −14.0 | 0.0 | 1.7 | 0.0 |
| PAN3 | 14.3 | 0.0 | −39.1 | 0.0 | 5.8 | 0.0 |
| PCTAIRE1 | −15.6 | 0.0 | −0.2 | 0.0 | 9.0 | 0.0 |
| PCTAIRE1, PCTAIRE3 | −3.5 | 0.0 | 29.4 | 0.0 | 2.3 | 0.0 |
| PCTAIRE2, PCTAIRE3 | −8.9 | 0.0 | 5.1 | 0.0 | 20.3 | 0.0 |
| PEK | 7.9 | 0.0 | −16.3 | 0.0 | −12.9 | 0.0 |
| PFTAIRE1 | −2.4 | 0.0 | 8.8 | 0.0 | −5.1 | 0.0 |
| PHKg2 | −38.6 | 0.0 | −45.4 | 0.0 | −64.0 | 0.0 |
| PI4KA, PI4KAP2 | 24.7 | 0.0 | 0.1 | 0.0 | −2.9 | 0.0 |
| PI4KB | 0.0 | 0.0 | 13.0 | 0.0 | 8.6 | 0.0 |
| PIK3C3 | −32.5 | 0.0 | −13.2 | 0.0 | −15.0 | 0.0 |
| PIK3CB | 27.7 | 0.0 | 7.2 | 0.0 | 14.6 | 0.0 |
| PIK3CG | −74.9 | 0.0 | −146.5 | 0.0 | −64.0 | 0.0 |
| PIP4K2A | −5.5 | 0.0 | −16.5 | 0.0 | −4.6 | 0.0 |
| PIP4K2B | −31.5 | 0.0 | −47.1 | 0.0 | −8.9 | 0.0 |
| PIP4K2C | 90.6 | >90 | 85.4 | 75-90 | 90.2 | >90 |
| PIP5K3 | 79.7 | 75-90 | 84.7 | 75-90 | 91.7 | >90 |
| PITSLRE | −27.6 | 0.0 | −20.2 | 0.0 | −17.5 | 0.0 |
| PKCi | −15.0 | 0.0 | −49.1 | 0.0 | −41.2 | 0.0 |

TABLE 4-continued

KiNativ Assay IC$_{50}$ data

| Kinase | I-50 (10 µM) | % inhibition | I-51 (10 µM) | % inhibition | I-65 (10 µM) | % inhibition |
|---|---|---|---|---|---|---|
| PKCz | −1.7 | 0.0 | 2.1 | 0.0 | −12.4 | 0.0 |
| PKD2 | 51.5 | 50-75 | 73.2 | 50-75 | −33.4 | 0.0 |
| PKD3 | 69.7 | 50-75 | 74.8 | 50-75 | −24.2 | 0.0 |
| PKN1 | −39.9 | 0.0 | −72.1 | 0.0 | 35.9 | ND |
| PKR | 1.8 | 0.0 | 3.8 | 0.0 | −7.6 | 0.0 |
| PLK1 | −11.1 | 0.0 | −20.6 | 0.0 | −10.1 | 0.0 |
| PRP4 | −17.9 | 0.0 | 10.2 | 0.0 | −19.3 | 0.0 |
| PRPK | −23.6 | 0.0 | −47.4 | 0.0 | −55.9 | 0.0 |
| PYK2 | 31.5 | 0.0 | 30.1 | 0.0 | 38.7 | 35-40 |
| RSK1 domain1 | −4.6 | 0.0 | 5.4 | 0.0 | 59.9 | 50-75 |
| RSK1 domain1, RSK2 domain1, RSK3 domain1 | 15.8 | 0.0 | 25.8 | 0.0 | 68.4 | 50-75 |
| RSK1 domain2 | 1.0 | 0.0 | 11.0 | 0.0 | −0.7 | 0.0 |
| RSK2 domain1 | 21.0 | 0.0 | 49.9 | 35-40 | 79.4 | 75-90 |
| RSK2 domain2 | −1.4 | 0.0 | 9.9 | 0.0 | 7.2 | 0.0 |
| RSKL1 | 3.2 | 0.0 | −22.1 | 0.0 | −10.6 | 0.0 |
| SGK3 | 11.2 | 0.0 | 26.3 | 0.0 | 13.5 | 0.0 |
| SLK | 70.6 | 50-75 | 85.6 | 75-90 | 97.8 | >90 |
| SMG1 | 30.8 | 0.0 | 55.8 | 50-75 | 68.8 | 50-75 |
| SNRK | 33.2 | 0.0 | −26.2 | 0.0 | 1.1 | 0.0 |
| SRPK1 | −9.2 | 0.0 | −11.5 | 0.0 | −25.4 | 0.0 |
| SRPK2 | 1.8 | 0.0 | −41.0 | 0.0 | −29.4 | 0.0 |
| STLK3 | −12.3 | 0.0 | −5.0 | 0.0 | 31.4 | 0.0 |
| STLK5 | −22.3 | 0.0 | −17.1 | 0.0 | −38.6 | 0.0 |
| STLK6 | −15.0 | 0.0 | −15.0 | 0.0 | −15.9 | 0.0 |
| TAK1 | 39.1 | 35-40 | 30.0 | 0.0 | 35.0 | 35-40 |
| TAO1, TAO3 | 17.8 | 0.0 | 80.4 | 75-90 | 14.4 | 0.0 |
| TAO2 | 9.0 | 0.0 | 40.9 | 35-40 | 8.3 | 0.0 |
| TBK1 | 31.4 | 0.0 | 35.8 | 35-40 | 74.6 | 50-75 |
| TLK1 | −7.5 | 0.0 | −11.8 | 0.0 | −1.2 | 0.0 |
| TLK2 | −3.0 | 0.0 | −20.1 | 0.0 | −3.5 | 0.0 |
| TYK2 domain2 | −21.0 | 0.0 | −23.9 | 0.0 | −8.4 | 0.0 |
| ULK1 | 28.8 | 0.0 | 40.0 | 35-40 | 22.2 | 0.0 |
| ULK3 | −14.2 | 0.0 | 1.8 | 0.0 | 30.6 | 0.0 |
| Wnk1, Wnk2, Wnk3 | 15.9 | 0.0 | 0.2 | 0.0 | −8.3 | 0.0 |
| ZAK | 6.6 | 0.0 | 58.3 | 50-75 | 36.2 | 35-40 |
| ZC1/HGK, ZC2/TNIK, ZC3/MINK | 96.3 | >90 | 97.2 | >90 | 96.6 | >90 |
| ZC3/MINK | 57.6 | 50-75 | 63.4 | 50-75 | 66.6 | 50-75 |

Example 65: Cell Viability and Proliferation Assay

Cell Culture and Reagents

Cell lines and culture. The MM cell lines H929 and KMS20 were available in the Laboratory. MM Dex-sensitive (MM.1 S) human MM cell lines were kindly provided by Dr. Steven Rosen (Northwestern University, Chicago, Ill., United States). The cell lines were routinely tested for *Mycoplasma*, and genotyped with two different methods. All MM cell lines were cultured in RPMI-1640 media (EuroClone, Pero, Italy) containing 10% fetal bovine serum (FBS, GIBCO, Life technologies, Carlsbad, Calif., United States), and a mix of penicillin and streptomycin to 1% from EuroClone (ECB3001).

H929 and MM.1S cell lines presented low levels of YAP1, while KMS20 cell line presented a focal genetic lesion affecting the YAP1 locus, hence in this cell line YAP1 is not present at the RNA and protein level. RPMI/8226, OPM-2 and U266 cell lines were also tested.

Cell Proliferation Assays and Growth Assays

MM. 1S, KMS20, H929 MM cells, RPMI/8226, OPM-2 and U266 were counted and diluted to a final concentration of 400,000 cells/mL. The cell were plated in 96-well plates and mixed with an equal volume of culture media containing DMSO or increasing concentration of a compound of the present application diluted in DMSO (the final DMSO concentration is equal between all tested samples), using a STARlet Robot (Hamiltonrobotics, Reno, Nev., United States). Cells with increasing concentration of compound of the present application and DMSO were harvested at different time points (24 hrs to 72 hrs). Viability was assessed by MTT or Cell Titer 96® AQueous One Solution cell proliferation assay (Promega). Specifically, for the MTT assay, the 3-[4,5 dimethylthiazol-2-yl]-2,5 diphenyltetrazolium bromide-MTT (Sigma-Aldrich, St. Louis, Mo., Unites States) colorimetric survival assay was used. At the various time points (24-72 hrs), 10 µL of 5 mg/mL MTT were added to cells. After 4 hrs incubation at 37° C., medium was discarded and 100 µL MTT stop solution (DMSO or Isopropanol with 1 N HCl) was used to dissolve MTT metabolic products. Absorbance was read at 570/630 nm. For the Promega assay, at the various time points, 20 µL of Cell Titer solution is added to the cells. After 4 hrs of incubation at 37° C. absorbance was read at 690 nM.

Figure 6:
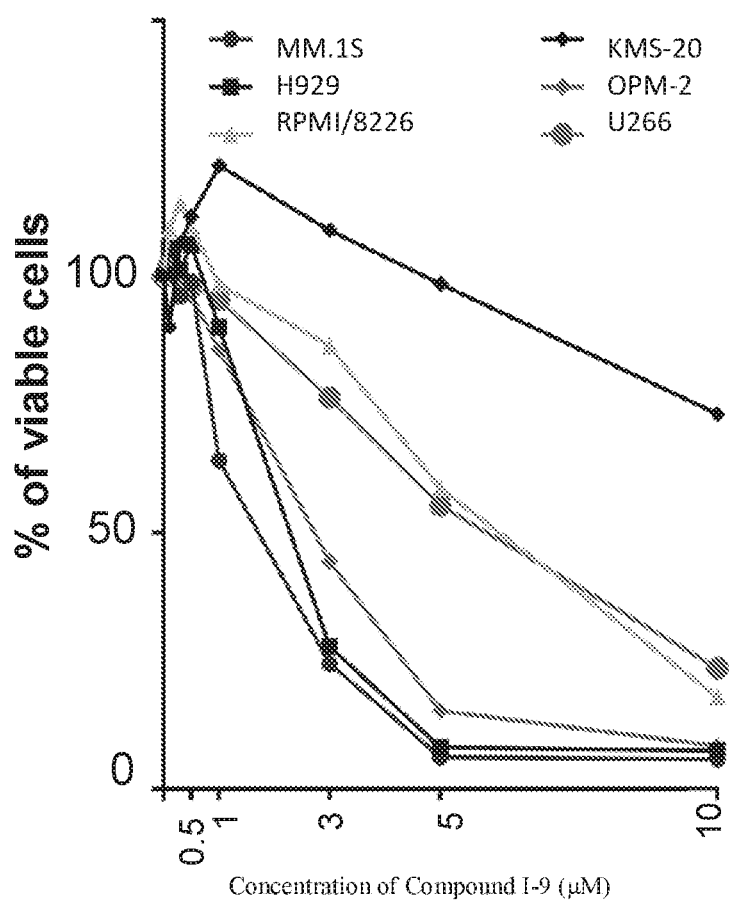
FIG. 6 is a graph showing the viability of MM.1 S, KMS20, H929, RPMI/8226, OPM-2, and U266 cells when treated with varying concentrations of Compound I-9.
Figure 9:
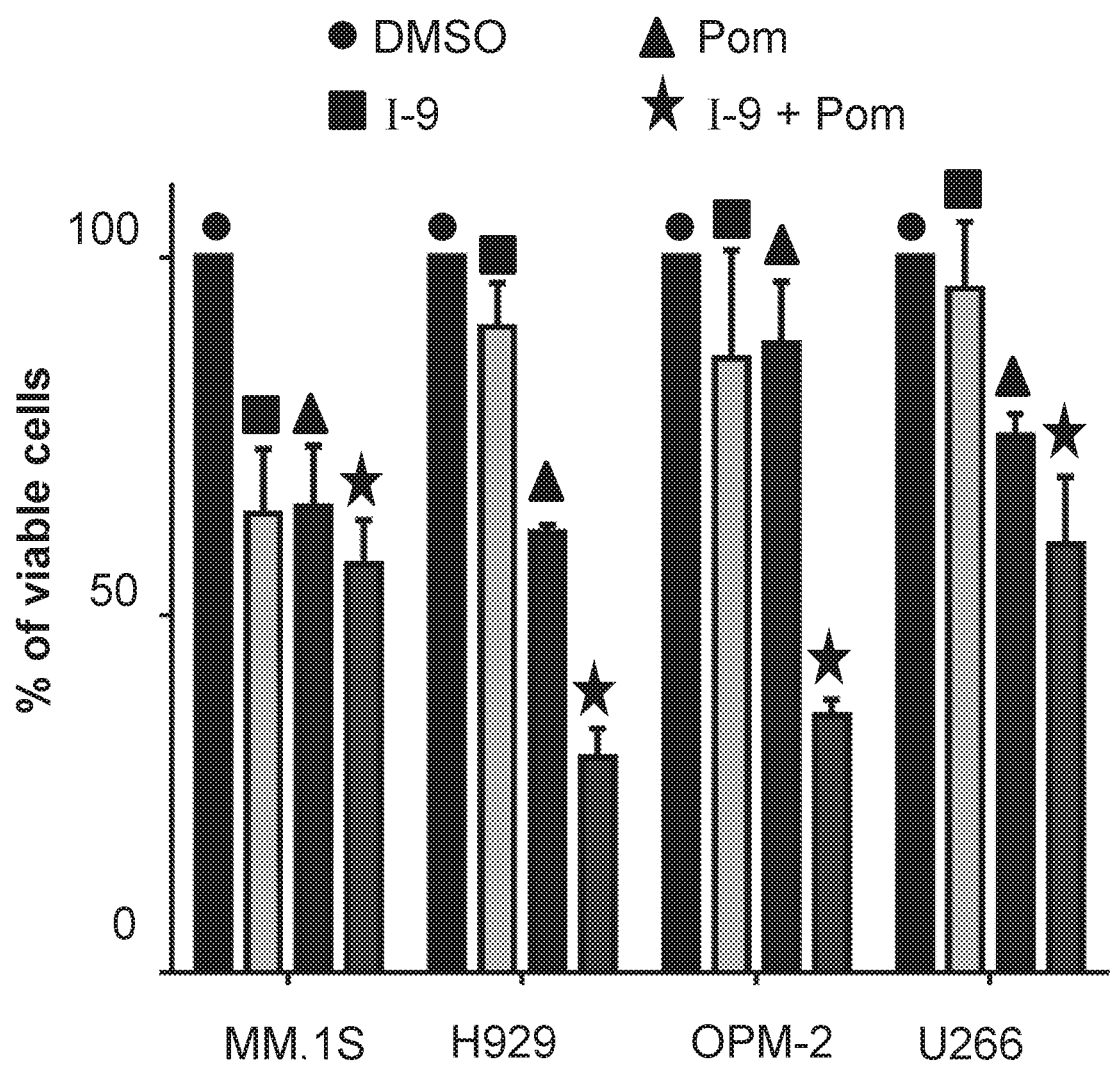
FIG. 9 is a graph showing the viability of MM.1S, KMS20, OPM-2, and H929 cells when treated with DMSO (control), Compound I-9, Pomalidomide (POM), and Compound I-9 and Pomalidomide.

The cell viability of MM.1S, KMS20, and H929 MM cells treated with varying concentrations of Compounds I-1, I-2, I-3, I-5, I-6, I-8, I-9, I-11, I-12, I-13, I-14, I-15, I-16, I-18, I-19, I-20, I-21, I-22, I-23, I-27, I-28, I-30, I-31, I-39, I-45, I-46, I-47, I-48, I-49, I-52, I-53, I-56, I-57, I-60, I-61, I-62, I-63, I-72, I-74, I-76, I-77 is shown in FIGS. 1-6, 10B, 11A-11M, 14A-25, and 27. The cell viability of MM.1S, KMS20, H929 MM, RPMI/8226, OPM-2 and U266 cells treated with varying concentrations of Compound I-9 is shown in FIG. 6. Cell viability of MM. 1S, KMS20, OPM-2, and H929 cells when treated with DMSO (control), Compound I-9, Pomalidomide, and Compound I-9 and Pomalidomide is shown in FIG. 9.

Western Blotting

Figure 8:
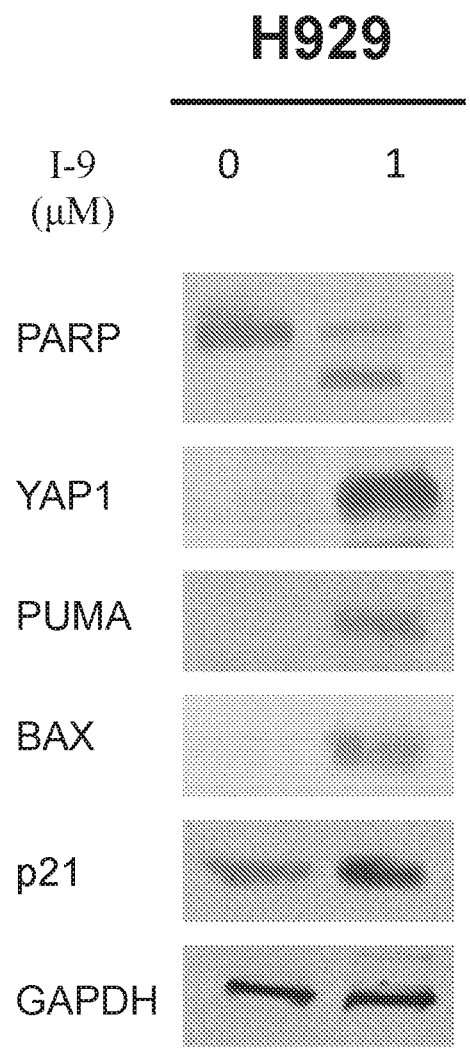
FIG. 8 is a Western blot showing the levels of PARP total and cleaved, YAP1, PUMA, BAX, p21, and GAPDH in untreated H929 cells and cells after treatment with Compound I-9 for 24 hours.

MM.1S, KMS20 and H929 cells were counted, diluted and plated in six-well plates to a final concentration of 500,000 cells/well. Cells were then harvested with DMSO or different concentration of a compound of the present application for 6 hrs, 24 hrs or 48 hrs. MM cells were then collected and centrifuged for 5 min, 1300 rpm at RT. The pellets were re-suspended in lysis buffer Laemli 1× (Laemli 5×: SDS 10%, DTT 500 mM, Tris-HCl pH6.8 0.4M, BromoFenol Blue, Glycerol 50%). Cell lysates were subjected to sodium dodecyl sulfate-polyacrylamide gel electrophoresis SDS-PAGE, transferred to nitrocellulose membranes, and immunoblotted with different antibodies: YAP1 (#4912), p-YAP1 (S127) (#13008), LATS1 (#9153), p-LATS1 (Thr1079) (#8654), MOB1 (#3863), p-MOB1 (Thr12) (#8843), p-MST1/p-MST2 (Thr183/Thr180) (#3681), p21 (#2947), PARP (#9532), ERK, STAT, and GAPDH (#5174) from Cell Signaling, Beverly, Mass., United States; STK4 (ab57836) (from Abcam, Cambridge, Mass., United States); PUMA (sc-28226), BAX (sc-20067), from Santa Cruz, Dallas, Tex., United States; β-actin from Sigma-Aldrich (St. Louis, Mo., United States). All antibodies were diluted 1:500, except for β-actin antibody (1:50,000 dilution). In FIG. 8, H929 cells were treated with Compound I-9 or DMSO at 1 μM concentration for 24 hours. Lysates were then obtained and immunoblot was performed using antibodies against PARP, YAP1, PUMA, BAX. p21, and GAPDH. As can be seen in FIG. 8, Compound I-9 caused upregulation of protein levels of YAP1, PUMA, BAX, and p21 and induction of PARP cleavage in H929 cells.

Figure 10A:
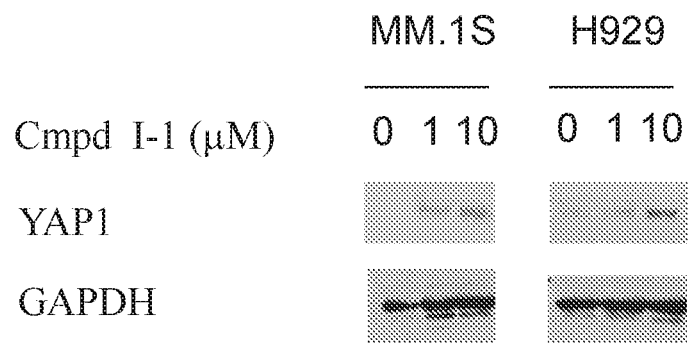
FIG. 10A is a Western blot showing the levels of YAP 1 and GAPDH 1 in untreated MM.1S and H929 cells and MM.1S and H929 cells after treatment with Compound I-1 for 16 hours.
Figure 10B:
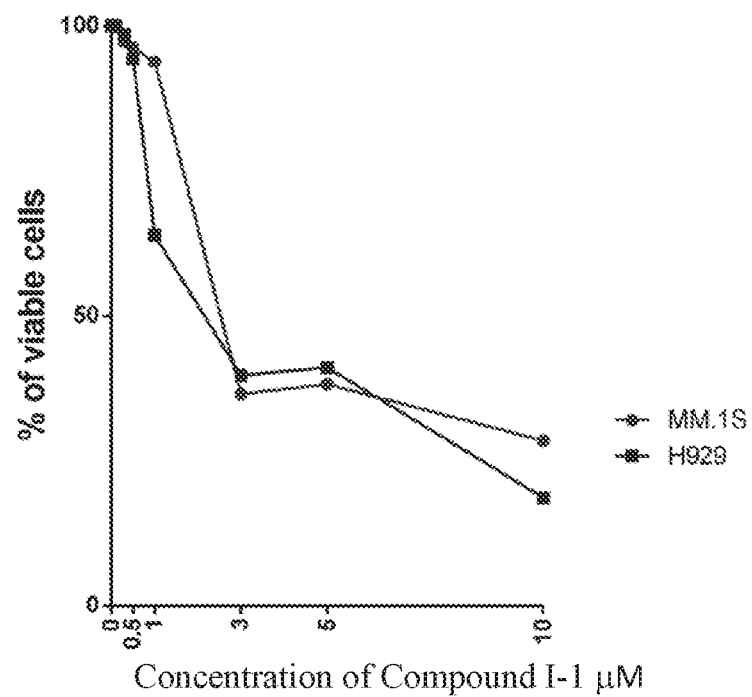
FIG. 10B is a graph showing the viability of MM.1S and H929 cells when treated with Compound I-1.
Figure 11A:
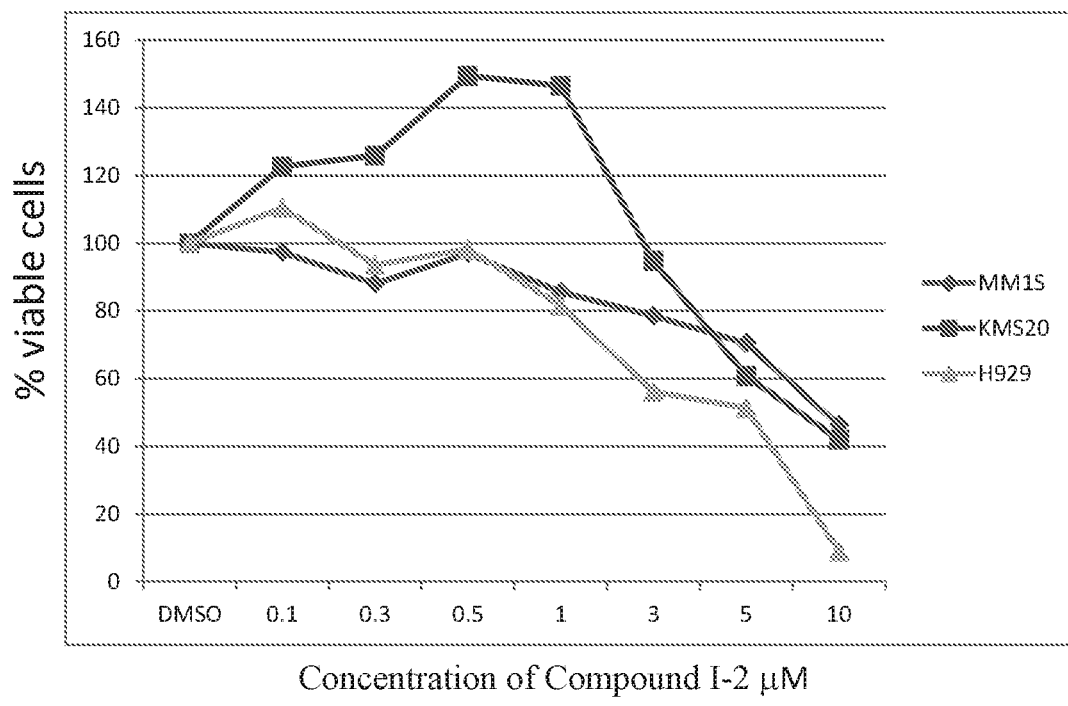
Figure 11B:
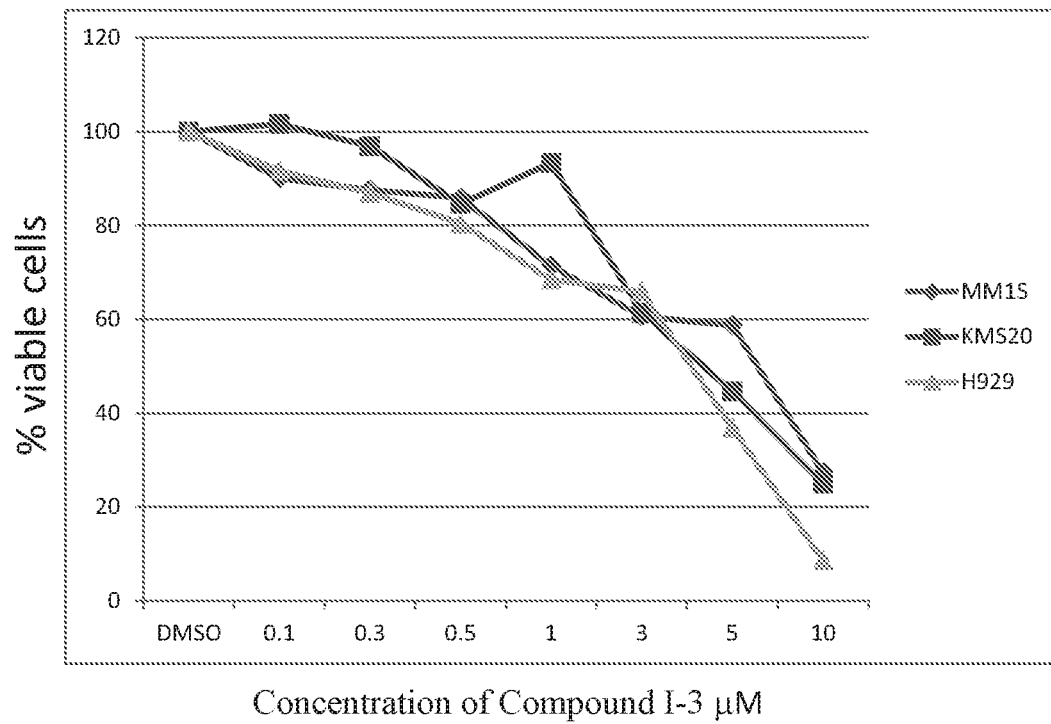
Figure 11C:
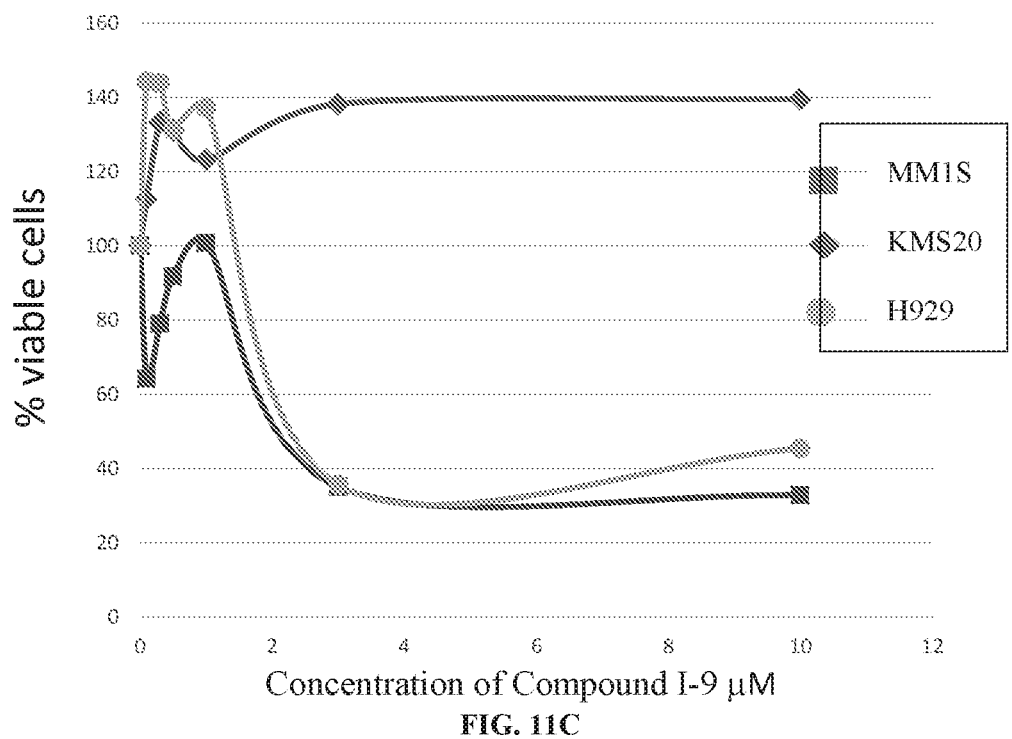
Figure 11D:
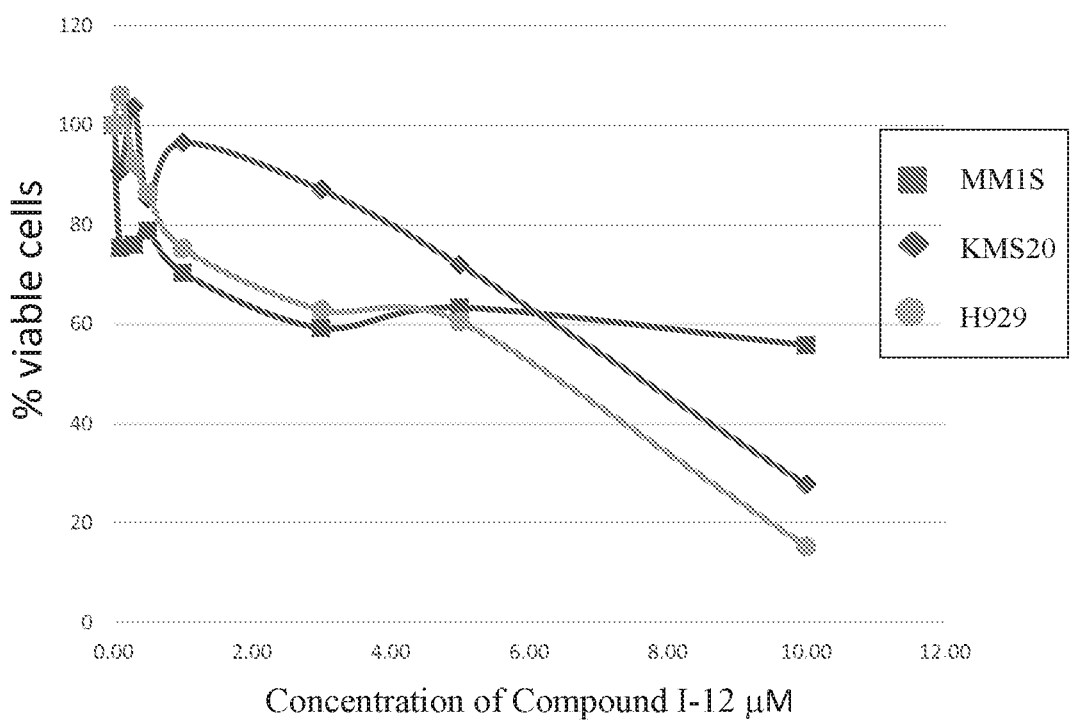
Figure 11E:
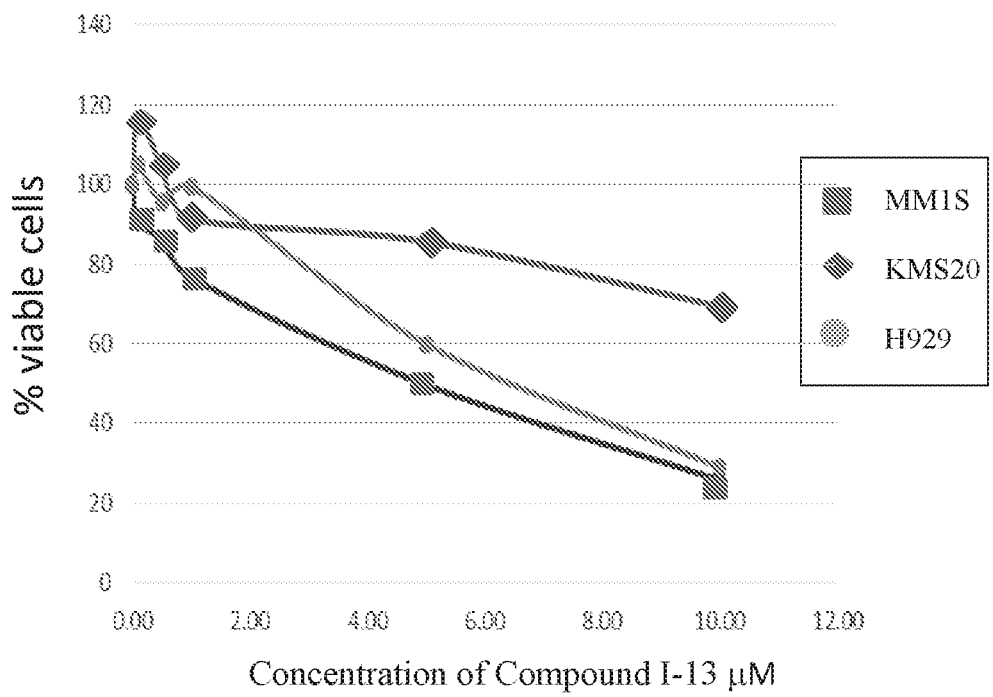
Figure 11F:
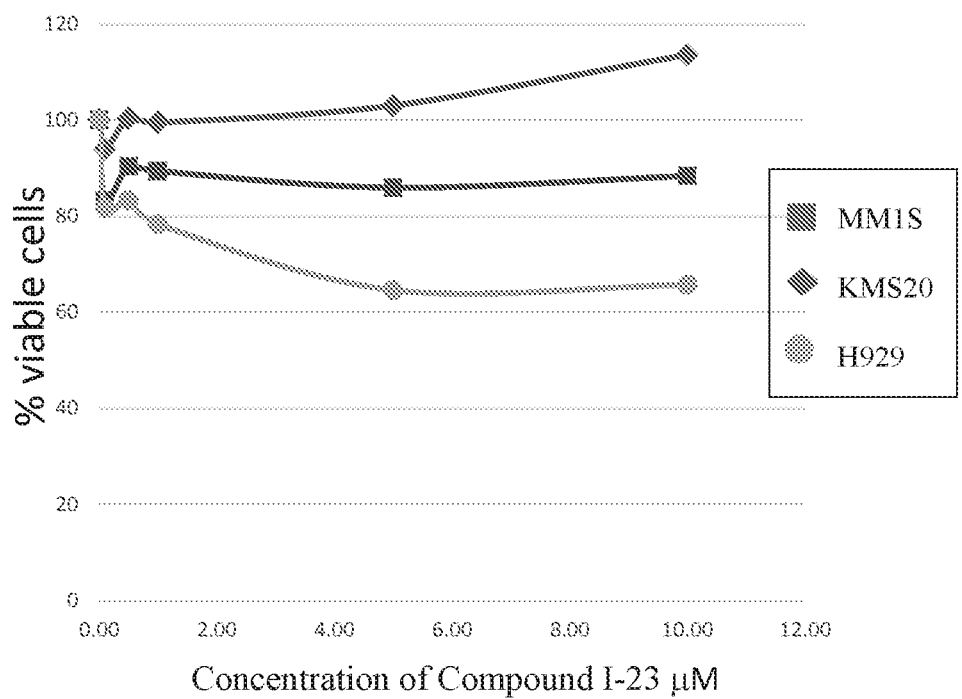
Figure 11G:
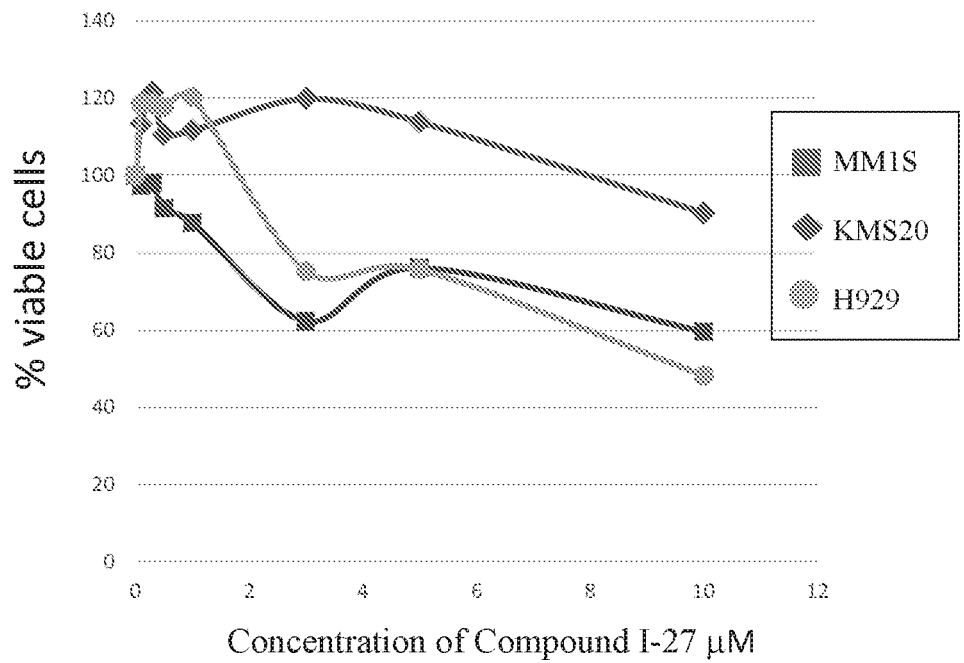
Figure 11H:
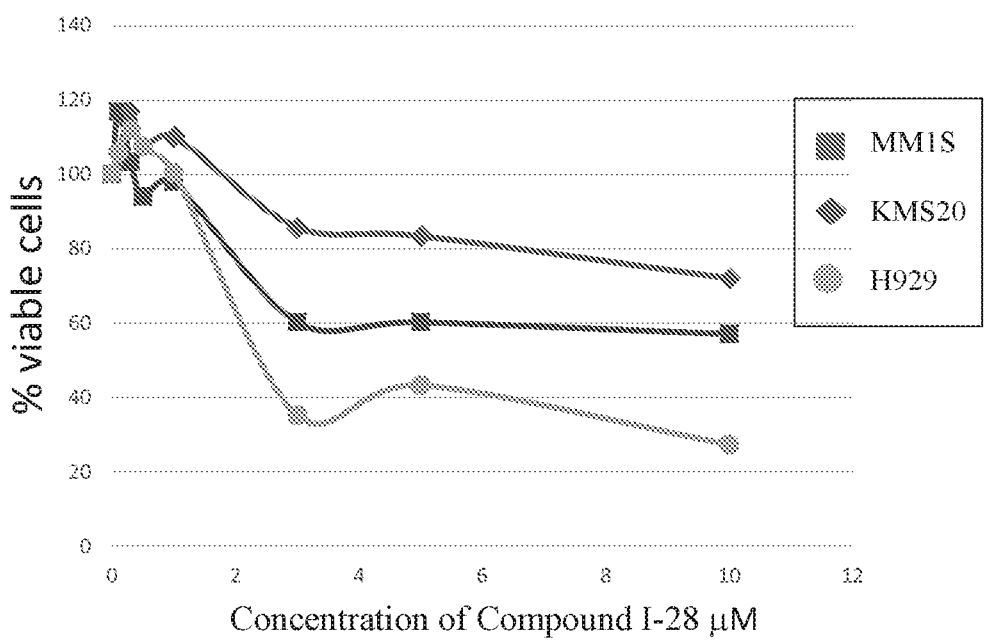
Figure 11I:
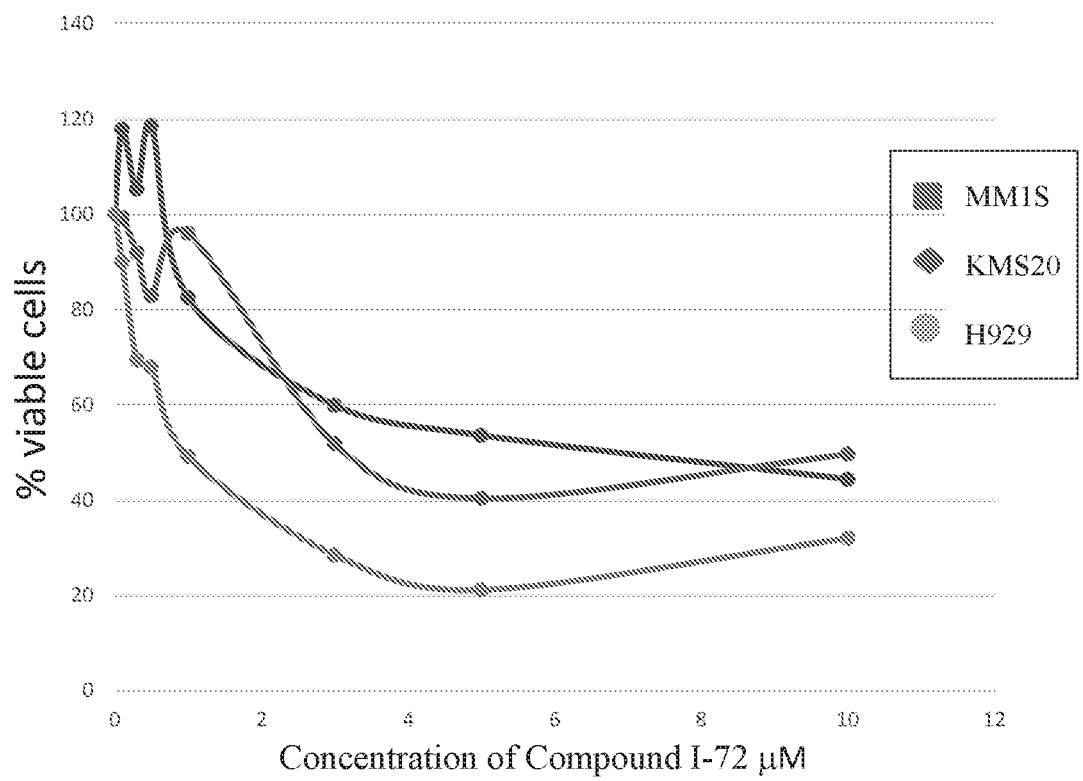
Figure 11J:
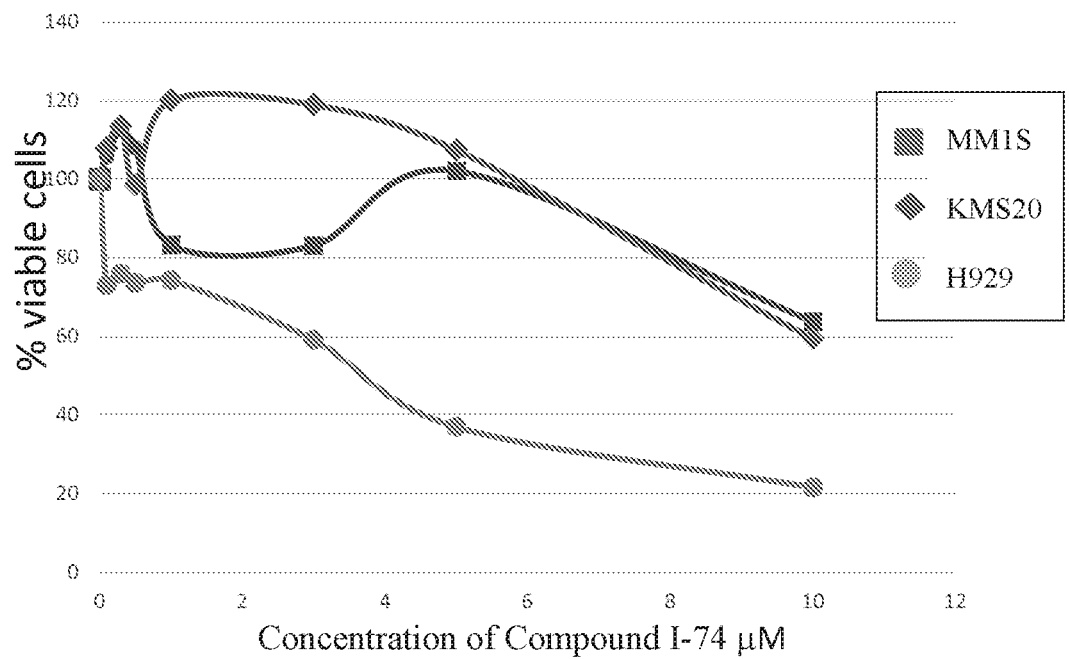
Figure 11K:
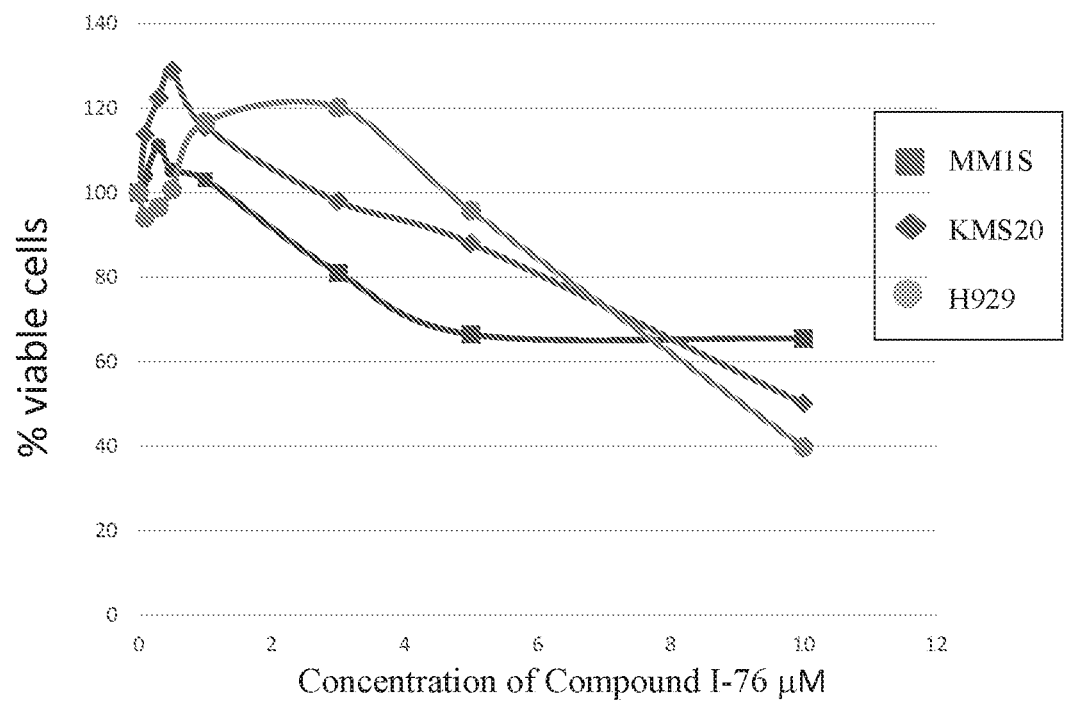
Figure 11L:
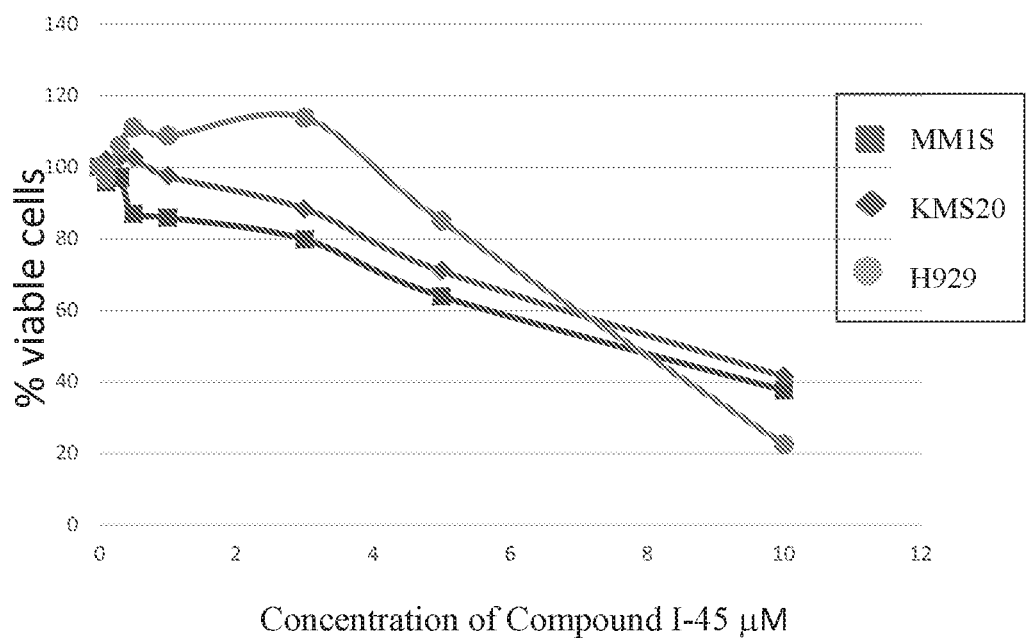
Figure 11M:
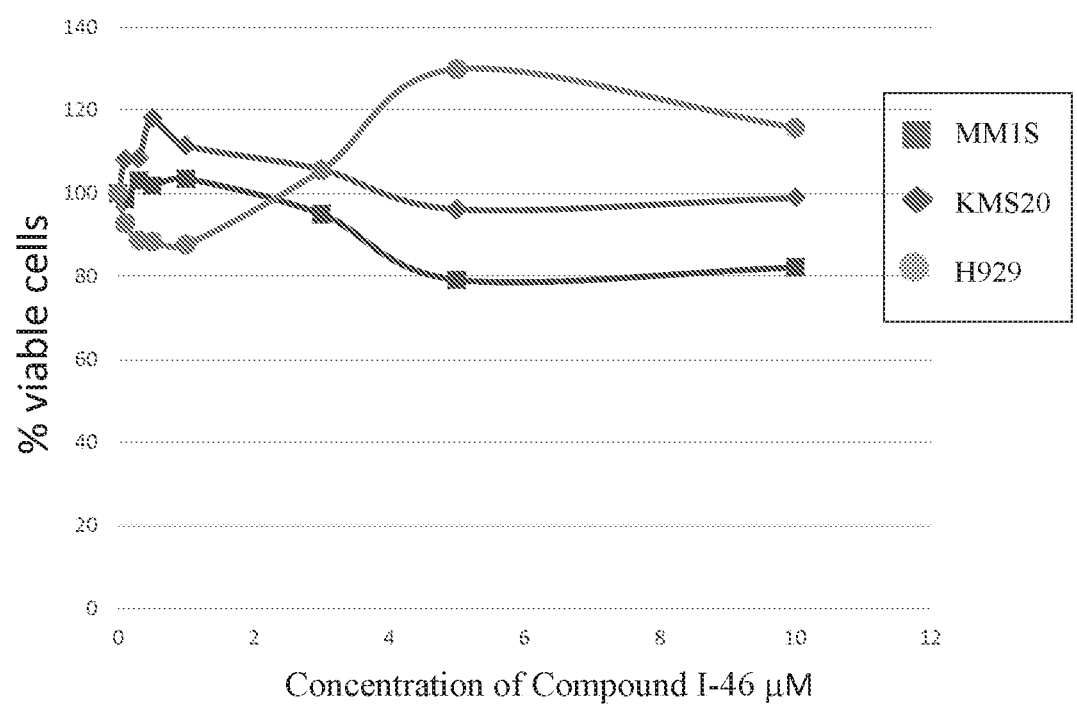

In FIG. 10A, H929 and MM.1S cells were treated with Compound I-1 or DMSO at 1 μM and 10 μM concentrations for 16 hours. Lysates were then obtained and immunoblot was performed using antibodies against YAP1 and GAPDH. As can be seen in FIG. 10A, Compound I-1 caused upregulation of protein levels of YAP1 in H929 cells and MM.1S cells.

Figure 12:
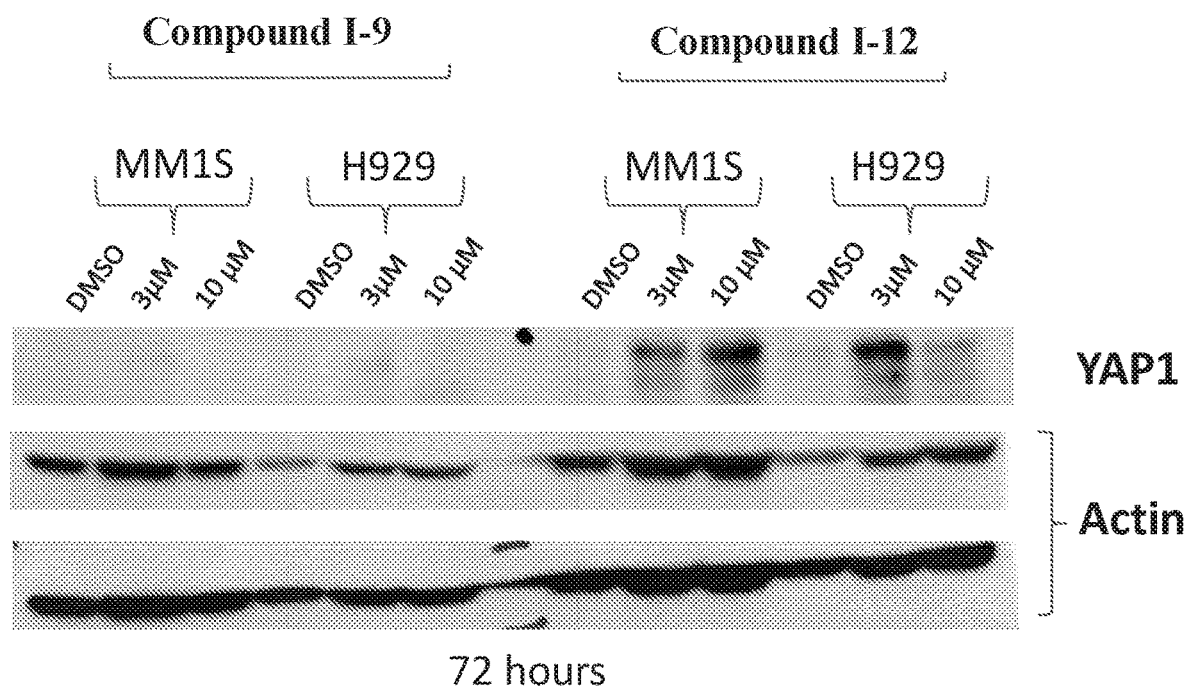
FIG. 12 is a Western blot showing the levels of YAP1 and Actin in untreated MM.1S and H929 cells and MM.1S and H929 cells after treatment with Compound I-9 or Compound I-12 for 72 hours.

In FIG. 12, H929 and MM. 1S cells were treated with Compound I-9, Compound I-12, or DMSO at 3 μM and 10 μM concentrations for 72 hours. Lysates were then obtained and immunoblot was performed using antibodies against YAP1 and Actin as loading control. As can be seen in FIG. 12, YAP1 levels for Compound I-9 were low at both concentrations, while Compound I-12 caused upregulation of protein levels of YAP1 in H929 cells and MM.1S cells.

Figure 13:
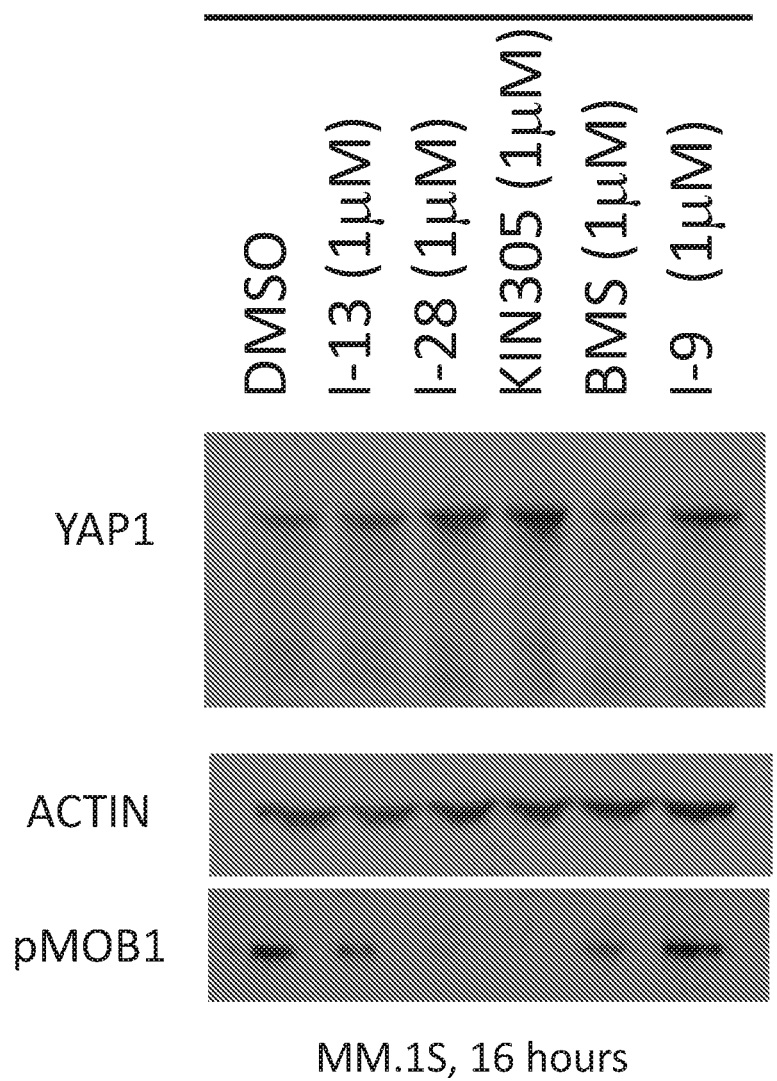
FIG. 13 is a Western blot showing the levels of YAP1, Actin, and pMOB1 in untreated MM.1S cells and MM.1S cells after treatment with Compound I-13, Compound I-28, KIN001-305, BMS536924, or Compound I-9 for 16 hours.
Figure 14A:
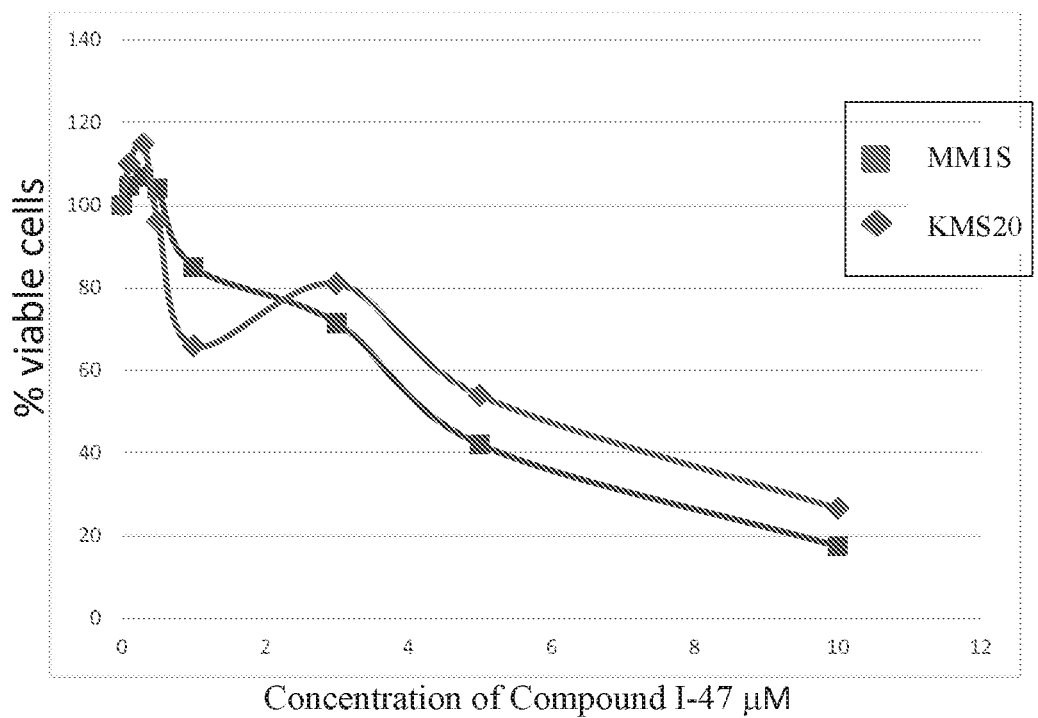
FIG. 14A is a graph showing the viability of MM.1 S and KMS20 cells when treated with Compound I-47.
Figure 14B:
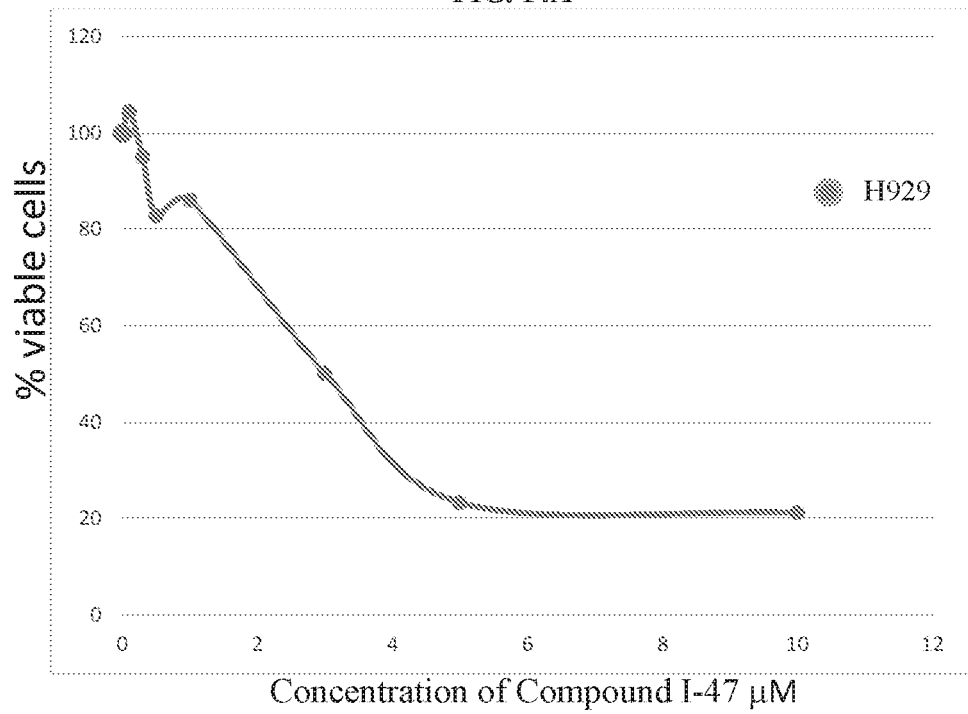
FIG. 14B is a graph showing the viability of H929 cells when treated with Compound I-47.
Figure 15A:
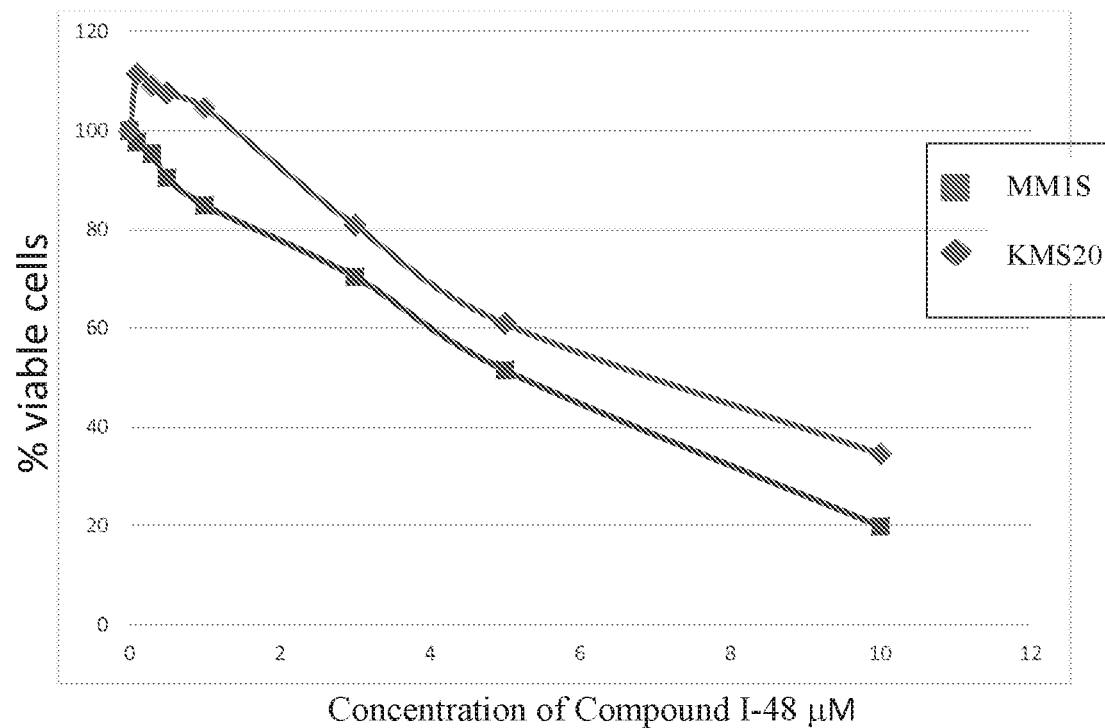
FIG. 15A is a graph showing the viability of MM.1S and KMS20 cells when treated with Compound I-48.
Figure 15B:
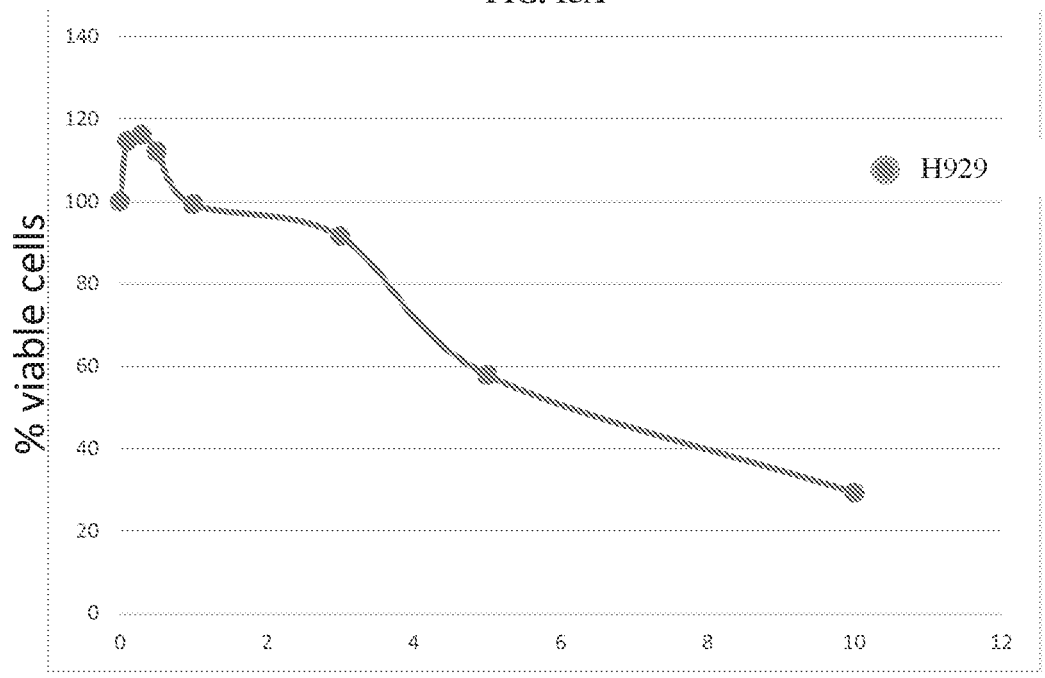
FIG. 15B is a graph showing the viability of H929 cells when treated with Compound I-48.
Figure 16A:
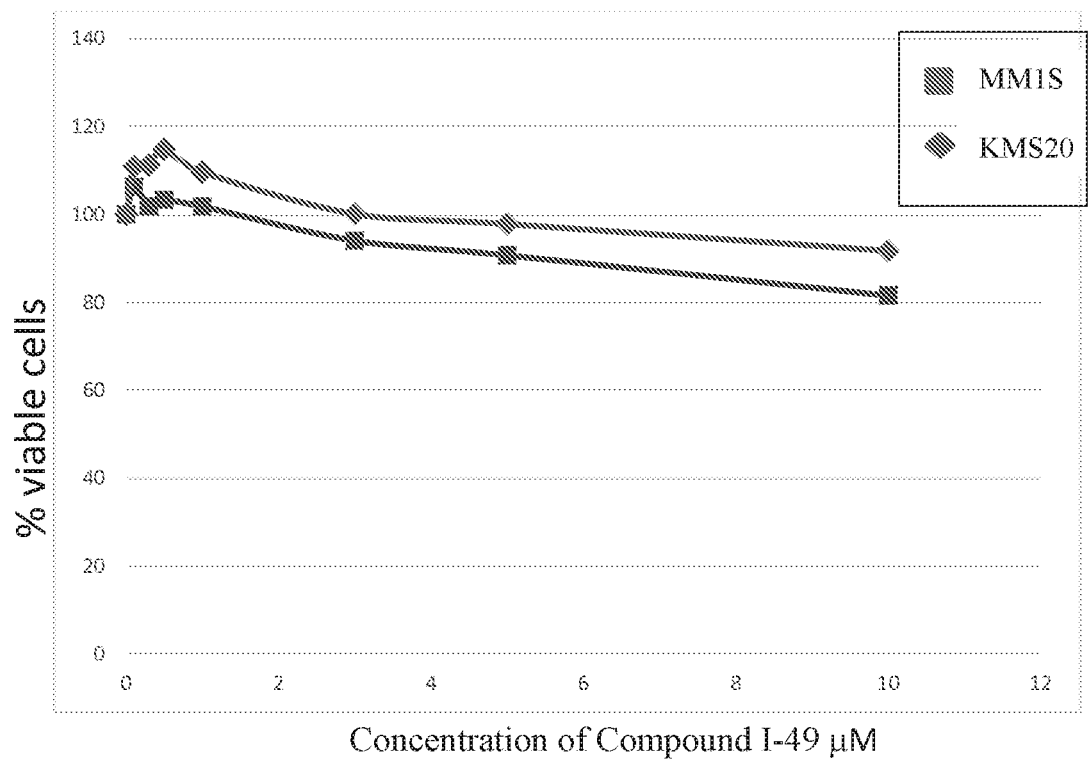
FIG. 16A is a graph showing the viability of MM.1S and KMS20 cells when treated with Compound I-49.
Figure 16B:
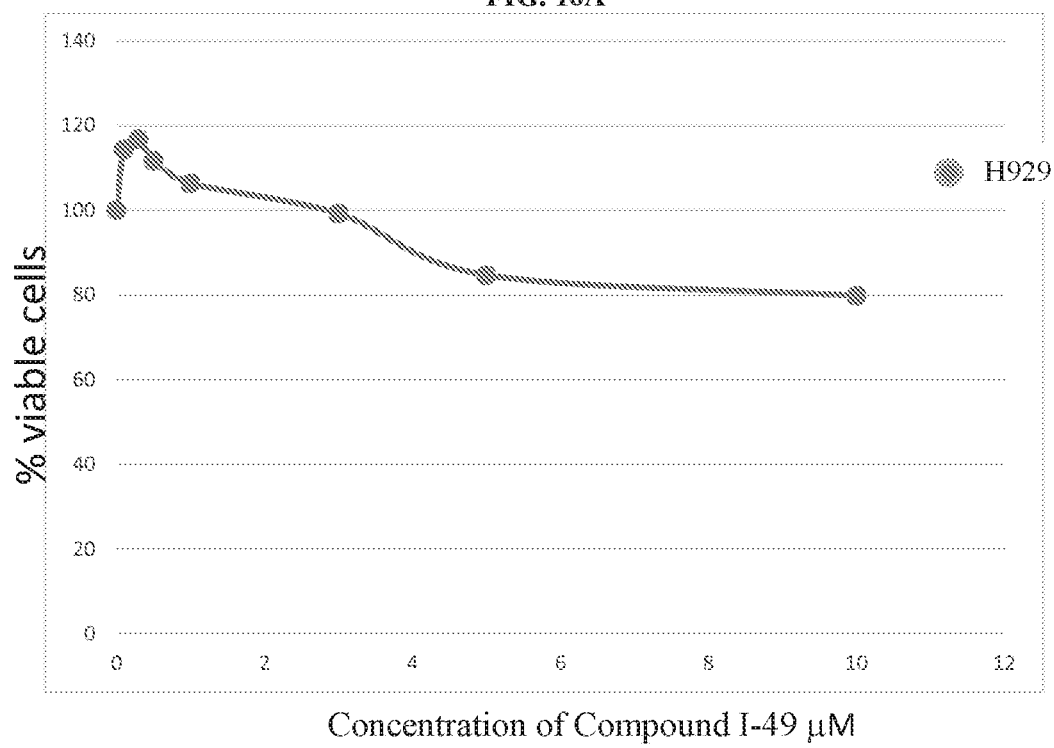
FIG. 16B is a graph showing the viability of H929 cells when treated with Compound I-49.
Figure 17A:
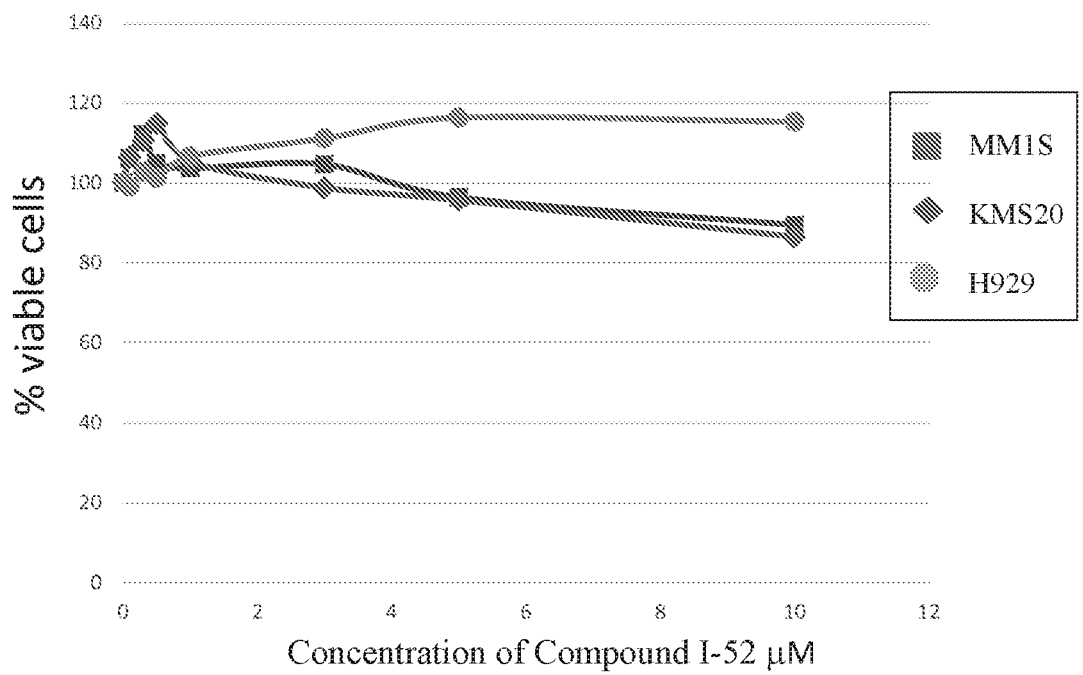
FIG. 17A is a graph showing the viability of MM.1S and KMS20 cells when treated with Compound I-52.
Figure 17B:
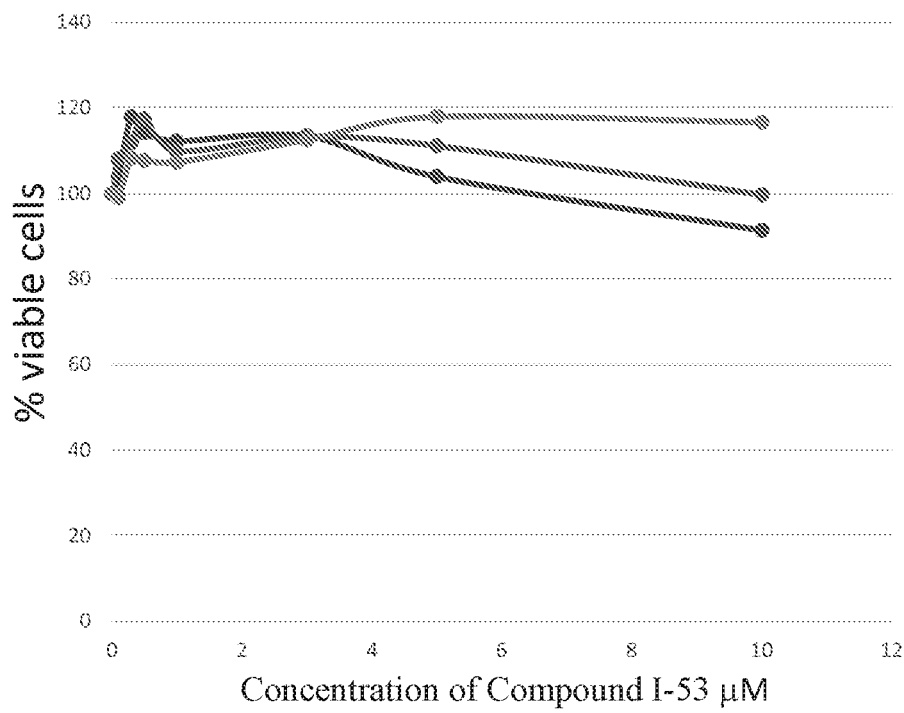
FIG. 17B is a graph showing the viability of H929 cells when treated with Compound I-52.
Figure 18A:
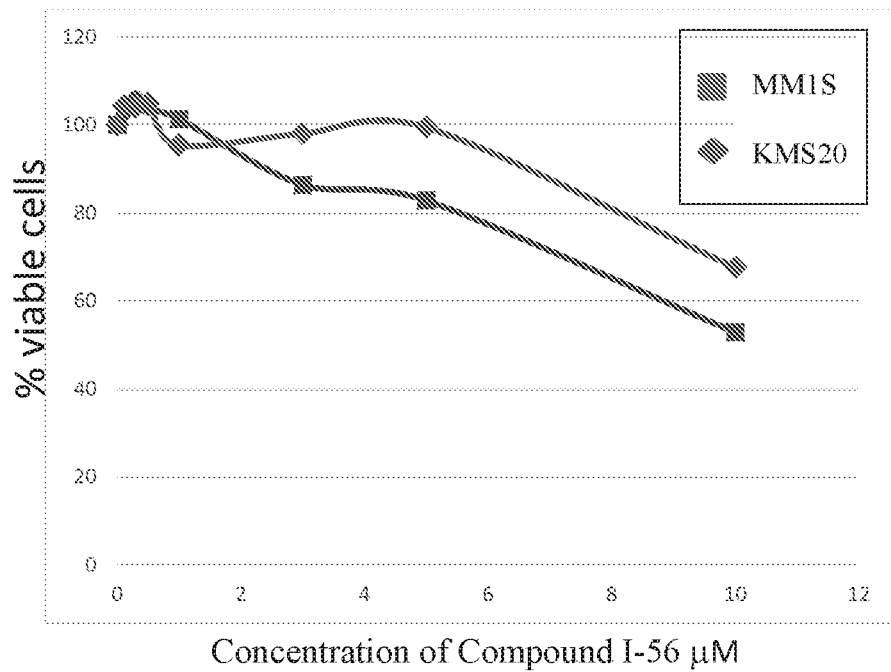
FIG. 18A is a graph showing the viability of MM.1S and KMS20 cells when treated with Compound I-56.
Figure 18B:
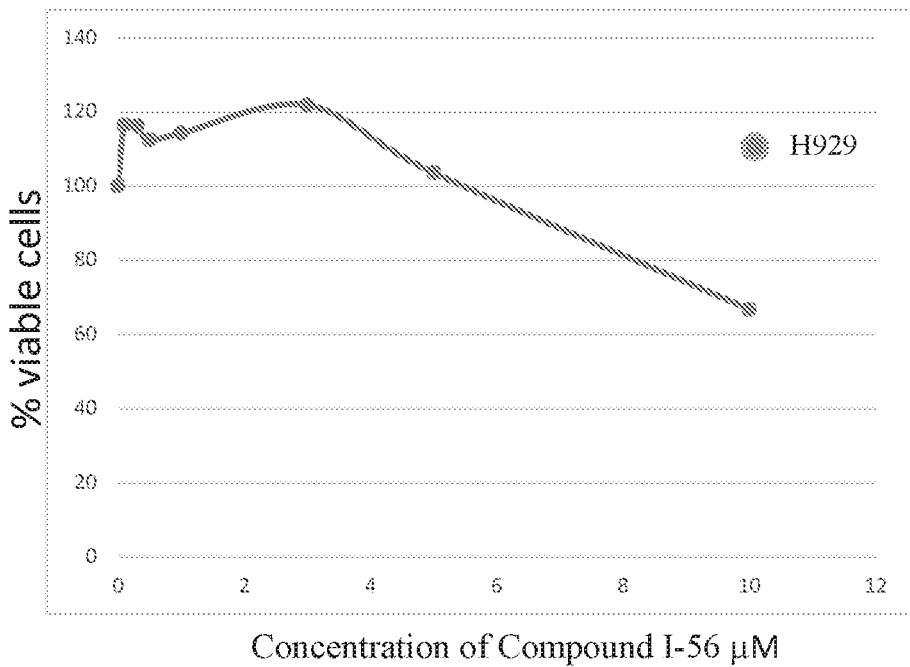
FIG. 18B is a graph showing the viability of H929 cells when treated with Compound I-56.
Figure 19A:
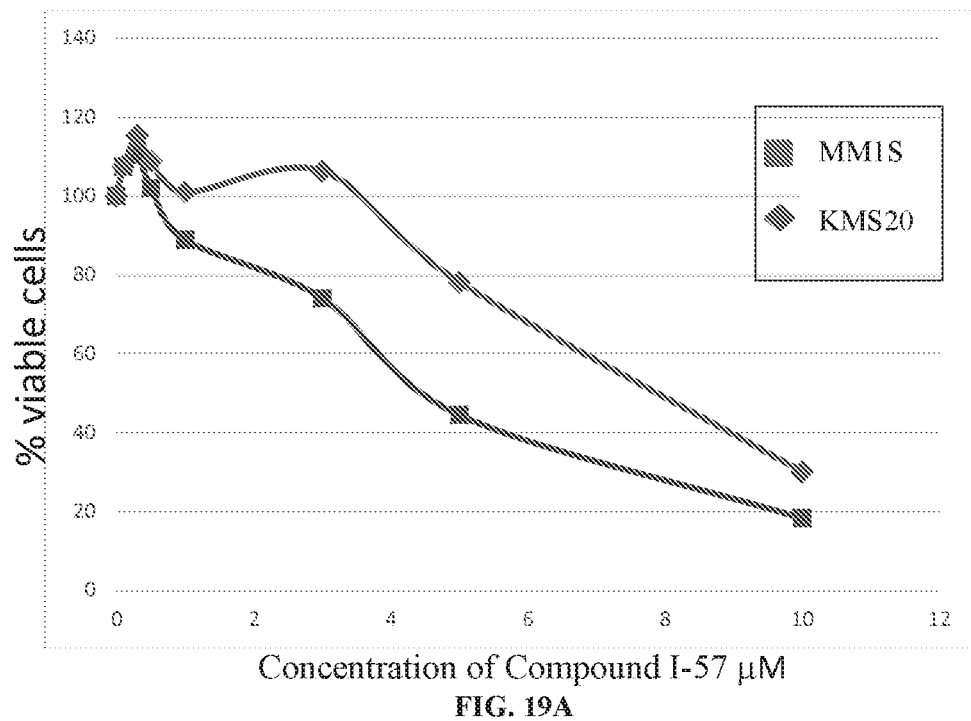
FIG. 19A is a graph showing the viability of MM.1S and KMS20 cells when treated with Compound I-57.
Figure 19B:
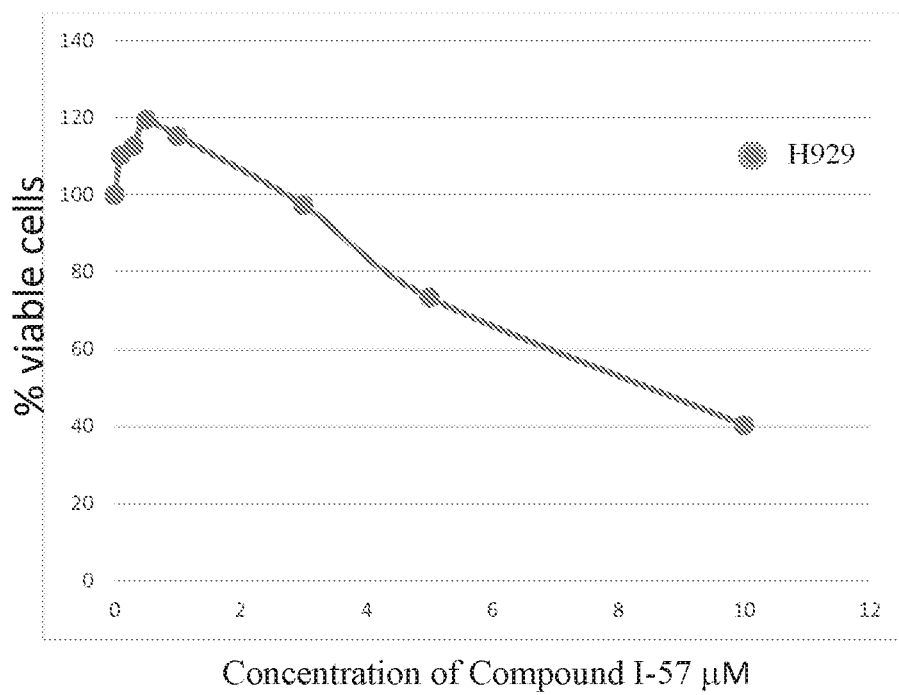
FIG. 19B is a graph showing the viability of H929 cells when treated with Compound I-57.
Figure 20A:
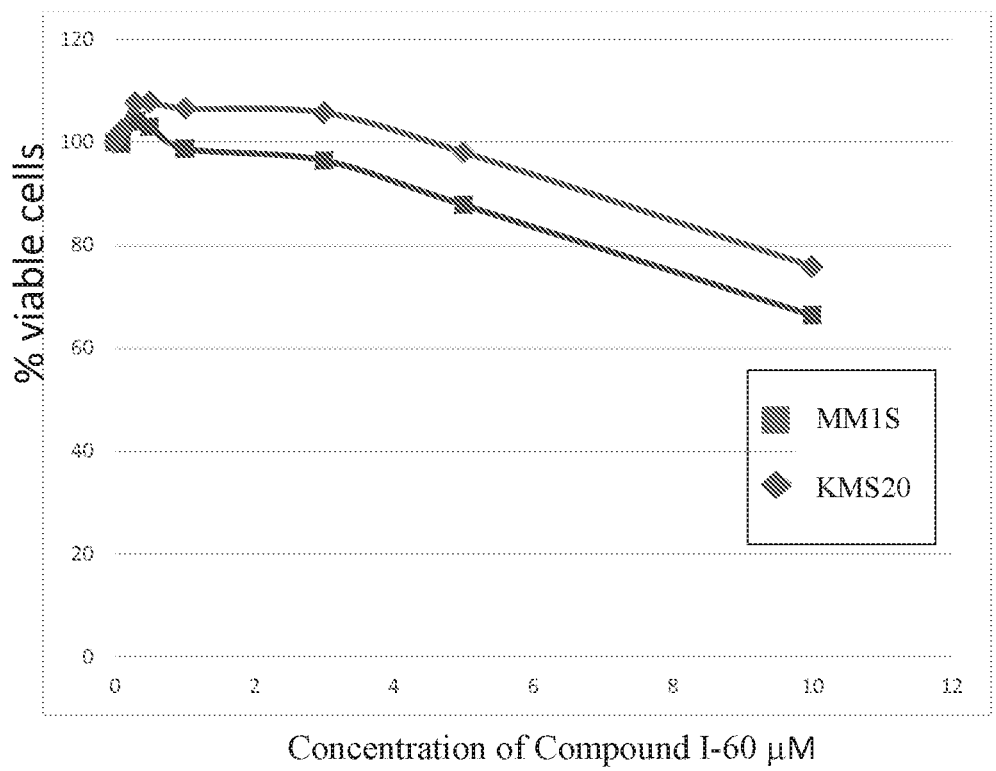
FIG. 20A is a graph showing the viability of MM.1S and KMS20 cells when treated with Compound I-60.
Figure 20B:
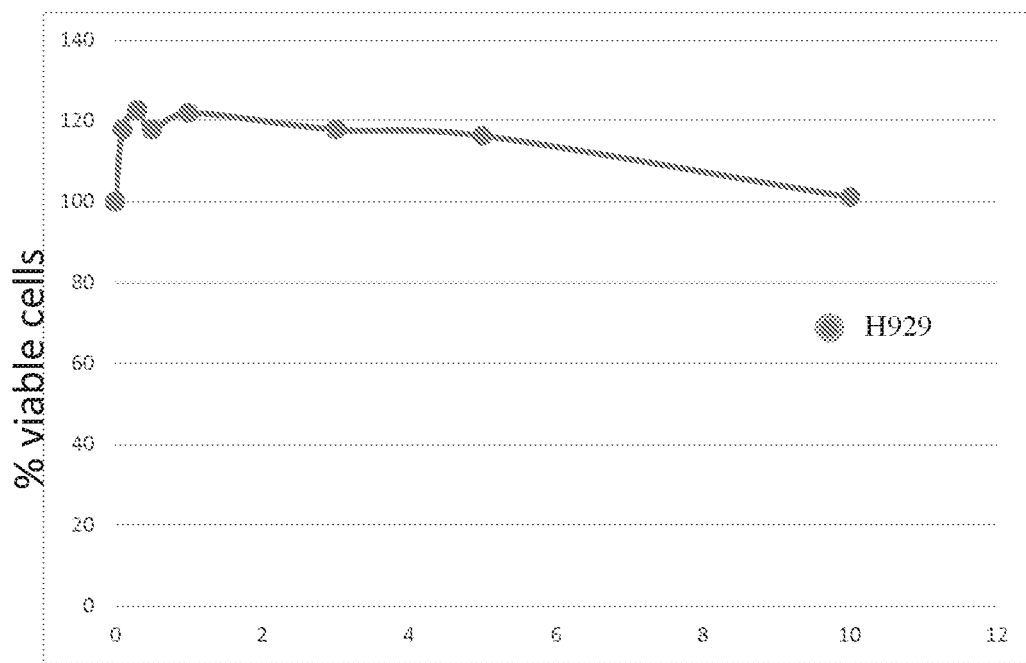
FIG. 20B is a graph showing the viability of H929 cells when treated with Compound I-60.
Figure 21:
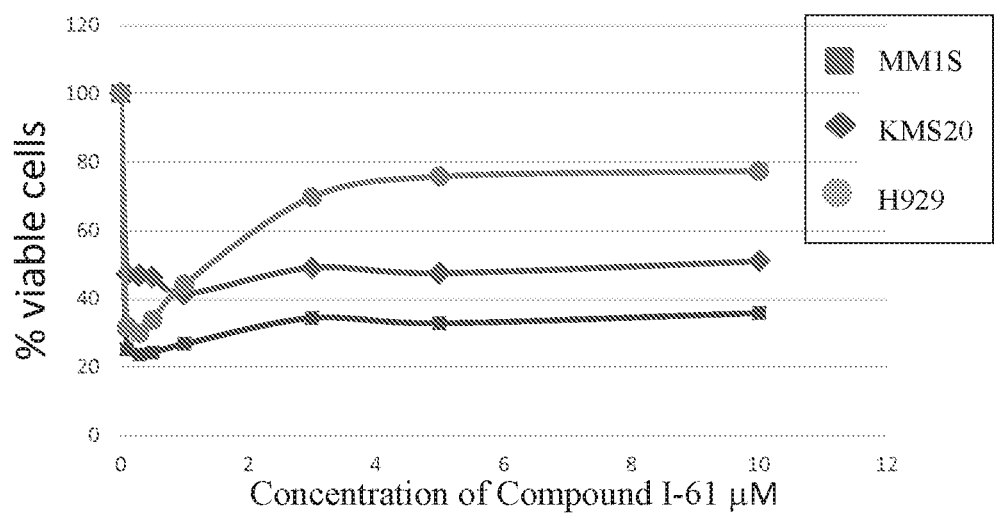
FIG. 21 is a graph showing the viability of MM.1S, KMS20, and H929 cells when treated with Compound I-61.
Figure 22A:
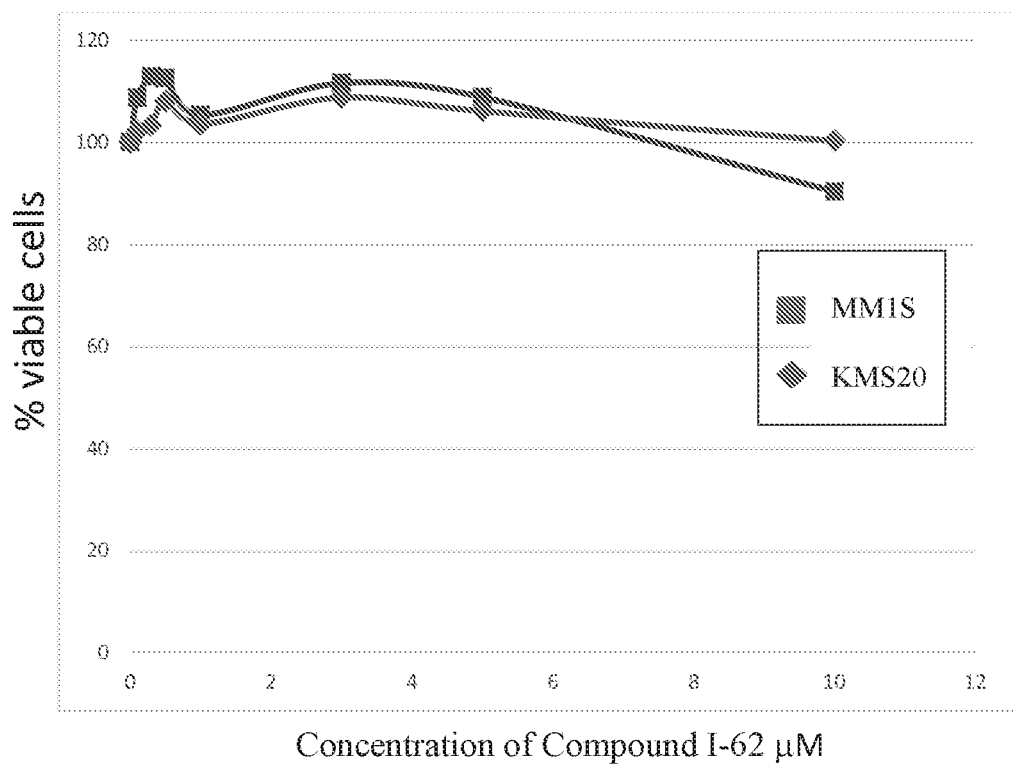
FIG. 22A is a graph showing the viability of MM.1S and KMS20 cells when treated with Compound I-62.
Figure 22B:
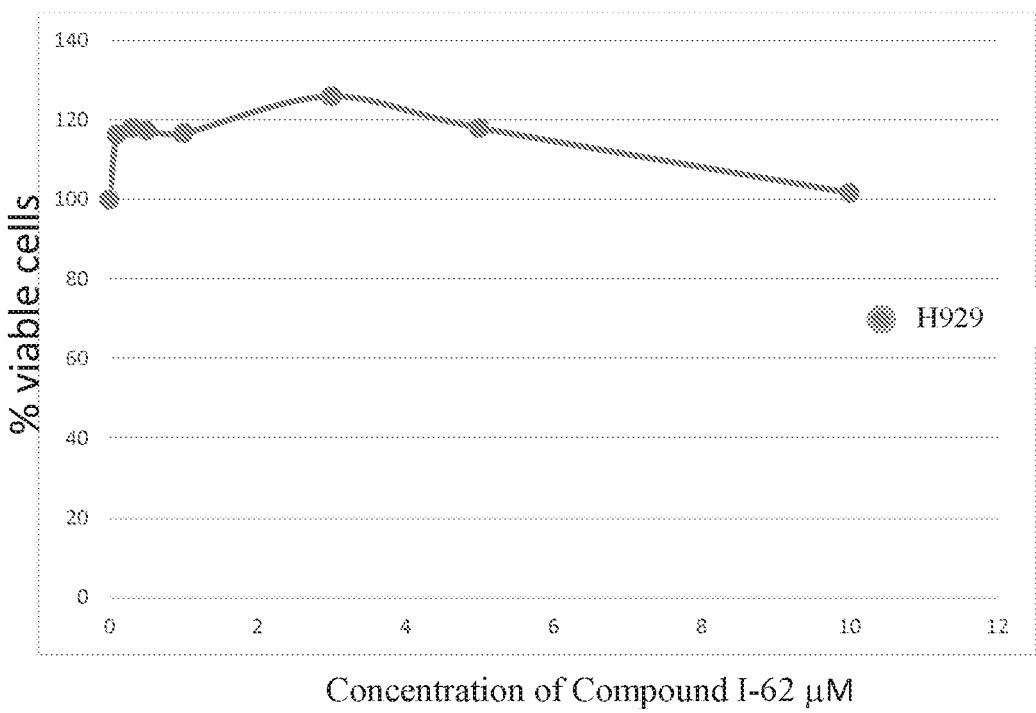
FIG. 22B is a graph showing the viability of H929 cells when treated with Compound I-62.
Figure 23A:
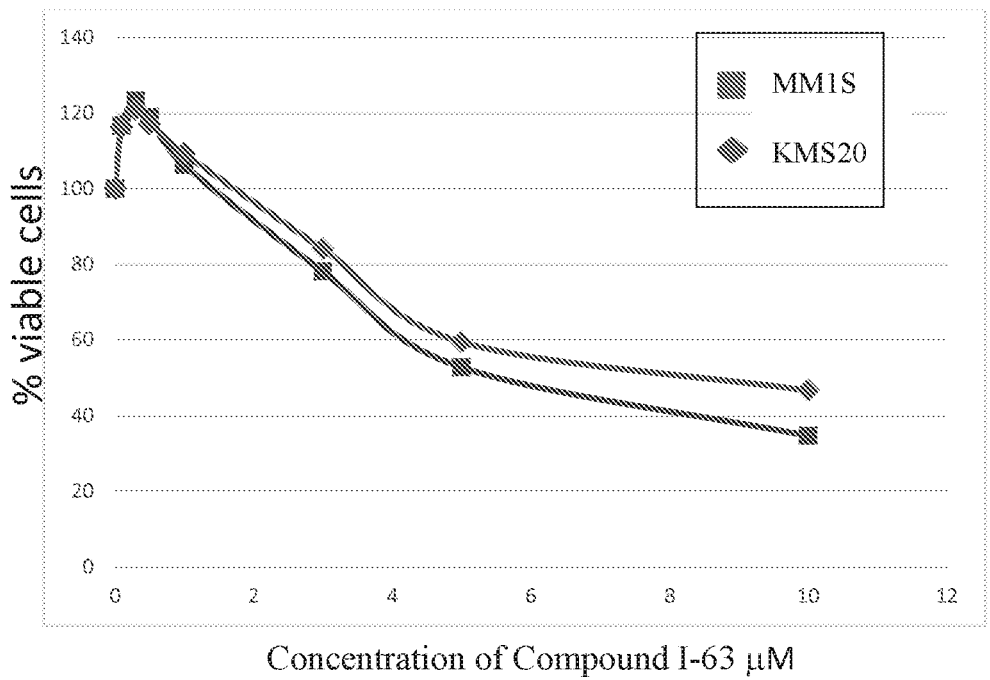
FIG. 23A is a graph showing the viability of MM.1S and KMS20 cells when treated with Compound I-63.
Figure 23B:
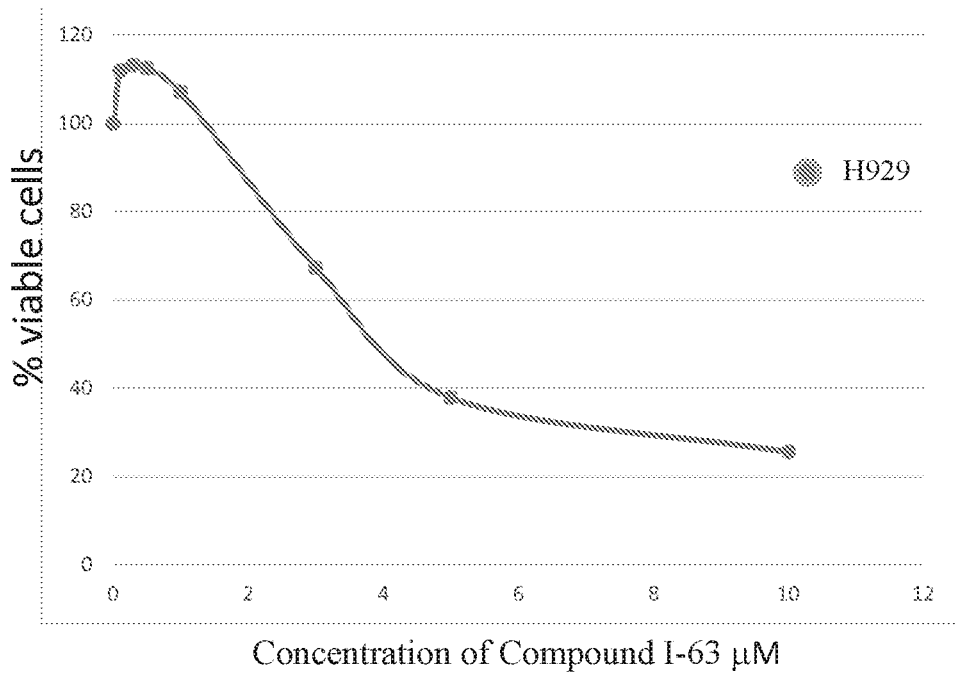
FIG. 23B is a graph showing the viability of H929 cells when treated with Compound I-63.
Figure 24A:
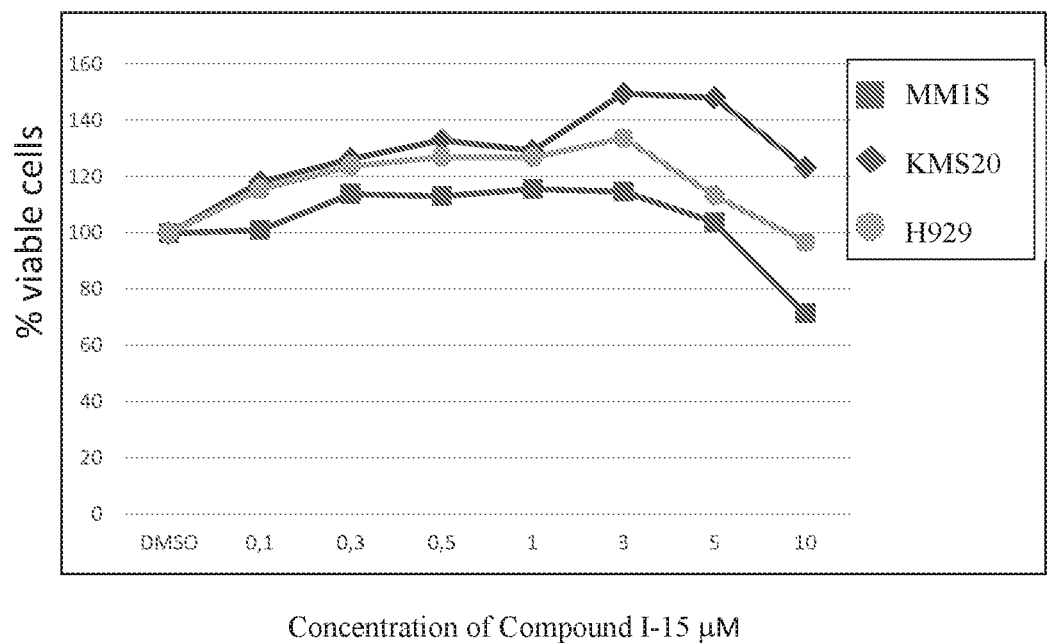
FIG. 24A is a graph showing the viability of MM.1S, KMS20, and H929 cells when treated with Compound I-15 for 72 hours.
Figure 24B:
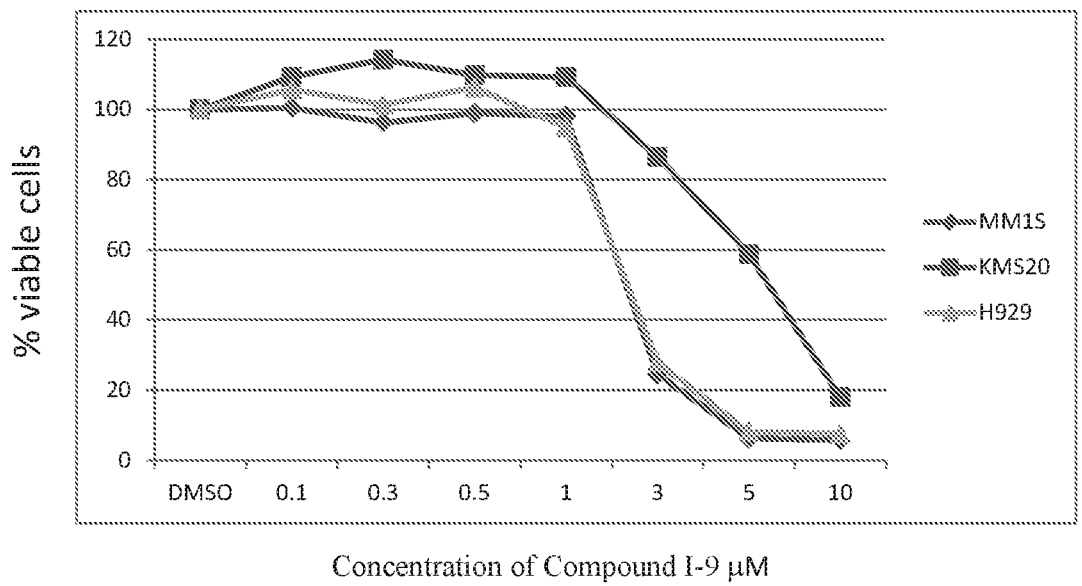
FIG. 24B is a graph showing the viability of MM.1S, KMS20, and H929 cells when treated with Compound I-9 for 72 hours.
Figure 24C:
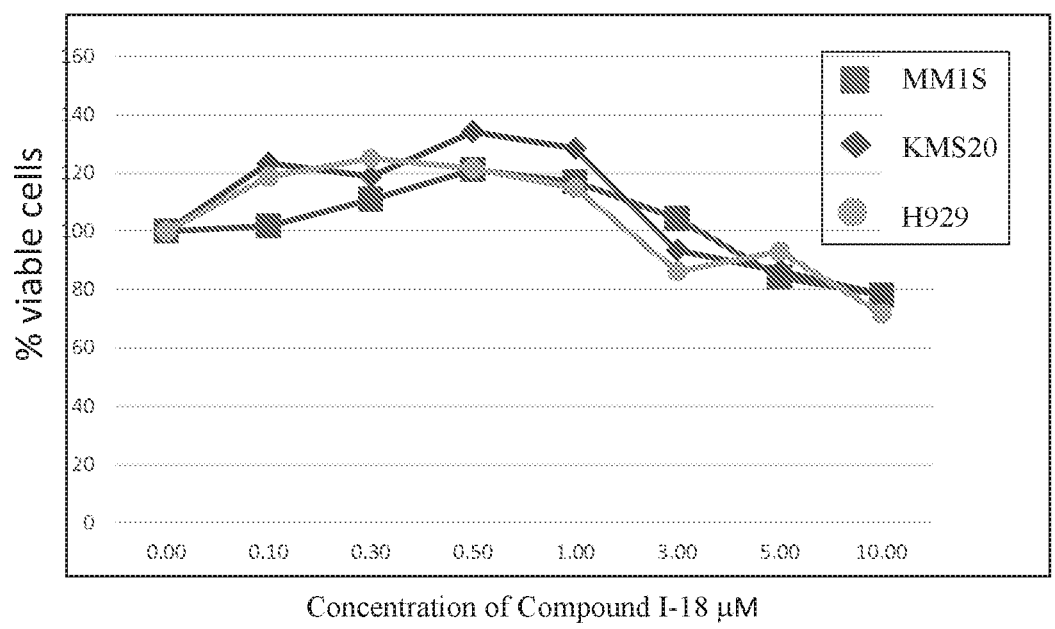
FIG. 24C is a graph showing the viability of MM.1S, KMS20, and H929 cells when treated with Compound I-18 for 72 hours.
Figure 25A:
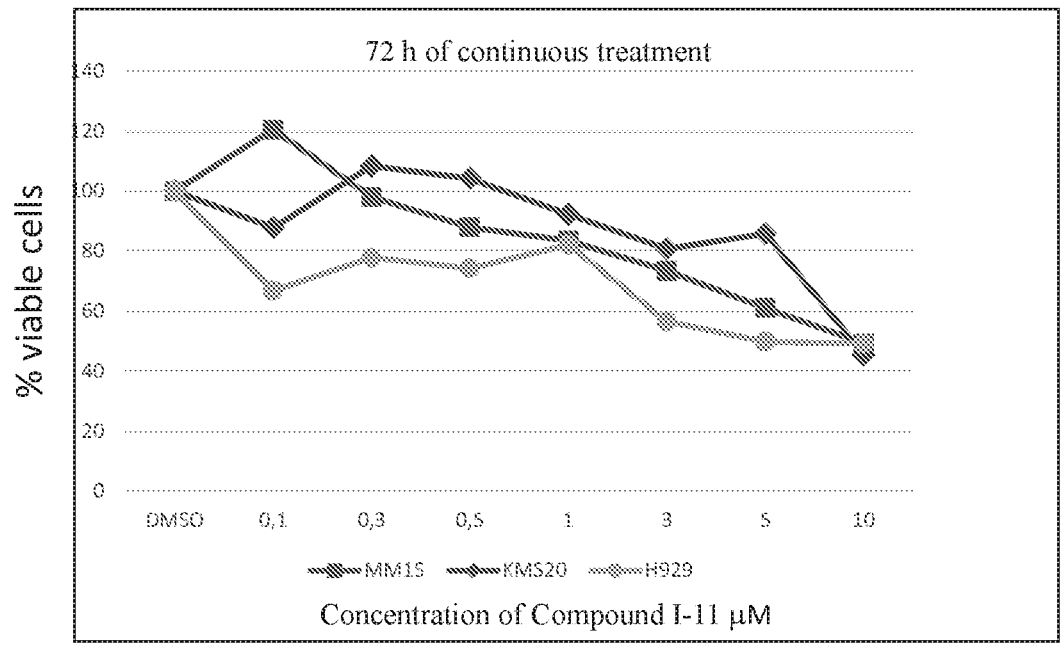
FIG. 25A-FIG. 25W are graphs showing the viability of MM.1S, KMS20, and H929 cells when treated with Compound I-11 (FIG. 25A), Compound I-13 (FIG. 25B), Compound I-14 (FIG. 25C), Compound I-16 (FIG. 25D), Compound I-15 (FIG. 25E), Compound I-18 (FIG. 25F), Compound I-19 (FIG. 25G), Compound I-20 (FIG. 25H), Compound I-21 (FIG. 25I), Compound I-5 (FIG. 25J), Compound I-6 (FIG. 25K), Compound I-8 (FIG. 25L), Compound I-39 (FIG. 25M), Compound I-6 (FIG. 25N), Compound I-31 (FIG. 25O), Compound I-30 (FIG. 25P), Compound I-22 (FIG. 25Q), Compound I-27 (FIG. 25R), Compound I-1 (FIG. 25S), Compound I-23 (FIG. 25T), Compound I-13 (FIG. 25U), Compound I-28 (FIG. 25V), and Compound I-9 (FIG. 25W), for 72 hours.
Figure 25B:
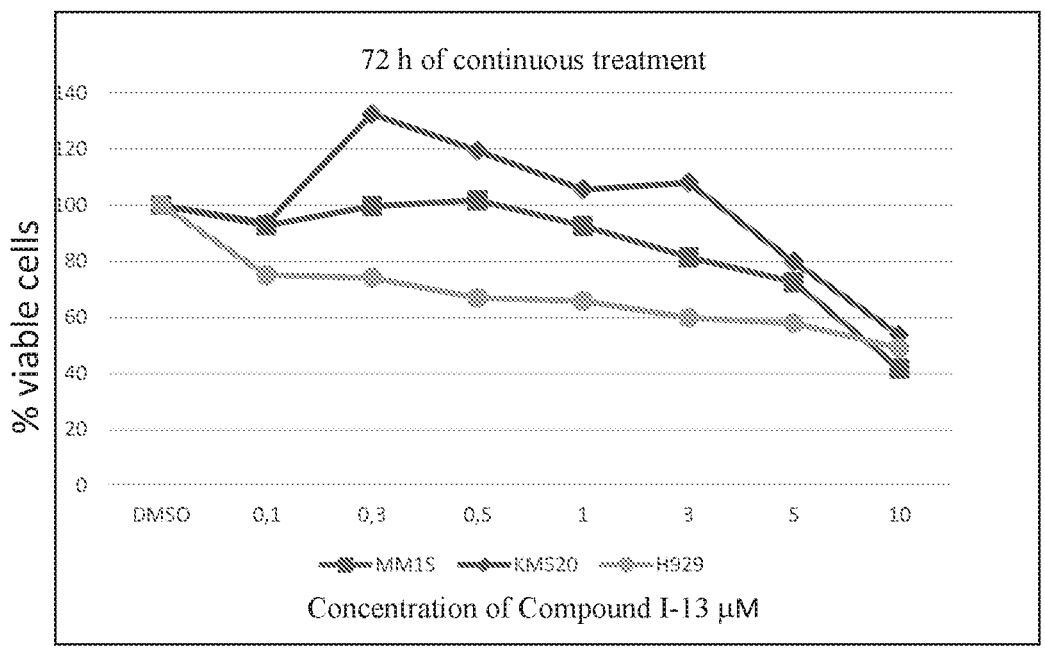
Figure 25C:
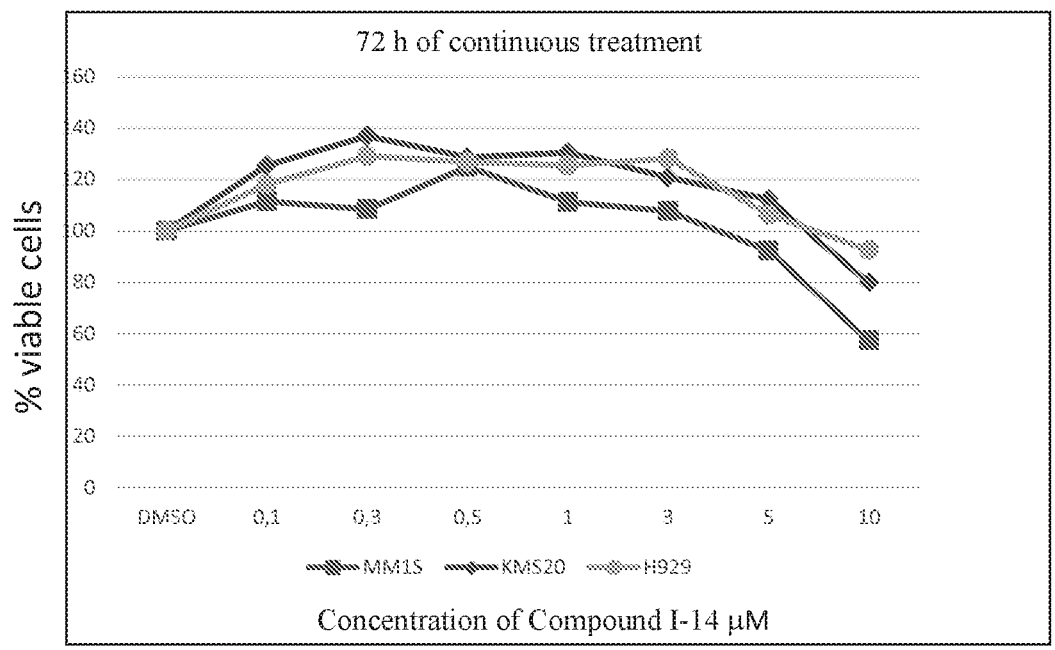
Figure 25D:
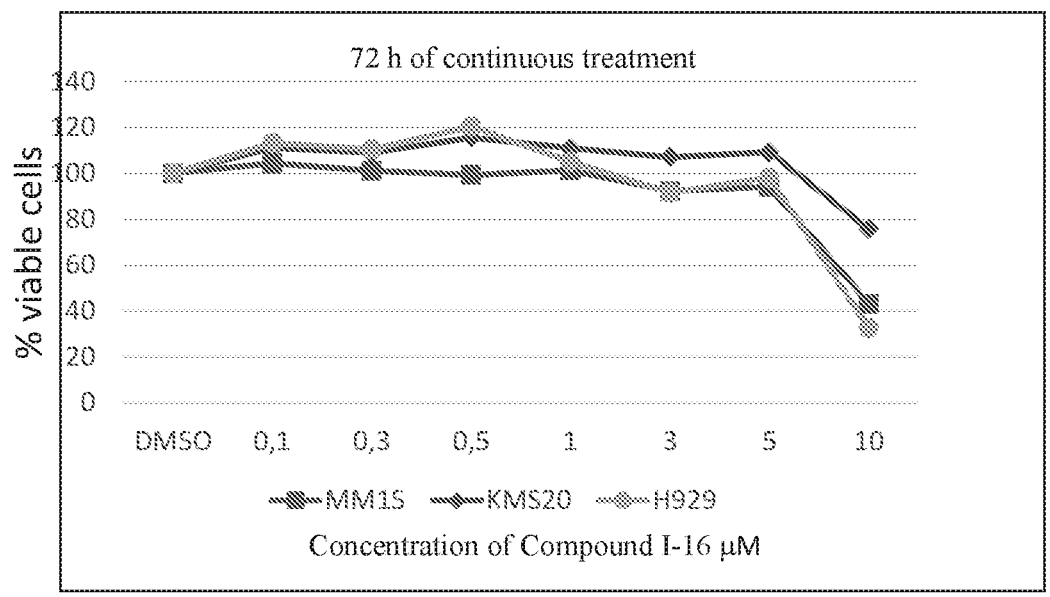
Figure 25E:
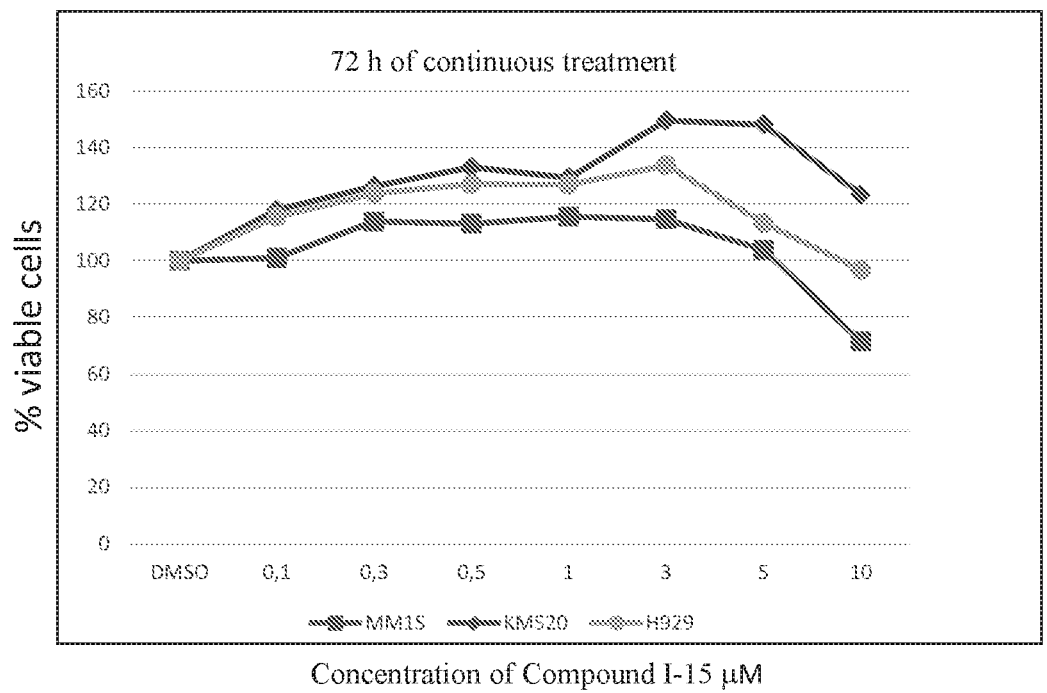
Figure 25F:
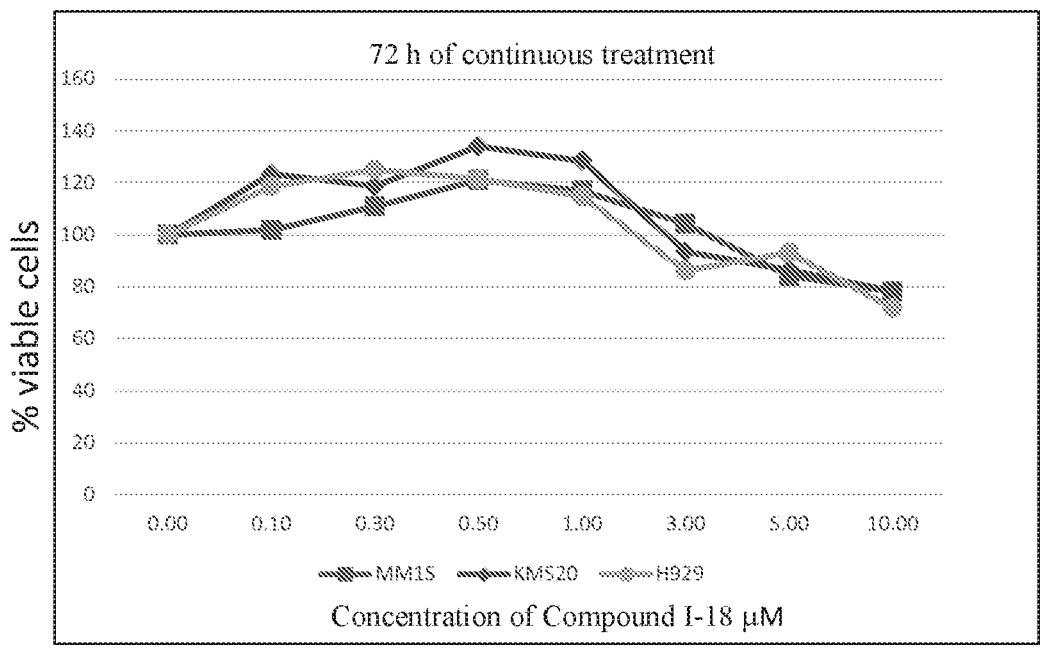
Figure 25G:
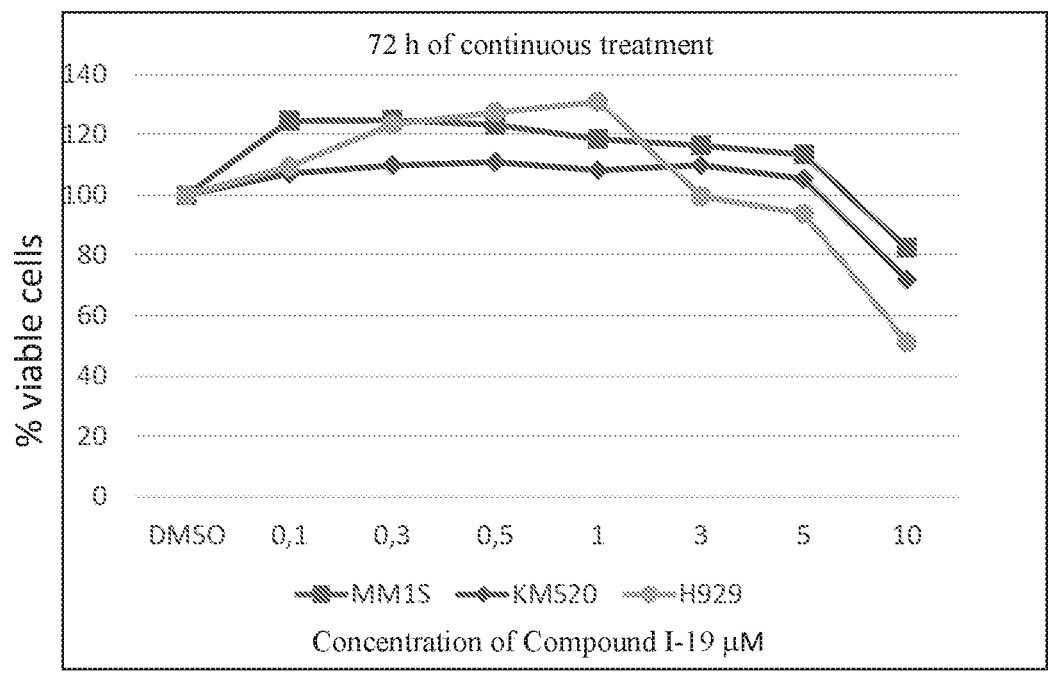
Figure 25H:
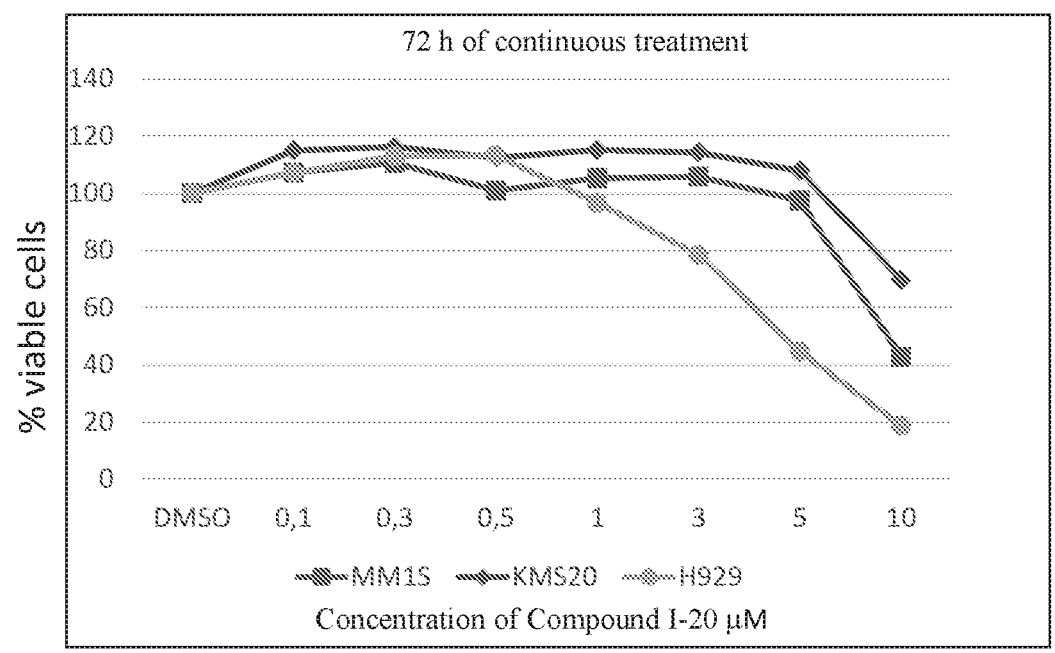
Figure 25I:
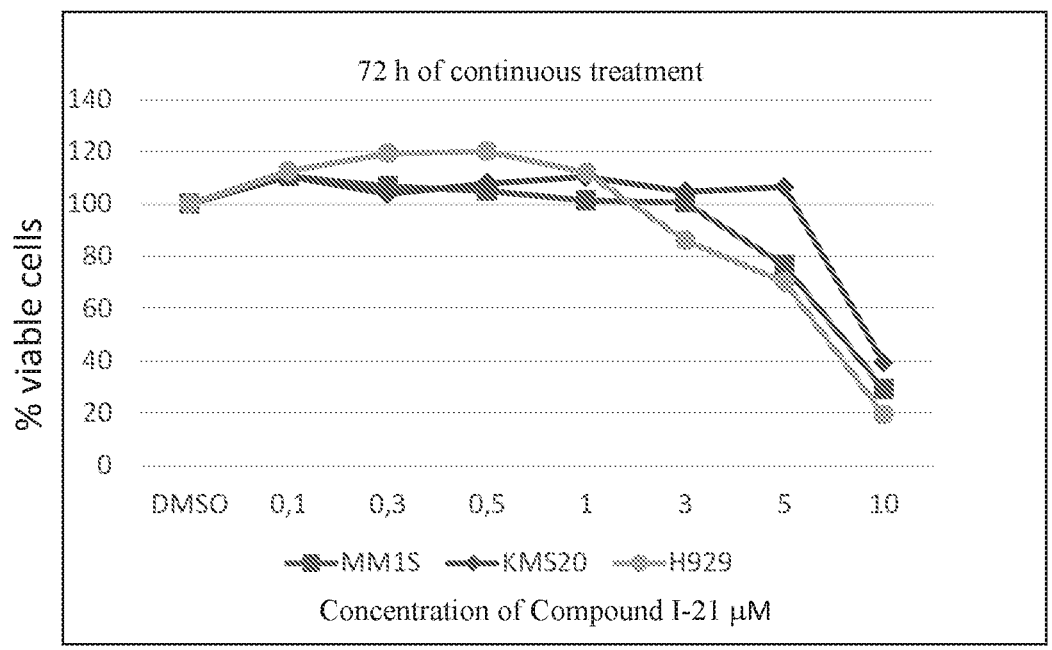
Figure 25J:
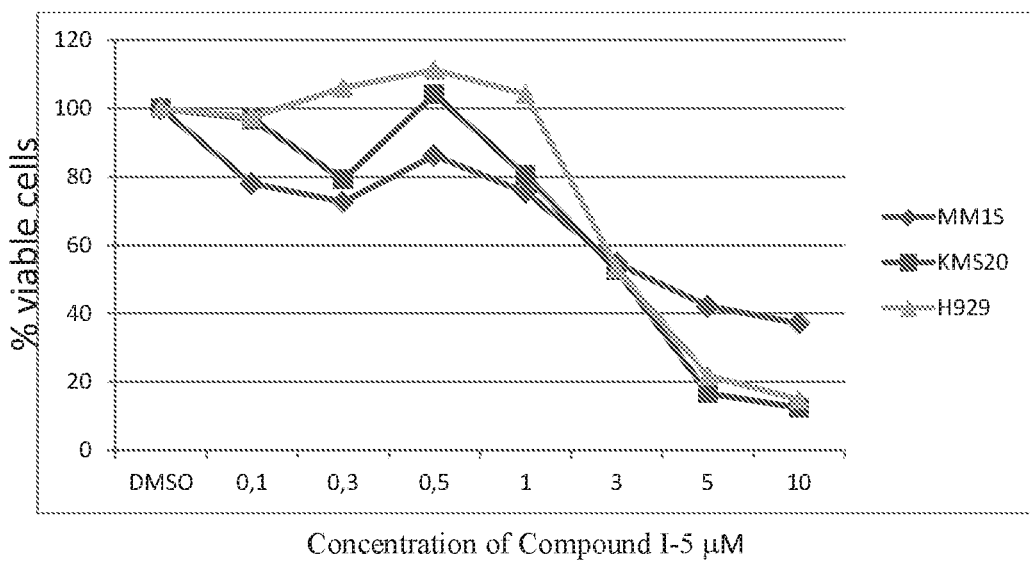
Figure 25K:
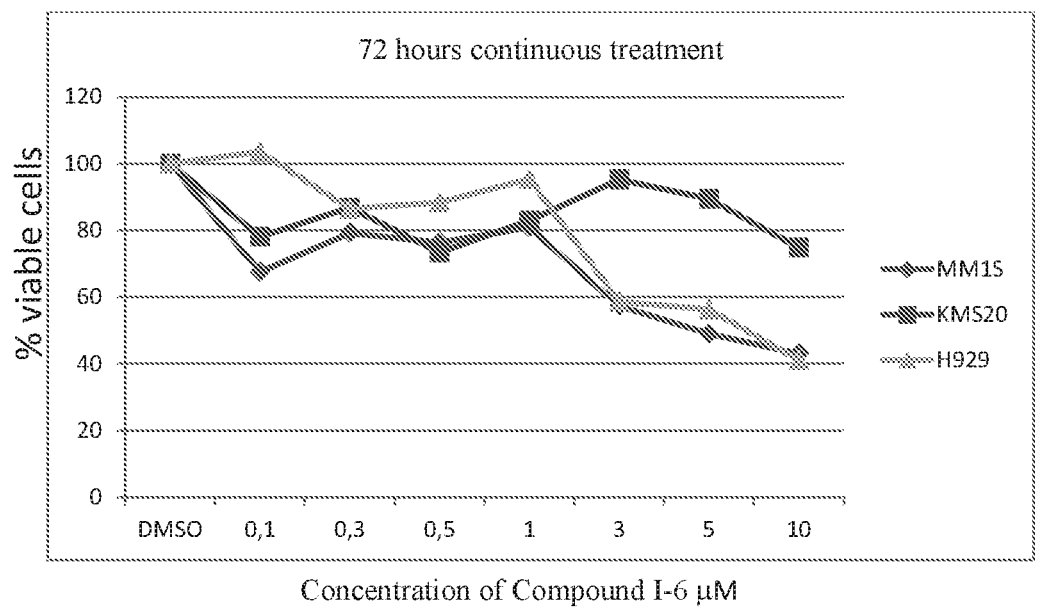
Figure 25L:
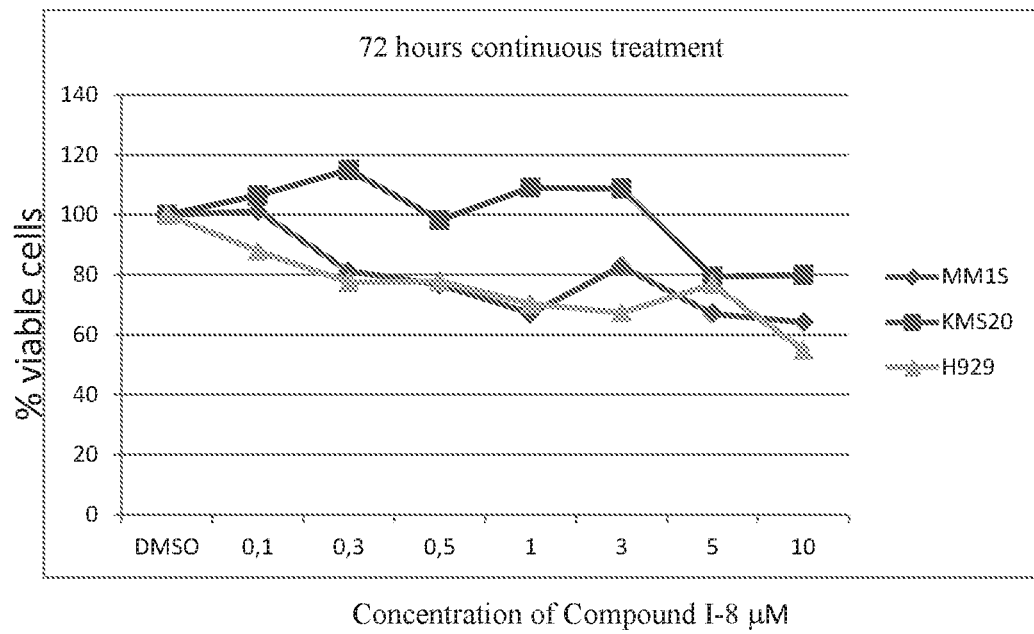
Figure 25M:
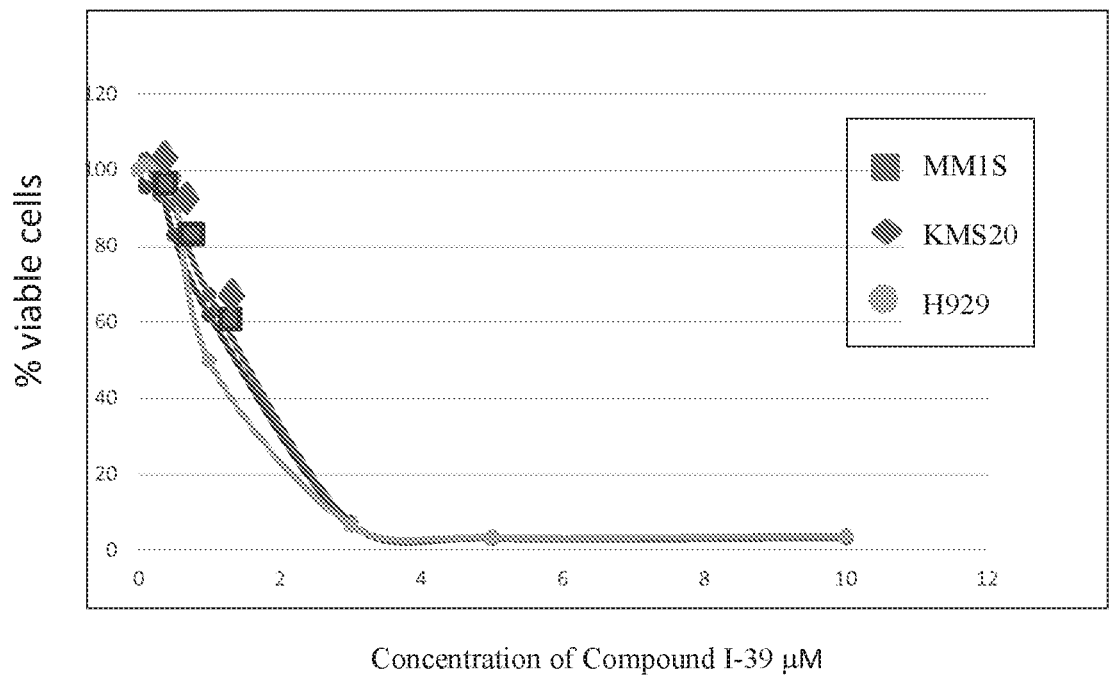
Figure 25N:
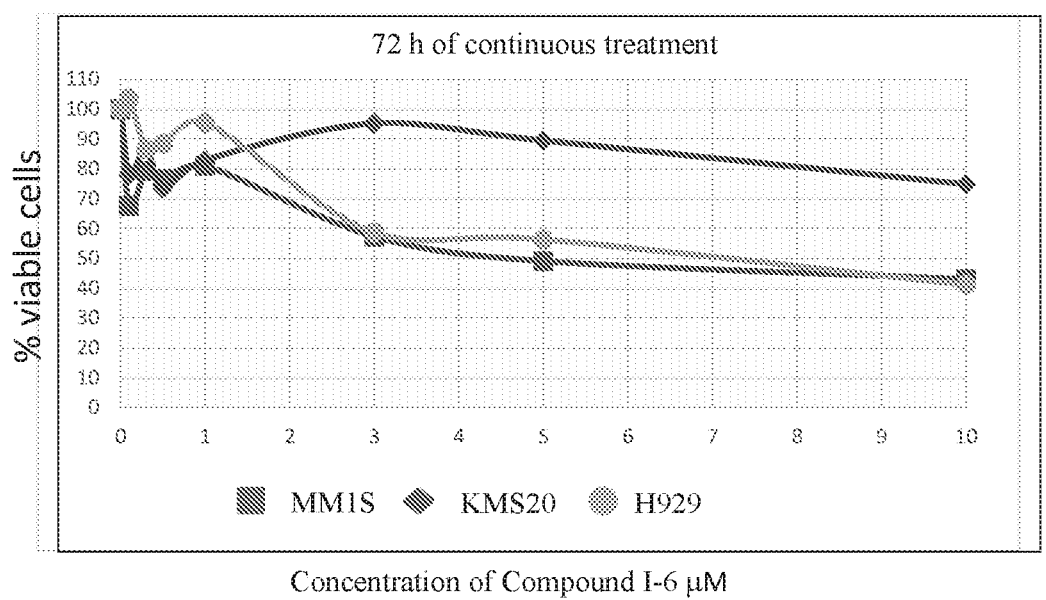
Figure 25O:
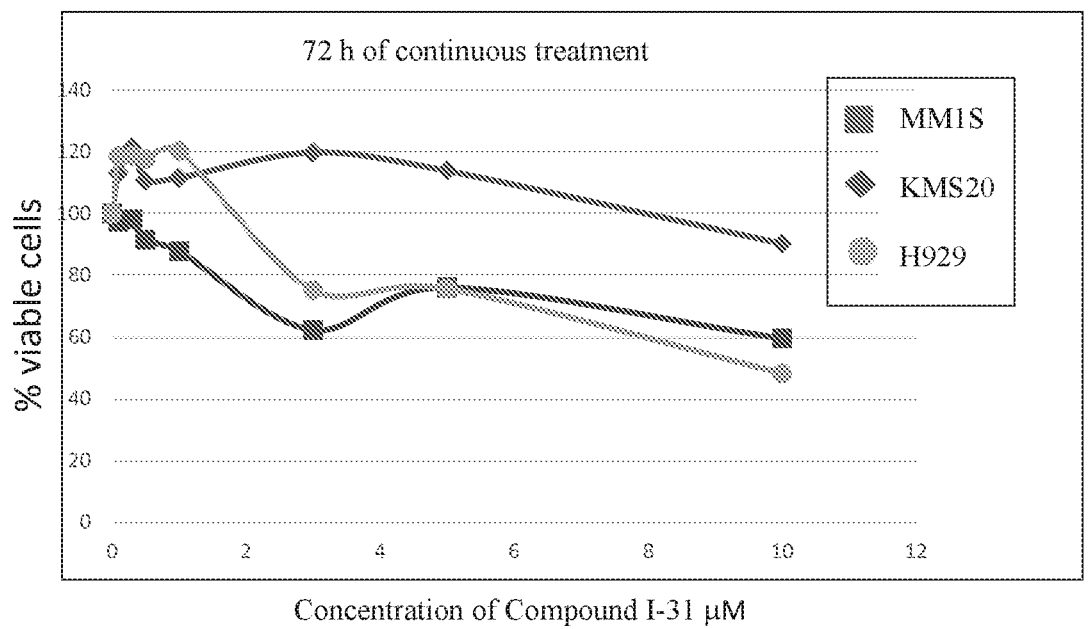
Figure 25P:
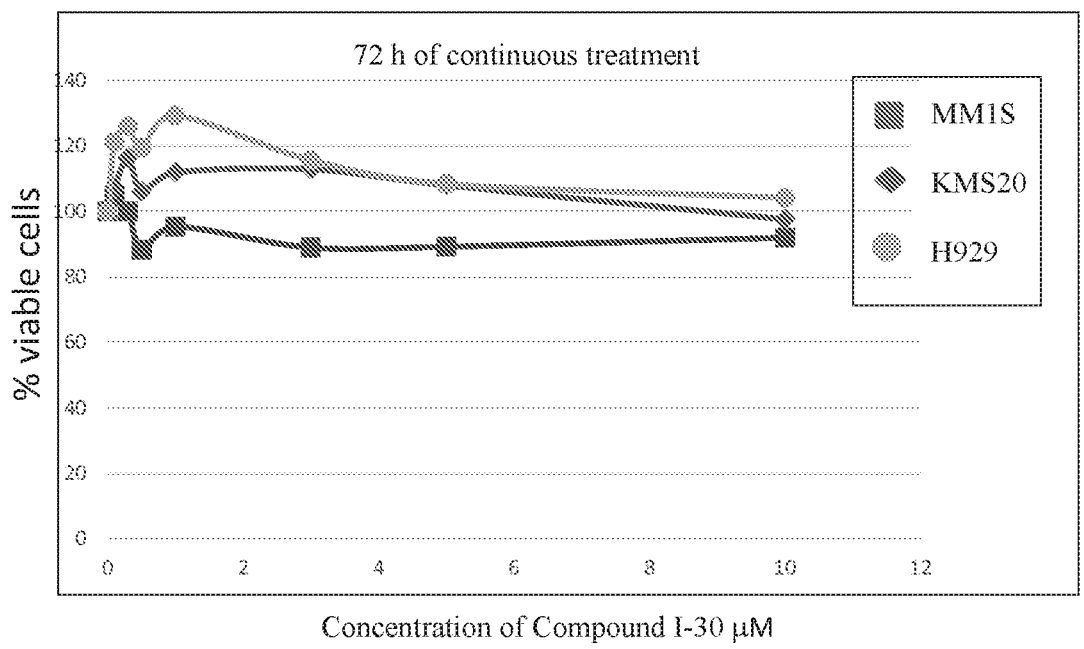
Figure 25Q:
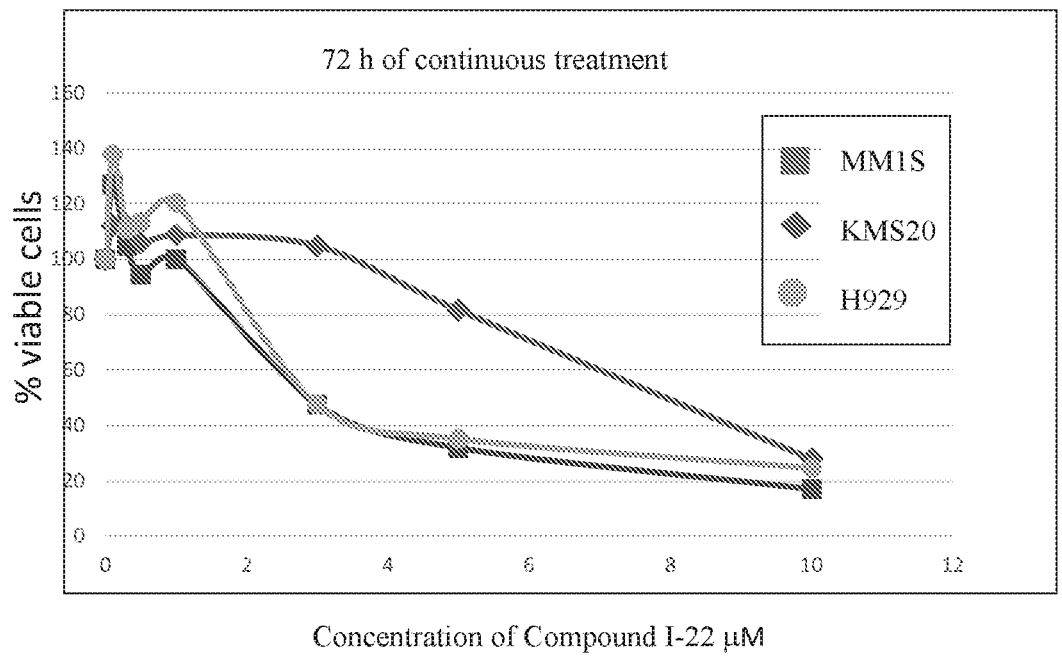
Figure 25R:
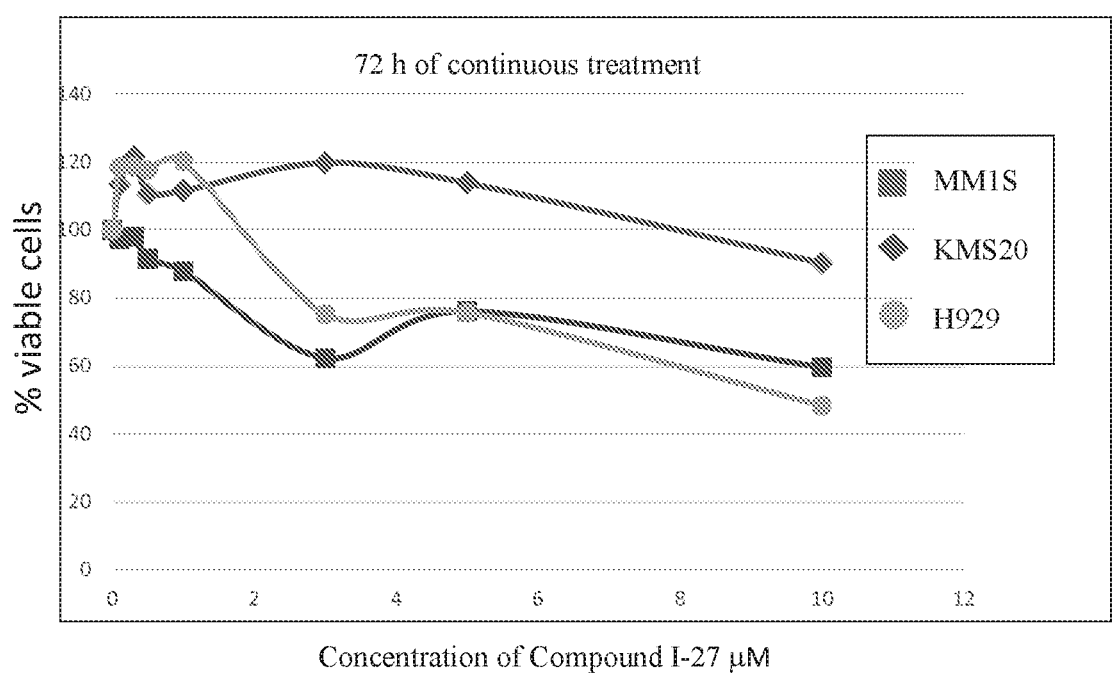
Figure 25S:
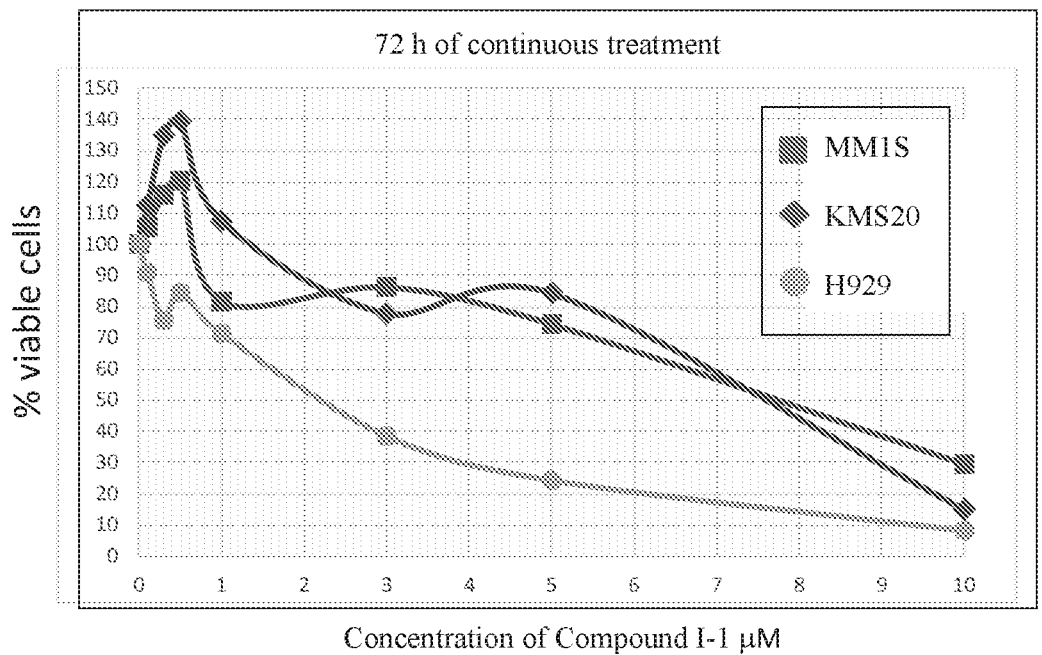
Figure 25T:
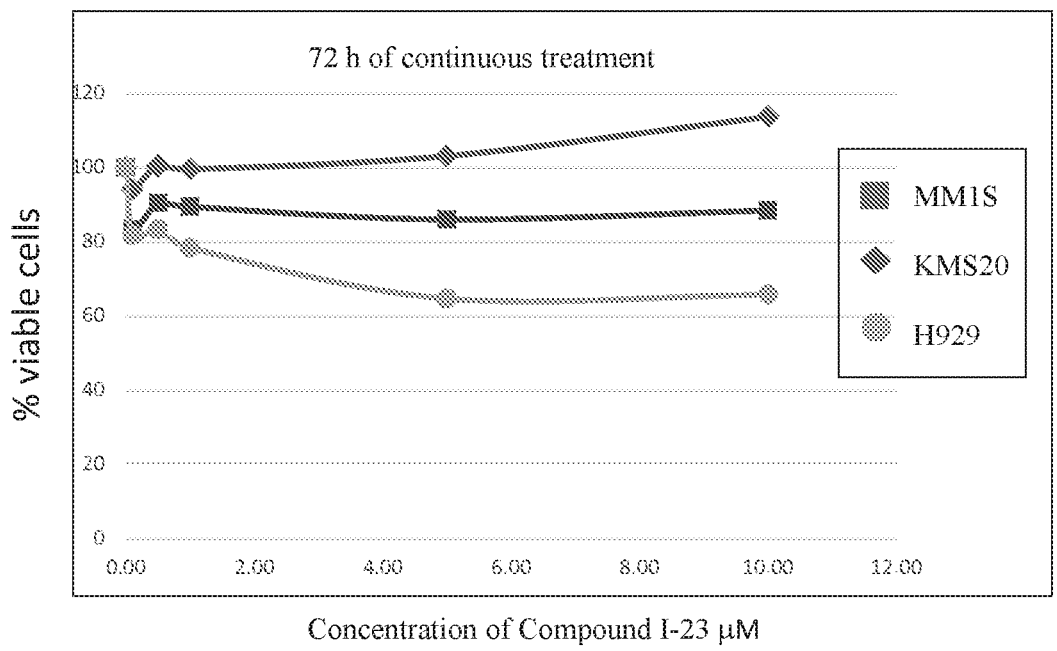
Figure 25U:
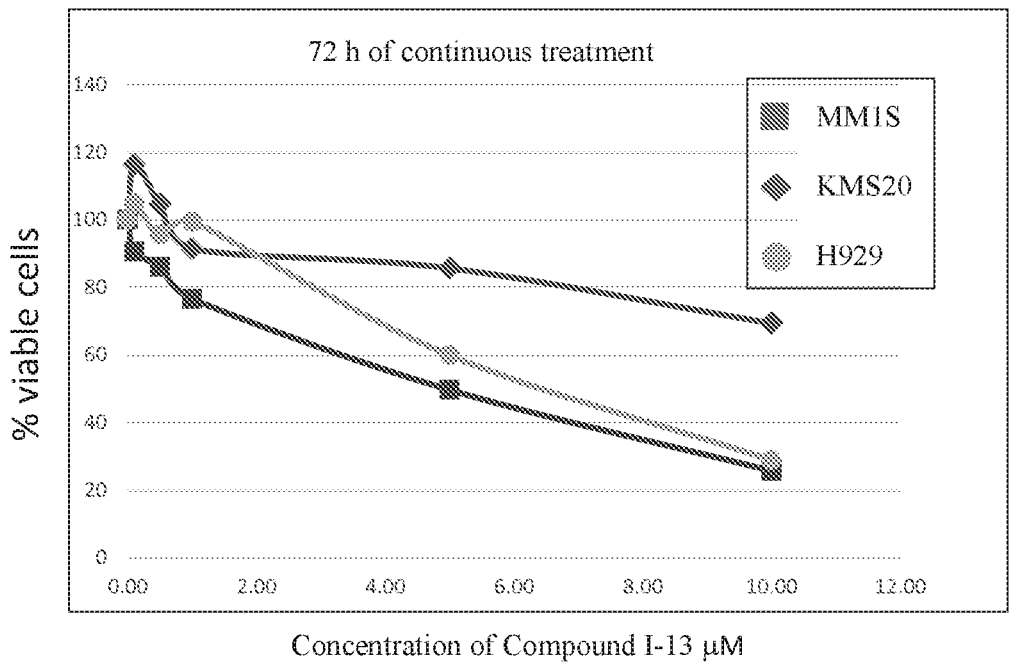
Figure 25V:
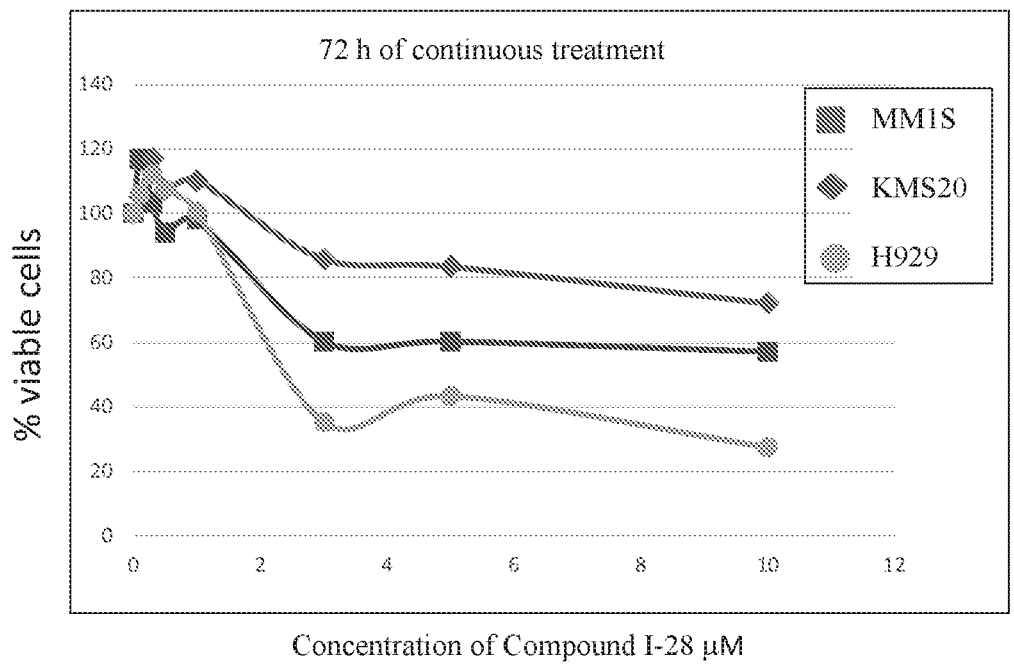
Figure 25W:
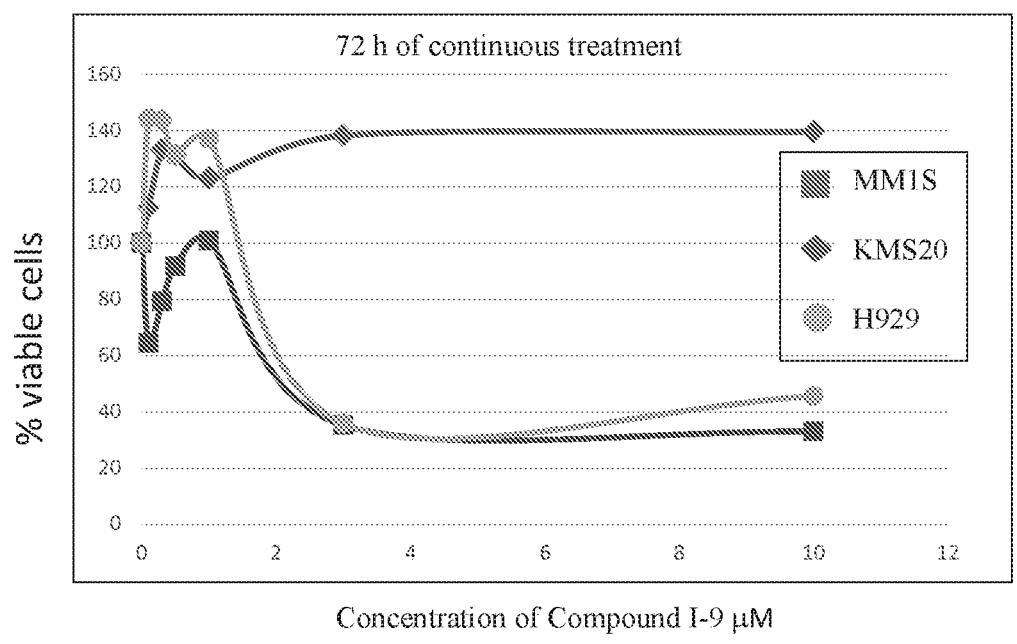
Figure 26A:
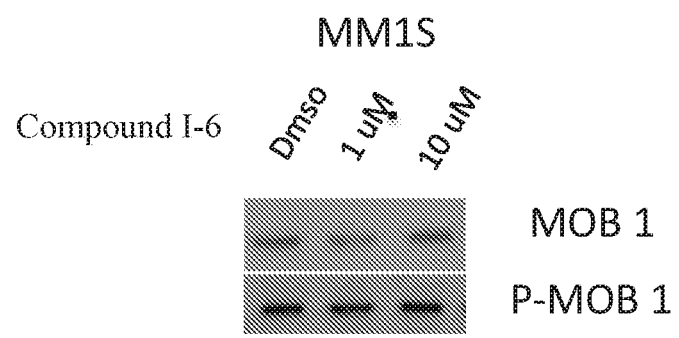
FIG. 26A-FIG. 26J are Western blots showing the levels of MOB1 and P-MOB 1 in untreated MM.1S cells and cells after treatment with Compound I-6 (FIG. 26A), Compound I-31 (FIG. 26B), Compound I-30 (FIG. 26C), Compound I-22 (FIG. 26D), Compound I-27 (FIG. 26E), Compound I-1 (FIG. 26F), Compound I-23 (FIG. 26G), Compound I-13 (FIG. 26H), Compound I-28 (FIG. 26I), and Compound I-9 (FIG. 26J) for 6 hours.
Figure 26B:
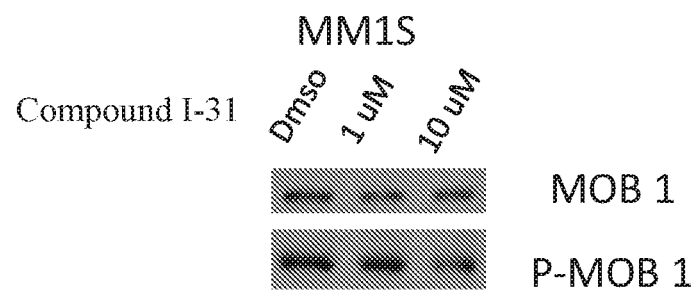
Figure 26C:
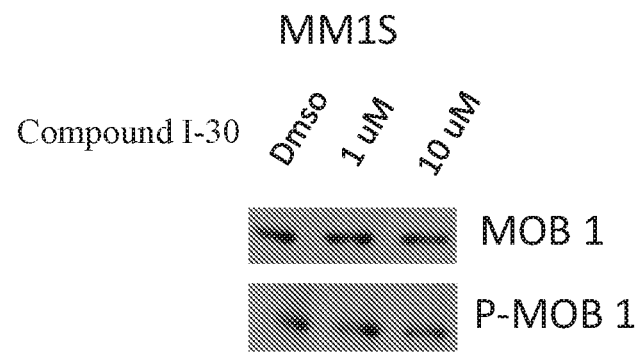
Figure 26D:
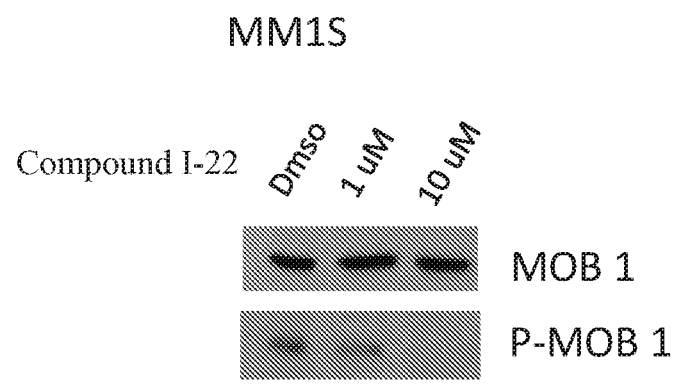
Figure 26E:
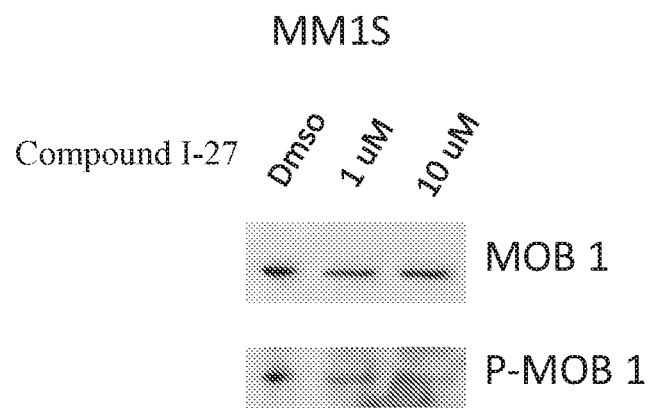
Figure 26F:
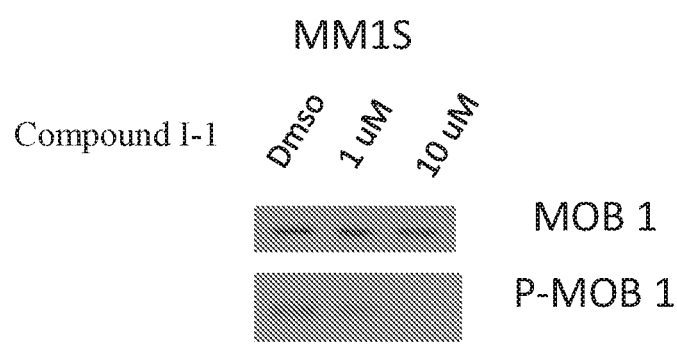
Figure 26G:
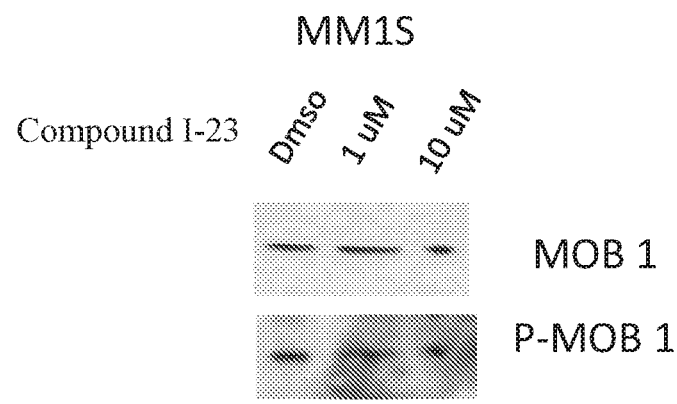
Figure 26H:
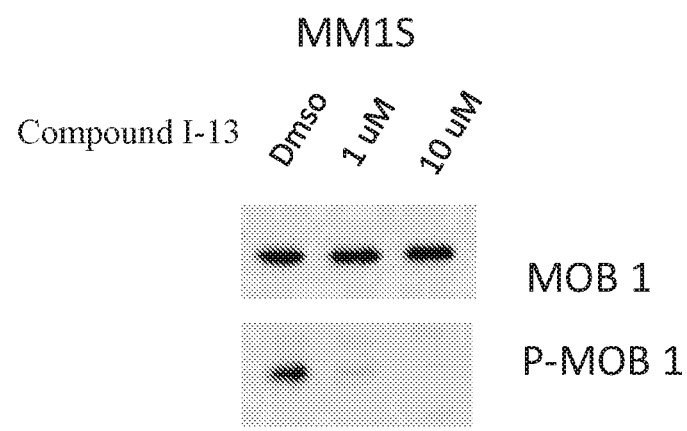
Figure 26I:
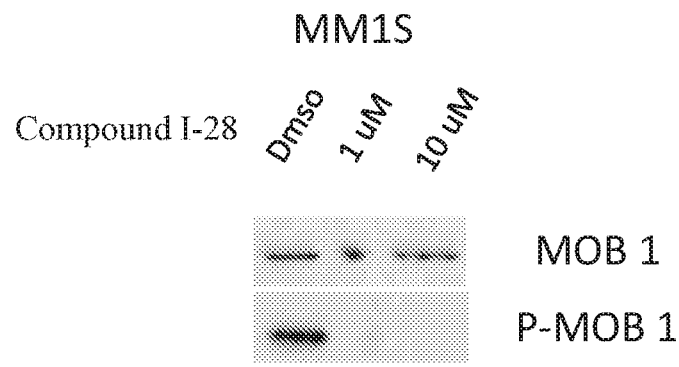
Figure 26J:
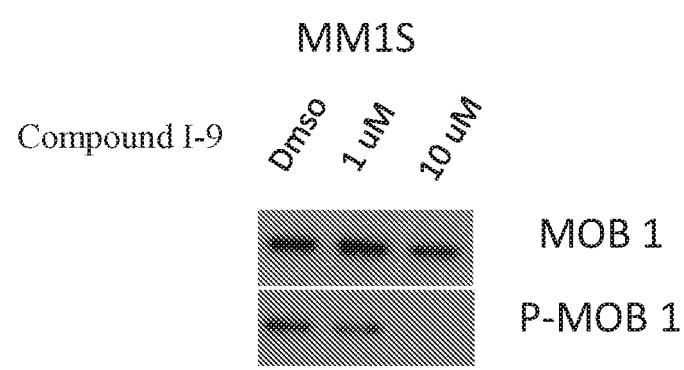
Figure 27A:
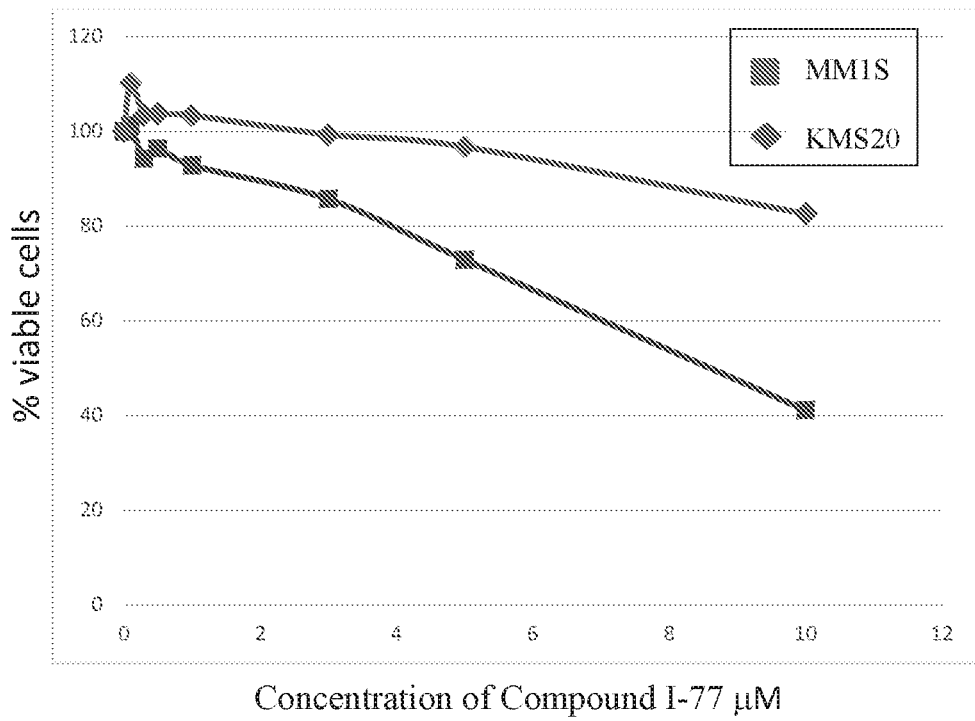
FIG. 27A is a graph showing the viability of MM.1S and KMS20 cells when treated with Compound I-77.
Figure 27B:
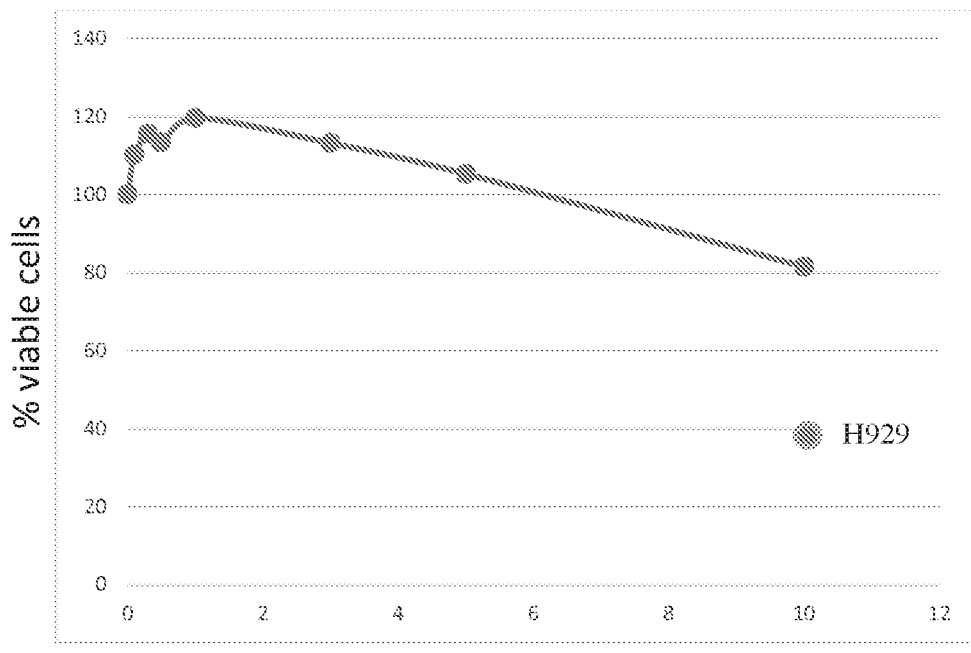
FIG. 27B is a graph showing the viability of H929 cells when treated with Compound I-77.

FIG. 13 show a Western blot of H929 and MM.1S cells treated with Compound I-13, Compound I-28, Compound I-9, KIN001-305, BMS536924, or DMSO at 1 μM concentration for 16 hours. Lysates were then obtained and immunoblot was performed using antibodies against YAP1, Actin, and pMOB1. As shown in FIG. 13, an increase in YAP1 levels were observed in cells treated with Compound I-9, 1-13, and 1-28, and this increase was lower than cells treated with KIN305, but higher than BMS536924.

In FIGS. 26A-26J, MM.1S cells were treated with Compound I-6, Compound I-31, Compound I-30, Compound I-22, Compound I-27, Compound I-1, Compound I-23, Compound I-13, Compound I-28, Compound I-9, or DMSO at 1 μM and 10 μM concentrations for 6 hours. Lysates were then obtained and immunoblot was performed using antibodies against MOB1 and p-MOB1. As shown from FIGS. 26A-26J, Compound I-22, Compound I-27, Compound I-1, Compound I-23, Compound I-13, Compound I-28, and Compound I-9 reduced PMOB1 levels at different concentrations.

Figure 28A:
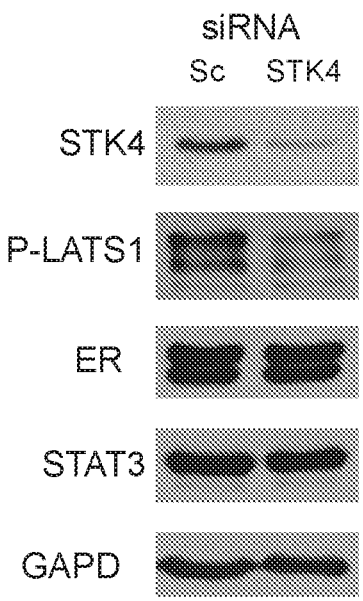
FIG. 28A is a Western blot showing the levels of STK4, P-LATS1, ERK, STAT3, and GAPDH, in H929 cells transfected with scrambled (Sc) or STK4 siRNA after 72 hours of incubation.
Figure 28B:
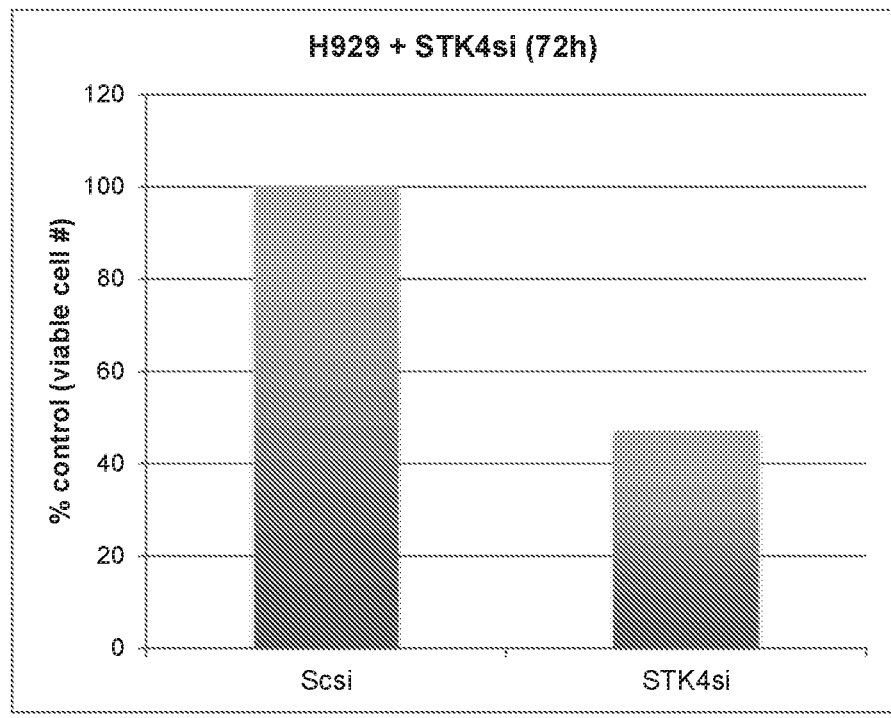
FIG. 28B is a graph showing the viability of H929 cells transfected with scrambled (Sc) or STK4 siRNA after 72 hours of incubation. The number of cell was estimated by Trypan-blue exclusion test.
Figure 29:
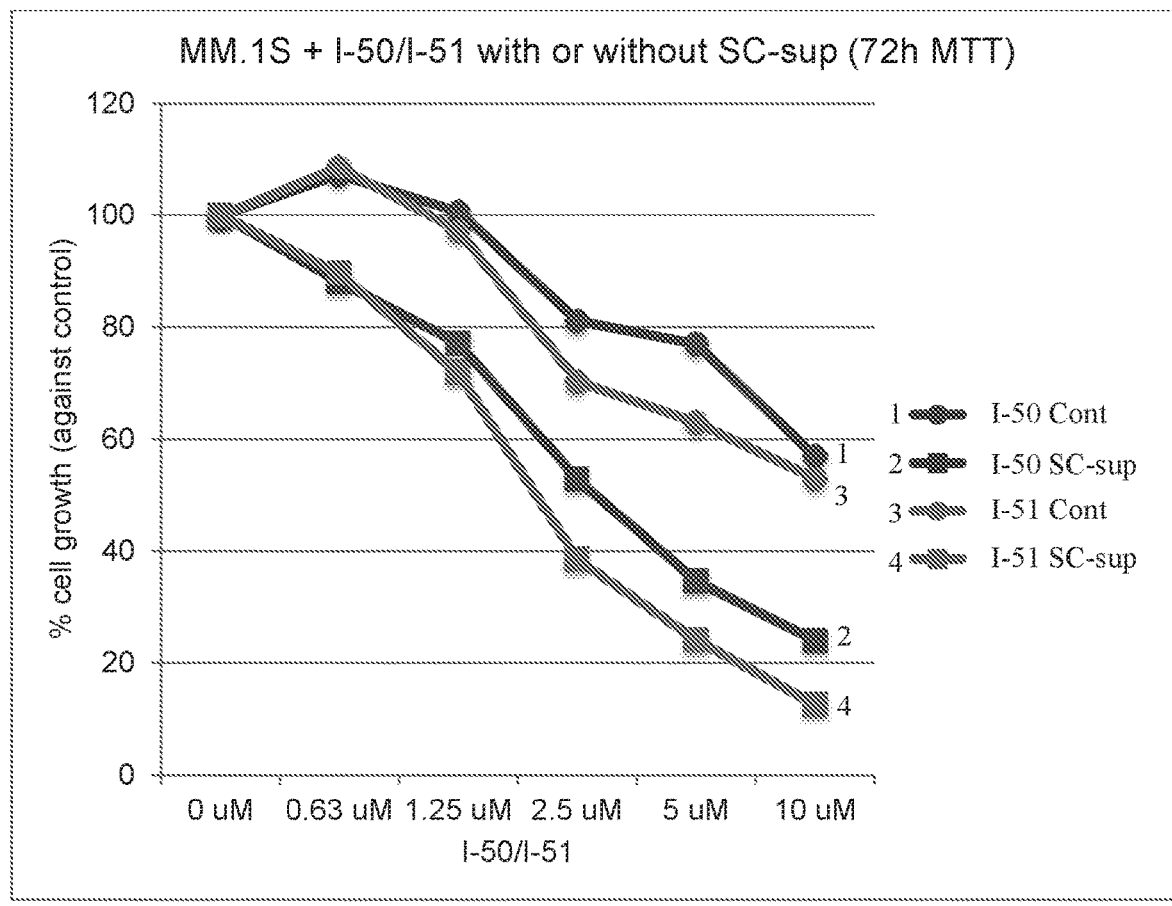
FIG. 29 is a graph showing cell growth of MM.1S cells treated for 72 hours with Compound I-50 or I-51 alone or in combination with stromal cell supernatant in an MTT assay in triplicate. Co-culture with stromal cell supernatant enhanced the susceptibility of cells to Compounds I-50 and I-51.
Figure 30:
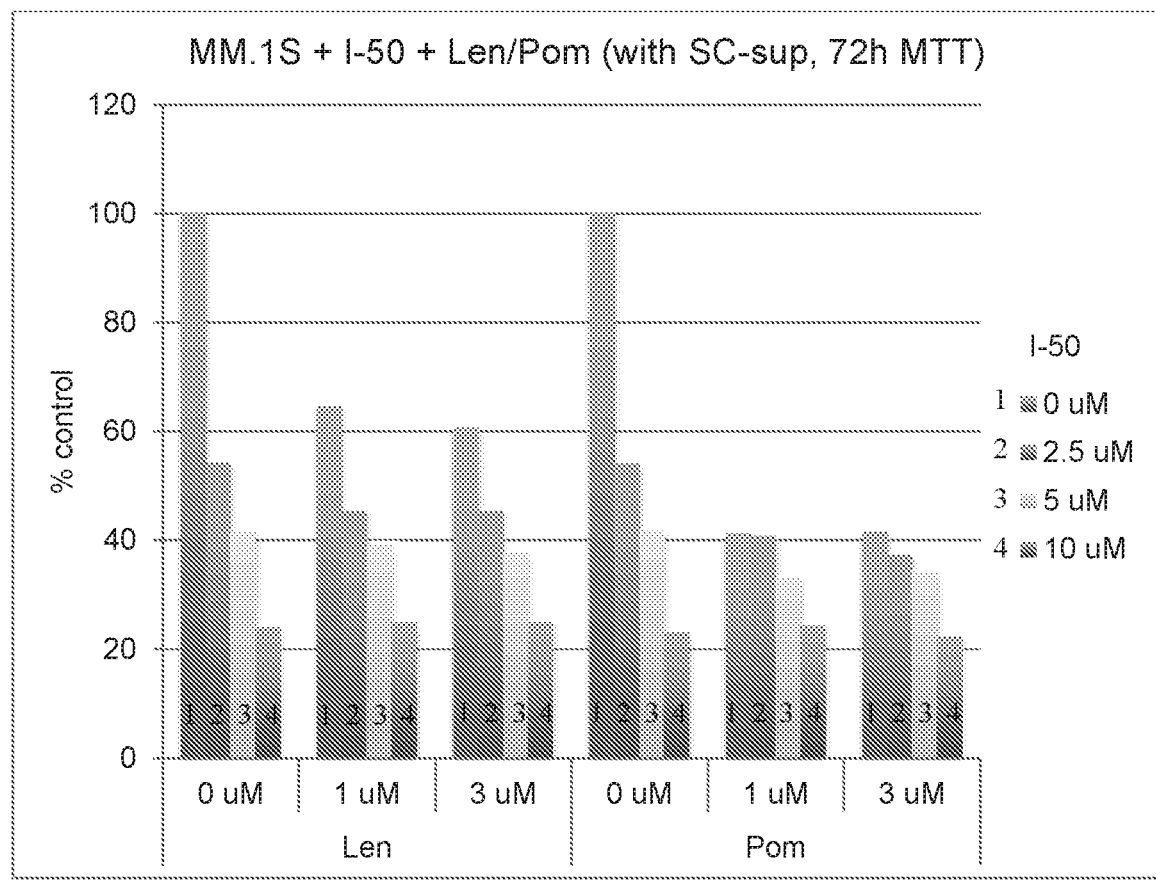
FIG. 30 is a graph showing cell growth of MM.1S cells treated for 72 hours with Lenalidomide/Pomalidomide in the presence of stromal cell supernatant alone or in combination with Compound I-50 in an MTT assay in triplicate. Compound I-50 enhanced the growth inhibitory effect of Lenalidomide/Pomalidomide in the presence of stromal cell supernatant.
Figure 31:
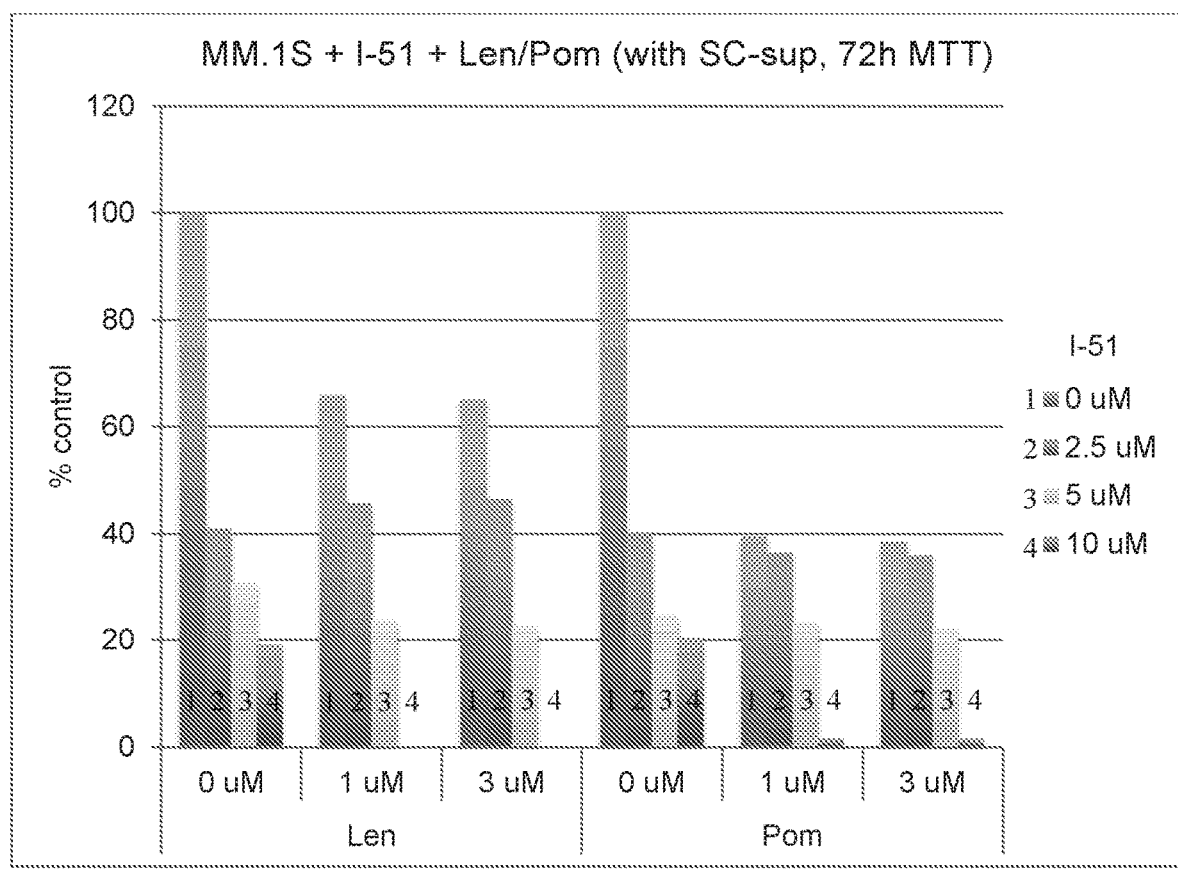
FIG. 31 is a graph showing cell growth of MM.1S cells treated for 72 hours with Lenalidomide/Pomalidomide in the presence of stromal cell supernatant alone or in combination with Compound I-51 in an MTT assay in triplicate. Compound I-51 enhanced the growth inhibitory effect of Lenalidomide/Pomalidomide in the presence of stromal cell supernatant.
Figure 32A:
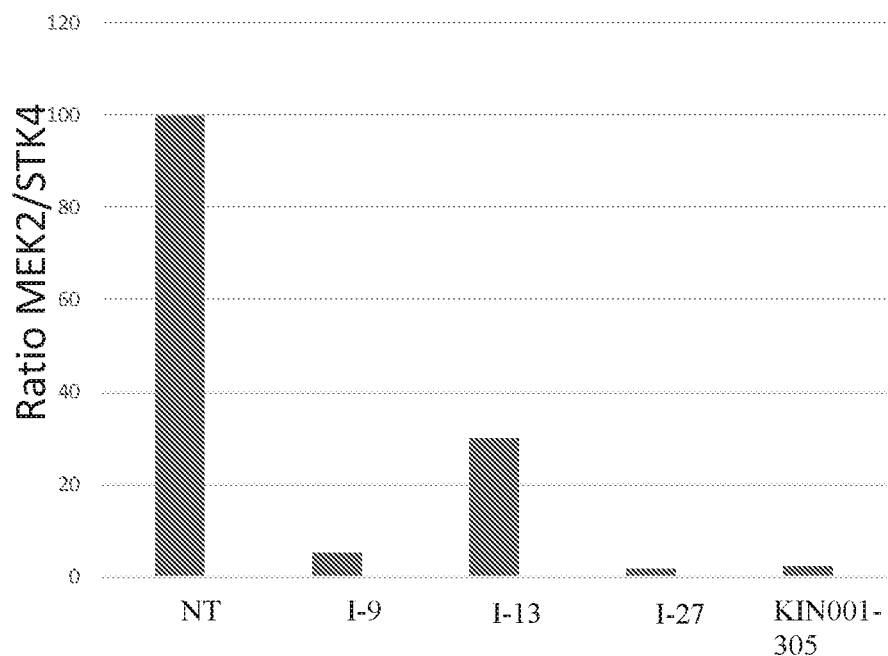
FIG. 32A and FIG. 32B show the results of a KiNativ™ Platform experiment obtained after incubating MM.1S cell lysates with 10 µM of the indicated compounds for 20 minutes, followed by incubation with biotinylated ATP for 10 minutes.
Figure 32B:
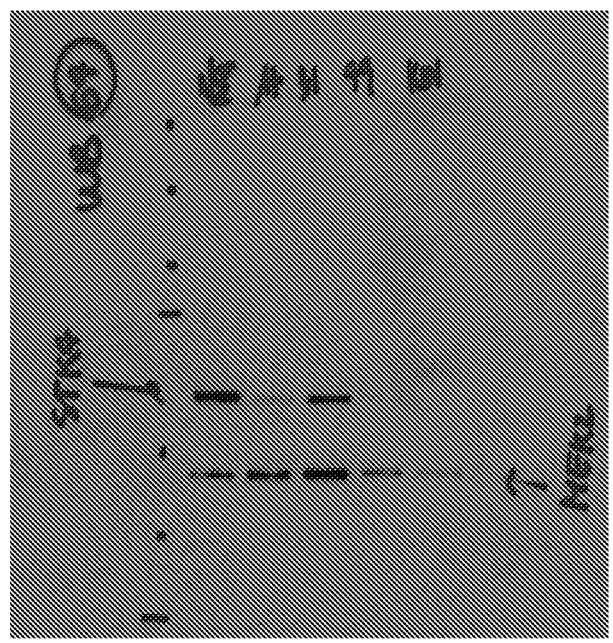

In FIGS. 28A and 28B, H929 cells were transfected with scrambled (Sc) or STK4 siRNA. After 72h incubation, whole cell lysates were subjected to immunoblotting using the indicated antibodies (i.e., STK4, P-LATS1, ERK, STAT3, and GAPDH). The results show that STK4 knockdown inhibits cell growth of H929 cells.

Apoptosis Assays

Apoptosis was quantified using Annexin-V-FITC-PI staining. In particular, cells were washed twice with room-temperature PBS, resuspended in 100 μL of Annexin binding buffer, and stained with specific antibodies for 20 minutes. After adding other 400 μL of Annexin binding buffer, samples were acquired using FACS Canto II machine from Becton Dickinson, BD, and analyzed with FCS EXPRESS 4 Flow Research Edition software. The percentage of cells undergoing apoptosis after treatment with a compound of the present application was defined as the sum of early apoptotic (AnnexinV+,PI−) and late apoptotic (Annexin V+PI+) cells.

Figure 7:
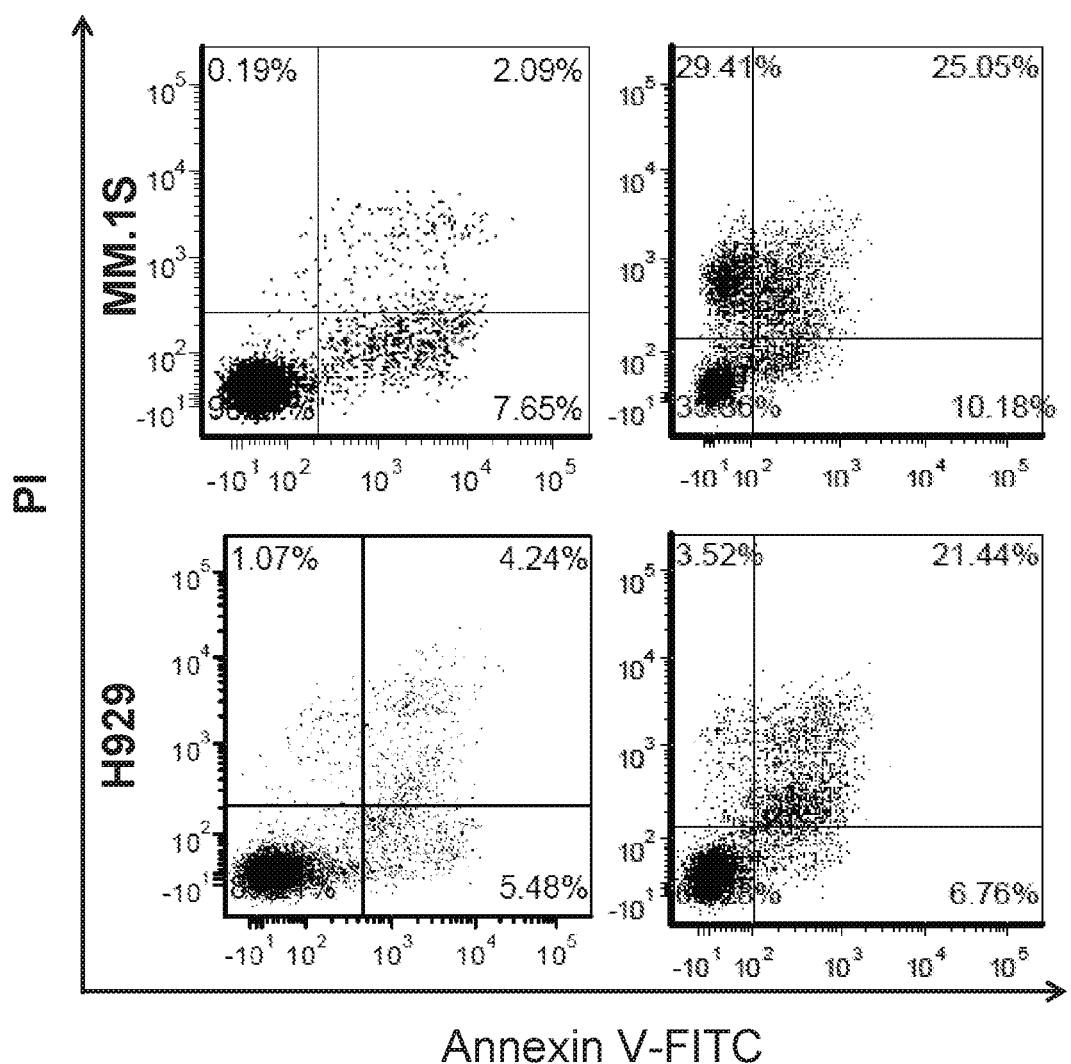
FIG. 7 is a graph showing apoptosis in MM.1S and H929 cell line when treated with Compound I-9. Annexin V-PI staining is performed after 48 hour treatment.

FIG. 7 shows apoptosis in MM.1S and H929 cells when treated with Compound I-9.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of the following formula:

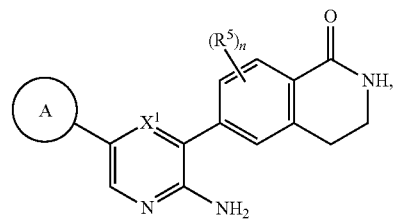

or a pharmaceutically acceptable salt, hydrate, solvate, stereoisomer, or tautomer thereof, wherein:

is

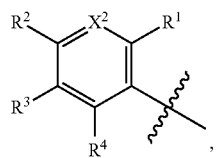

$X^1$ is N or CH;
$X^2$ is N or $CR^6$;
$R^1$ is H, $(C_1-C_3)$ alkyl, $(C_1-C_3)$ alkoxy, $NO_2$, halogen, O—$(C_3-C_7)$ cycloalkyl, or O-benzyl;
$R^2$ is H, $(C_1-C_2)$ alkyl, $(C_2-C_4)$ alkenyl, $(C_2-C_4)$ alkynyl, $(C_1-C_2)$ alkoxy, $(CH_2)_{0-2}$-heterocycloalkyl, halogen, $NO_2$, CN, $NR^9C(O)R^{10}$, $NR^9R^{10}$, $S(O)_m NR^9R^{10}$, $NHS(O)_m$—$(C_3-C_7)$ cycloalkyl, or $(CH_2)_{0-2}$-heteroaryl wherein the heteroaryl comprises a 5- to 6-membered ring and is optionally substituted with one or more substituents selected from halogen, $(C_1-C_3)$ alkyl, and $(C_1-C_3)$ alkoxy, wherein the alkyl, alkenyl, or alkynyl is optionally substituted with one or more substituents selected from $NH_2$, $NH(C_1-C_3)$ alkyl, and $N((C_1-C_3)$ alkyl$)_2$;
$R^3$ is H, halogen, $(C_1-C_3)$ alkyl, $(C_1-C_3)$ alkoxy, $NO_2$, $C(O)NR^{11}R^{12}$, $NR^{11}(O)R^{12}$, $C(O)OR^{11}$, $S(O)_m R^{12}$, $S(O)_m NR^{11}R^{12}$, $NHS(O)_m$—$(C_3-C_7)$ cycloalkyl, CN, or a 5- to 6-membered heteroaryl optionally substituted with one or more substituents selected from halogen, $(C_1-C_3)$ alkyl, and $(C_1-C_3)$ alkoxy, wherein the alkyl is optionally substituted with one or more substituents selected from $NH_2$, $NH(C_1-C_3)$ alkyl, and $N((C_1-C_3)$ alkyl$)_2$;
$R^4$ is H, $(C_1-C_3)$ alkyl, $(C_1-C_3)$ alkoxy, $NO_2$, halogen, O—$(C_3-C_7)$ cycloalkyl, or O-benzyl;
$R^6$ is H, halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_m R^{12}$, $S(O)_m NR^{11}R^{12}$, $NHS(O)_m$—$(C_3-C_7)$ cycloalkyl, CN, or a 5- to 6-membered heteroaryl optionally substituted with one or more substituents selected from halogen, $(C_1-C_3)$ alkyl, and $(C_1-C_3)$ alkoxy, wherein the alkyl is optionally substituted with one or more substituents selected from $NH_2$, $NH(C_1-C_3)$ alkyl, and $N((C_1-C_3)$ alkyl$)_2$; or
$R^2$ and $R^3$, together with the atoms to which they are attached, form a 6-membered heterocycloalkyl optionally substituted with one or more $R^7$, or a 5- to 6-membered heteroaryl optionally substituted with one or more $R^7$; or
$R^2$ and $R^6$, together with the atoms to which they are attached, form a 6-membered heterocycloalkyl optionally substituted with one or more $R^7$, or a 5- to 6-membered heteroaryl optionally substituted with one or more $R^7$; or
$R^3$ and $R^4$, together with the atoms to which they are attached, form a 5- to 6-membered heteroaryl optionally substituted with one or more $R^8$; or
$R^1$ and $R^6$, together with the atoms to which they are attached, form a 5- to 6-membered heteroaryl optionally substituted with one or more $R^8$;
each $R^7$ is independently $(C_1-C_3)$ alkyl, $(C_1-C_3)$ alkoxy, or halogen, or two $R^7$, together with the carbon atom to which they are attached, form C(O);
each $R^8$ is independently $(C_1-C_3)$ alkyl, $(C_1-C_3)$ alkoxy, or halogen, or two $R^8$, together with the carbon atom to which they are attached, form C(O);

$R^9$ and $R^{10}$ are each independently H, $(C_1-C_4)$ alkyl, $(CH_2)_{0-2}$-aryl, $(CH_2)_{0-2}$-heteroaryl, $(CH_2)_{0-2}$—$(C_3-C_7)$ cycloalkyl, or $(CH_2)_{0-2}$-heterocycloalkyl;
$R^{11}$ and $R^{12}$ are each independently H, $(C_1-C_4)$ alkyl, $(C_3-C_7)$ cycloalkyl, or heterocycloalkyl;
each $R^5$ is independently $(C_1-C_4)$ alkyl, $C(O)NR^{14}R^{15}$, CN, OH, or halogen;
$R^{14}$ and $R^{15}$ are each independently H or $(C_1-C_4)$ alkyl;
m is 0, 1, or 2; and
n is 1, 2, or 3
wherein at least one of $R^1$, $R^2$, $R^3$, $R^4$, and $R^6$ is not H; and
provided that
when $R^2$ is $S(O)_2NR^9R^{10}$ or F, then $R^4$ and $R^1$ are not simultaneously H, and
when $R^2$ is $S(O)_2NR^9R^{10}$, then $R^4$ or $R^1$ is not Cl.
2. The compound of claim 1, wherein the compound is of the following formula:

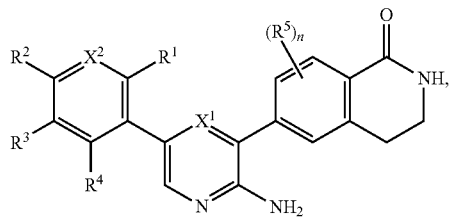

or a pharmaceutically acceptable salt, hydrate, solvate, stereoisomer, or tautomer thereof, wherein:
$X^1$ is N or CH;
$X^2$ is N or $CR^6$;
$R^1$ is H, $(C_1-C_3)$ alkyl, $(C_1-C_3)$ alkoxy, $NO_2$, or halogen;
$R^2$ is H, $(C_1-C_2)$ alkyl, $(C_1-C_2)$ alkoxy, $(CH_2)_{0-2}$-heterocycloalkyl, halogen, $NR^9C(O)R^{10}$, $NR^9R^{10}$, or $S(O)_m NR^9R^{10}$, wherein the alkyl is optionally substituted with one or more substituents selected from $NH_2$, $NH(C_1-C_3)$ alkyl, and $N((C_1-C_3)$ alkyl$)_2$;
$R^3$ is H, halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_m R^{12}$, $S(O)_m NR^{11}R^{12}$, or CN, wherein the alkyl is optionally substituted with one or more substituents selected from $NH_2$, $NH(C_1-C_3)$ alkyl, and $N((C_1-C_3)$ alkyl$)_2$;
$R^4$ is H, $(C_1-C_3)$ alkyl, $(C_1-C_3)$ alkoxy, $NO_2$, or halogen;
$R^6$ is H, halogen, $(C_1-C_3)$ alkyl, $(C_1-C_3)$ alkoxy, $NO_2$, $C(O)NR^{11}R^{12}$, $NR^{11}C(O)R^{12}$, $C(O)OR^{11}$, $S(O)_m R^{12}$, $S(O)_m NR^{11}R^{12}$, or CN, wherein the alkyl is optionally substituted with one or more substituents selected from $NH_2$, $NH(C_1-C_3)$ alkyl, and $N((C_1-C_3)$ alkyl$)_2$; or
$R^2$ and $R^3$, together with the atoms to which they are attached, form a 6-membered heterocycloalkyl optionally substituted with one or more $R^7$, or a 5- to 6-membered heteroaryl optionally substituted with one or more $R^7$; or
$R^2$ and $R^6$, together with the atoms to which they are attached, form a 6-membered heterocycloalkyl optionally substituted with one or more $R^7$, or a 5- to 6-membered heteroaryl optionally substituted with one or more $R^7$; or R³ and R⁴, together with the atoms to which they are attached, form a 5- to 6-membered heteroaryl optionally substituted with one or more R⁸; or R¹ and R⁶, together with the atoms to which they are attached, form a 5- to 6-membered heteroaryl optionally substituted with one or more R⁸;

each R⁷ is independently $(C_1-C_3)$ alkyl, $(C_1-C_3)$ alkoxy, or halogen, or two R⁷, together with the carbon atom to which they are attached, form C(O);

each R⁸ is independently $(C_1-C_3)$ alkyl, $(C_1-C_3)$ alkoxy, or halogen, or two R⁸, together with the carbon atom to which they are attached, form C(O);

R⁹ and R¹⁰ are each independently H, $(C_1-C_4)$ alkyl, $(CH_2)_{0-2}$-aryl, $(CH_2)_{0-2}$-heteroaryl, $(CH_2)_{0-2}$—$(C_3-C_7)$ cycloalkyl, or $(CH_2)_{0-2}$-heterocycloalkyl;

R¹¹ and R¹² are each independently H, $(C_1-C_4)$ alkyl, $(C_3-C_7)$ cycloalkyl, or heterocycloalkyl;

each R⁵ is independently $(C_1-C_4)$ alkyl, $C(O)NR^{14}R^{15}$, CN, OH, or halogen;

R¹⁴ and R¹⁵ are each independently H or $(C_1-C_4)$ alkyl;

m is 0, 1, or 2; and n is 1, 2, or 3;

wherein at least one of R¹, R², R³, R⁴, and R⁶ is not H; and provided that when R² is $S(O)_2NR^9R^{10}$ or F, then R⁴ and R¹ are not simultaneously H, and when R² is $S(O)_2NR^9R^{10}$, then R⁴ or R¹ is not Cl.

3. The compound of claim 1, wherein R⁵ is selected from OH, CN, Cl, and $C(O)NH_2$.

4. The compound of claim 1, wherein R¹ is selected from H, F, Cl, $NO_2$, and $OCH_3$.

5. The compound of claim 1, wherein R⁴ is selected from H, F, Cl, $NO_2$, and $OCH_3$.

6. The compound of claim 1, wherein R² is selected from H, $CH_3$, F, Cl, NHBn, $CH_2N(CH_3)_2$, $NHC(O)CH_3$, morpholinyl, $CH_2$-morpholinyl, $NO_2$, $S(O)_2N(CH_3)$cyclopropyl, and $OCH_3$.

7. The compound of claim 1, wherein R³ is selected from H, F, Cl, $NO_2$, CN, $C(O)NHCH_2CH_3$, $NHC(O)(CH_3)_2$, $CH_2N(CH_3)_2$, $C(O)OCH_3$, $S(O)_2N(CH_3)$cyclopropyl, and $OCH_3$.

8. The compound of claim 1, wherein R⁶ is selected from H, F, Cl, $NO_2$, CN, $C(O)NHCH_2CH_3$, $NHC(O)(CH_3)_2$, $CH_2N(CH_3)_2$, $C(O)OCH_3$, $S(O)_2N(CH_3)$cyclopropyl, and $OCH_3$.

9. The compound of claim 1, wherein R¹ and R⁶, together with the atoms to which they are attached, form an optionally substituted 5- to 6-membered heteroaryl.

10. The compound of claim 1, wherein R² and R³, together with the atoms to which they are attached, form an optionally substituted 6-membered heterocycloalkyl.

11. The compound of claim 1, wherein R² and R³, together with the atoms to which they are attached, form an optionally substituted optionally substituted 5- to 6-membered heteroaryl.

12. The compound of claim 1, wherein the compound is one of the following formulae:

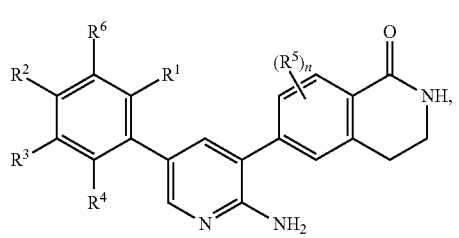

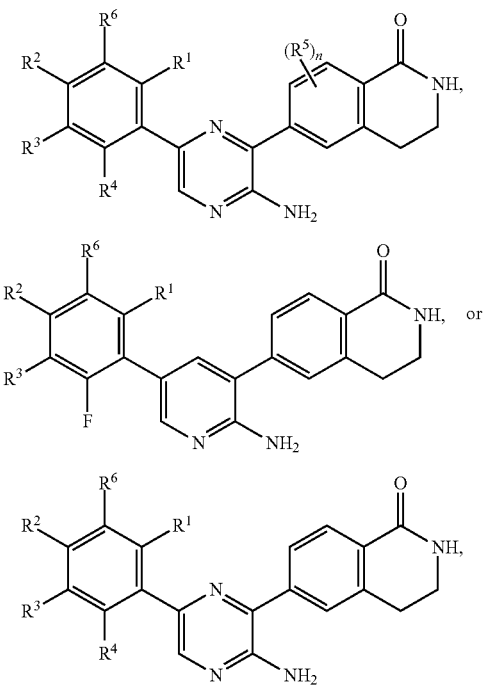

or a pharmaceutically acceptable salt, hydrate, solvate, stereoisomer, or tautomer thereof.

13. A compound selected from the group consisting of:

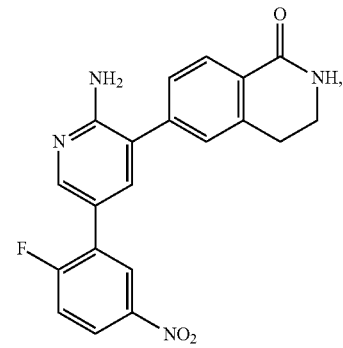

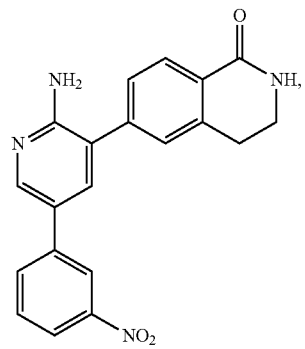

237
-continued
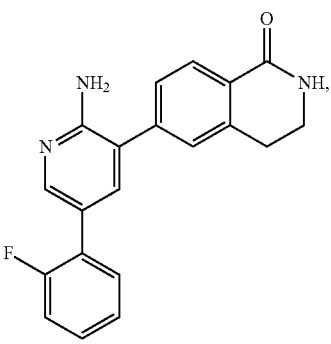
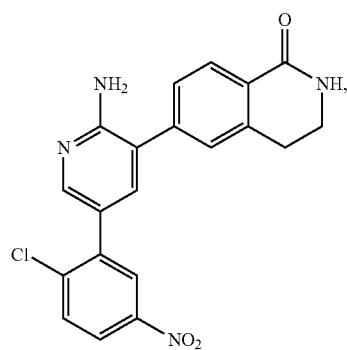
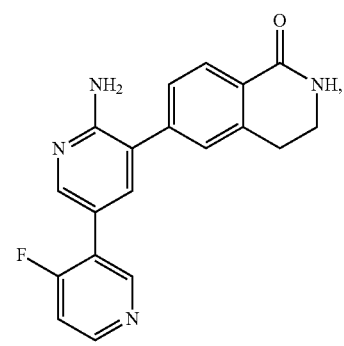
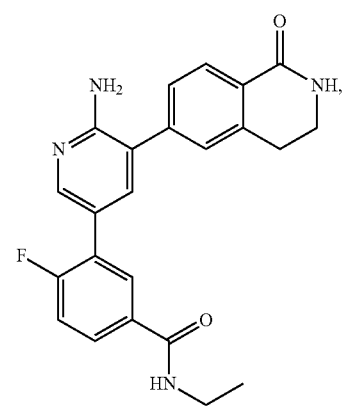
238
-continued
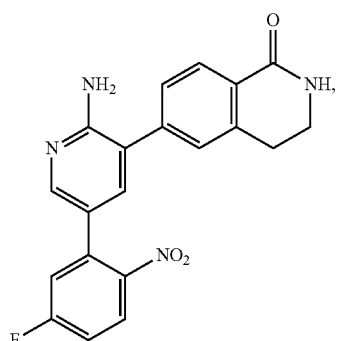
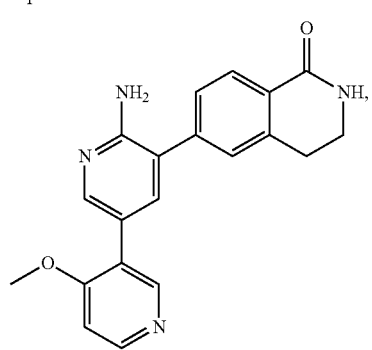
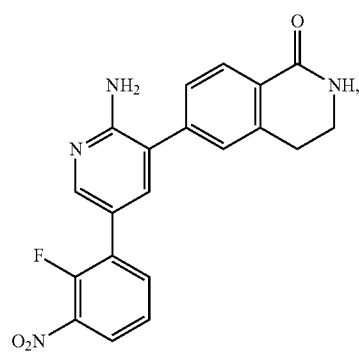
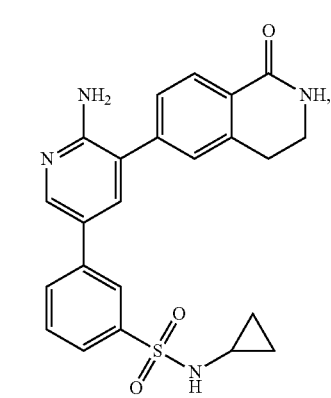

-continued
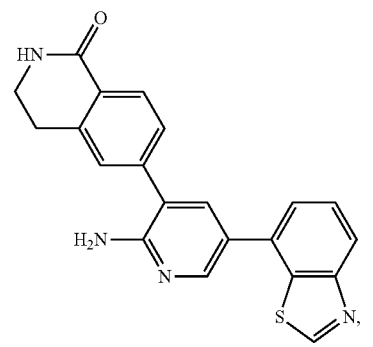
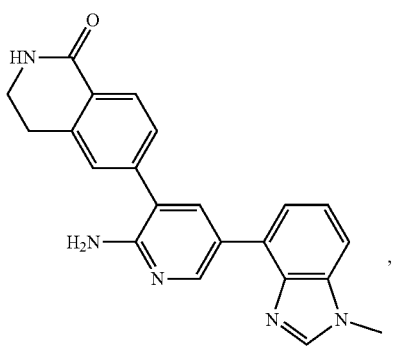
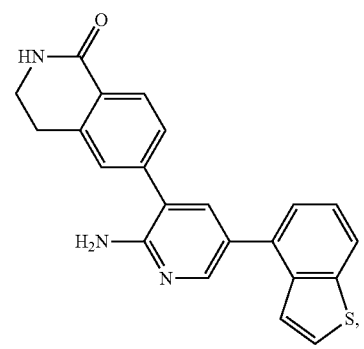
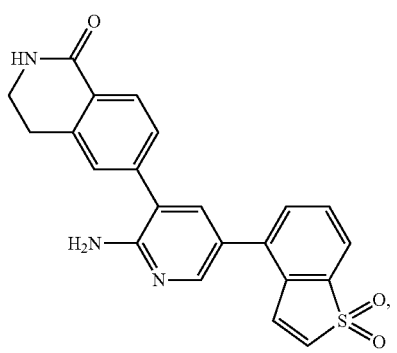
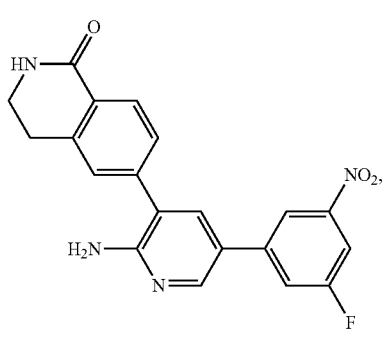
-continued
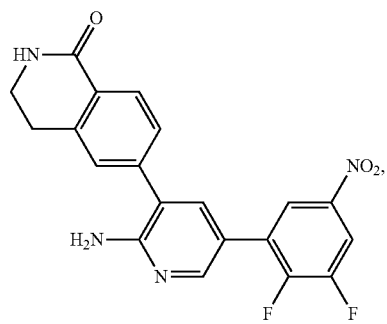
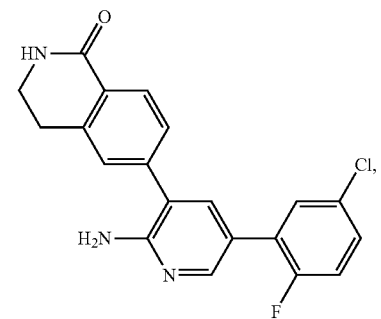
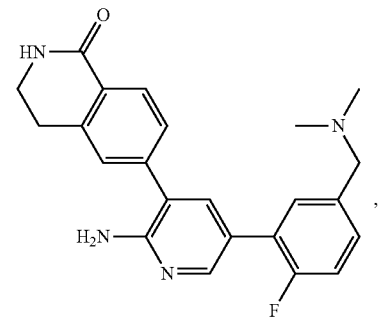
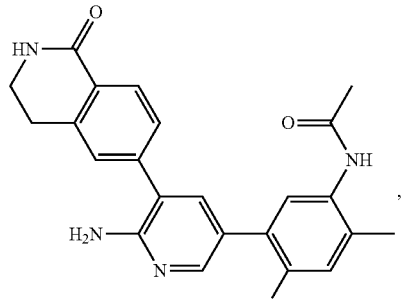
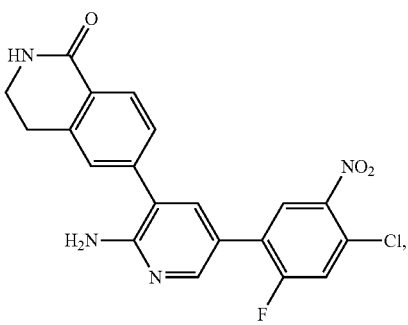

-continued
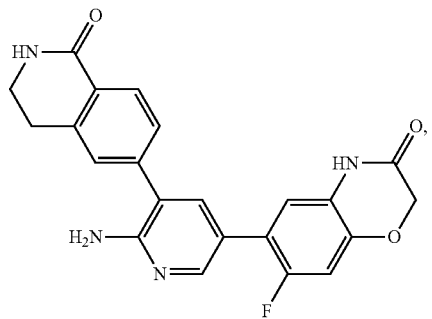
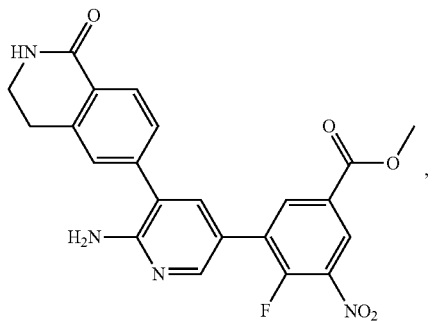
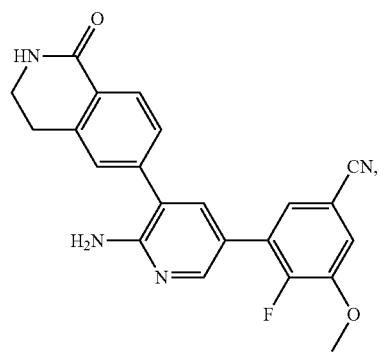
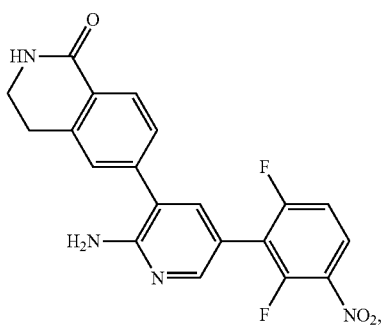
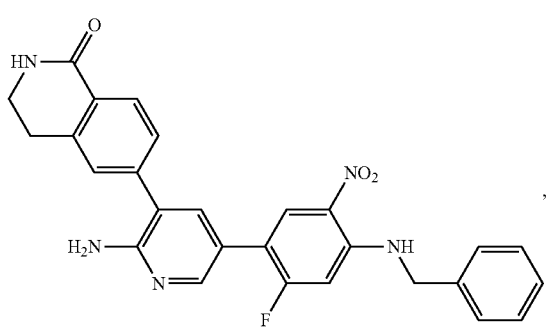
-continued
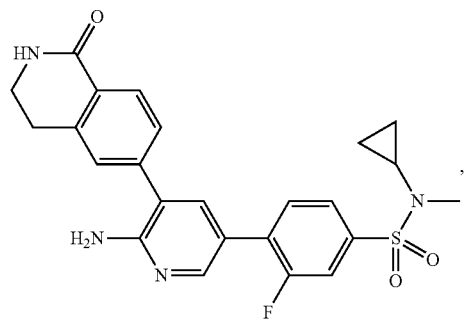
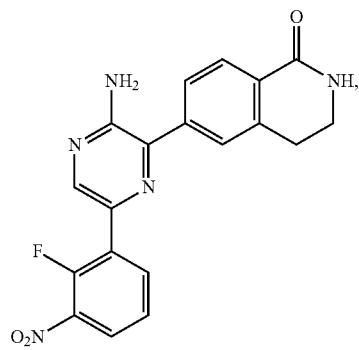
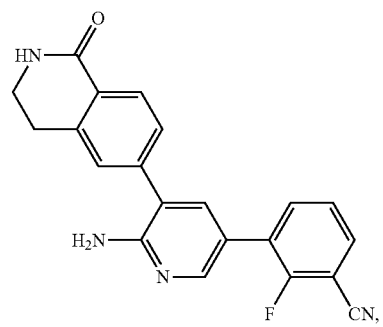
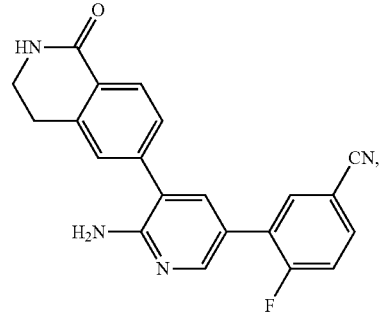
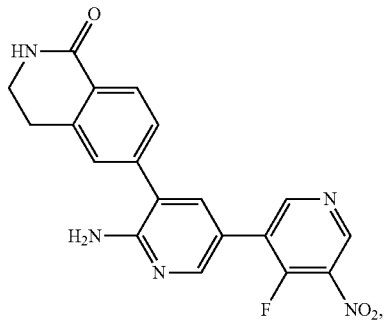

243
-continued
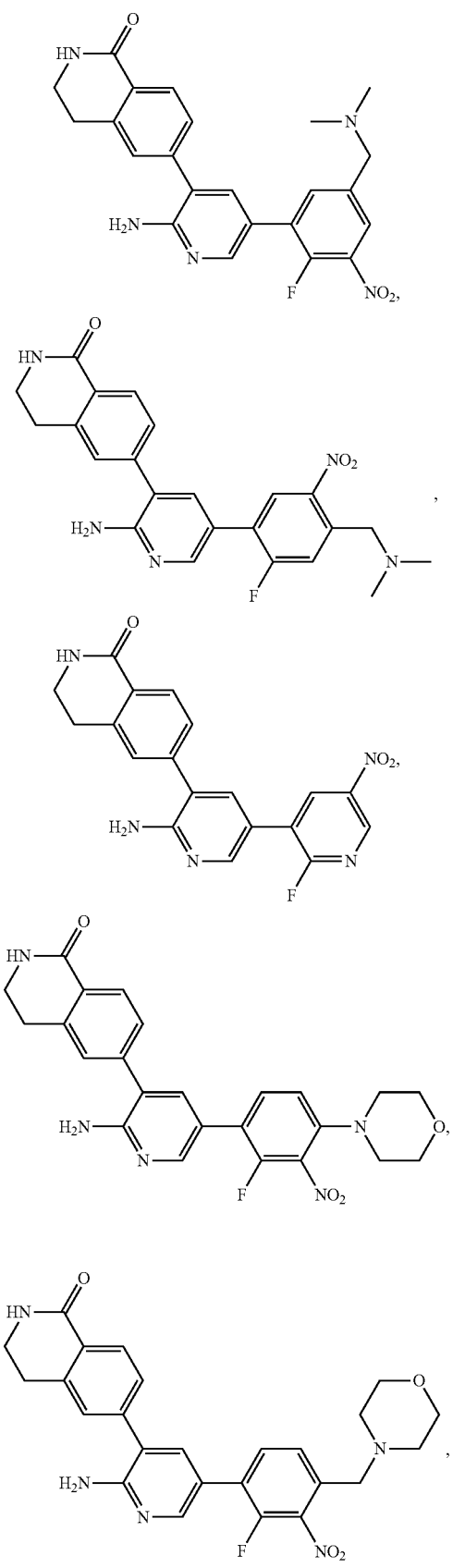
244
-continued
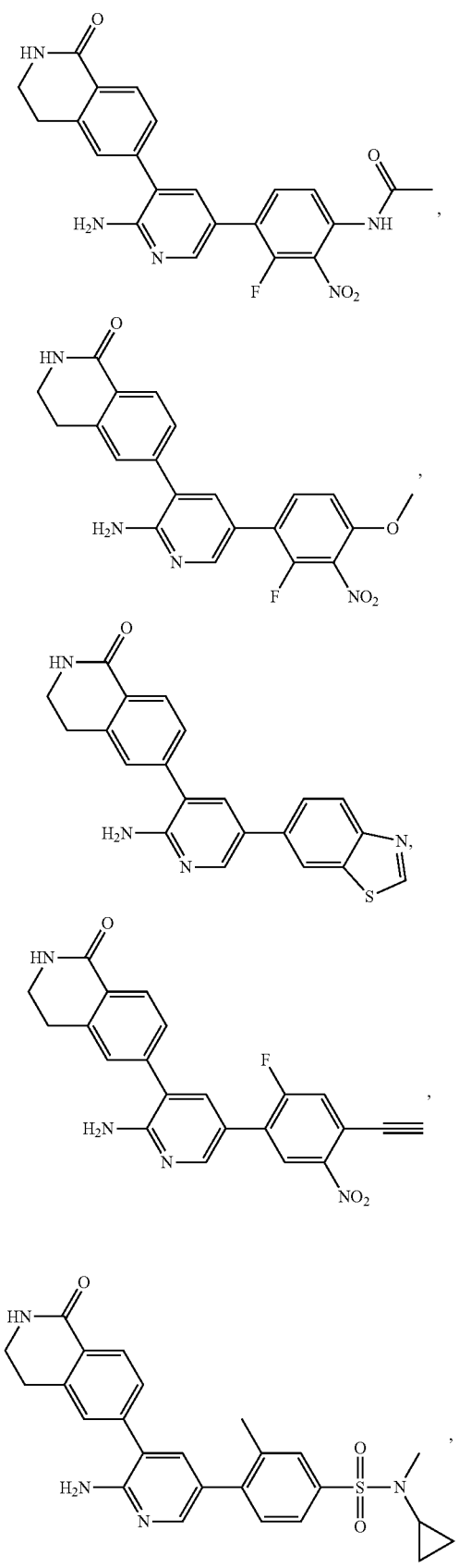

245
-continued
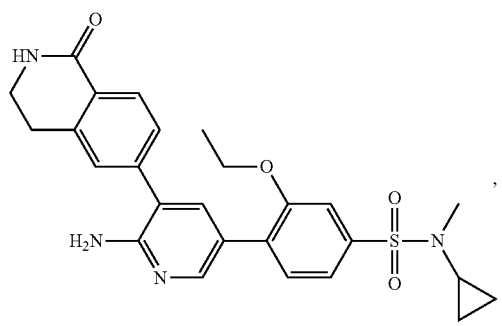
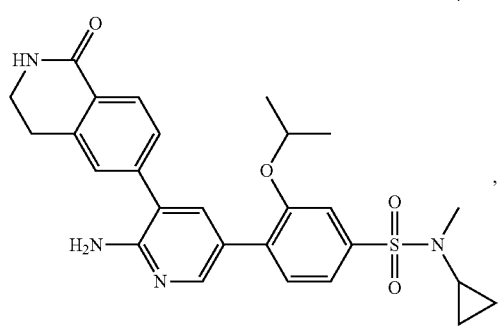
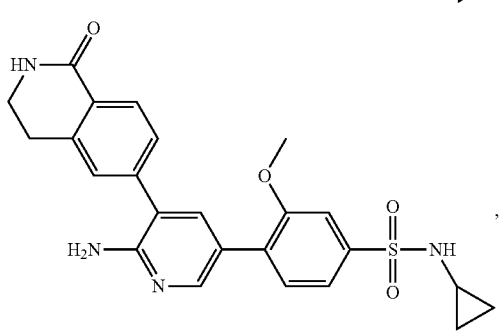
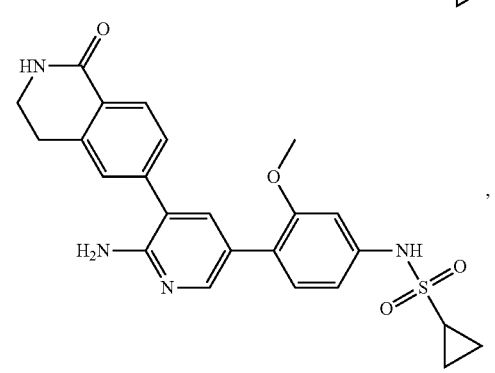
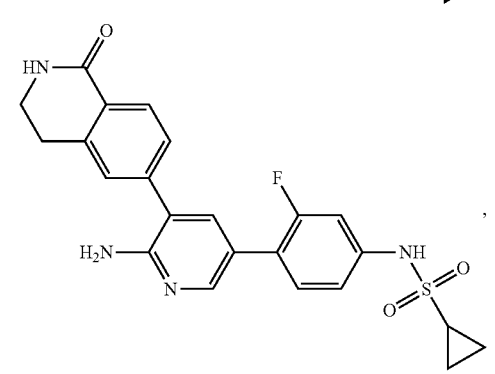
246
-continued
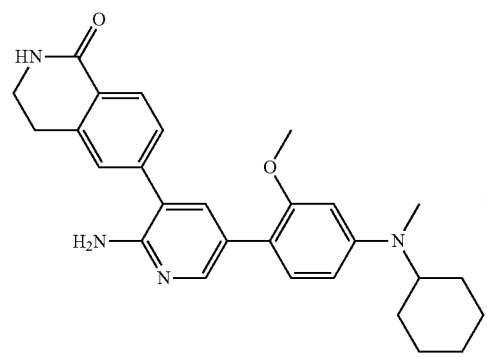
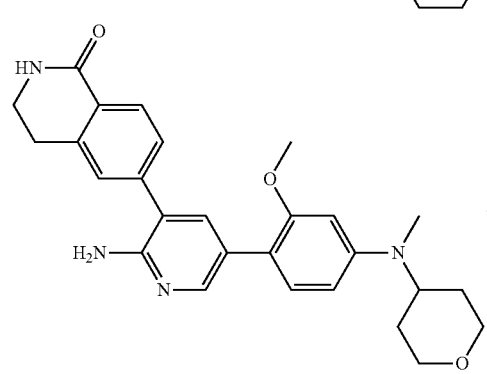
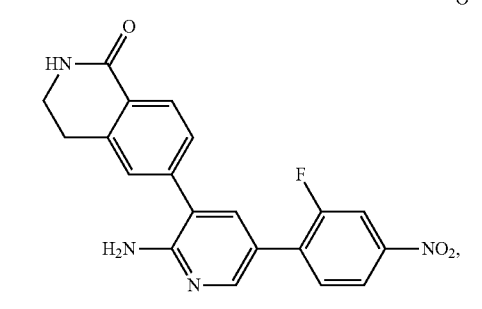
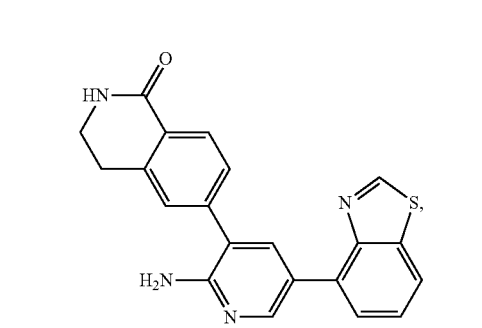
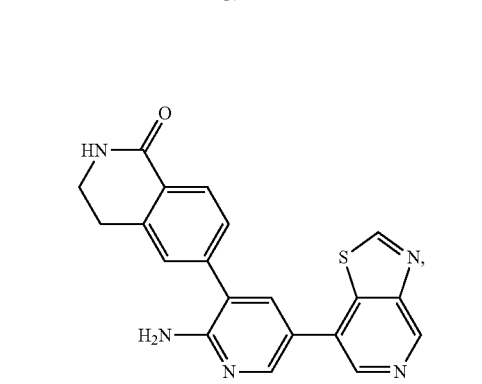

247
-continued
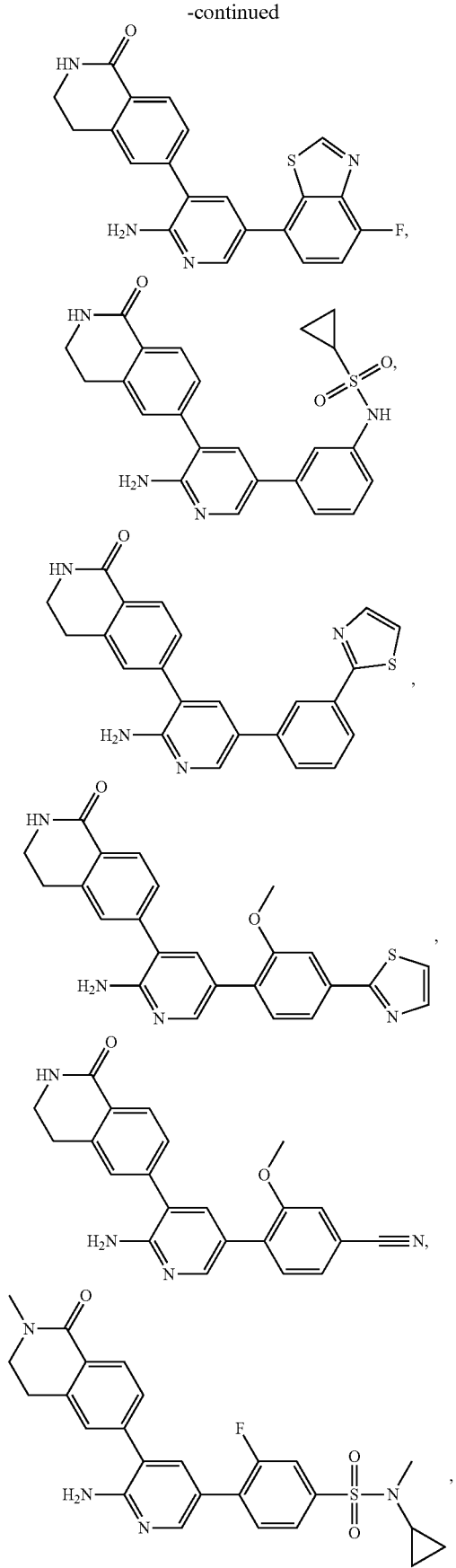
248
-continued
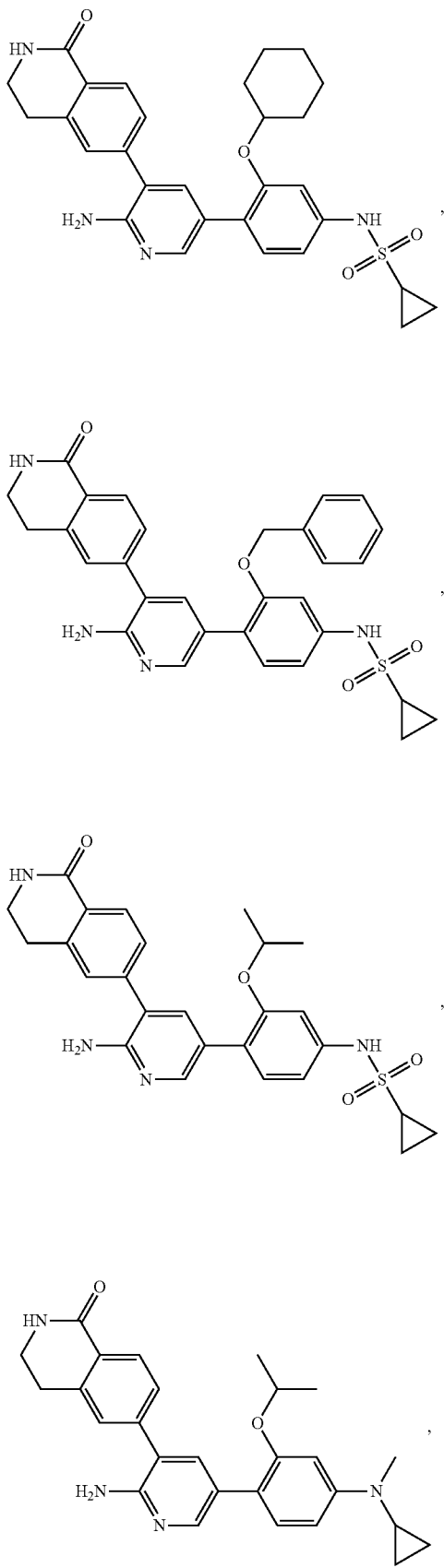

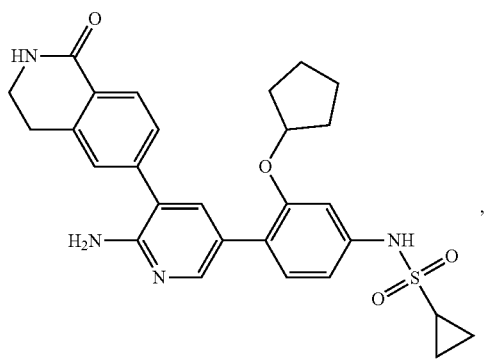

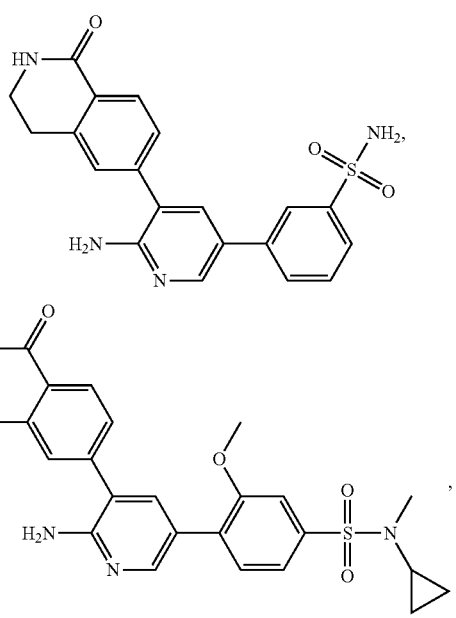

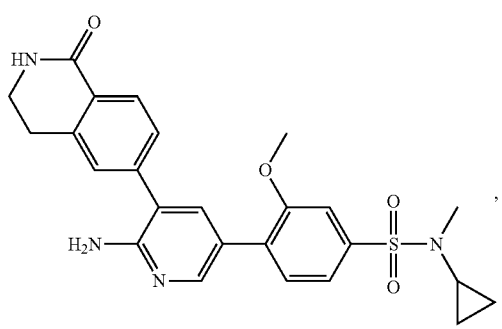

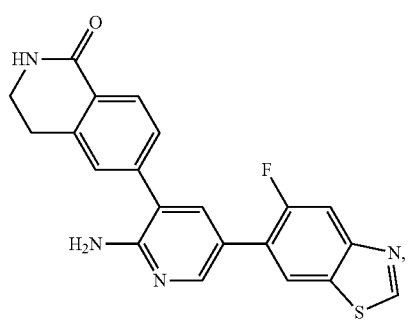

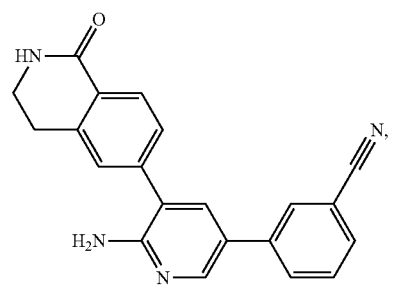

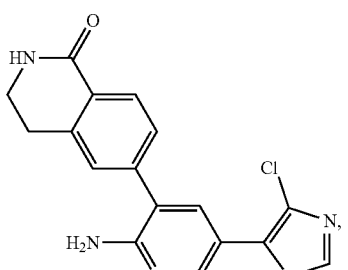

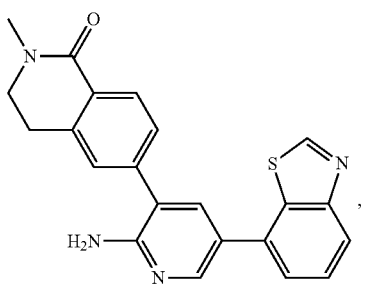

or a pharmaceutically acceptable salt, hydrate, solvate, stereoisomer, or tautomer thereof.

14. A pharmaceutical composition comprising the compound of claim 1 and a pharmaceutically acceptable carrier.

15. A method of treating cancer, a hyperproliferative disorder, or an autoimmune disorder, comprising administering to a subject in need thereof an effective amount of the compound of claim 1.

16. A method of modulating a kinase, comprising administering to a subject in need thereof an effective amount of the compound of claim 1.

17. The compound of claim 1, wherein the compound is

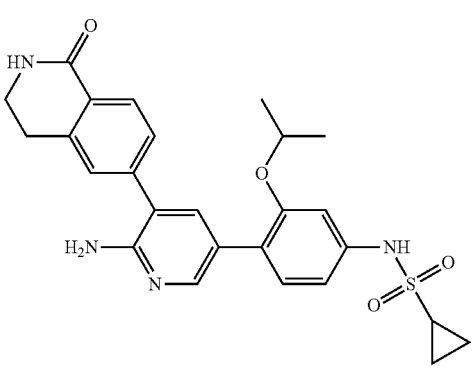 [SMILES: CC(C)Oc1cc(NS(=O)(=O)C2CC2)ccc1-c1cnc(N)c(-c2ccc3c(c2)CCNC3=O)c1]

or a pharmaceutically acceptable salt, hydrate, solvate, stereoisomer, or tautomer thereof.

18. The compound of claim 1, wherein the compound is
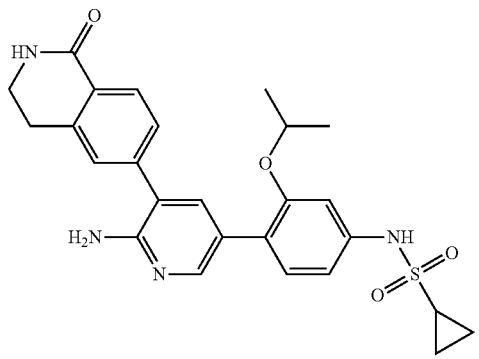 [SMILES: CC(C)Oc1cc(NS(=O)(=O)C2CC2)ccc1-c1cnc(N)c(-c2ccc3c(c2)CCNC3=O)c1]
or a pharmaceutically acceptable salt thereof.
19. A compound selected from the group consisting of:
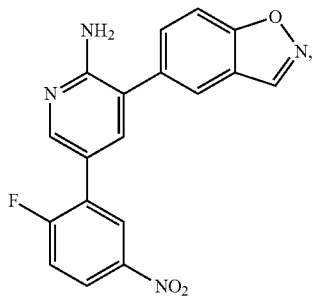
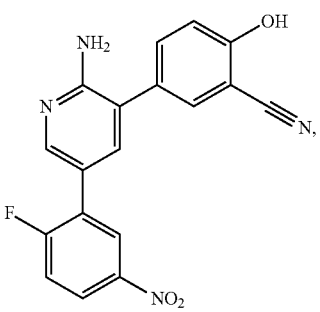
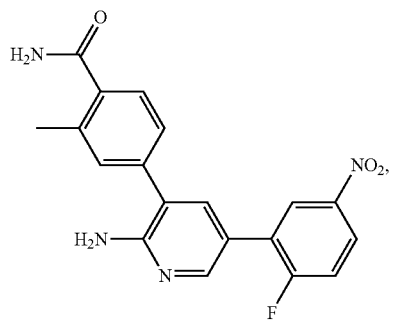
-continued
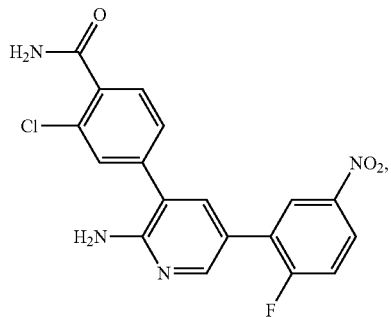
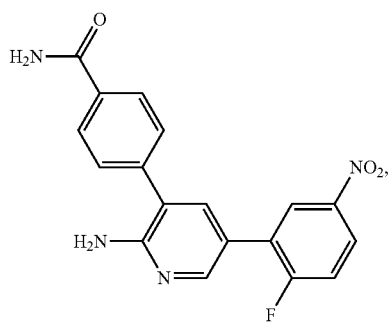
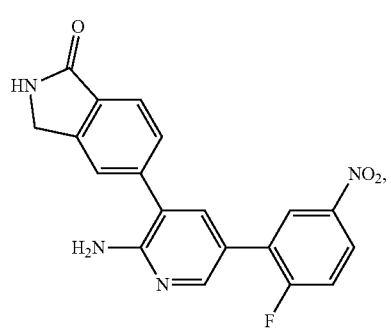
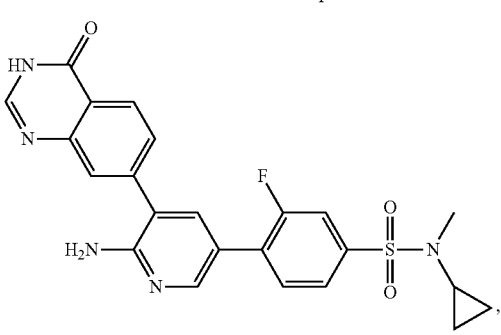
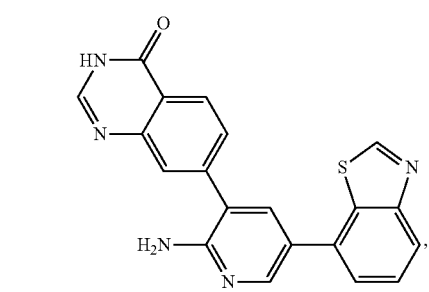

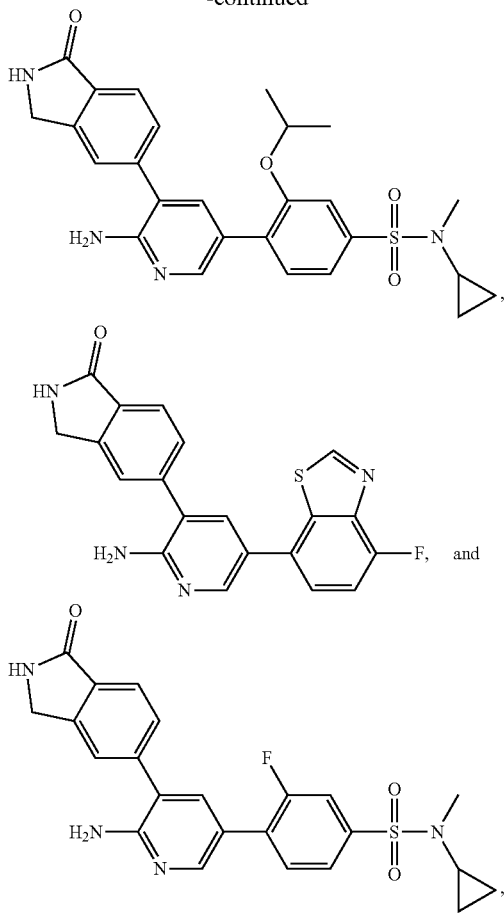

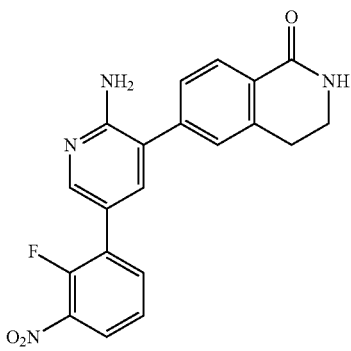 [SMILES: Nc1ncc(-c2cccc([N+](=O)[O-])c2F)cc1-c1ccc2c(c1)CCNC2=O]

or a pharmaceutically acceptable salt, hydrate, solvate, stereoisomer, or tautomer thereof.

20. The method of claim 15, wherein the cancer is a hematopoietic cancer.

21. The compound of claim 1, wherein the compound is or a pharmaceutically acceptable salt, hydrate, solvate, stereoisomer, or a tautomer thereof.

22. A pharmaceutical composition comprising the compound or pharmaceutically acceptable salt, hydtrate, solvate, stereoisomer, or tautomer thereof of claim 21, and a pharmaceutically acceptable carrier.

23. A method of treating cancer, a hyperproliferative disorder, or an autoimmmune disorder, comprising administering to the subject in need thereof an effective amount of the compound or pharmaceutically acceptable salt, hydrate, solcate, stereoisomer, or tautomer thereof of claim 21.

24. A method of modulating a kinase, comprising administering to a subject in need thereof an effective amount of the compound or pharmaceutically acceptable salt, hydrate, solvate, stereoisomer, or tautomer thereof of claim 21.

* * * * *

UNITED STATES PATENT AND TRADEMARK OFFICE
CERTIFICATE OF CORRECTION

Page 1 of 2

PATENT NO. : 10,710,978 B2
APPLICATION NO. : 15/562961
DATED : July 14, 2020
INVENTOR(S) : Nathanael S. Gray et al.

It is certified that error appears in the above-identified patent and that said Letters Patent is hereby corrected as shown below:

In the Claims

In Column 236, Lines 20-28:
Delete the following structure:

" 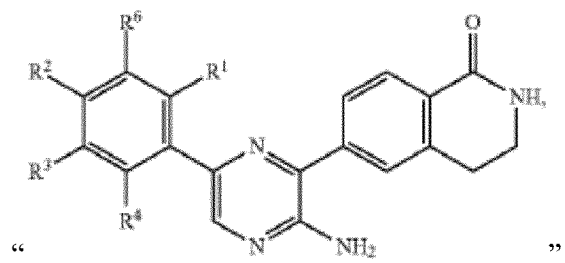 "

Replace with the following structure:

-- 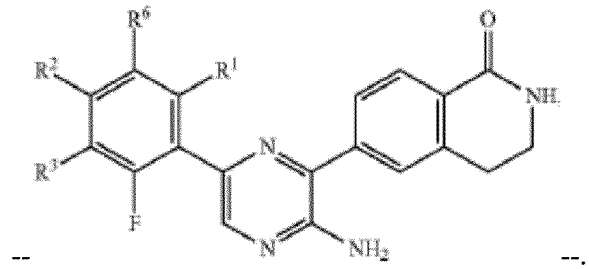 --.

Signed and Sealed this
Fifth Day of January, 2021

Andrei Iancu
*Director of the United States Patent and Trademark Office*

CERTIFICATE OF CORRECTION (continued)
U.S. Pat. No. 10,710,978 B2

In Column 246, Lines 2-28:
Delete the following structures:

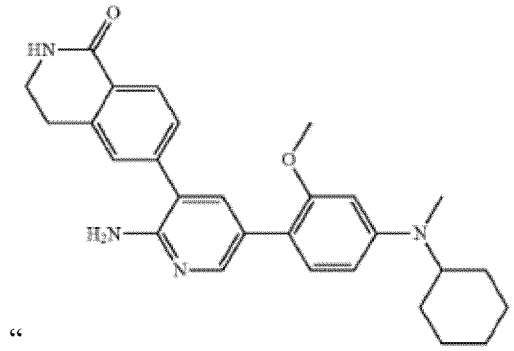
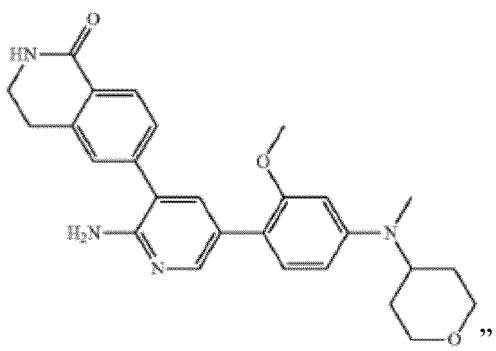

"

Replace with the following structures:

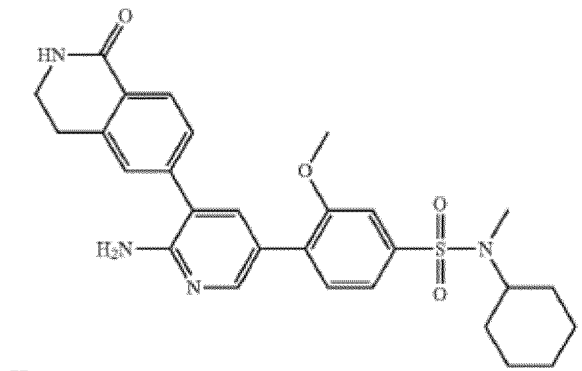
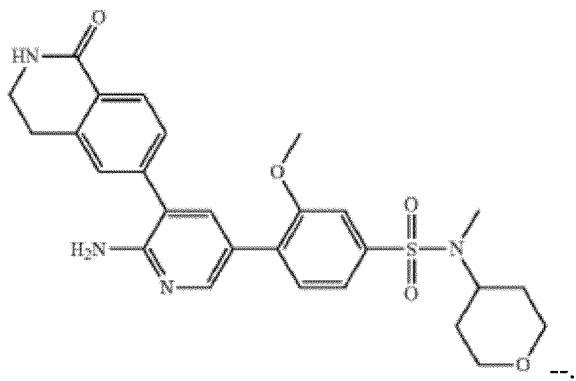

--

In Column 248, Lines 54-66:
Delete the following structure:

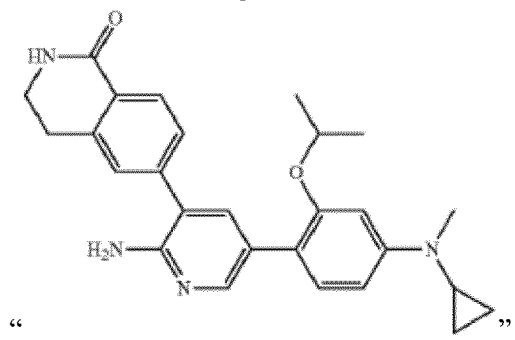

"

Replace with the following structure:

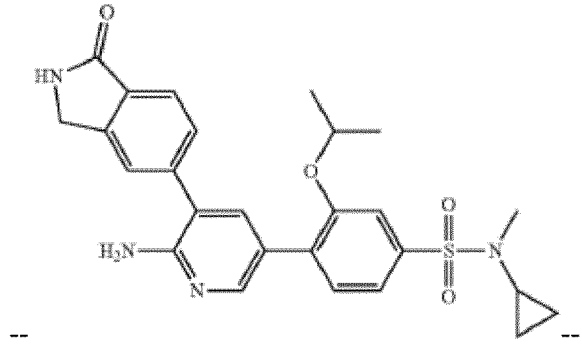

--.